US011489125B2

(12) United States Patent
Uno

(10) Patent No.: US 11,489,125 B2
(45) Date of Patent: Nov. 1, 2022

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-Si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 567 days.

(21) Appl. No.: 16/403,308

(22) Filed: May 3, 2019

(65) Prior Publication Data

US 2019/0363263 A1 Nov. 28, 2019

(30) Foreign Application Priority Data

May 28, 2018 (KR) ........................ 10-2018-0060192

(51) Int. Cl.
*C07D 495/10* (2006.01)
*H01L 51/00* (2006.01)
(Continued)

(52) U.S. Cl.
CPC ............ *H01L 51/0094* (2013.01); *C07F 7/10* (2013.01); *H01L 51/006* (2013.01); (Continued)

(58) Field of Classification Search
None
See application file for complete search history.

(56) References Cited

U.S. PATENT DOCUMENTS 6,329,082 B1 * 12/2001 Kreuder ................ C07F 7/0812 428/690
6,461,748 B1 * 10/2002 Suzuki .................. C09K 11/06 257/103
(Continued)

FOREIGN PATENT DOCUMENTS

CN 105154067 A 12/2015
CN 105778891 A 7/2016
(Continued)

OTHER PUBLICATIONS

Machine translation of CN-105154067, translation generated Apr. 2021, 31 pages. (Year: 2021).*
(Continued)

*Primary Examiner* — Robert S Loewe
(74) *Attorney, Agent, or Firm* — Lewis Roca Rothgerber Christie LLP

(57) ABSTRACT

An organic electroluminescence device of an embodiment includes a first electrode, a second electrode provided on the first electrode, and a plurality of organic material layers provided between the first electrode and the second electrode, wherein at least one organic material layer among the plurality of organic material layers include a monoamine compound, and the monoamine compound includes a core structure including two condensed rings which are combined to form a spiro structure, where each condensed ring has a condensed structure of three or more pentagonal or hexagonal rings. High emission efficiency may be achieved.

19 Claims, 2 Drawing Sheets

(51) Int. Cl.
*C07F 7/10* (2006.01)
*H01L 51/50* (2006.01)

(52) U.S. Cl.
CPC ...... *H01L 51/0052* (2013.01); *H01L 51/0061* (2013.01); *H01L 51/0072* (2013.01); *H01L 51/0073* (2013.01); *H01L 51/0074* (2013.01); *H01L 51/5012* (2013.01); *H01L 51/5056* (2013.01); *H01L 51/5072* (2013.01)

(56) References Cited

U.S. PATENT DOCUMENTS

| | | | | |
|---|---|---|---|---|
| 7,014,925 | B2 * | 3/2006 | Thoms | C07D 221/20 252/301.16 |
| 2004/0209115 | A1 | 10/2004 | Thompson et al. | |
| 2015/0162542 | A1 | 6/2015 | Ryu et al. | |
| 2016/0035986 | A1 * | 2/2016 | Chung | C07D 493/10 257/40 |
| 2016/0329507 | A1 * | 11/2016 | Stoessel | H01L 51/0073 |
| 2018/0287068 | A1 | 10/2018 | Ha et al. | |
| 2018/0309067 | A1 * | 10/2018 | Wolohan | C07D 519/00 |
| 2018/0315942 | A1 * | 11/2018 | Wolohan | C07D 245/04 |
| 2018/0337343 | A1 * | 11/2018 | Wolohan | C07B 59/002 |

FOREIGN PATENT DOCUMENTS

| | | | | |
|---|---|---|---|---|
| CN | 105906640 | A | 8/2016 | |
| CN | 105154067 | * | 8/2017 | C07D 495/10 |
| CN | 107586307 | A | 1/2018 | |
| CN | 108976244 | A | 12/2018 | |
| EP | 2 980 182 | A1 | 2/2016 | |
| KR | 10-2014-0025120 | A | 3/2014 | |
| KR | 10-2015-0106501 | A | 9/2015 | |
| KR | 10-2017-0082824 | A | 7/2017 | |
| KR | 10-1781739 | B1 | 9/2017 | |
| KR | 10-2017-0114369 | A | 10/2017 | |
| KR | 10-2017-0134163 | A | 12/2017 | |
| KR | 10-2017-0138799 | A | 12/2017 | |
| WO | WO 2010/061315 | A1 | 6/2010 | |
| WO | WO 2013/139431 | A1 | 9/2013 | |

OTHER PUBLICATIONS

Partial European Search Report for corresponding European Patent Application No. 19173390.6, dated Jul. 16, 2019, 11 pages.

* cited by examiner

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATIONS

This application claims priority to and the benefit of Korean Patent Application No. 10-2018-0060192, filed on May 28, 2018, in the Korean Intellectual Property Office, the entire content of which is hereby incorporated by reference.

BACKGROUND

1. Field

The present disclosure herein relates to an organic electroluminescence device and a monoamine compound utilized in the organic electroluminescence device.

2. Description of the Related Art

The development of an organic electroluminescence device as an image display device is being actively conducted. Different from a liquid crystal display device, the organic electroluminescence device is a so-called self-luminescent display device, in which holes and electrons injected from a first electrode and a second electrode recombine in an emission layer, and a light emission material including an organic compound in the emission layer emits light to attain a display.

In the application of an organic electroluminescence device to a display device, the decrease of a driving voltage, and the increase of an emission efficiency and life (e.g., lifespan) are desired, and the development of a material for stably accomplishing these desires for an organic electroluminescence device is continuously pursued.

In addition, the development of a material for a hole transport layer for accomplishing an organic electroluminescence device having high efficiency is being conducted.

SUMMARY

Aspects according to embodiments of the present disclosure are directed toward an organic electroluminescence device and a monoamine compound utilized in the organic electroluminescence device.

According to an embodiment of the inventive concept, an organic electroluminescence device includes a first electrode, a second electrode on the first electrode, and a plurality of organic material layers between the first electrode and the second electrode, wherein at least one organic material layer among the plurality of organic material layers includes a monoamine compound, and the monoamine compound includes a core structure including two condensed rings which are combined to form a spiro structure, where each condensed ring has a condensed structure of three or more pentagonal or hexagonal rings.

In an embodiment, a central atom of the spiro structure may be carbon or silicon.

When the central atom is carbon, the core structure may include two condensed rings which are combined to form a spiro structure, where each condensed ring has a condensed structure of three or more hexagonal rings, and when the central atom is silicon, the core structure may include two condensed rings which are combined to form a spiro structure, where each condensed ring has a condensed structure of three or more pentagonal or hexagonal rings.

In an embodiment, the organic material layers may include a hole transport region on the first electrode, an emission layer on the hole transport region, and an electron transport region on the emission layer, wherein the hole transport region includes the monoamine compound.

In an embodiment, the hole transport region may include a hole injection layer, and a hole transport layer between the hole injection layer and the emission layer, wherein the hole transport layer includes the monoamine compound.

In an embodiment, the hole transport layer may include a plurality of organic layers, and an organic layer adjacent to the emission layer among the plurality of organic layers may include the monoamine compound.

In an embodiment, the monoamine compound may be represented by following Formula 1:

Formula 1

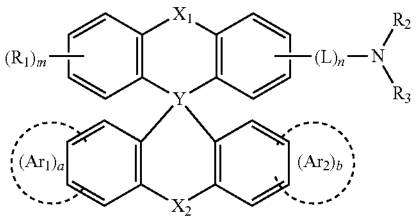

In Formula 1, Y is C or Si, when Y is C, $X_1$ and $X_2$ are each independently O, S, or $SiR_4R_5$, and $X_1$ and $X_2$ are different from each other, and when Y is Si, $X_1$ and $X_2$ are each independently O, S, $SiR_4R_5$, or a direct linkage, and both $X_1$ and $X_2$ are direct linkages is excluded (i.e., a case where both $X_1$ and $X_2$ are direct linkages is excluded).

In Formula 1, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring, and L is a direct linkage, a substituted or unsubstituted arylene group having 6 to 30 carbon atoms, or a substituted or unsubstituted heteroarylene group having 2 to 30 carbon atoms for forming a ring.

In Formula 1, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, a, b and n are each independently 0 or 1, and m is an integer of 0 to 4.

In an embodiment, the monoamine compound represented by Formula 1 may be represented by following Formula 2 or Formula 3:

Formula 2

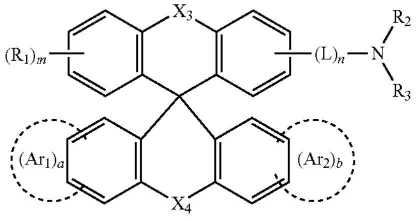

-continued

Formula 3

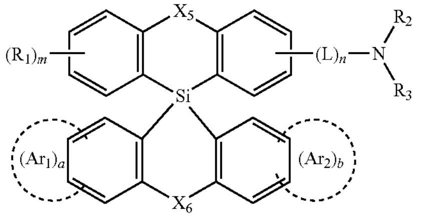

In Formula 2, $X_3$ and $X_4$ are each independently O, S, or $SiR_4R_5$, and $X_3$ and $X_4$ are different from each other.

In Formula 3, $X_5$ and $X_6$ are each independently O, S, $SiR_4R_5$, or a direct linkage, and both $X_5$ and $X_6$ are direct linkages is excluded.

In Formulae 2 and 3, $R_1$ to $R_5$, L, $Ar_1$, $Ar_2$, a, b, m and n are the same as respectively defined in association with Formula 1.

According to an embodiment of the inventive concept, an organic electroluminescence device includes a first electrode, a second electrode on the first electrode, and a plurality of organic material layers between the first electrode and the second electrode, wherein at least one organic material layer among the plurality of organic material layers comprises a monoamine compound represented by Formula 1 above.

According to an embodiment of the inventive concept, a monoamine compound is represented by Formula 1 above.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
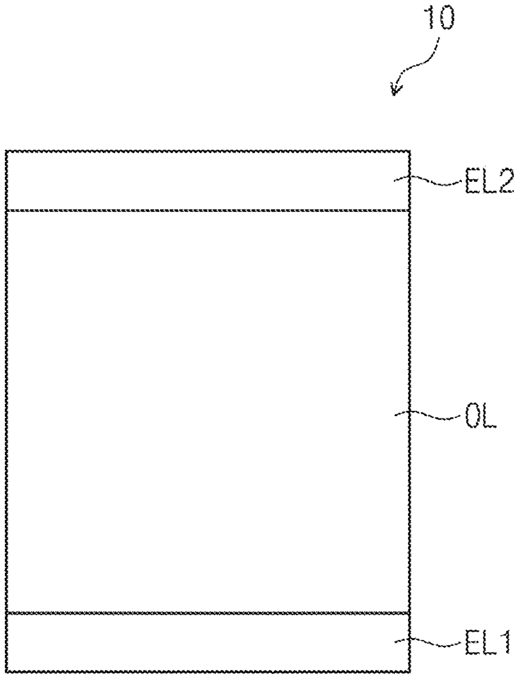
FIG. 1 is a cross-sectional view schematically illustrating an organic electroluminescence device according to an embodiment of the inventive concept.

The above aspects, other aspects, features and enhancements of the inventive concept will be easily understood from exemplary (e.g., preferred exemplary) embodiments with reference to the accompanying drawings. The inventive concept may, however, be embodied in different forms and should not be construed as limited to the embodiments set forth herein. Rather, exemplary embodiments are provided so that the contents disclosed herein become thorough and complete, and the spirit of the inventive concept is sufficiently described for a person skilled in the art.

Like reference numerals refer to like elements for explaining each drawing. In the drawings, the sizes of elements may be enlarged for clarity of the inventive concept. It will be understood that, although the terms "first," "second," etc., may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc., is referred to as being "on" another part, it can be "directly on" the other part, or intervening layers may also be present. Similarly, when a layer, a film, a region, a plate, etc., is referred to as being "under" another part, it can be "directly under" the other part, or intervening layers may also be present.

In the description, -* represents a part to be connected.

First, organic electroluminescence devices according to exemplary embodiments of the inventive concept will be explained by referring to FIG. 1 to FIG. 3.

FIG. 1 is a cross-sectional view schematically illustrating an organic electroluminescence device according to an embodiment of the inventive concept. FIG. 2 is a cross-sectional view schematically illustrating an organic electroluminescence device according to an embodiment of the inventive concept. FIG. 3 is a cross-sectional view schematically illustrating an organic electroluminescence device according to an embodiment of the inventive concept.

Figure 2:
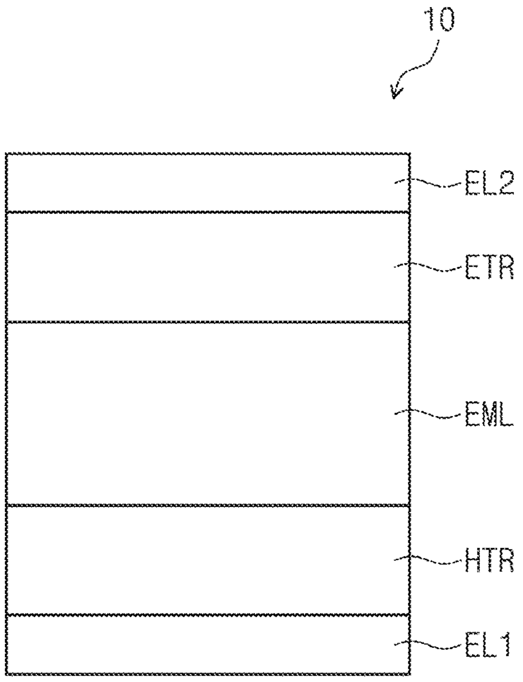
FIG. 2 is a cross-sectional view schematically illustrating an organic electroluminescence device according to an embodiment of the inventive concept.
Figure 3:
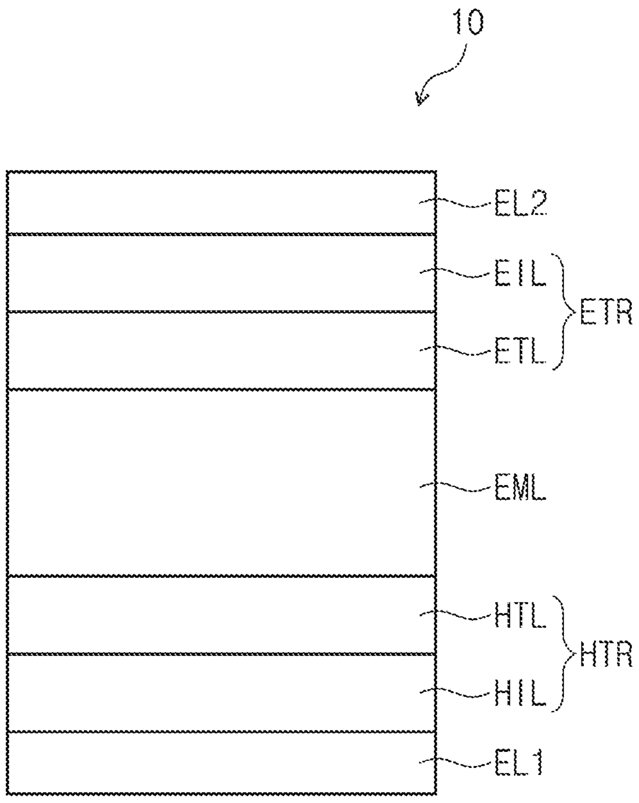
FIG. 3 is a cross-sectional view schematically illustrating an organic electroluminescence device according to an embodiment of the inventive concept.

Referring to FIG. 1 to FIG. 3, an organic electroluminescence device 10 according to an embodiment of the inventive concept includes a first electrode EL1, a plurality of organic material layers OL and a second electrode EL2.

The first electrode EL1 is oppositely disposed to the second electrode EL2, and the plurality of organic material layers OL may be disposed between the first electrode EL1 and the second electrode EL2.

Meanwhile, when compared to FIG. 1, FIG. 2 represents the cross-sectional view of an organic electroluminescence device 10 of an embodiment, in which a plurality of organic material layers OL include a hole transport region HTR, an emission layer EML and an electron transport region ETR. In addition, when compared to FIG. 1, FIG. 3 represents the cross-sectional view of an organic electroluminescence device 10 of an embodiment, in which a hole transport region HTR includes a hole injection layer HIL and a hole transport layer HTL, and an electron transport region ETR includes an electron injection layer EIL and an electron transport layer ETL.

The first electrode EL1 has conductivity. The first electrode EU may be a pixel electrode or an anode. The first electrode EU may be a transmissive electrode, a transflective electrode, or a reflective electrode. When the first electrode EL1 is the transmissive electrode, the first electrode EL1 may be formed utilizing a transparent metal oxide such as indium tin oxide (ITO), indium zinc oxide (IZO), zinc oxide (ZnO), and/or indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed utilizing the above materials, and a transparent conductive layer formed utilizing ITO, IZO, ZnO, or ITZO. For example, the first electrode EU may have a three-layer structure of ITO/Ag/ITO, but an embodiment of the inventive concept is not limited thereto.

The thickness of the first electrode EL1 may be from about 1,000 Å to about 10,000 Å, for example, from about 1,000 Å to about 3,000 Å.

On the first electrode EL1, a plurality of organic material layers OL are provided. The organic material layers OL may include a hole transport region HTR, an emission layer EML and an electron transport region ETR.

The hole transport region HTR is provided on the first electrode EL1. The hole transport region HTR may include at least one of a hole injection layer HIL, a hole transport layer HTL, a hole buffer layer or an electron blocking layer. The thickness of the hole transport region HTR may be, for example, from about 1,000 Å to about 1,500 Å.

In an embodiment, at least one layer among a plurality of organic material layers OL, for example, a hole transport region HTR, may include a monoamine compound, and the monoamine compound includes a core structure of two condensed rings which are combined to form a spiro structure, where each of the condensed ring is obtained by condensing three or more pentagonal or hexagonal rings. The monoamine compound according to embodiments of the inventive concept includes a core structure of two condensed rings which are combined to form a spiro structure, where each of the condensed ring is obtained by condensing three or more pentagonal or hexagonal rings. The monoamine compound has excellent durability at a high temperature and is not easily decomposed by heat under high temperature conditions, thereby contributing to the increase of device life (e.g., lifespan).

In the description, the term "substituted or unsubstituted" may refer to an unsubstituted group, or a group substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle (i.e., heterocyclic group). In addition, each of the substituents illustrated above may be substituted or unsubstituted. For example, a biphenyl group may be interpreted as an aryl group or a phenyl group substituted with a phenyl group. The heterocycle may be an aliphatic heterocycle or an aromatic heterocycle (e.g., a heteroaryl group).

In the description, the term "forming a ring via the combination with an adjacent group" may refer to forming a substituted or unsubstituted hydrocarbon ring, or a substituted or unsubstituted heterocycle via the combination with an adjacent group. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may be monocyclic or polycyclic. In addition, the ring formed via the combination with an adjacent group may be combined with another ring to form a Spiro structure.

In the description, the term "an adjacent group" may refer to a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, the two methyl groups may be interpreted as "adjacent groups" to each other, and in 1,1-diethylcyclopentane, the two ethyl groups may be interpreted as "adjacent groups" to each other.

In the description, examples of the halogen atom may include a fluorine atom, a chlorine atom, a bromine atom and/or an iodine atom.

In the description, the alkyl (i.e., the alkyl group) may be a linear chain, a branched chain or a cyclic group. The carbon number of the alkyl may be 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without being limited thereto.

In the description, the alkenyl (i.e., alkenyl group) may be a linear chain or a branched chain. The carbon number is not specifically limited but may be 2 to 30, 2 to 20, or 2 to 10. Examples of the alkenyl include vinyl, 1-butenyl, 1-pentenyl, 1,3-butadienyl aryl, styrenyl, styrylvinyl, etc., without being limited thereto.

In the description, the aryl (i.e., aryl group) refers to an optional functional group or substituent derived from an aromatic hydrocarbon ring. The aryl may be a monocyclic aryl or a polycyclic aryl. The carbon number for forming a ring in the aryl may be 6 to 60, 6 to 30, 6 to 20, or 6 to 15. Examples of the aryl may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without being limited thereto.

In the description, the heterocycle may include at least one of B, O, N, P, Si or S as a heteroatom for forming a ring. When the heterocycle includes two or more heteroatoms, the two or more heteroatoms may be the same or different. The heterocycle may be monocyclic heterocycle or polycyclic heterocycle, and may include a heteroaryl group. The carbon number for forming a ring of the heterocycle may be 2 to 30, 2 to 20, or 2 to 10. Examples of the heterocycle may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without being limited thereto.

In the description, the silyl (i.e., silyl group) may be an alkyl silyl or an aryl silyl. Examples of the silyl may include trimethylsilyl, triethylsilyl, t-butyldimethylsilyl, vinyldimethylsilyl, propyldimethylsilyl, triphenylsilyl, diphenylsilyl, phenylsilyl, etc. However, an embodiment of the inventive concept is not limited thereto.

In the description, the carbon number of the amino group is not specially limited, but may be 1 to 30. The amino group may be an alkyl amino group or an aryl amino group. Examples of the amino group may include a methylamino group, a dimethylamino group, a phenylamino group, a diphenylamino group, a naphthylamino group, a 9-methyl-anthracenylamino group, a triphenylamino group, etc., without being limited thereto.

In the description, the explanation on the aryl is applied to the arylene, except that the arylene is a divalent group.

In the description, the explanation on the heteroaryl is applied to the heteroarylene, except that the heteroarylene is a divalent group.

In the above-described core structure of the monoamine compound, the central atom of the spiro structure may be carbon or silicon.

When the central atom of the spiro structure is carbon (C), the core structure may have a spiro structure of two condensed rings each of which is a condensed ring of three or more hexagonal rings.

When the central atom of the spiro structure is silicon (Si), the core structure may have a spiro structure of two condensed rings, each of which is a condensed ring of three or more pentagonal or hexagonal rings. When the central atom of the spiro structure is silicon, different from the case where the central atom of the spiro structure is carbon, the condensed ring of the core structure may include pentagonal rings as well as hexagonal rings, and may be a condensed ring of three or more hexagonal rings or of one or more pentagonal rings and two or more hexagonal rings.

The monoamine compound may have, for example, a structure represented by the following Formula 1:

Formula 1

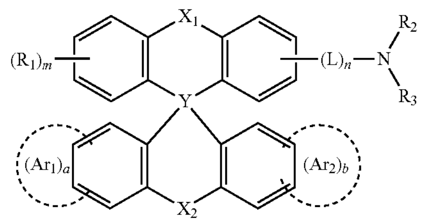

In Formula 1, Y may be C or Si.

In Formula 1, when Y is C, $X_1$ and $X_2$ may be each independently O, S, or $SiR_4R_5$. However, if the monoamine compound has a large degree of molecular symmetry, distance between molecules may be decreased due to intermolecular interaction. Accordingly, hole mobility rate may be degraded and emission efficiency may be deteriorated. Accordingly, $X_1$ and $X_2$ of Formula 1 may be selected as different atoms to decrease the degree of molecular symmetry of the monoamine compound, and to further decrease the intermolecular interaction and crystallinity, thereby providing an organic electroluminescence device having excellent emission efficiency.

In Formula 1, when Y is Si, $X_1$ and $X_2$ may be each independently O, S, $SiR_4R_5$, or a direct linkage. Because Si has a relatively greater atomic radius than C, and the core structure itself may have a twisted conformation and may have a small degree of molecular symmetry irrespective of the kind of $X_1$ and $X_2$. Accordingly, different from the case where Y is C, $X_1$ and $X_2$ may be the same atom. However, in view of the stability of molecules, a case where both $X_1$ and $X_2$ are direct linkages is excluded.

In Formula 1, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring.

In Formula 1, L is a direct linkage, a substituted or unsubstituted arylene group having 6 to 30 carbon atoms, or a substituted or unsubstituted heteroarylene group having 2 to 30 carbon atoms for forming a ring, and n is 0 or 1.

When n is 0, L may be a direct linkage, and when n is 1, L may be a substituted or unsubstituted arylene group having 6 to 30 carbon atoms, or a substituted or unsubstituted heteroarylene group having 2 to 30 carbon atoms for forming a ring.

When L is the substituted or unsubstituted arylene group having 6 to 30 carbon atoms, or the substituted or unsubstituted heteroarylene group having 2 to 30 carbon atoms for forming a ring, L may be represented by one of the following Formula L-1 to Formula L-4.

L-1

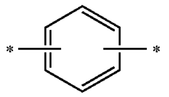

L-2

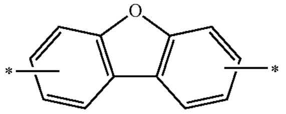

L-3

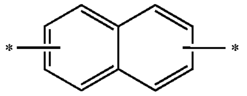

L-4

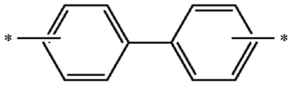

In Formula 1, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, and a and b are each independently 0 or 1.

When a and b are each 0, the monoamine compound represented by Formula 1 may have a structure in which two condensed rings with three condensed pentagonal or hexagonal rings each are combined to form a spiro structure. When a and/or b is 1, the monoamine compound represented by Formula 1 may have a structure in which a condensed ring of three condensed pentagonal or hexagonal rings and a condensed ring of four pentagonal or hexagonal rings are combined to form a spiro structure.

In Formula 1, m is an integer of 0 to 4.

In Formula 1, when Y is carbon, the monoamine compound represented by Formula 1 may be, for example, represented by the following Formula 2:

Formula 2

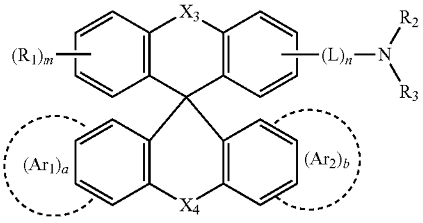

In Formula 2, $X_3$ and $X_4$ may be each independently O, S, or $SiR_4R_5$. However, $X_3$ and $X_4$ are different from each other. In Formula 2, $R_1$ to $R_5$, L, $Ar_1$, $Ar_2$, a, m and n are the same as respectively defined in association with Formula 1.

In Formula 1, when Y is silicon, the monoamine compound represented by Formula 1 may be, for example, represented by the following Formula 3:

Formula 3

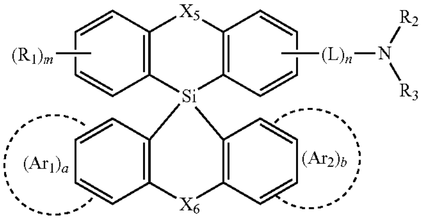

In Formula 3, $X_5$ and $X_6$ are each independently O, S, $SiR_4R_5$, or a direct linkage, and a case where both $X_5$ and $X_6$ are direct linkages is excluded. In Formulae 3, $R_1$ to $R_5$, L, $Ar_1$, $Ar_2$, a, b, m and n are the same as respectively defined in association with Formula 1.

The monoamine compound represented by Formula 2 may be, for example, represented by any one of the following Formulae 2-1 to 2-6:

Formula 2-1

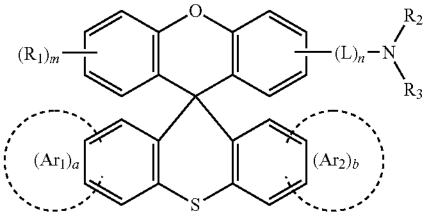

Formula 2-2

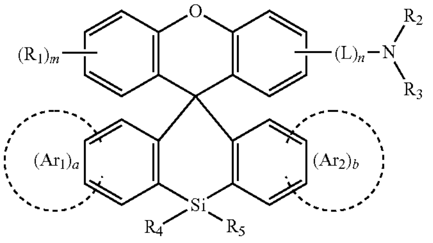

-continued

Formula 2-3

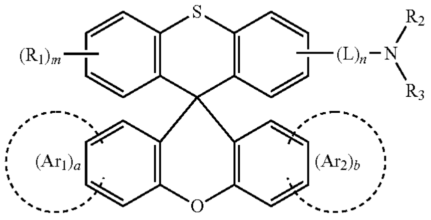

Formula 2-4

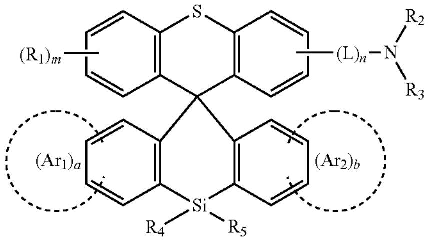

Formula 2-5

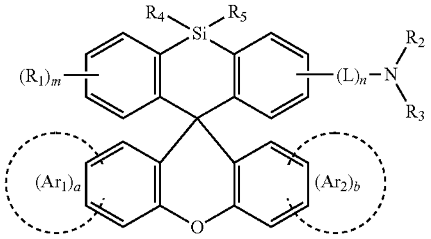

Formula 2-6

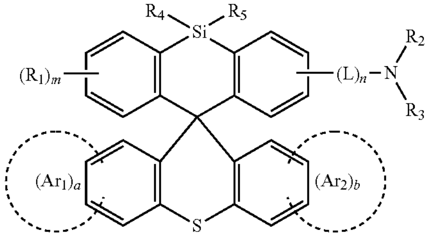

In Formulae 2-1 to 2-6, $R_1$ to $R_5$, L, $Ar_1$, $Ar_2$, a, b, m and n are the same as respectively defined in association with Formula 1.

The monoamine compound represented by Formula 3 may be, for example, represented by any one of the following Formulae 3-1 to 3-11:

[Formula 3-1]

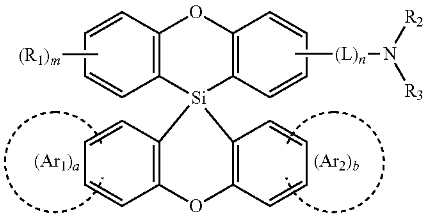

-continued

[Formula 3-2]

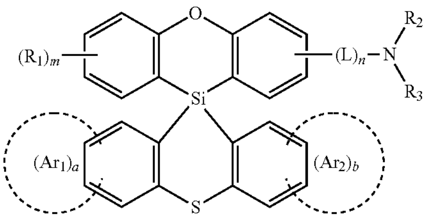

[Formula 3-3]

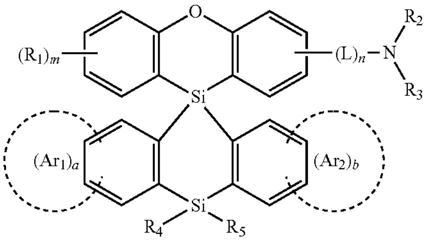

[Formula 3-4]

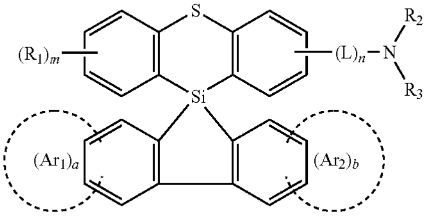

[Formula 3-5]

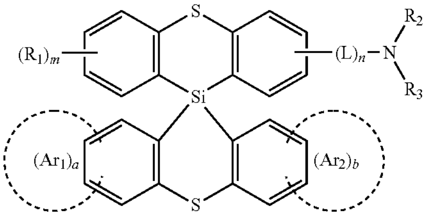

[Formula 3-6]

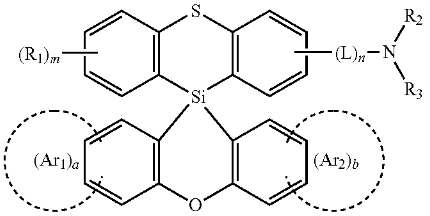

[Formula 3-7]

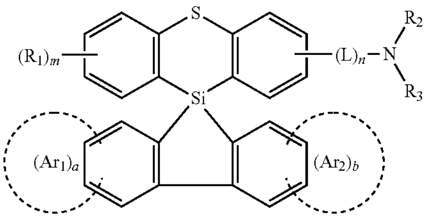

-continued

[Formula 3-8]

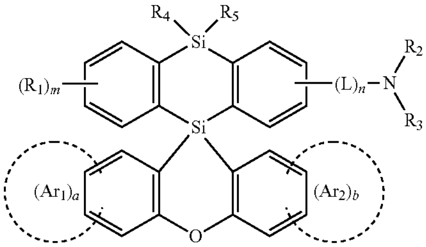

[Formula 3-9]

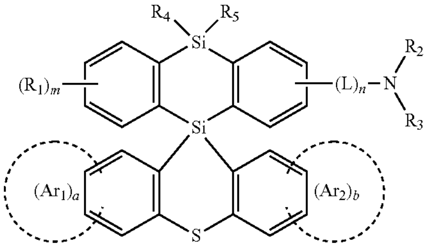

[Formula 3-10]

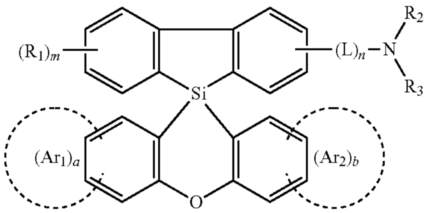

[Formula 3-11]

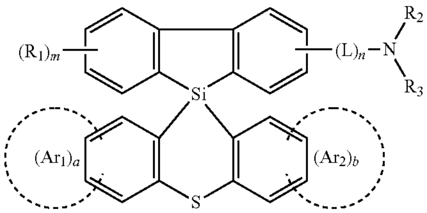

In Formulae 3-1 to 3-11, $R_1$ to $R_5$, L, $Ar_1$, $Ar_2$, a, b, n and m are the same as respectively defined in association with Formula 1.

The monoamine compound may be selected from the compounds represented in Compound Group 1 and Compound Group 2 below. However, an embodiment of the inventive concept is not limited thereto.

[Compound Group 1]

A1

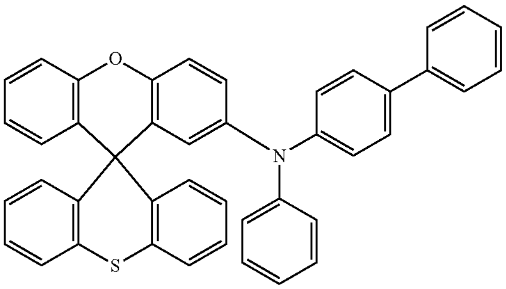

-continued
A2
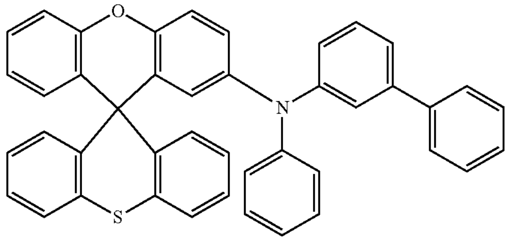
A3
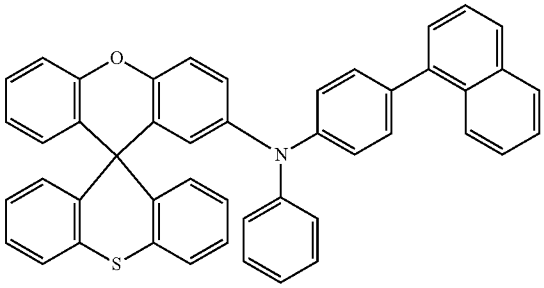
A4
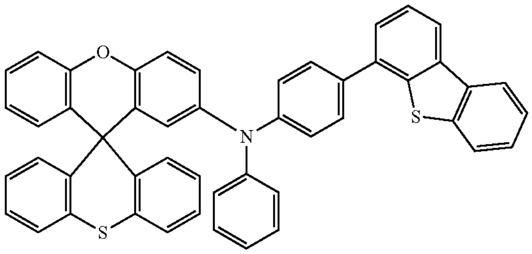
A5
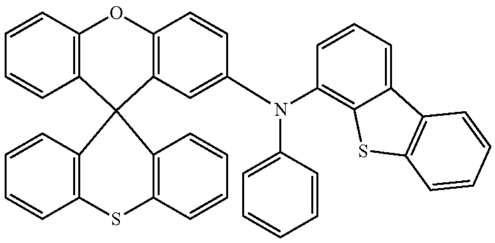
A6
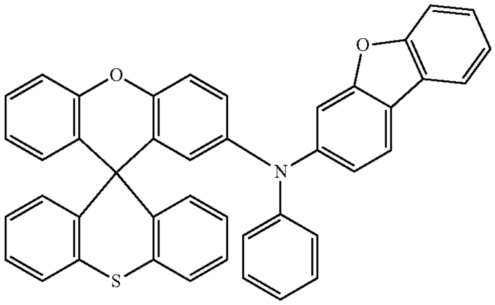
-continued
A7
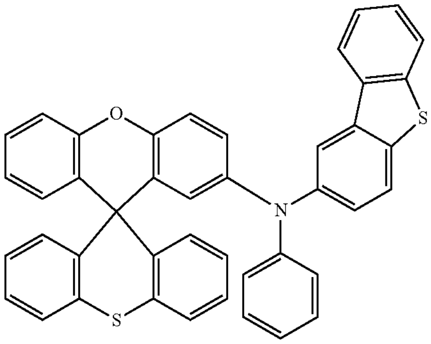
A8
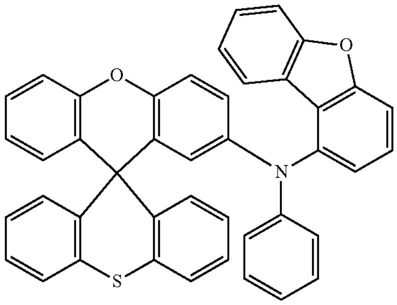
A9
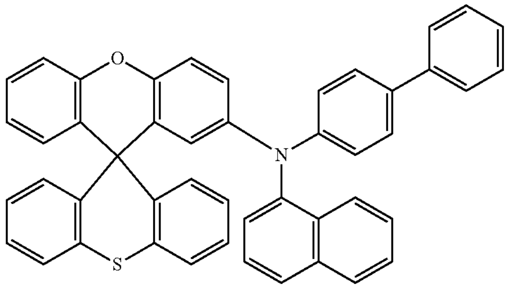
A10
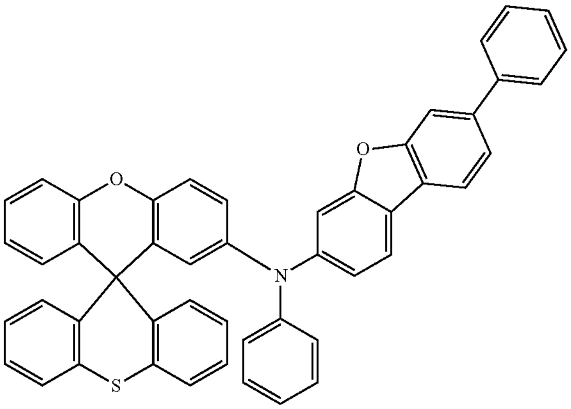

-continued
A11
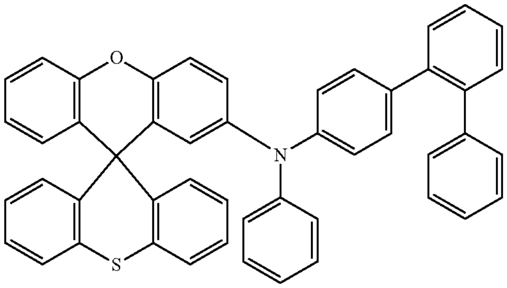
A12
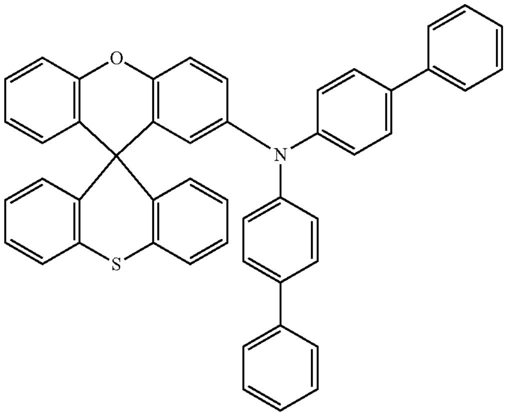
A13
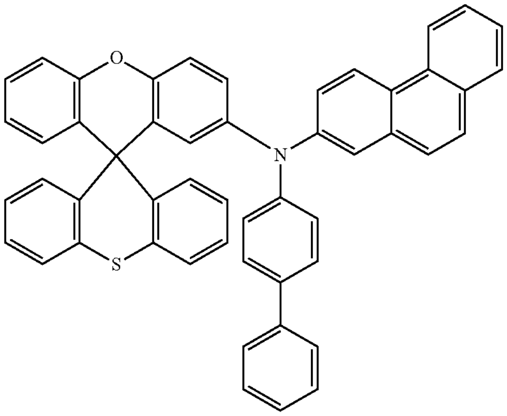
A14
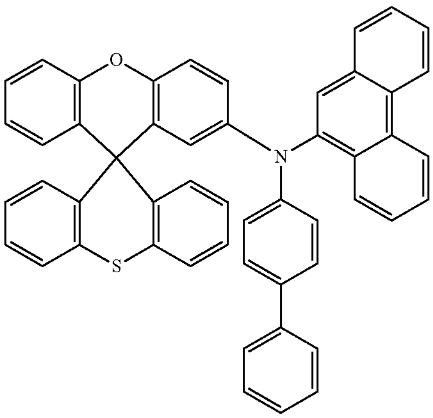
-continued
A15
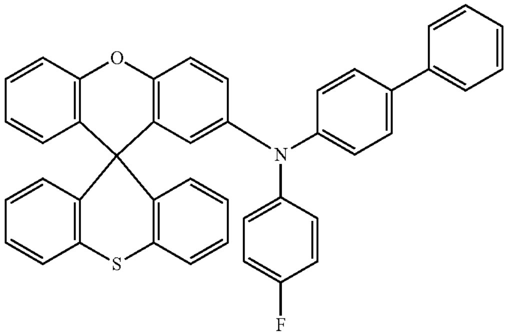
A16
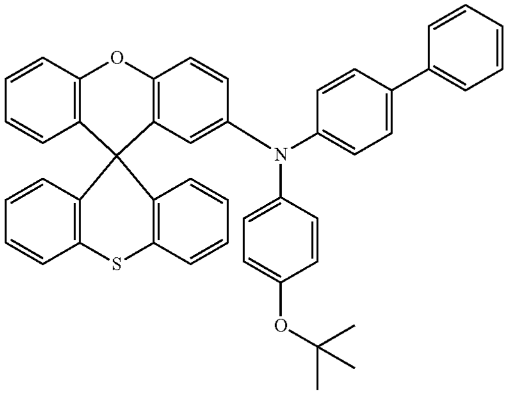
A17
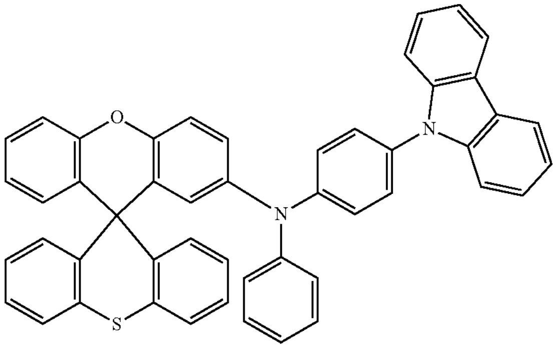
A18
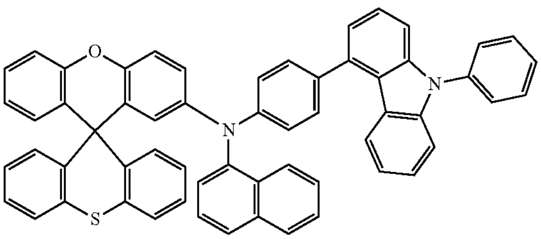

-continued
A19
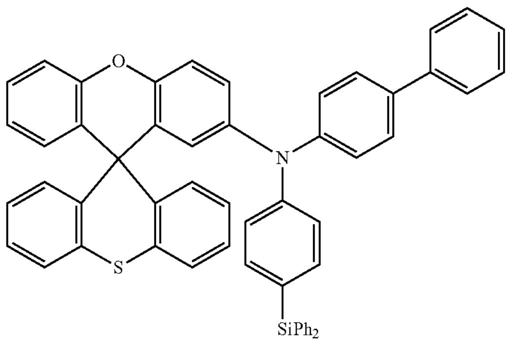
A20
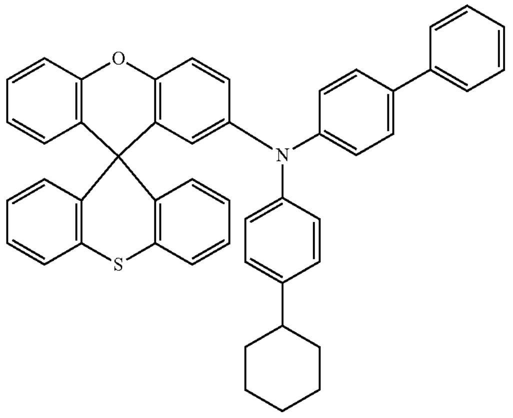
A21
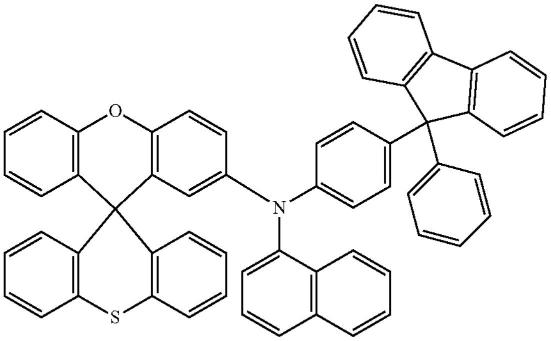
A22
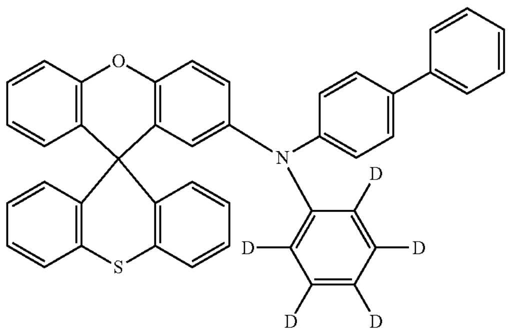
-continued
A23
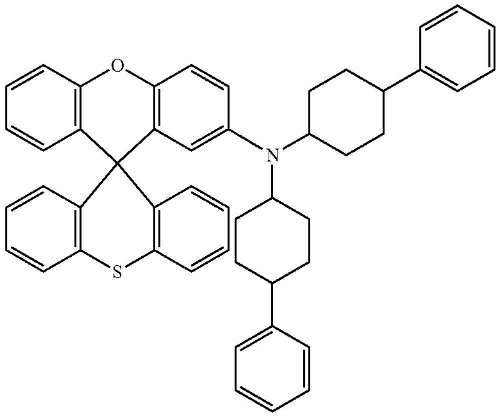
A24
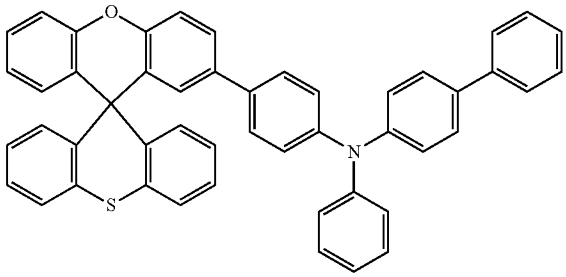
A25
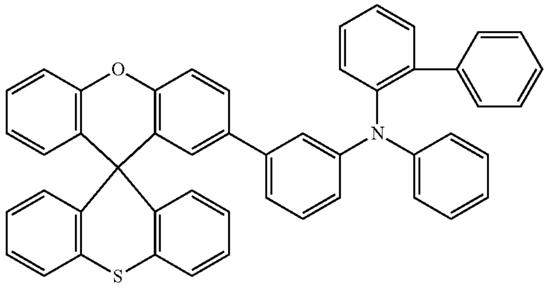
A26
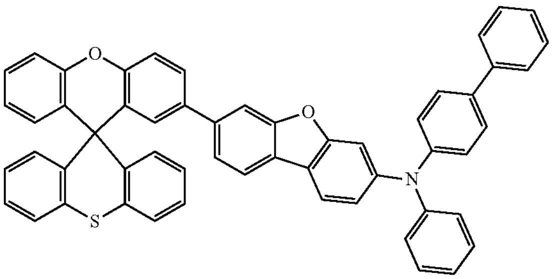

-continued
A27
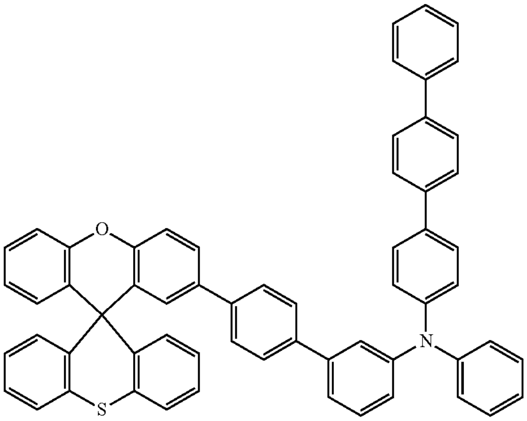
A28
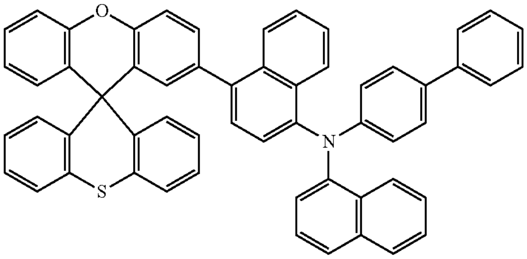
A29
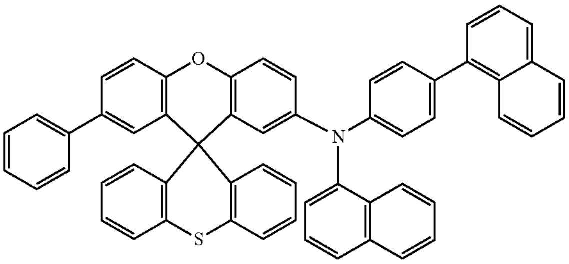
A30
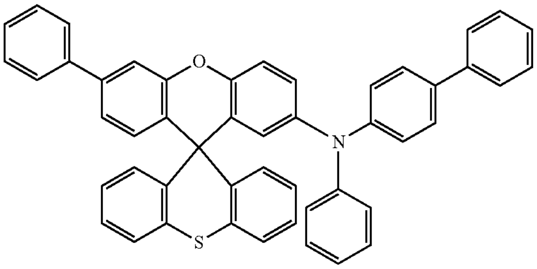
-continued
A31
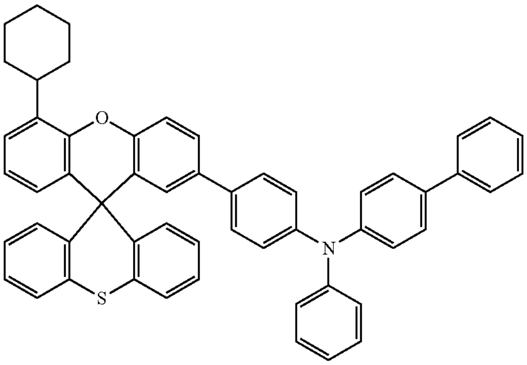
A32
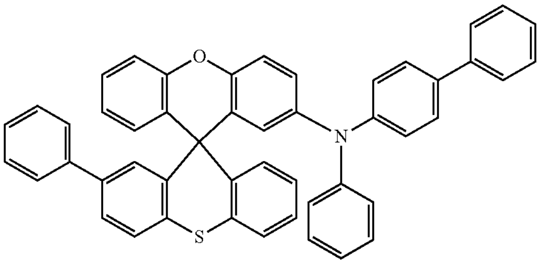
A33
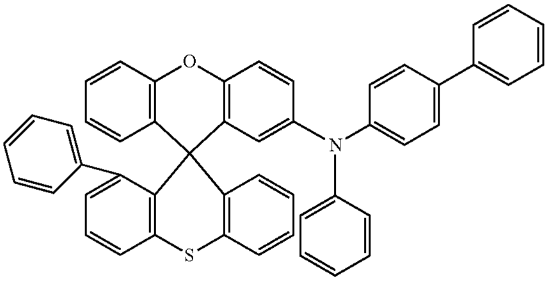
A34
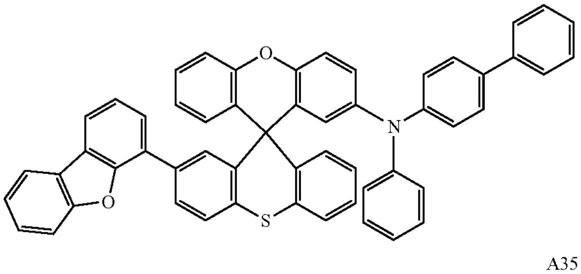
A35
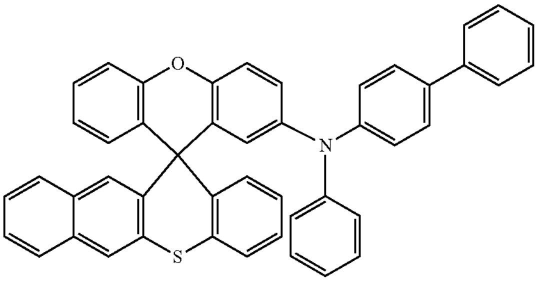

-continued
A36
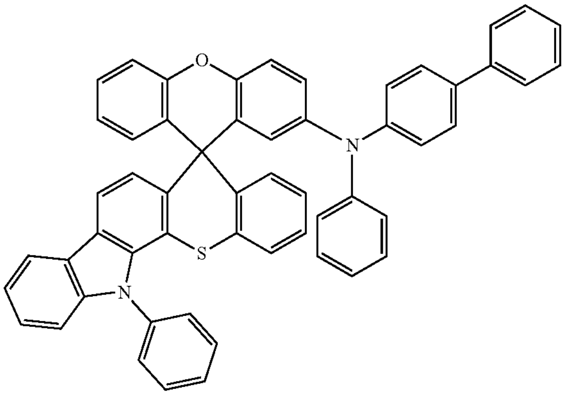
A37
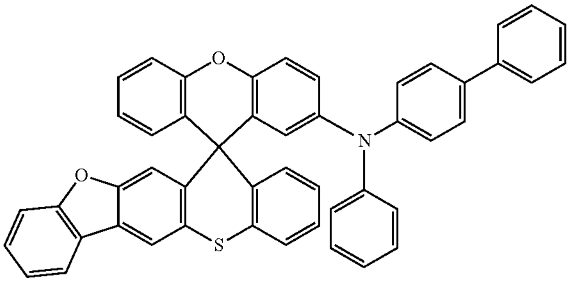
A38
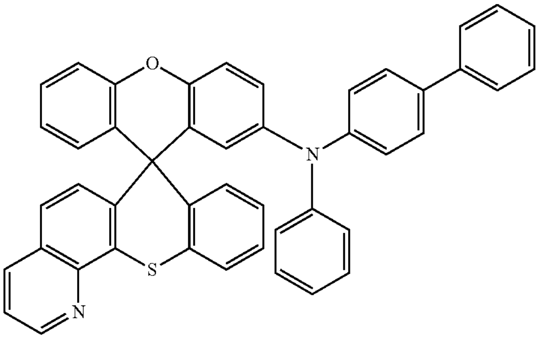
A39
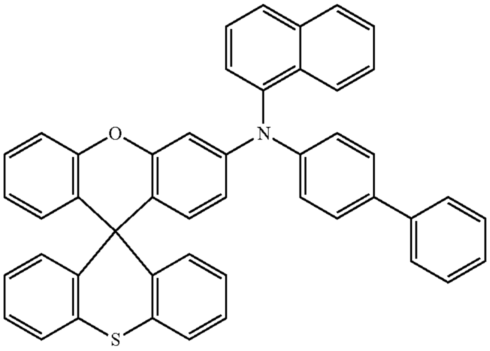
-continued
A40
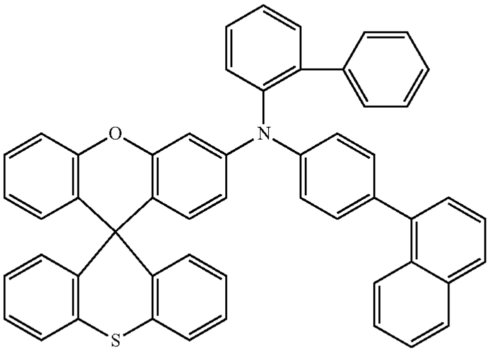
A41
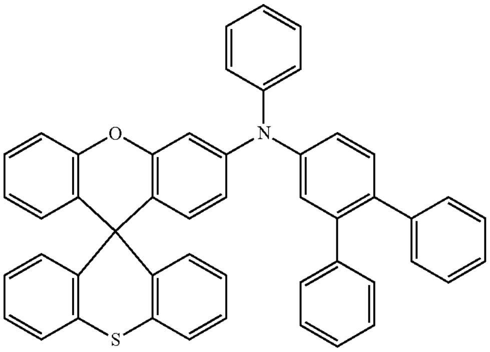
A42
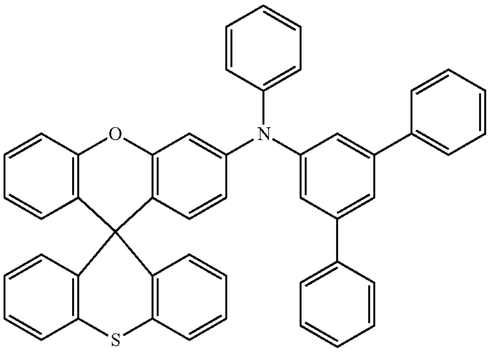
A43
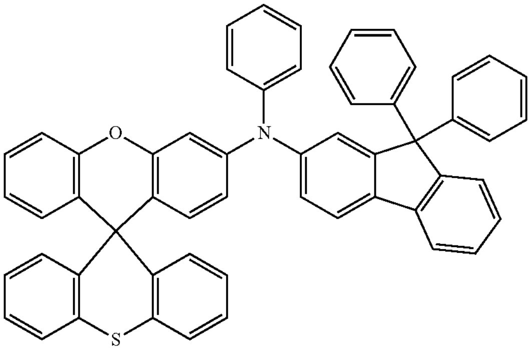

-continued
A44
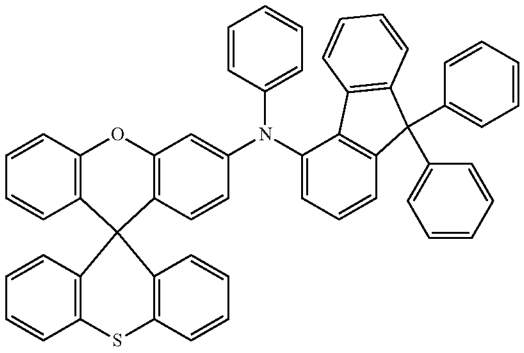
A45
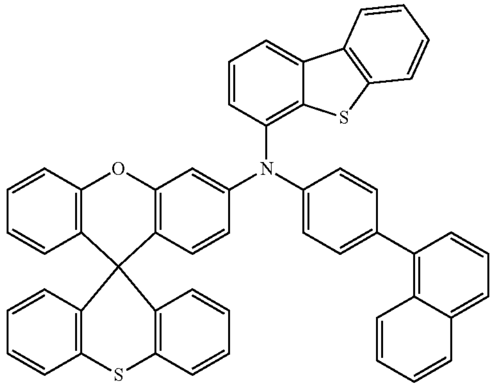
A46
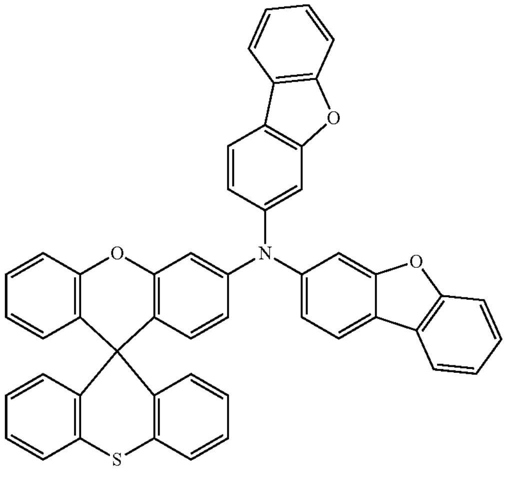
-continued
A47
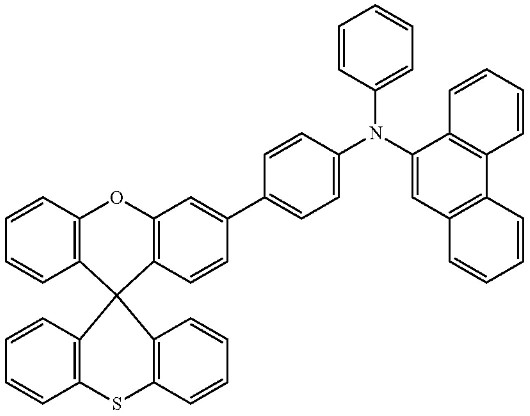
A48
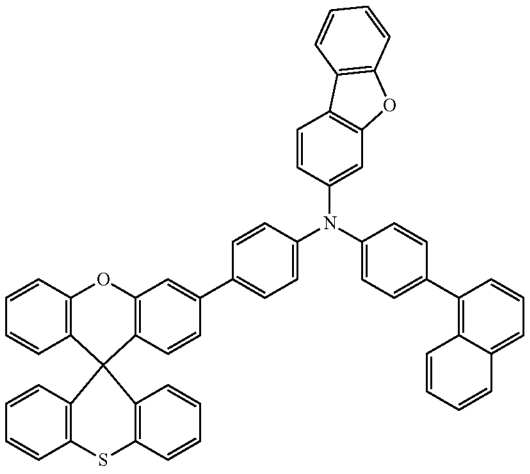
A49
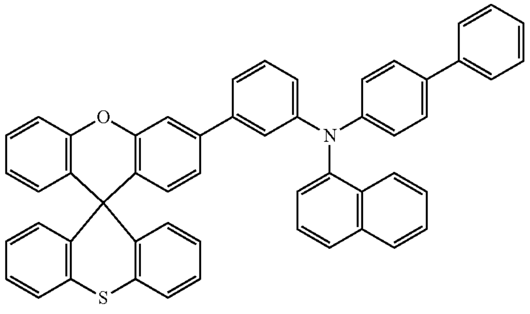

-continued
A50
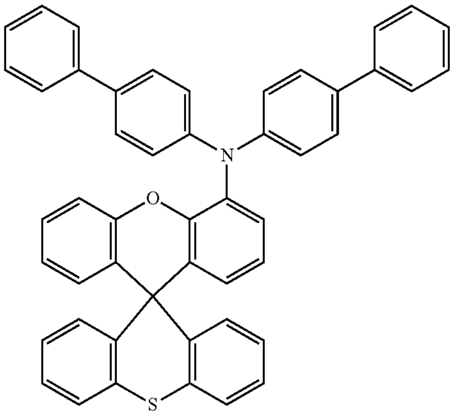
A51
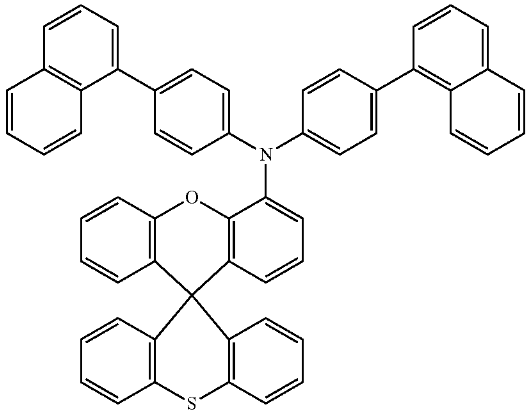
A52
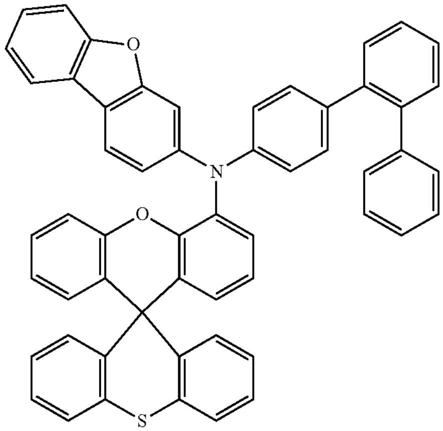
-continued
A53
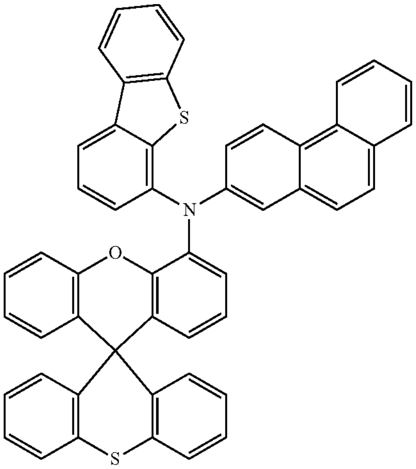
A54
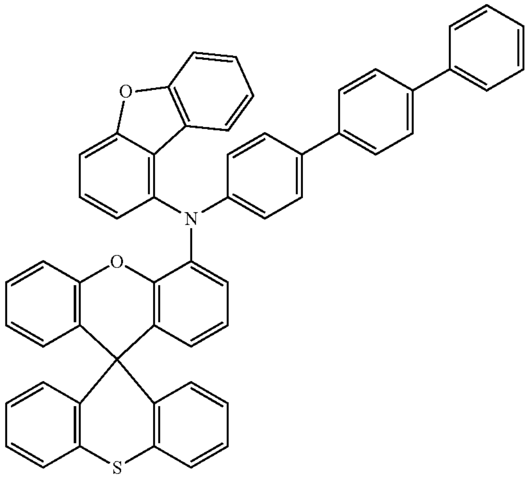
A55
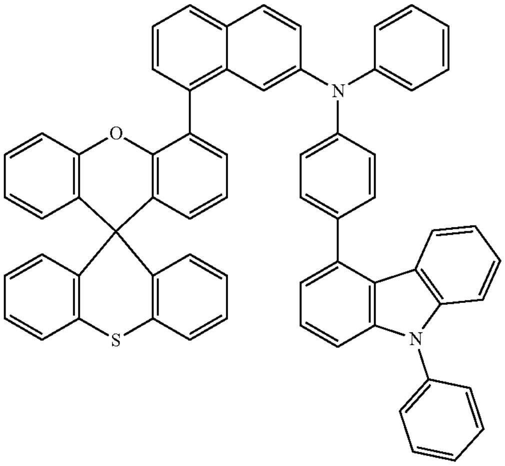

-continued
A56
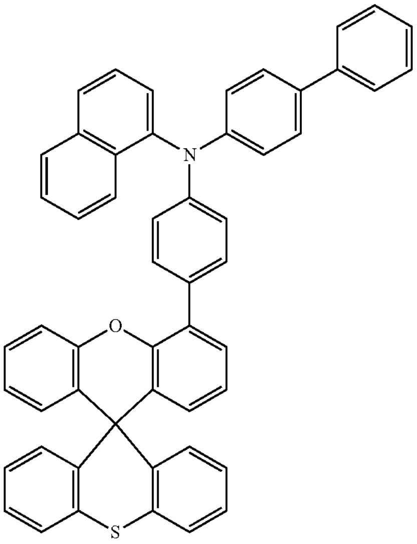
A57
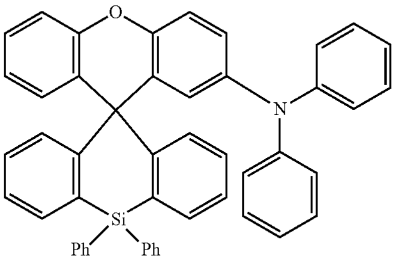
A58
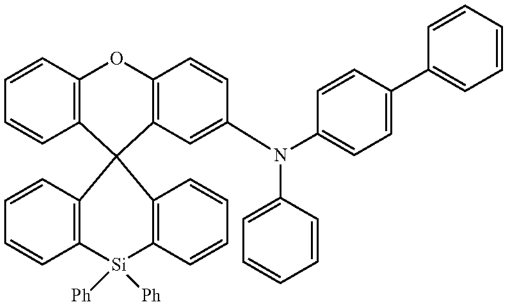
A59
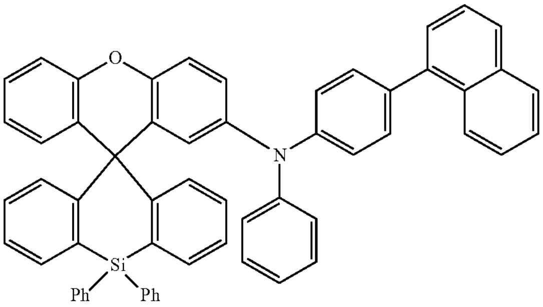
-continued
A60
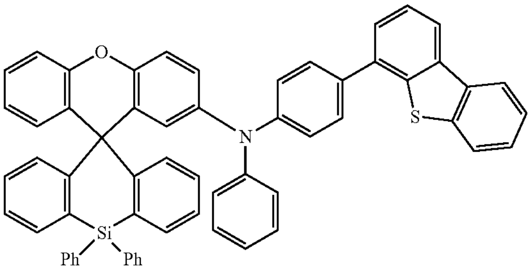
A61
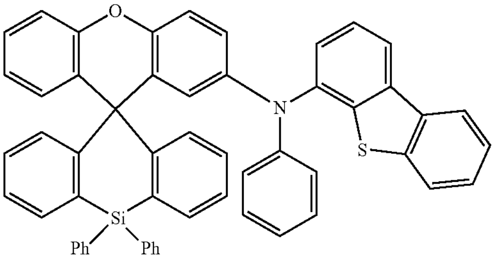
A62
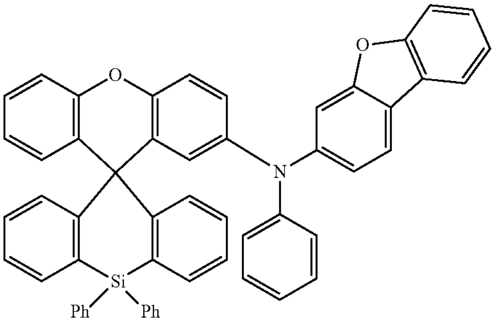
A63
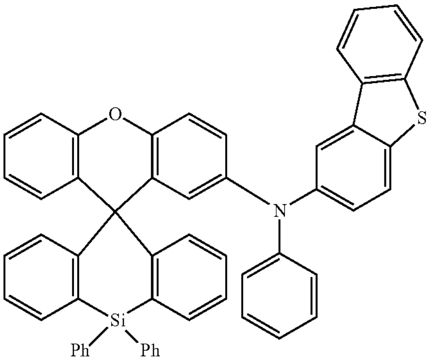
A64
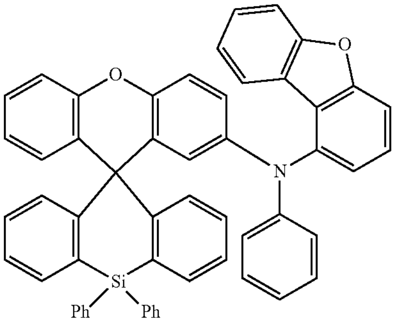

-continued
A65
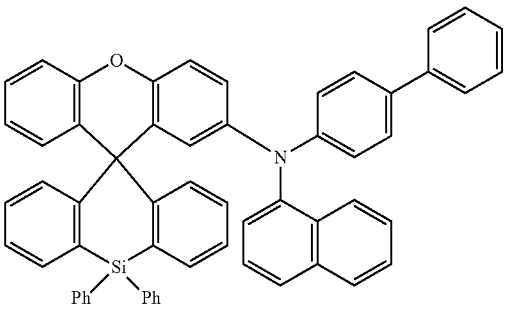
A66
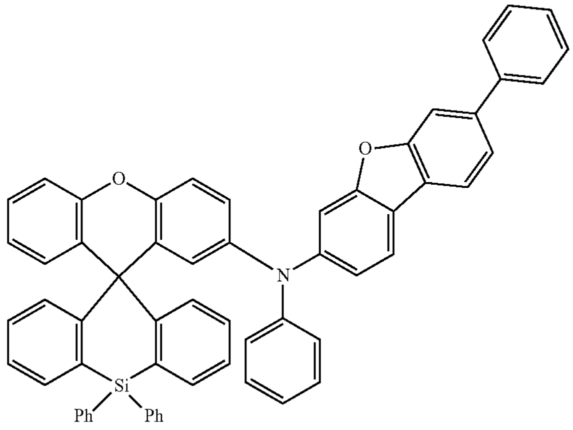
A67
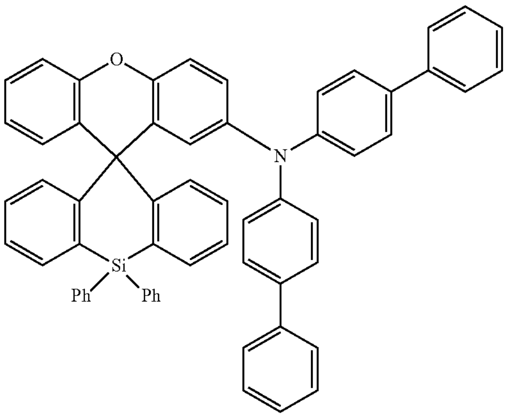
A68
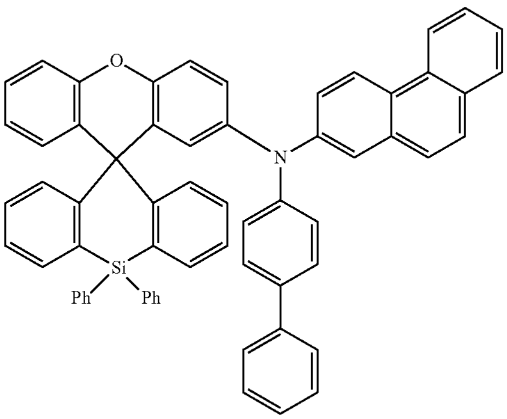
-continued
A69
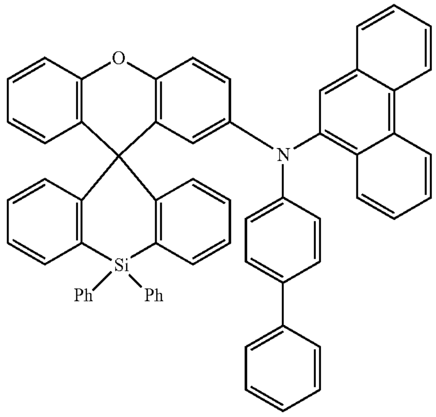
A70
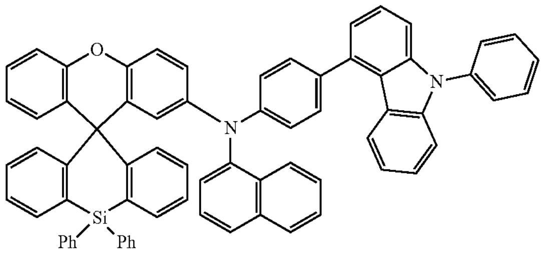
A71
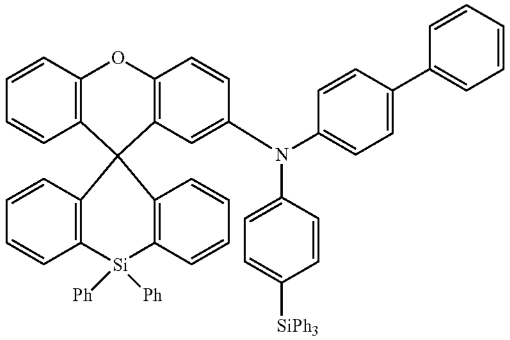
A72
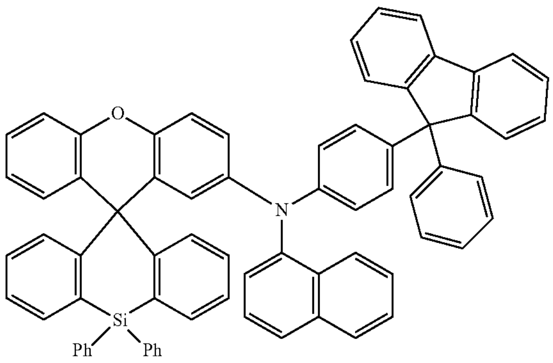

-continued
A73
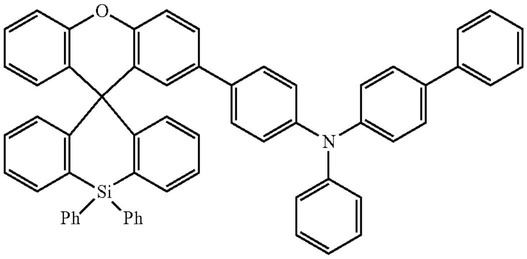
A74
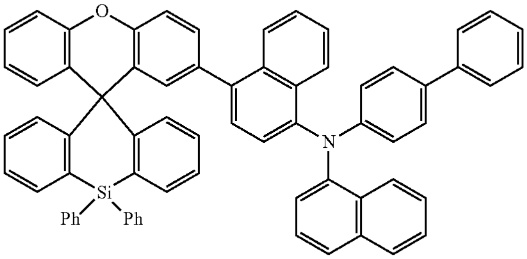
A75
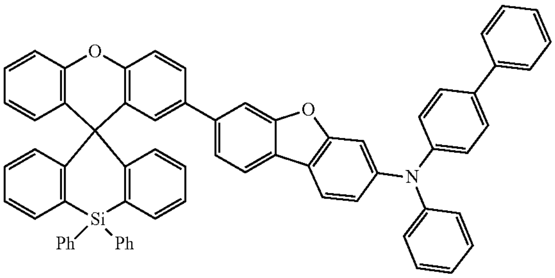
A76
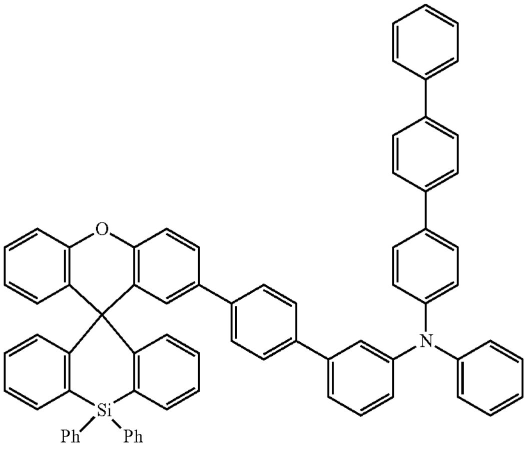
A77
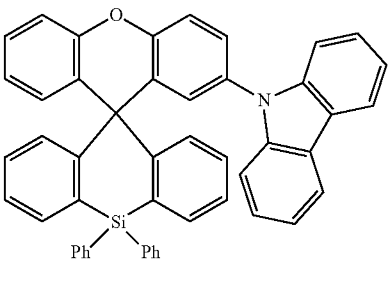
-continued
A78
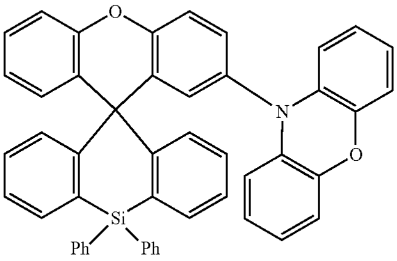
A79
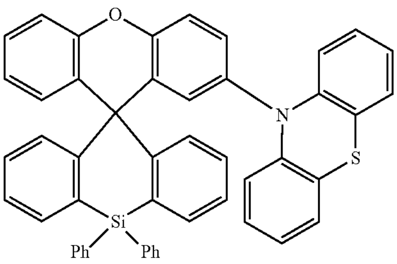
A80
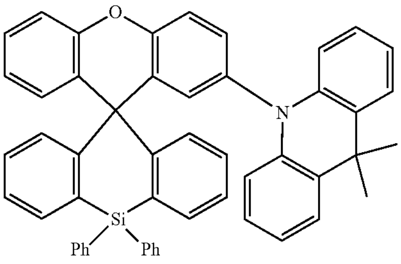
A81
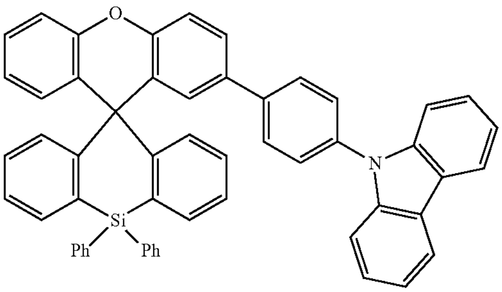
A82
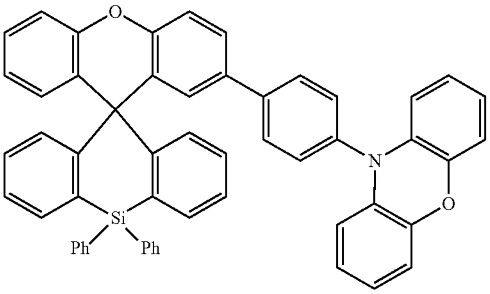

-continued
A83
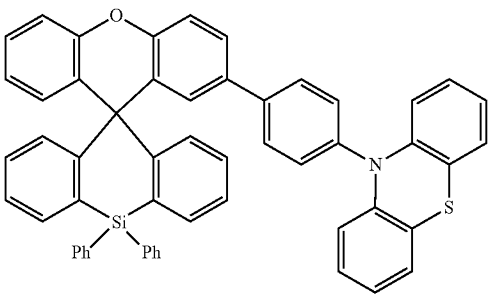
A84
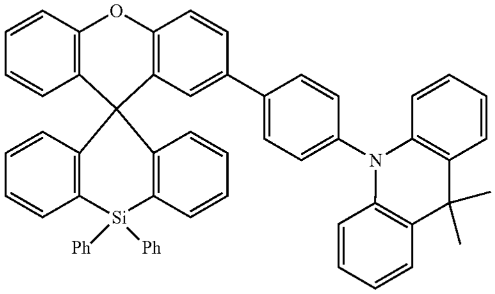
A85
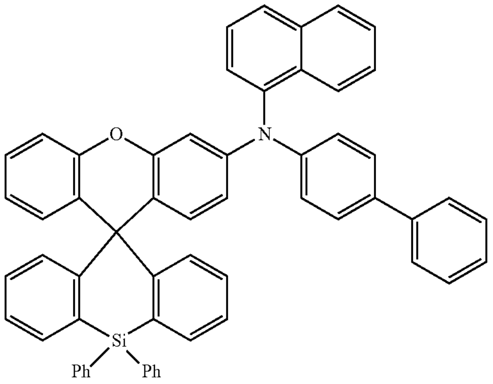
A86
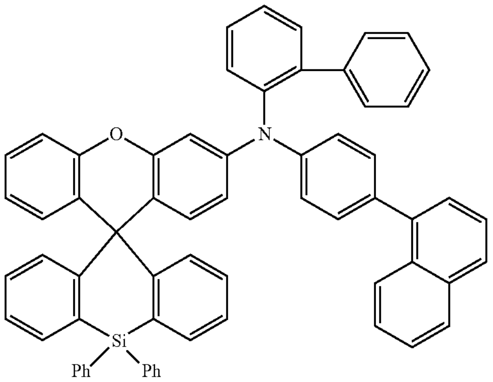
-continued
A87
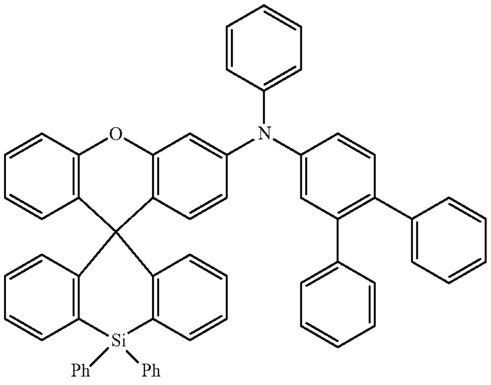
A88
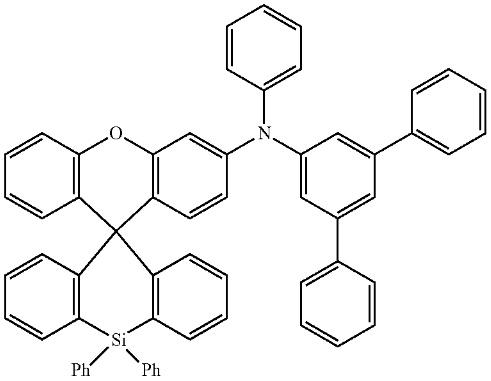
A89
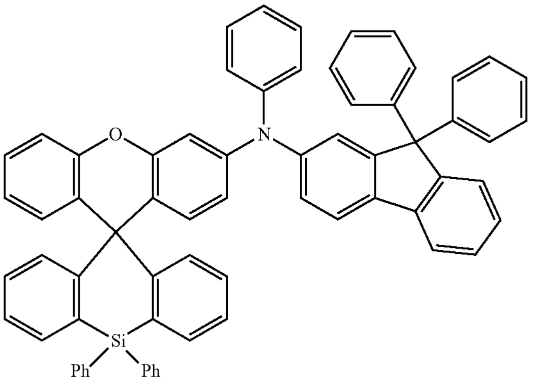
A90
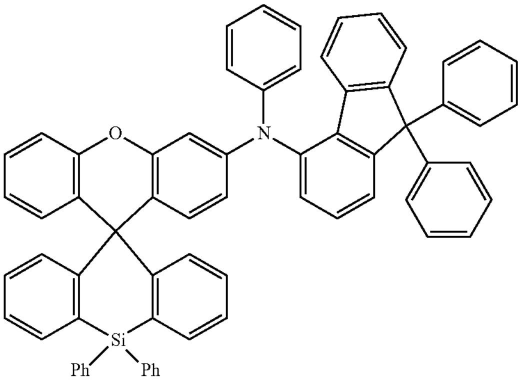

-continued
A91
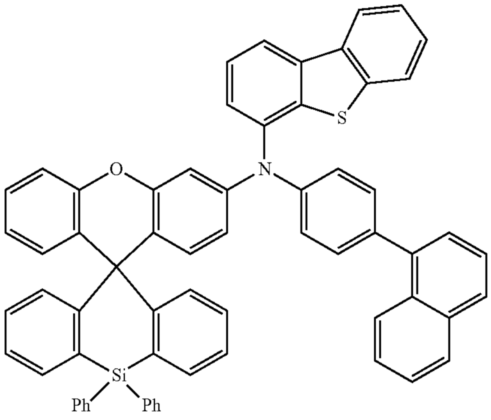
A92
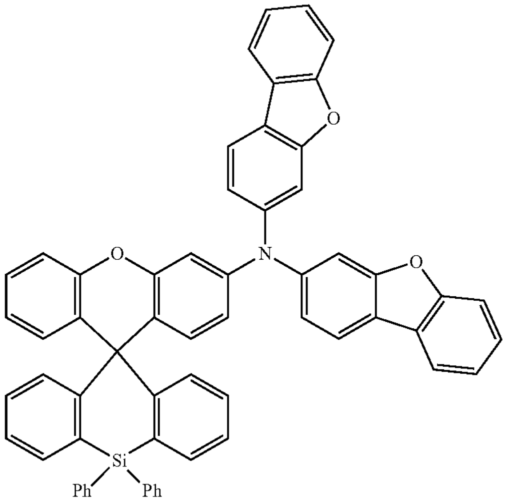
A93
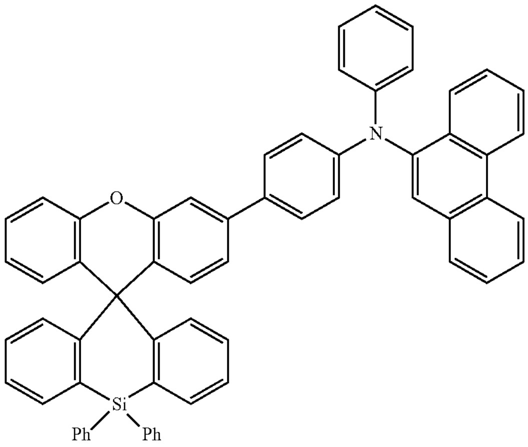
-continued
A94
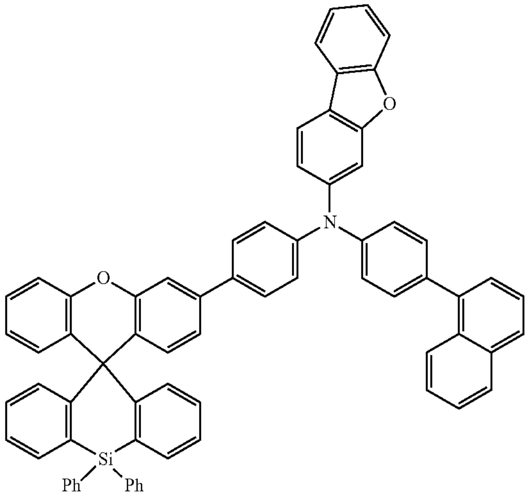
A95
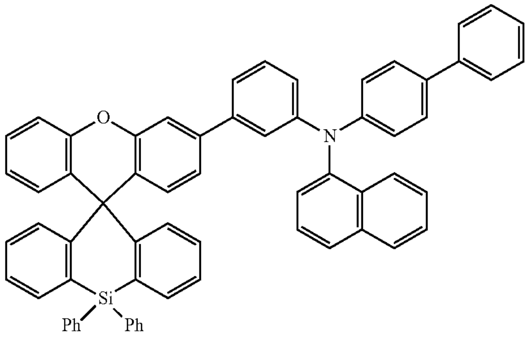
A96
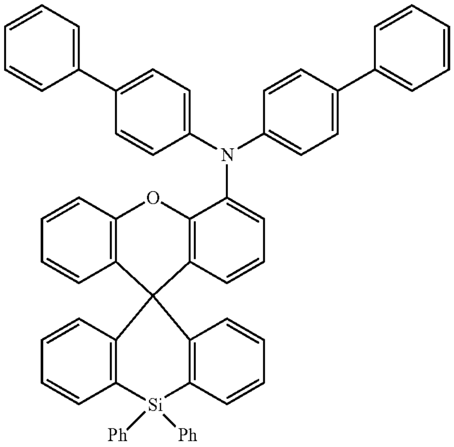

-continued
A97
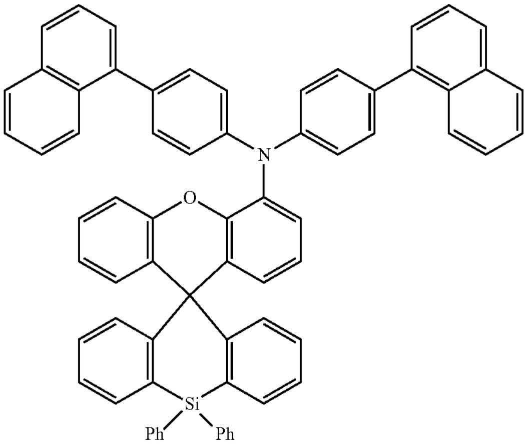
A98
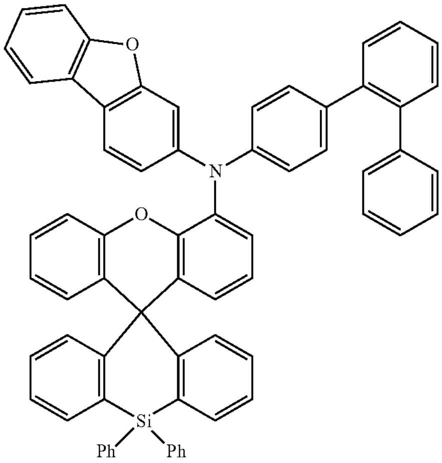
A99
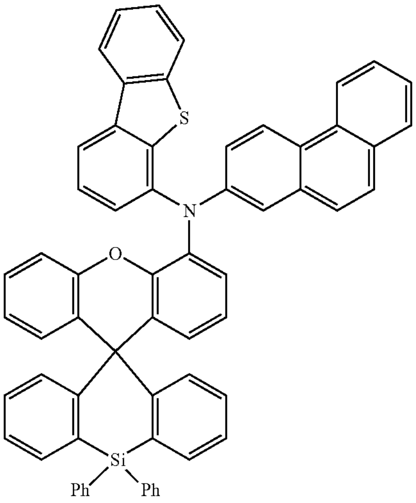
-continued
A100
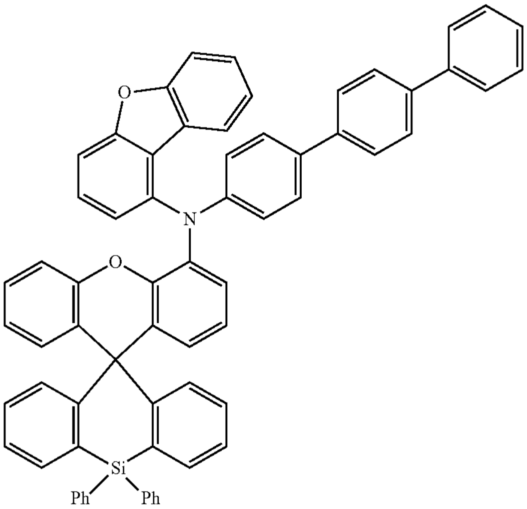
A101
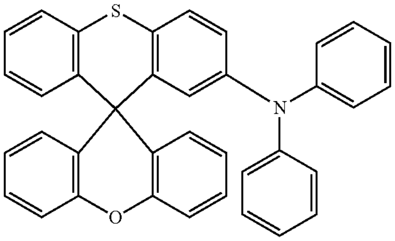
A102
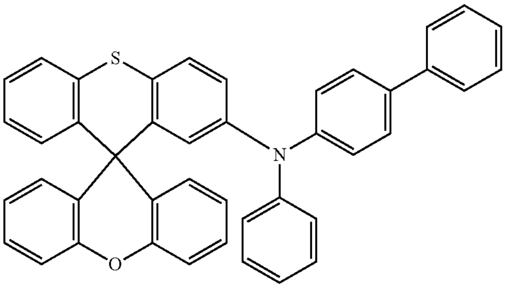
A103
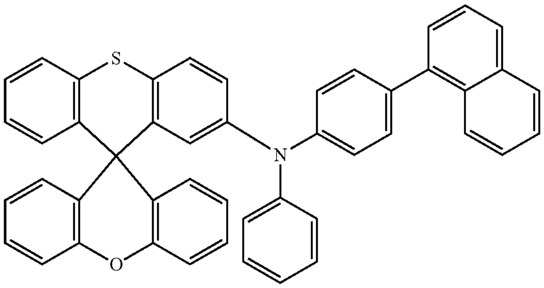

-continued
A104
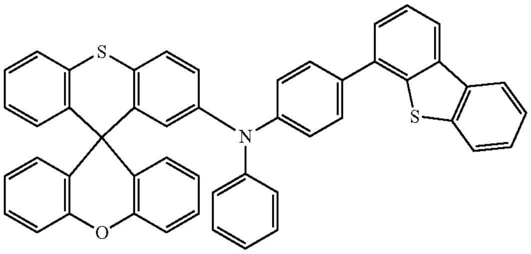
A105
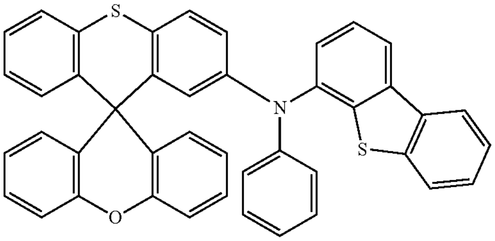
A106
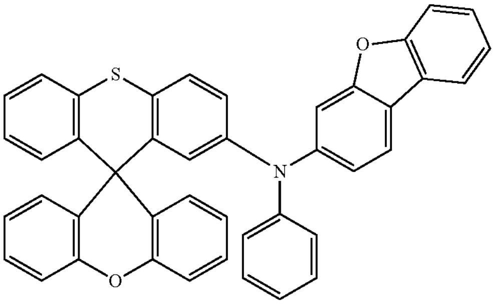
A107
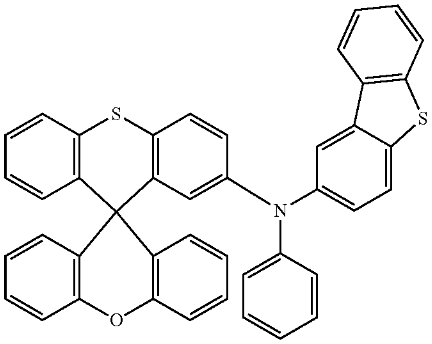
A108
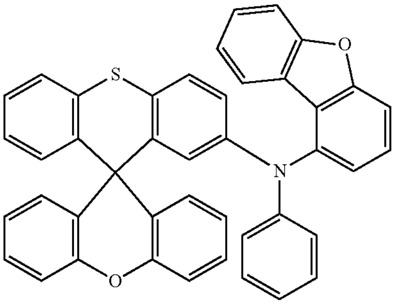
-continued
A109
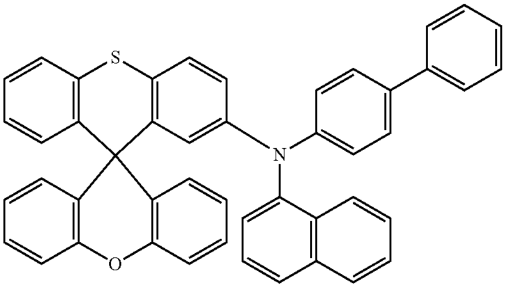
A110
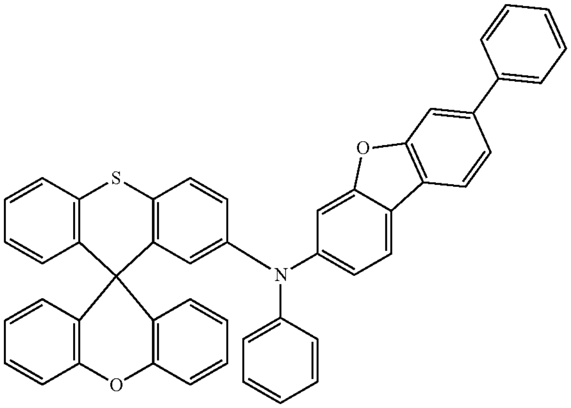
A111
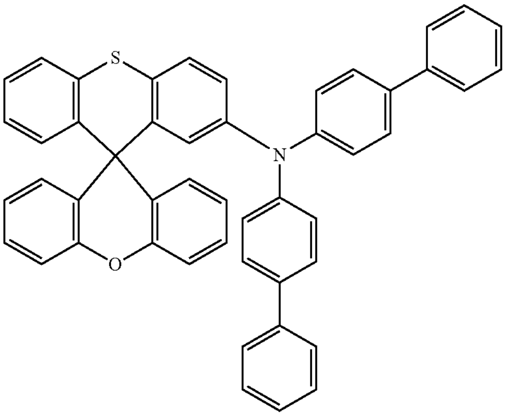
A112
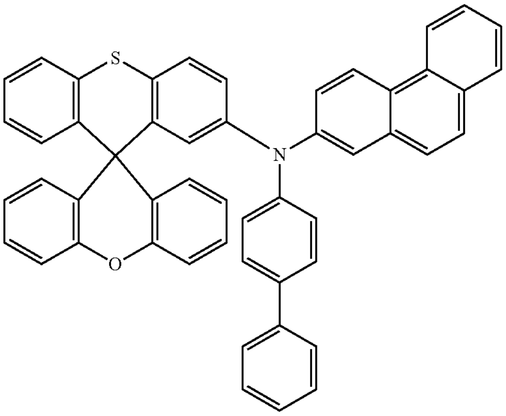

-continued
A113
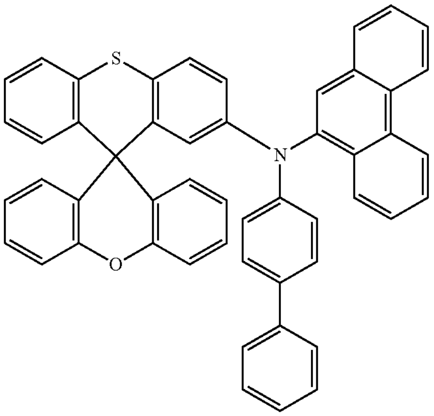
A114
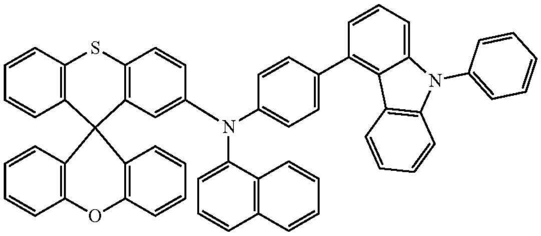
A115
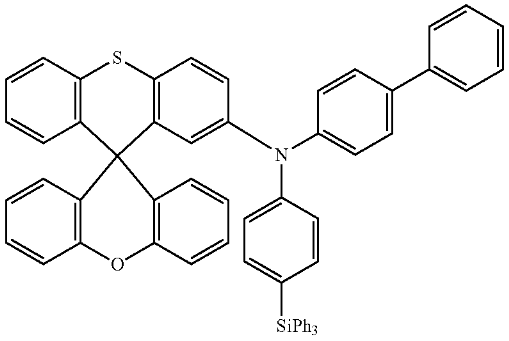
A116
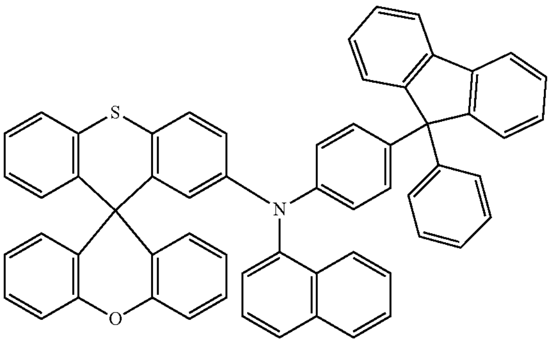
-continued
A117
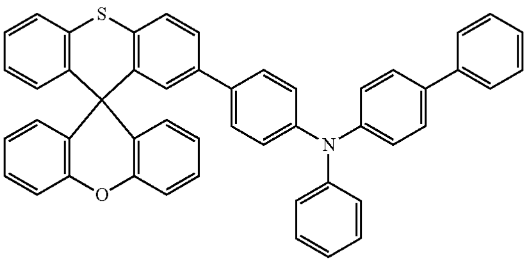
A118
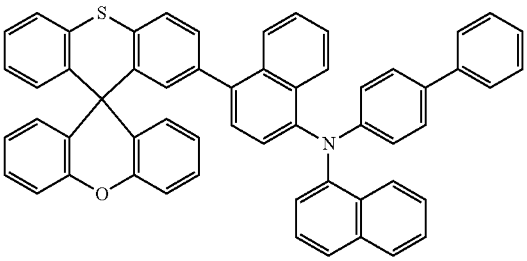
A119
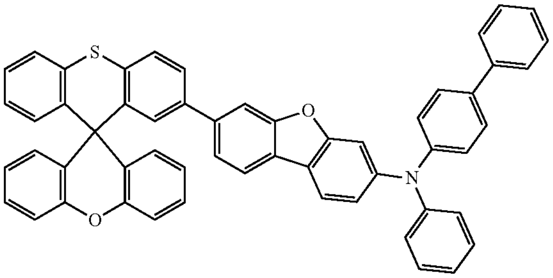
A120
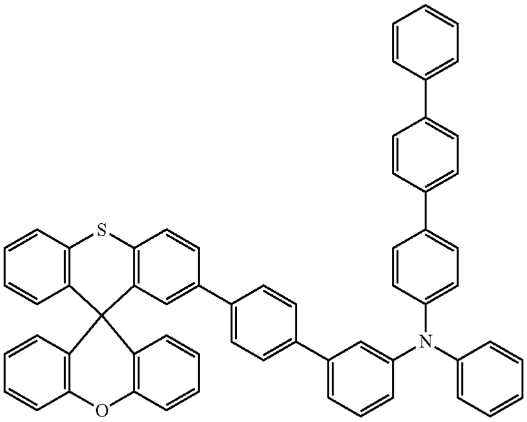
A121
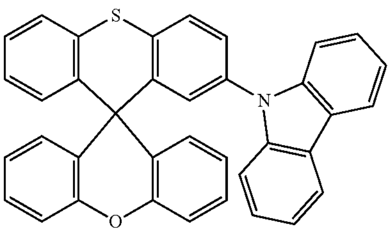

-continued
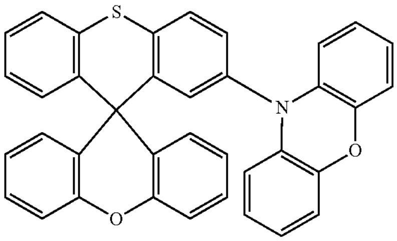
A122
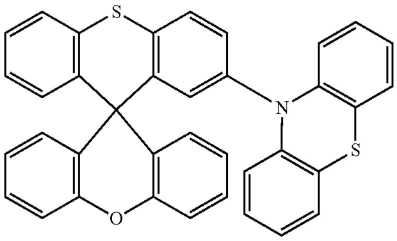
A123
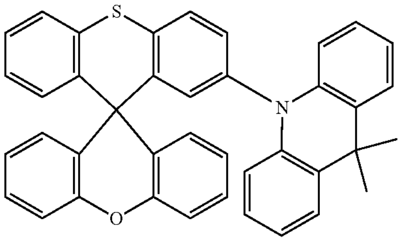
A124
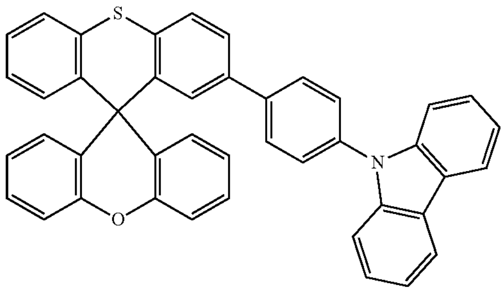
A125
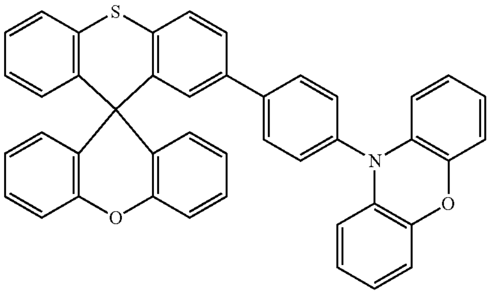
A126
-continued
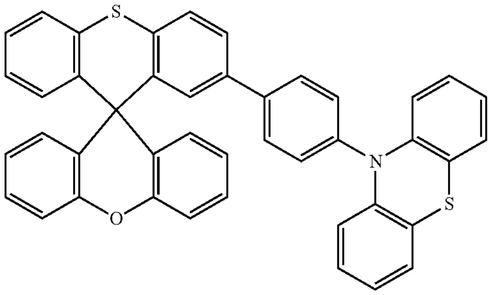
A127
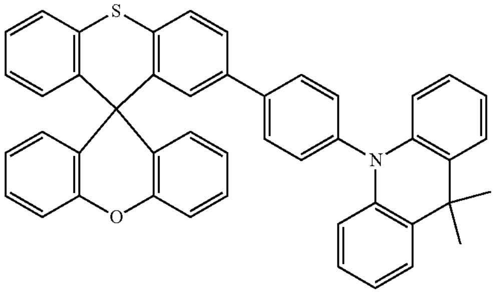
A128
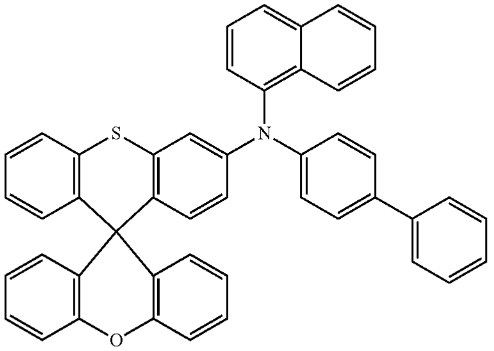
A129
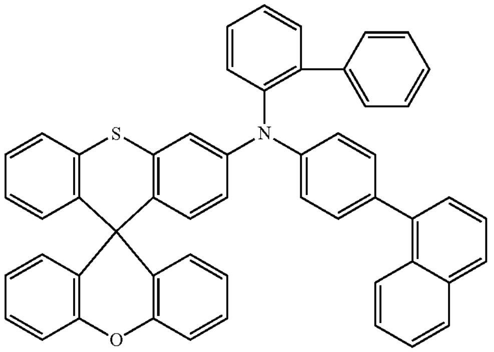
A130

-continued
A131
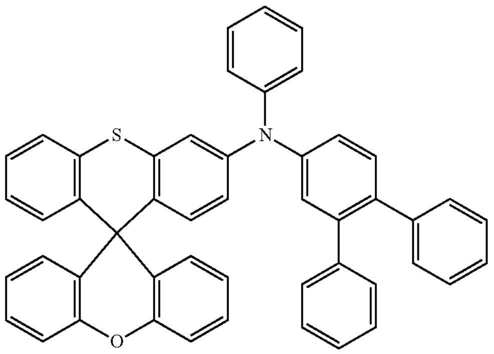
A132
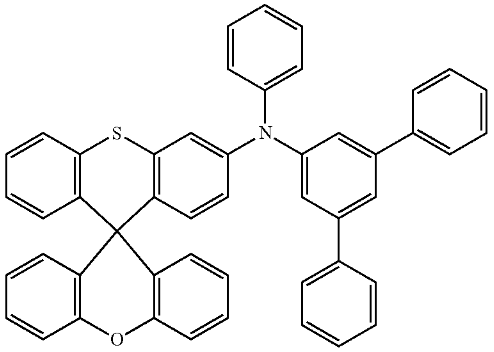
A133
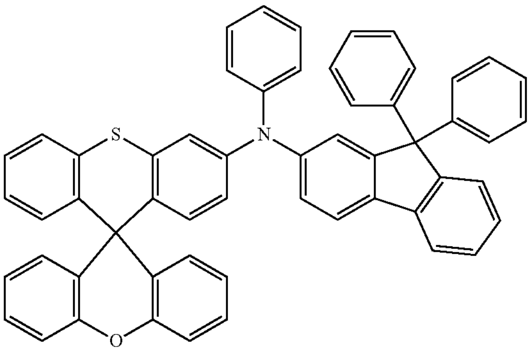
A134
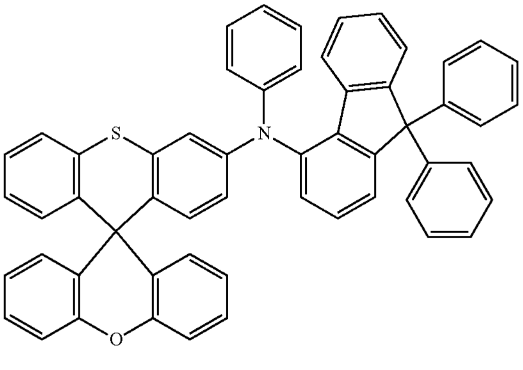
-continued
A135
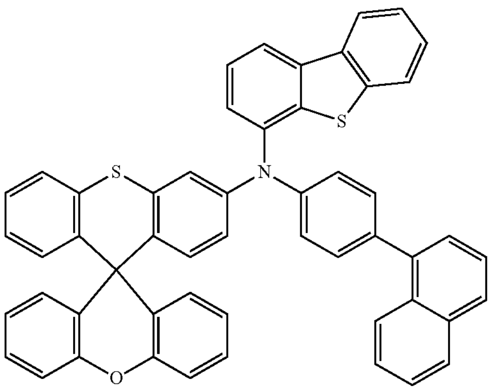
A136
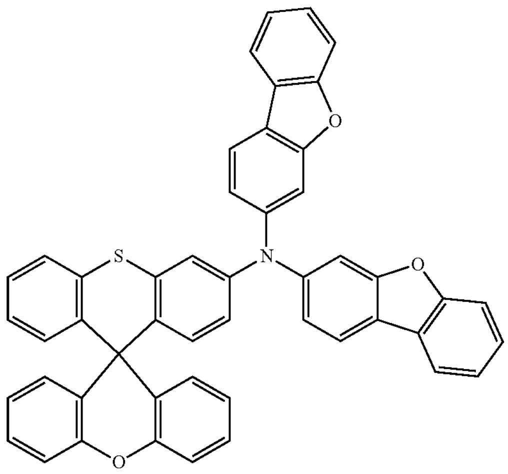
A137
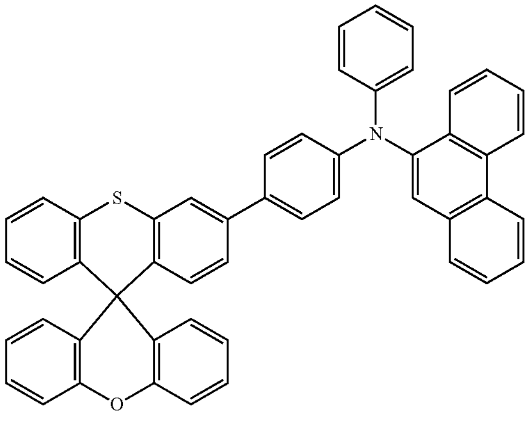

-continued
A138
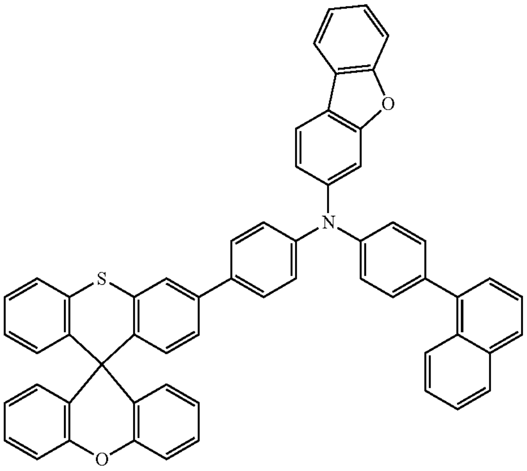
A139
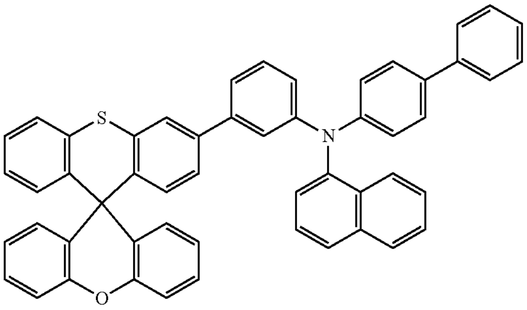
A140
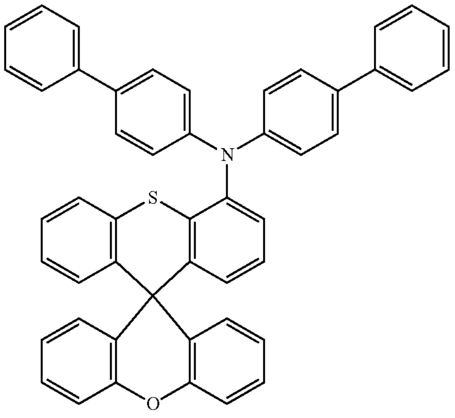
-continued
A141
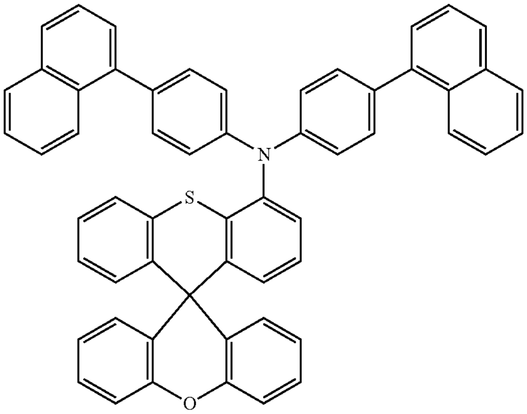
A142
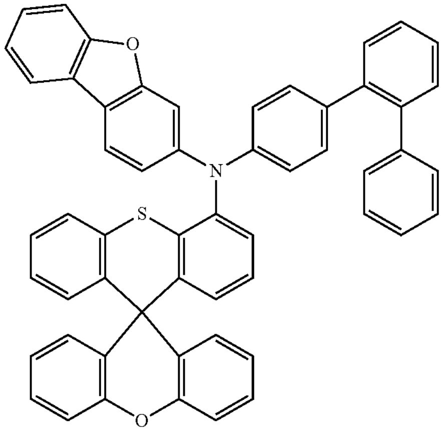
A143
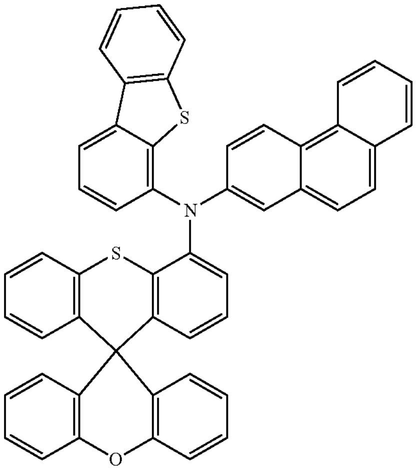

-continued
A144
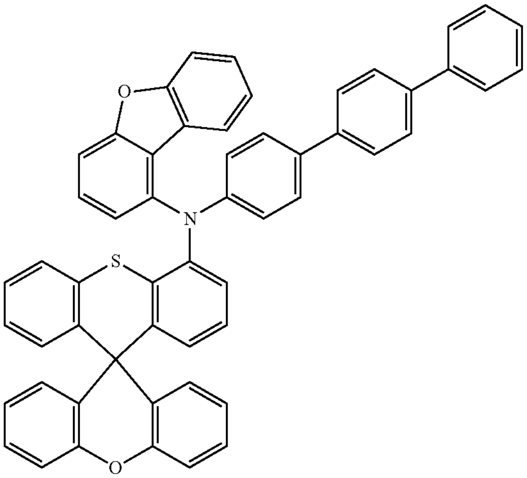
A145
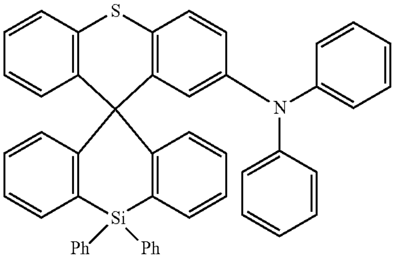
A146
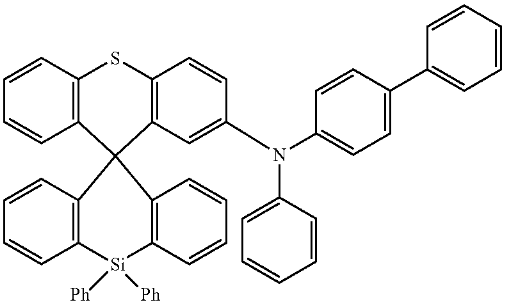
A147
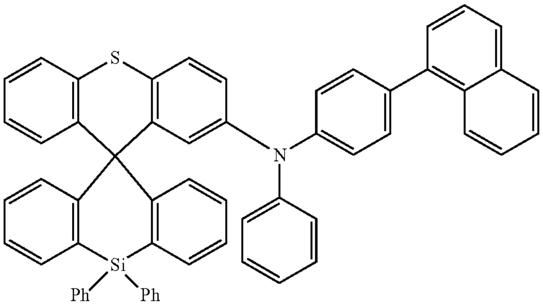
-continued
A148
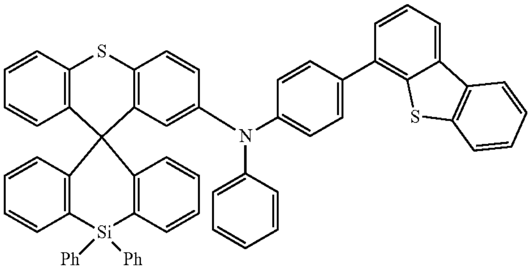
A149
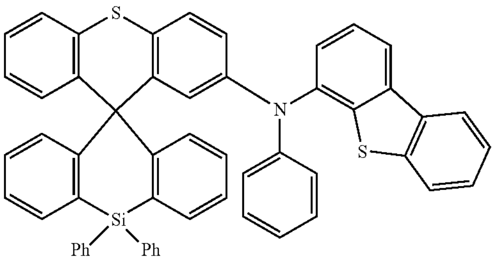
A150
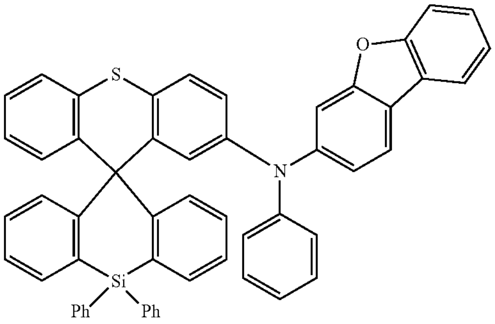
A151
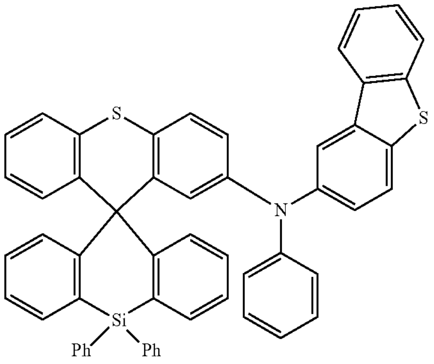
A152
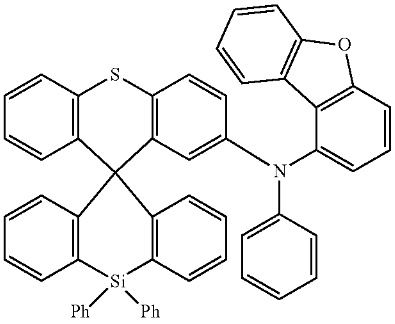

-continued
A153
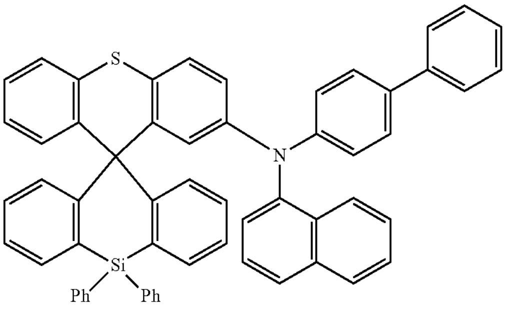
A154
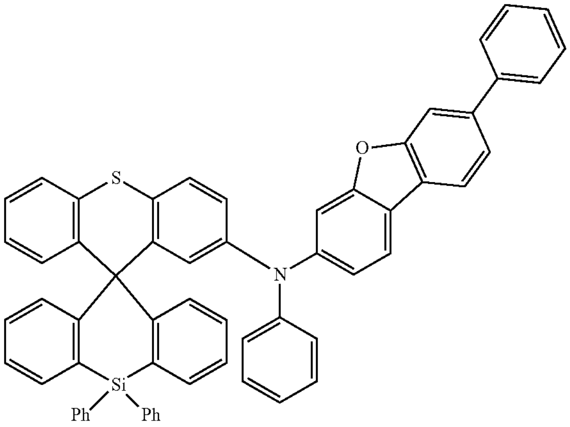
A155
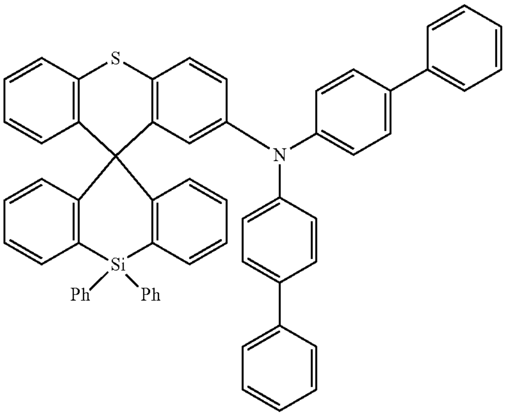
A156
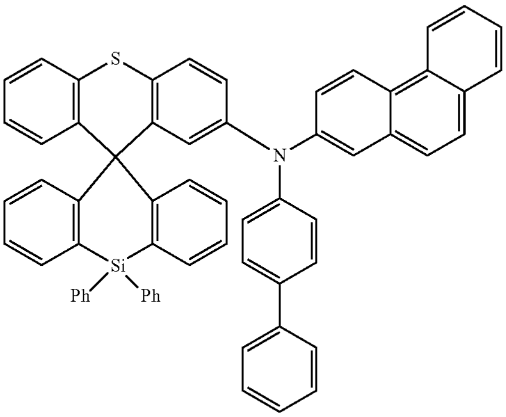
-continued
A157
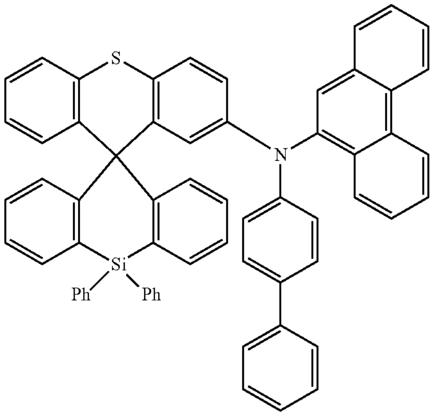
A158
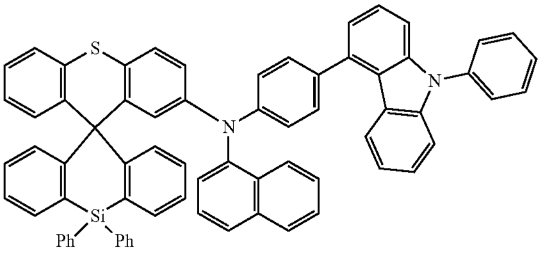
A159
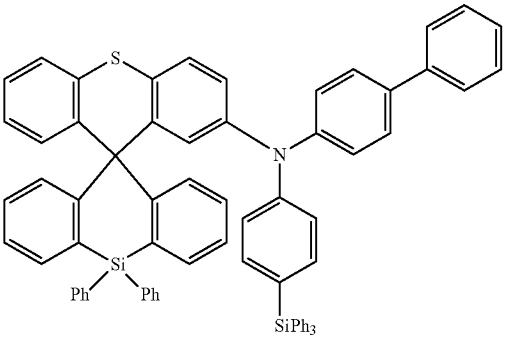
A160
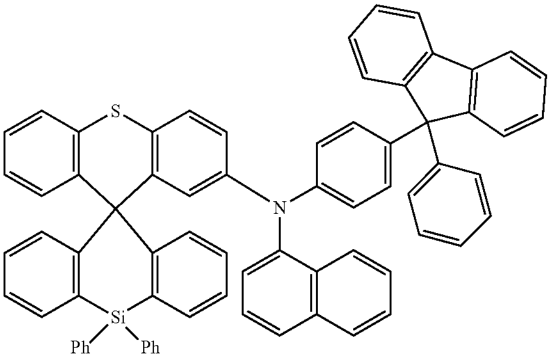

-continued
A161
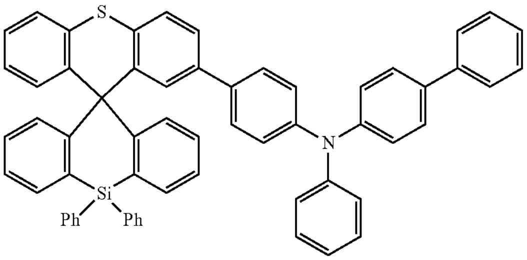
A162
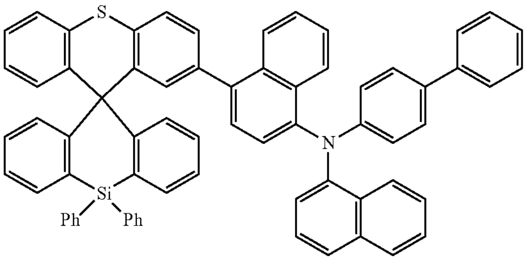
A163
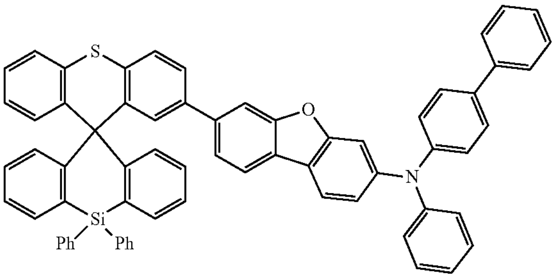
A164
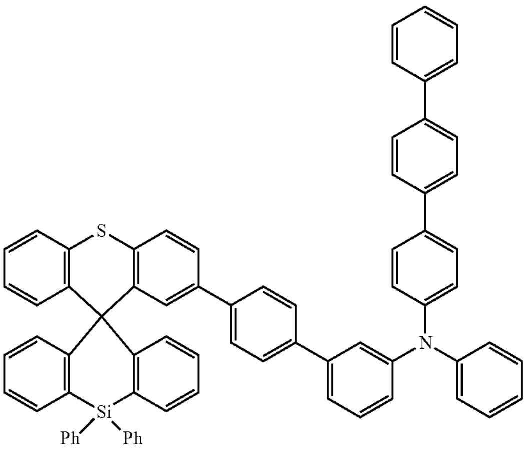
A165
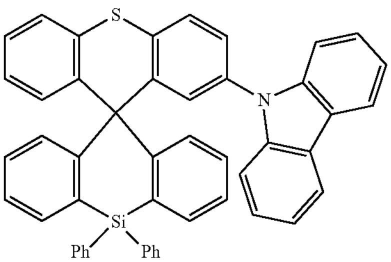
-continued
A166
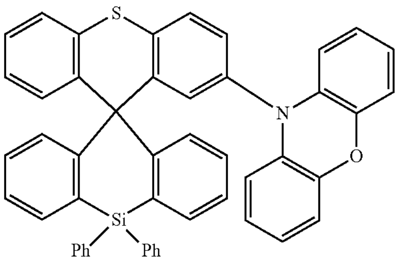
A167
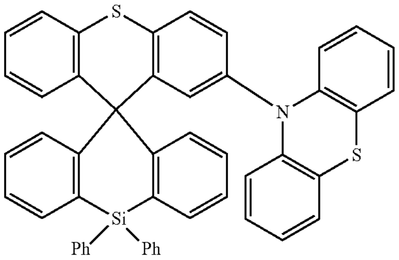
A168
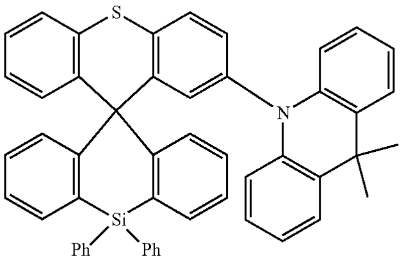
A169
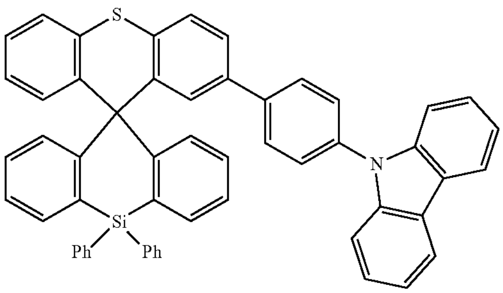
A170
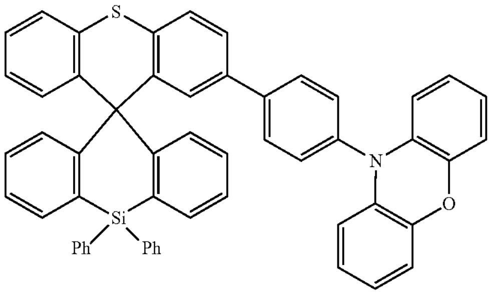

-continued
A171
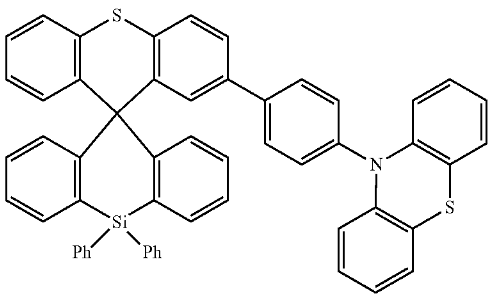
A172
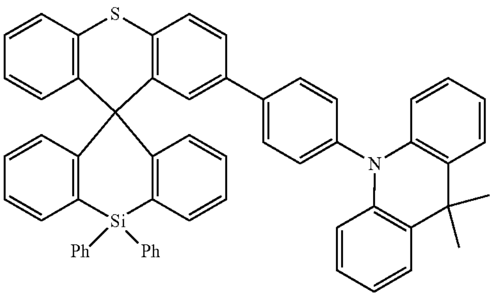
A173
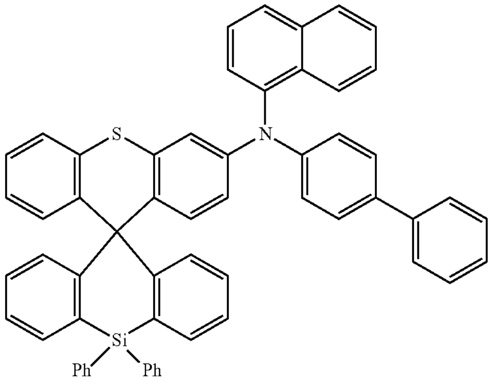
A174
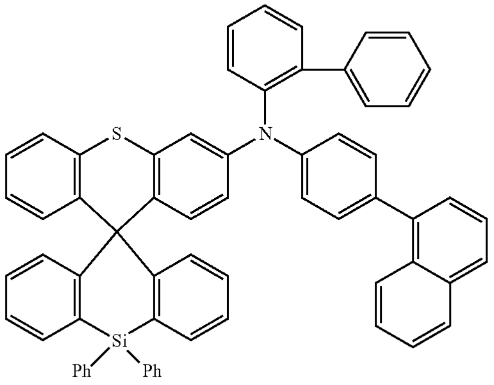
-continued
A175
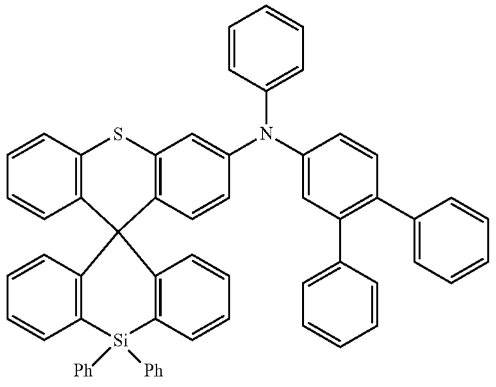
A176
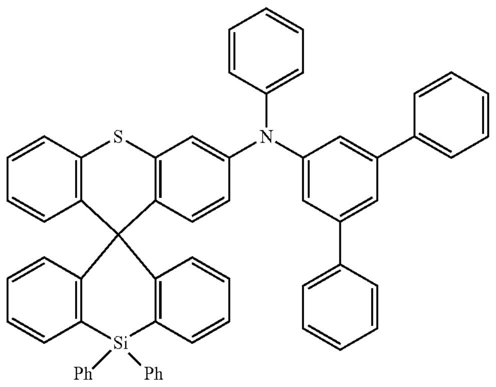
A177
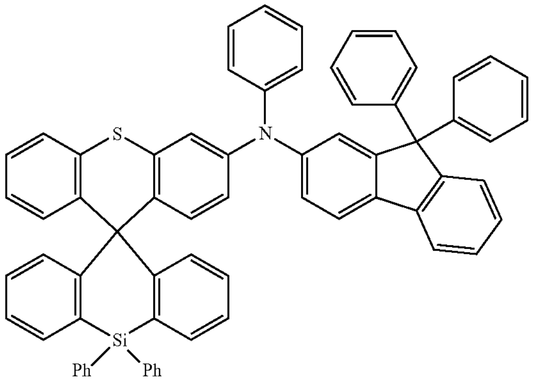
A178
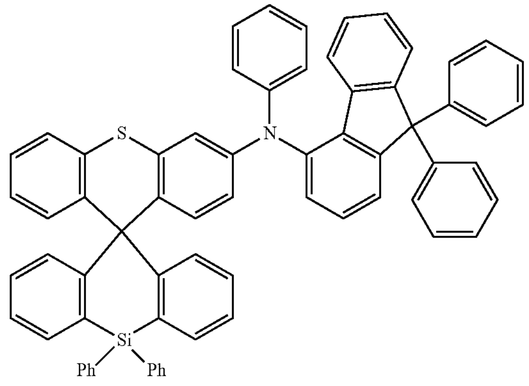

-continued
A179
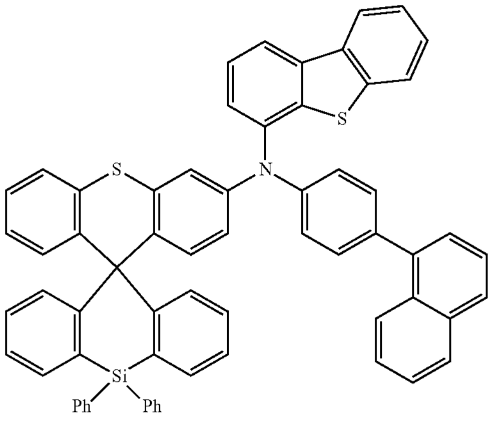
A180
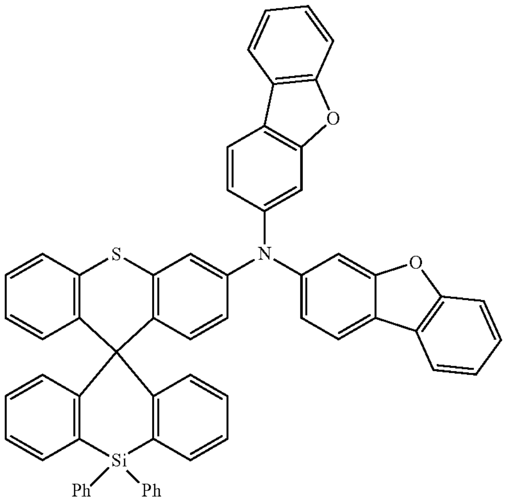
A181
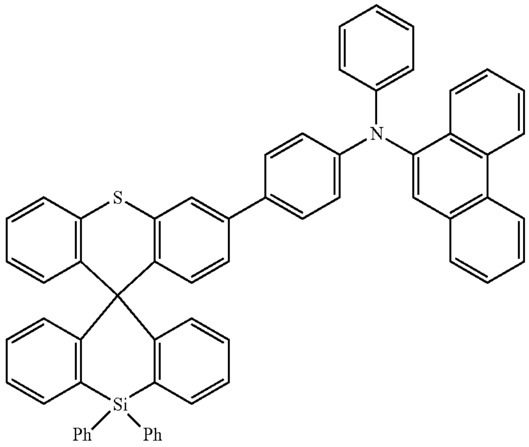
-continued
A182
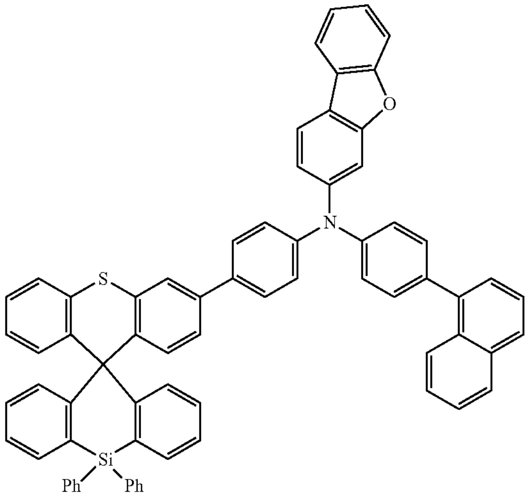
A183
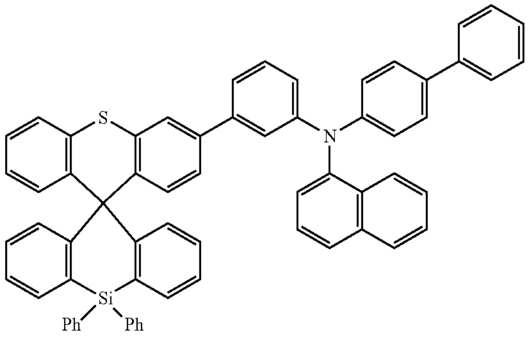
A184
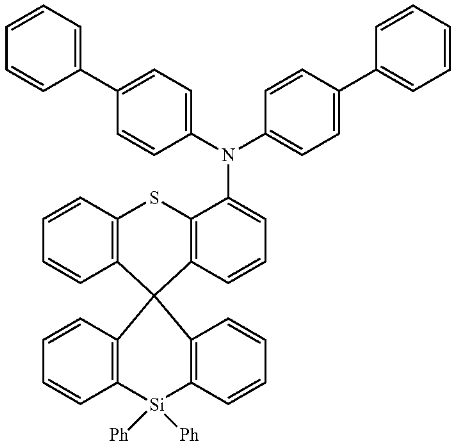

-continued
A185
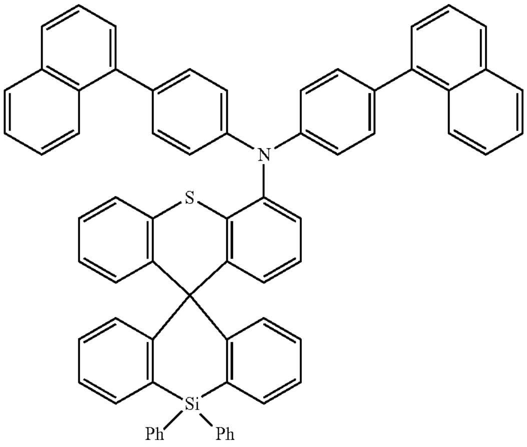
A186
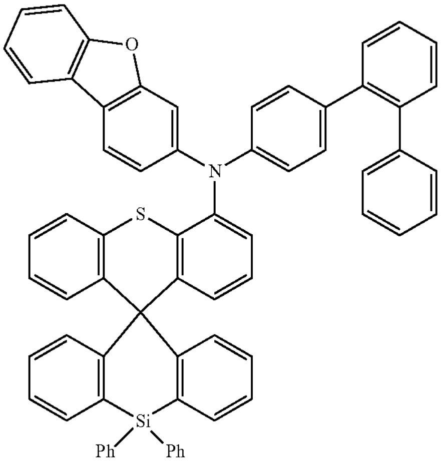
A187
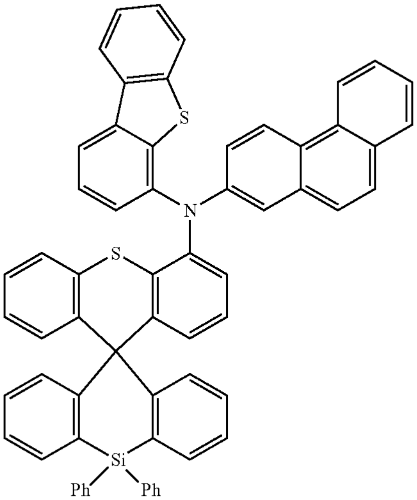
-continued
A188
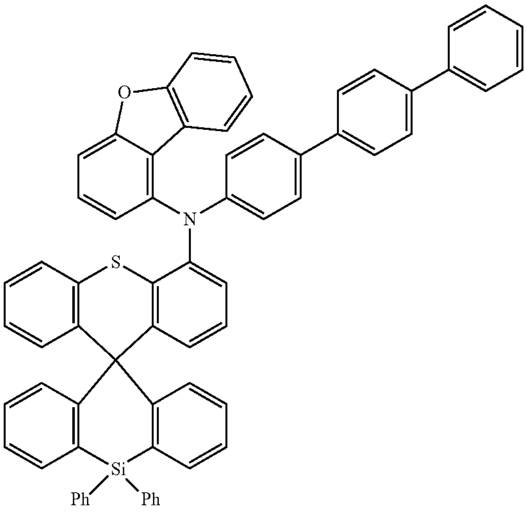
A189
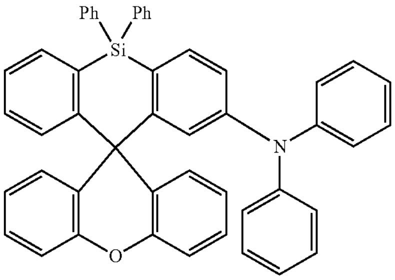
A190
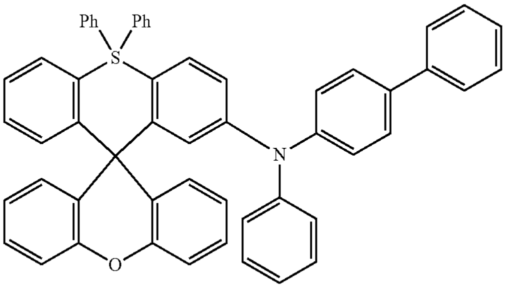
A191
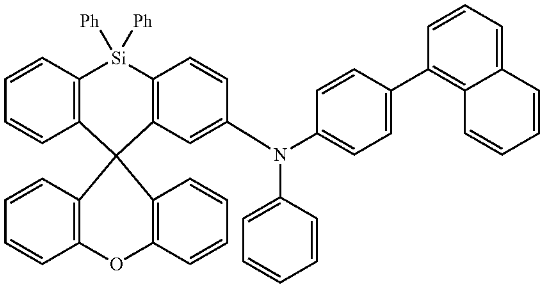

-continued
A192
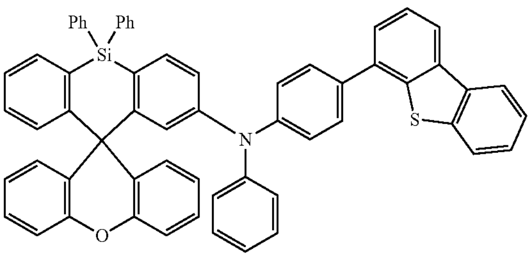
A193
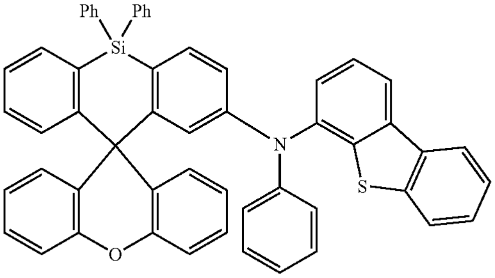
A194
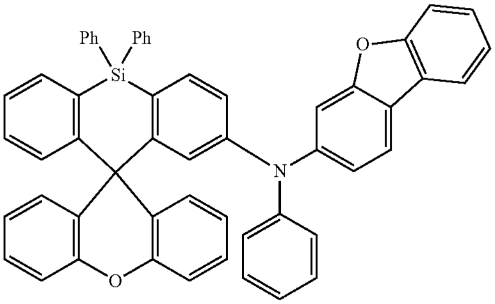
A195
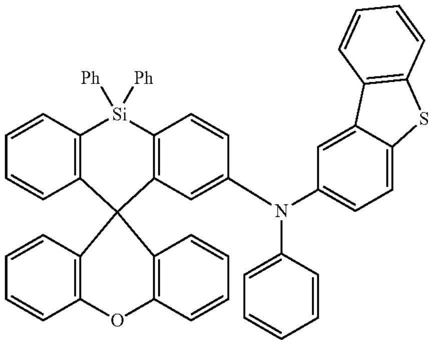
A196
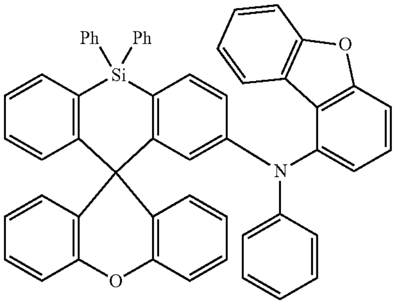
-continued
A197
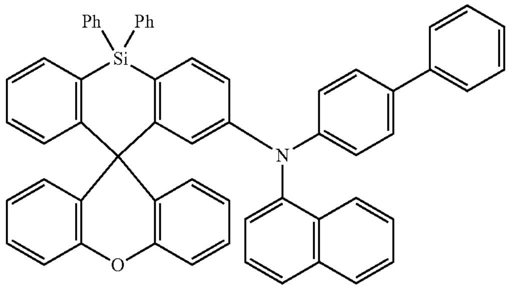
A198
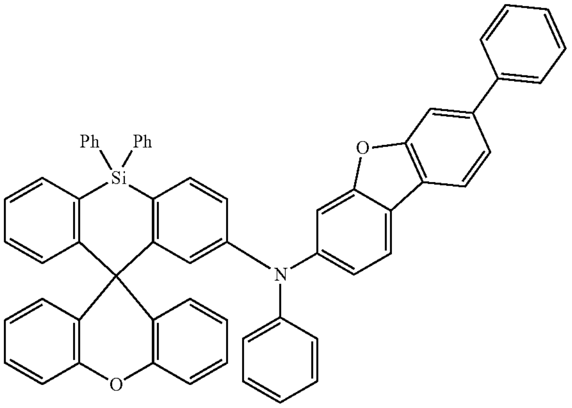
A199
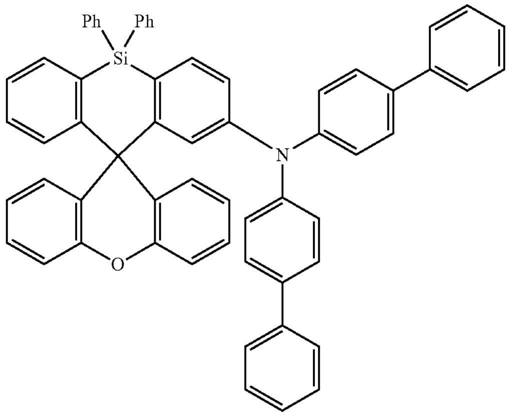
A200
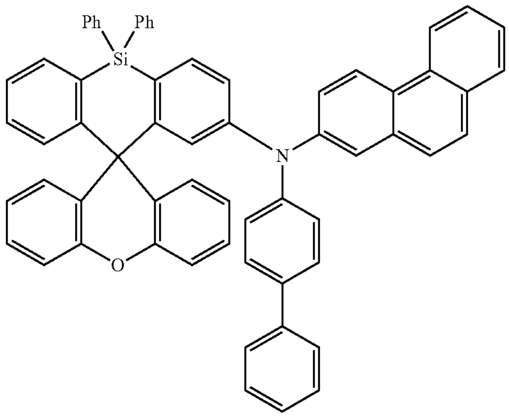

-continued
A201
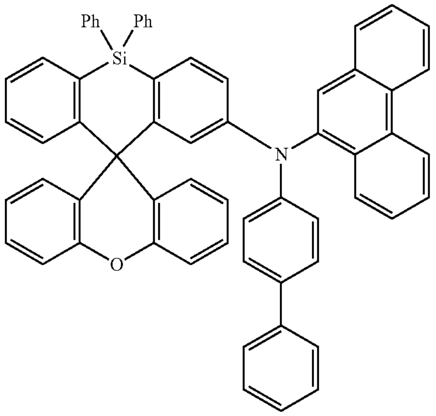
A202
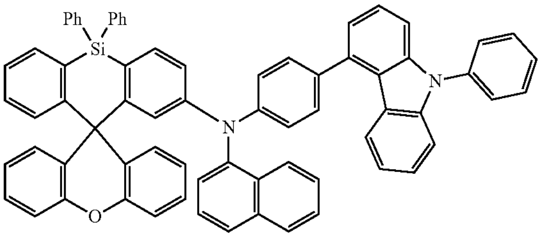
A203
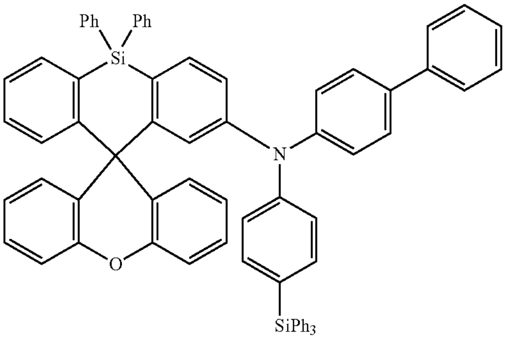
A204
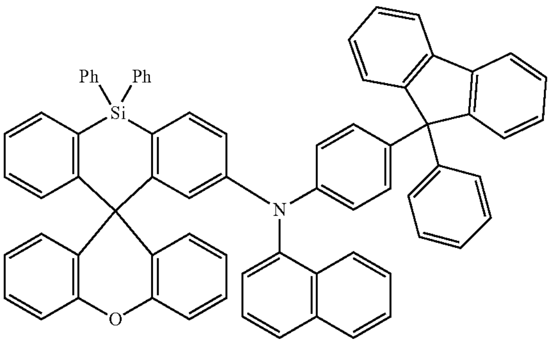
-continued
A205
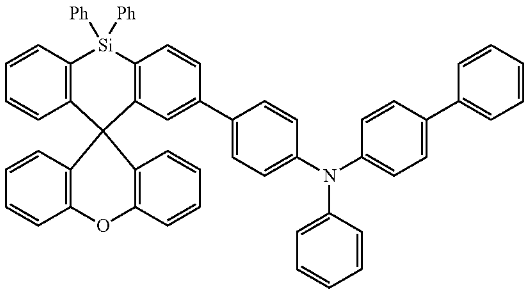
A206
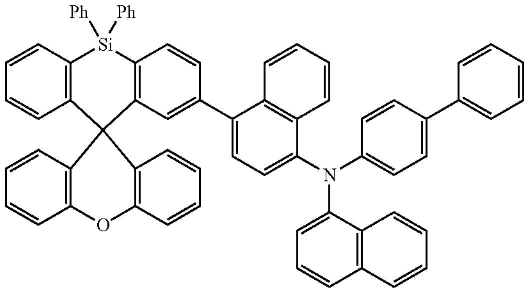
A207
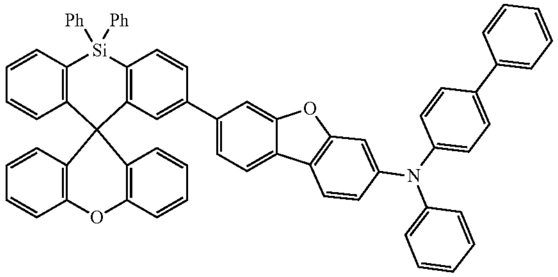
A208
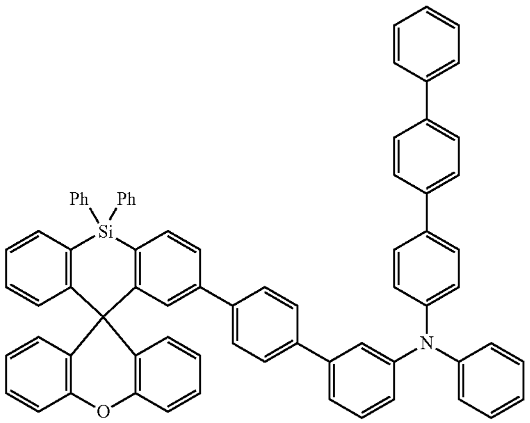
A209
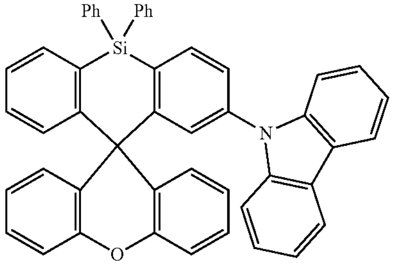

-continued
A210
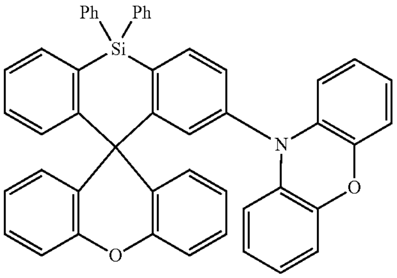
A211
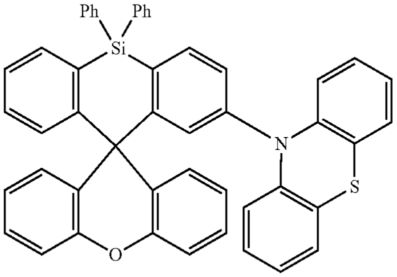
A212
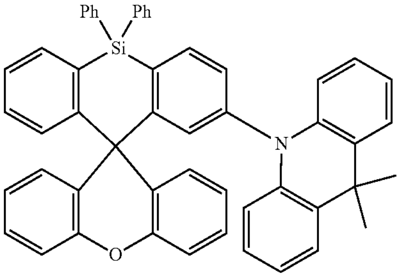
A213
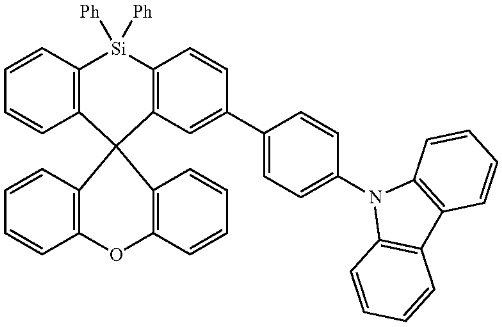
A214
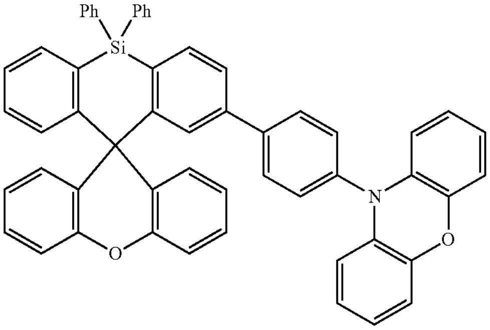
-continued
A215
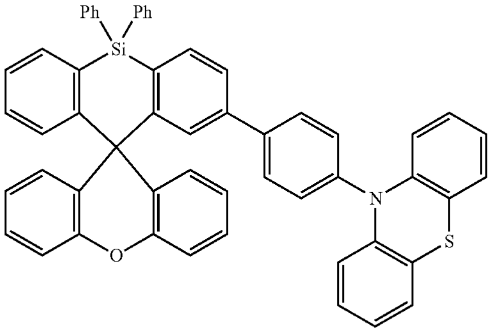
A216
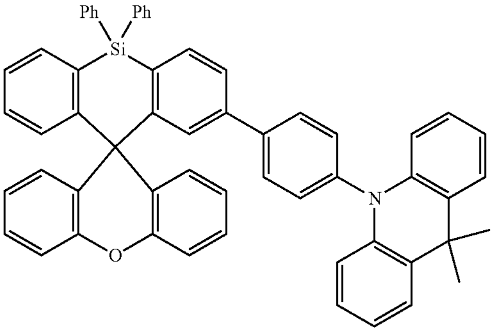
A217
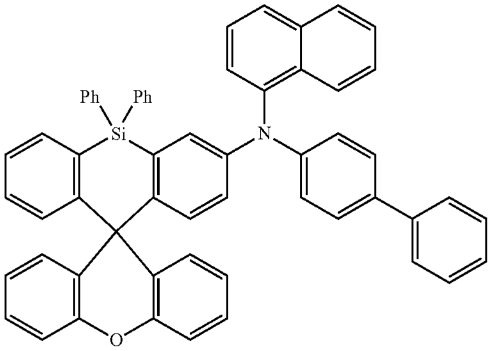
A218
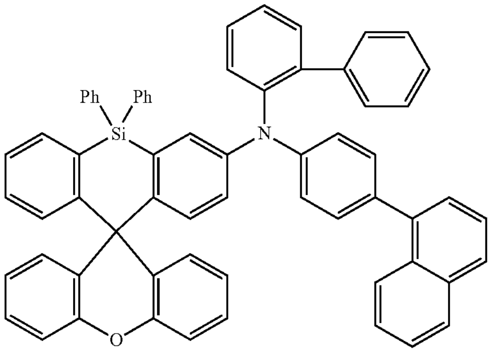

-continued
A219
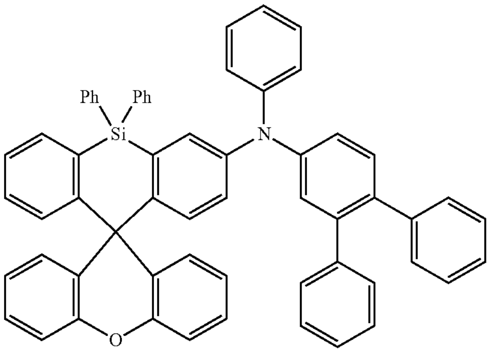
A220
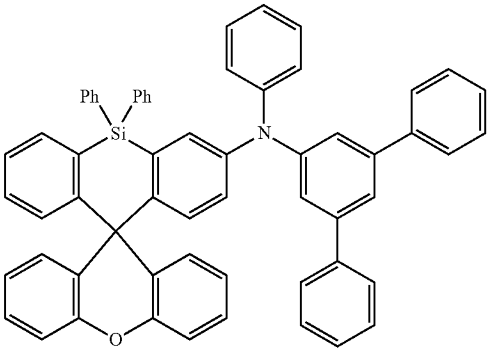
A221
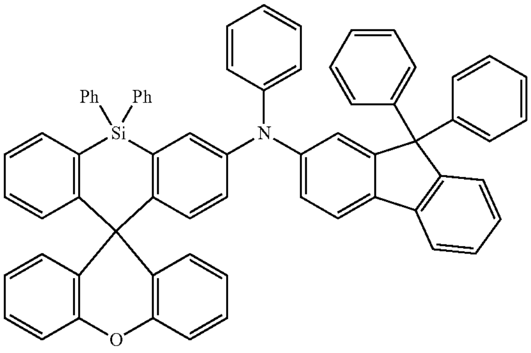
A222
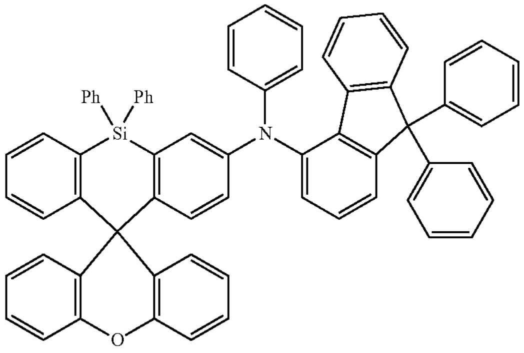
-continued
A223
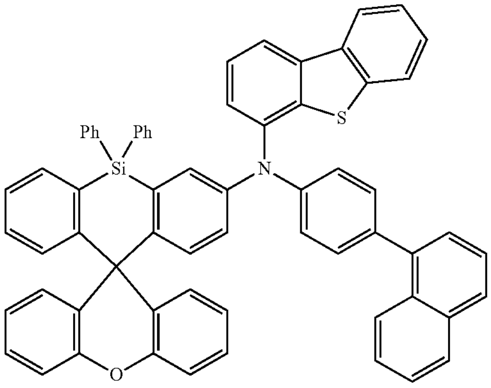
A224
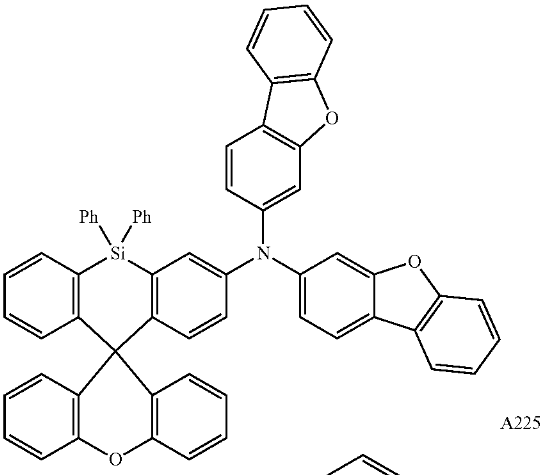
A225
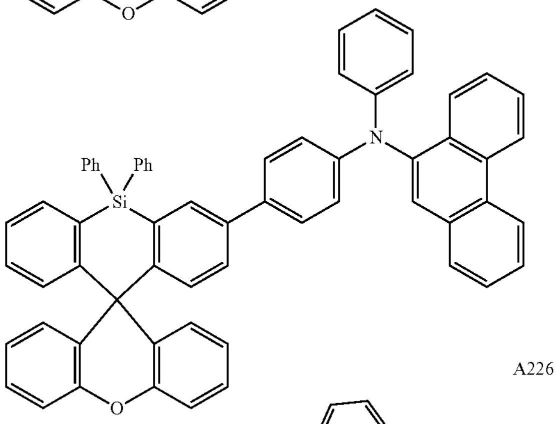
A226
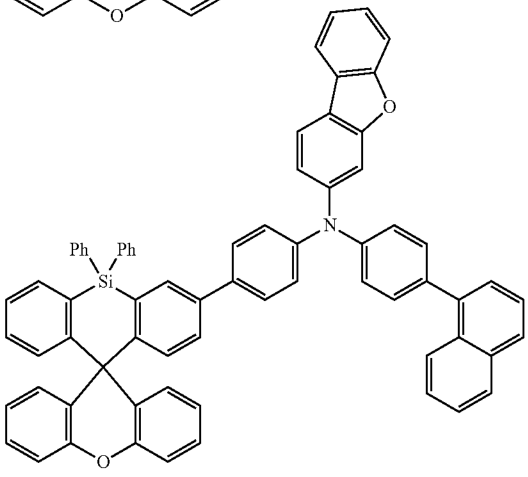

-continued
A227
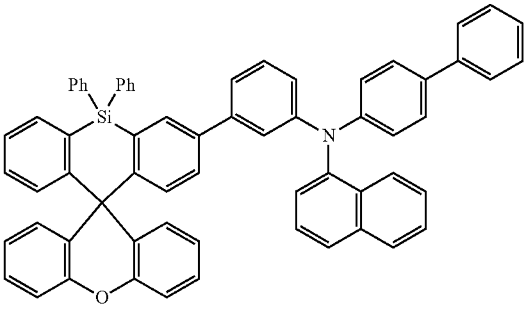
A228
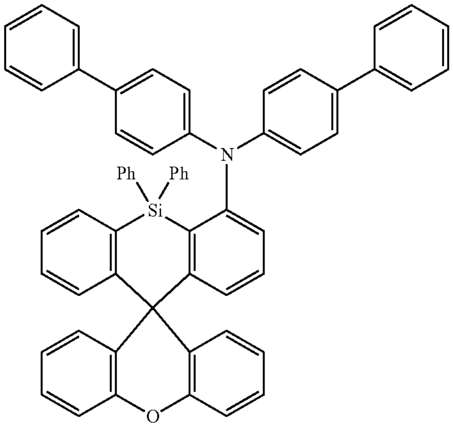
A229
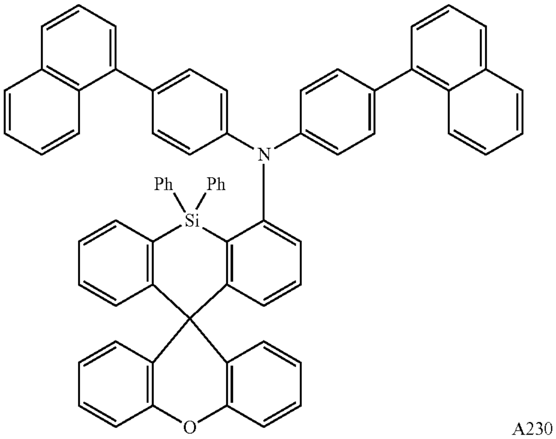
A230
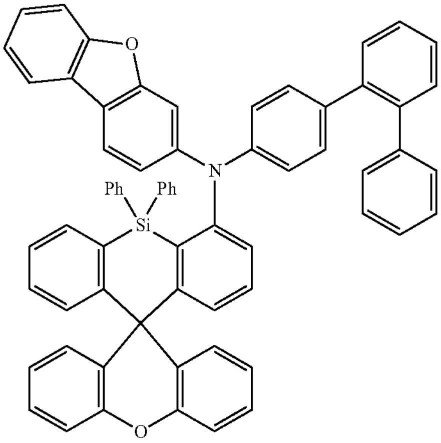
-continued
A231
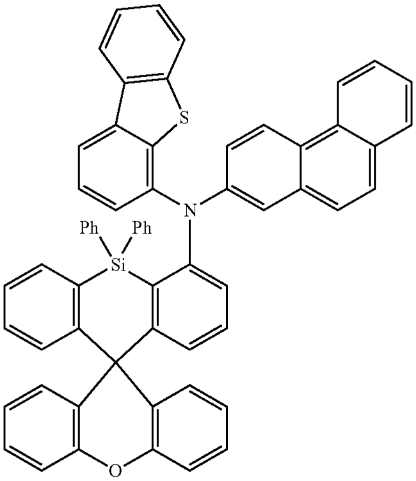
A232
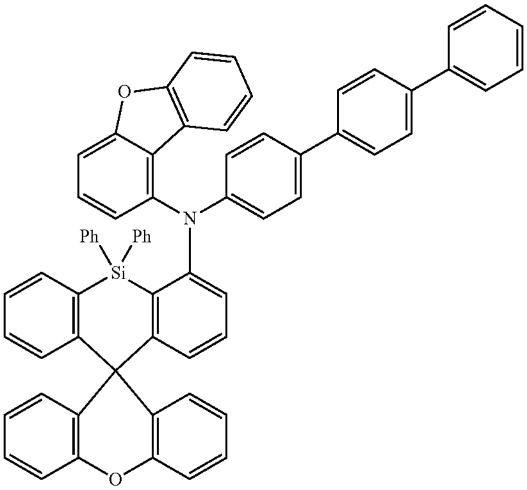
A233
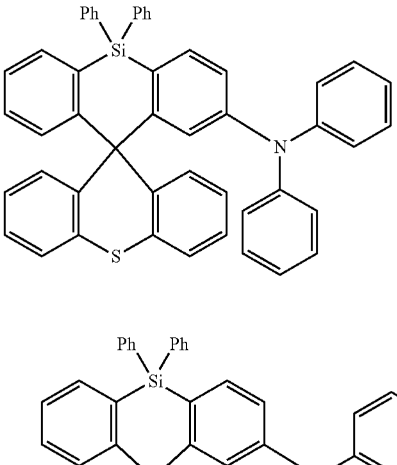
A234
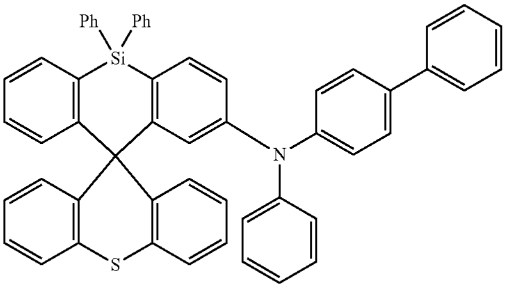

-continued
A235
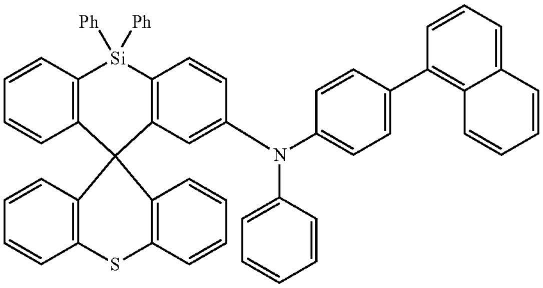
A236
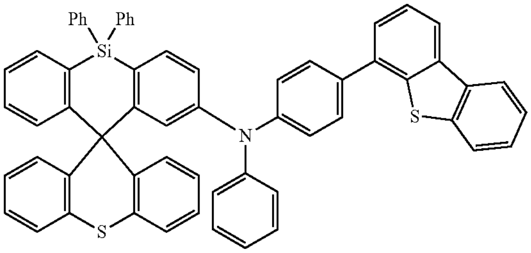
A237
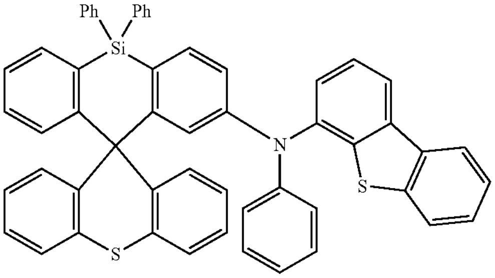
A238
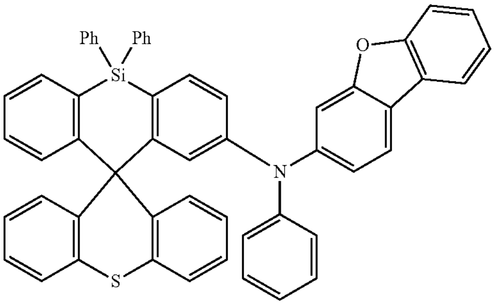
A239
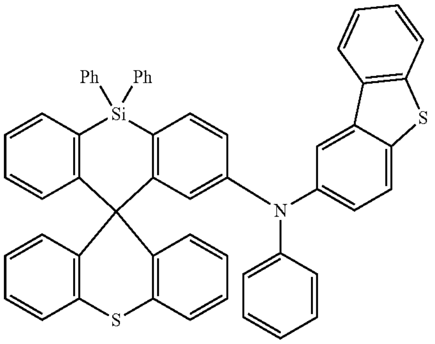
-continued
A240
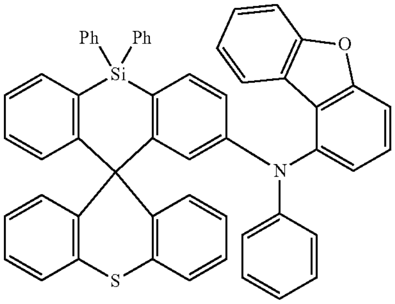
A241
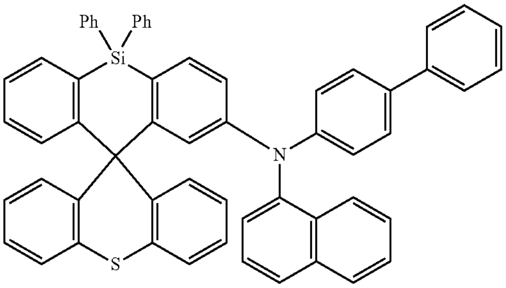
A242
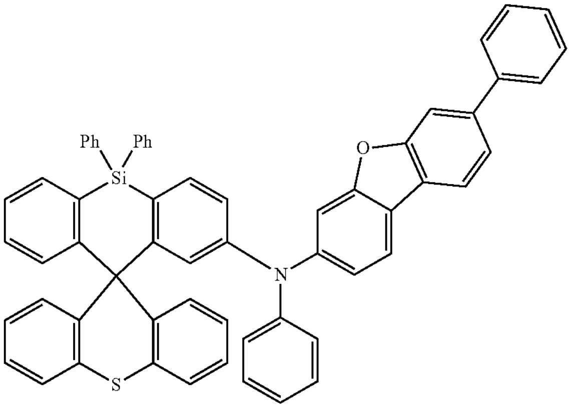
A243
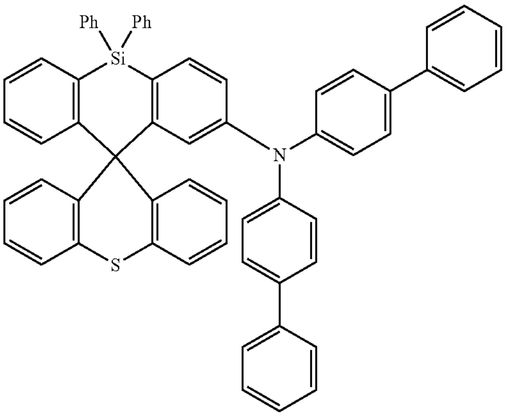

-continued
A244
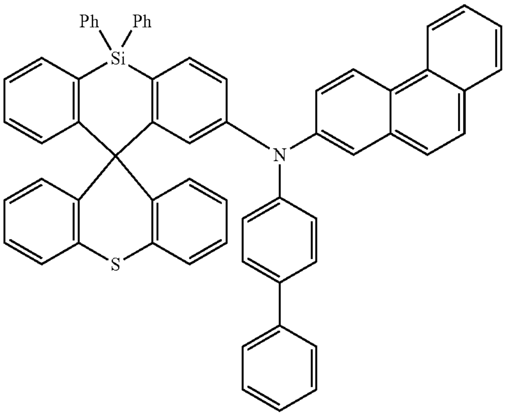
A245
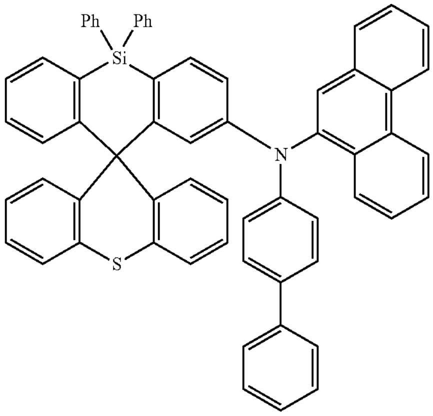
A246
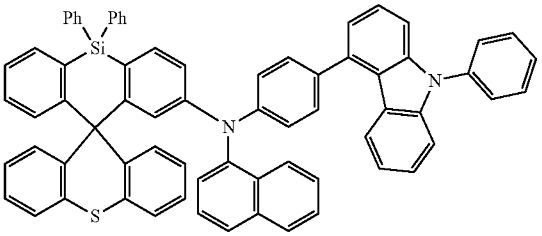
A247
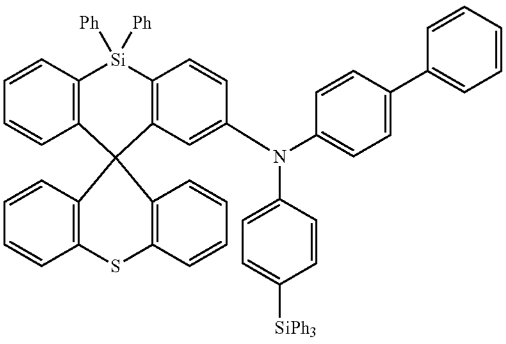
-continued
A248
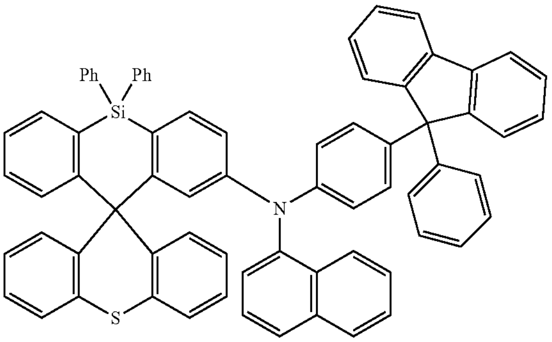
A249
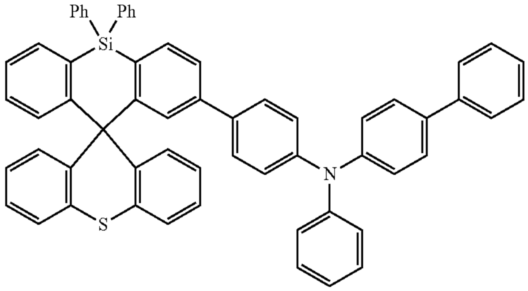
A250
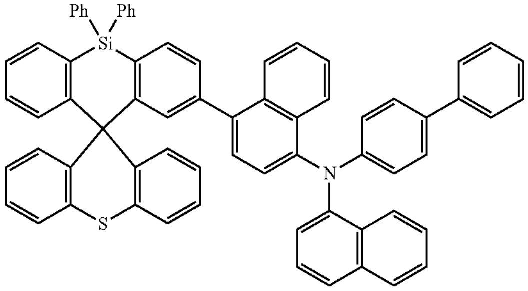
A251
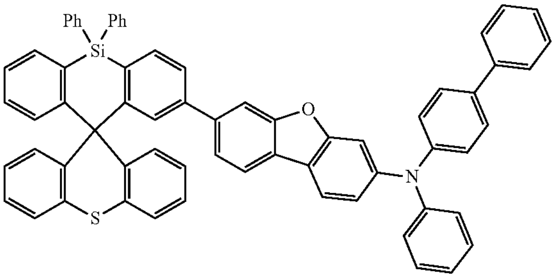

A252
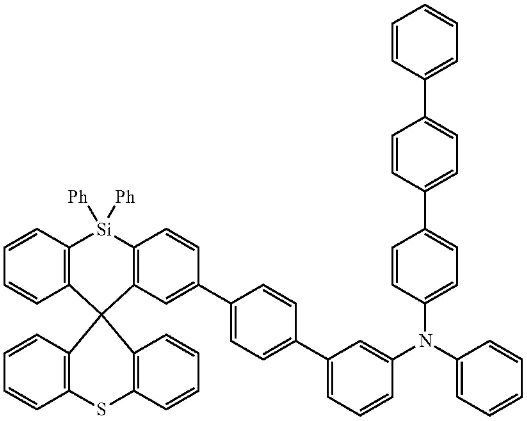
A253
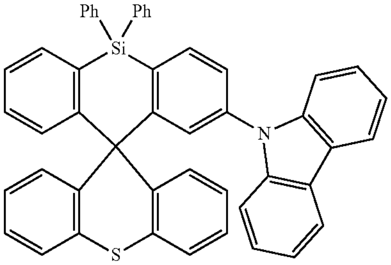
A254
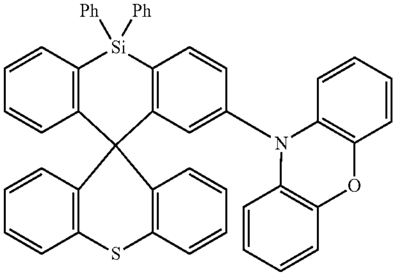
A255
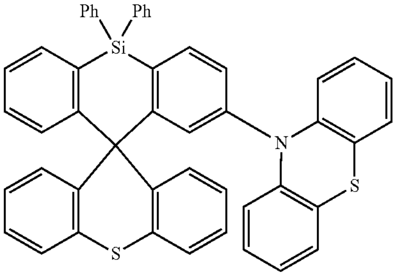
A256
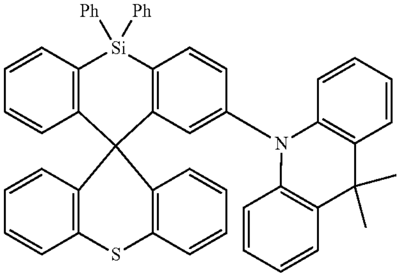
A257
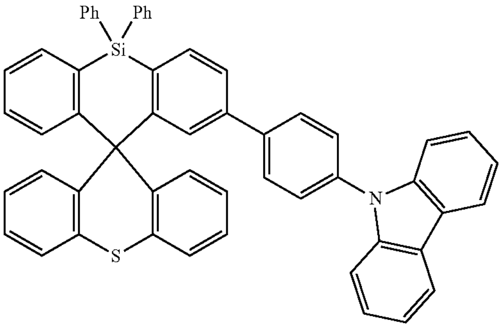
A258
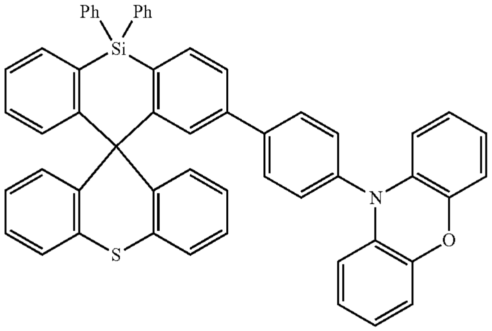
A259
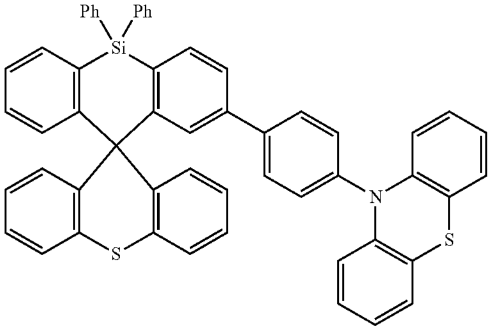
A260
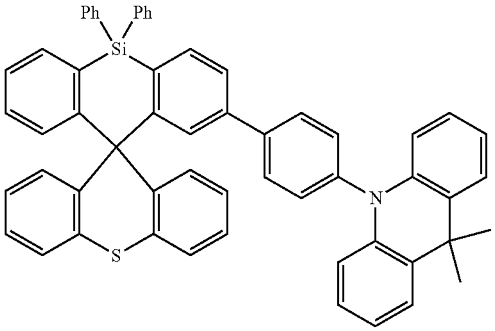

-continued
A261
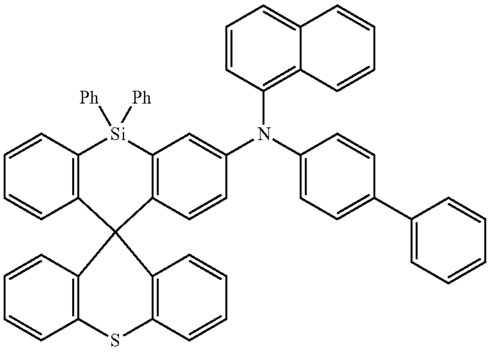
A262
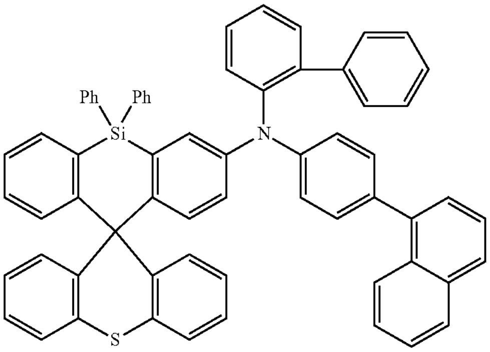
A263
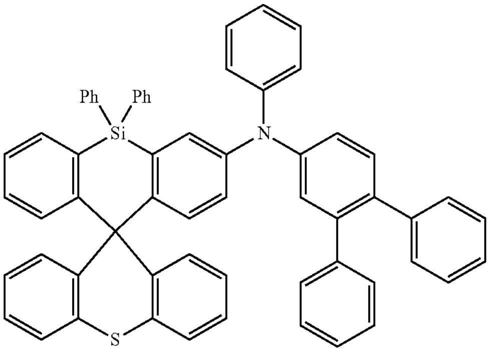
A264
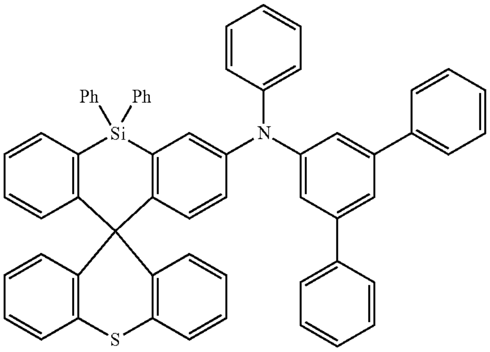
-continued
A265
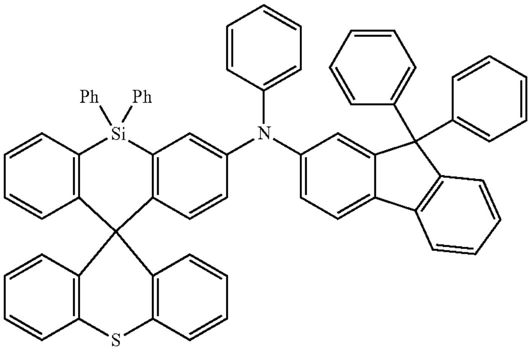
A266
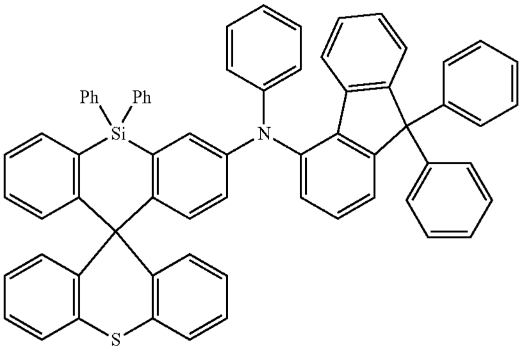
A267
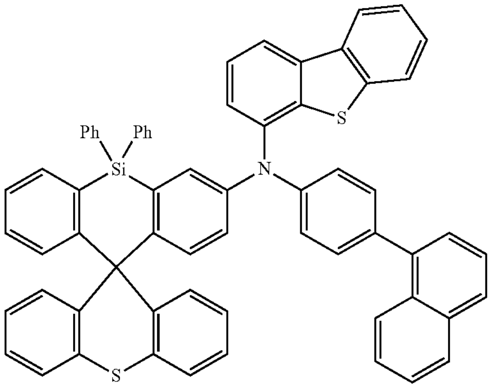
A268
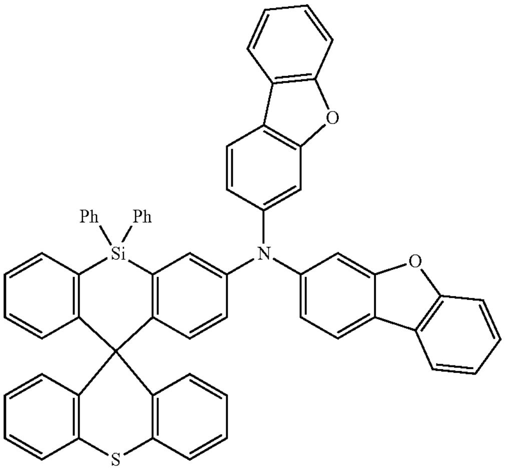

-continued
A269
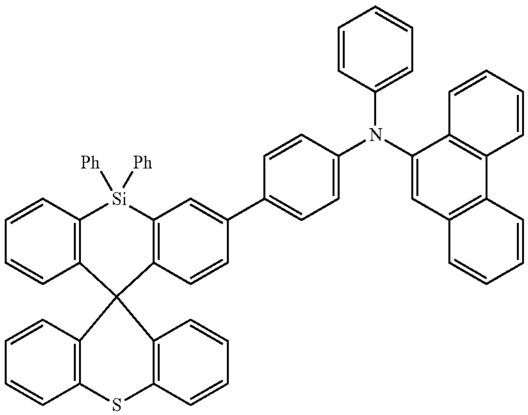
A270
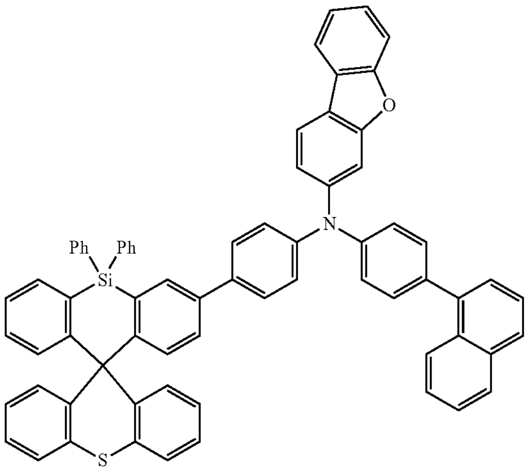
A271
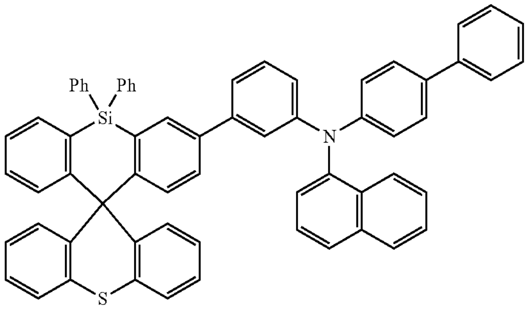
-continued
A272
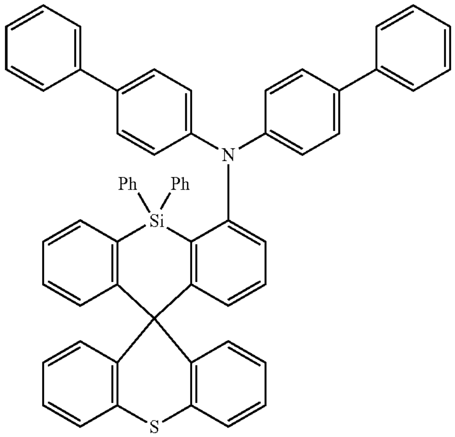
A273
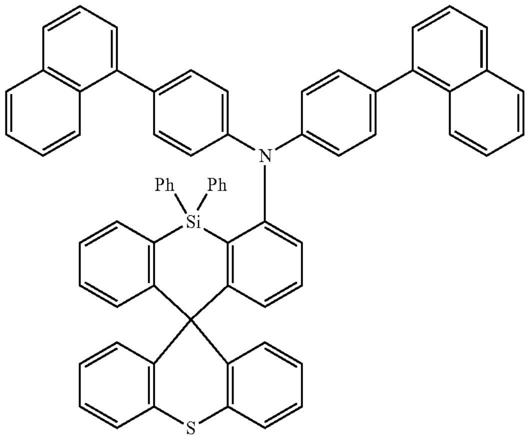
A274
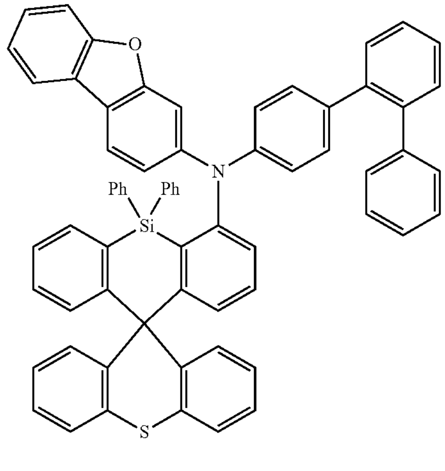

-continued
A275
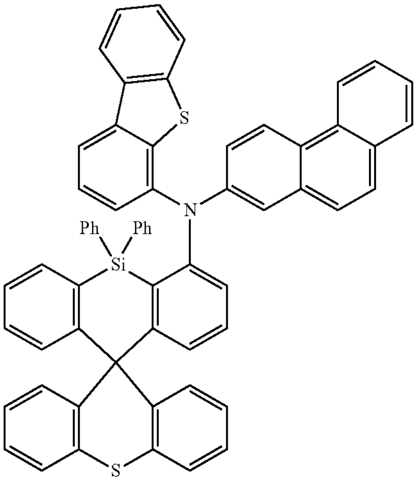
A276
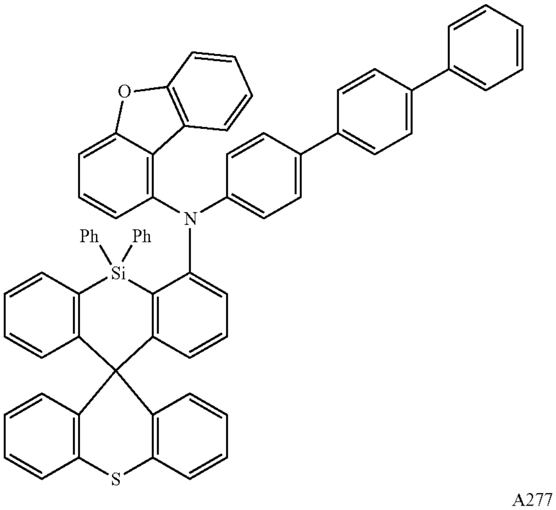
A277
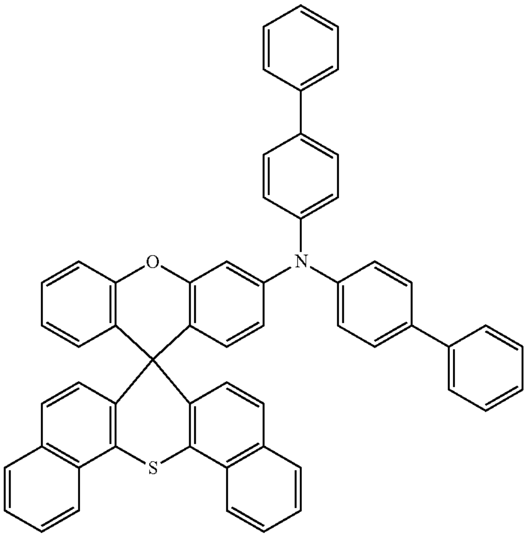
-continued
A278
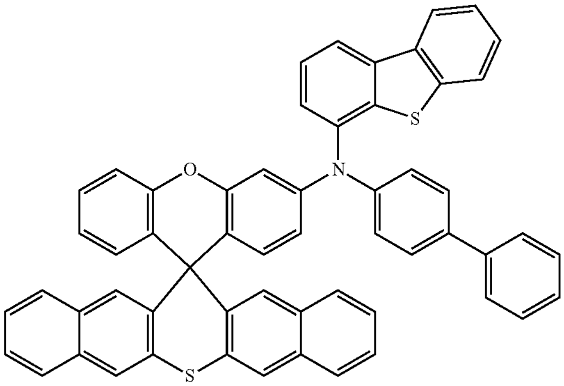
A279
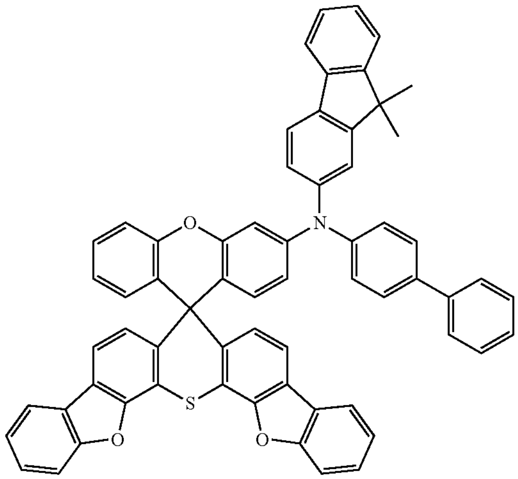
A280
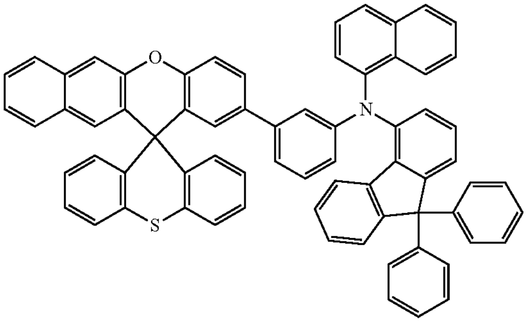
[Compound Group 2]
B1
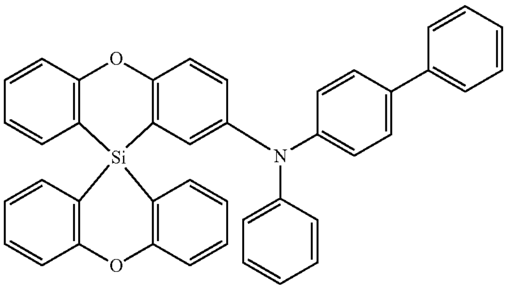

B2
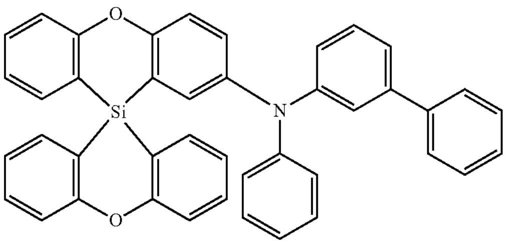
B3
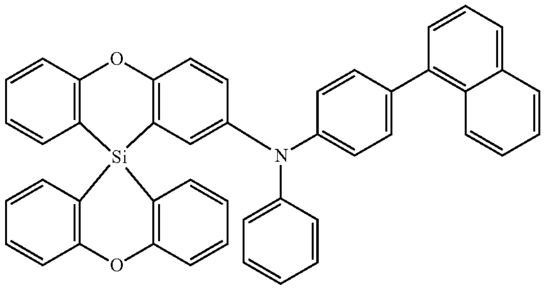
B4
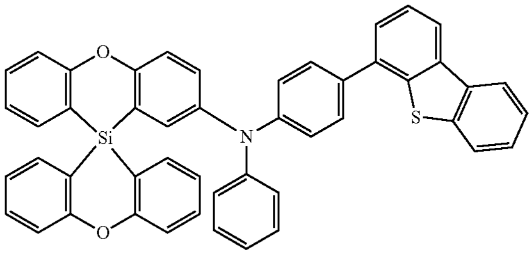
B5
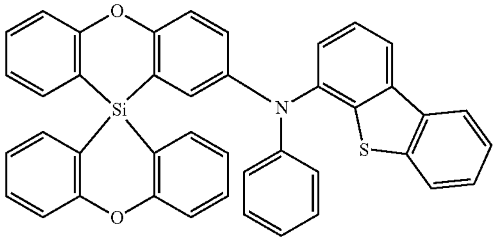
B6
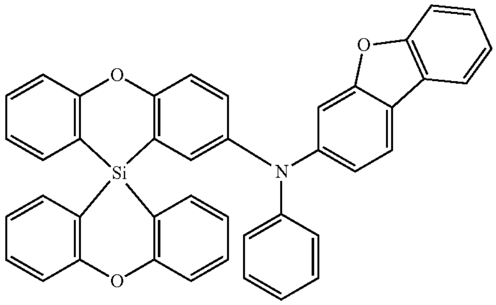
B7
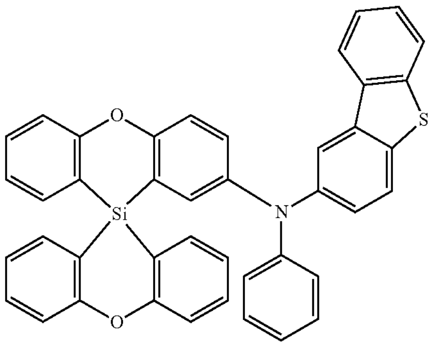
B8
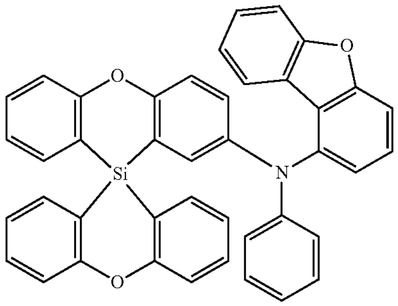
B9
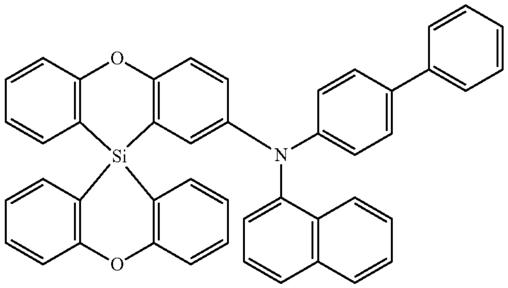
B10
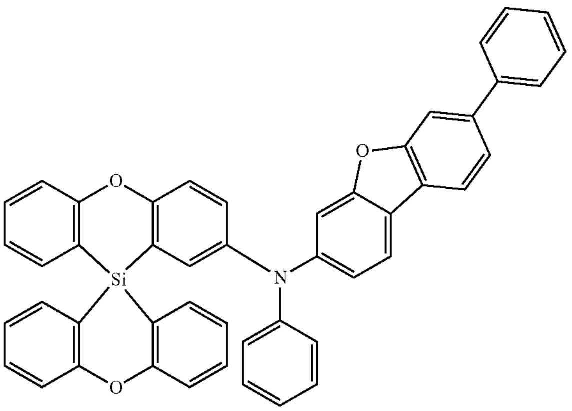

-continued
B11
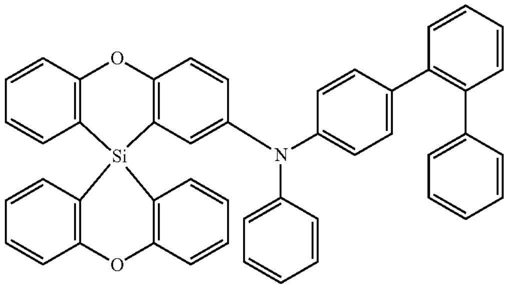
B12
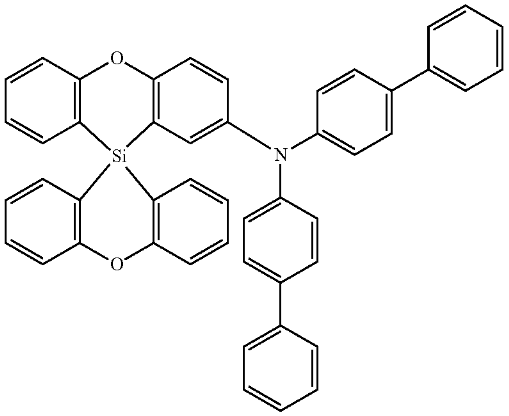
B13
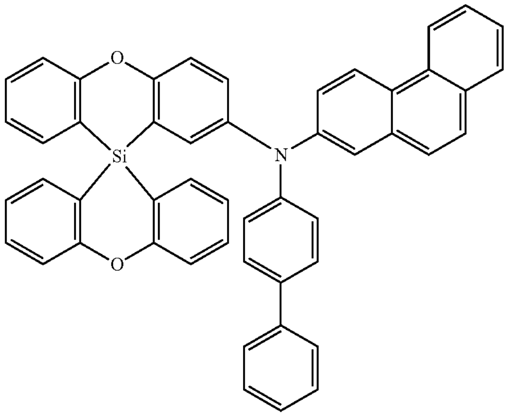
B14
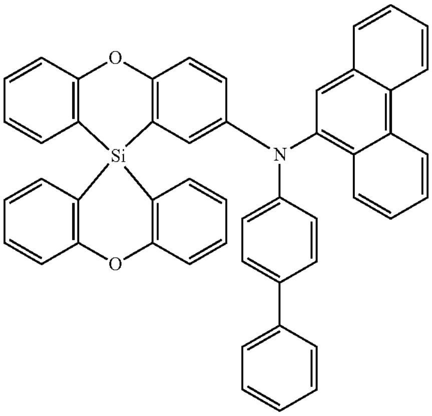
-continued
B15
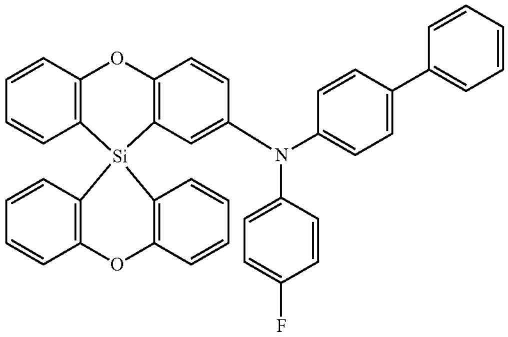
B16
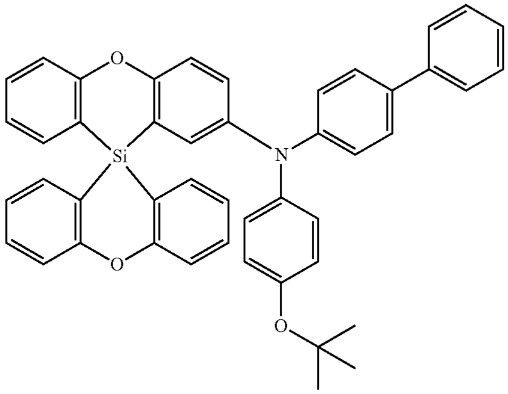
B17
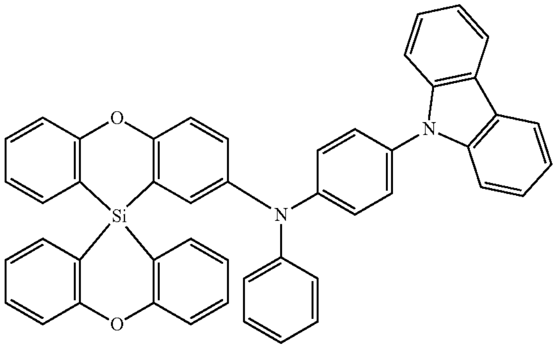
B18
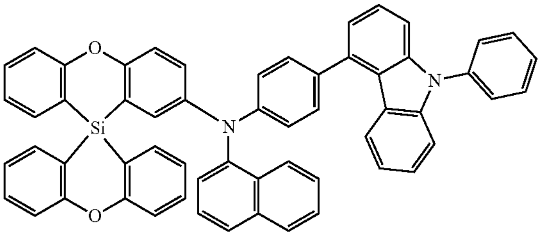

-continued
B19
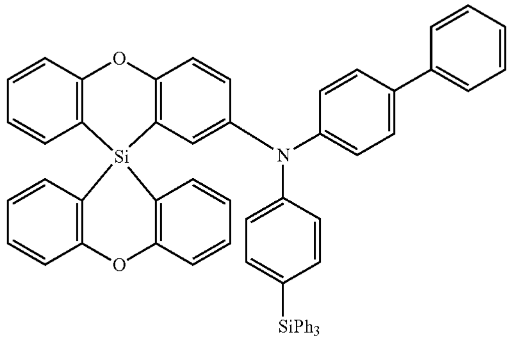
B20
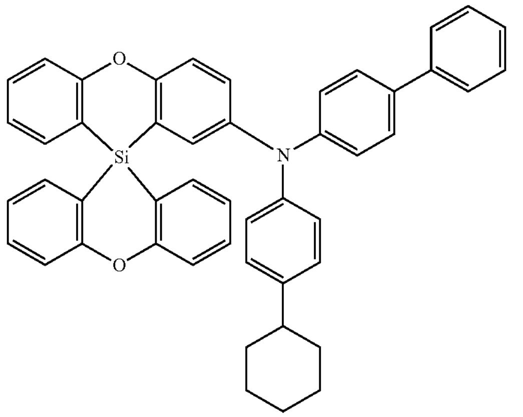
B21
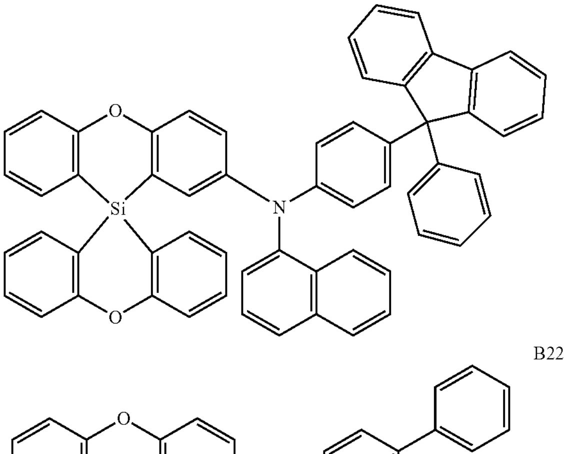
B22
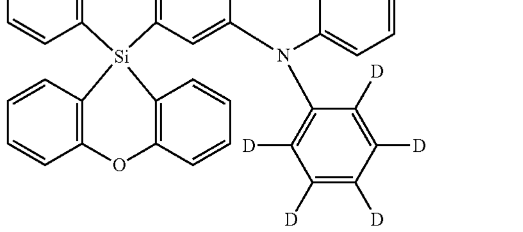
-continued
B23
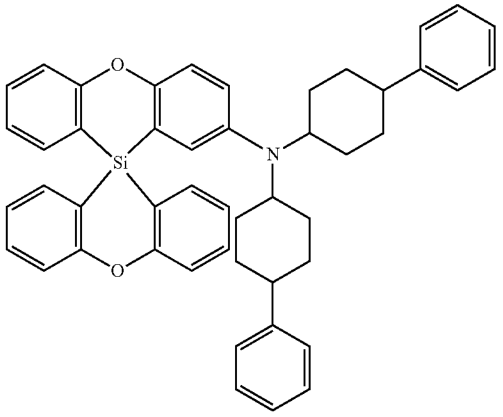
B24
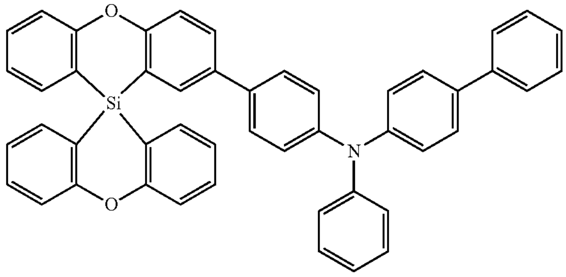
B25
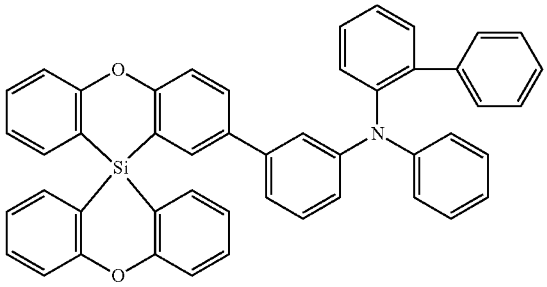
B26
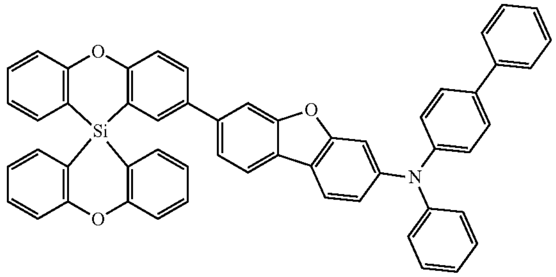

-continued
B27
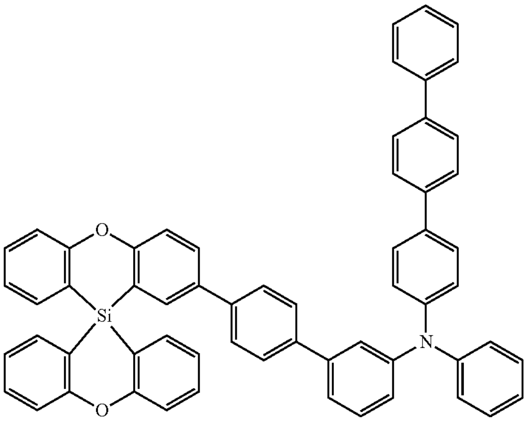
B28
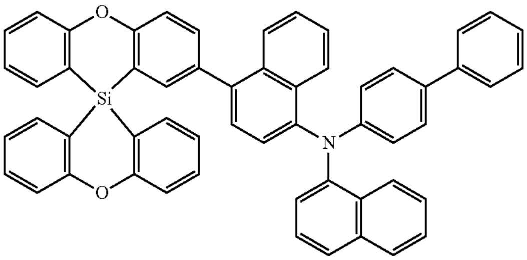
B29
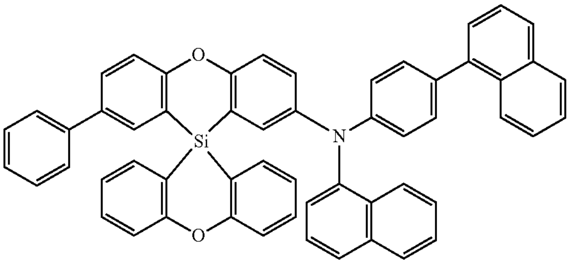
B30
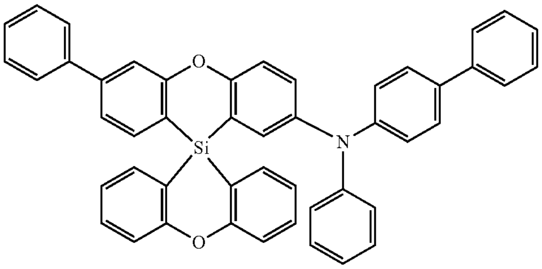
-continued
B31
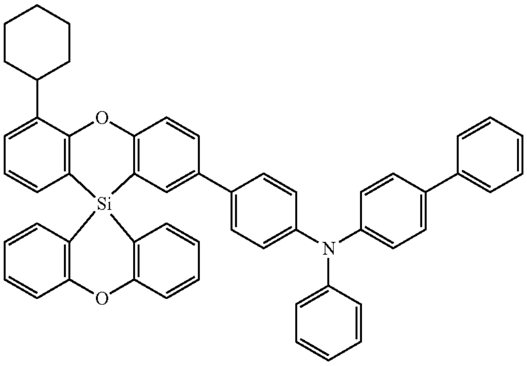
B32
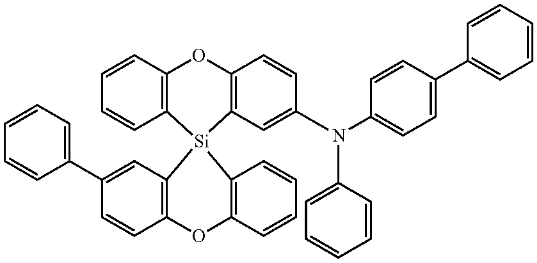
B33
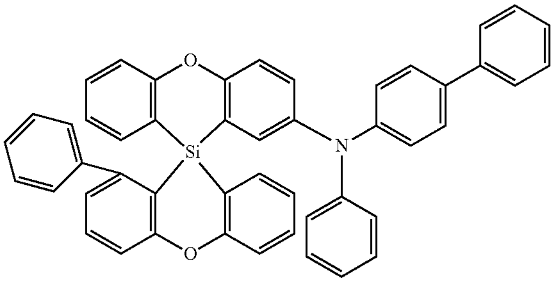
B34
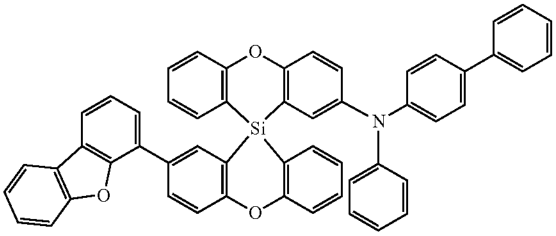
B35
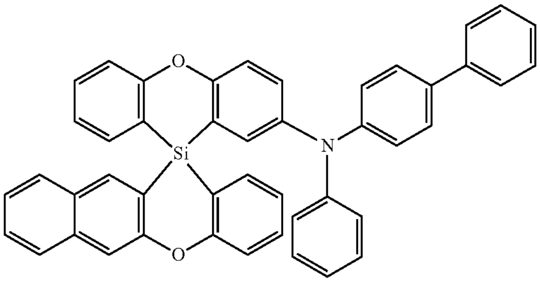

-continued
B36
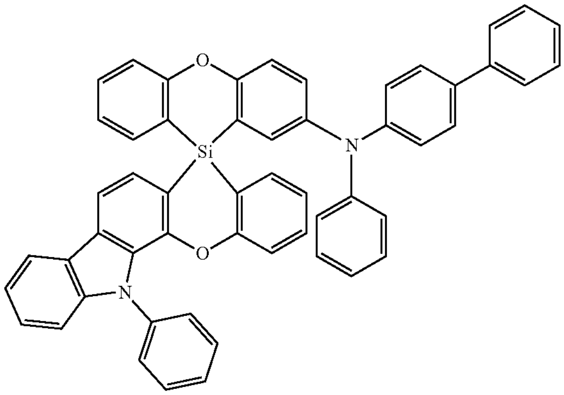
B37
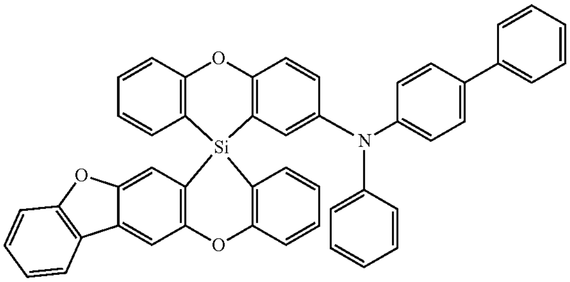
B38
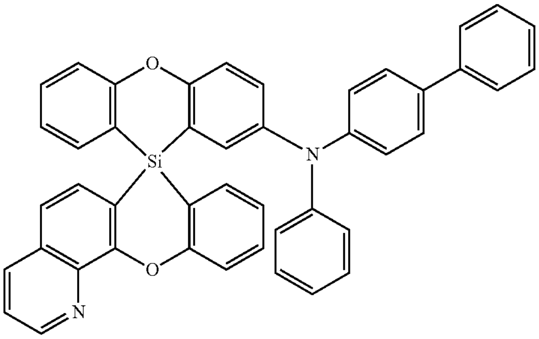
B39
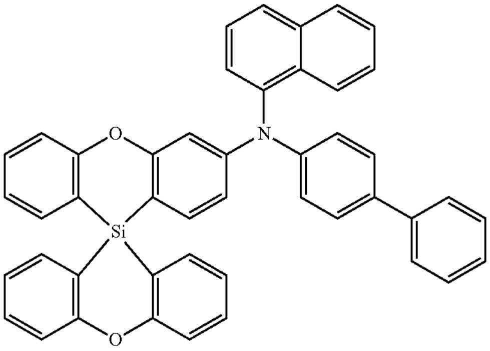
-continued
B40
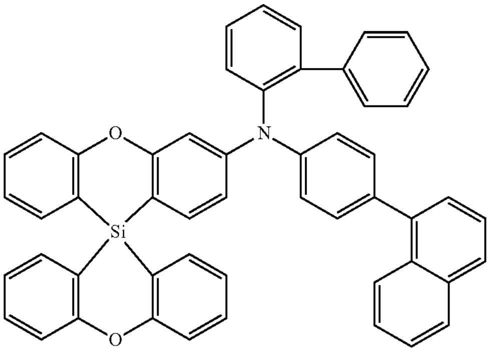
B41
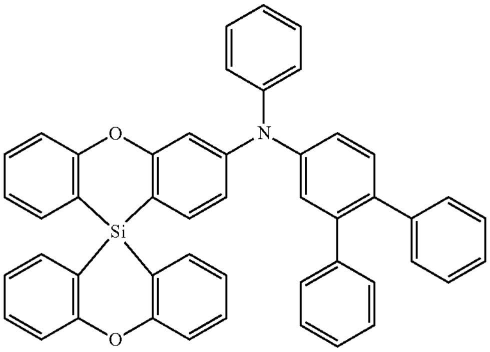
B42
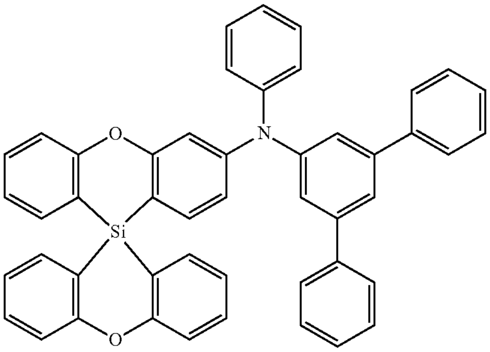
B43
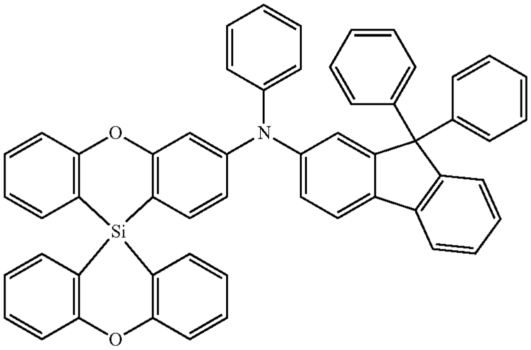

-continued
B44
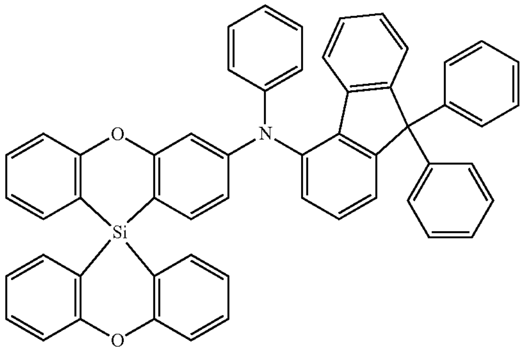
B45
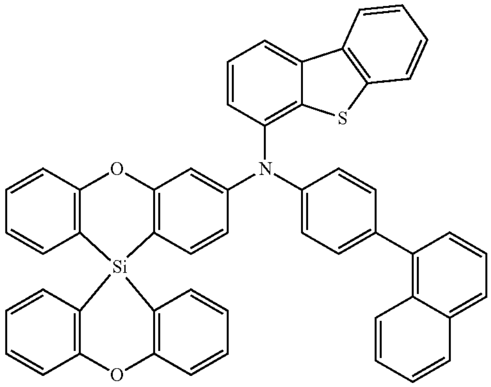
B46
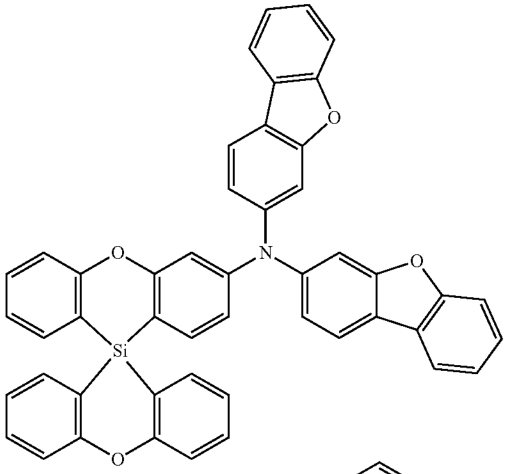
B47
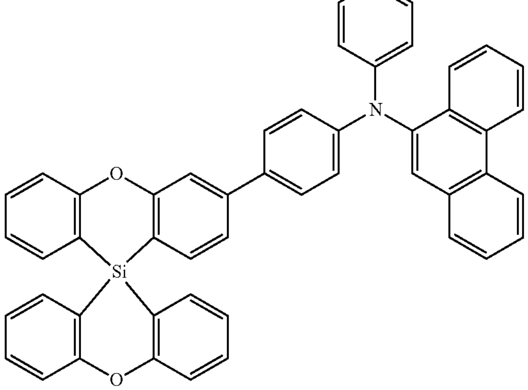
-continued
B48
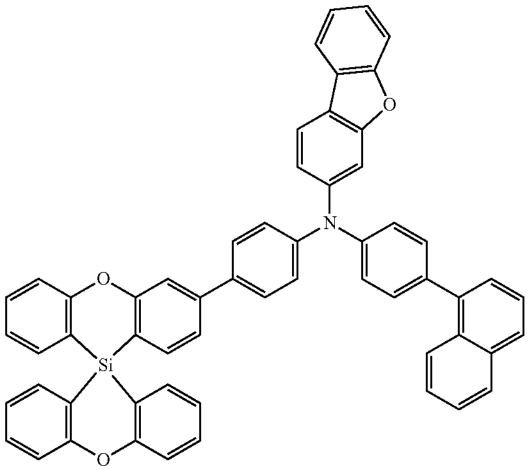
B49
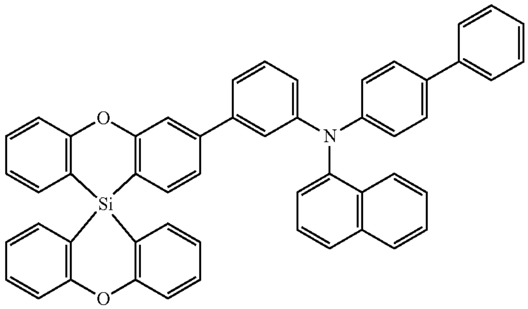
B50
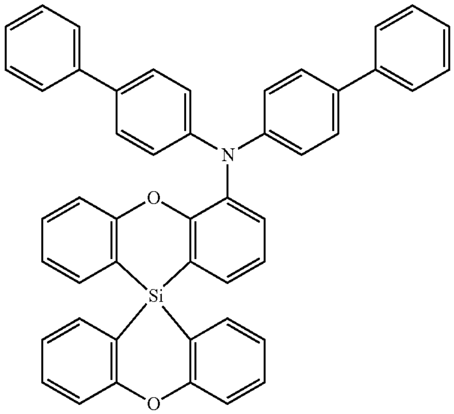

-continued
B51
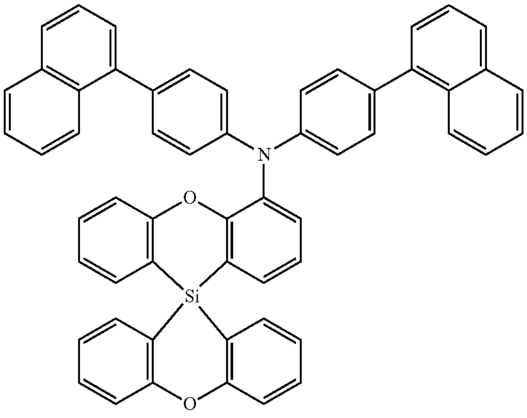
B52
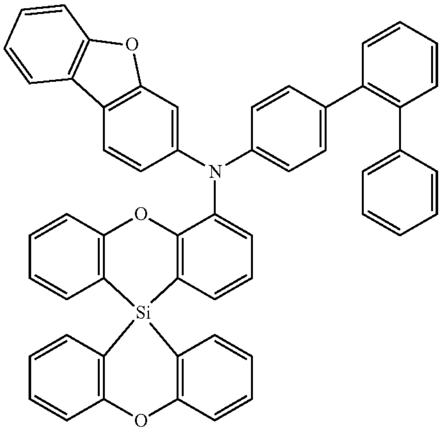
B53
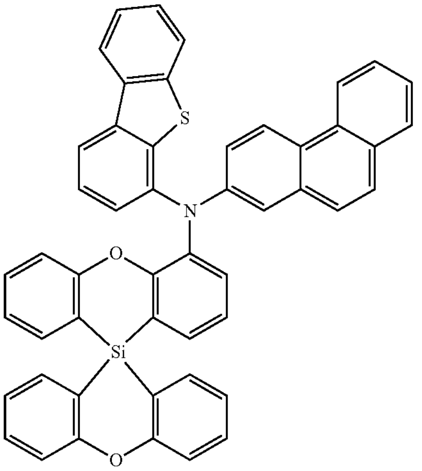
-continued
B54
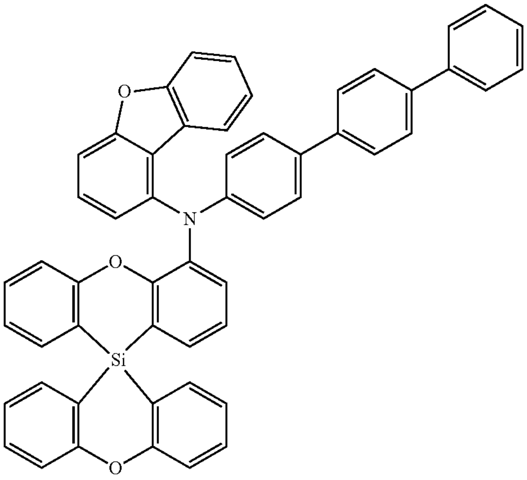
B55
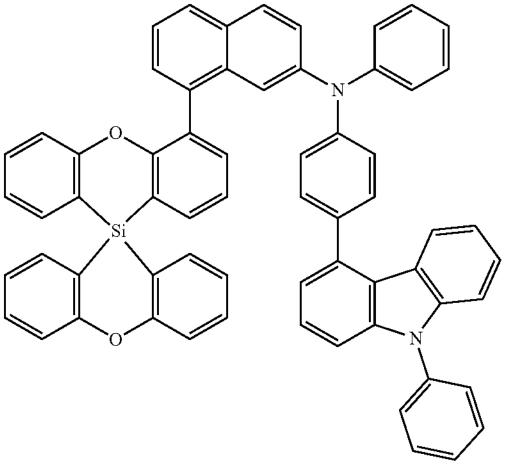
B56
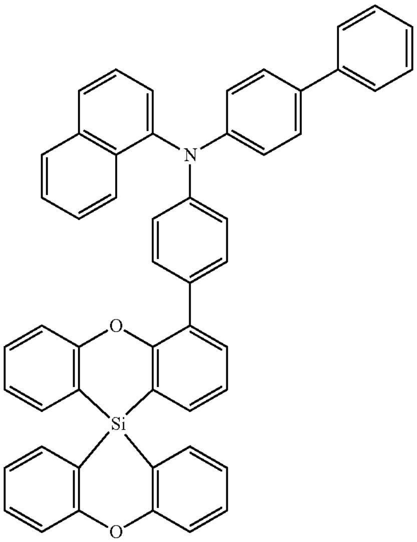

-continued
B57
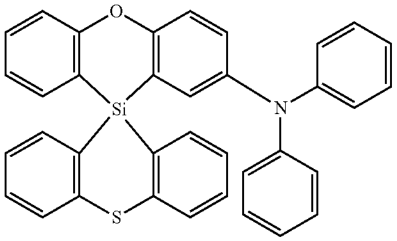
B58
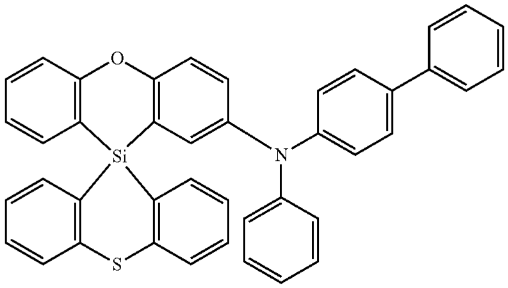
B59
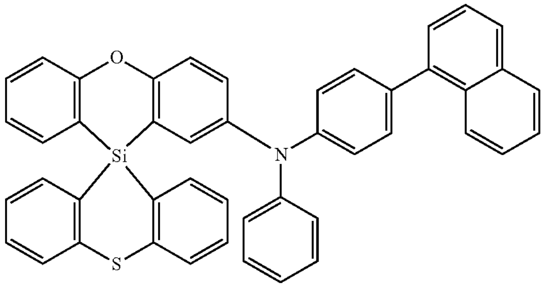
B60
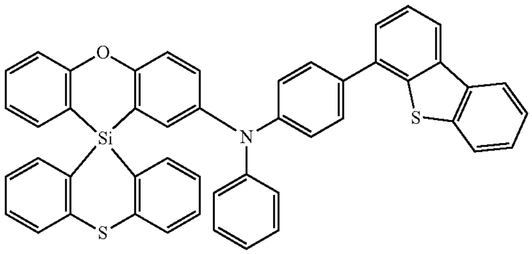
B61
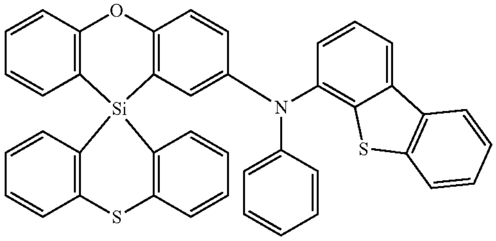
-continued
B62
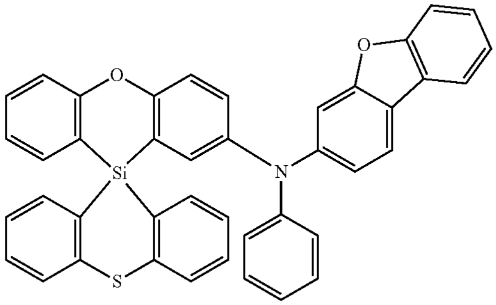
B63
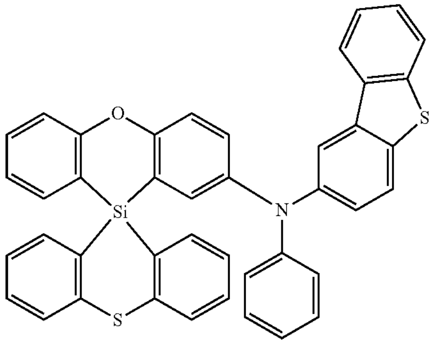
B64
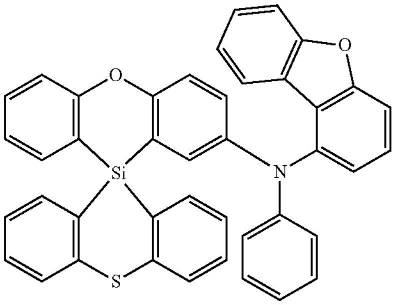
B65
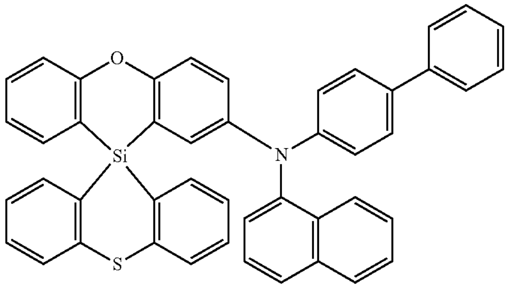

-continued
B66
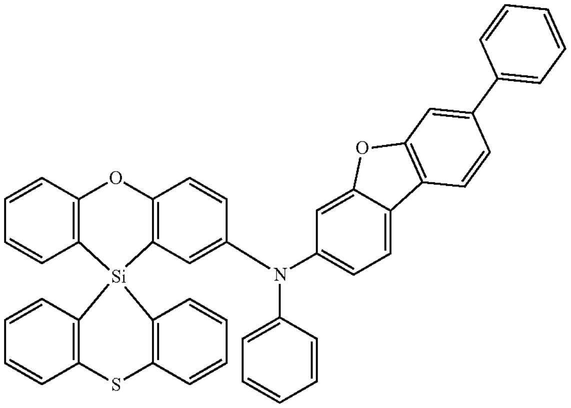
B67
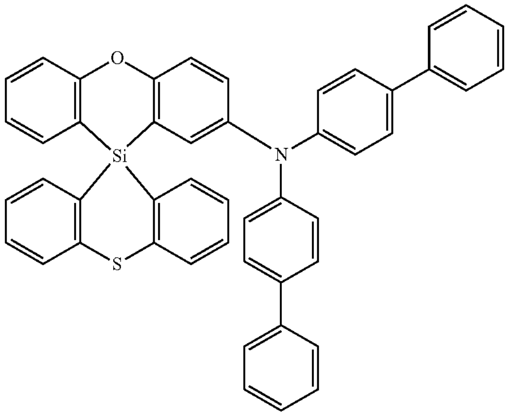
B68
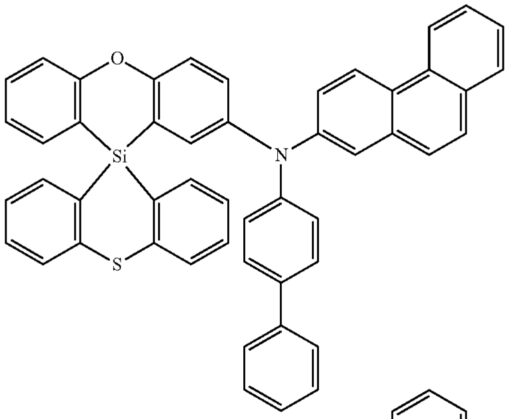
B69
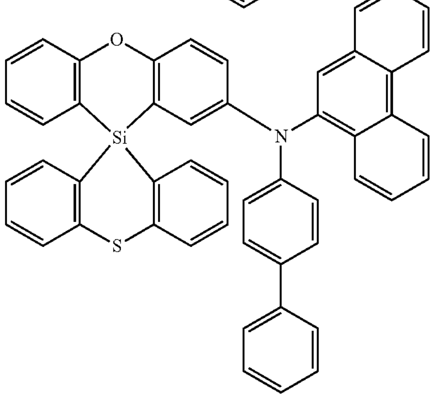
-continued
B70
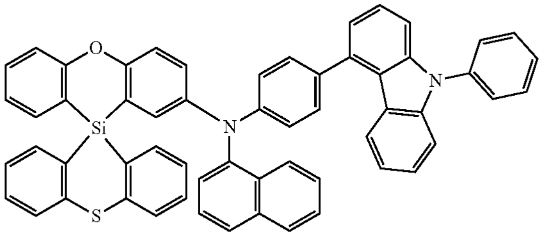
B71
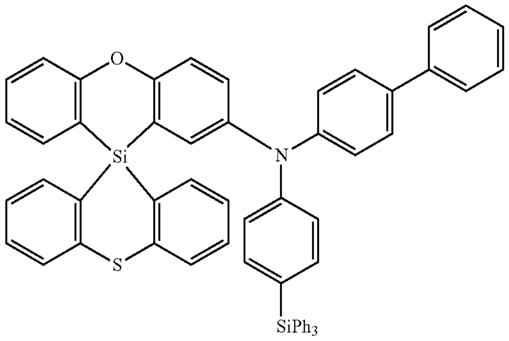
B72
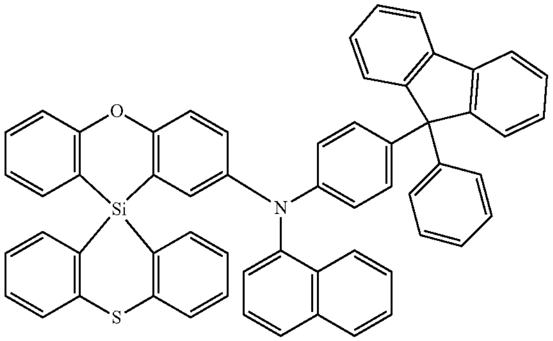
B73
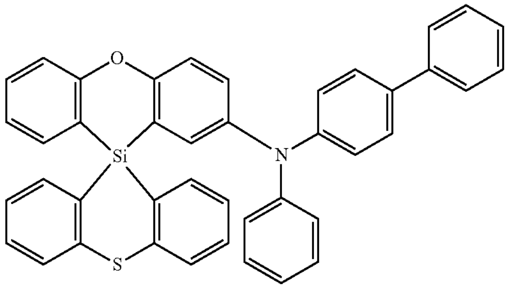
B74
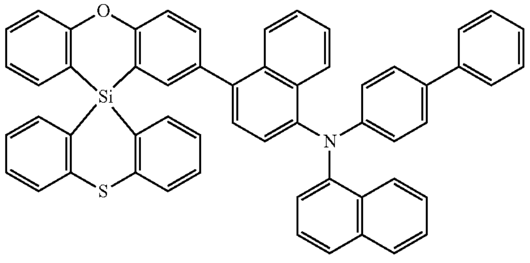

B75
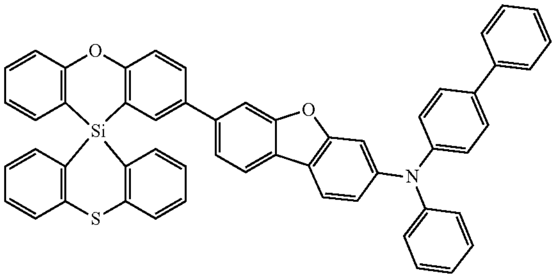
B76
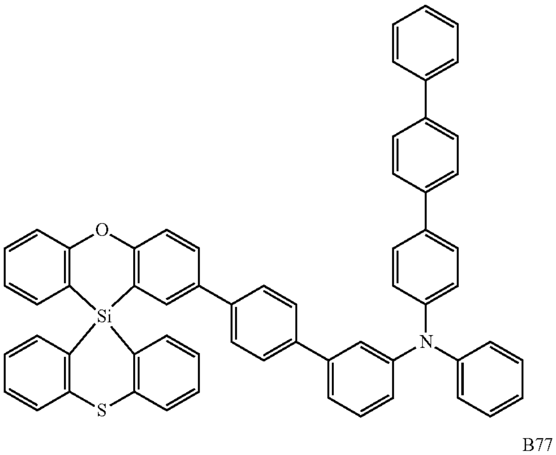
B77
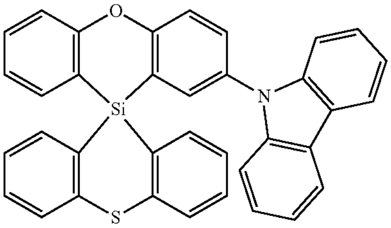
B78
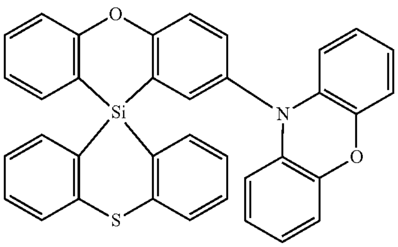
B79
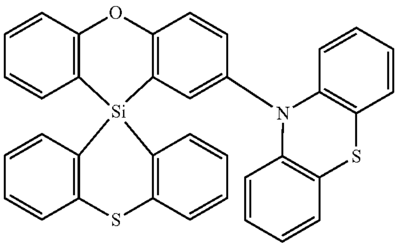
B80
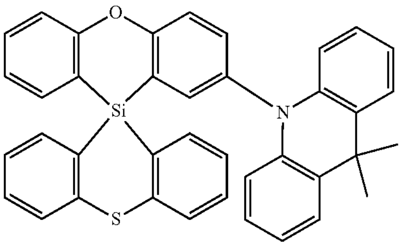
B81
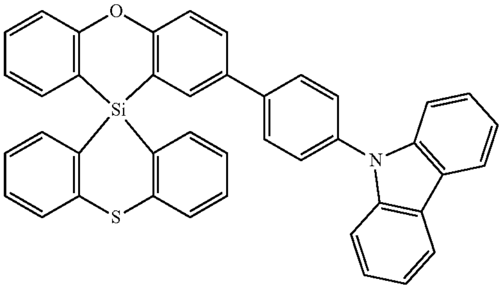
B82
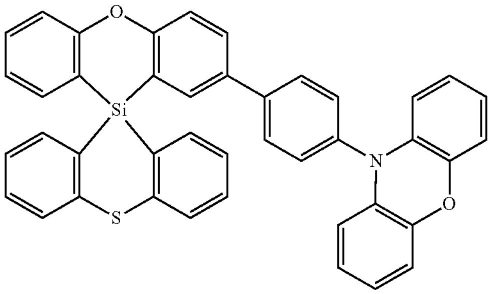
B83
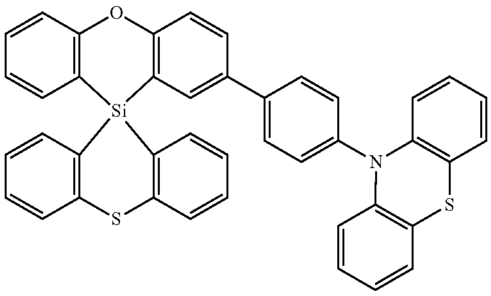
B84
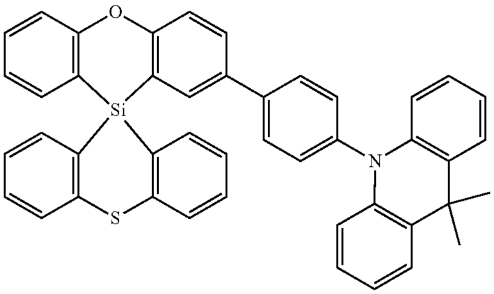

-continued
B85
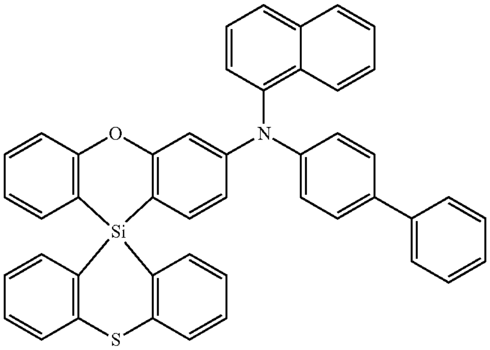
B86
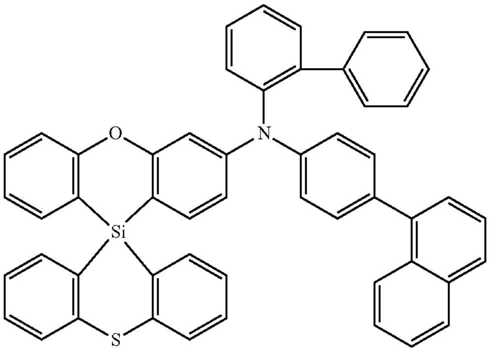
B87
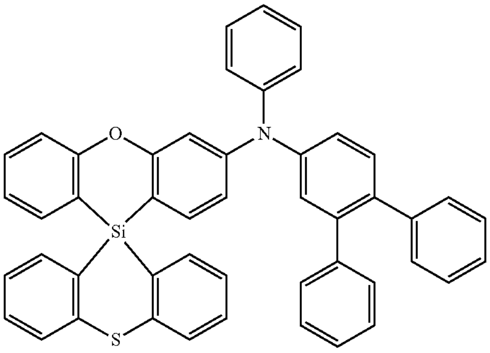
B88
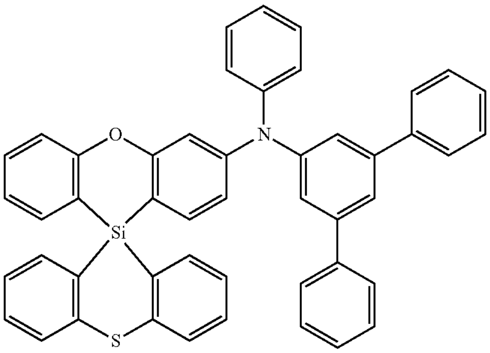
-continued
B89
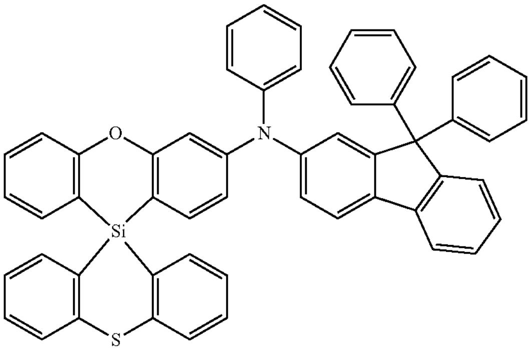
B90
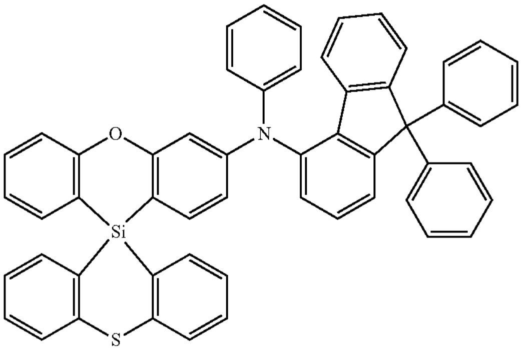
B91
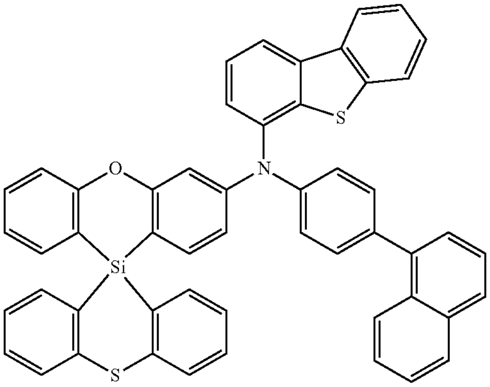
B92
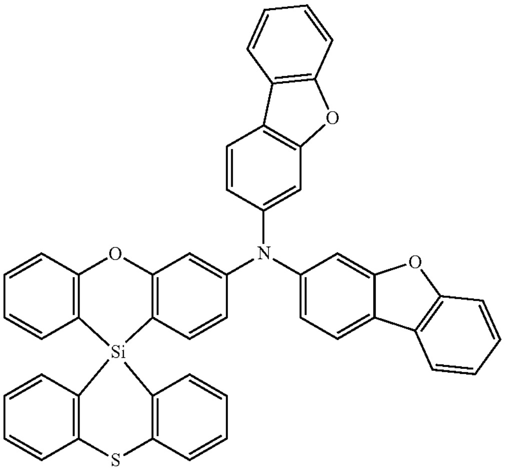

-continued
B93
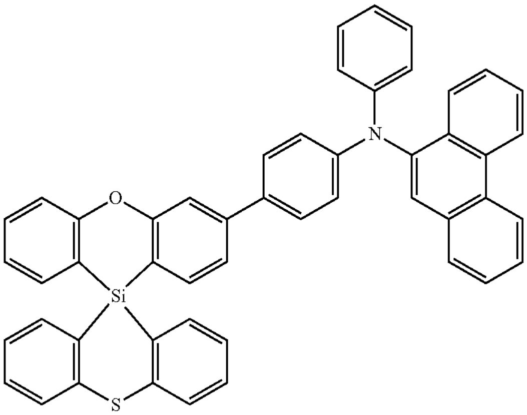
B94
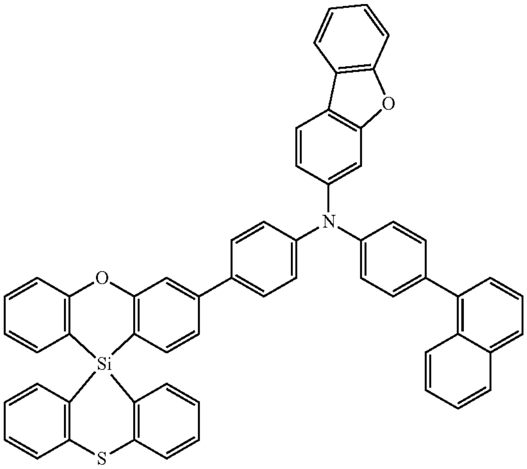
B95
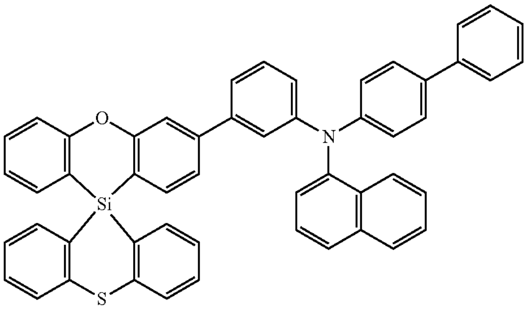
B96
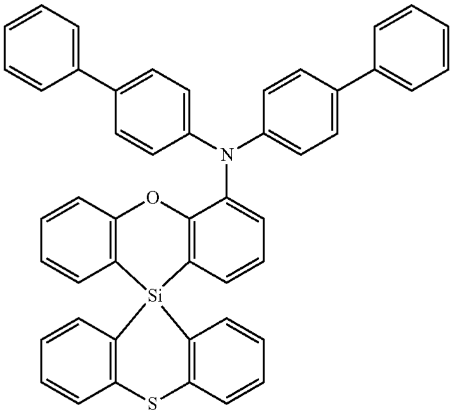
-continued
B97
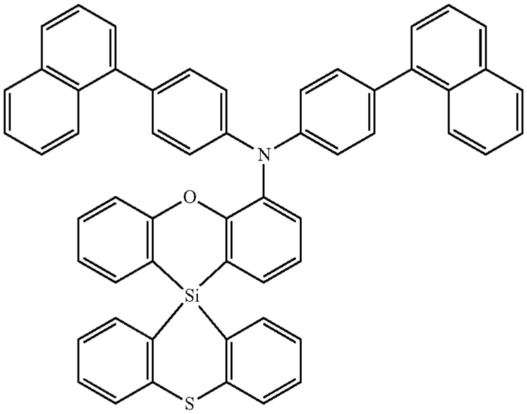
B98
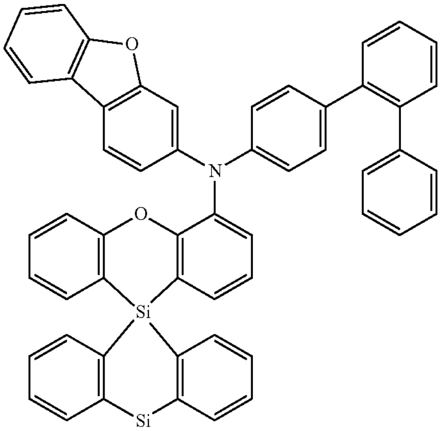
B99
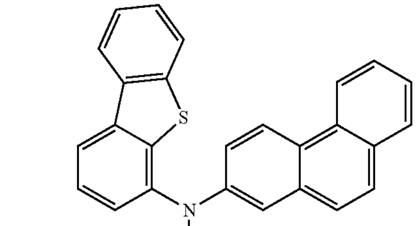
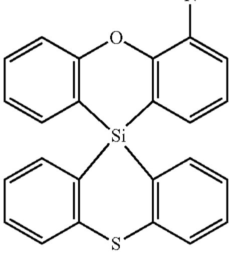

-continued
B100
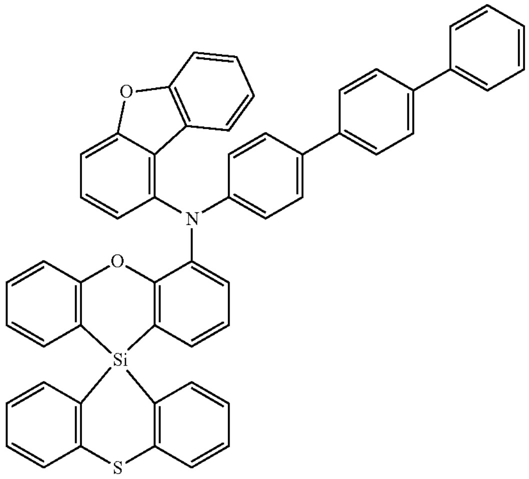
B101
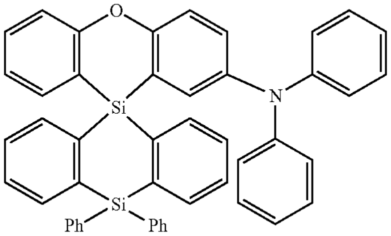
B102
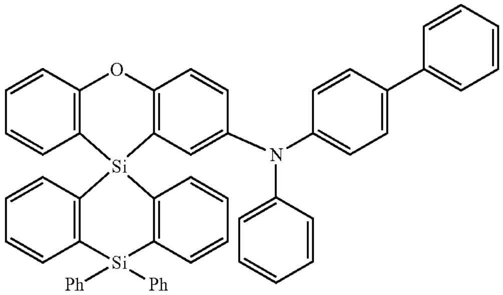
B103
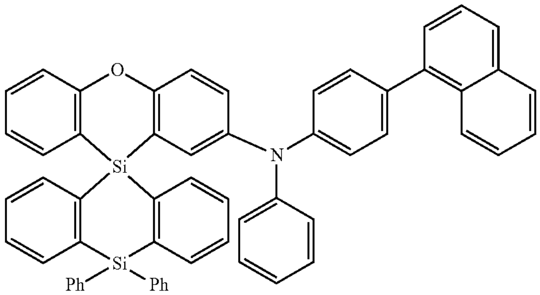
-continued
B104
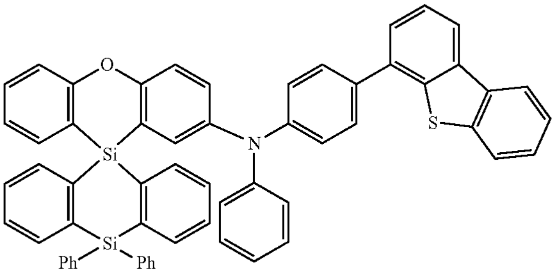
B105
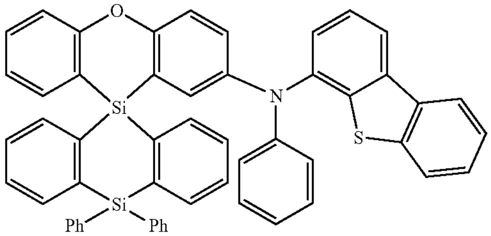
B106
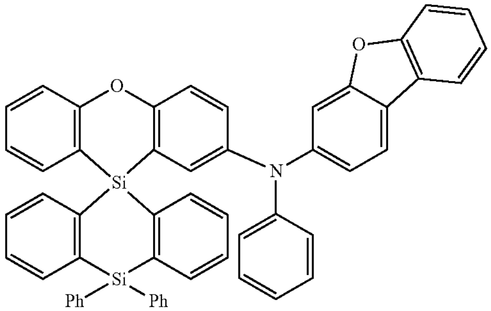
B107
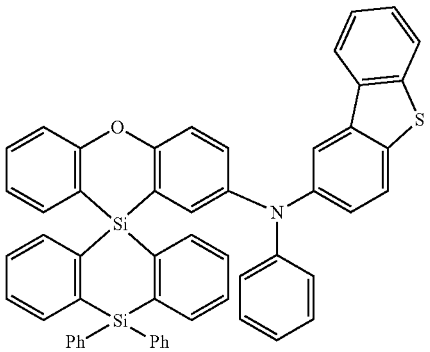
B108
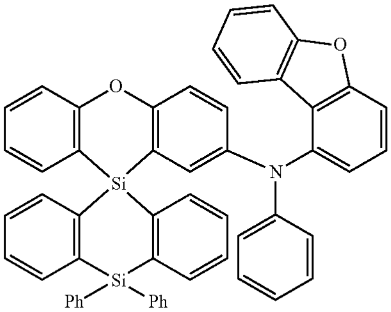

B109
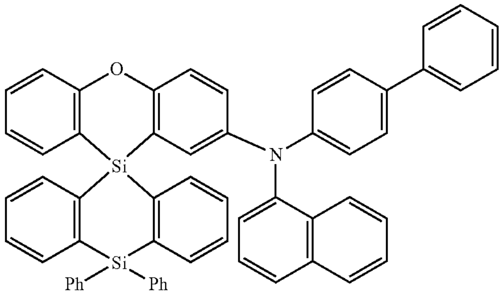
B110
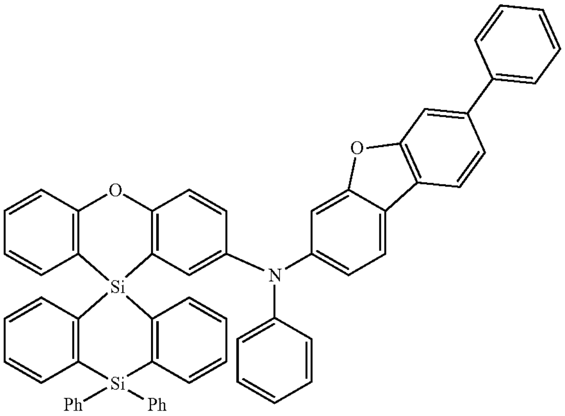
B111
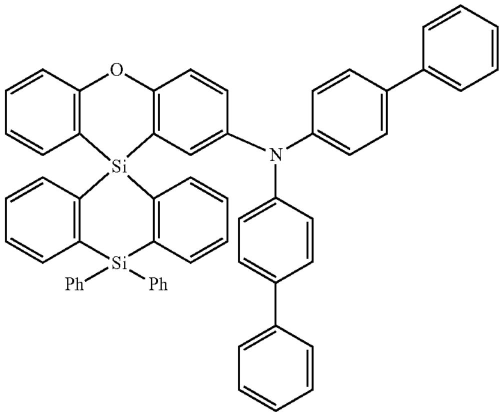
B112
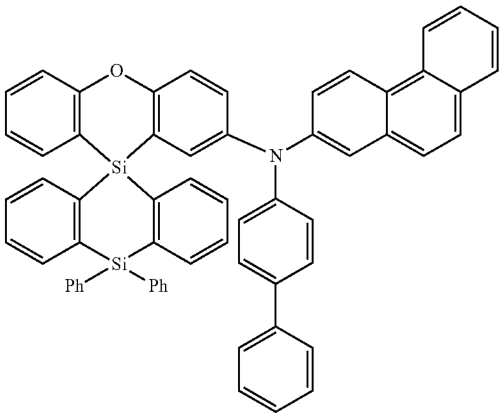
B113
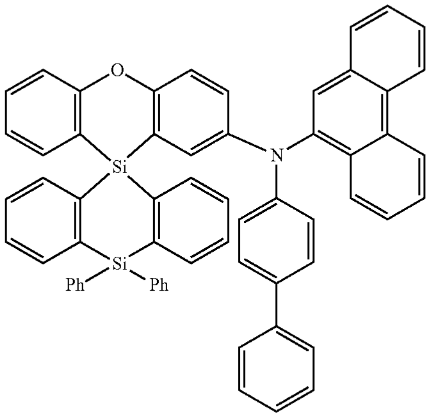
B114
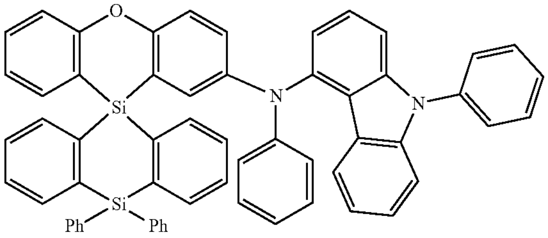
B115
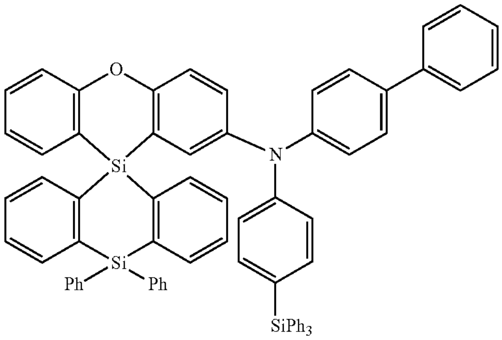
B116
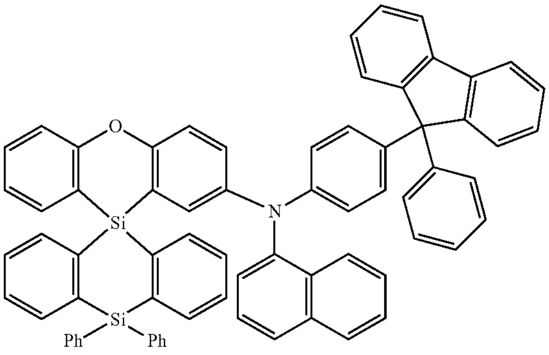

-continued
B117
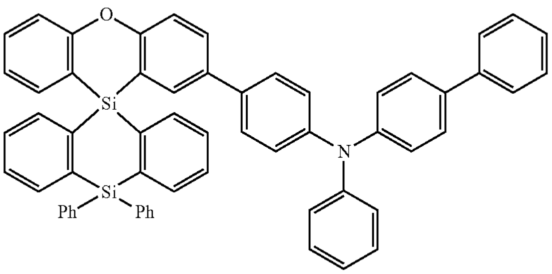
B118
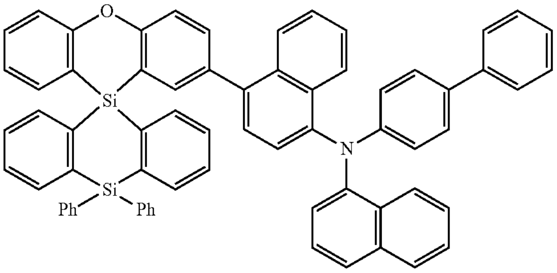
B119
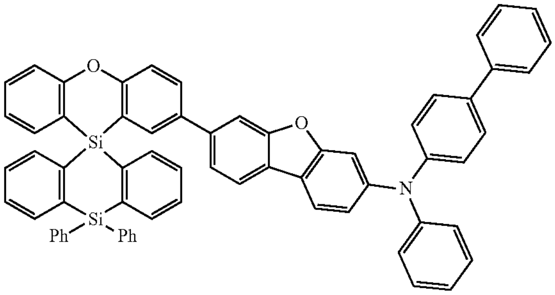
B120
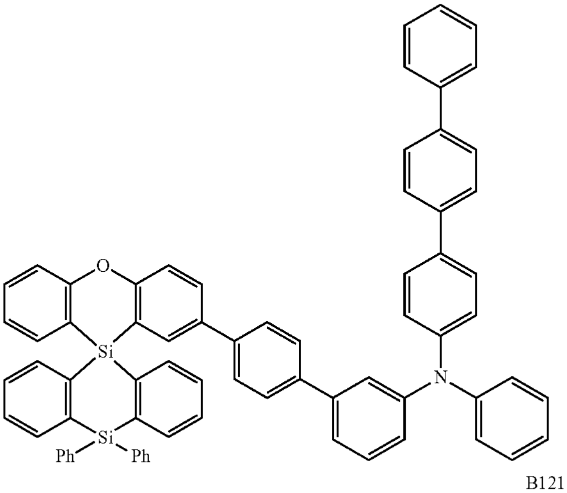
B121
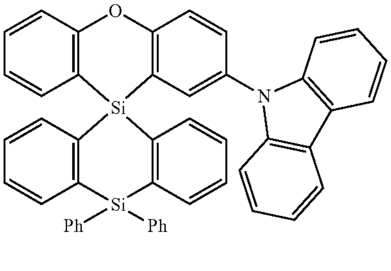
-continued
B122
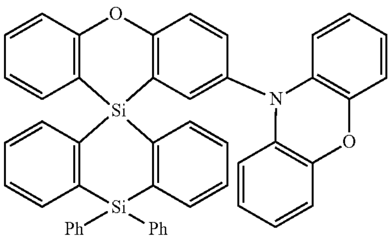
B123
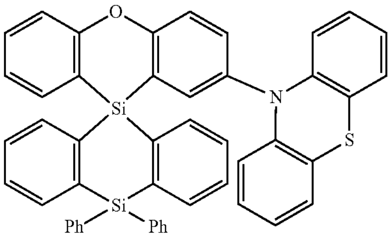
B124
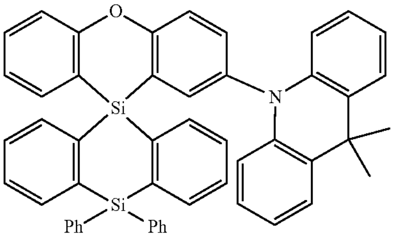
B125
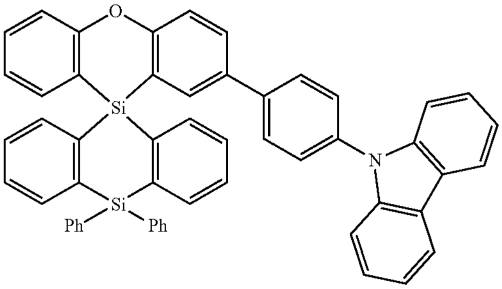
B126
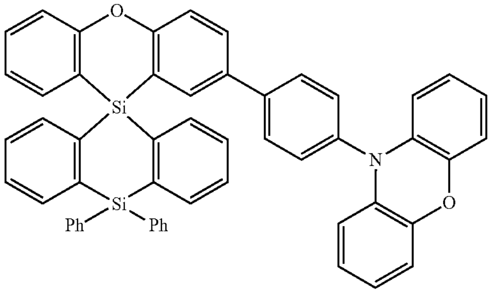

B127
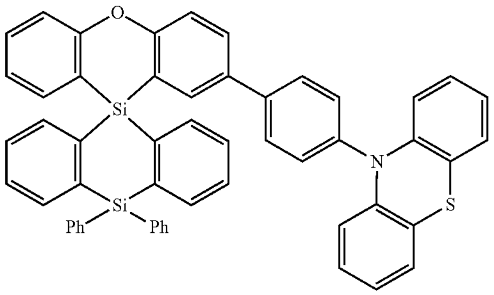
B128
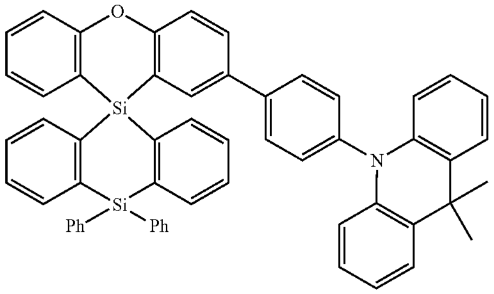
B129
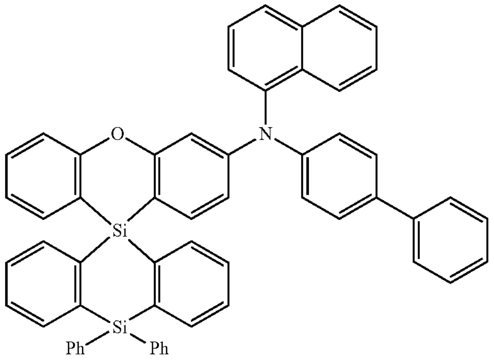
B130
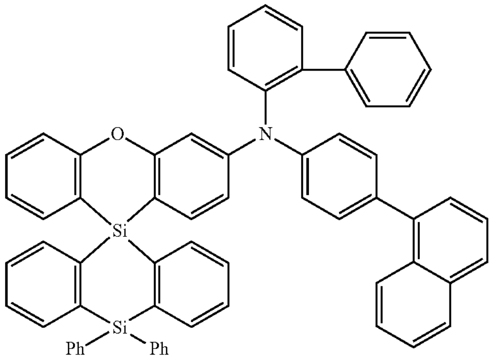
B131
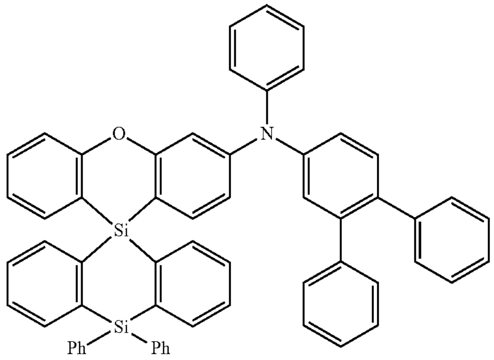
B132
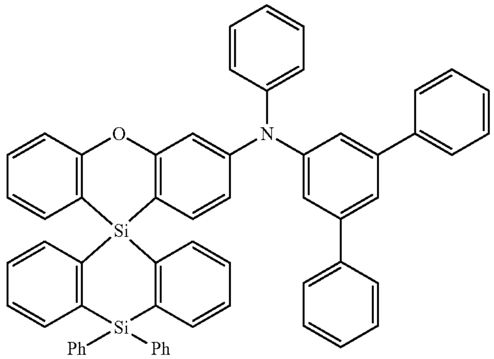
B133
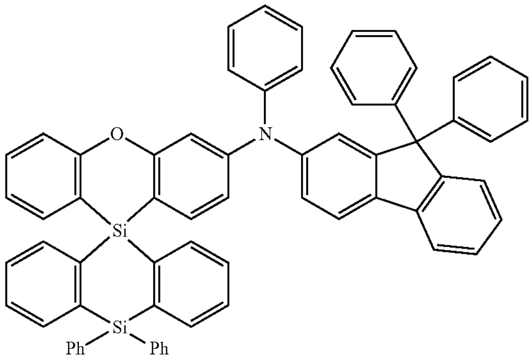
B134
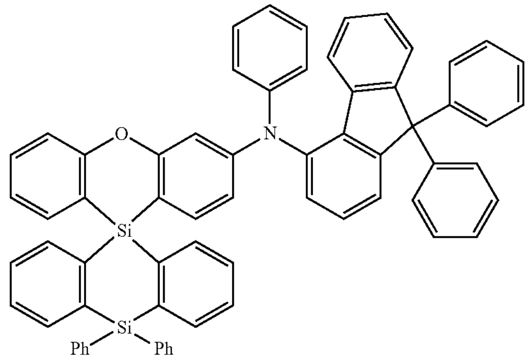

-continued
B135
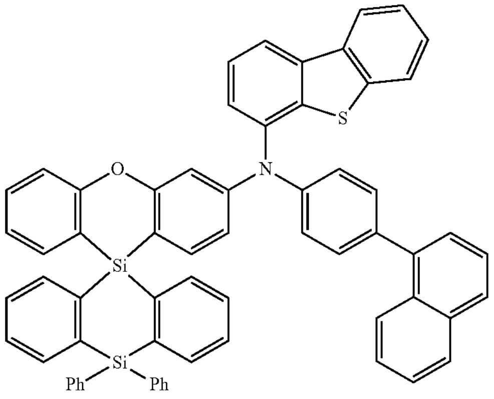
B136
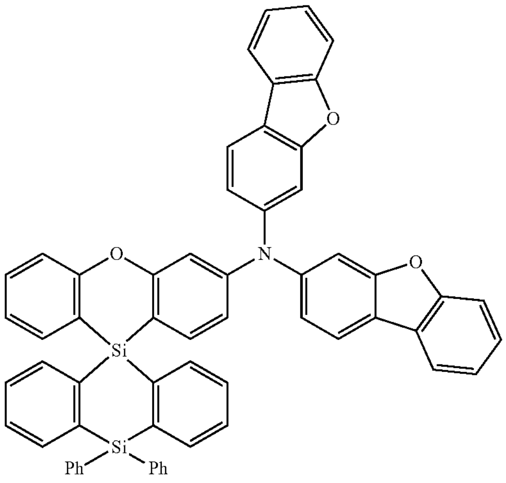
B137
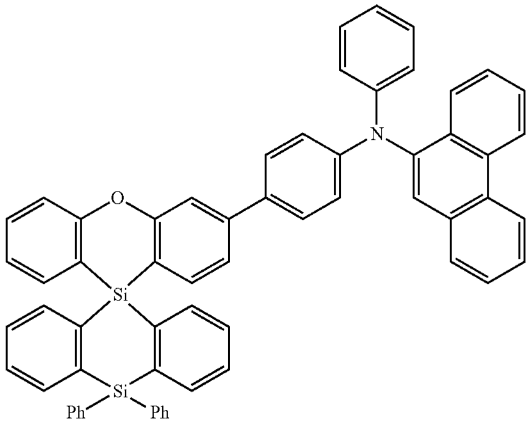
-continued
B138
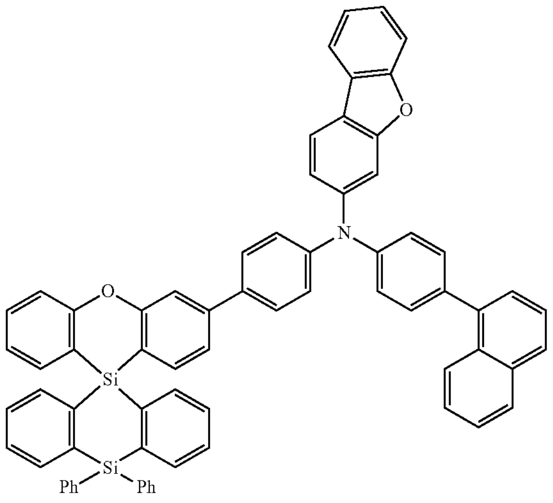
B139
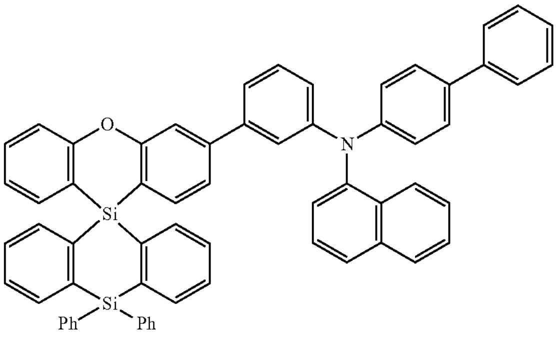
B140
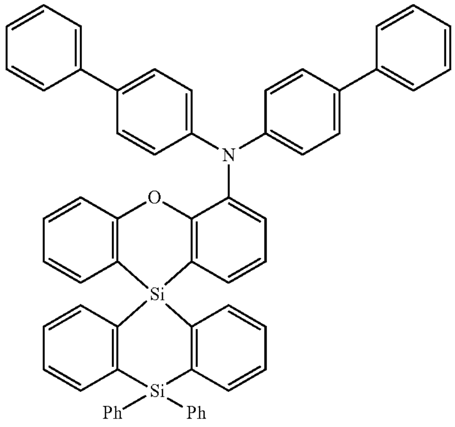

-continued
B141
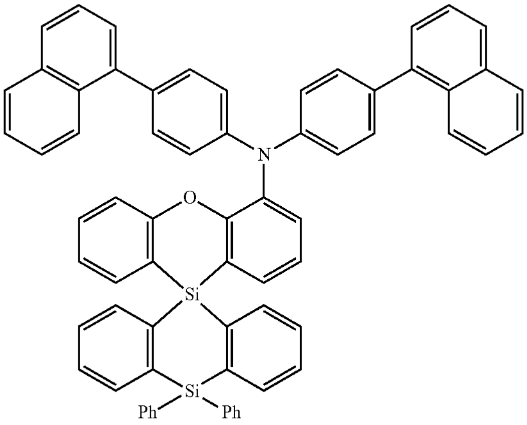
B142
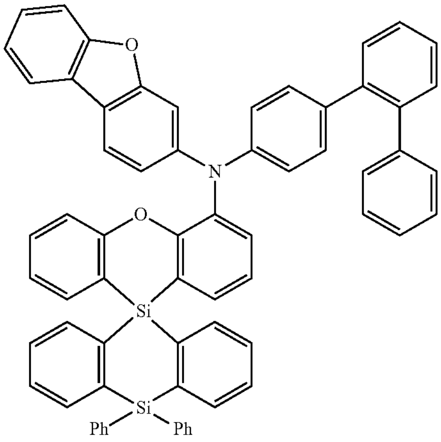
B143
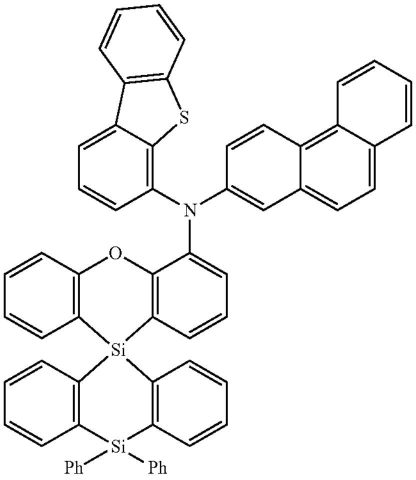
-continued
B144
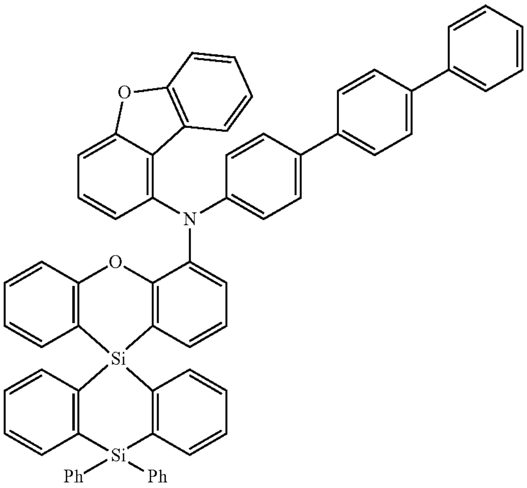
B145
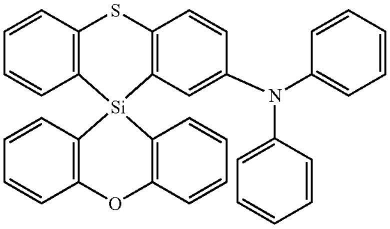
B146
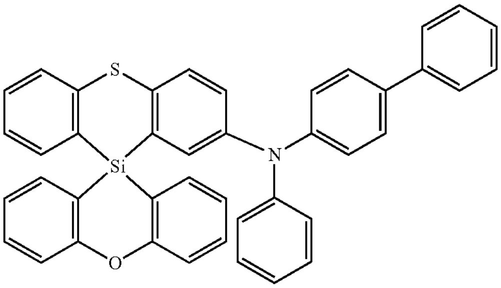
B147
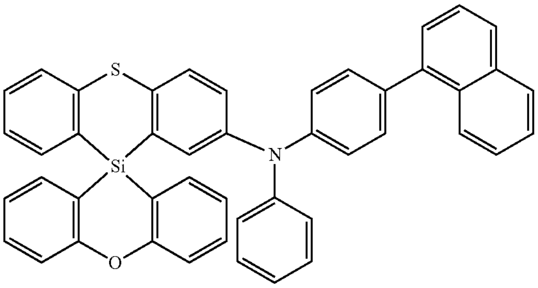

-continued
B148
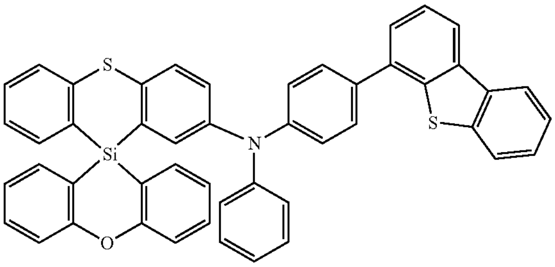
B149
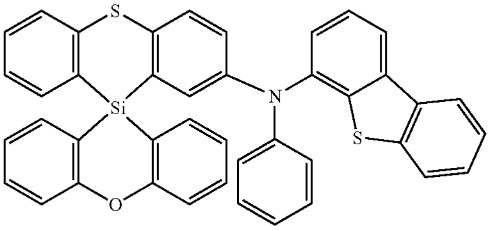
B150
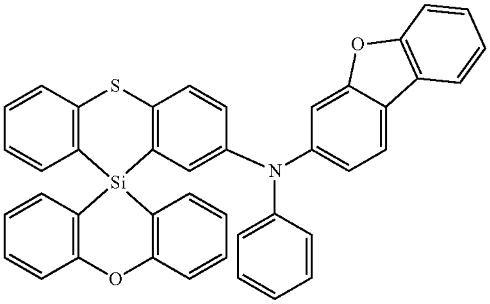
B151
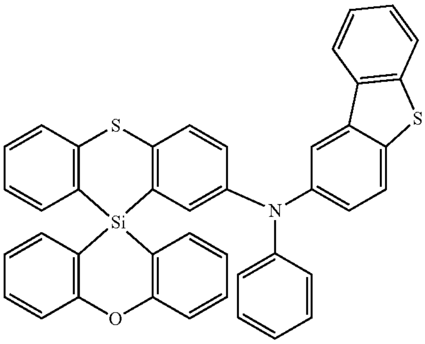
B152
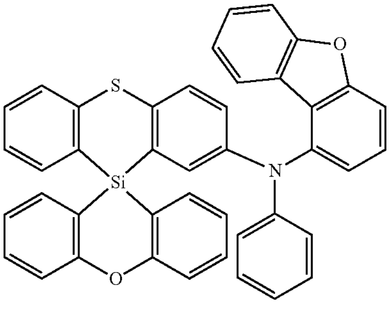
-continued
B153
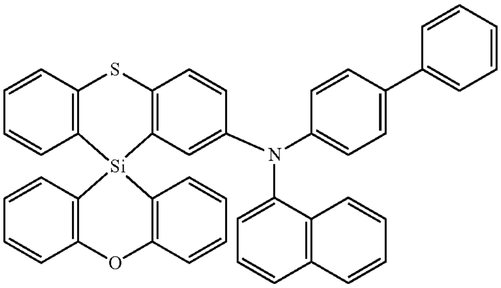
B154
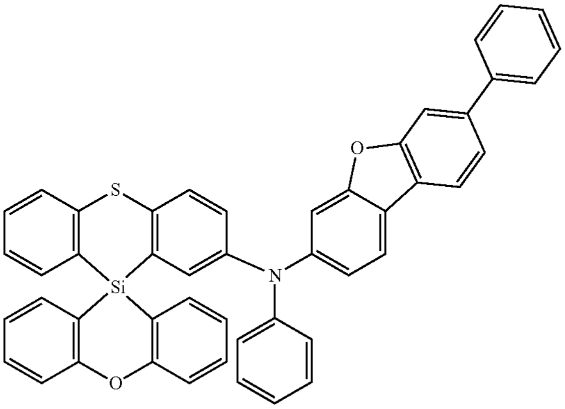
B155
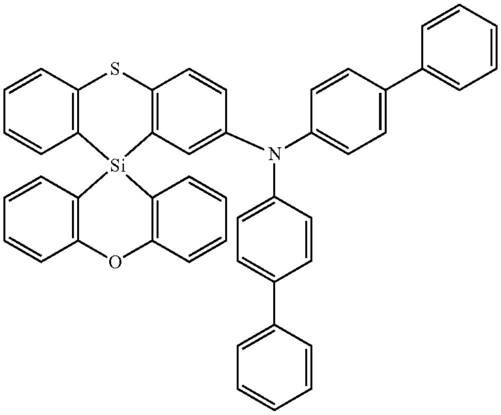
B156
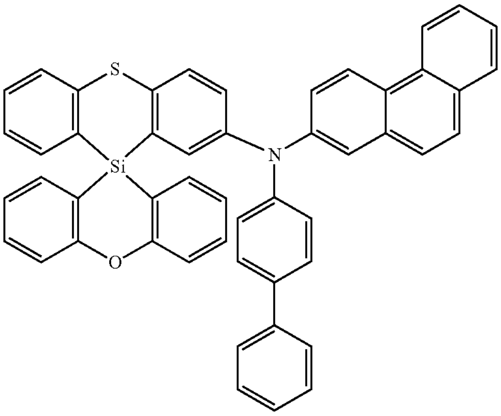

-continued
B157
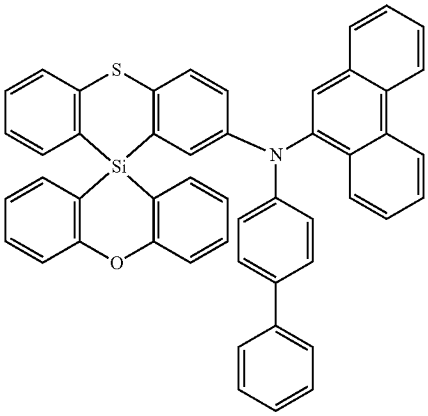
B158
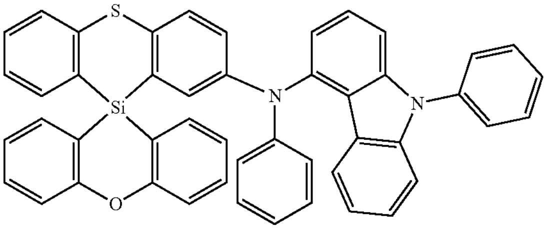
B159
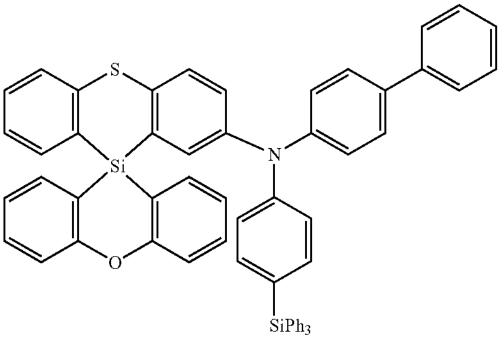
B160
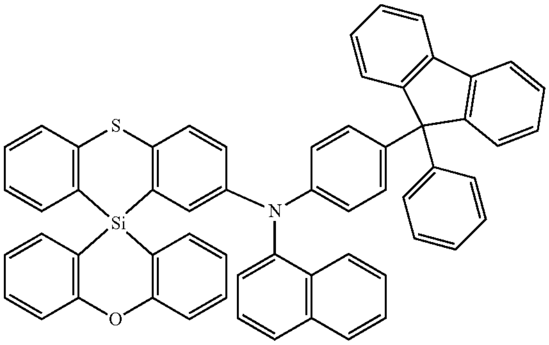
-continued
B161
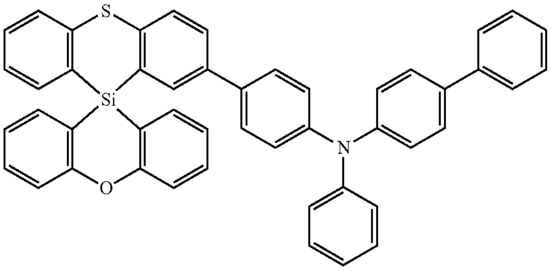
B162
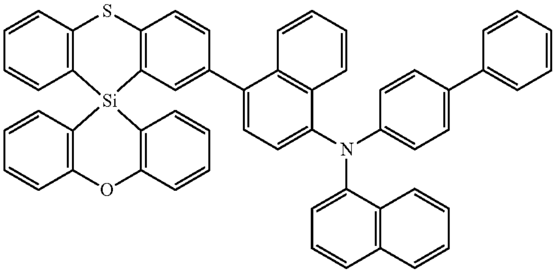
B163
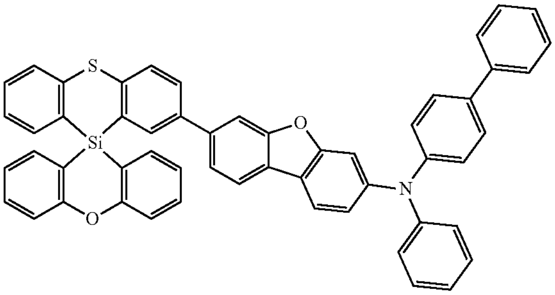
B164
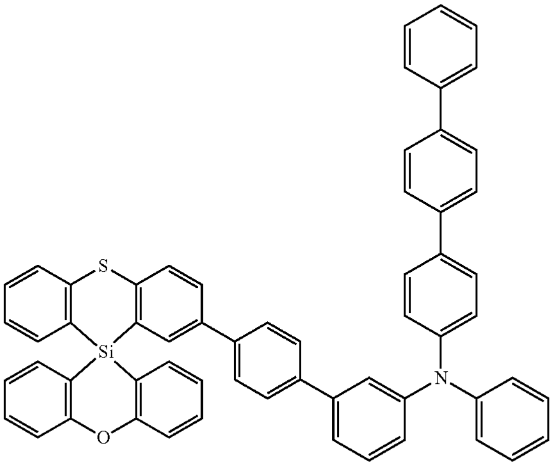
B165
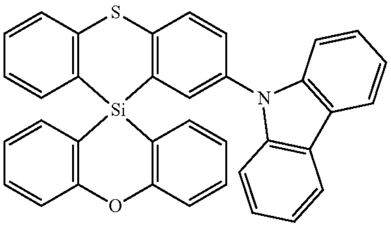

B166
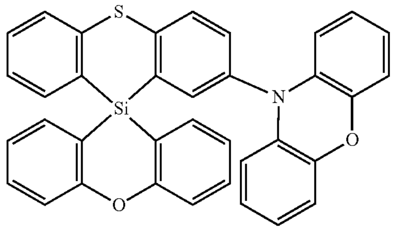
B167
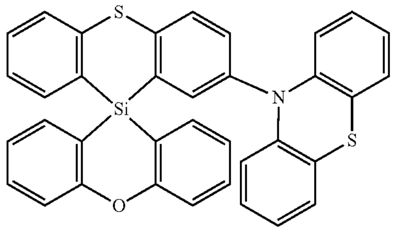
B168
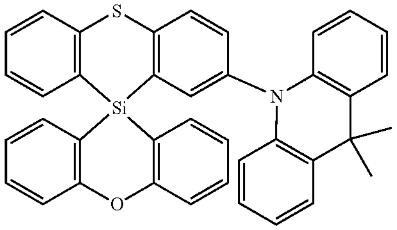
B169
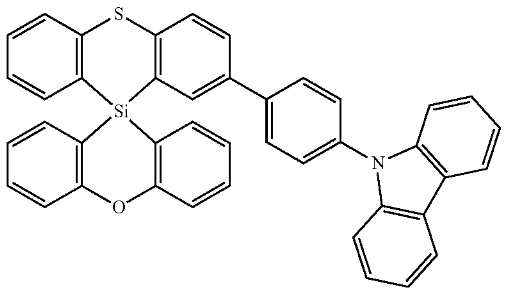
B170
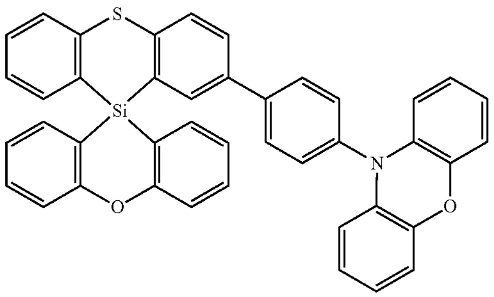
B171
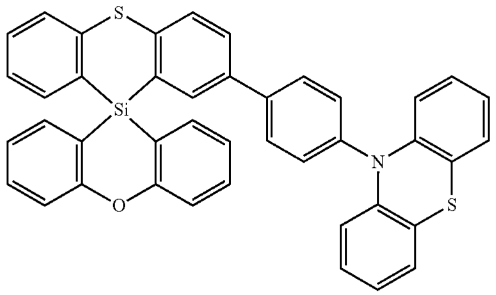
B172
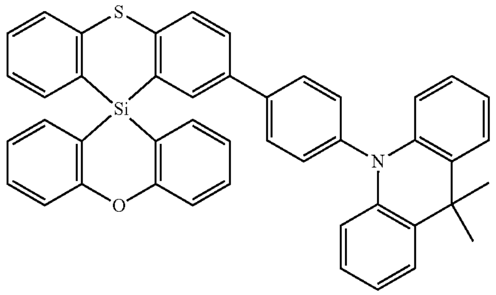
B173
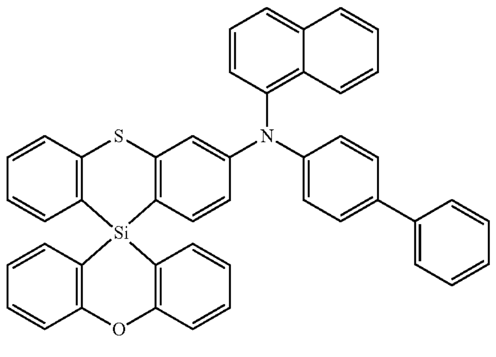
B174
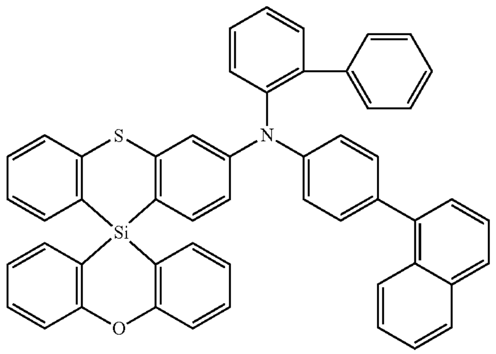

-continued
B175
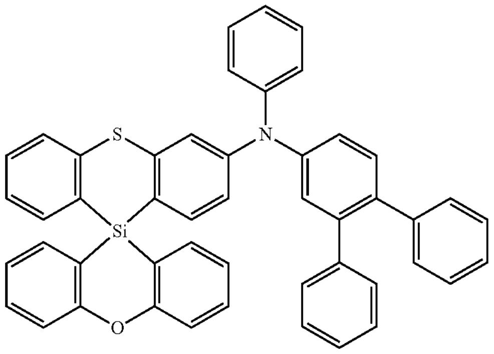
B176
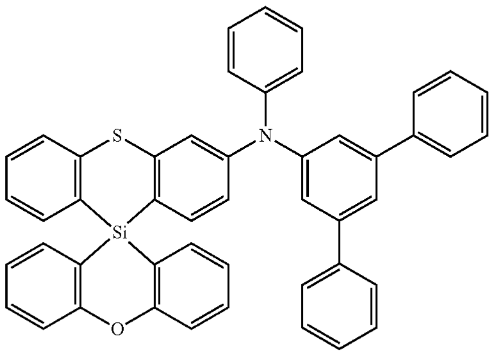
B177
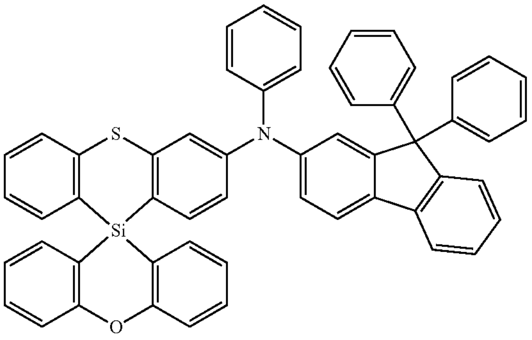
B178
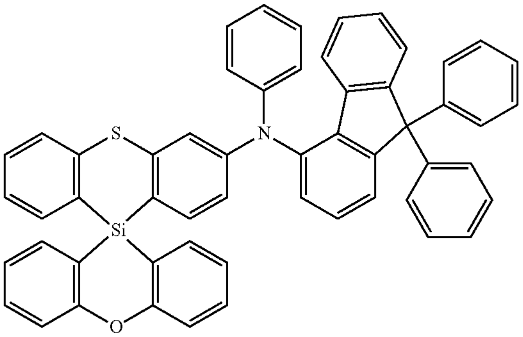
-continued
B179
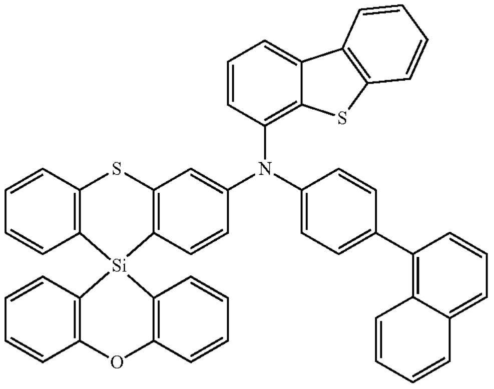
B180
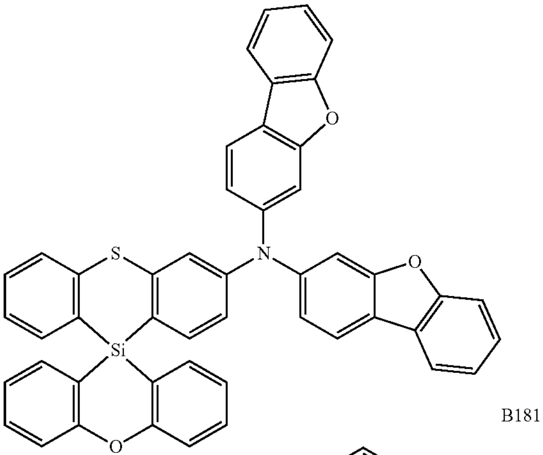
B181
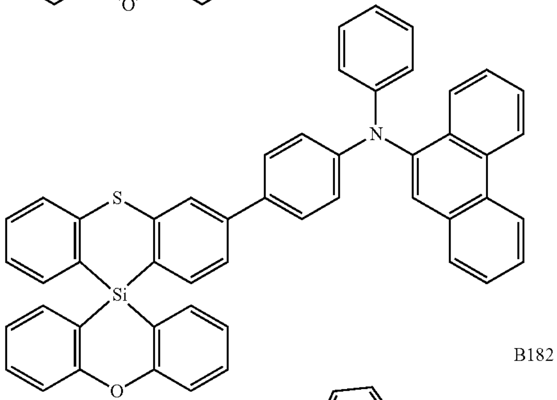
B182
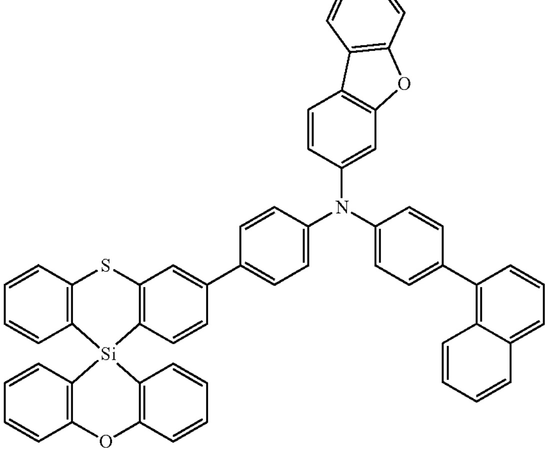

-continued
B183
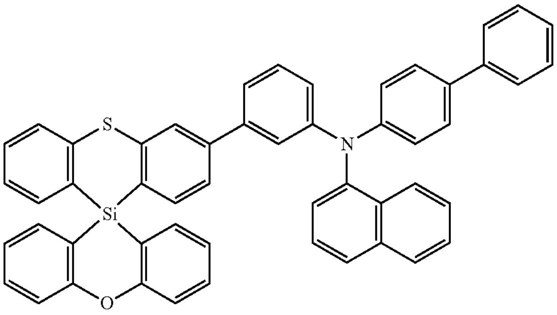
B184
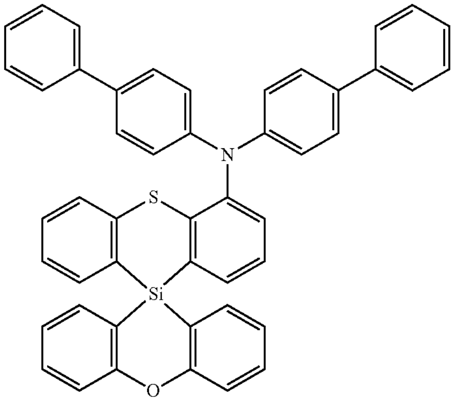
B185
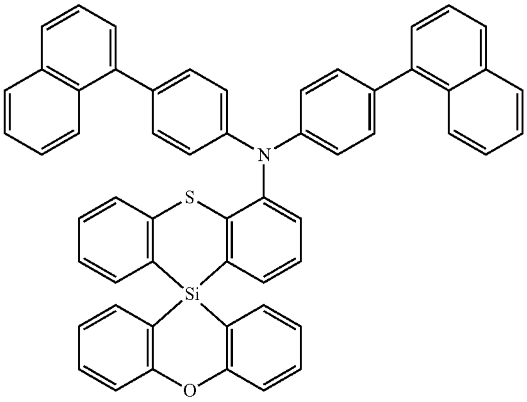
B186
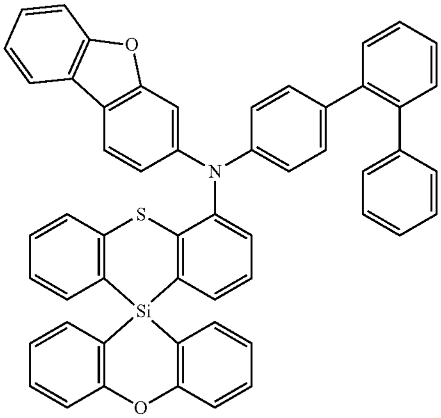
-continued
B187
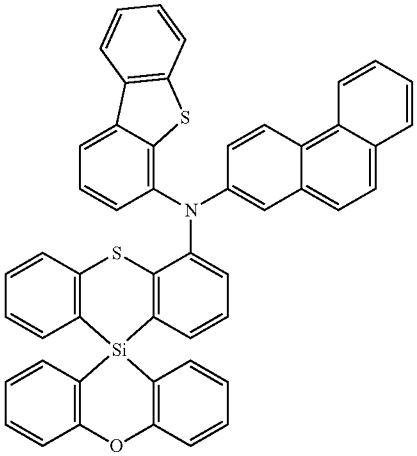
B188
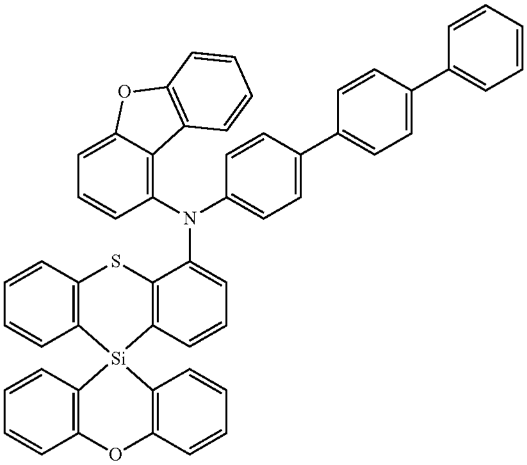
B189
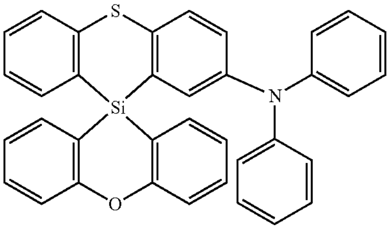
B190
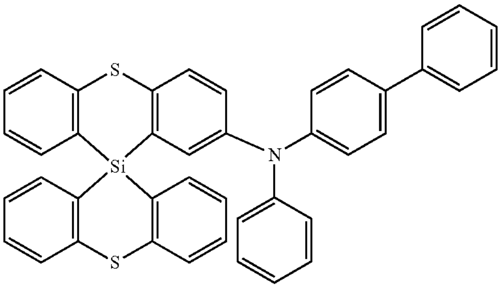

-continued
B191
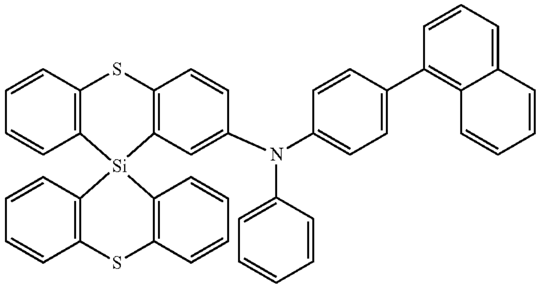
B192
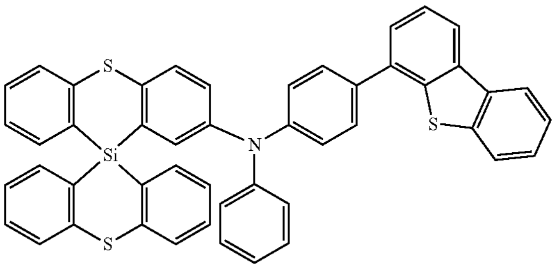
B193
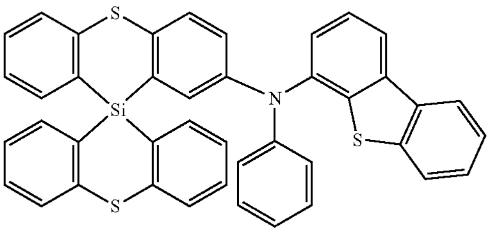
B194
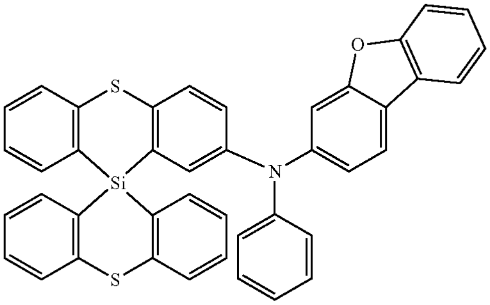
B195
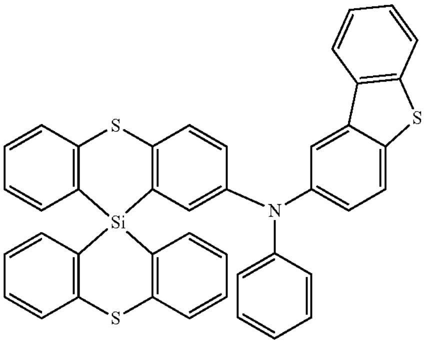
-continued
B196
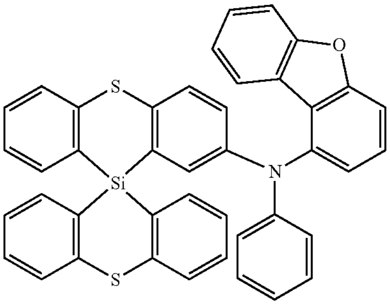
B197
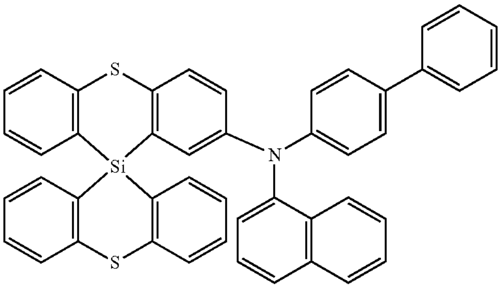
B198
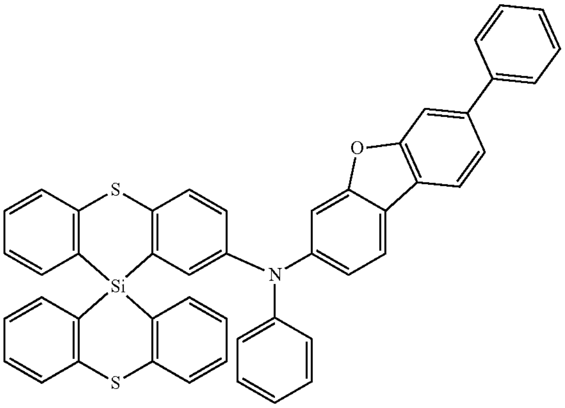
B199
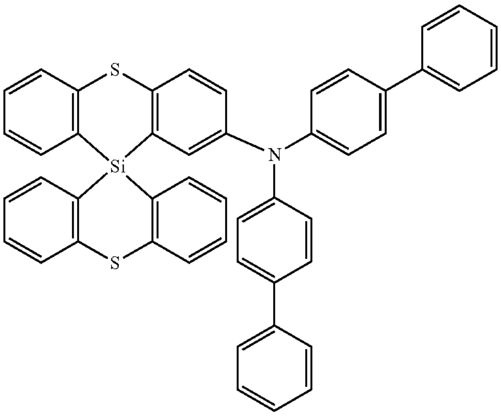

-continued
B200
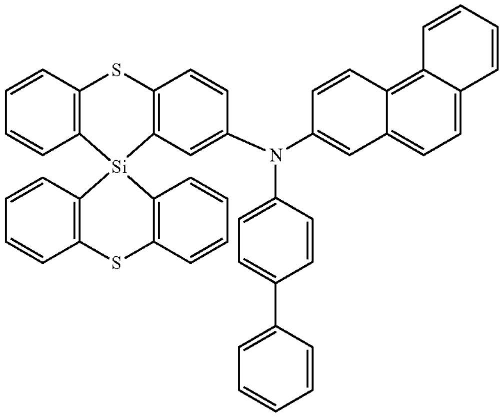
B201
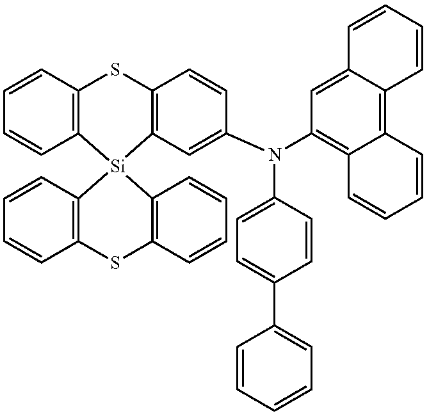
B202
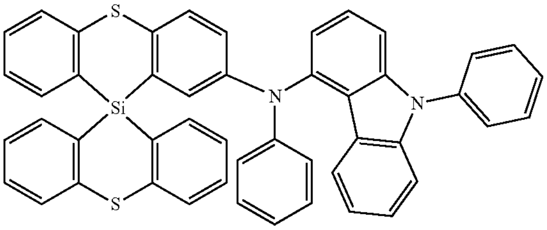
B203
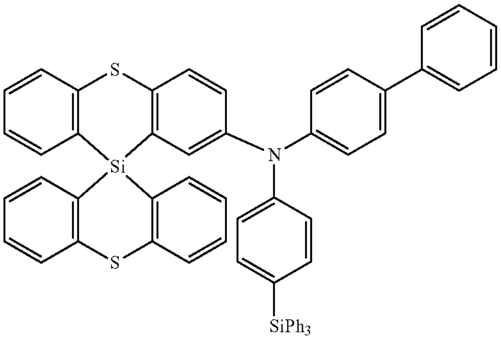
-continued
B204
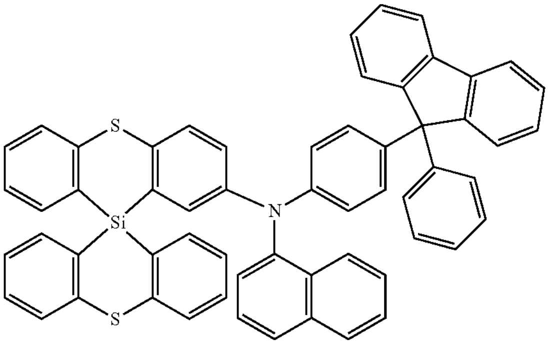
B205
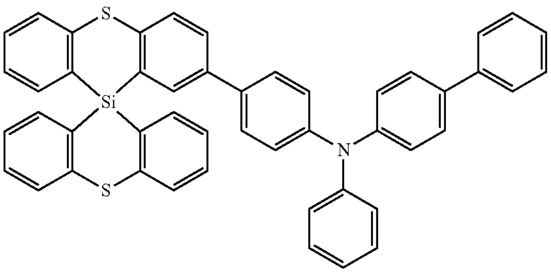
B206
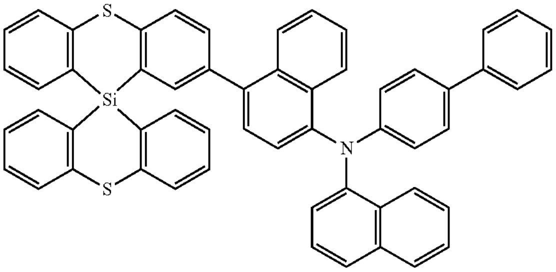
B207
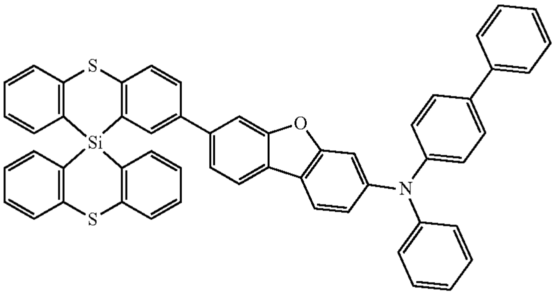

-continued
B208
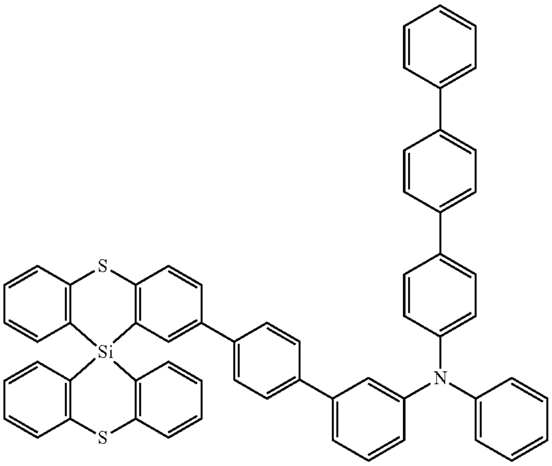
B209
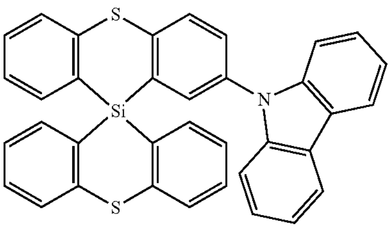
B210
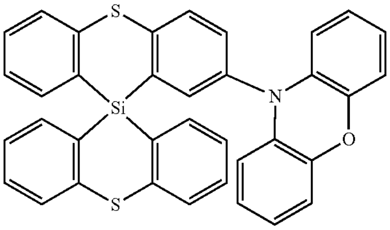
B211
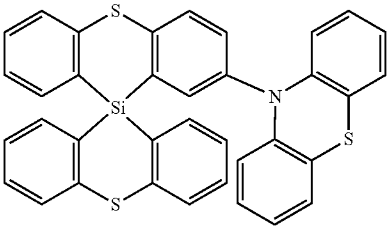
B212
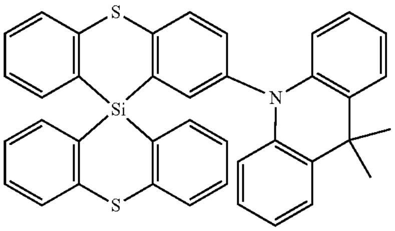
-continued
B213
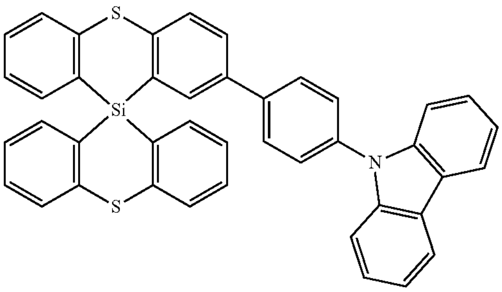
B214
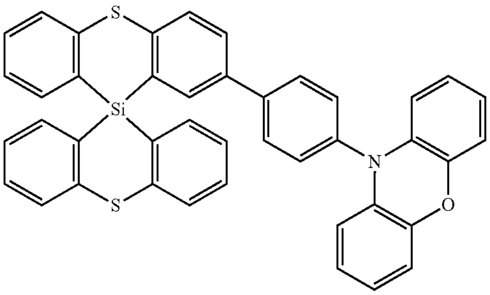
B215
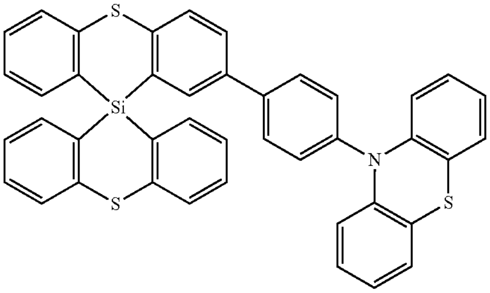
B216
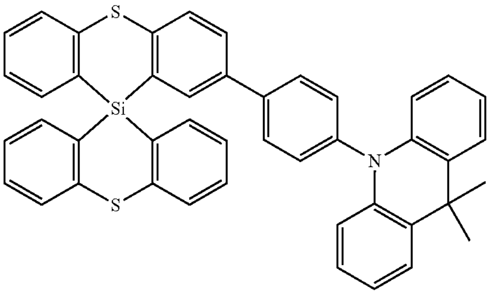
B217
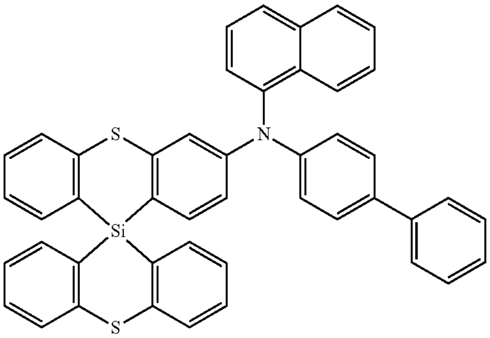

-continued
B218
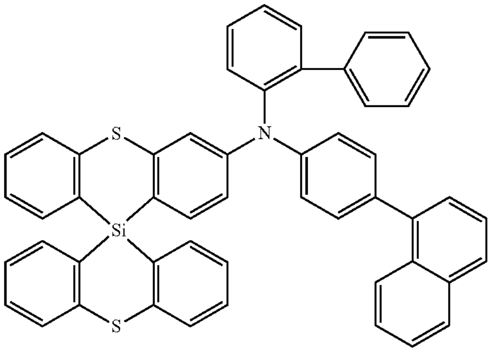
B219
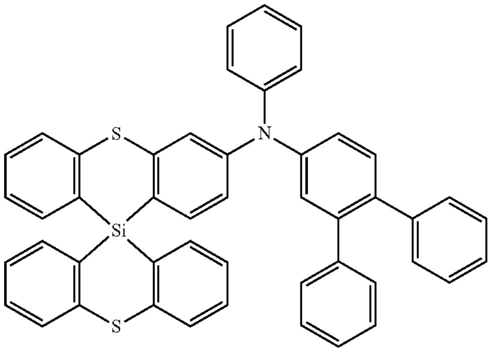
B220
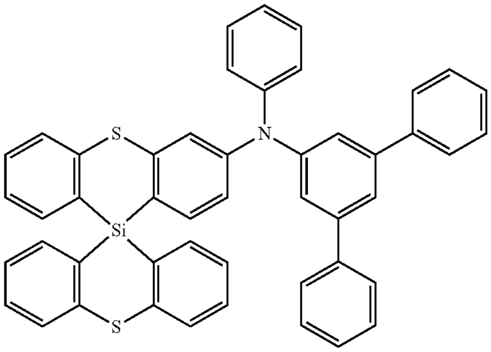
B221
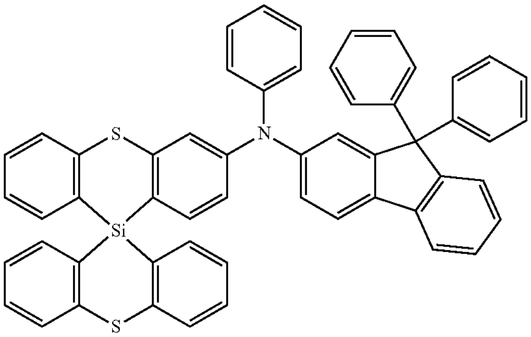
-continued
B222
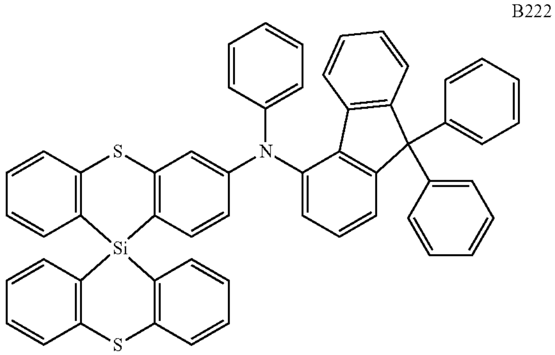
B223
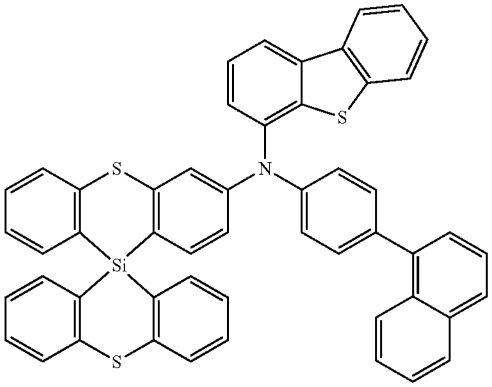
B224
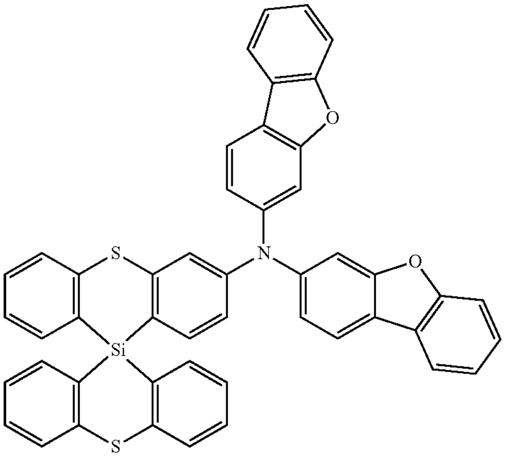
B225
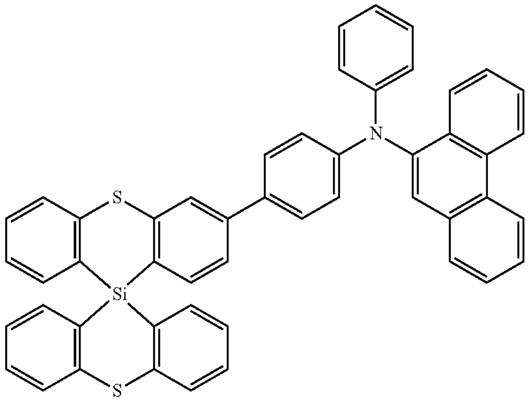

-continued
B226
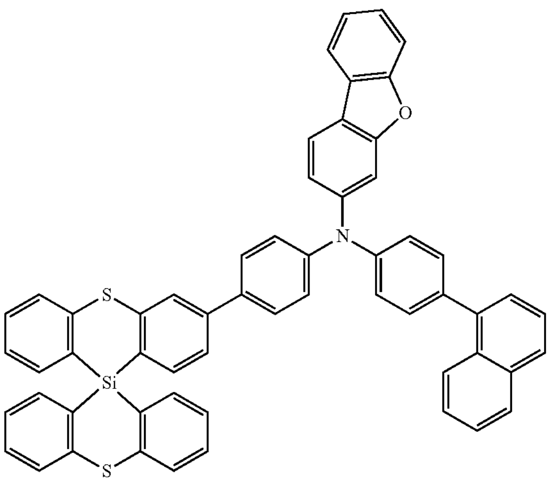
B227
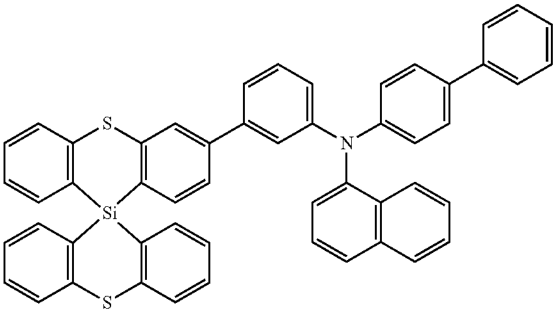
B228
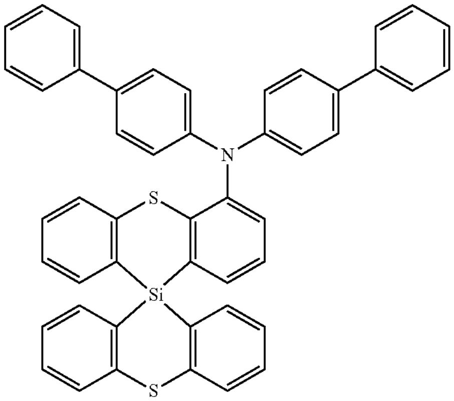
B229
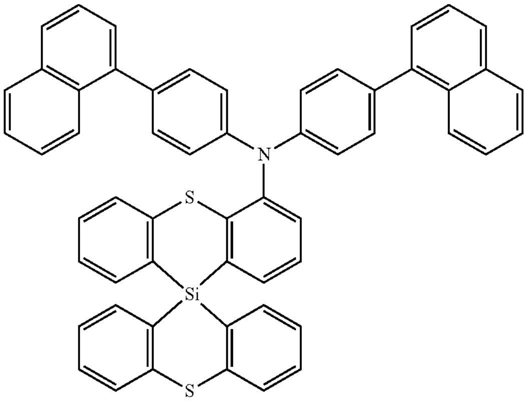
-continued
B230
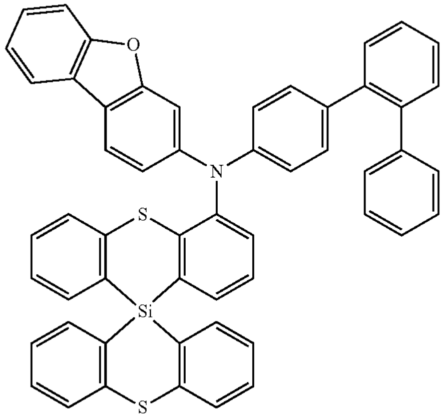
B231
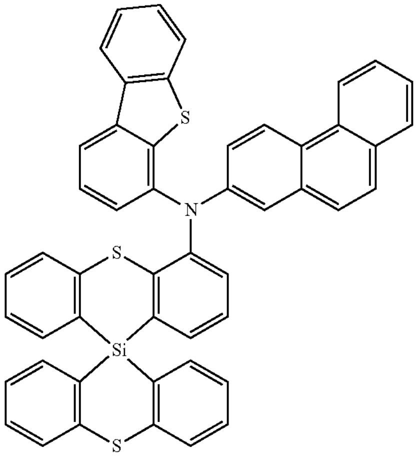
B232
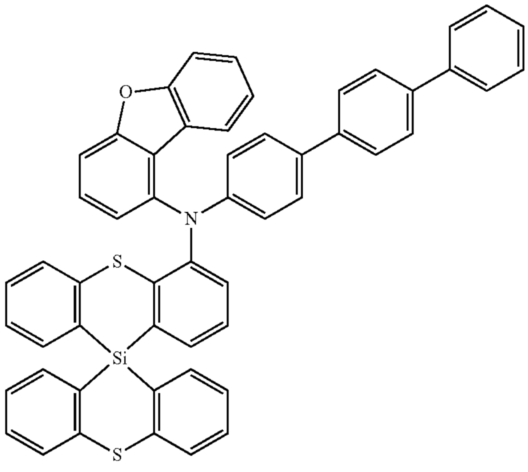
B233
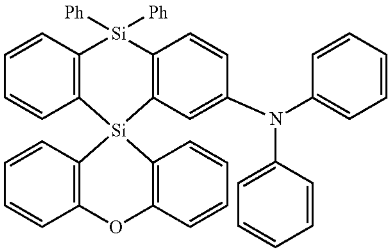

-continued
B234
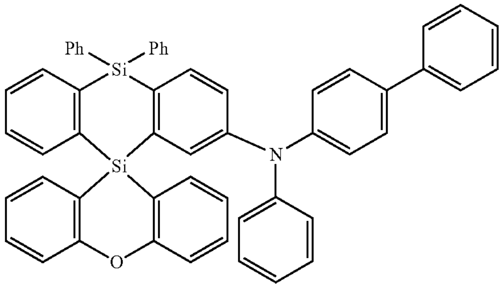
B235
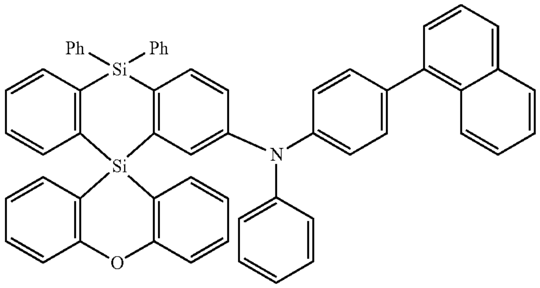
B236
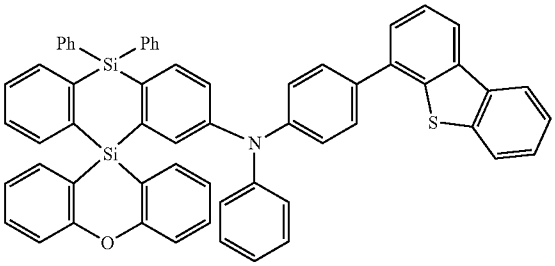
B237
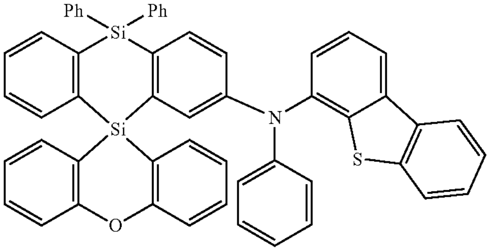
B238
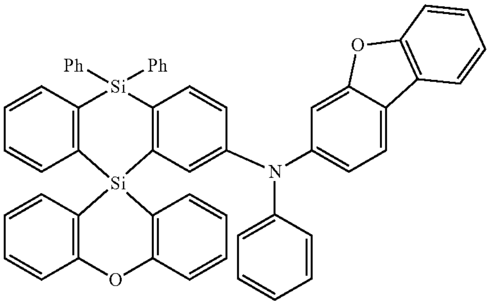
-continued
B239
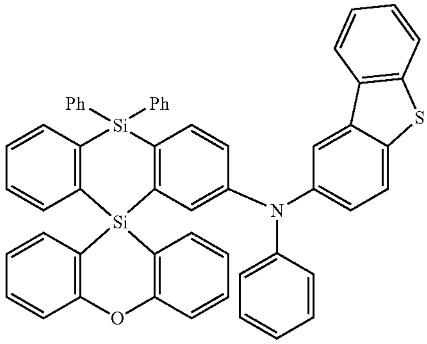
B240
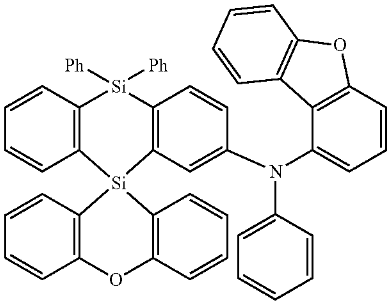
B241
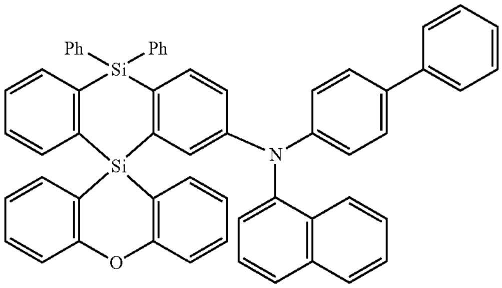
B242
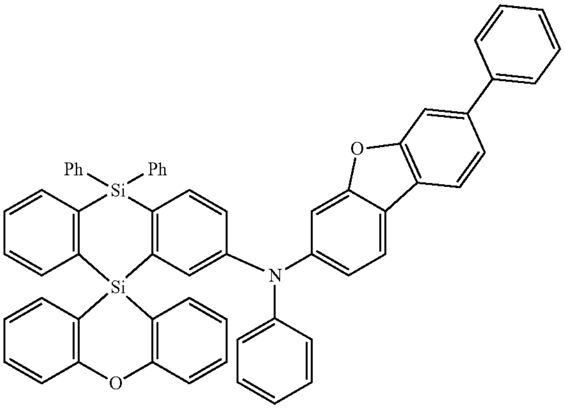

-continued
B243
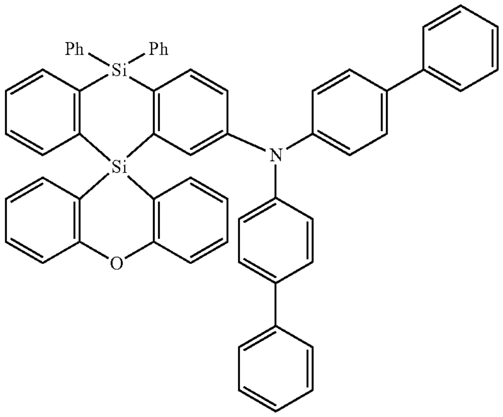
B244
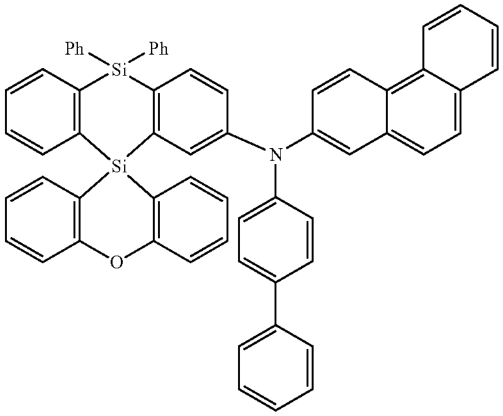
B245
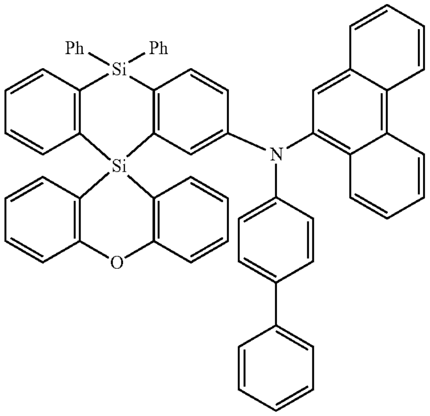
B246
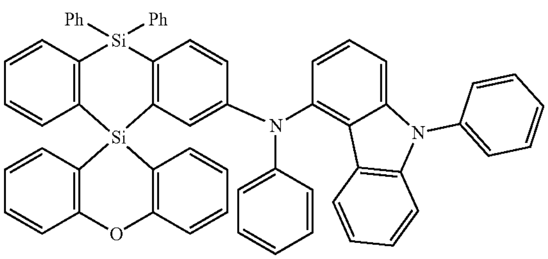
-continued
B247
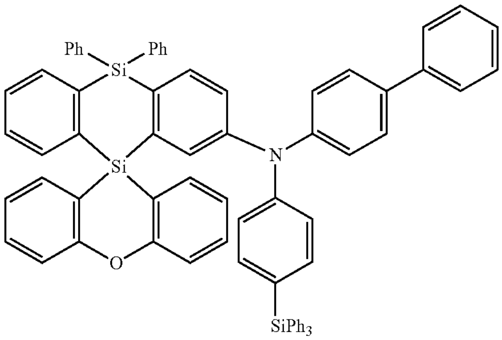
B248
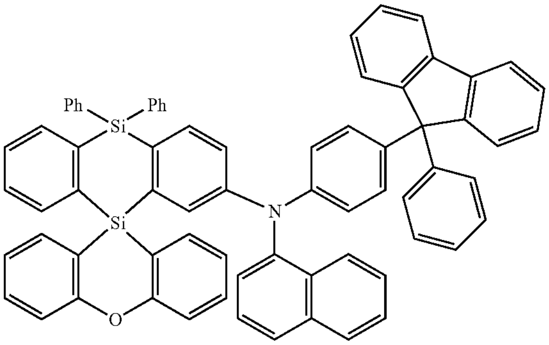
B249
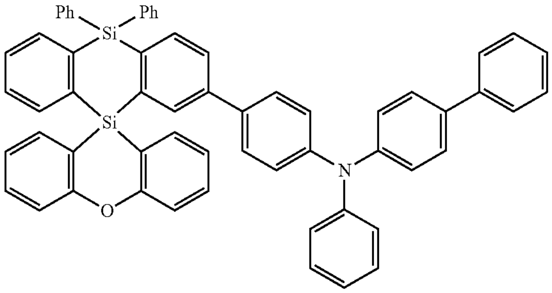
B250
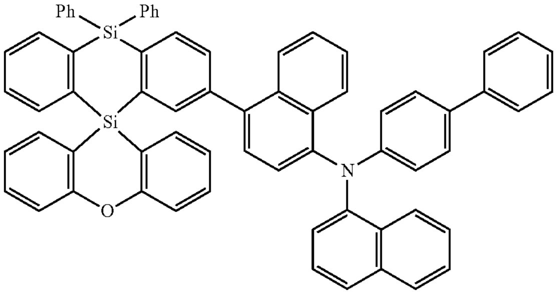

-continued
B251
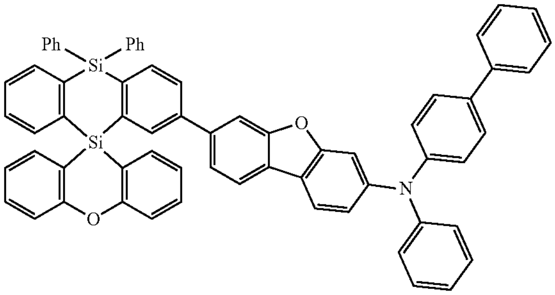
B252
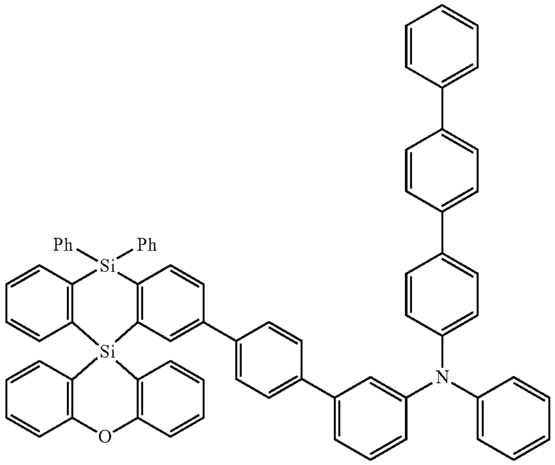
B253
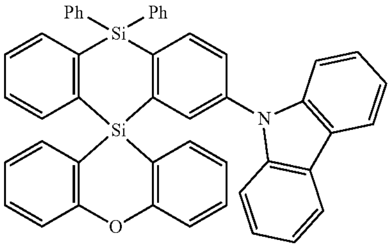
B254
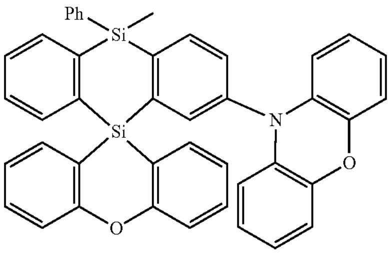
B255
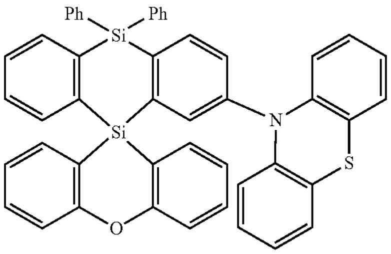
-continued
B256
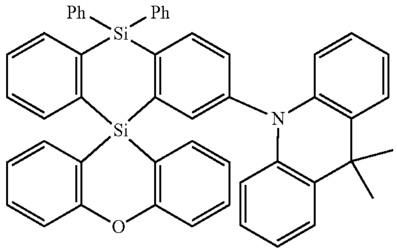
B257
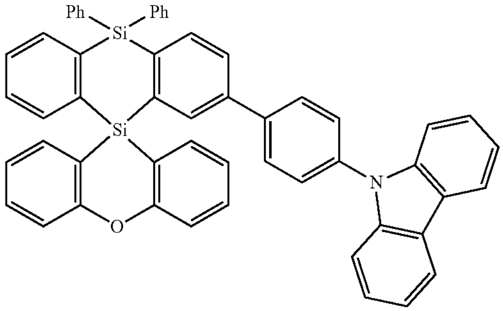
B258
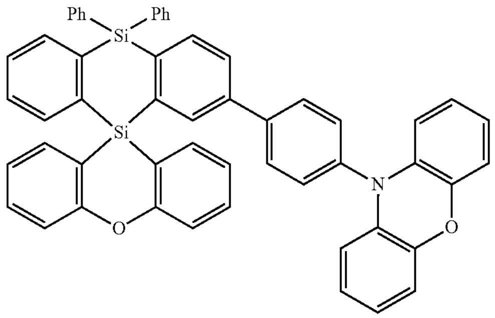
B259
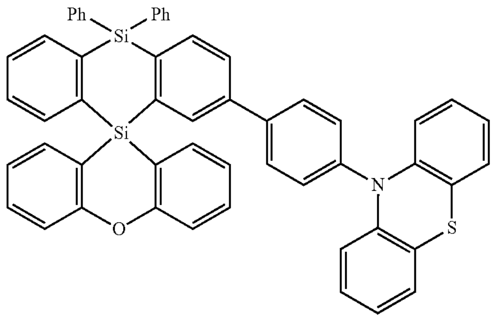
B260
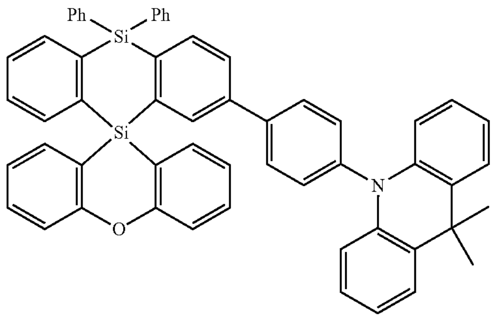

-continued
B261
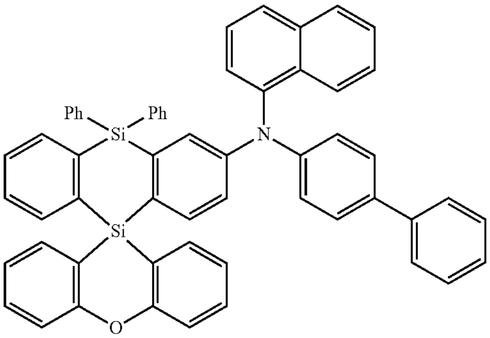
B262
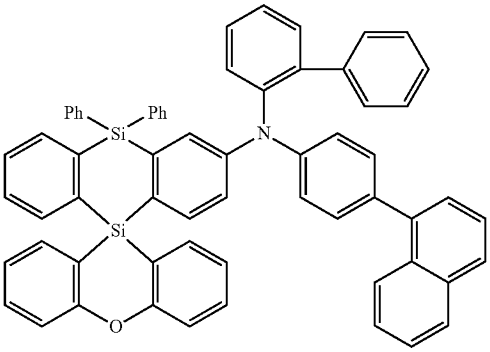
B263
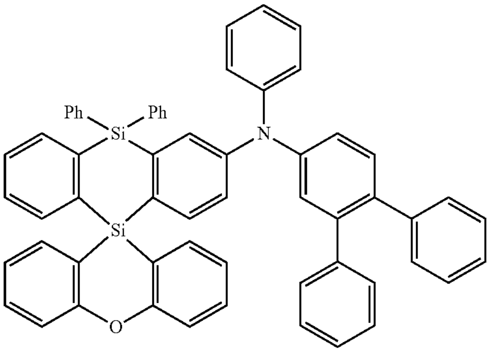
B264
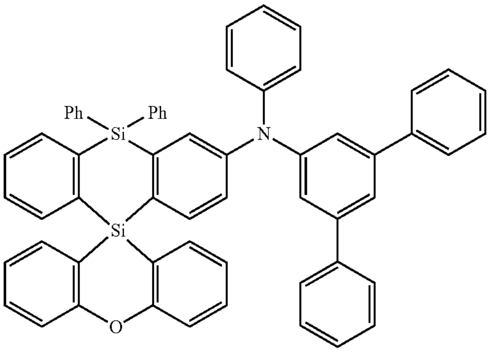
-continued
B265
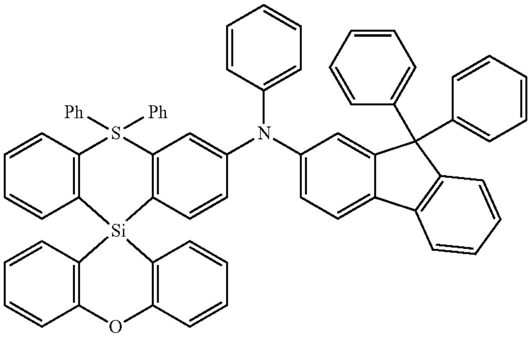
B266
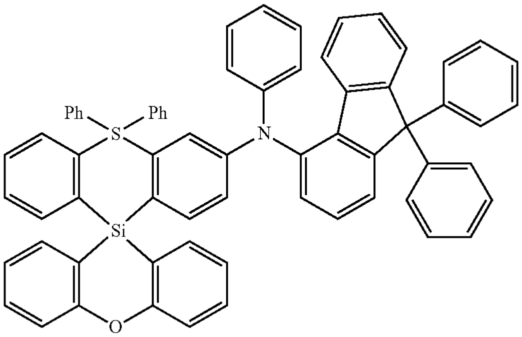
B267
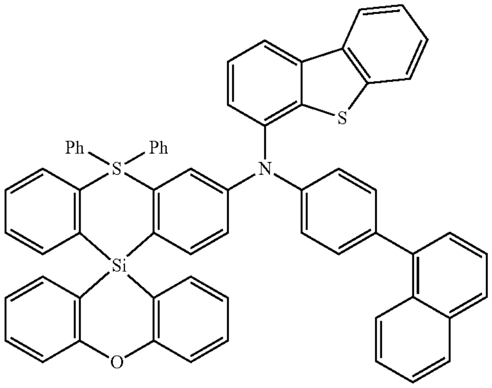
B268
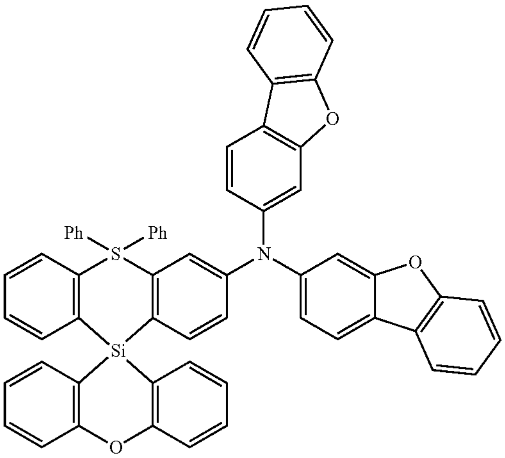

-continued
B269
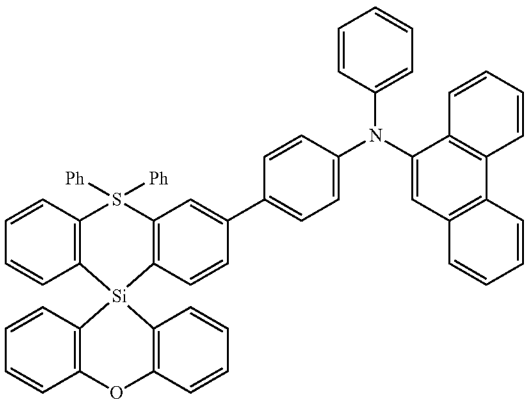
B270
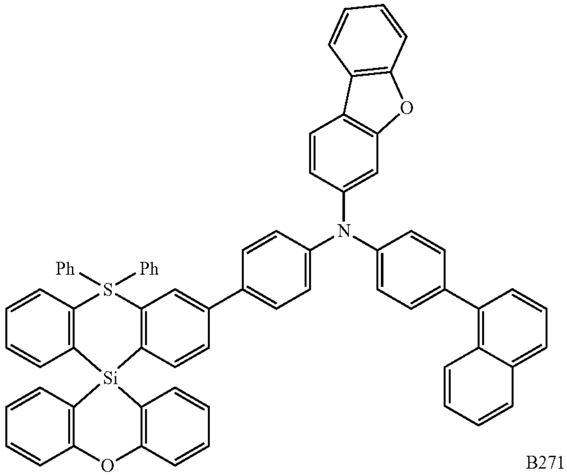
B271
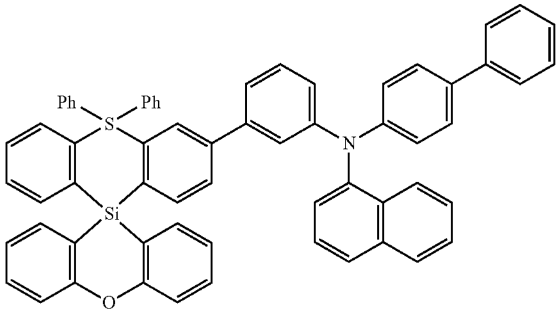
B272
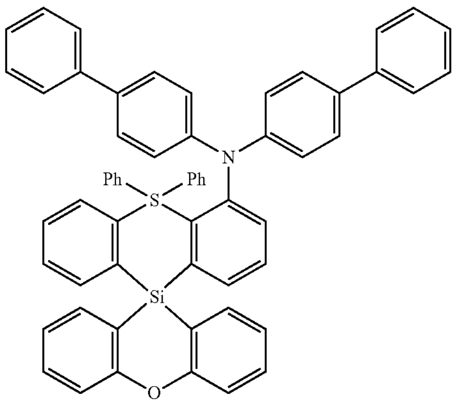
-continued
B273
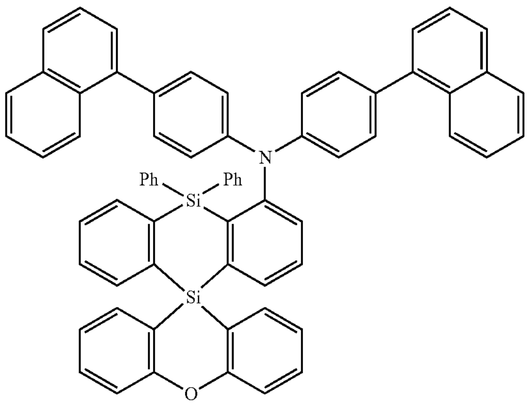
B274
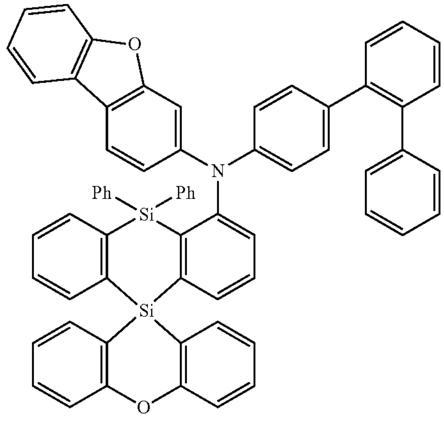
B275
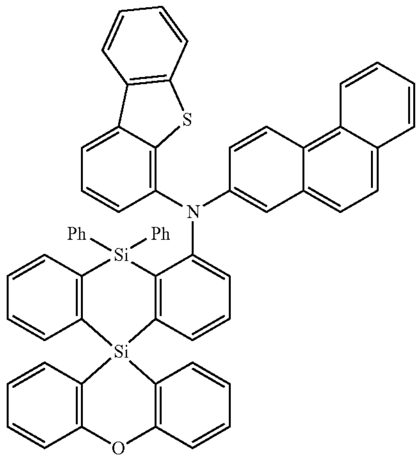

-continued
B276
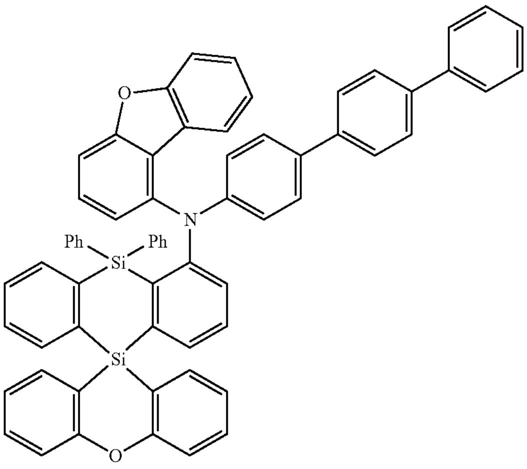
B277
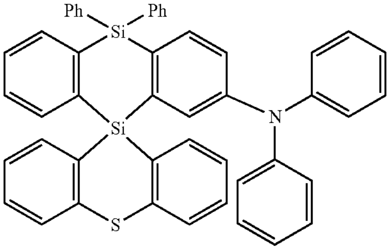
B278
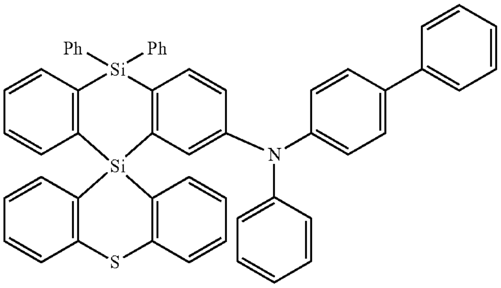
B279
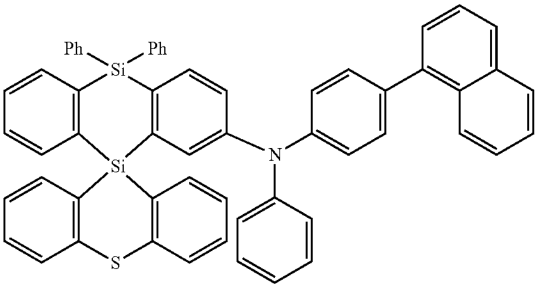
B280
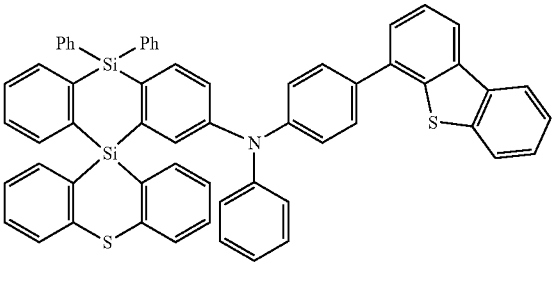
-continued
B281
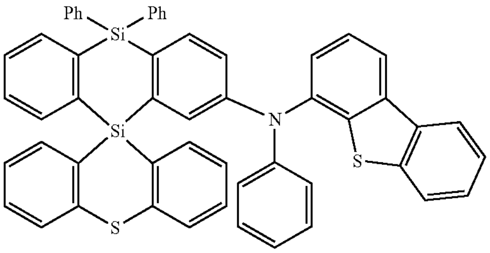
B282
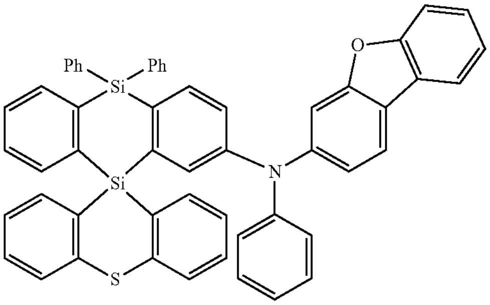
B283
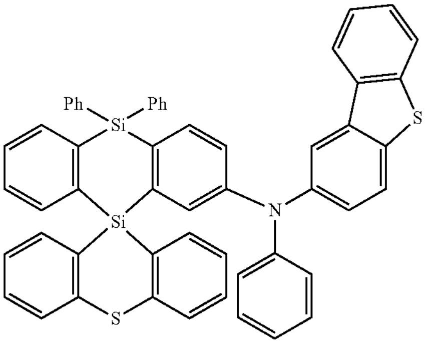
B284
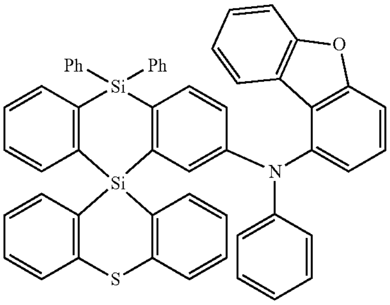
B329
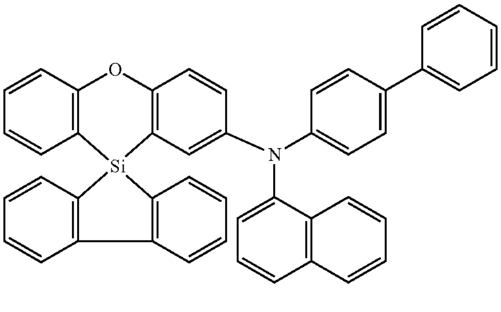

-continued
B330
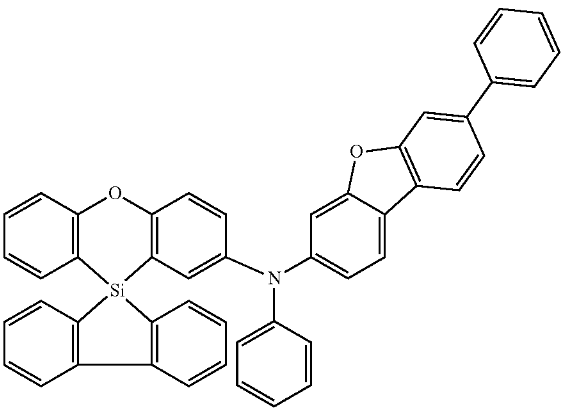
B331
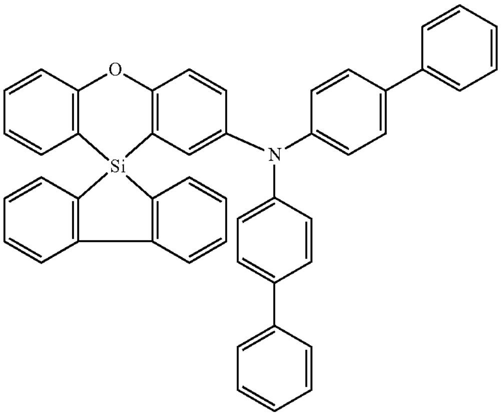
B332
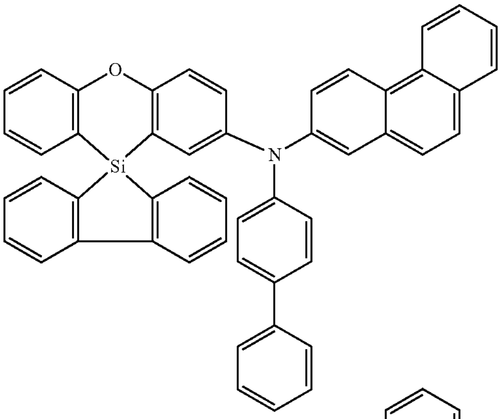
B289
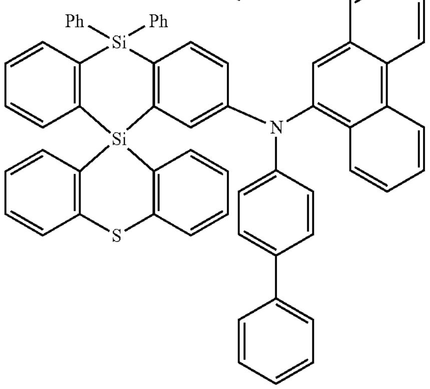
-continued
B290
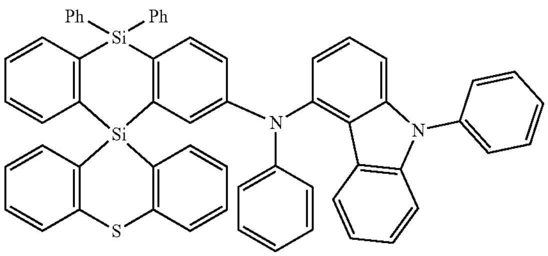
B291
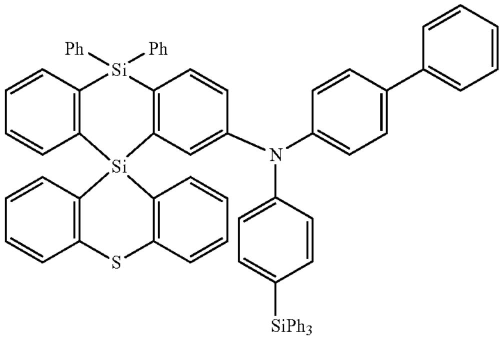
B292
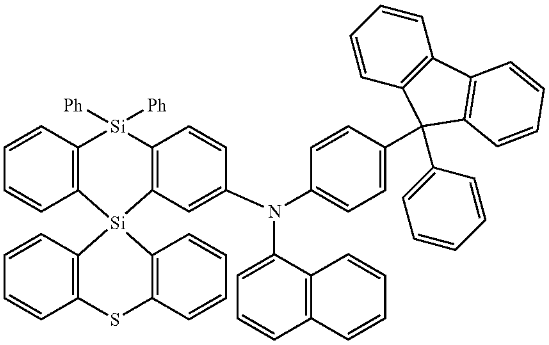
B293
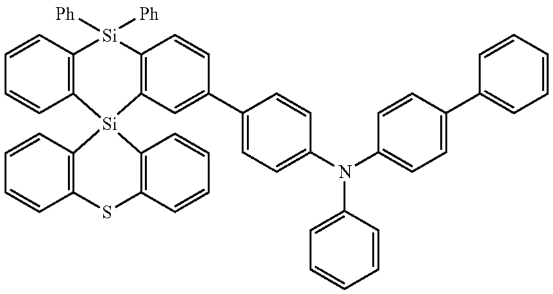
B294
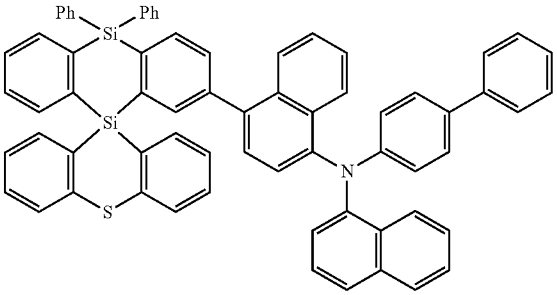

-continued
B295
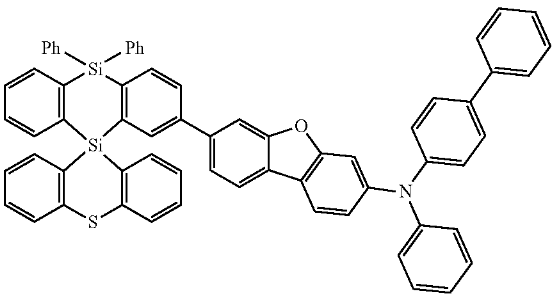
B296
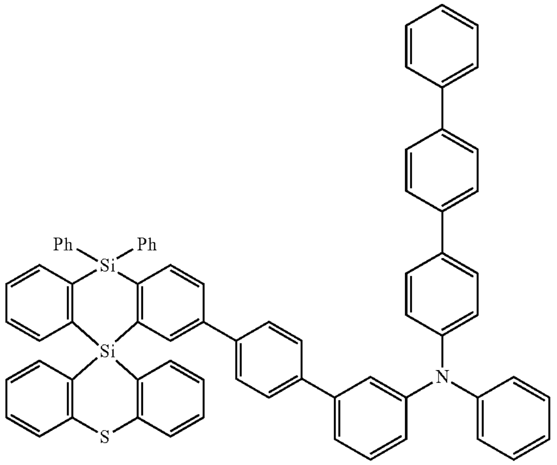
B297
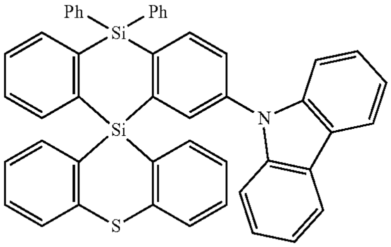
B298
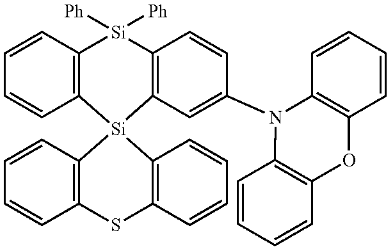
B299
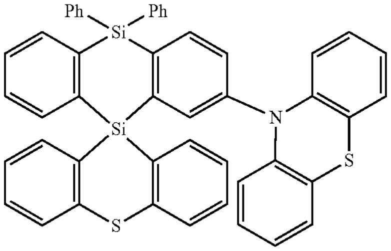
-continued
B300
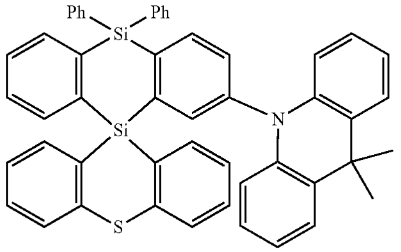
B301
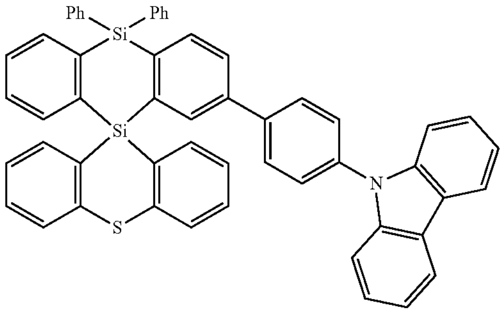
B302
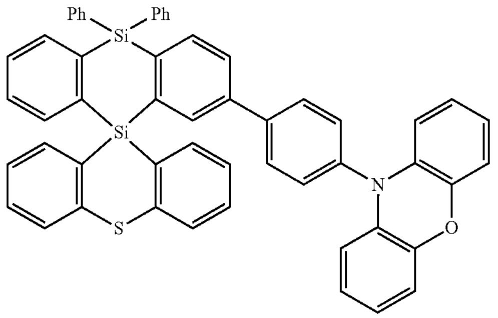
B303
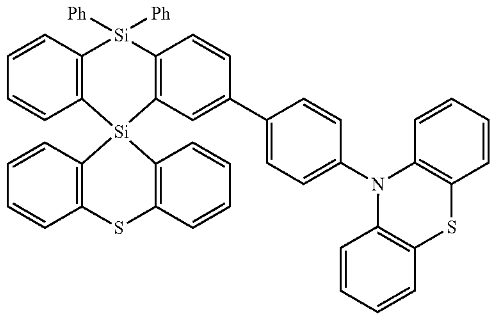
B304
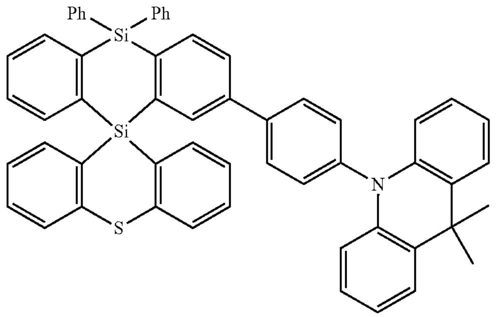

-continued
B305
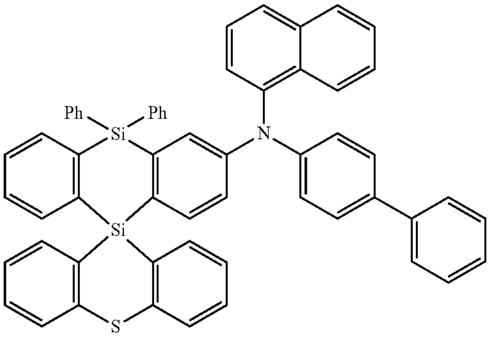
B306
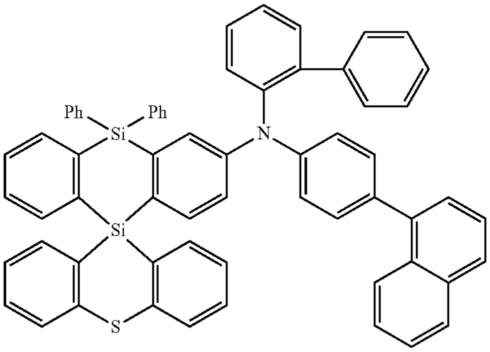
B307
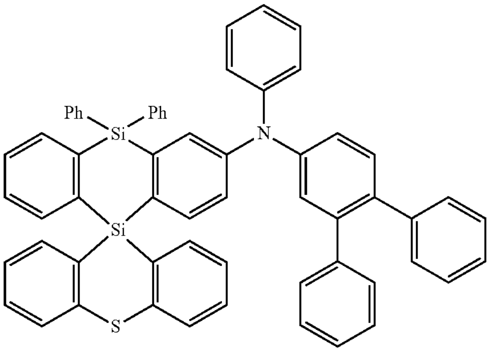
B308
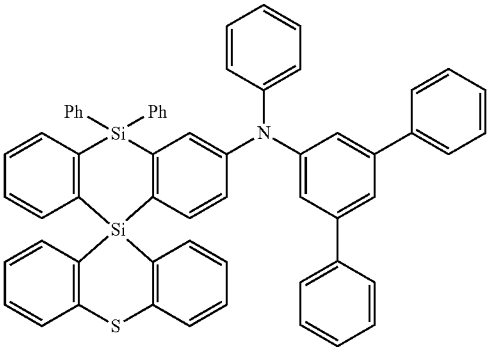
-continued
B309
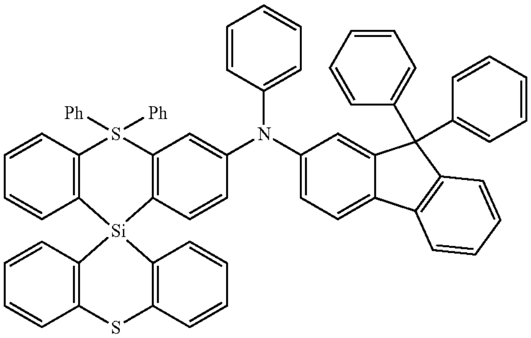
B310
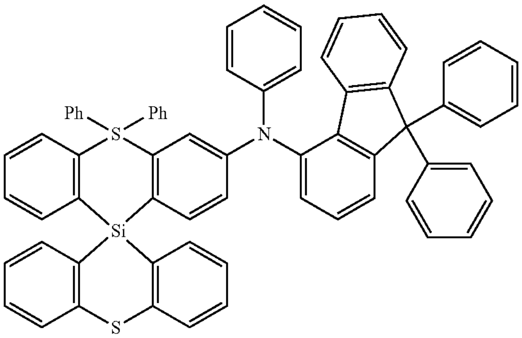
B311
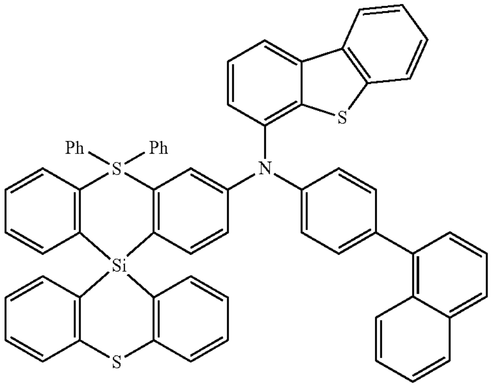
B312
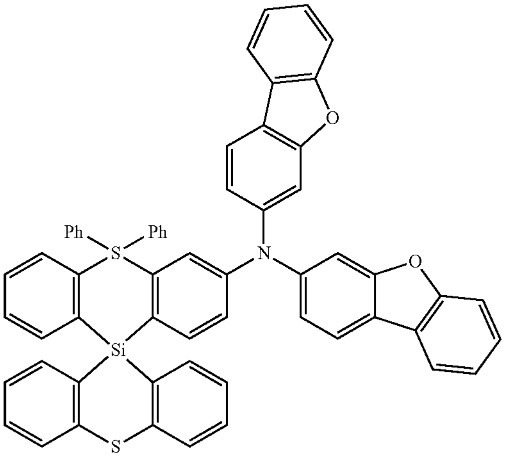

-continued
B313
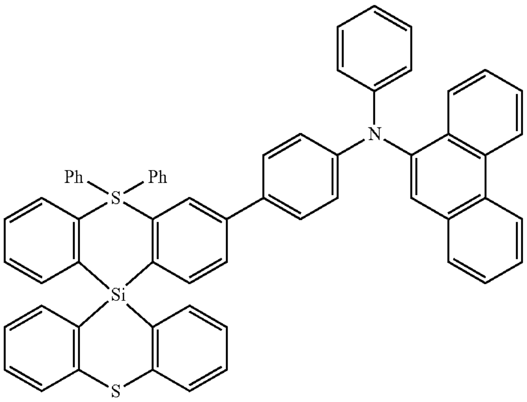
B314
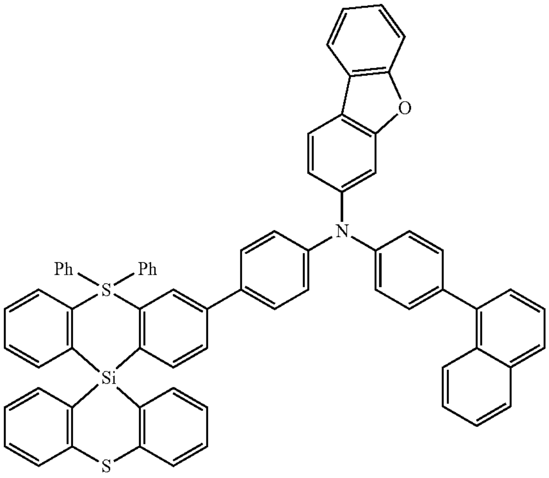
B315
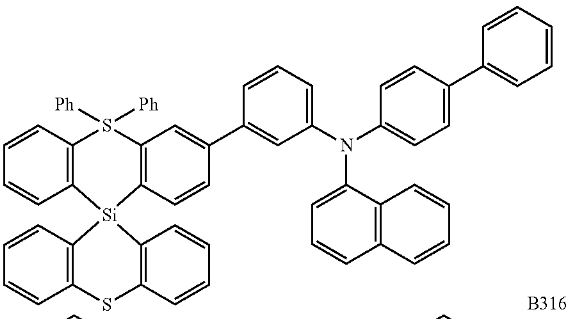
B316
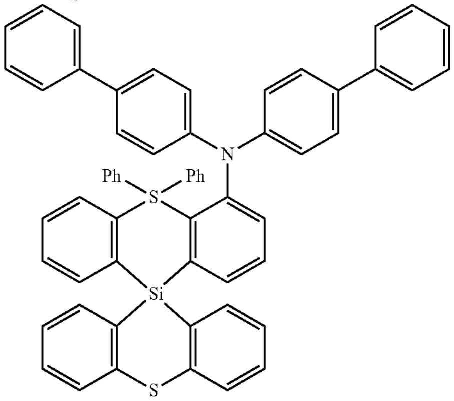
-continued
B317
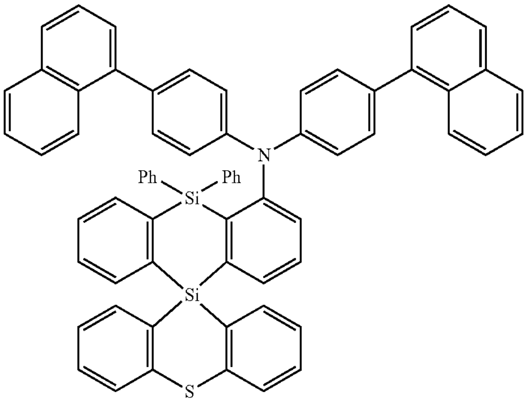
B318
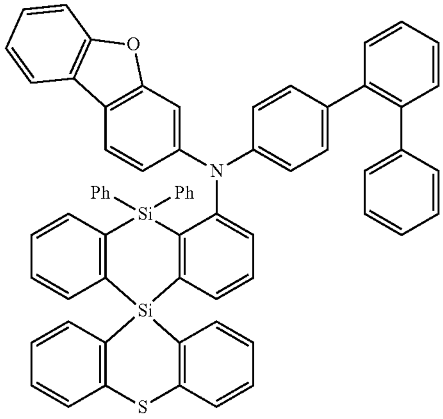
B319
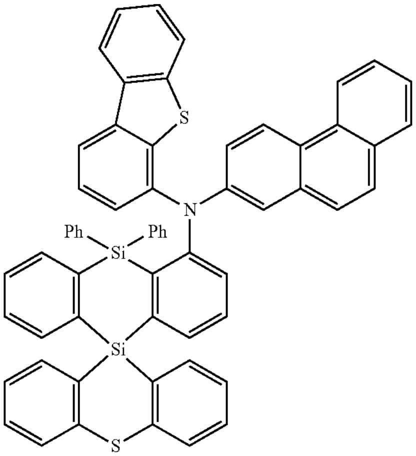

-continued
B320
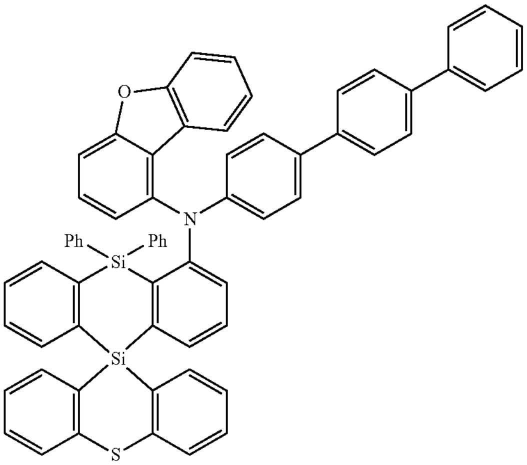
B321
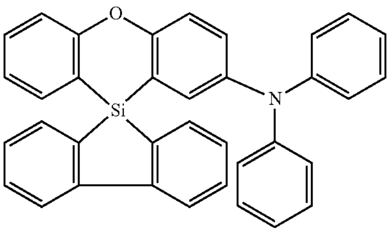
B322
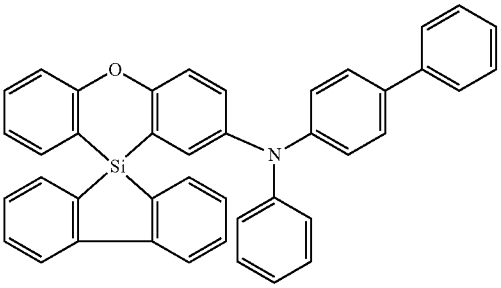
B323
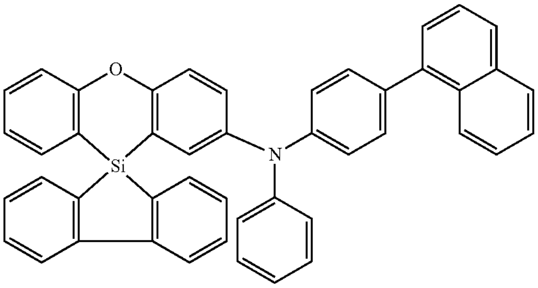
B324
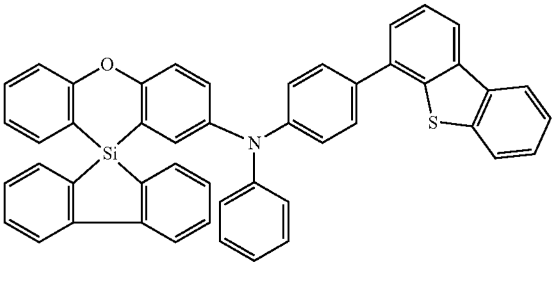
-continued
B325
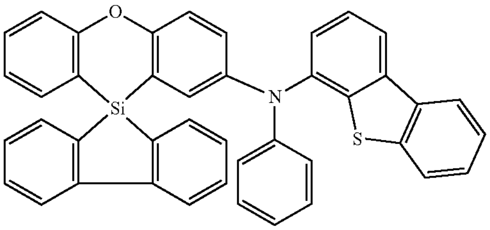
B326
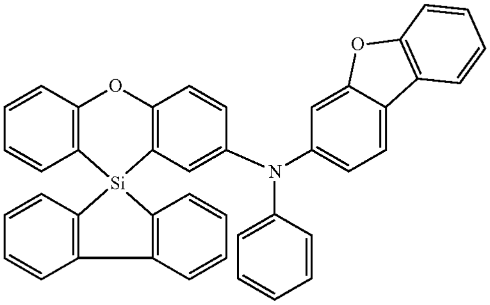
B327
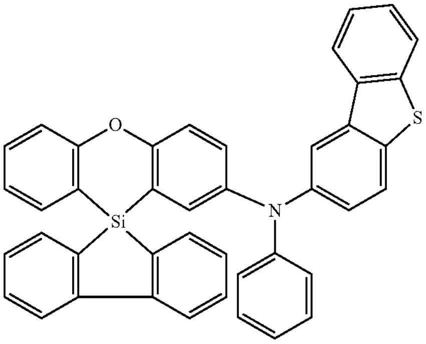
B328
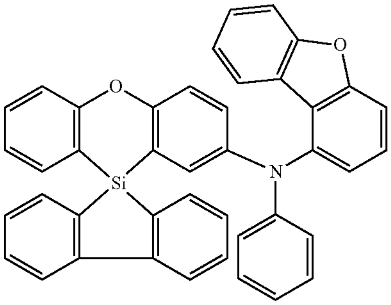
B329
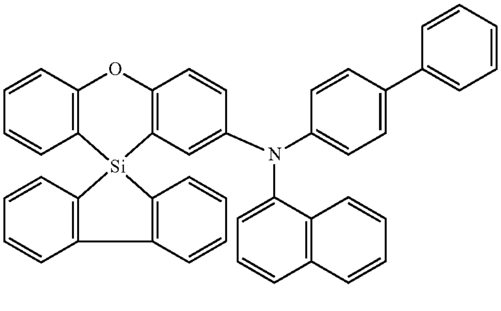

-continued
B330
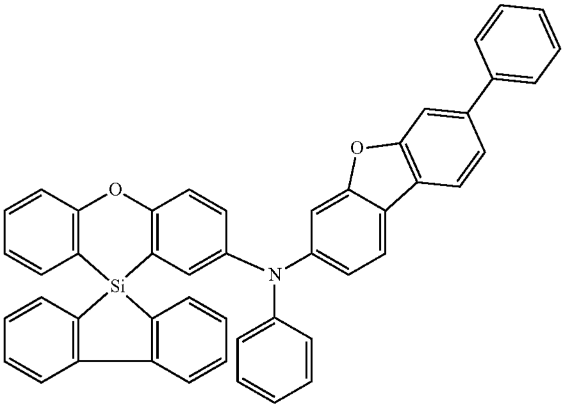
B331
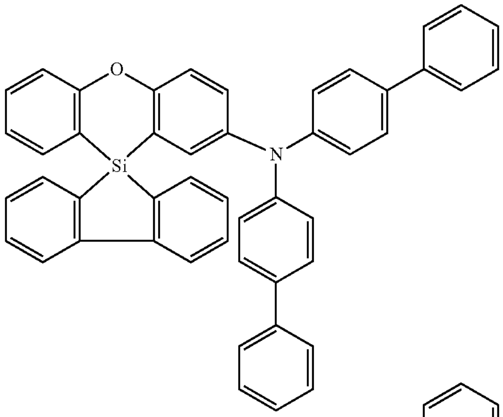
B332
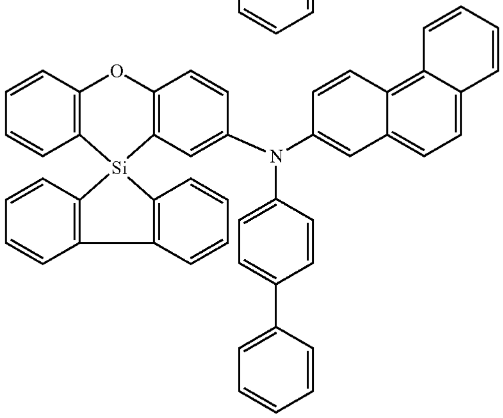
B333
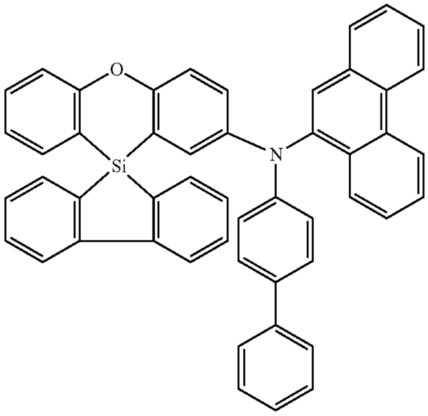
-continued
B334
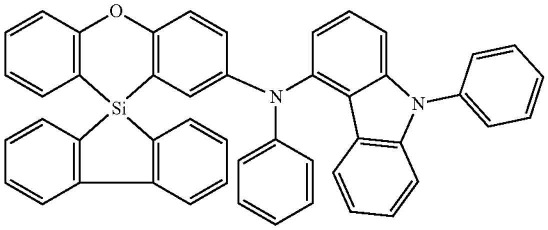
B335
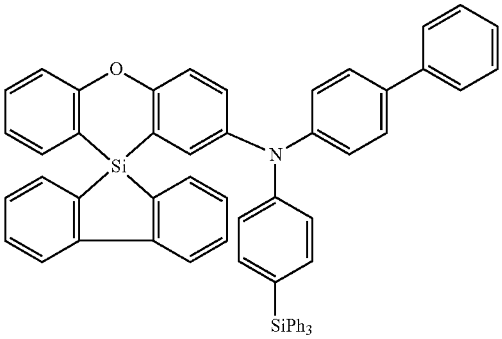
B336
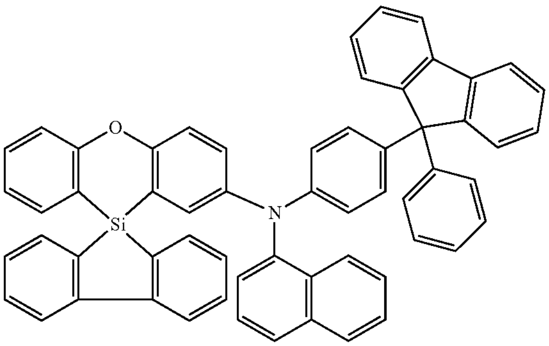
B337
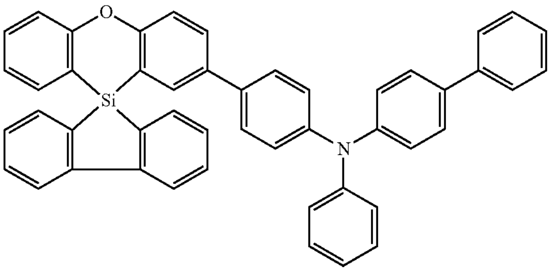
B338
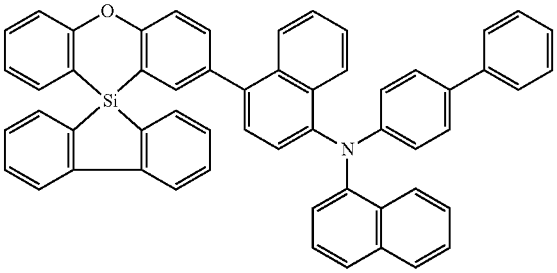

-continued
B339
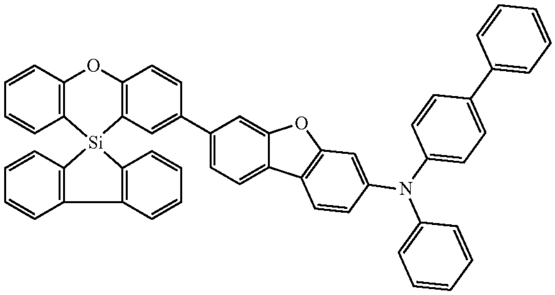
B340
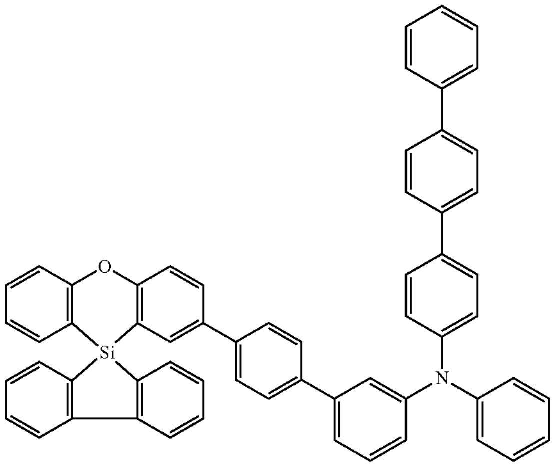
B341
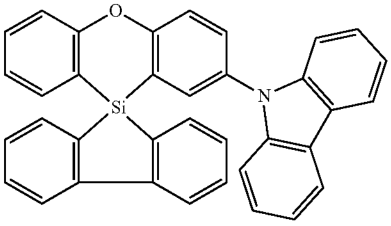
B342
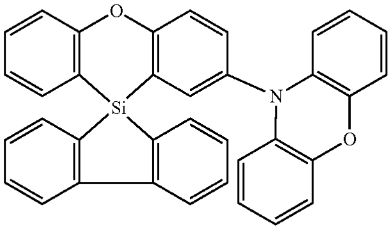
B343
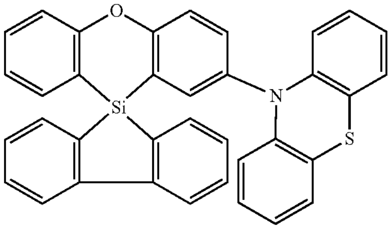
-continued
B344
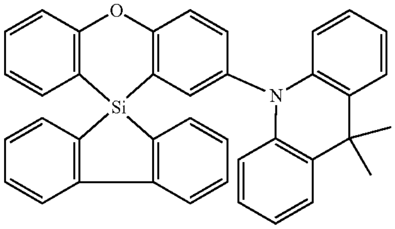
B345
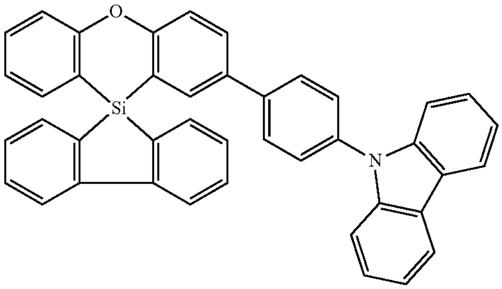
B346
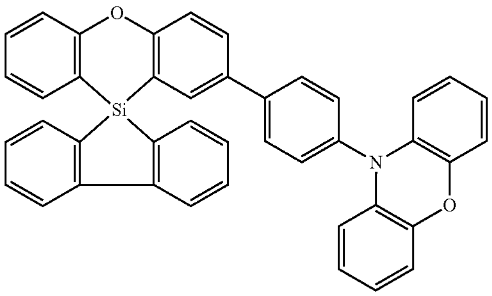
B347
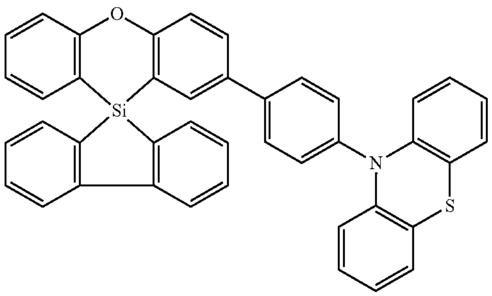
B348
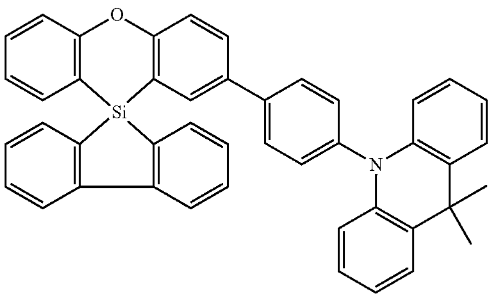

-continued
B349
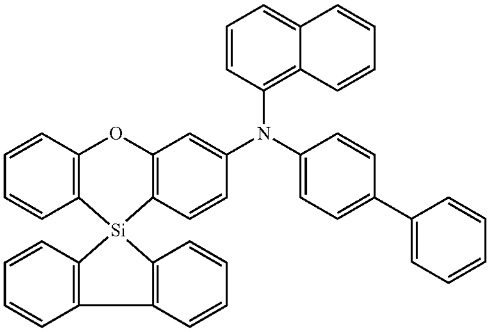
B350
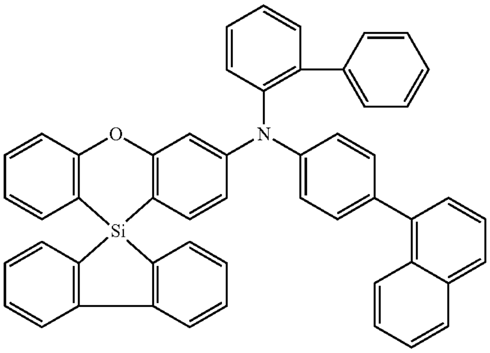
B351
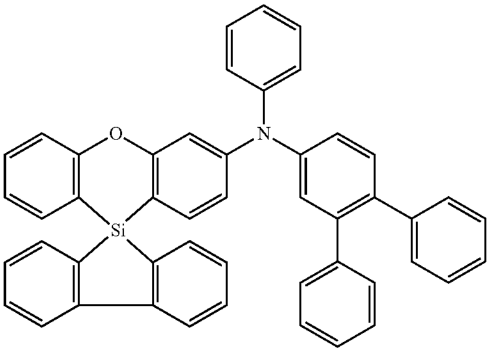
B352
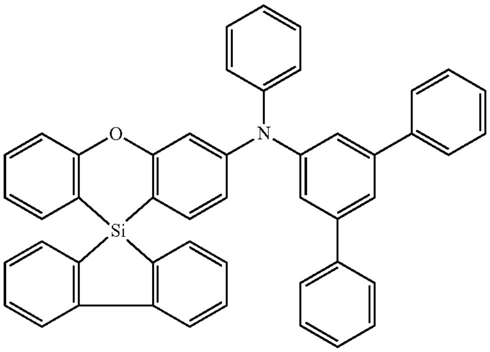
-continued
B353
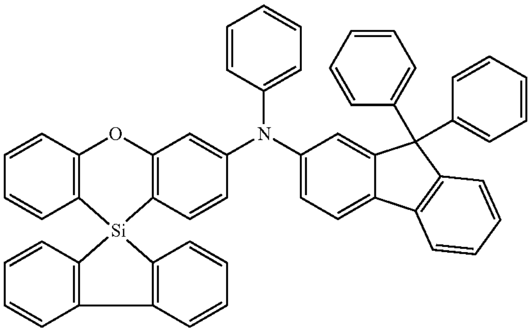
B354
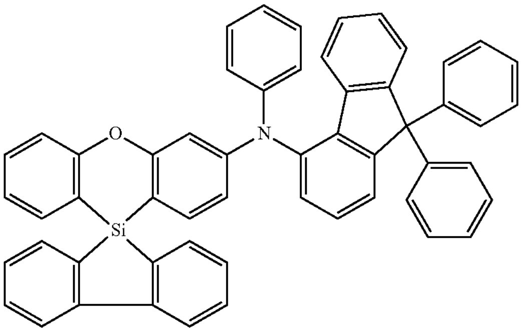
B355
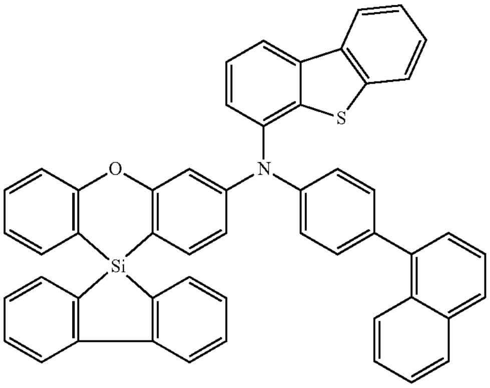
B356
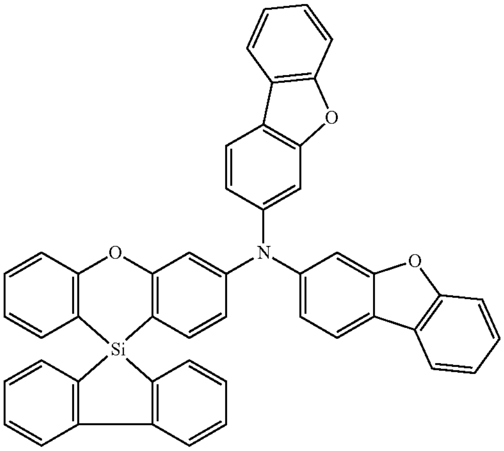

-continued
B357
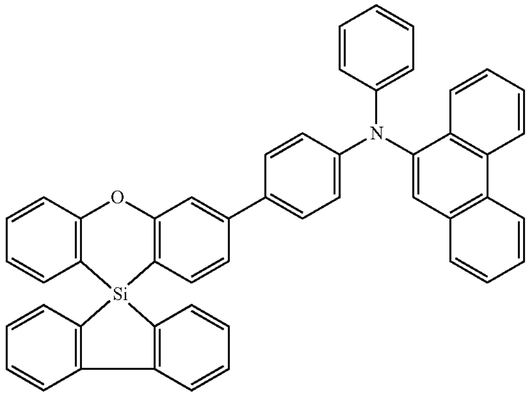
B358
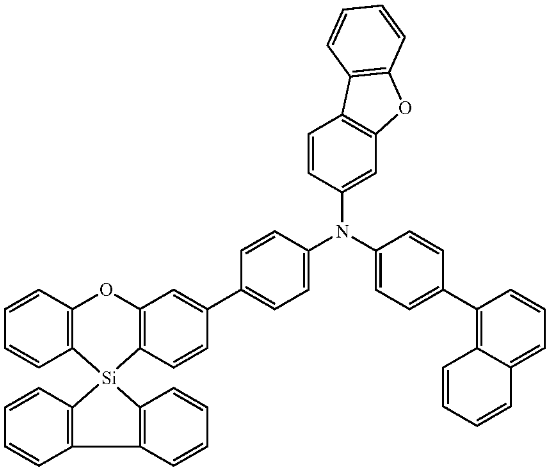
B359
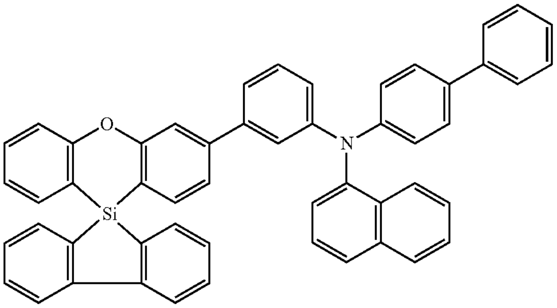
B360
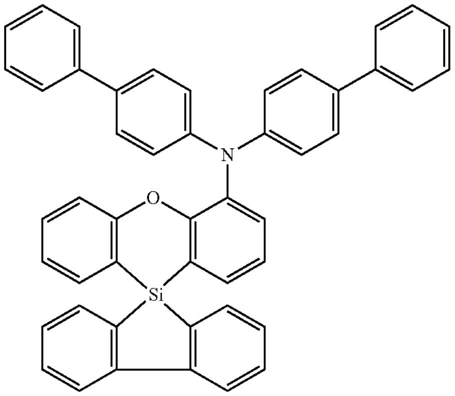
-continued
B361
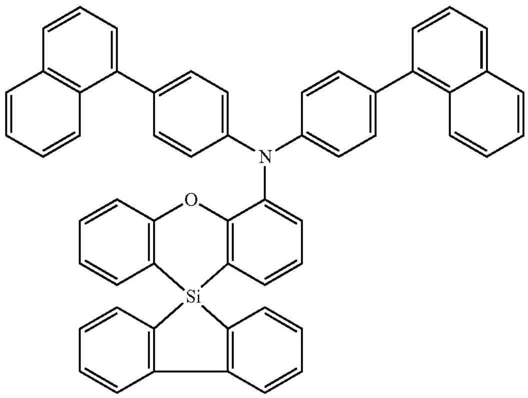
B362
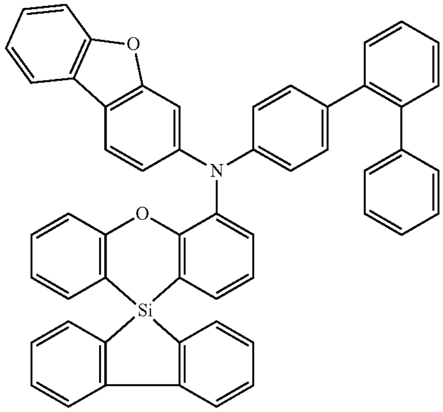
B363
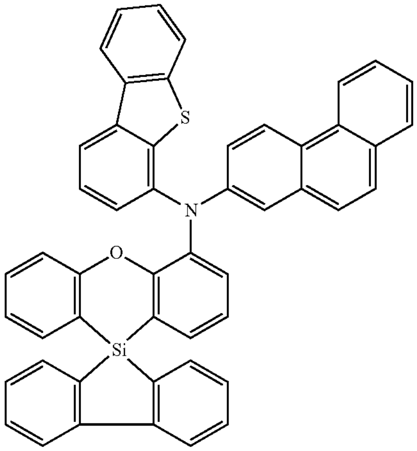

-continued
B364
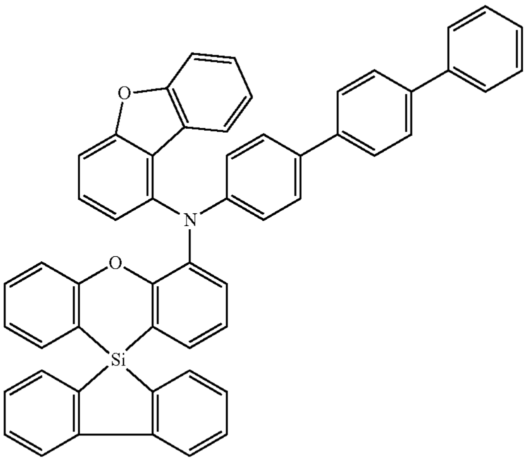
B365
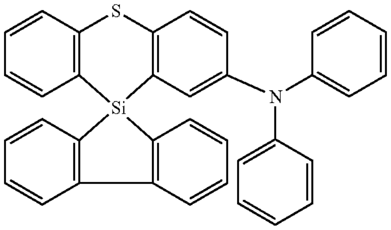
B366
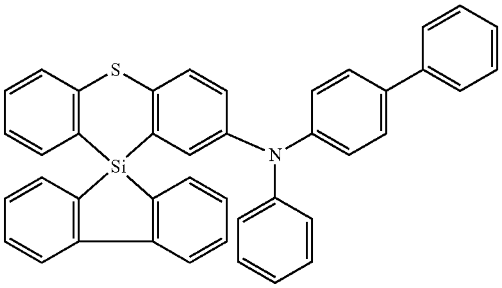
B367
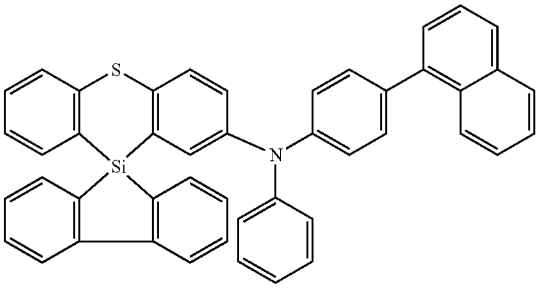
B368
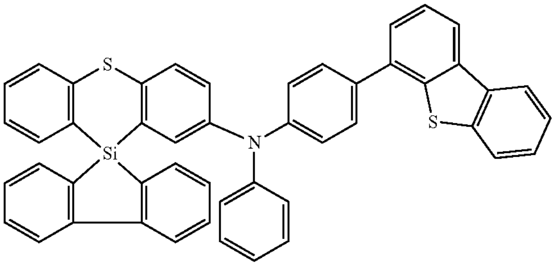
-continued
B369
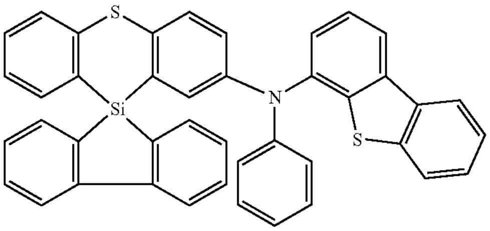
B370
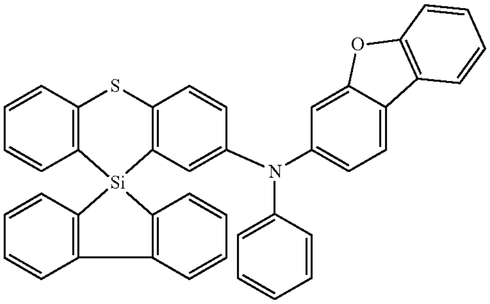
B371
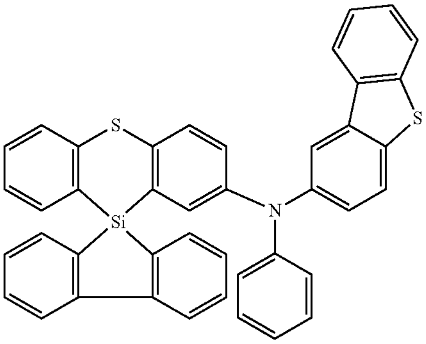
B372
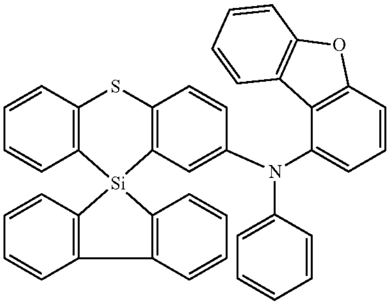
B373
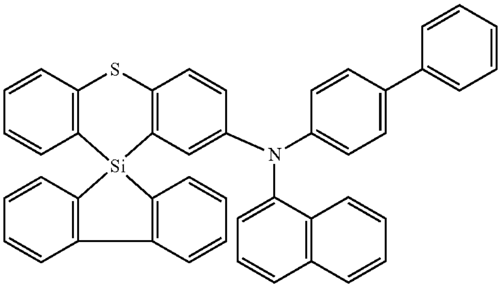

-continued
B374
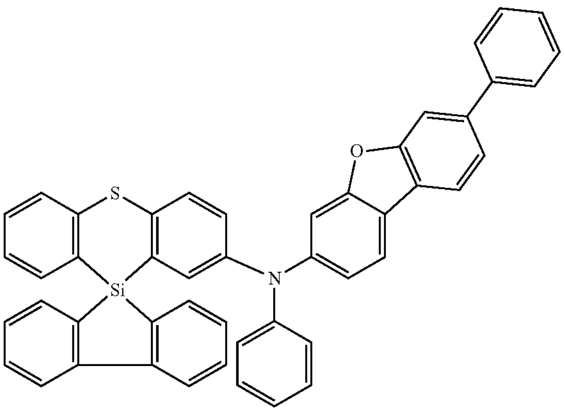
B375
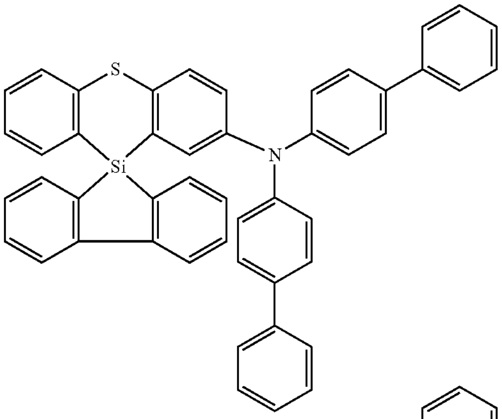
B376
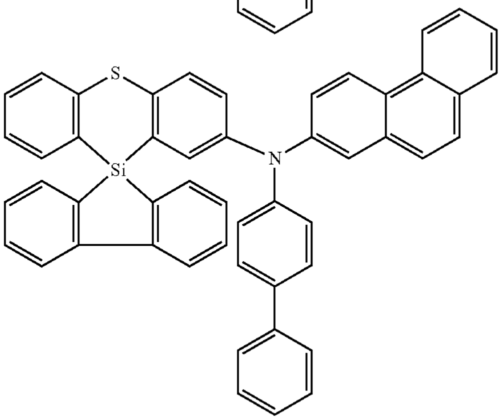
B377
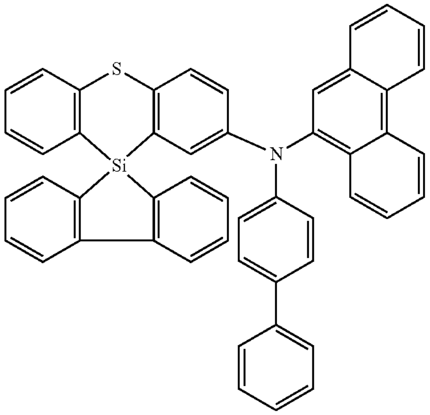
-continued
B378
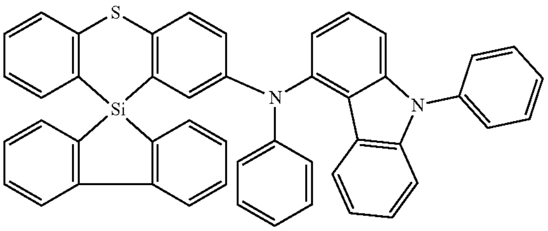
B379
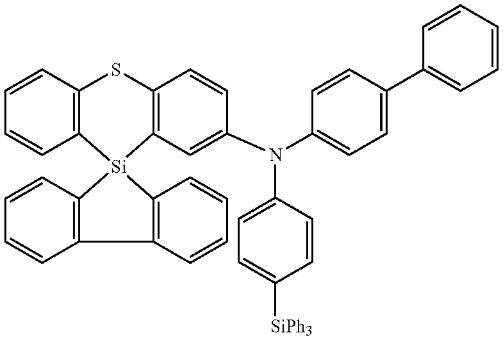
B380
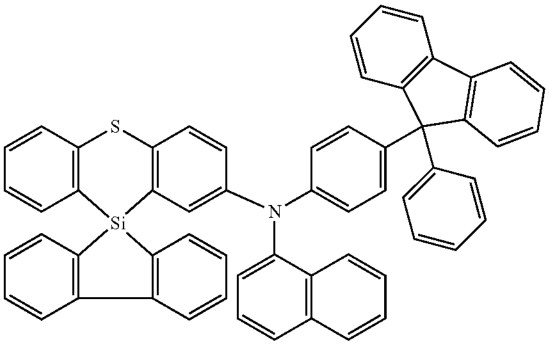
B381
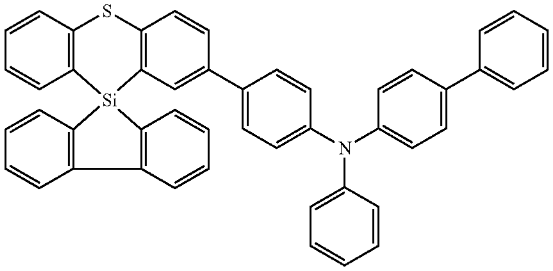
B382
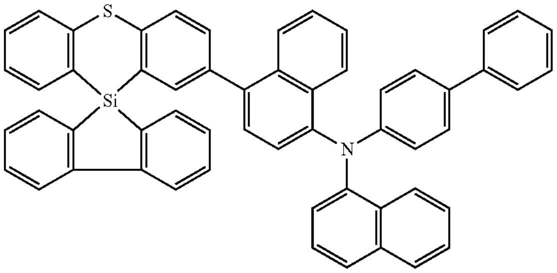

-continued
B383
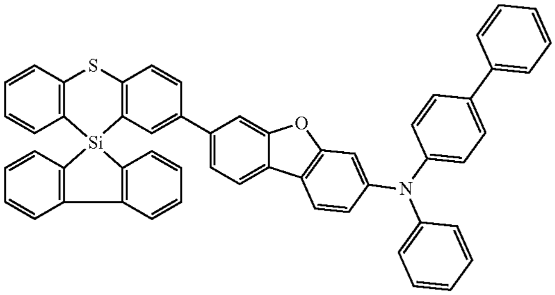
B384
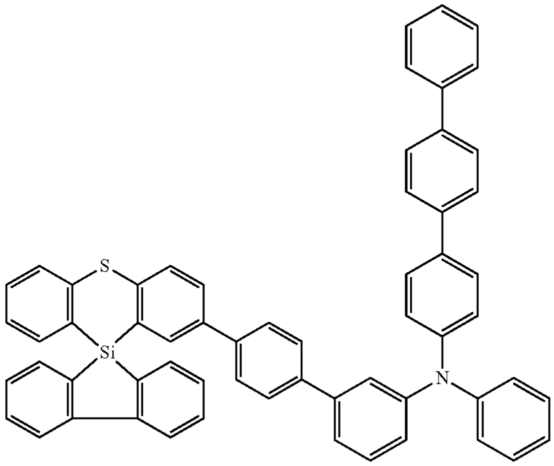
B385
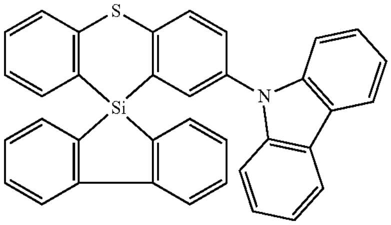
B386
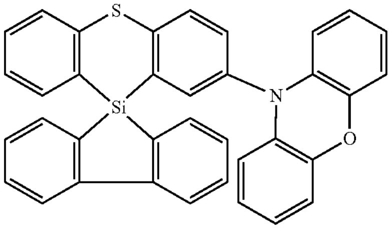
B387
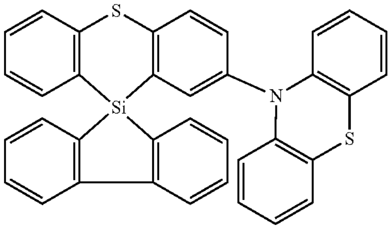
-continued
B388
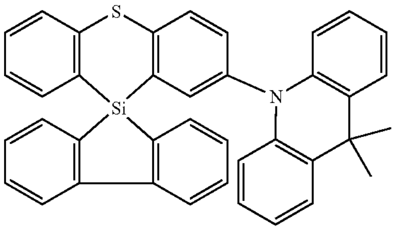
B389
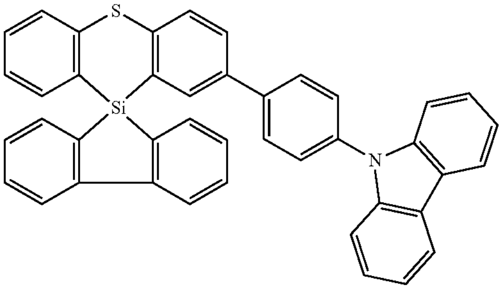
B390
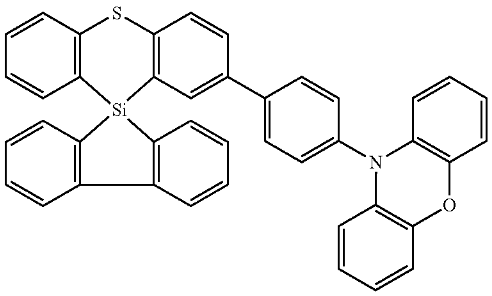
B391
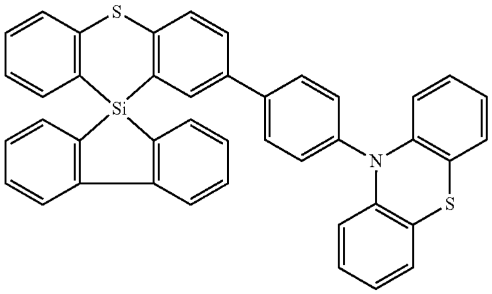
B392
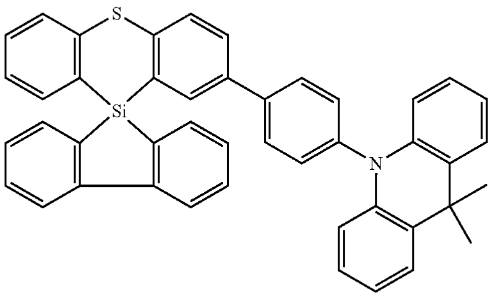

-continued
B393
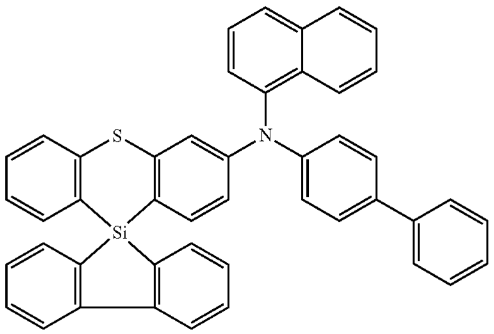
B394
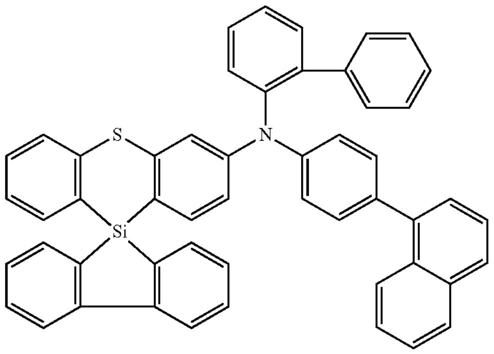
B395
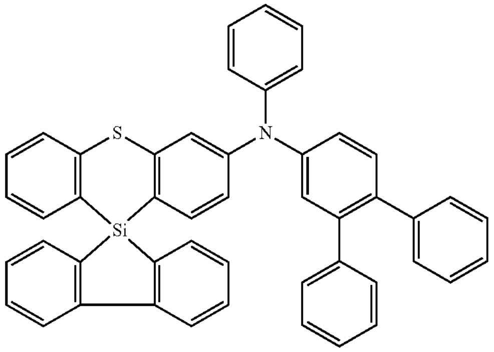
B396
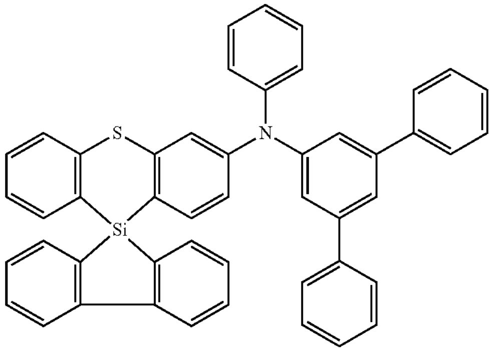
-continued
B397
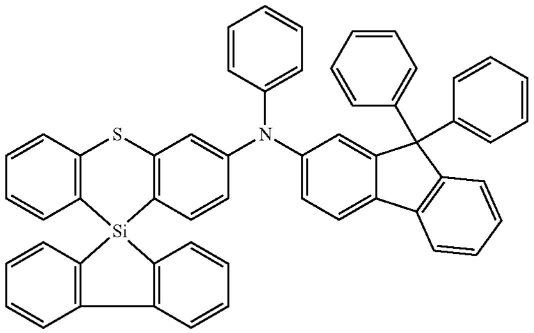
B398
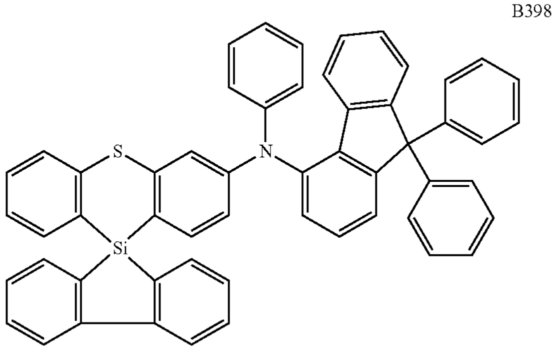
B399
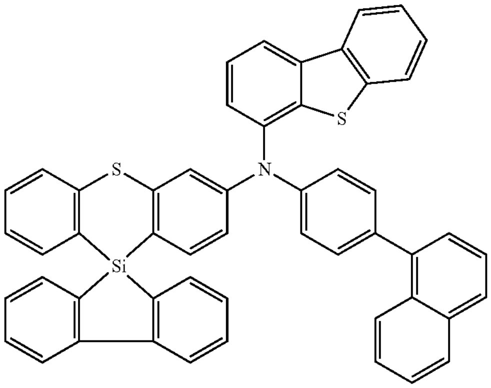
B400
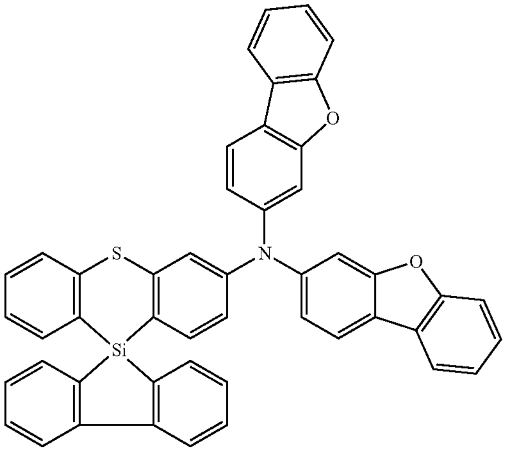

-continued
B401
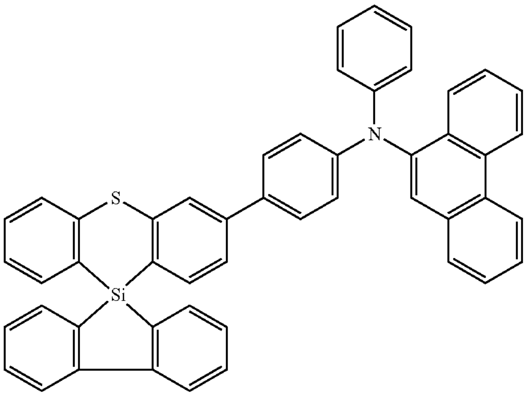
B402
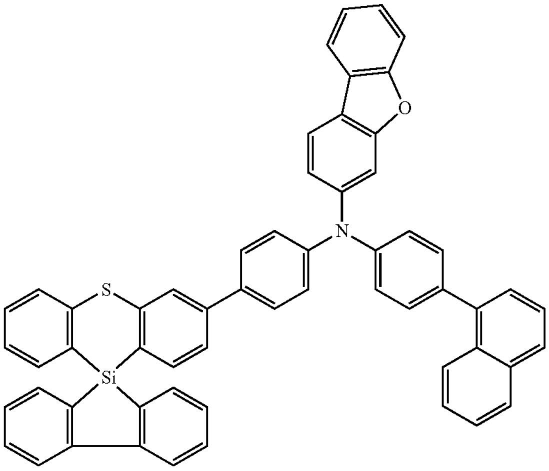
B403
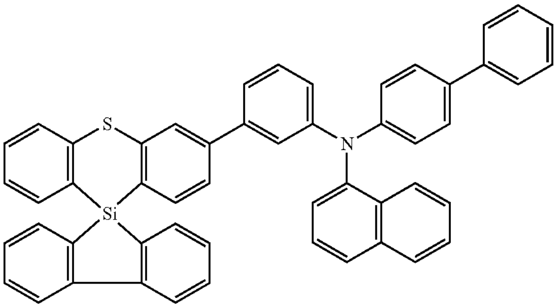
B404
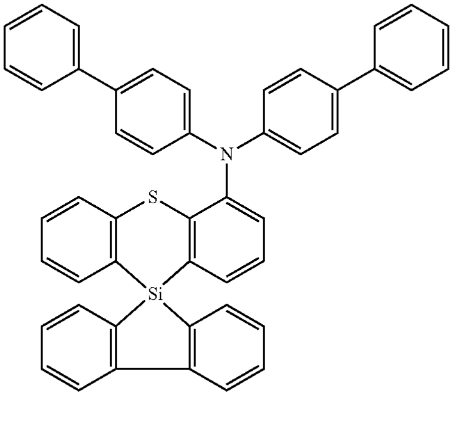
-continued
B405
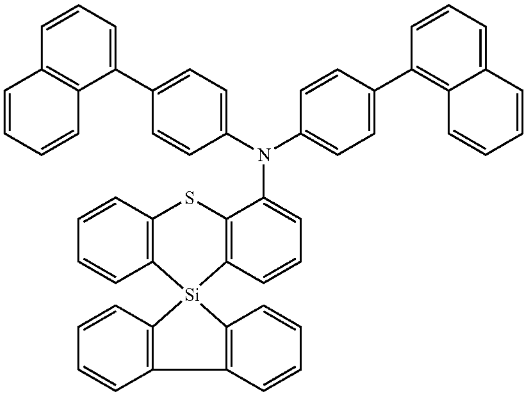
B406
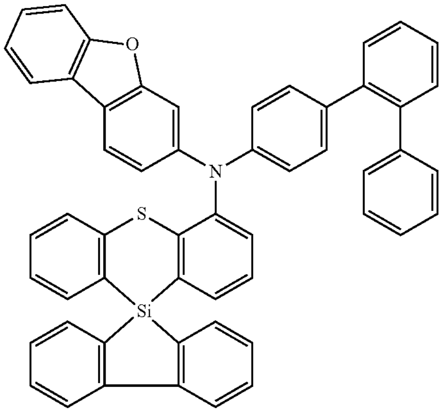
B407
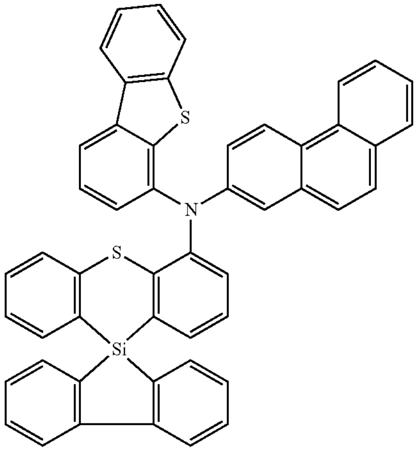

-continued
B408
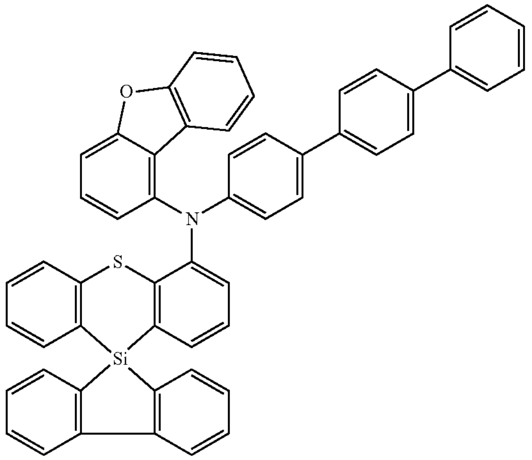
B409
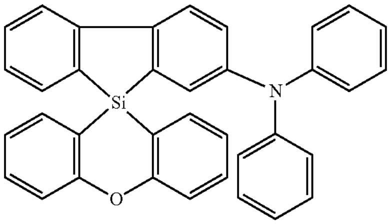
B410
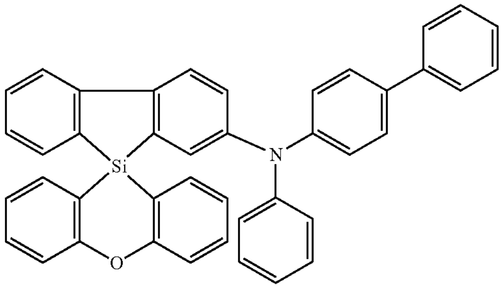
B411
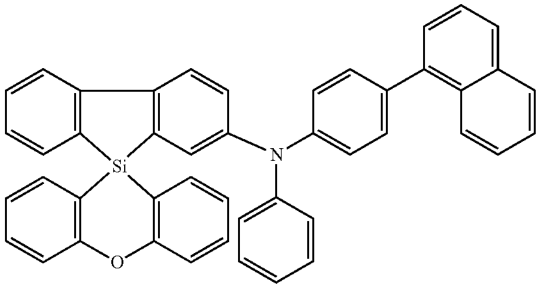
B412
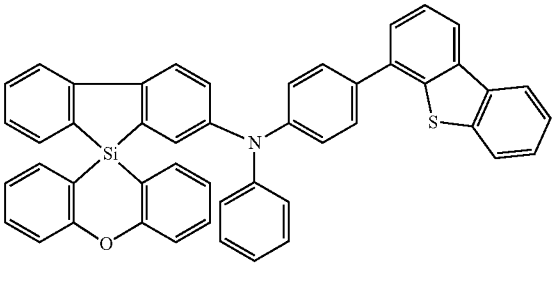
-continued
B413
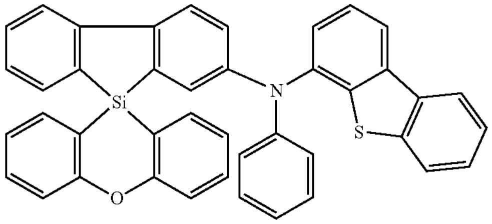
B414
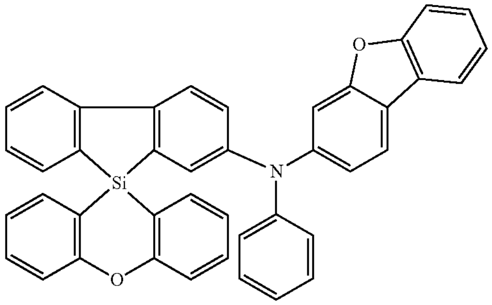
B415
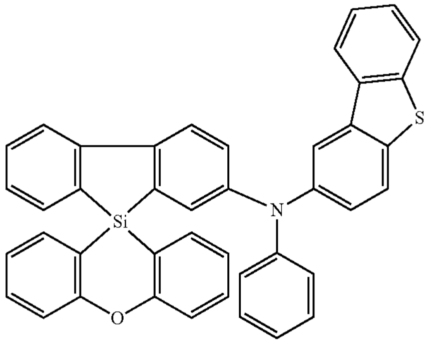
B416
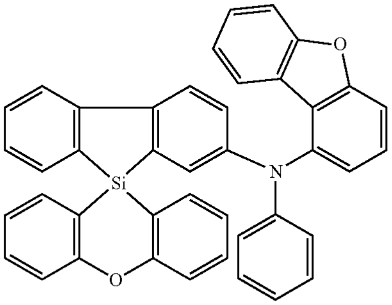
B417
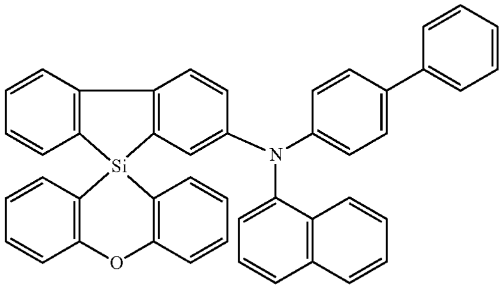

-continued
B418
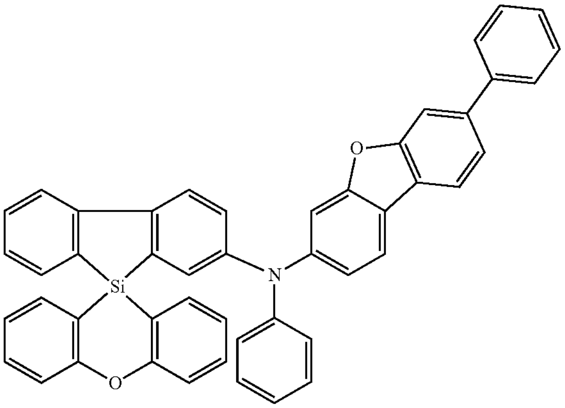
B419
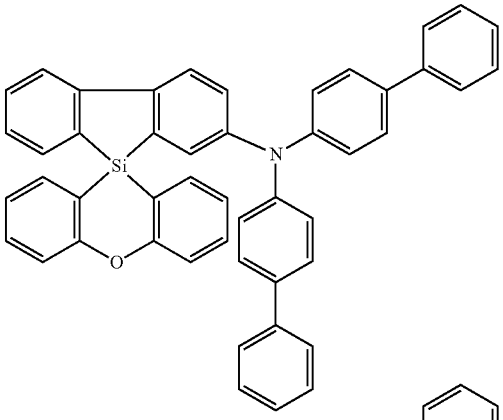
B420
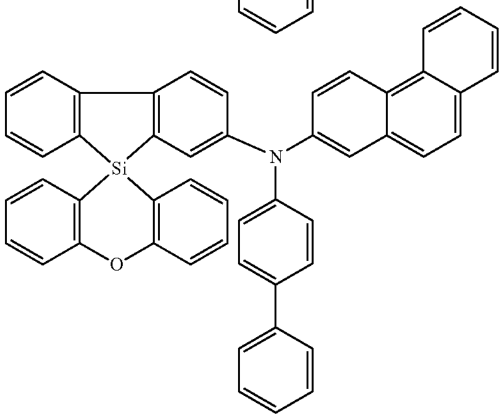
B421
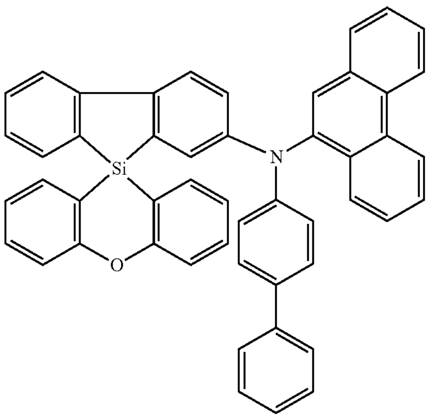
-continued
B422
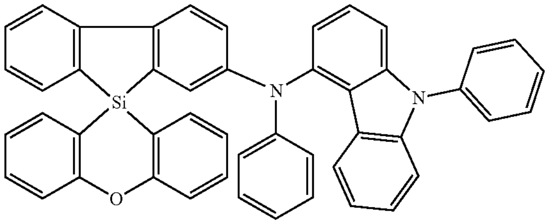
B423
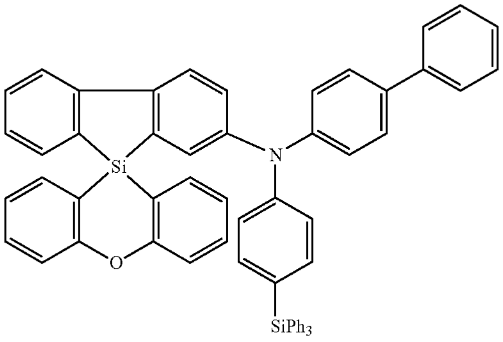
B424
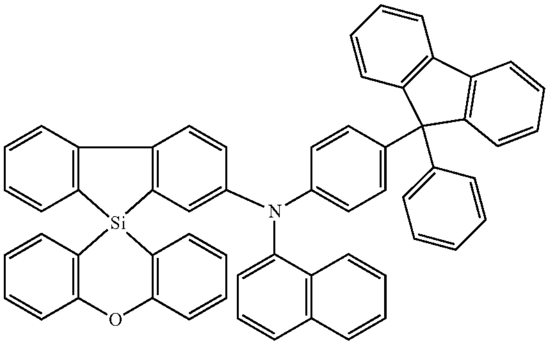
B425
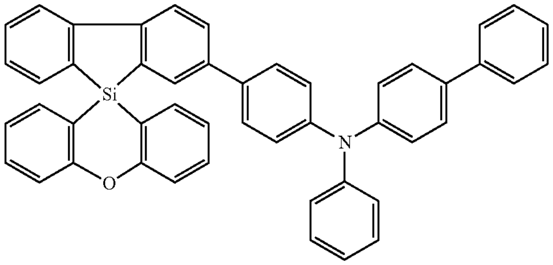
B426
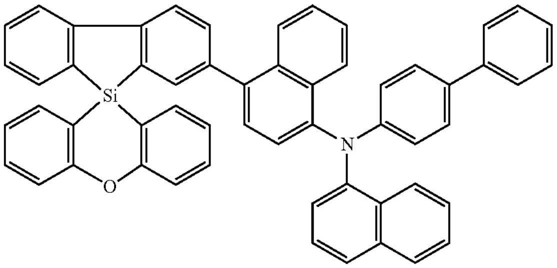

B427
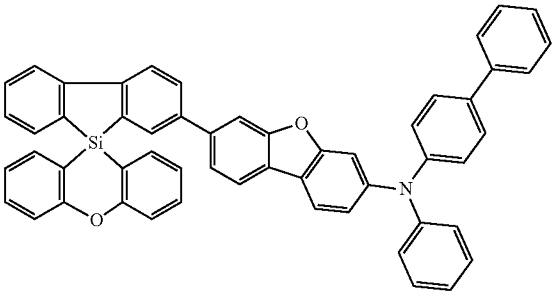
B428
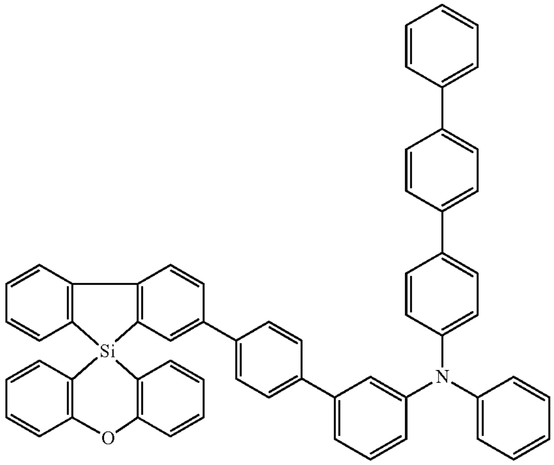
B429
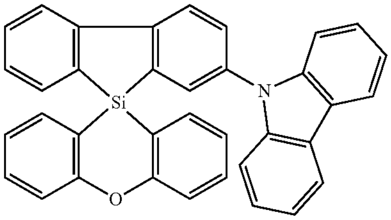
B430
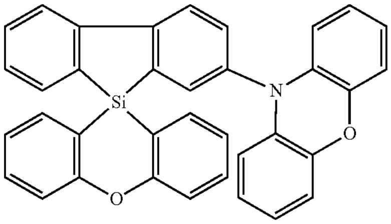
B431
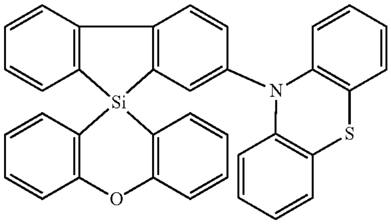
B432
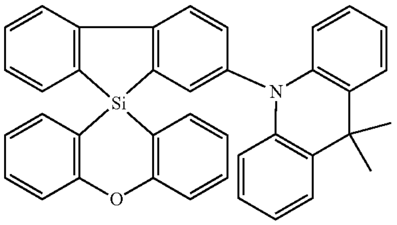
B433
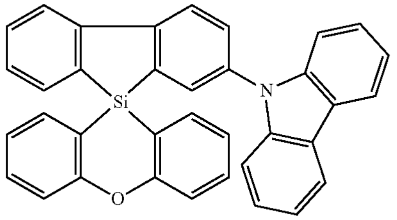
B434
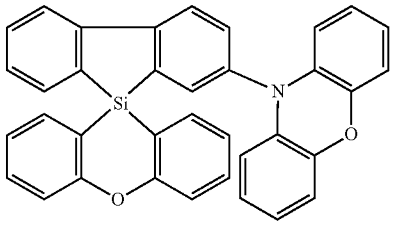
B435
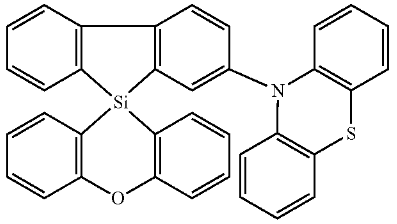
B436
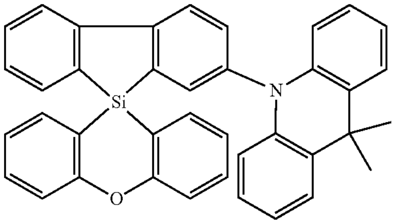
B437
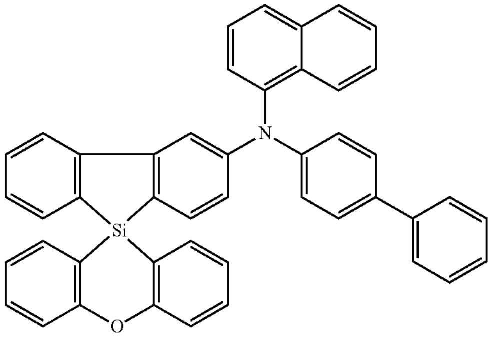

-continued
B438
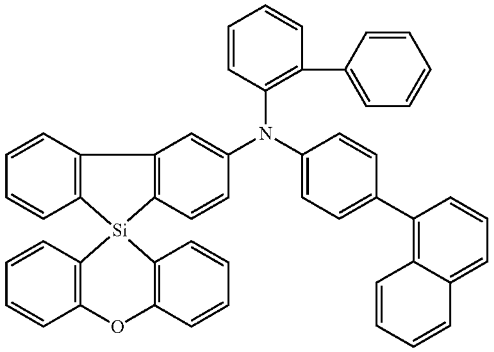
B349
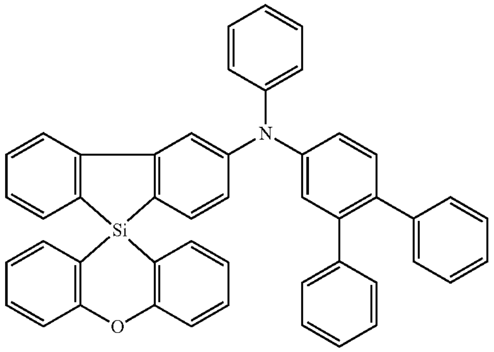
B440
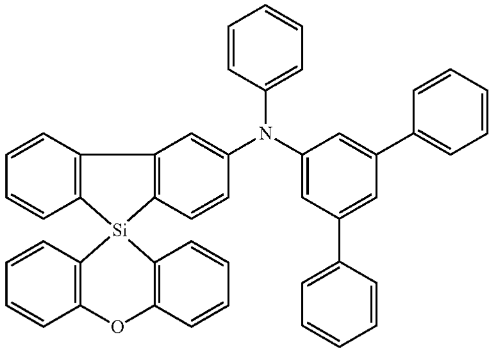
B441
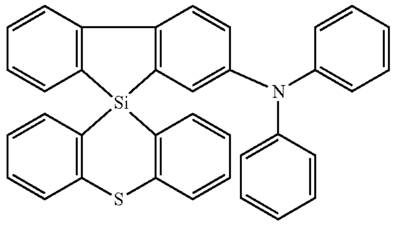
B442
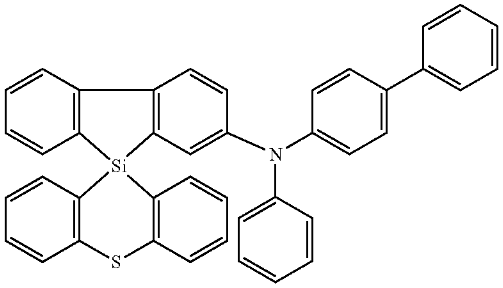
-continued
B443
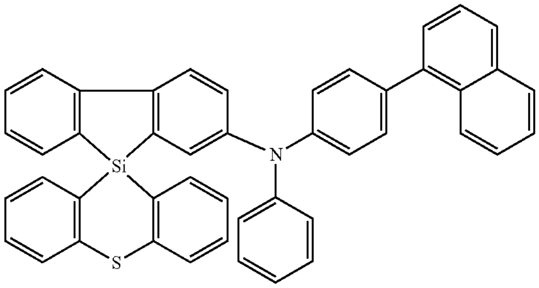
B444
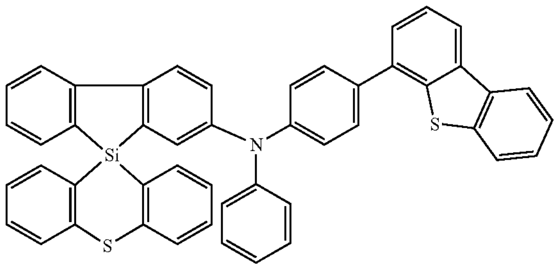
B445
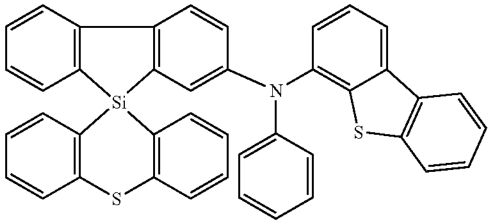
B446
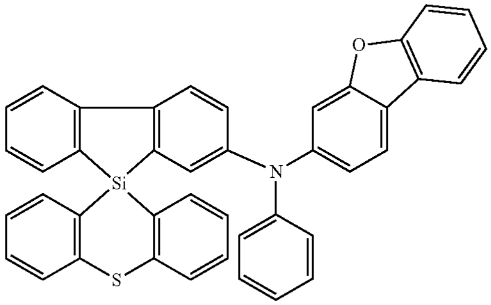
B447
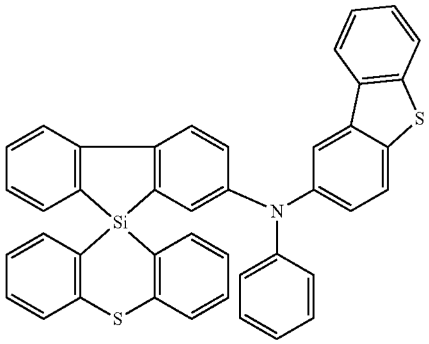

-continued
B448
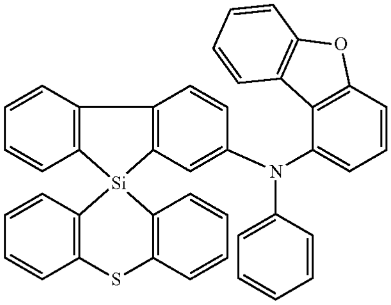
B449
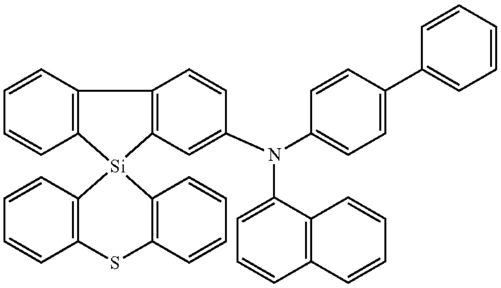
B450
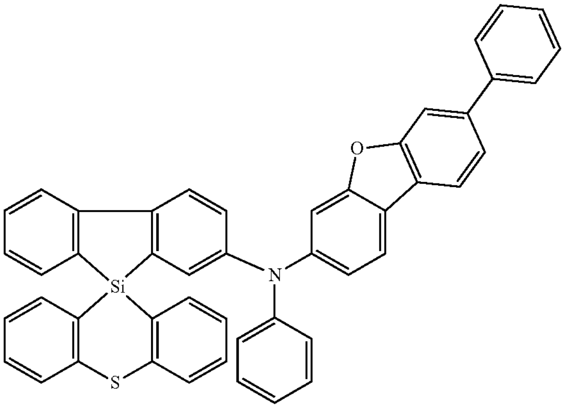
B451
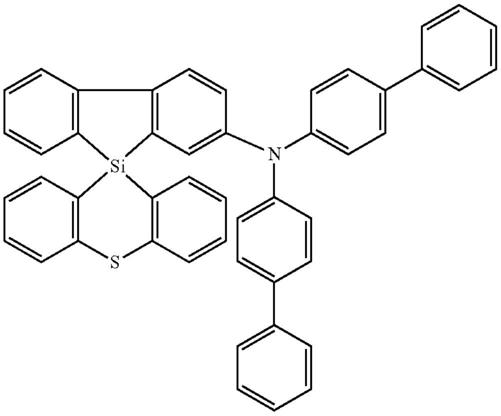
-continued
B452
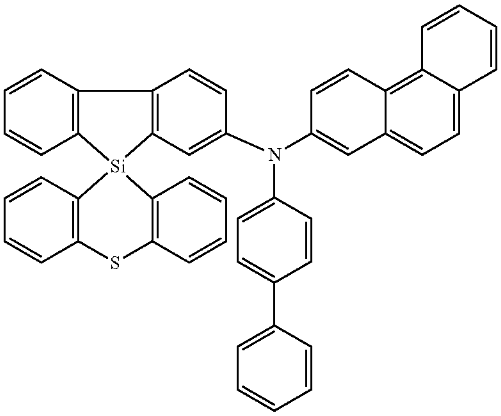
B453
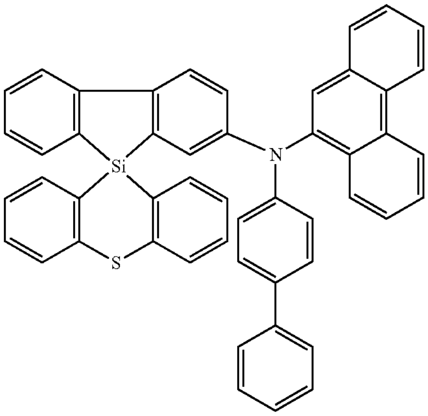
B454
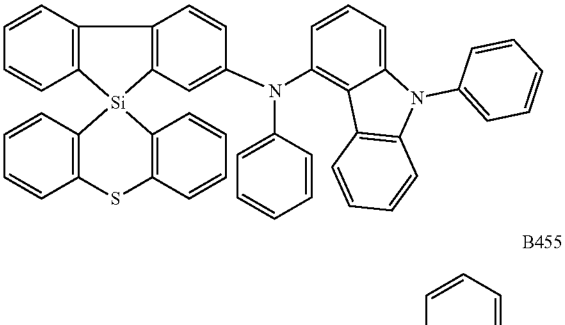
B455
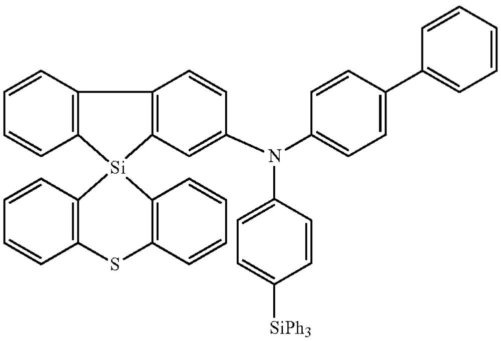

-continued
B456
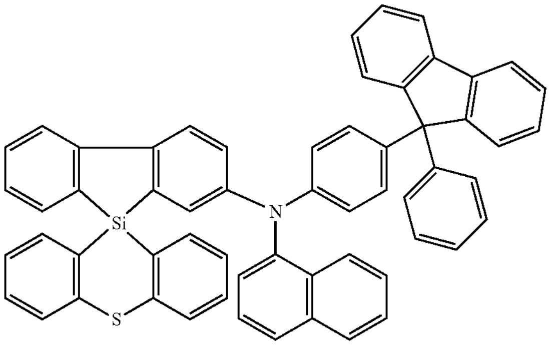
B457
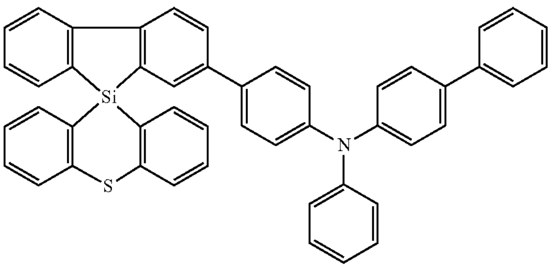
B458
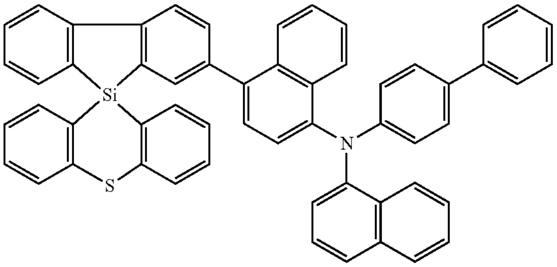
B459
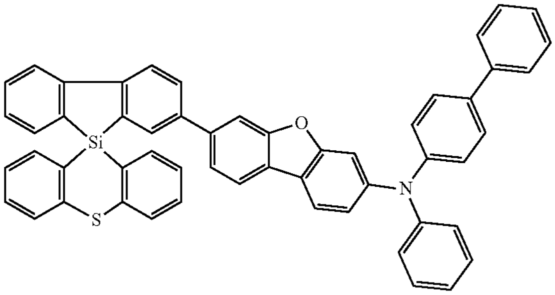
-continued
B460
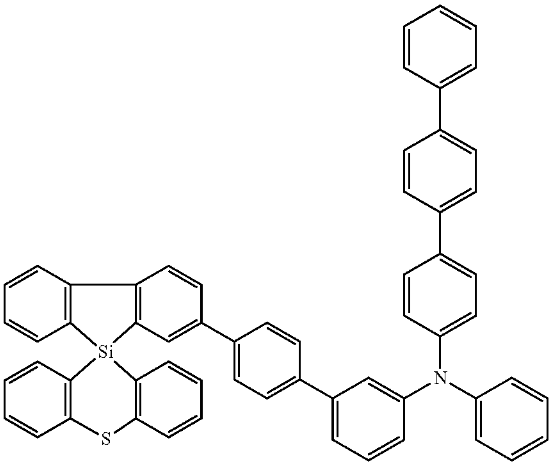
B461
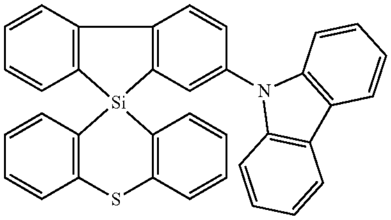
B462
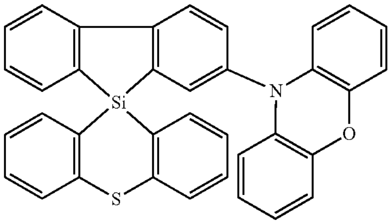
B463
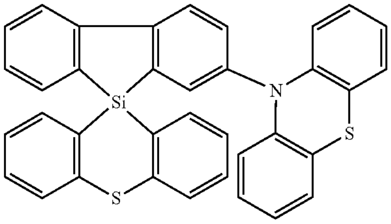
B464
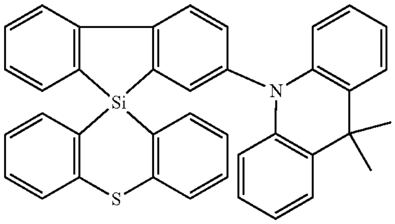

-continued
B101
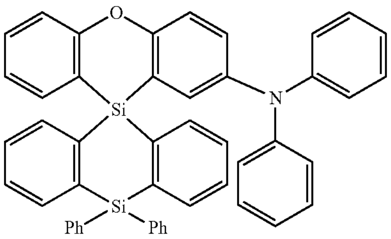
B102
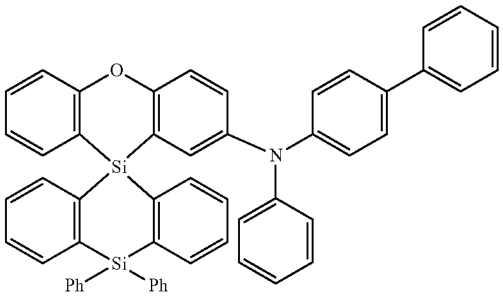
B103
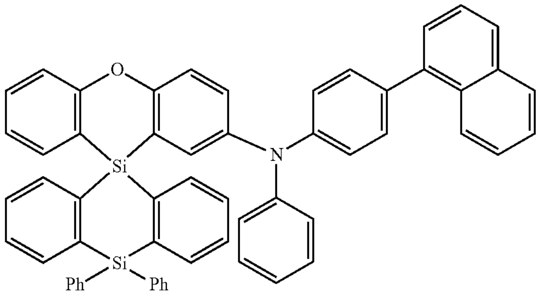
B104
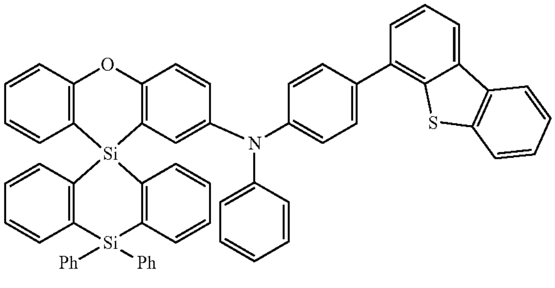
B105
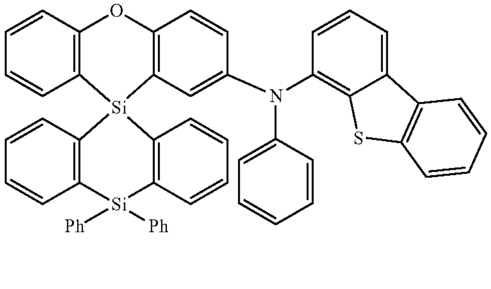
B106
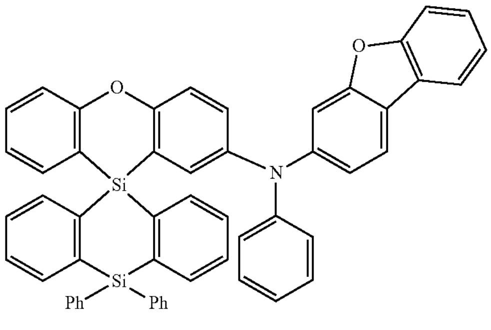
B107
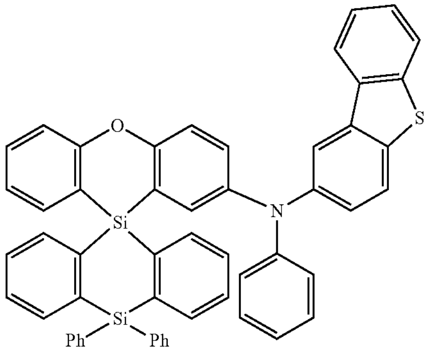
B108
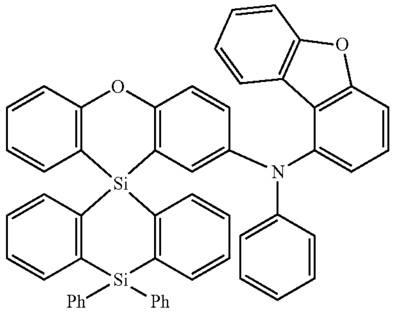
B109
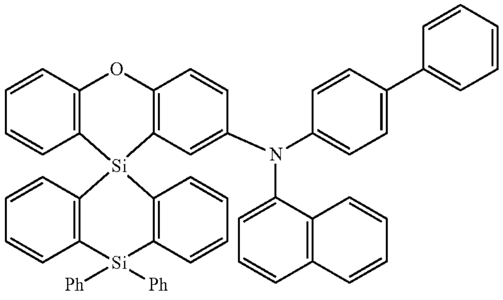

-continued
B110
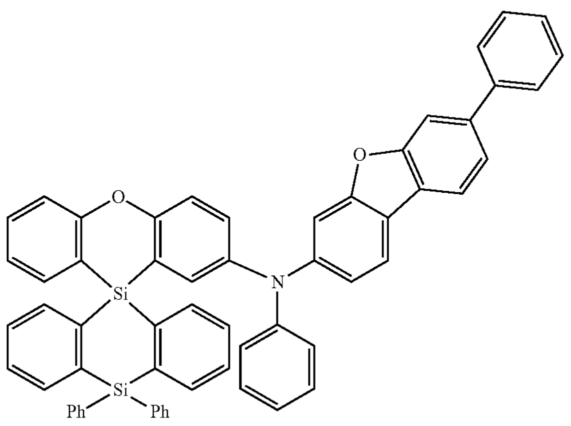
B111
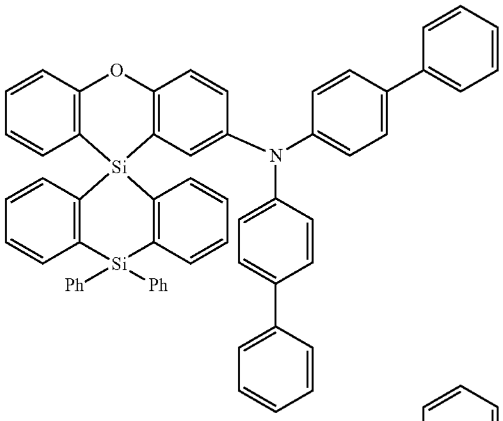
B112
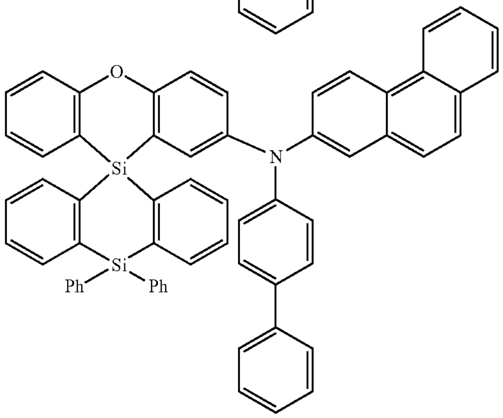
B113
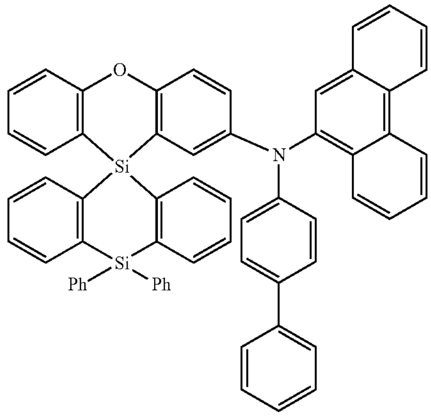
-continued
B114
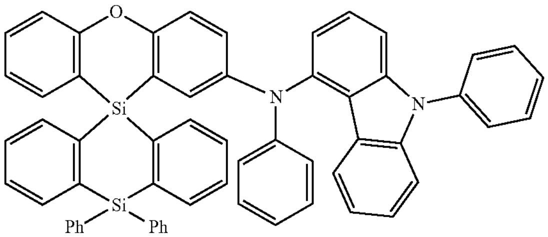
B115
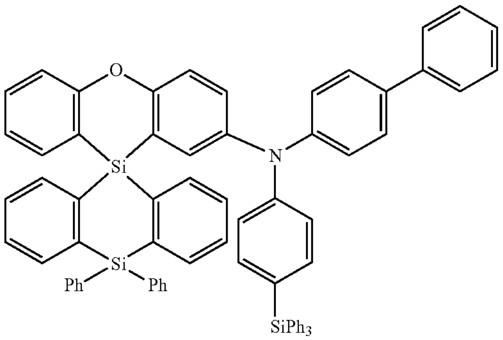
B116
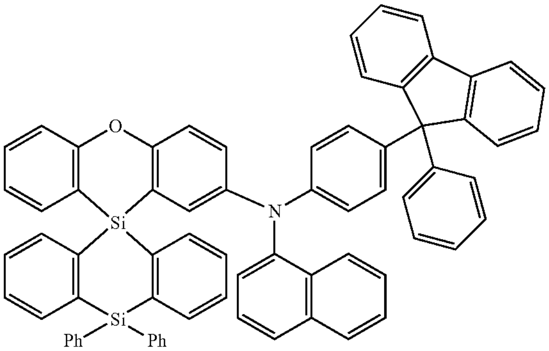
B117
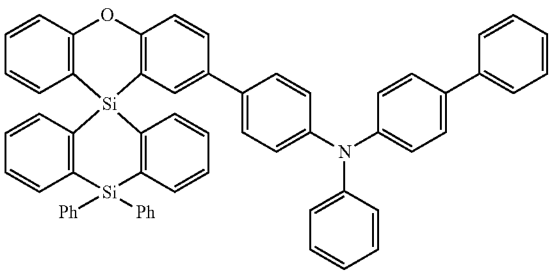
B118
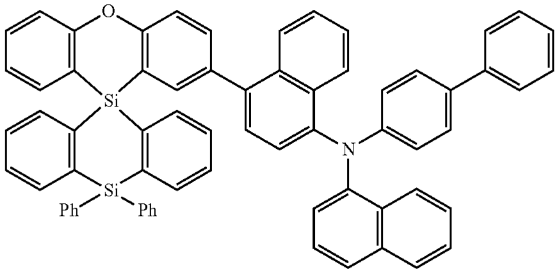

-continued
B119
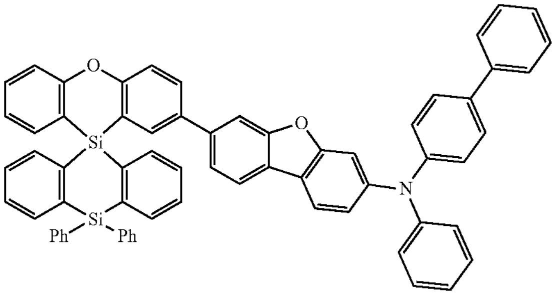
B120
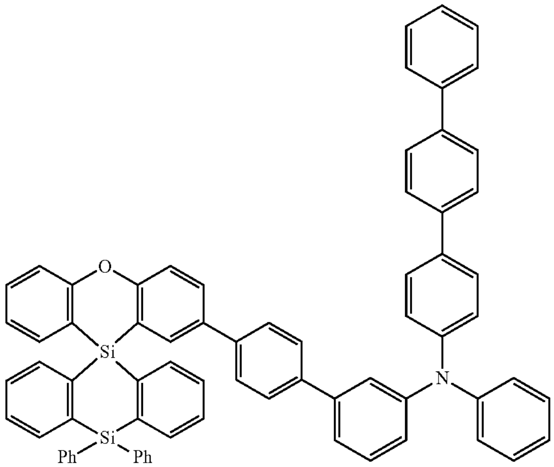
B121
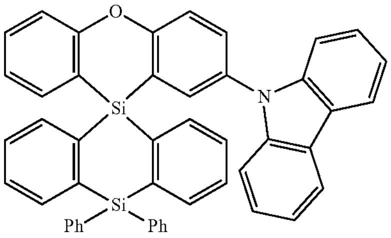
B122
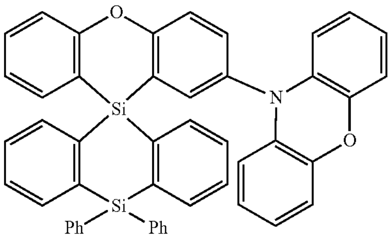
B123
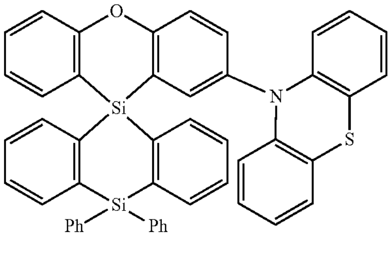
-continued
B124
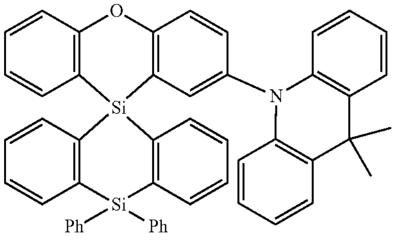
B125
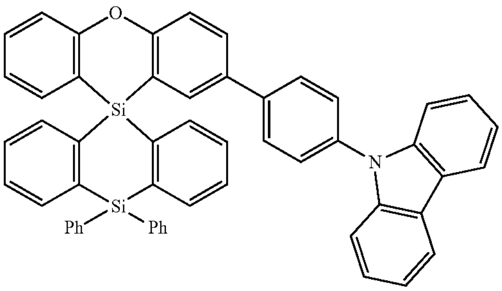
B126
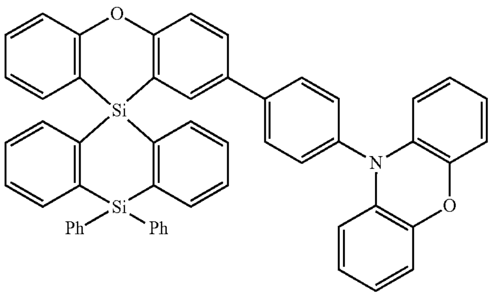
B127
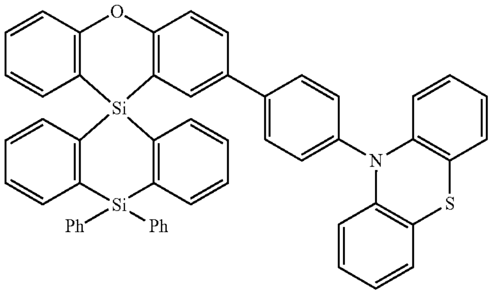
B128
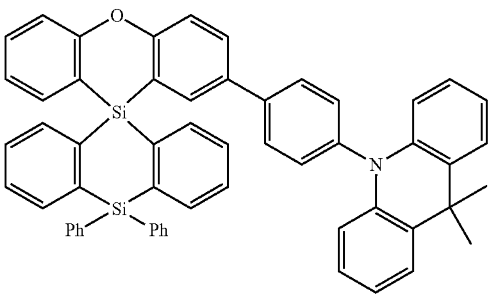

-continued
B129
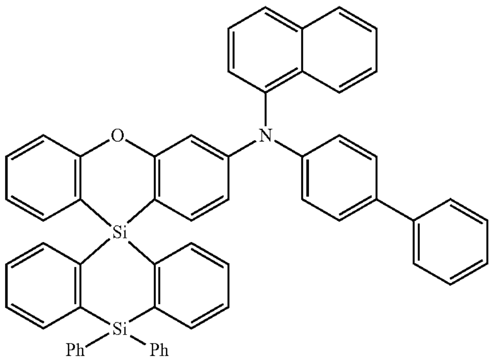
B130
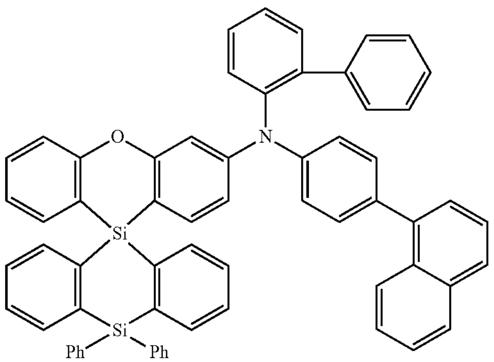
B131
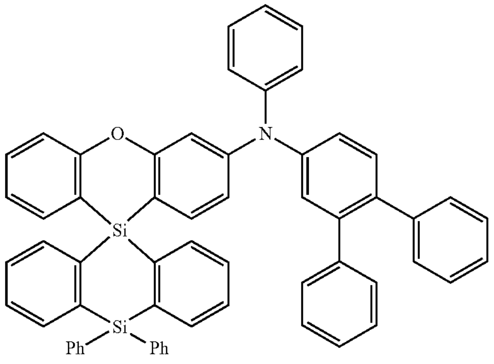
B132
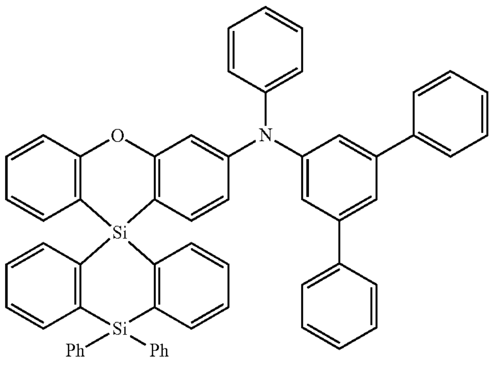
-continued
B133
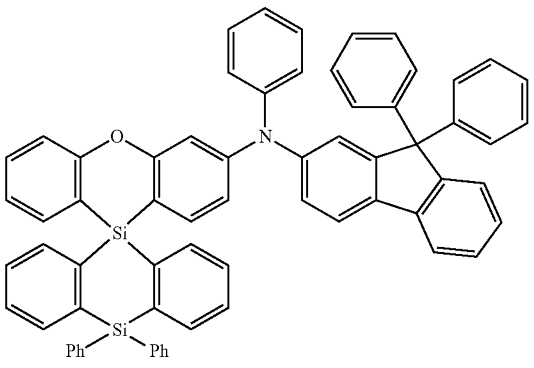
B134
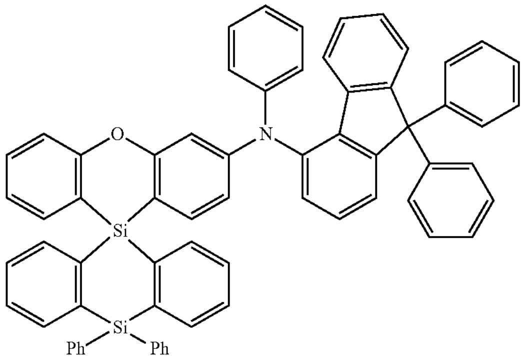
B135
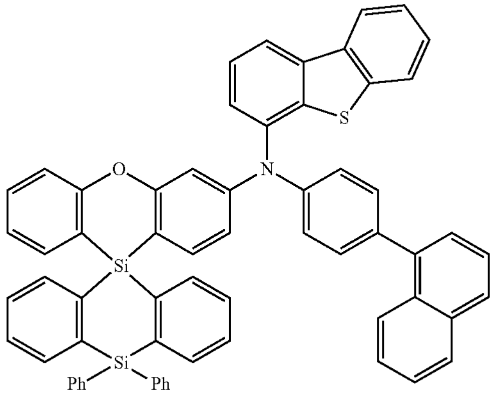
B136
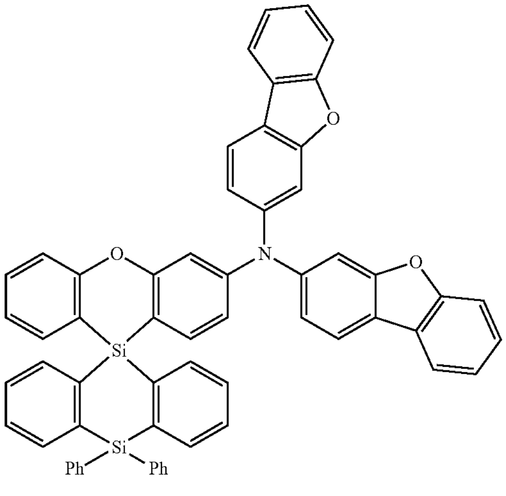

-continued
B137
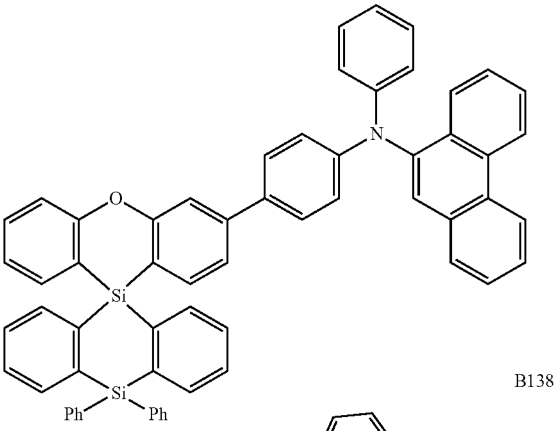
B138
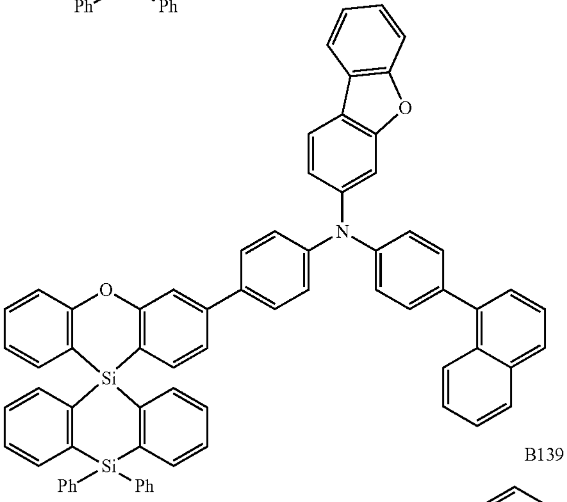
B139
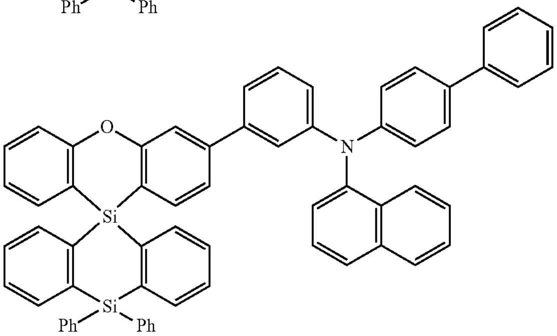
B140
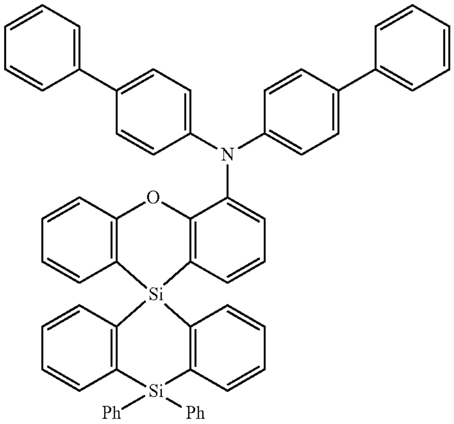
-continued
B141
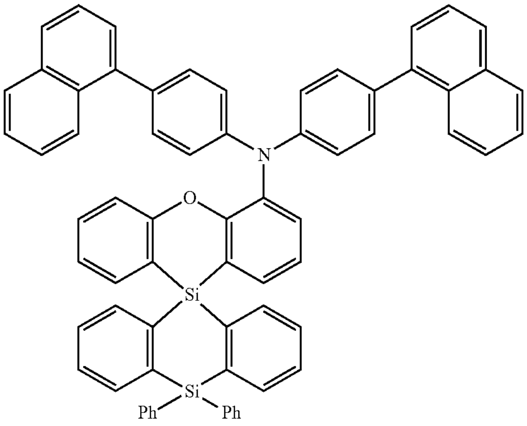
B142
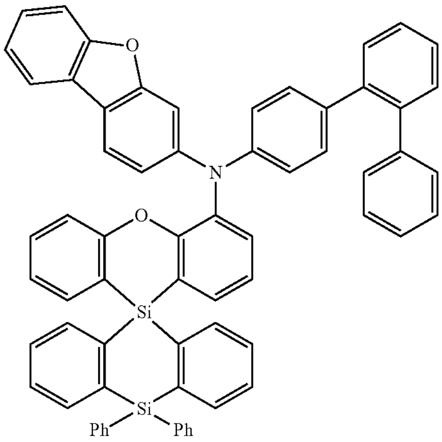
B143
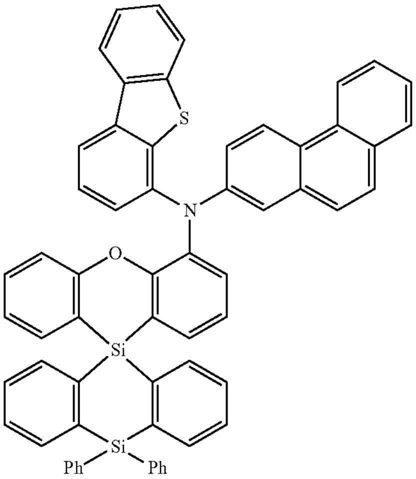

-continued
B144
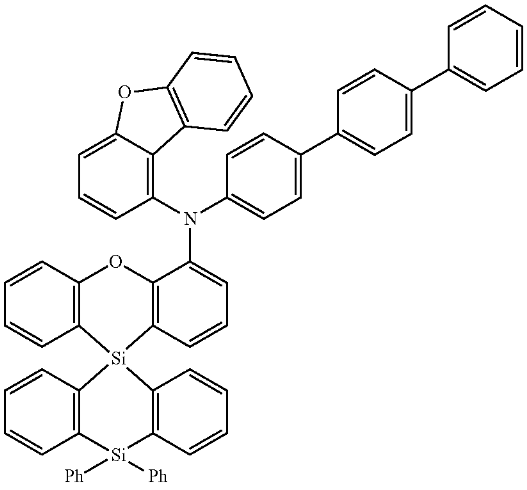
B145
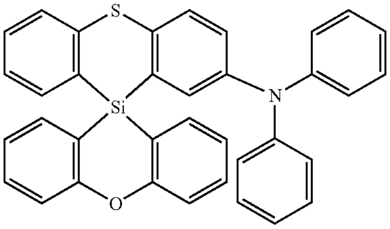
B146
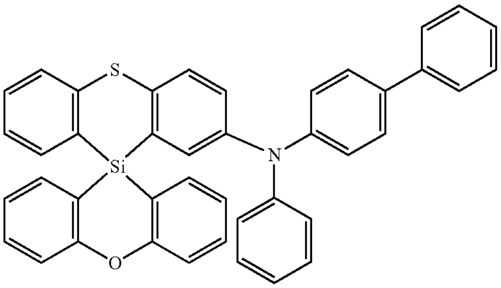
B147
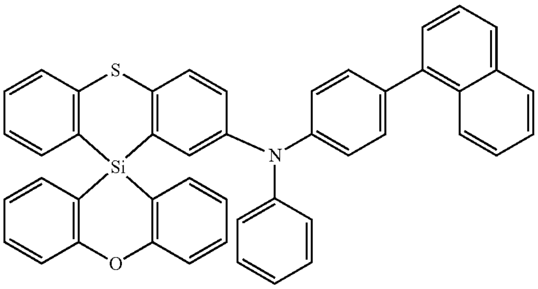
-continued
B148
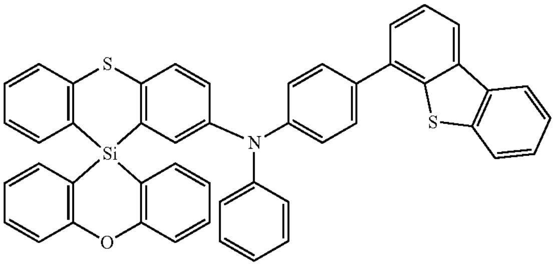
B149
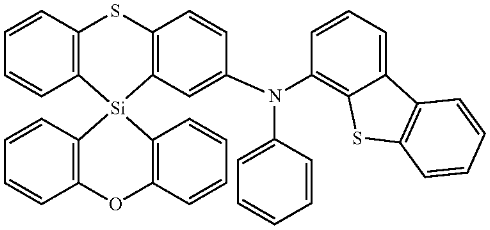
B150
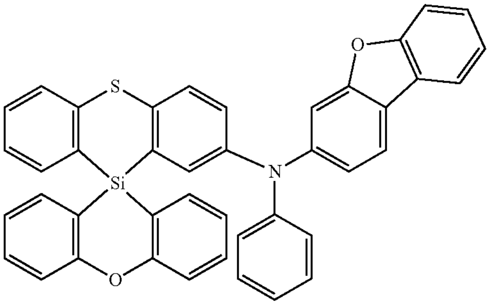
B151
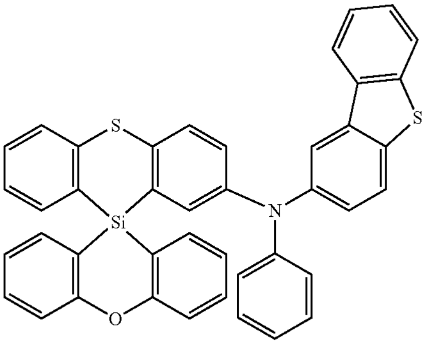
B152
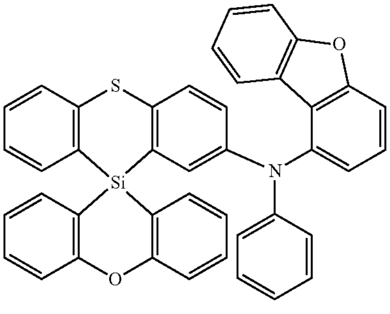

-continued
B153
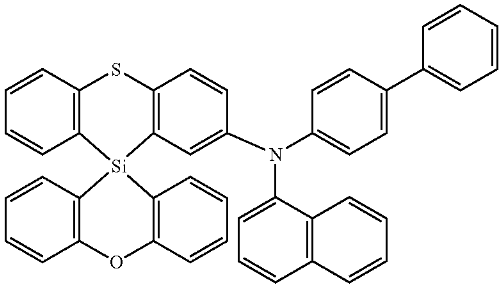
B154
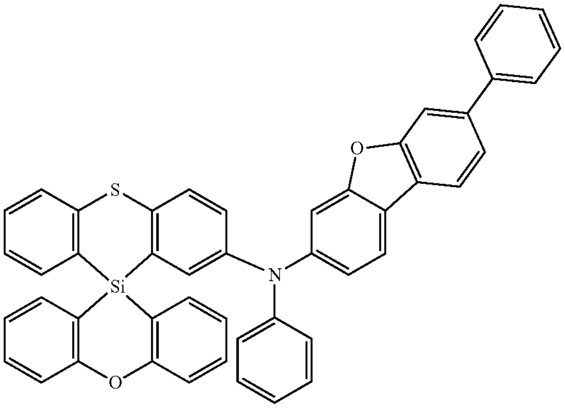
B155
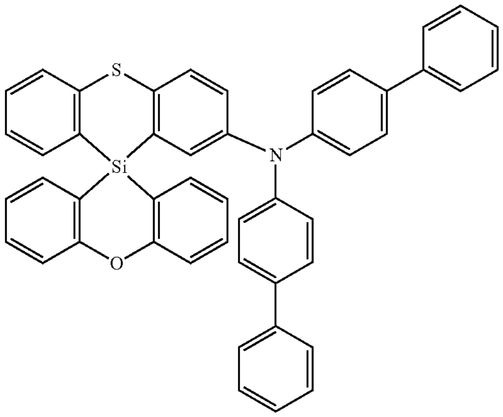
B156
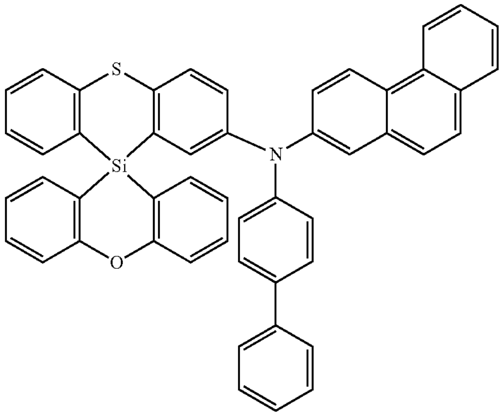
-continued
B157
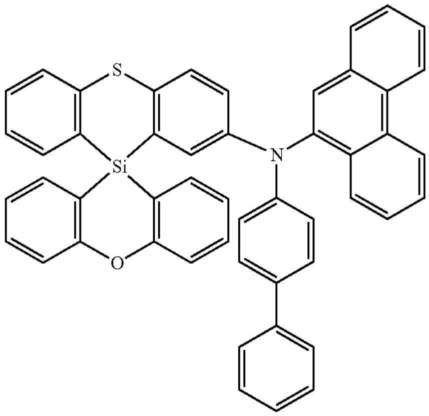
B158
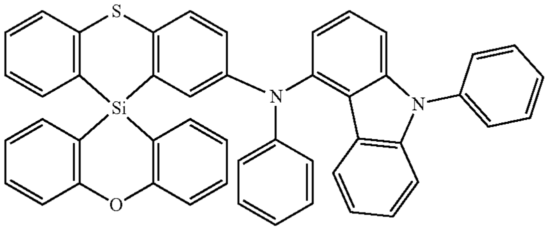
B159
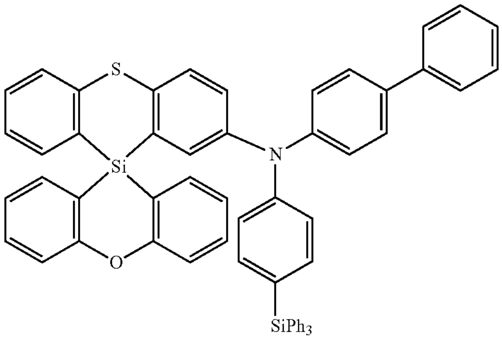
B160
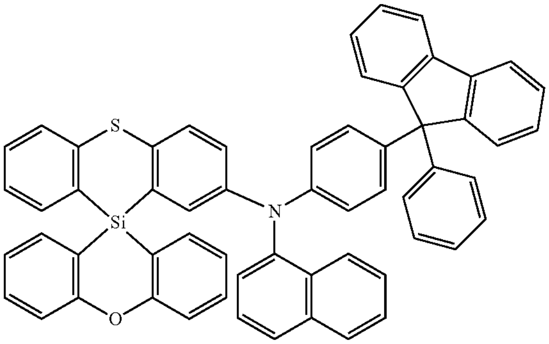

-continued
B161
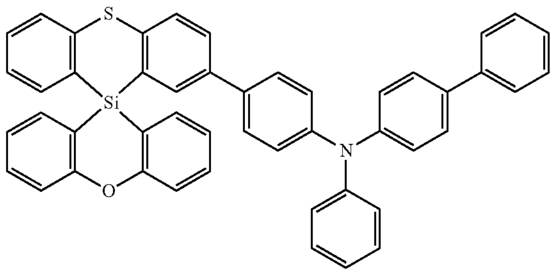
B162
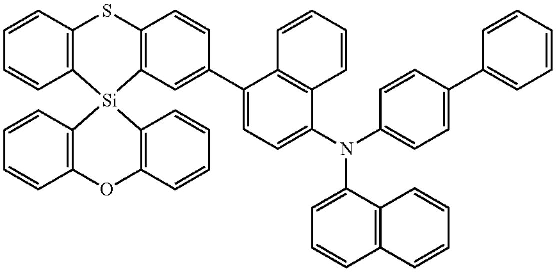
B163
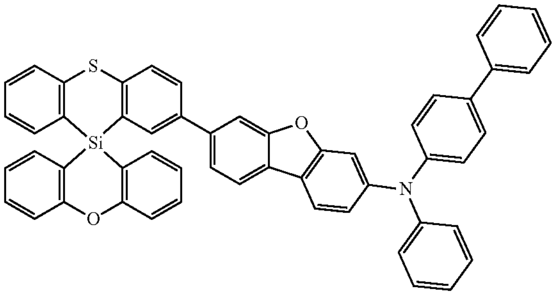
B164
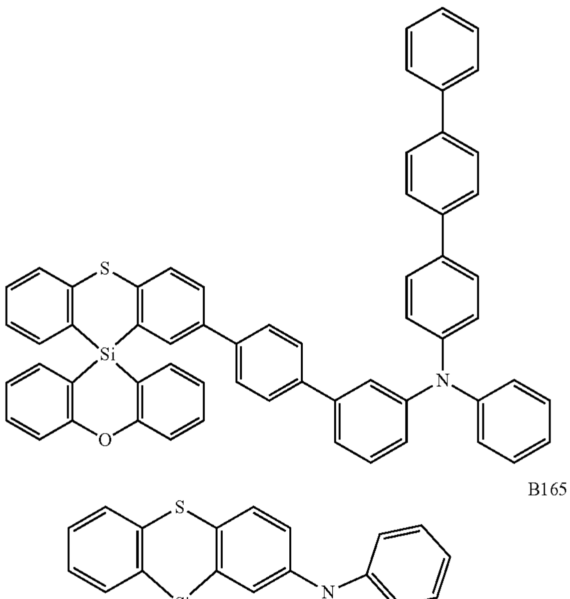
B165
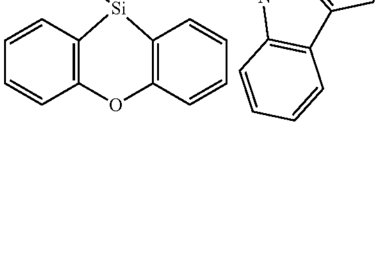
-continued
B166
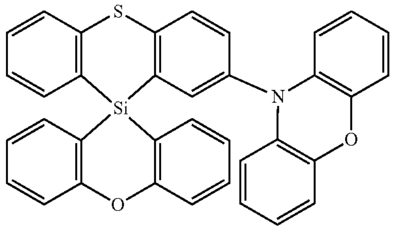
B167
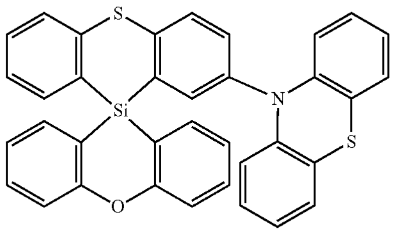
B168
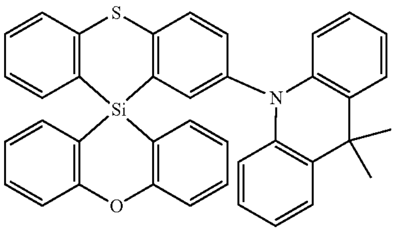
B169
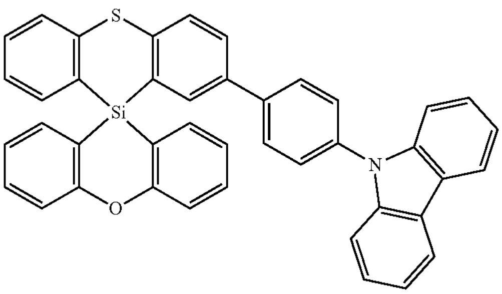
B170
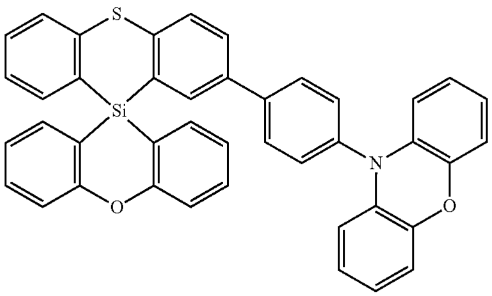
B171
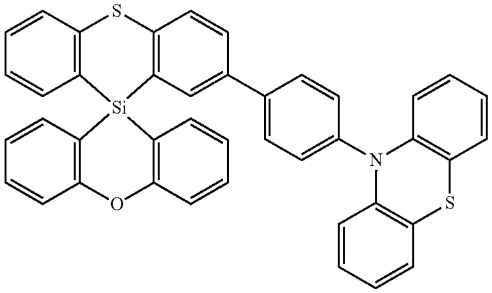

-continued
B172
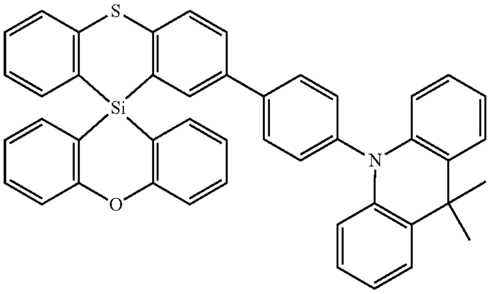
B173
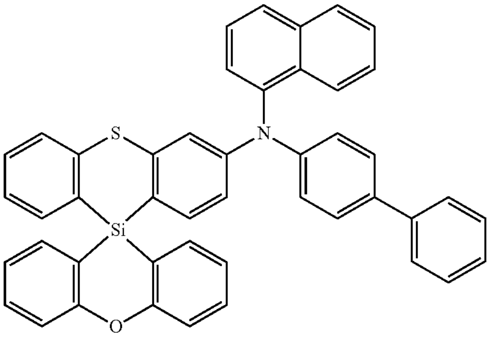
B174
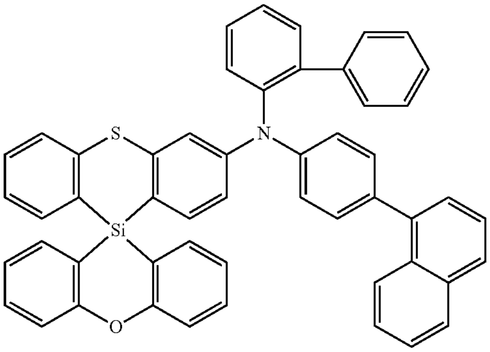
B175
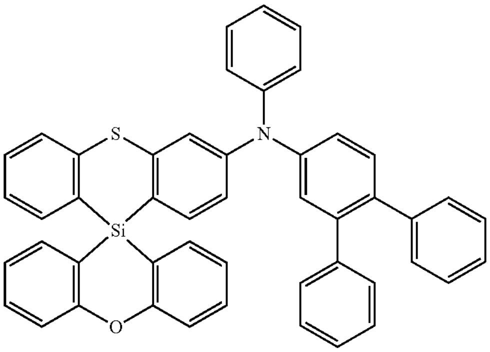
-continued
B176
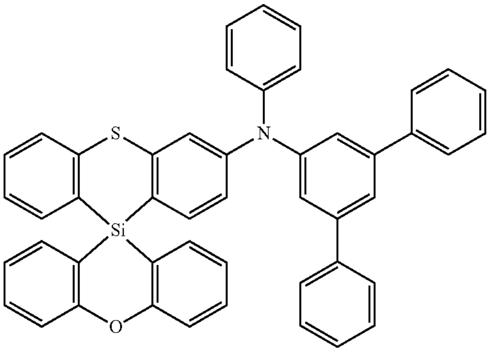
B177
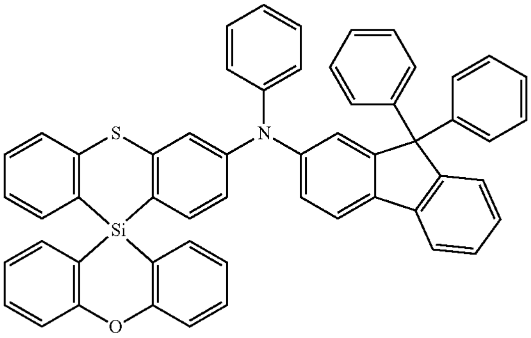
B178
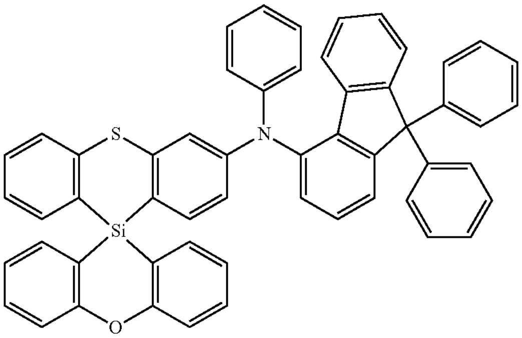
B179
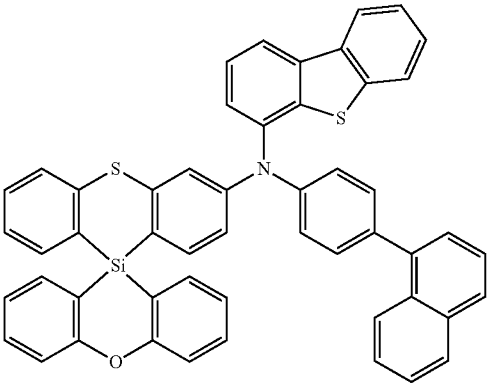

-continued
B180
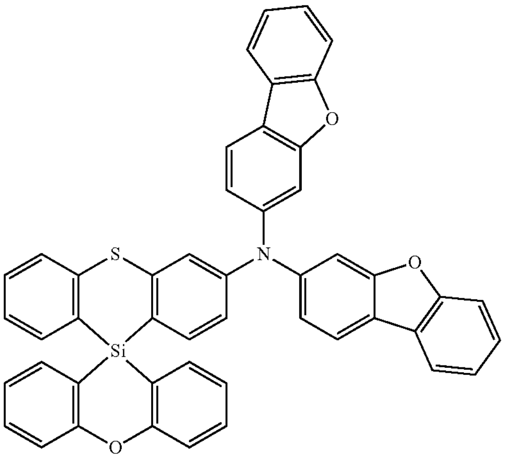
B181
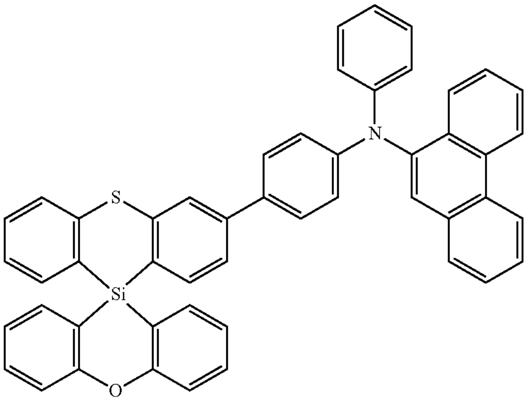
B182
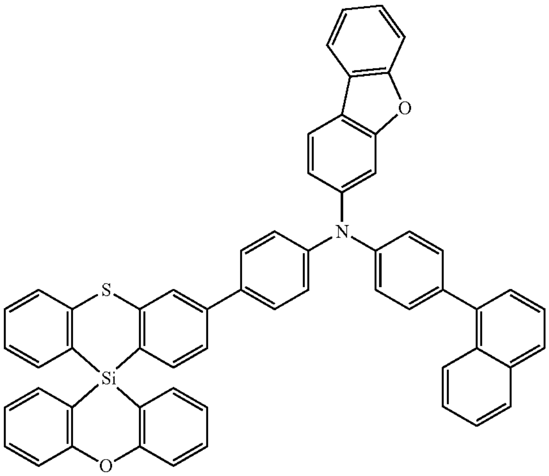
-continued
B183
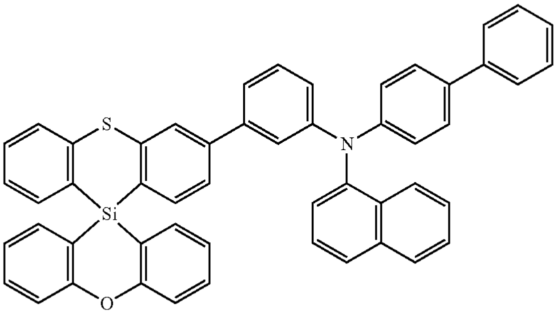
B184
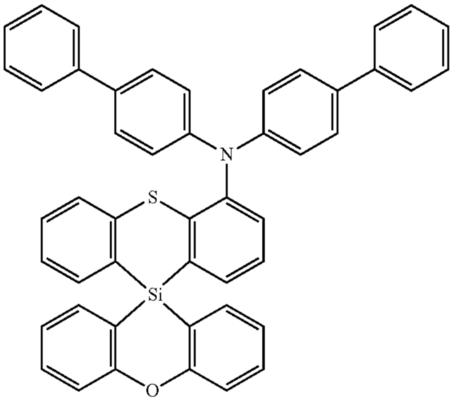
B185
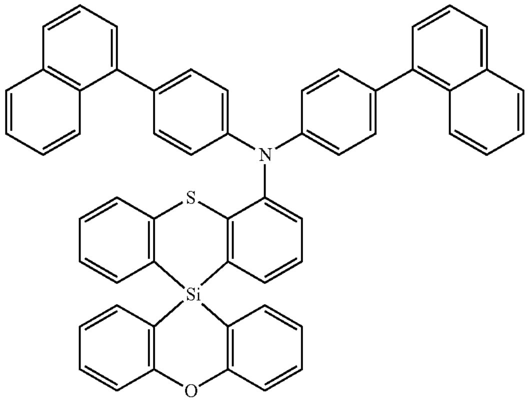
B186
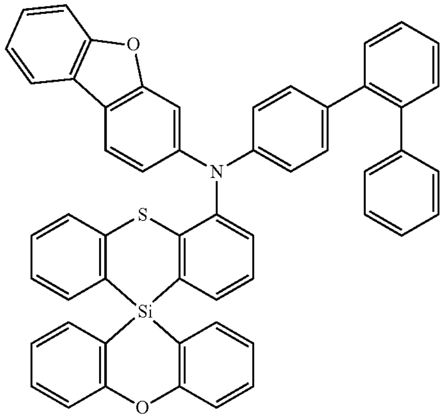

-continued
-continued
B187
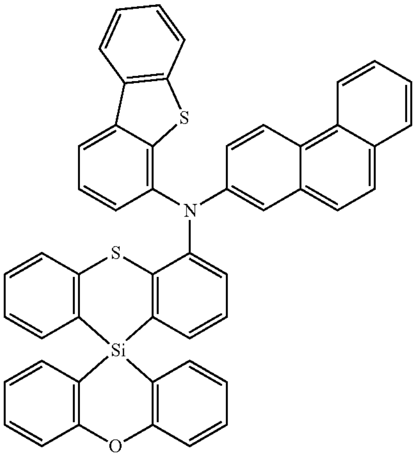
B188
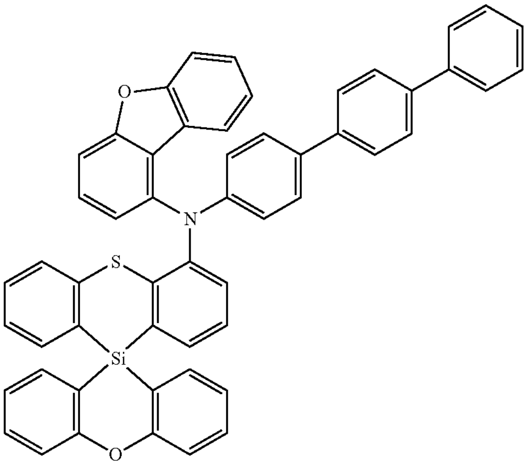
B189
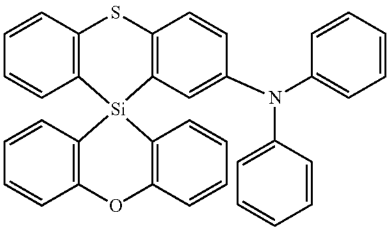
B190
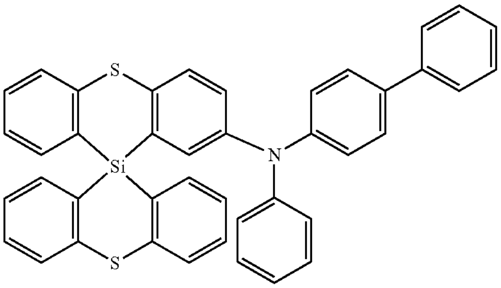
B191
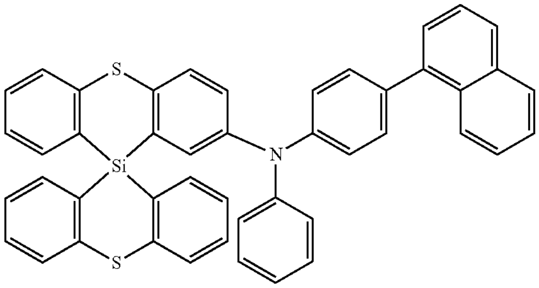
B192
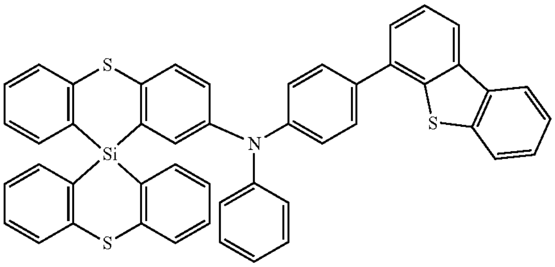
B193
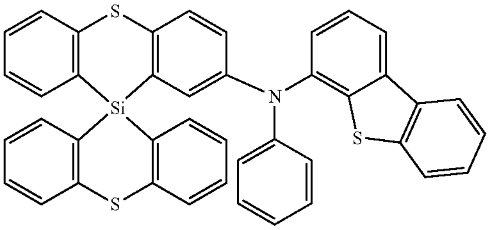
B194
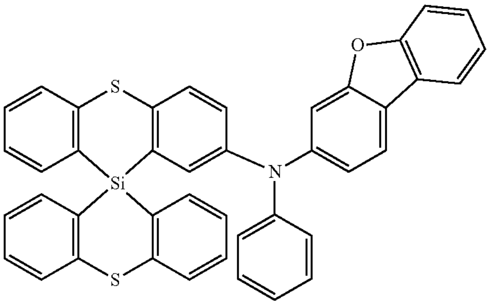
B195
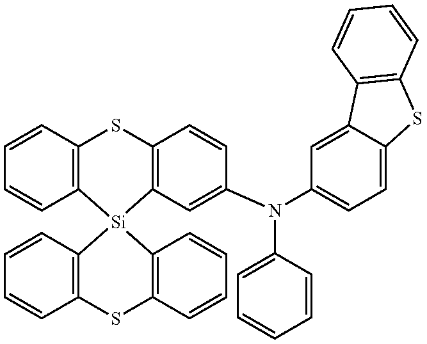

-continued
B196
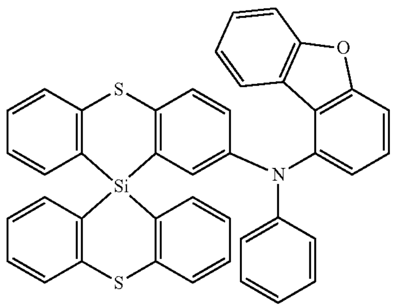
B197
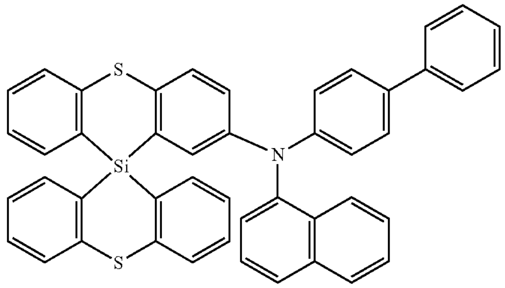
B198
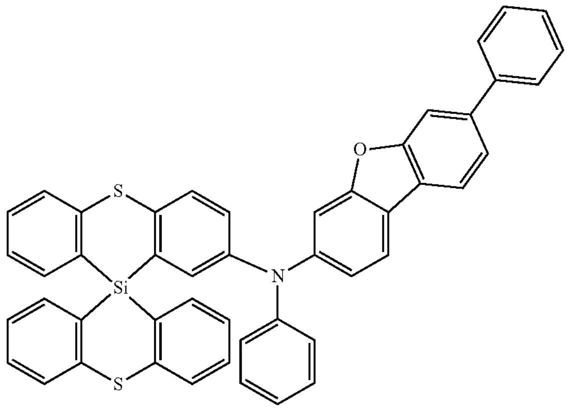
B199
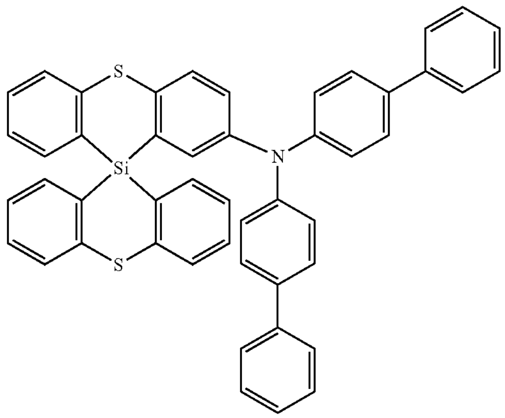
-continued
B200
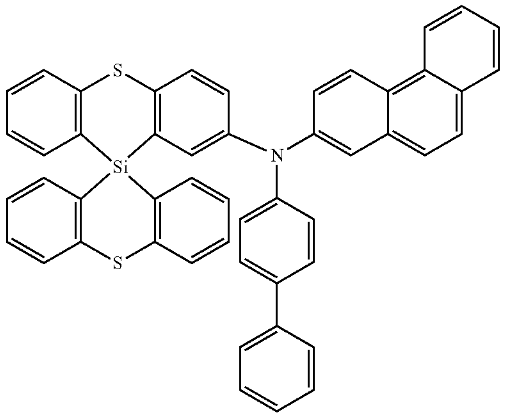
B201
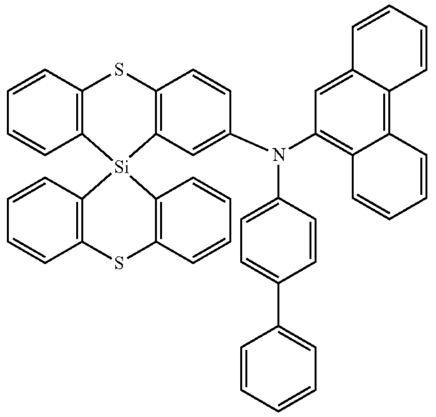
B202
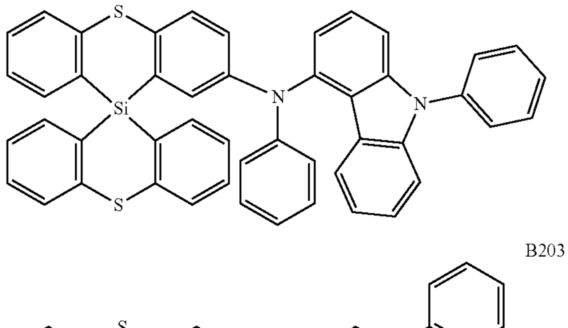
B203
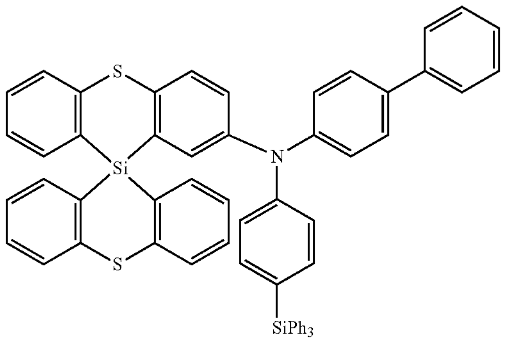

-continued
B204
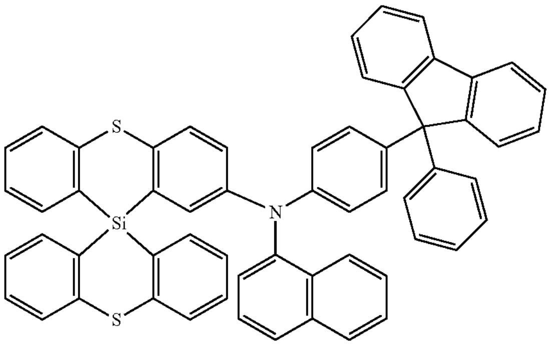
B205
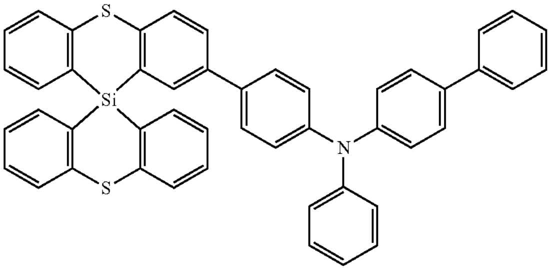
B206
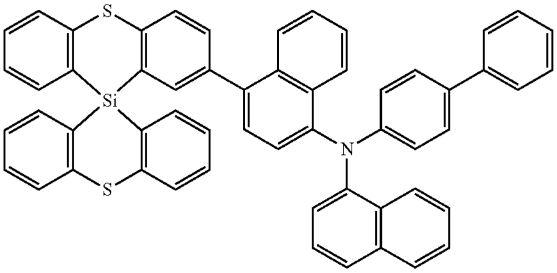
B207
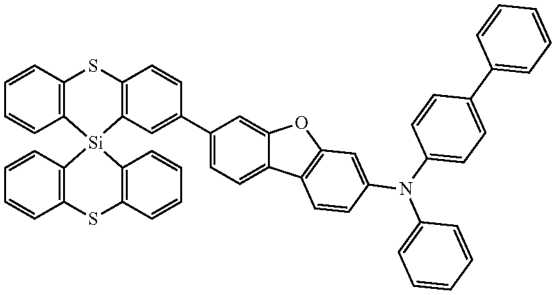
-continued
B208
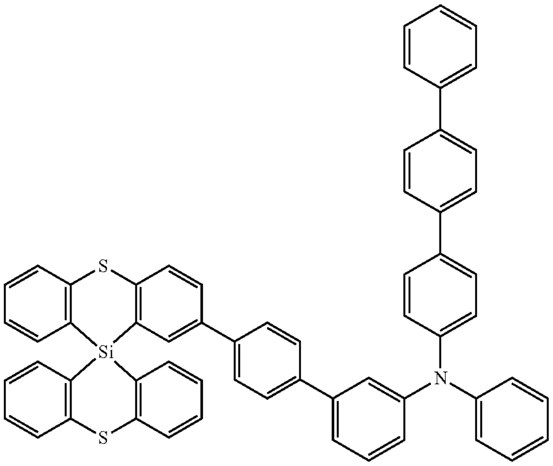
B209
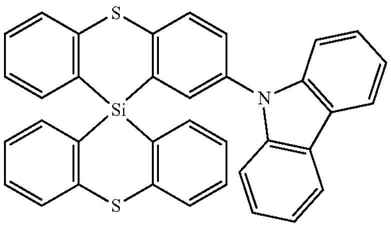
B210
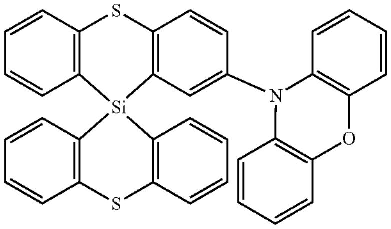
B211
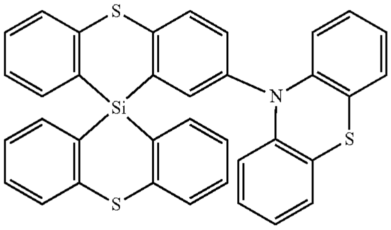
B212
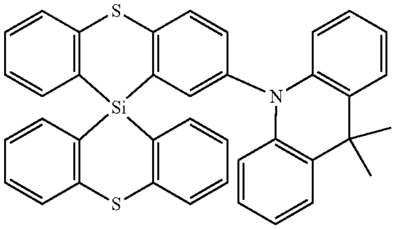

-continued
B213
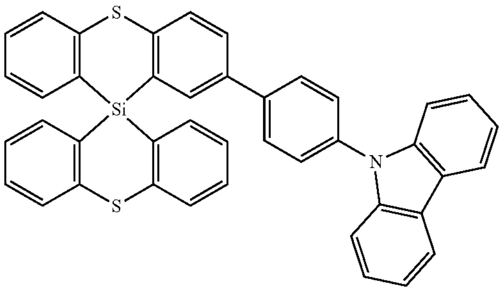
B214
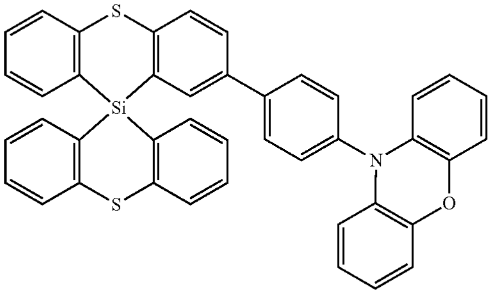
B215
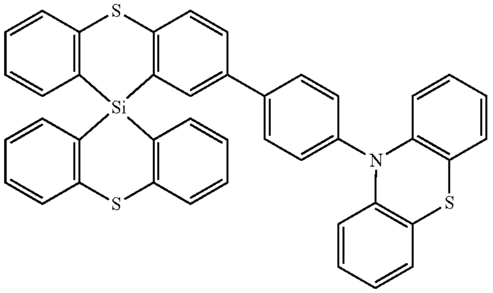
B216
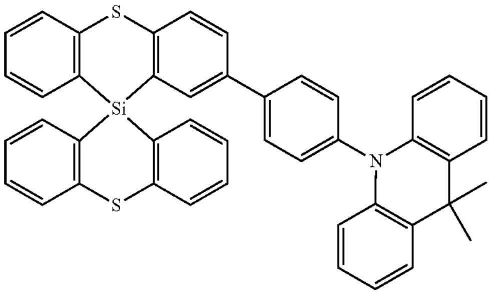
B217
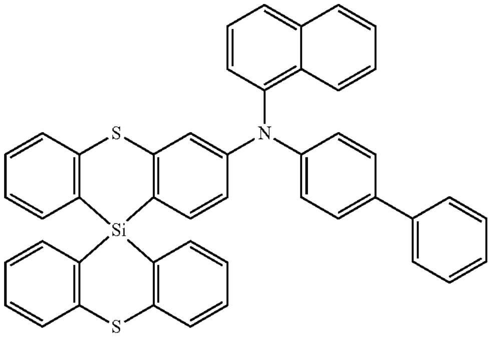
-continued
B218
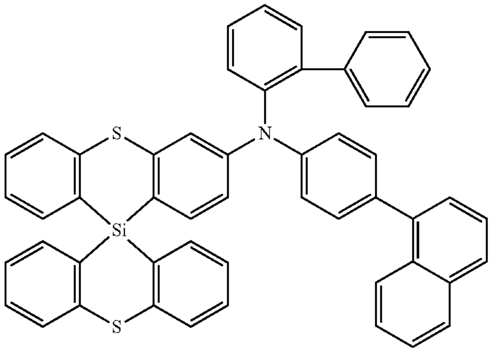
B219
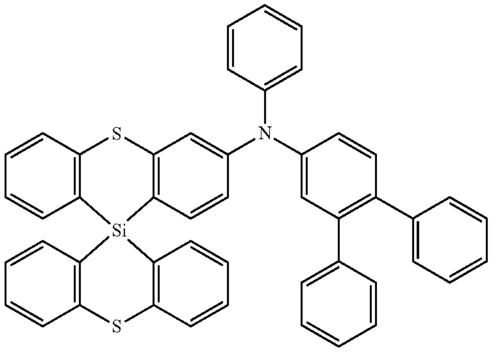
B220
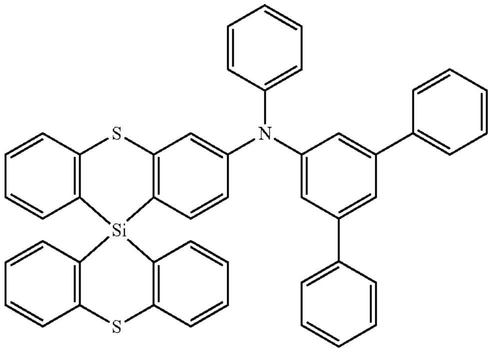
B221
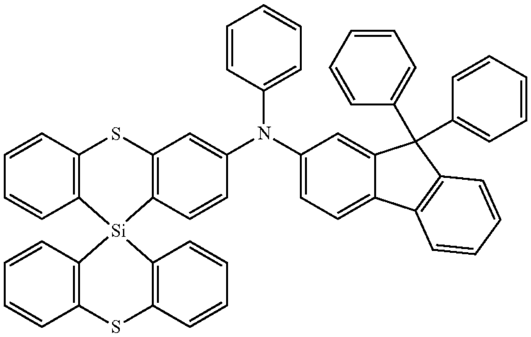

-continued
B222
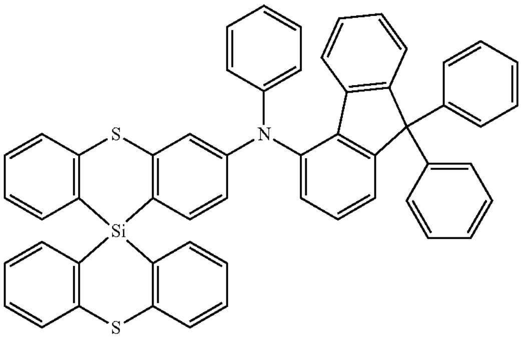
B223
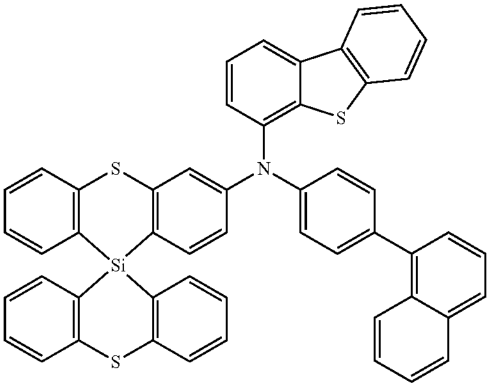
B224
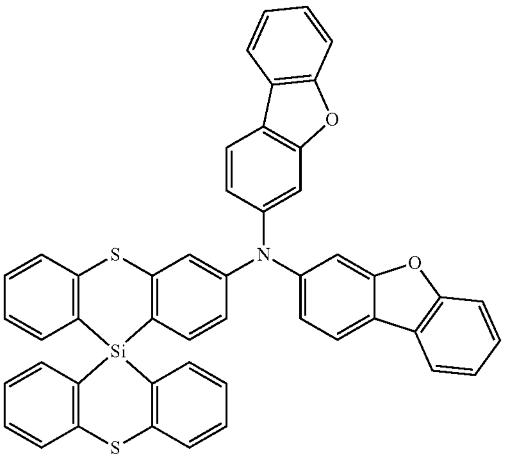
B225
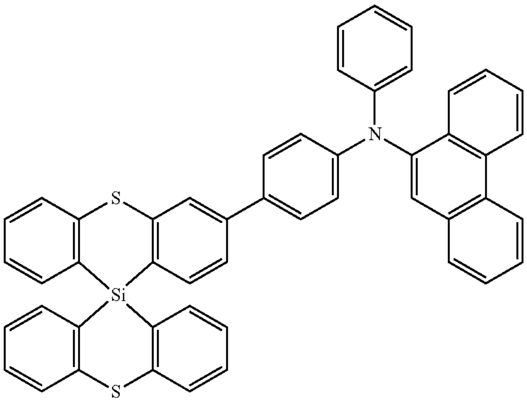
-continued
B226
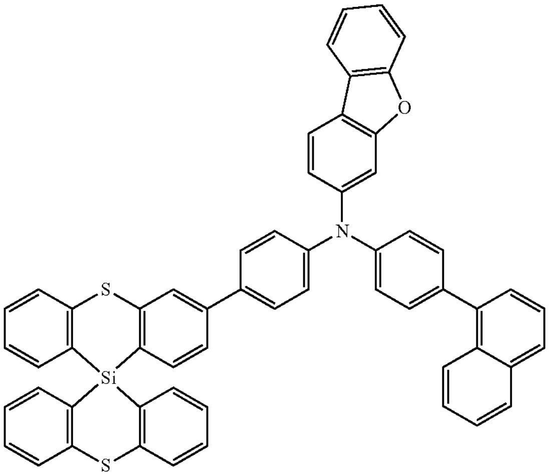
B227
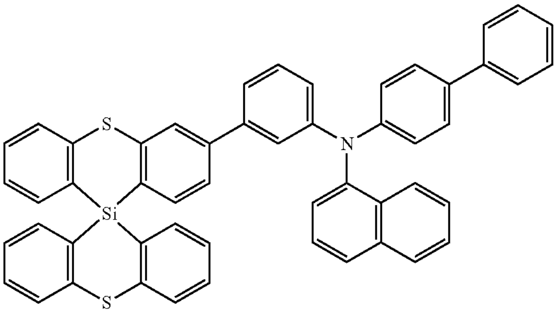
B228
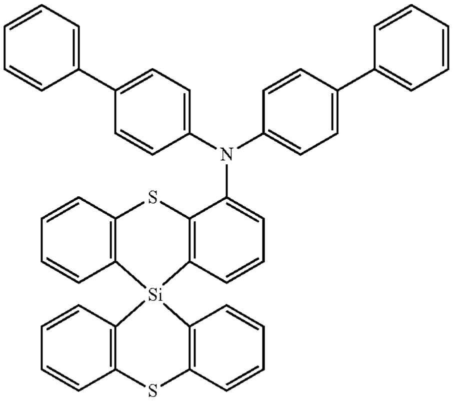
B229
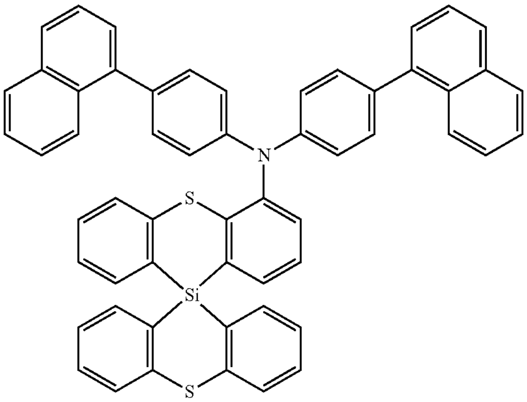

-continued
B230
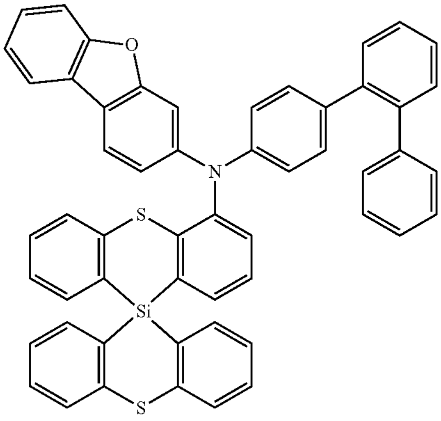
B231
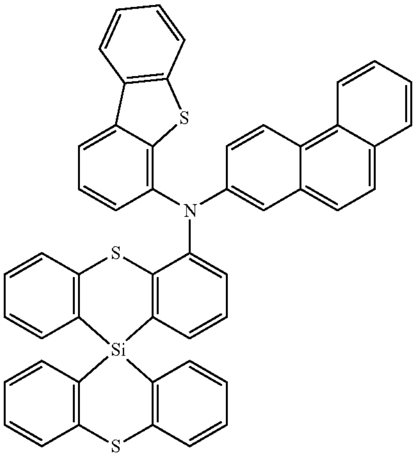
B232
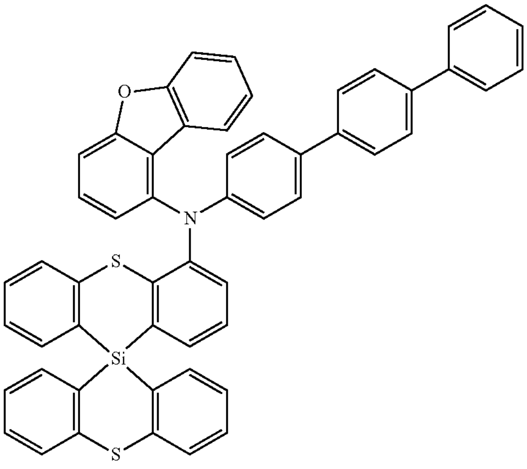
B233
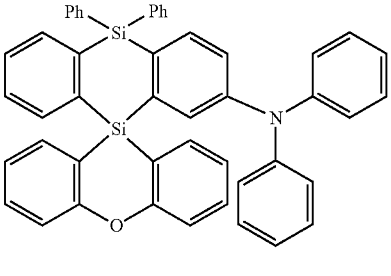
-continued
B234
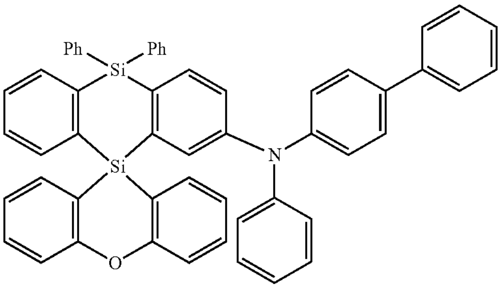
B235
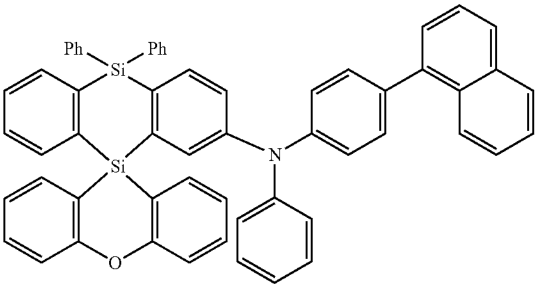
B236
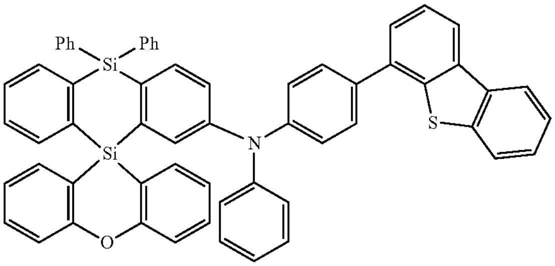
B237
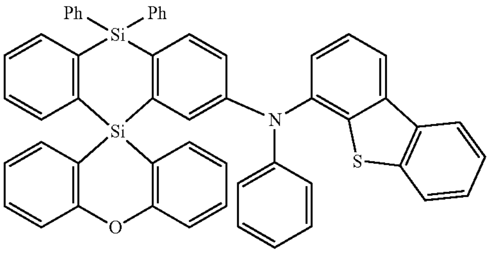
B238
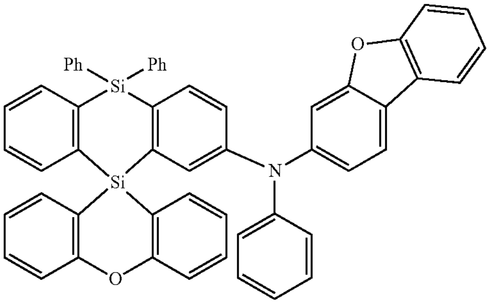

-continued
B239
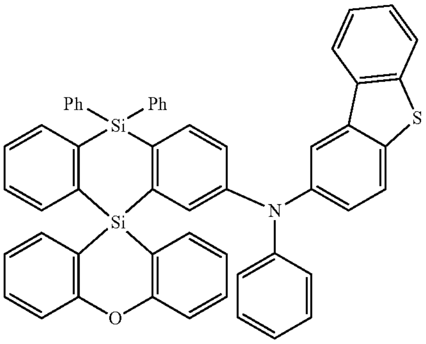
B240
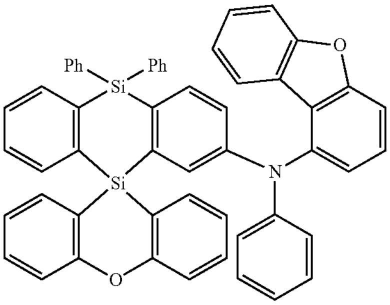
B241
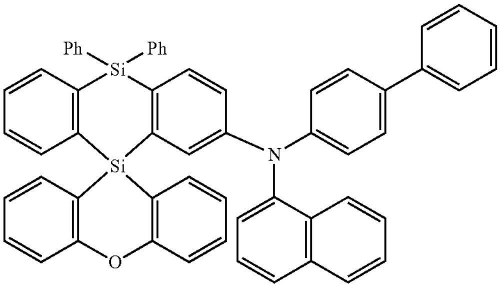
B242
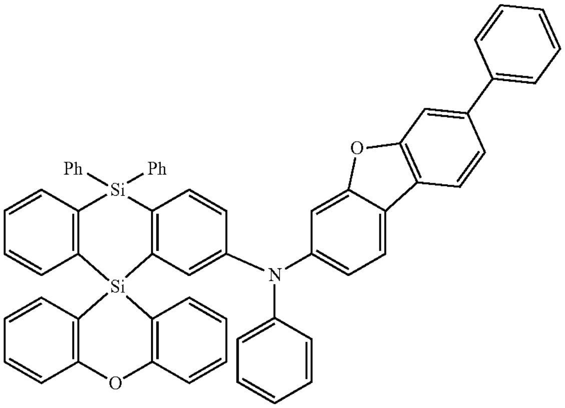
-continued
B243
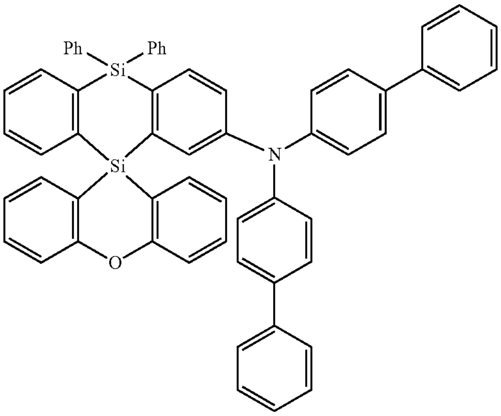
B244
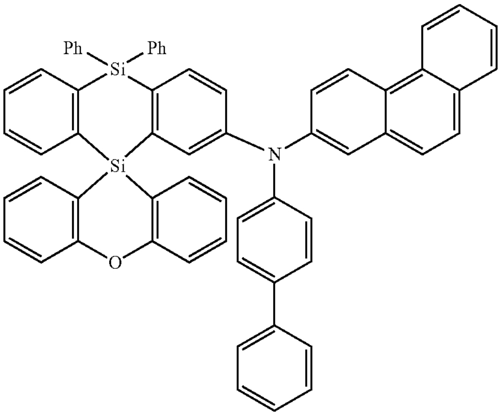
B245
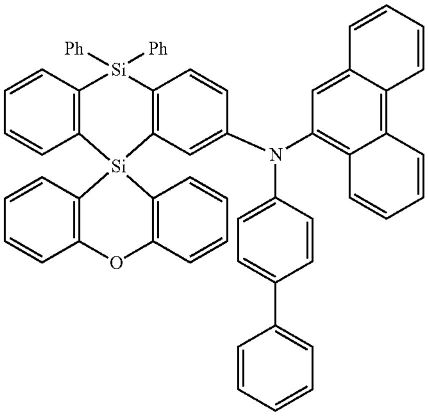
B246
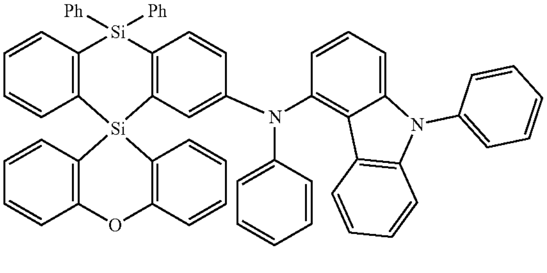

-continued
B247
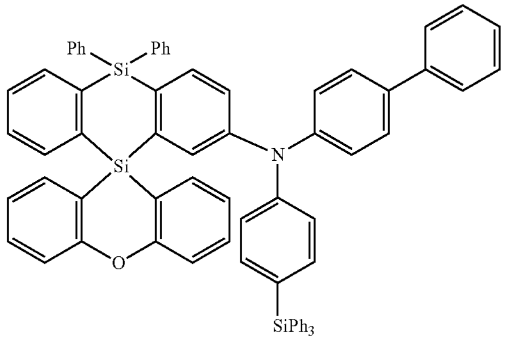
B248
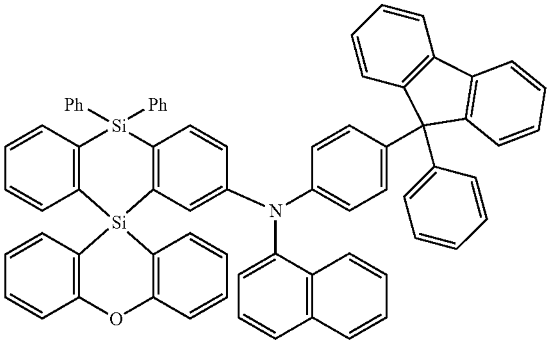
B249
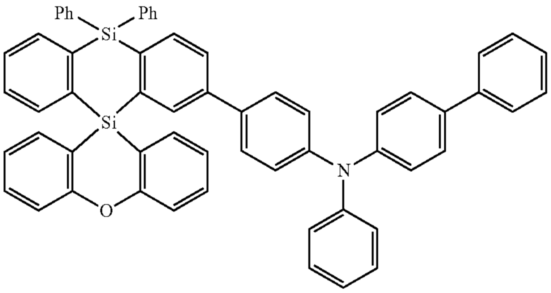
B250
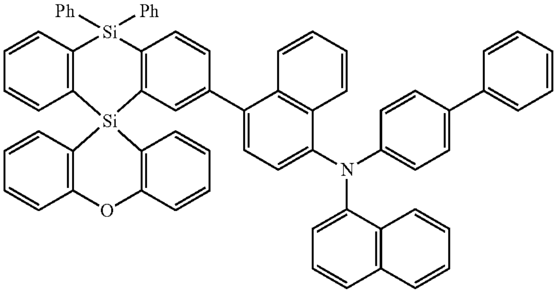
-continued
B251
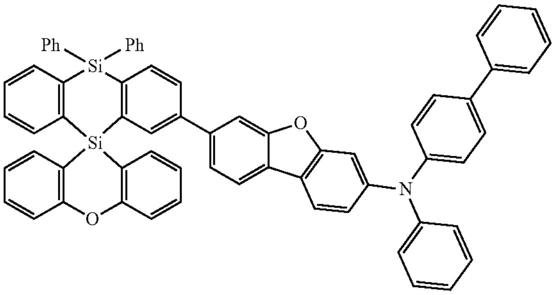
B252
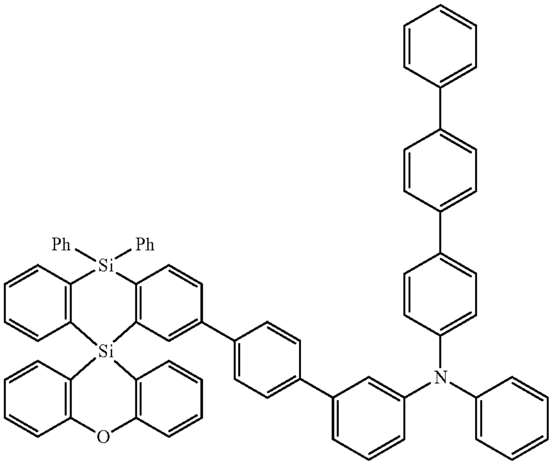
B253
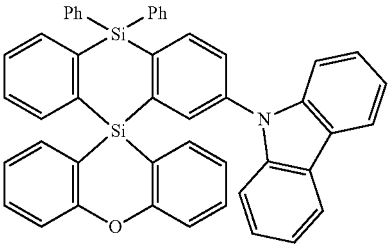
B254
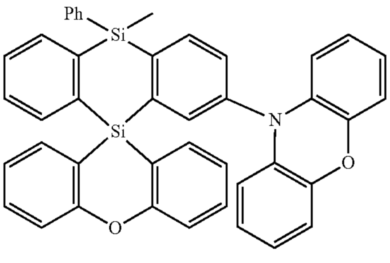
B255
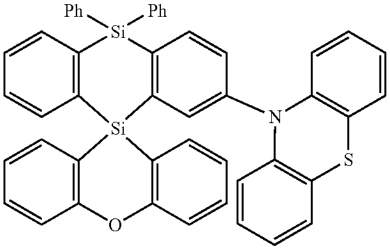

-continued
B256
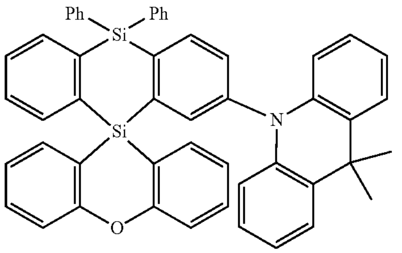
B257
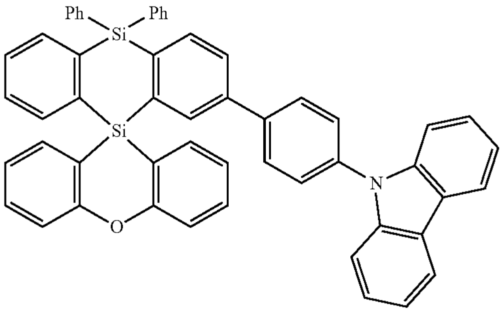
B258
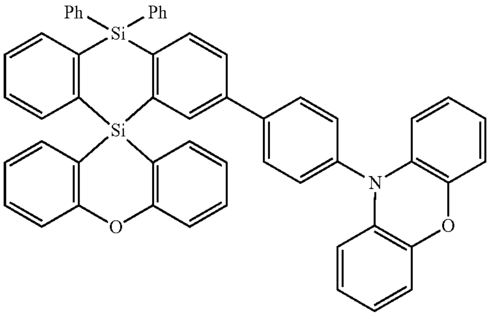
B259
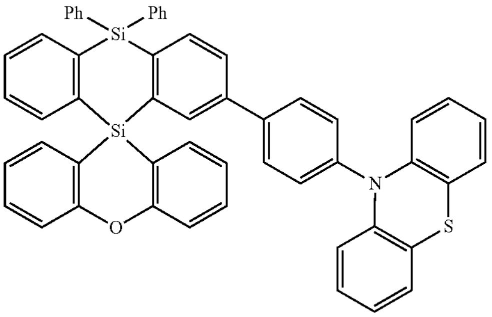
B260
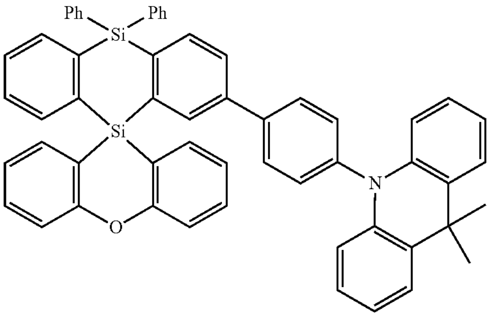
-continued
B261
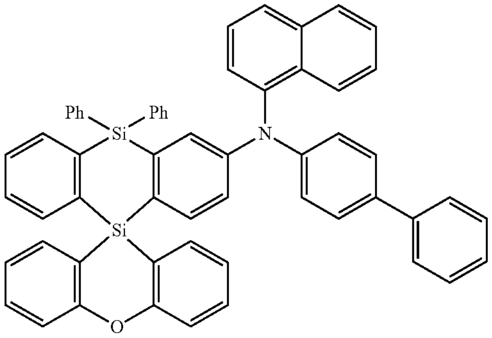
B262
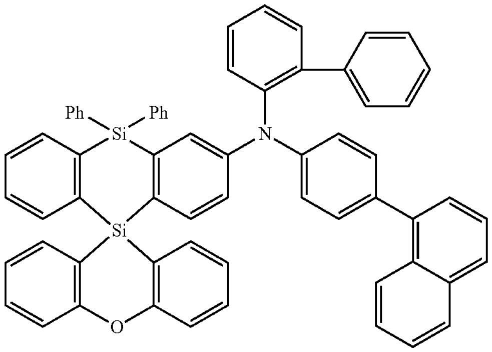
B263
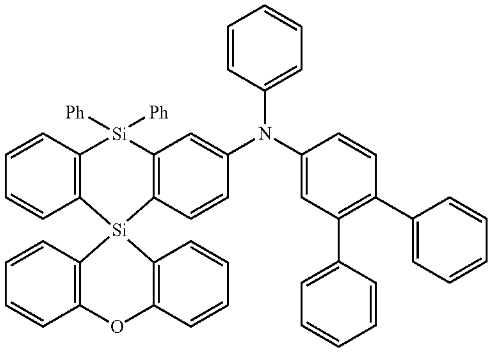
B264
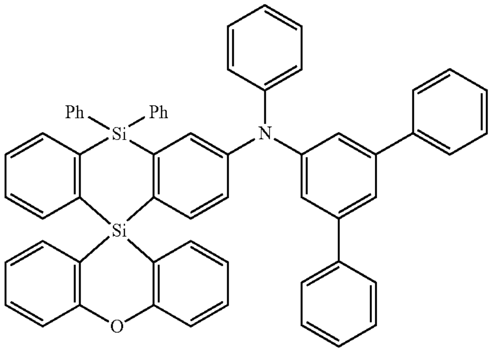

-continued
B265
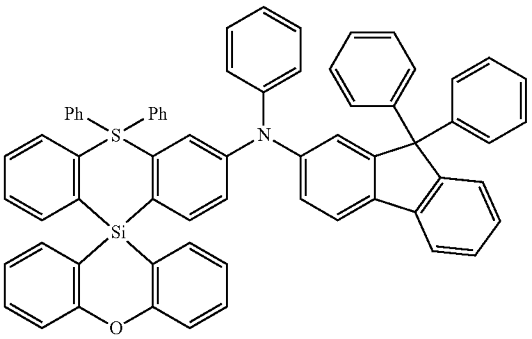
B266
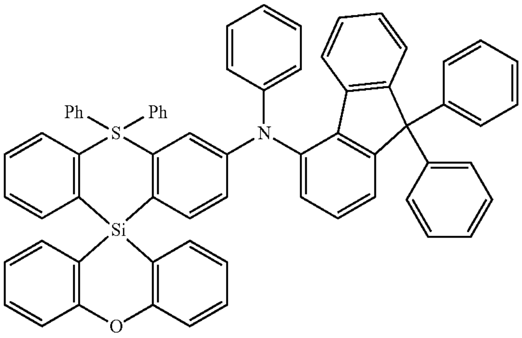
B267
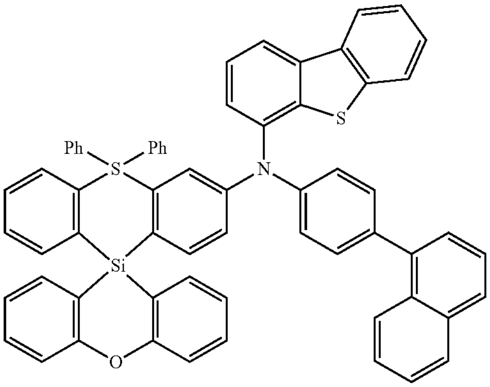
B268
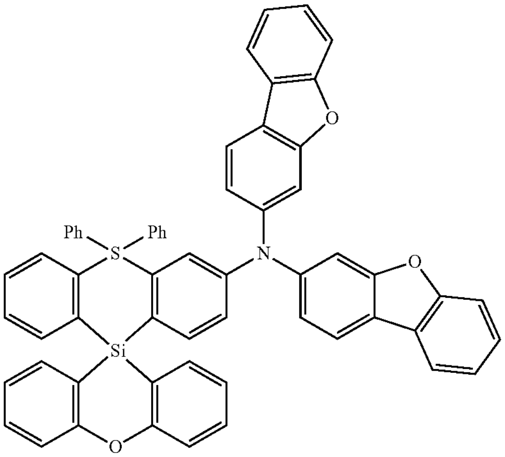
-continued
B269
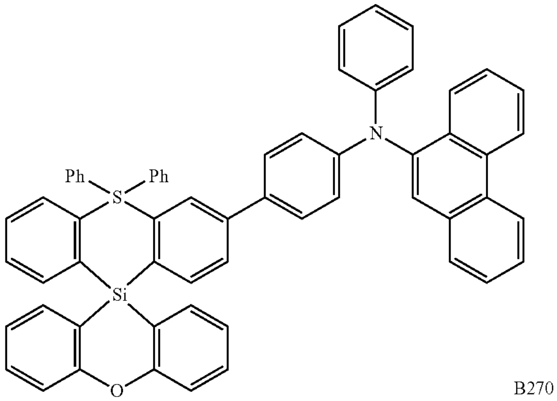
B270
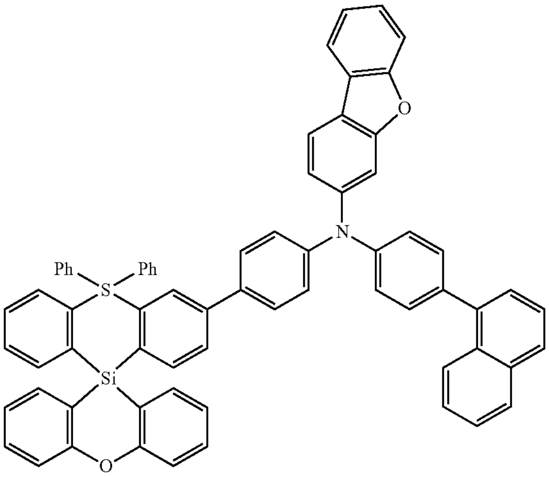
B271
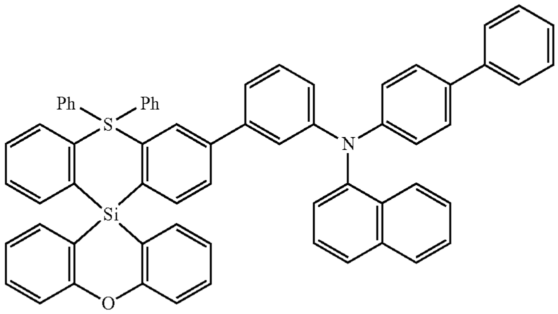
B272
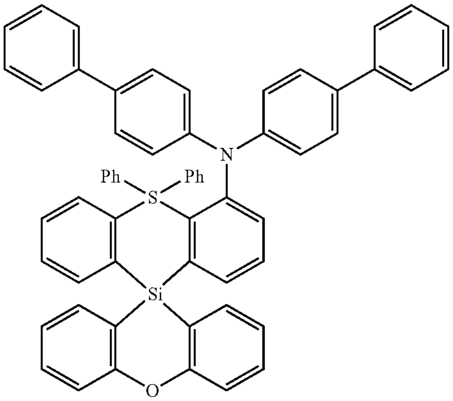

-continued
B273
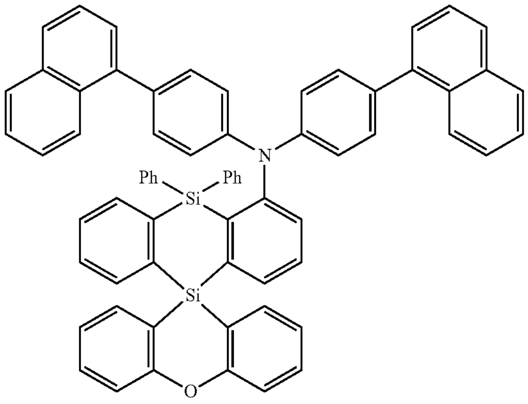
B274
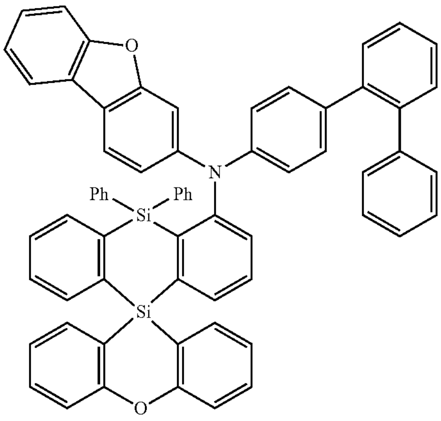
B275
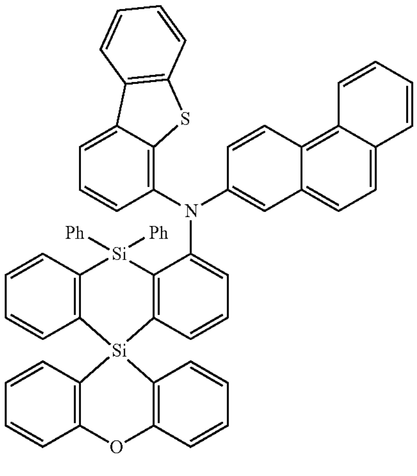
-continued
B276
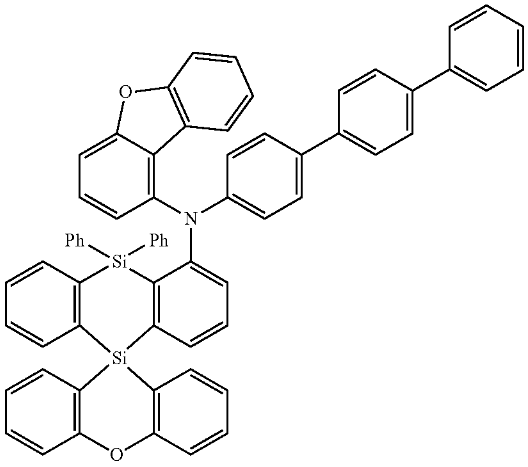
B277
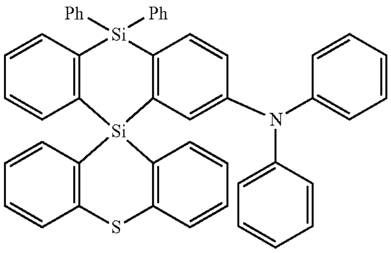
B278
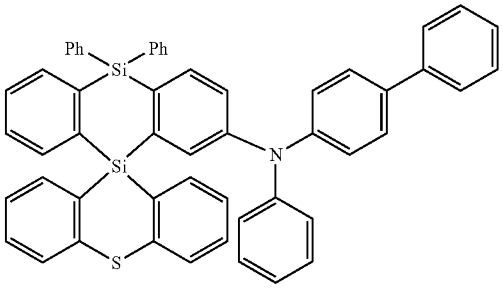
B279
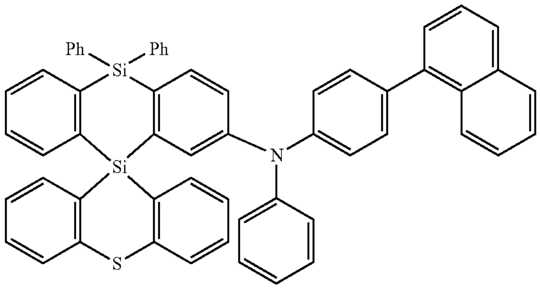
B280
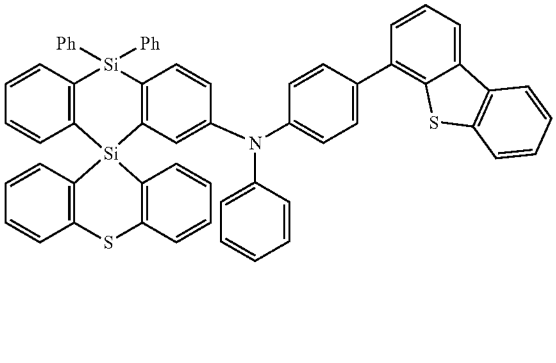

-continued
B281
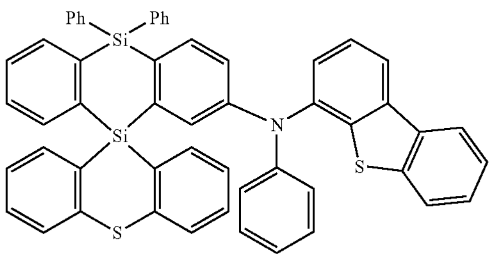
B282
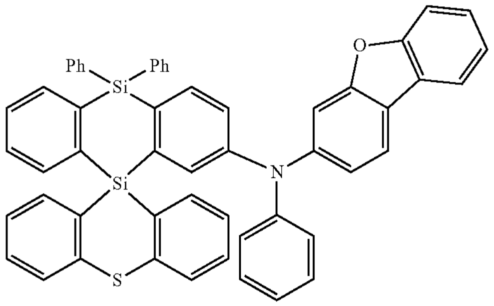
B283
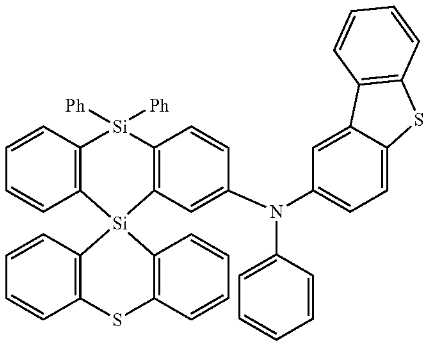
B284
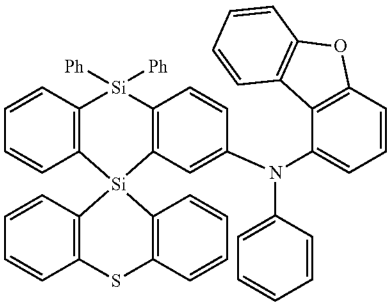
B285
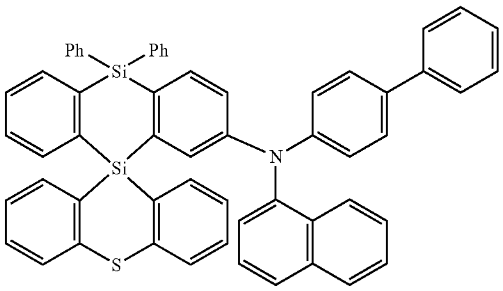
-continued
B286
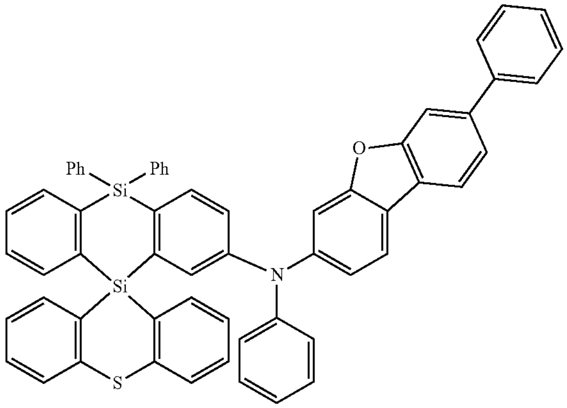
B287
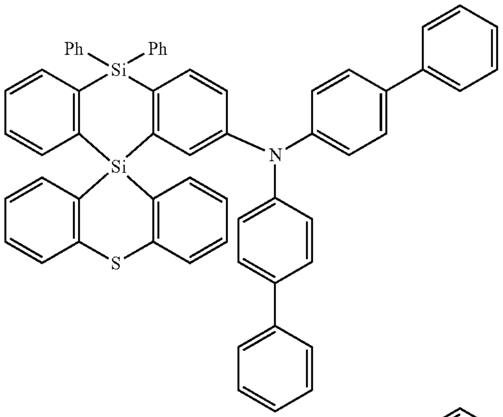
B288
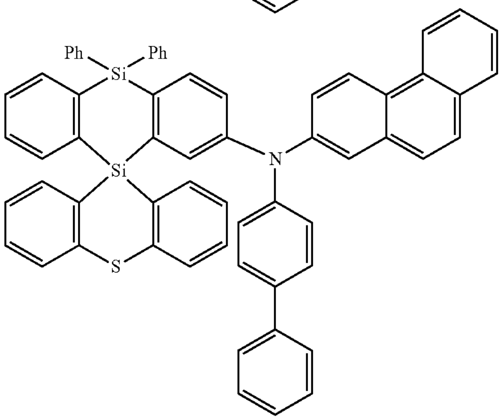
B289
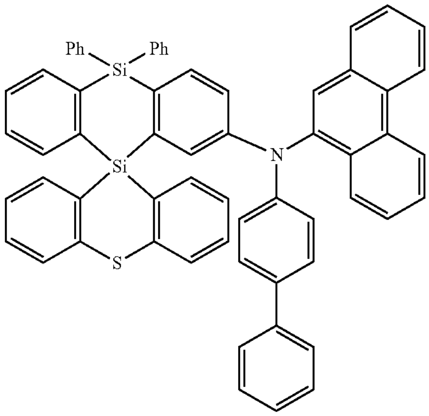

B290
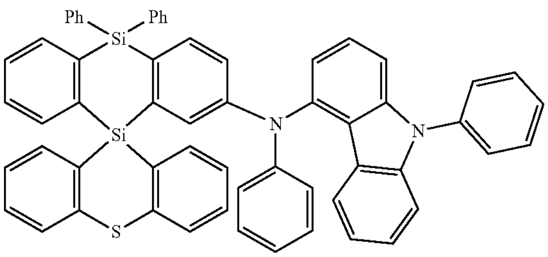
B291
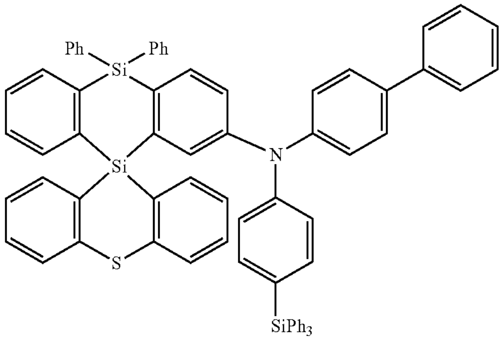
B292
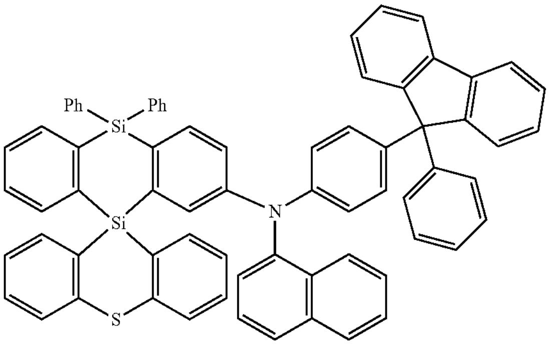
B293
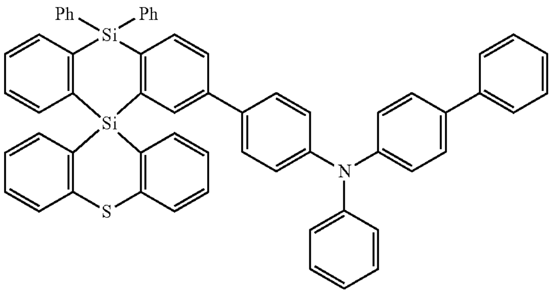
B294
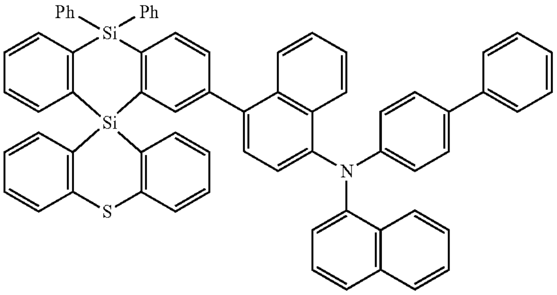
B295
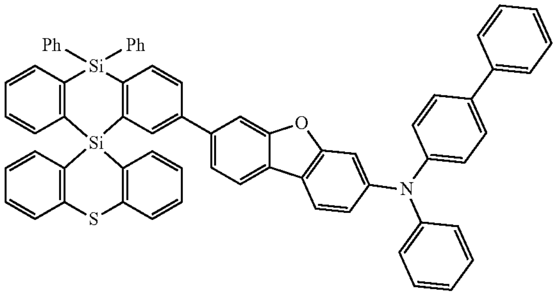
B296
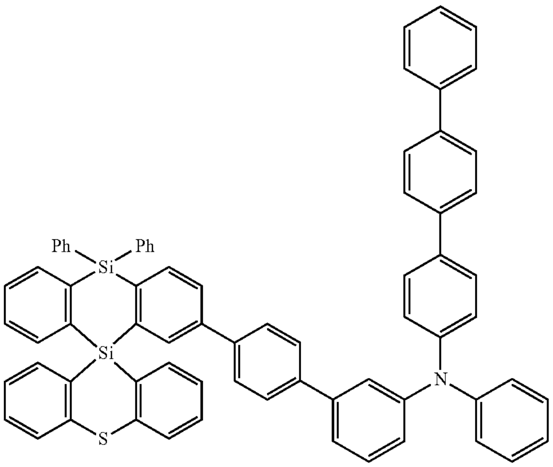
B297
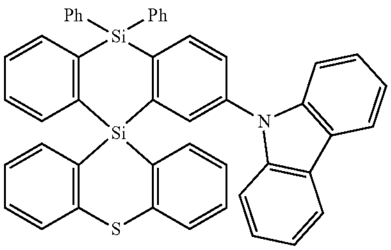
B298
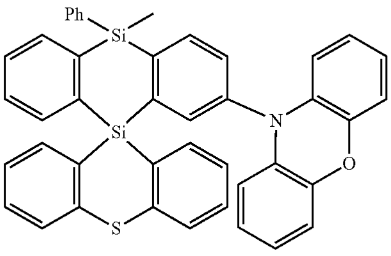
B299
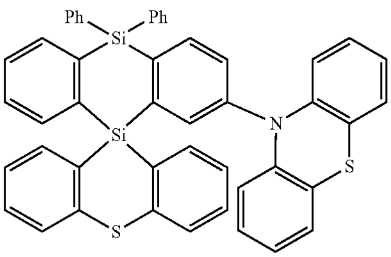

-continued
B300
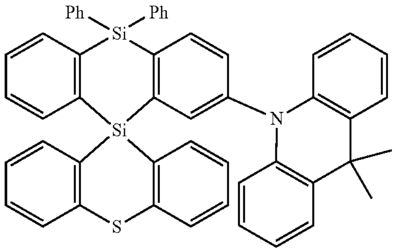
B301
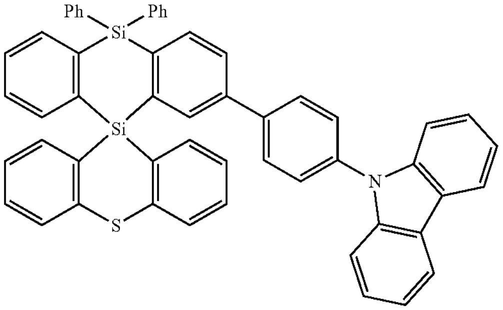
B302
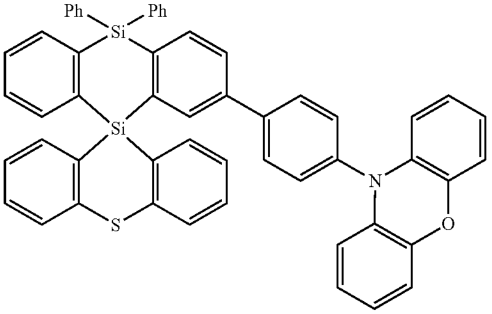
B303
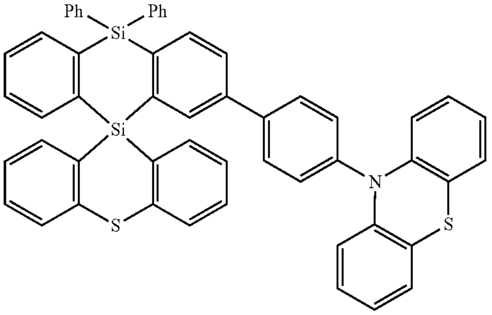
B304
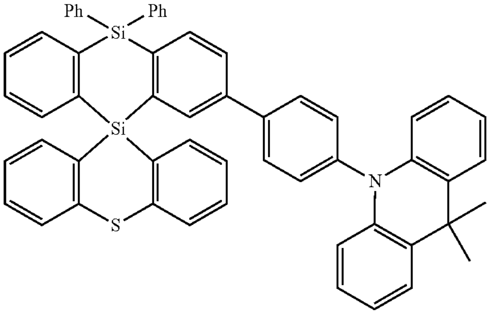
-continued
B305
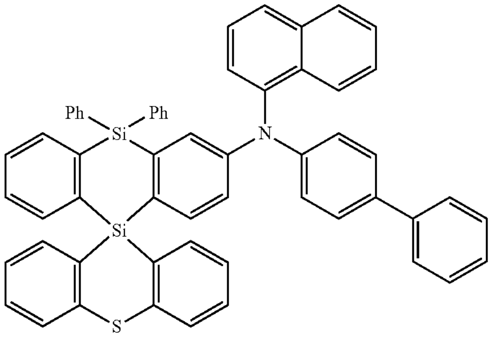
B306
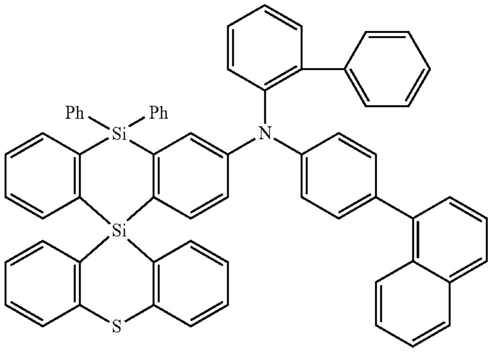
B307
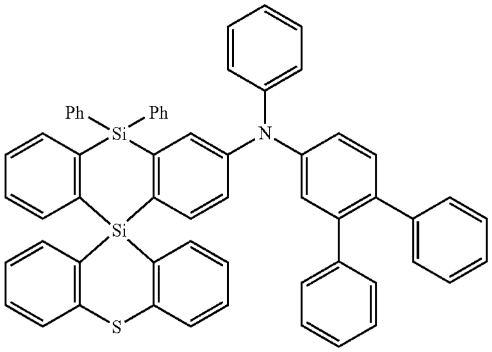
B308
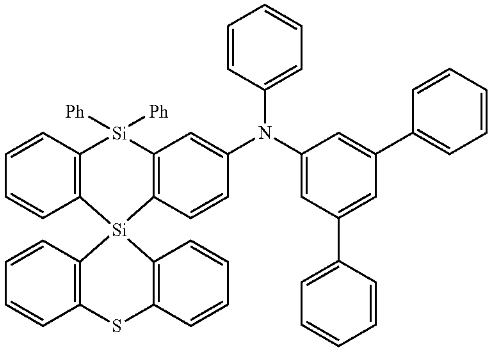

-continued
B309
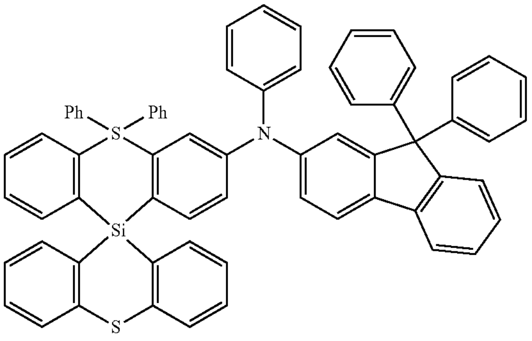
B310
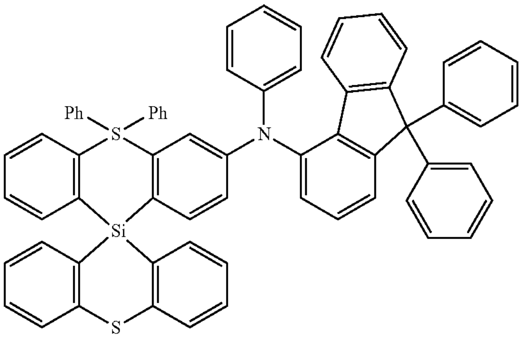
B311
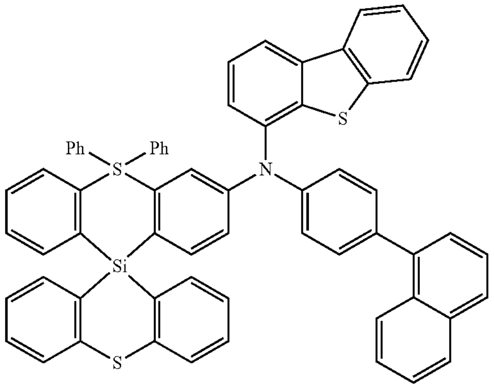
B312
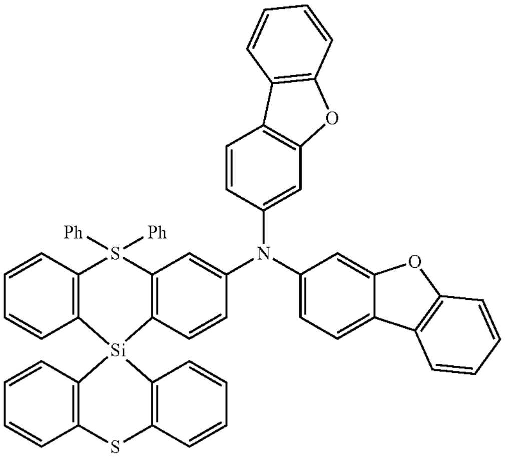
-continued
B313
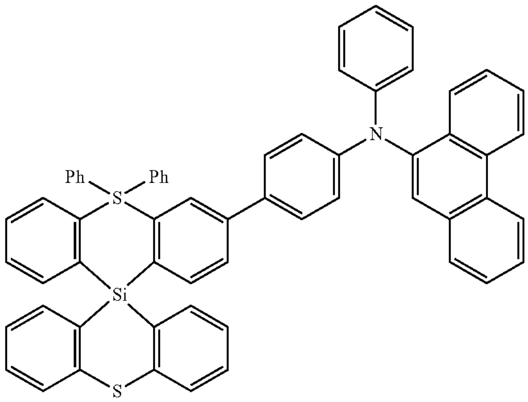
B314
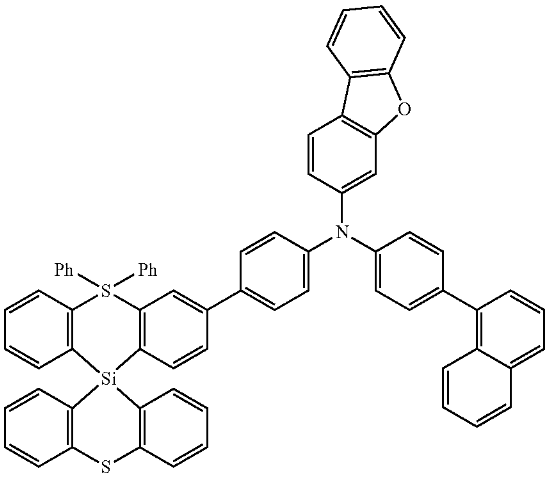
B315
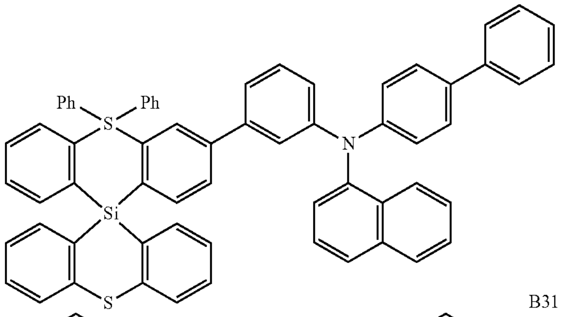
B316
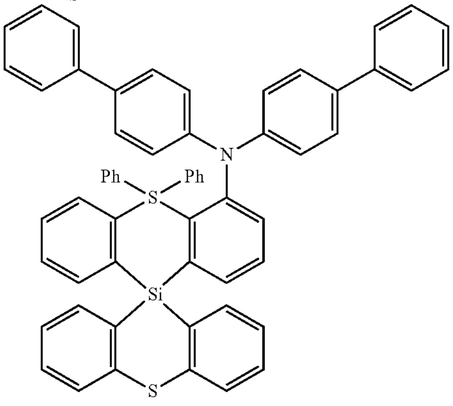

-continued
B317
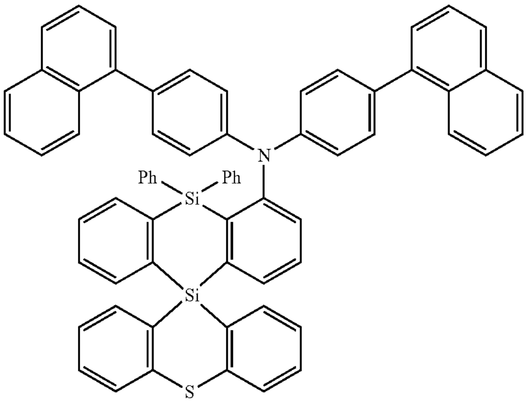
B318
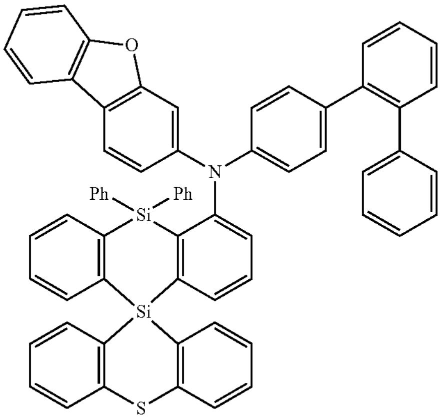
B319
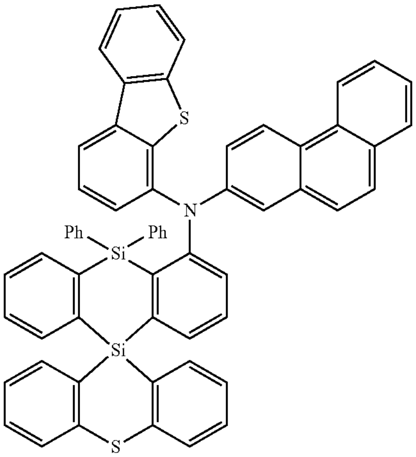
-continued
B320
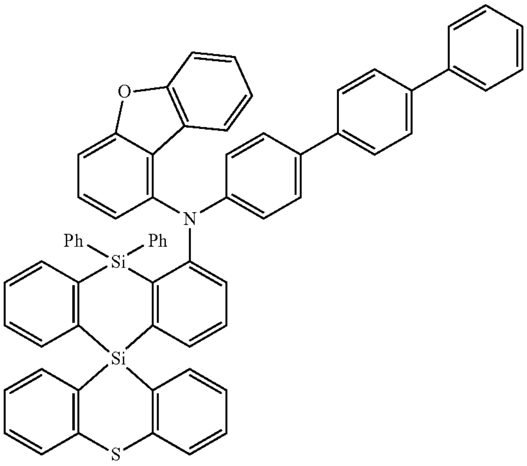
B321
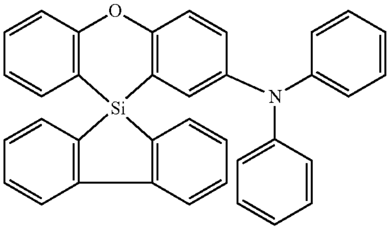
B322
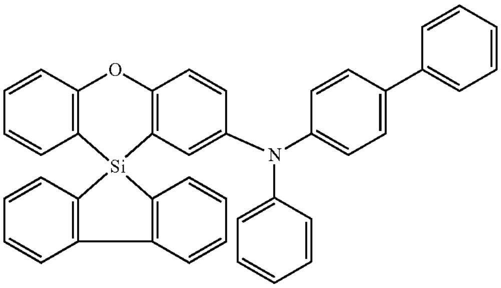
B323
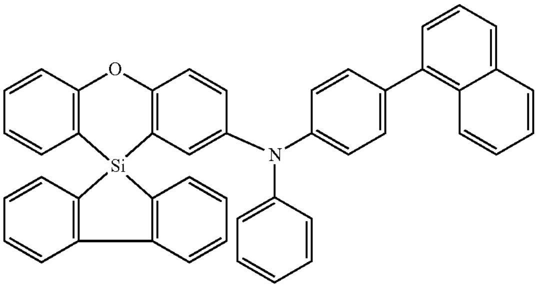
B324
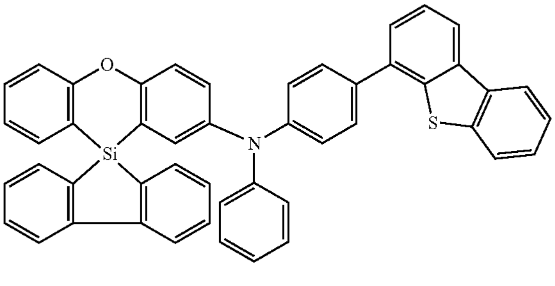

-continued
B325
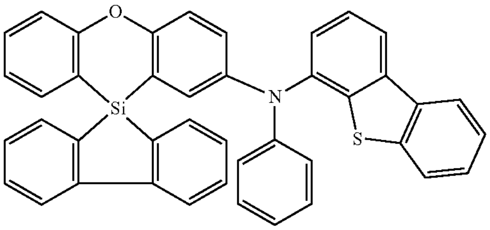
B326
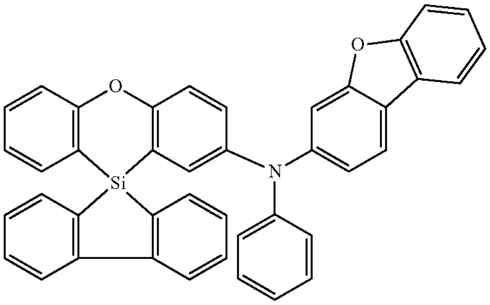
B327
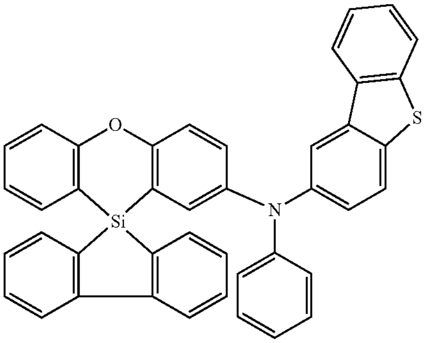
B328
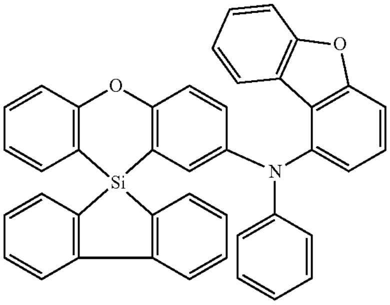
B329
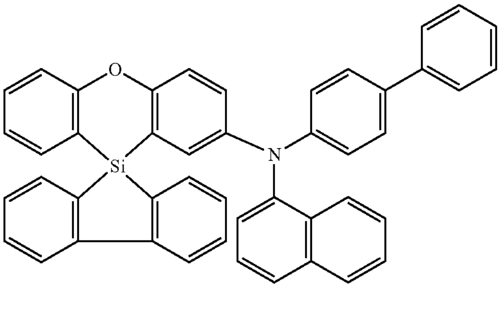
-continued
B330
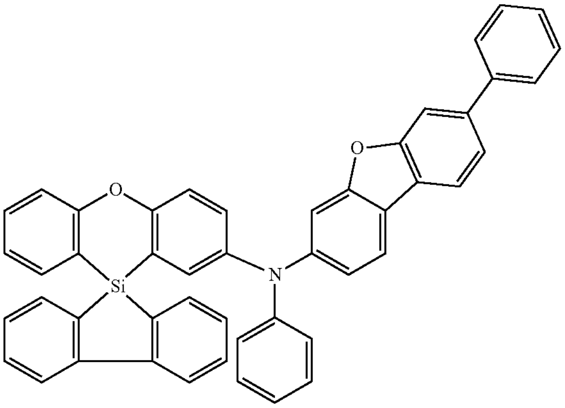
B331
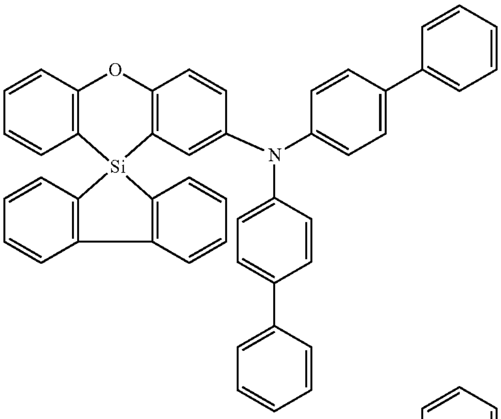
B332
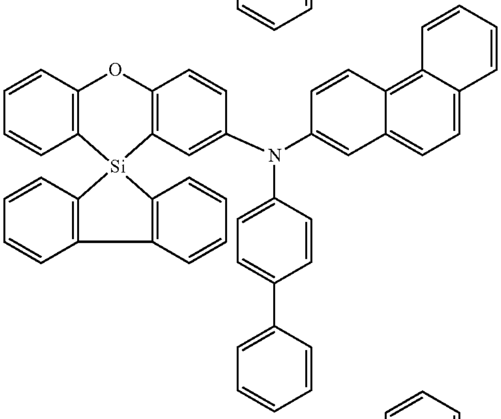
B333
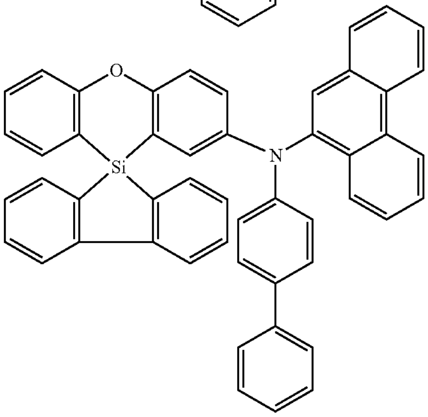

-continued
B334
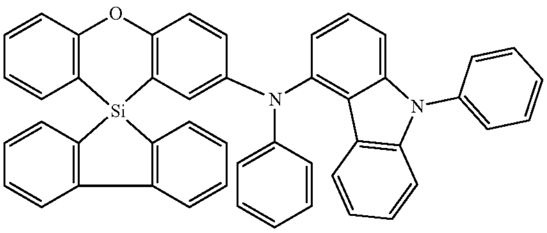
B335
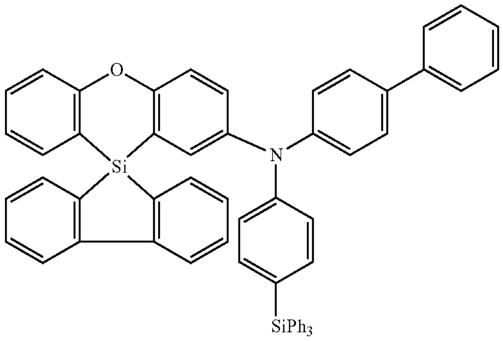
B336
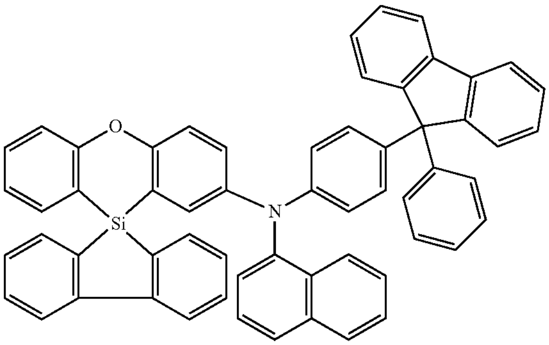
B337
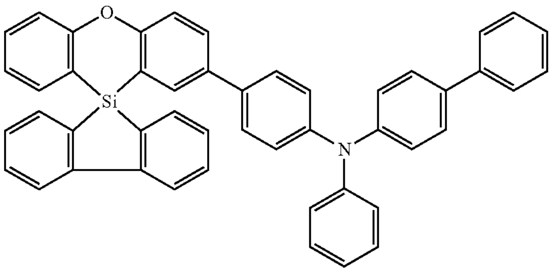
B338
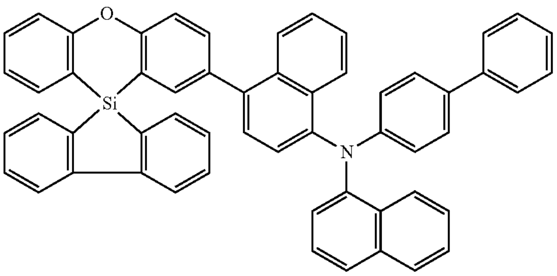
-continued
B339
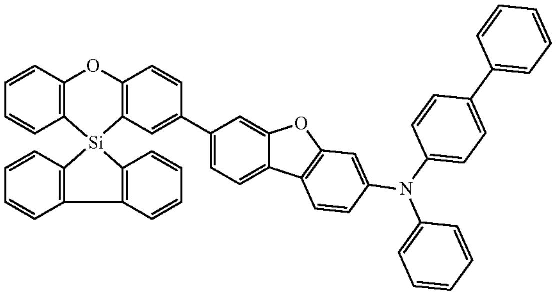
B340
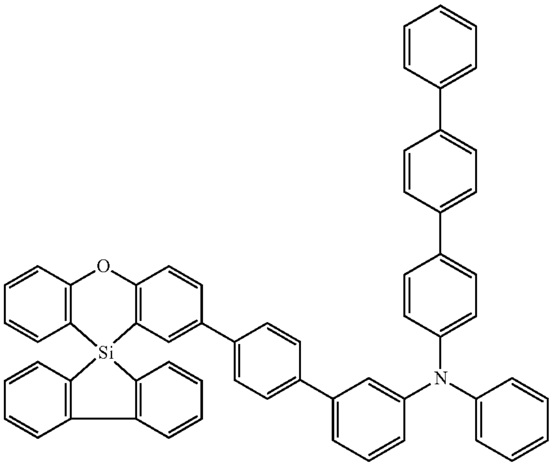
B341
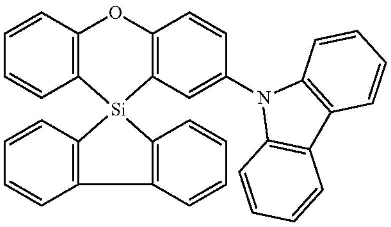
B342
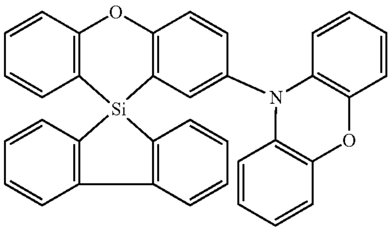
B343
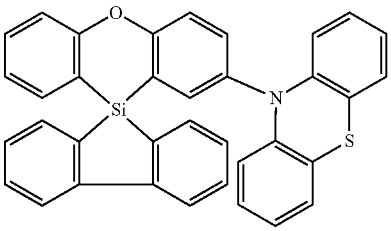

B344
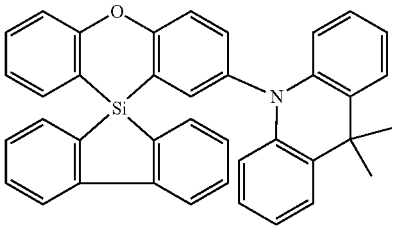
B345
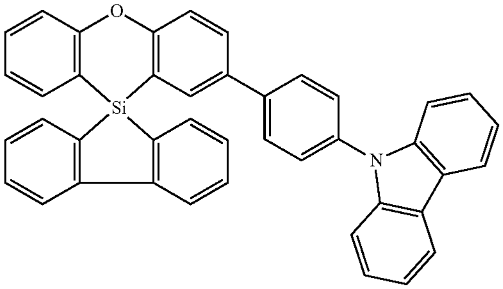
B346
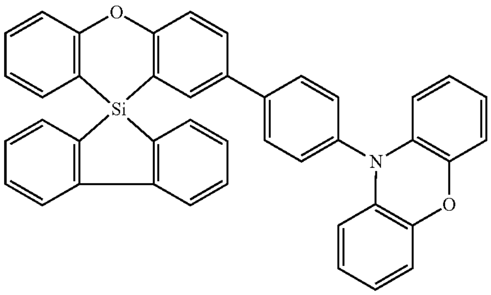
B347
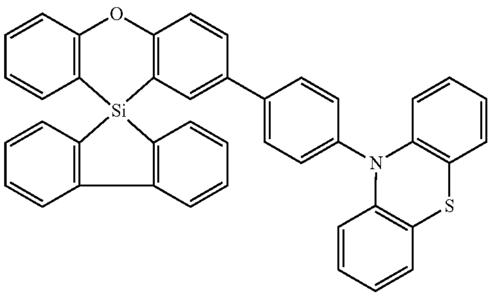
B348
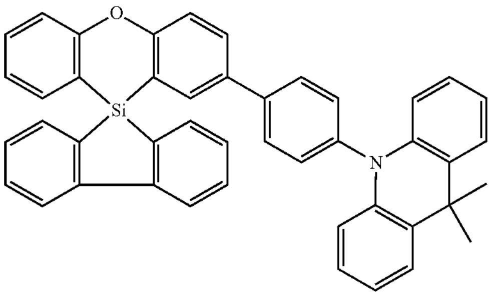
B349
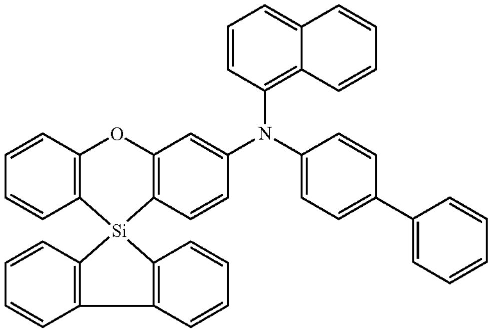
B350
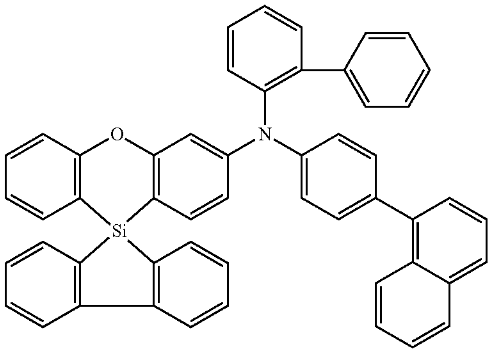
B351
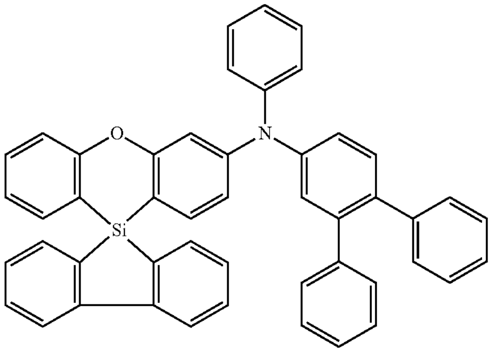
B352
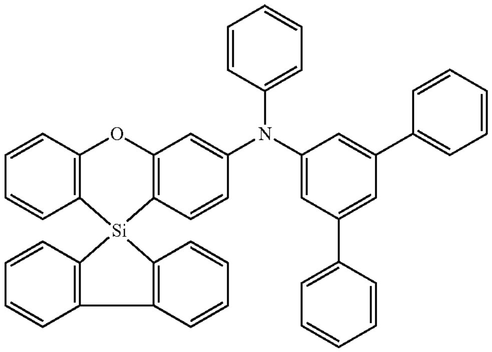

-continued
B353
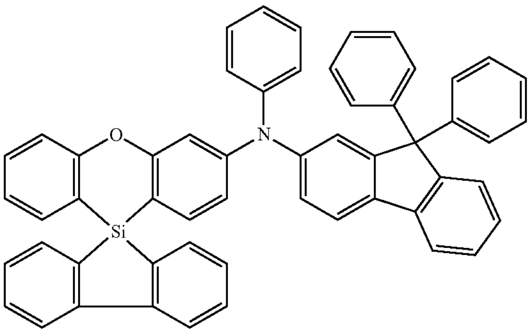
B354
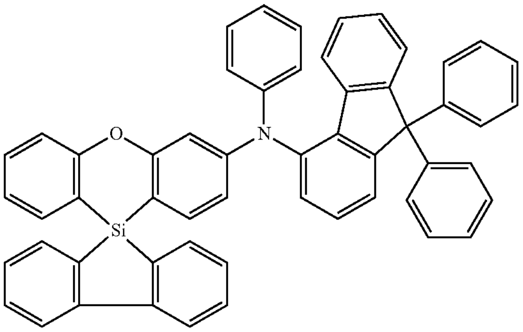
B355
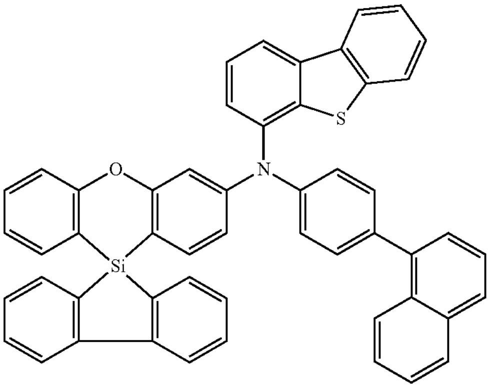
B356
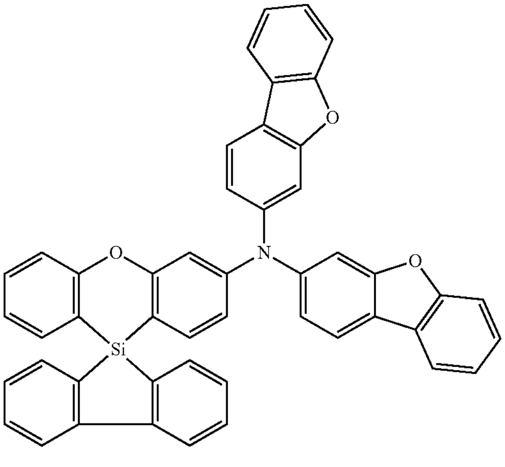
-continued
B357
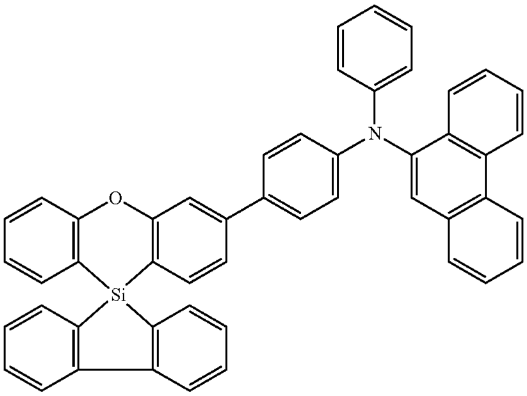
B358
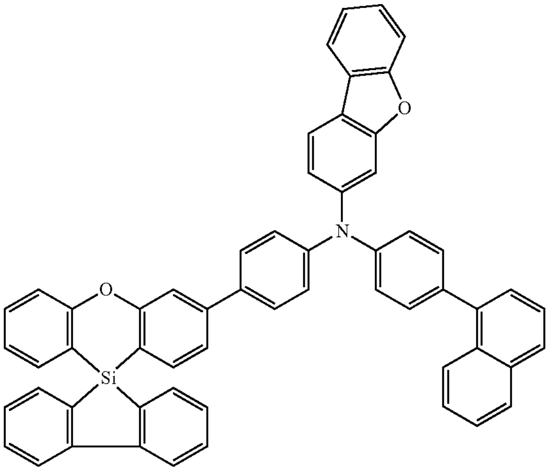
B359
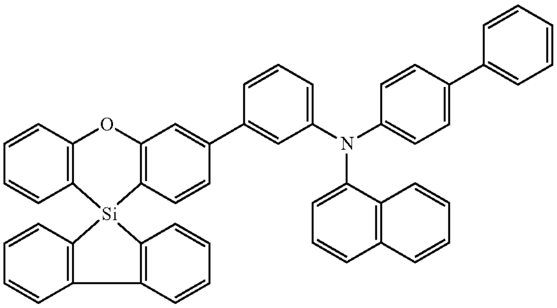
B360
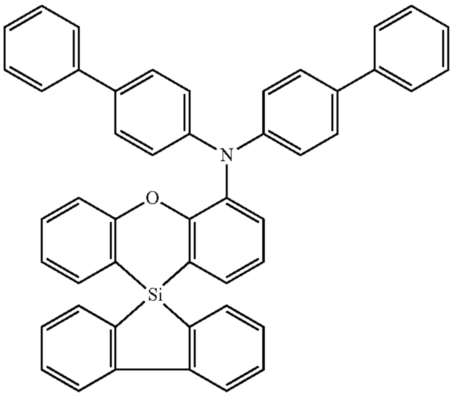

-continued
B361
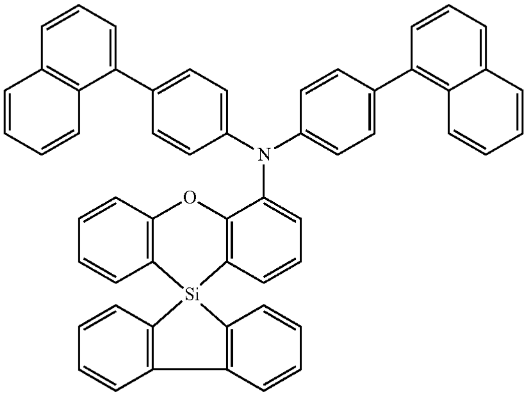
B362
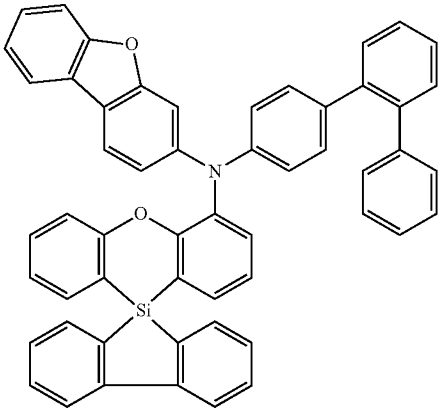
B363
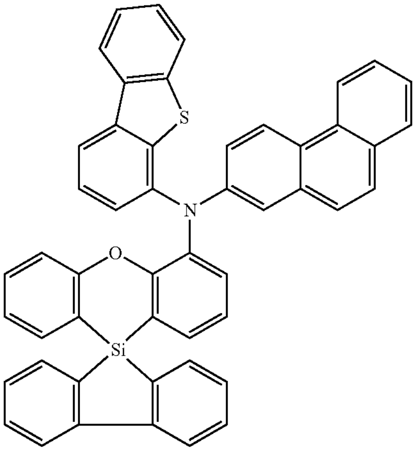
-continued
B364
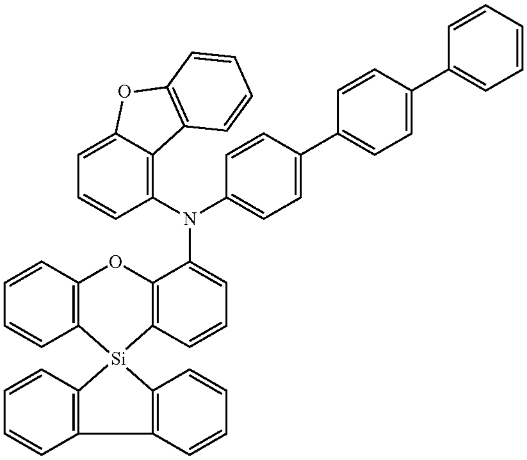
B365
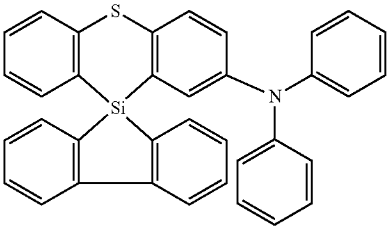
B366
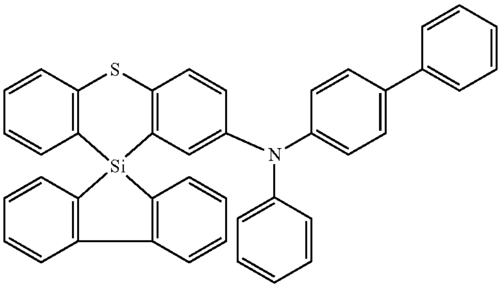
B367
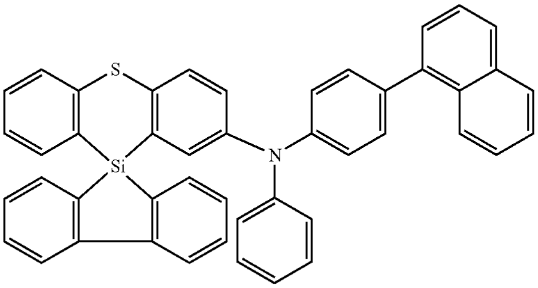
B368
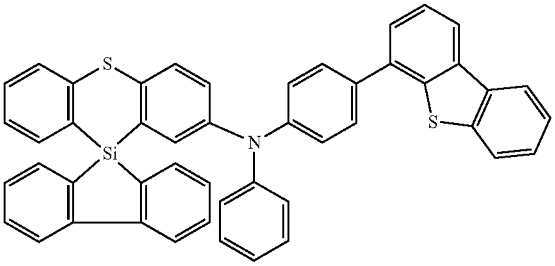

-continued
B369
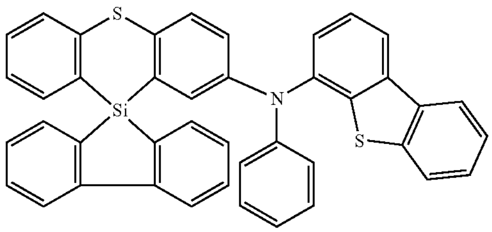
B370
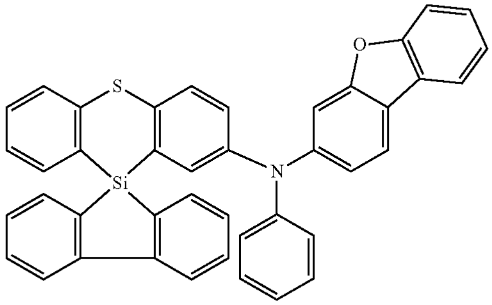
B371
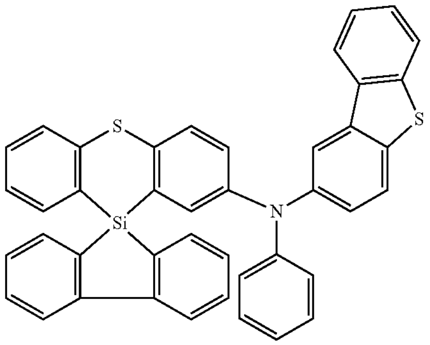
B372
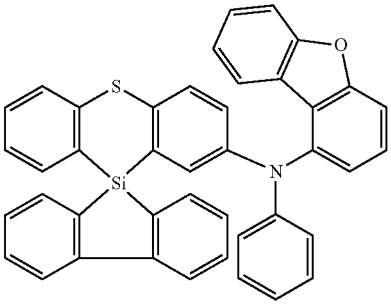
B373
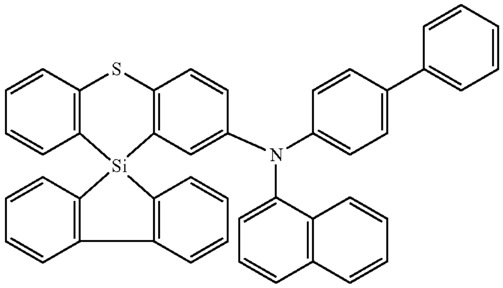
-continued
B374
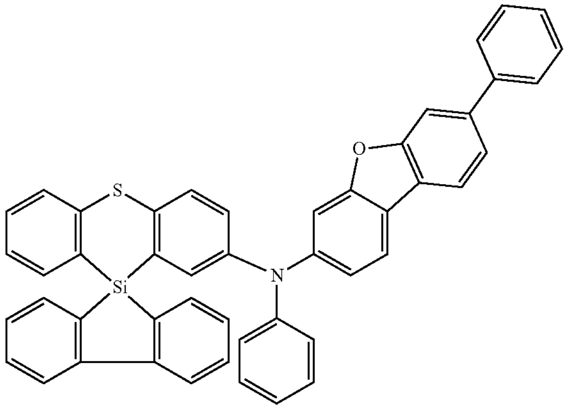
B375
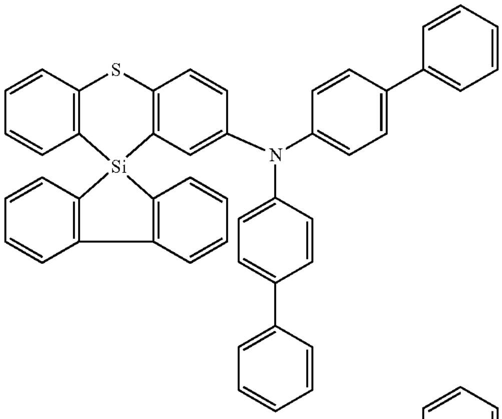
B376
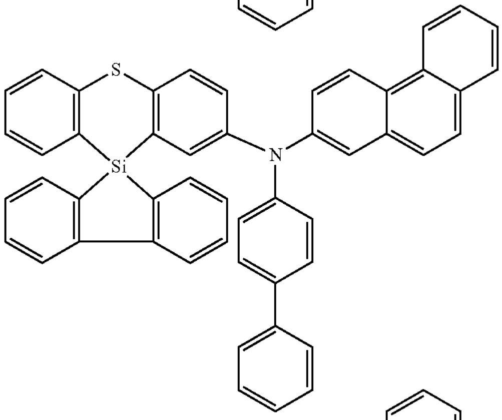
B377
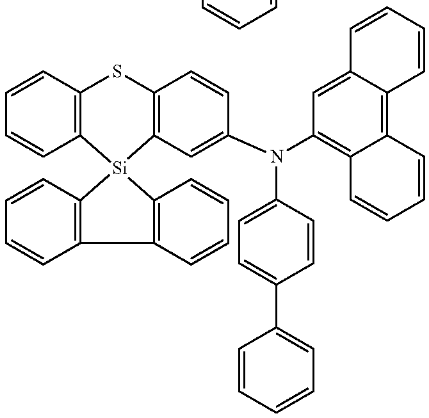

-continued
B378
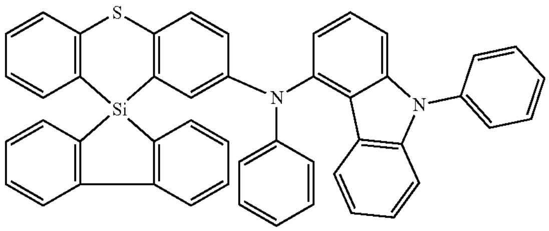
B379
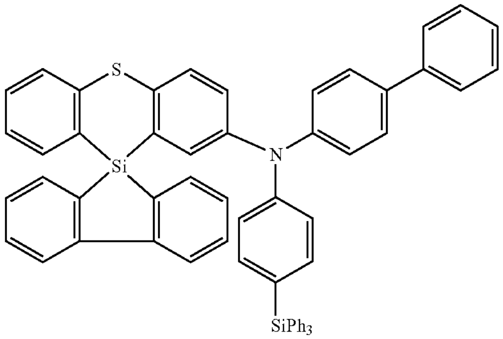
B380
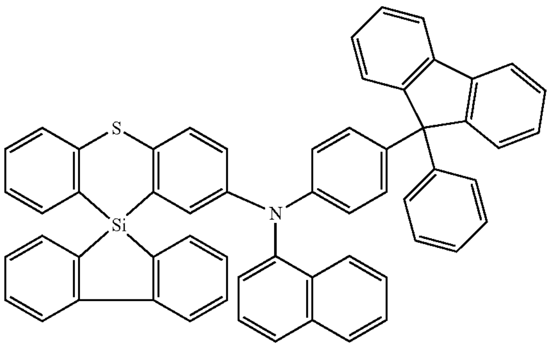
B381
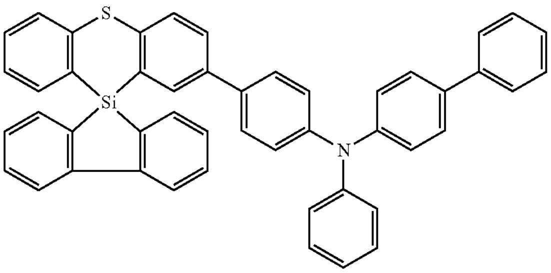
B382
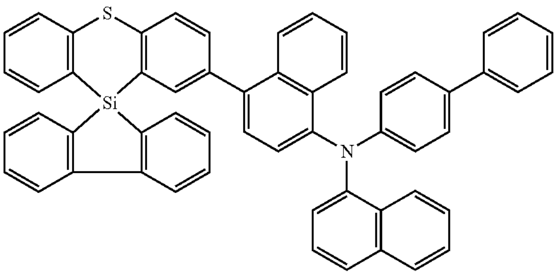
-continued
B383
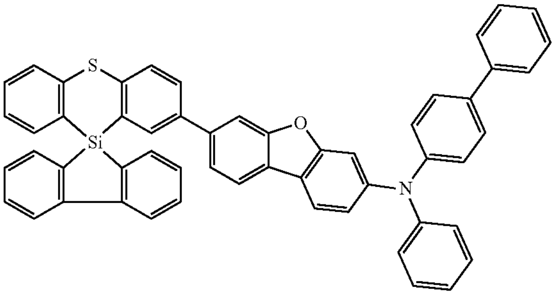
B384
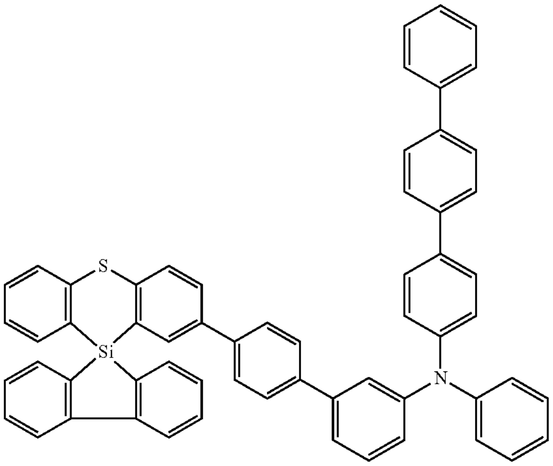
B385
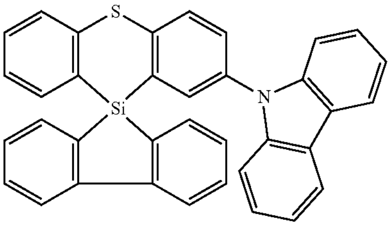
B386
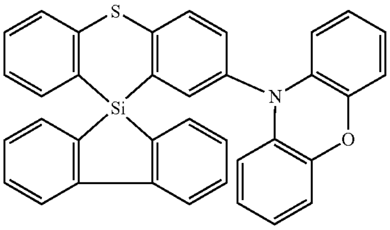
B387
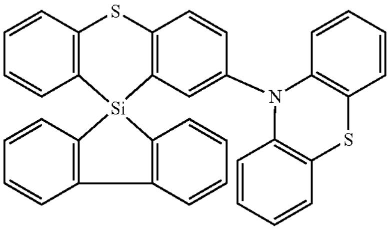

-continued
B388
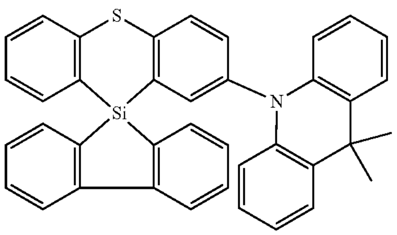
B389
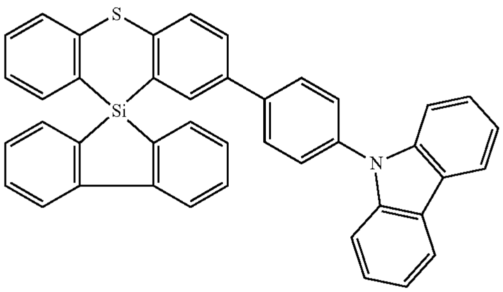
B390
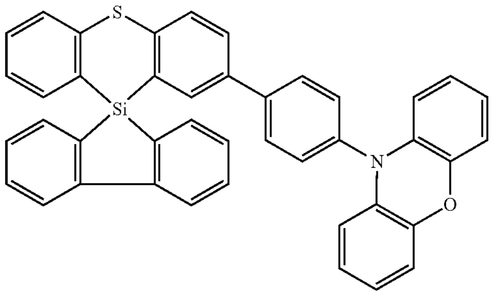
B391
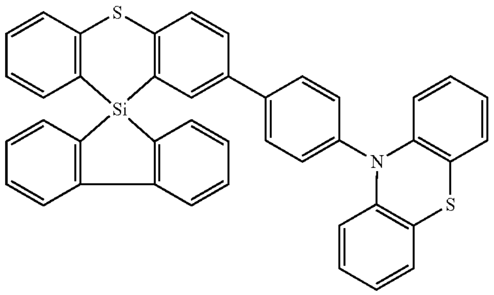
B392
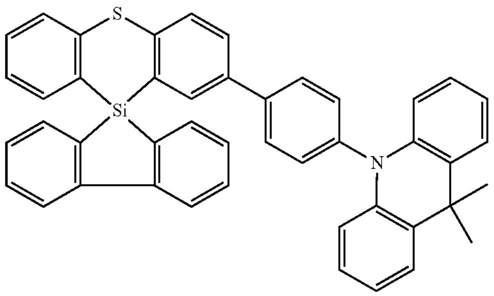
-continued
B393
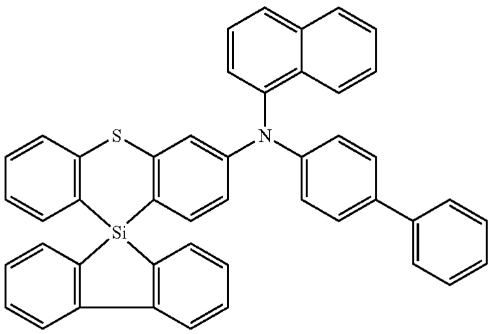
B394
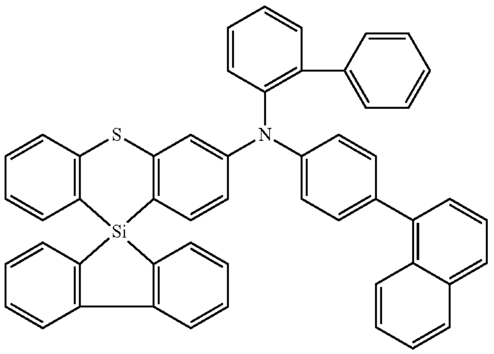
B395
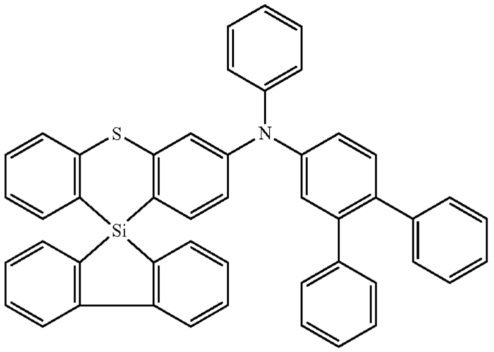
B396
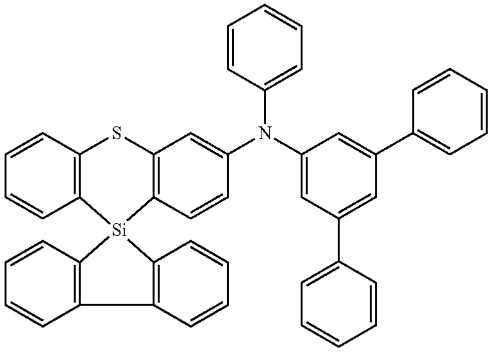

-continued
B397
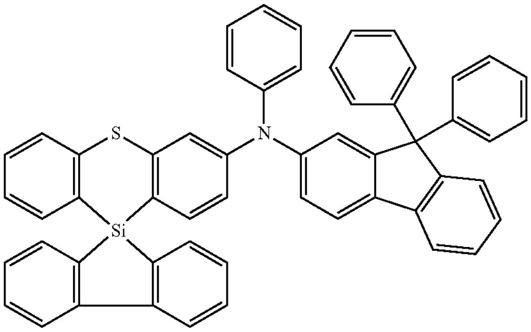
B398
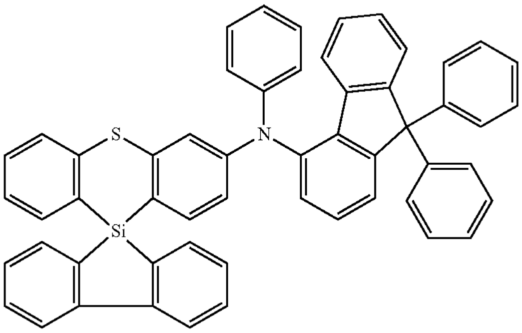
B399
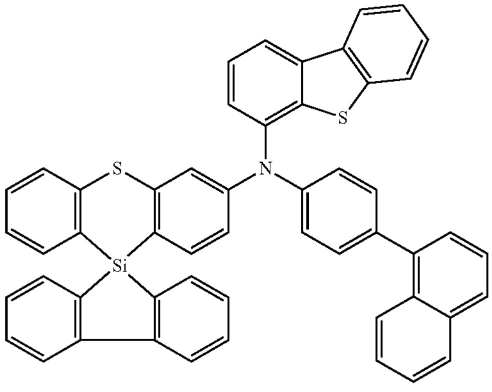
B400
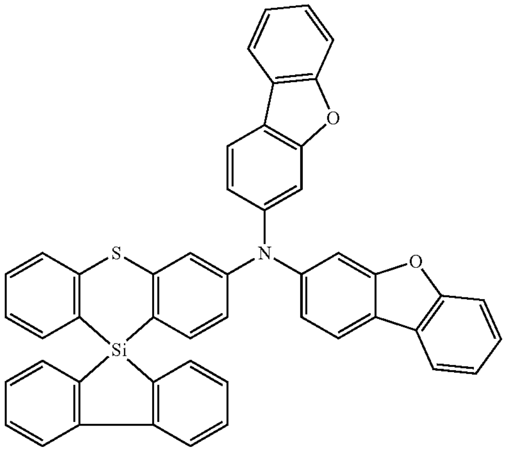
-continued
B401
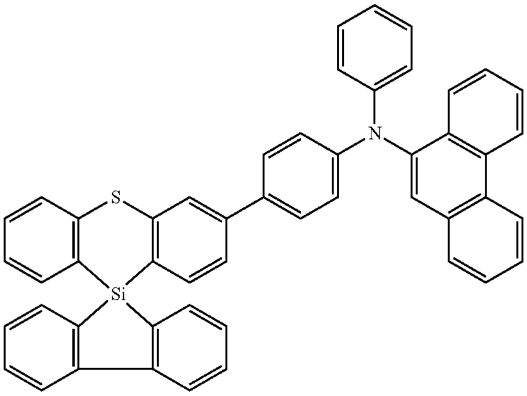
B402
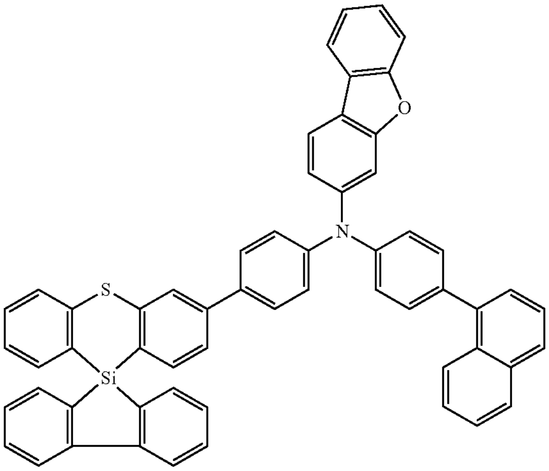
B403
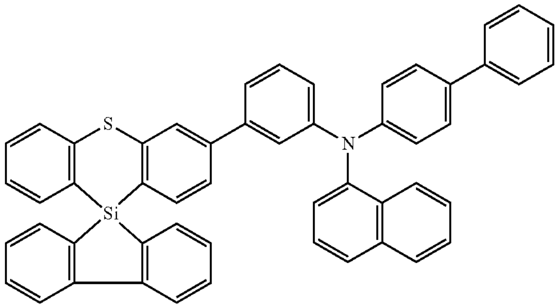
B404
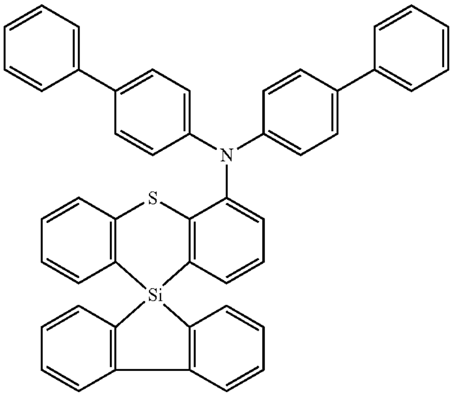

-continued
B405
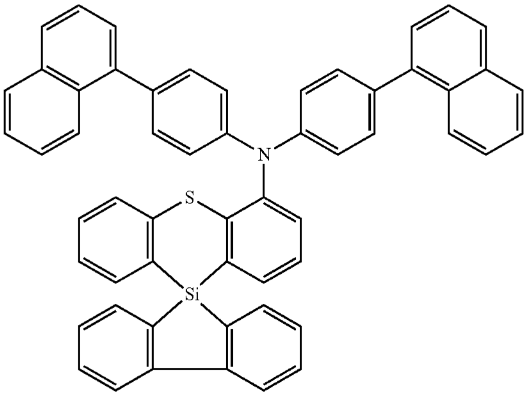
B406
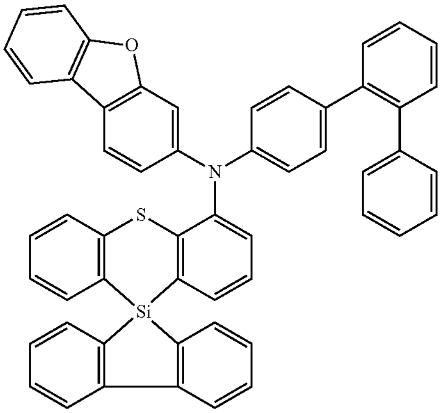
B407
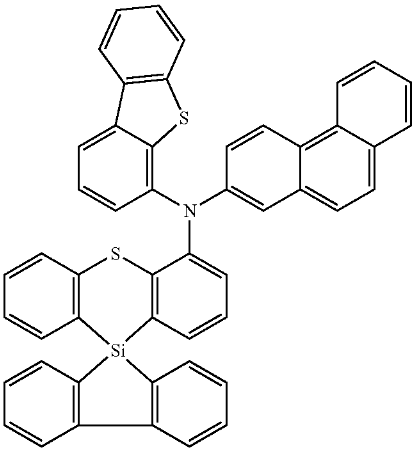
-continued
B408
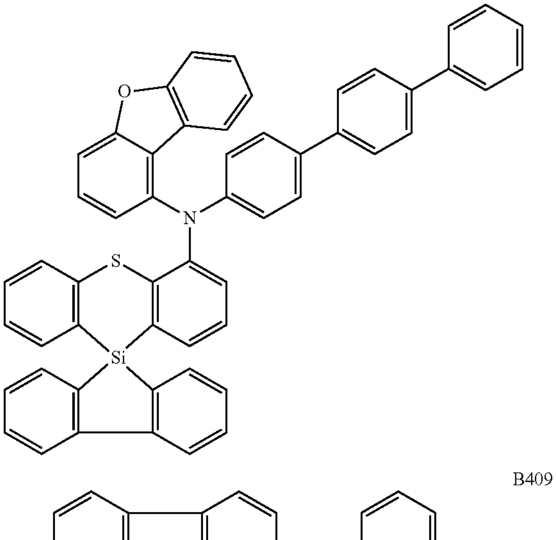
B409
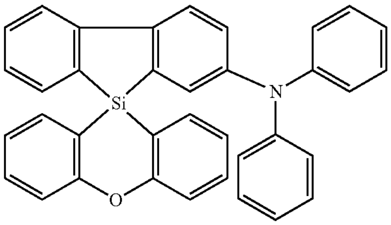
B410
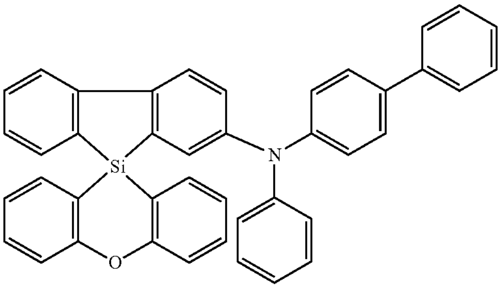
B411
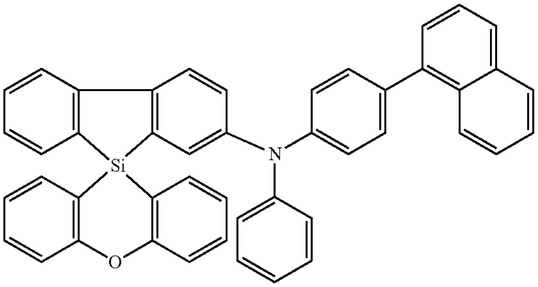
B412
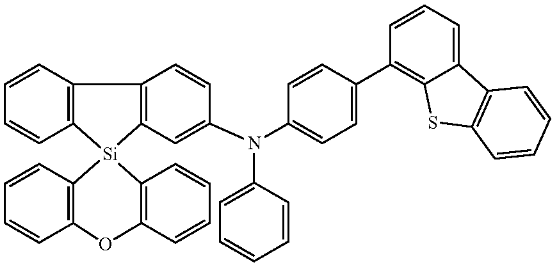

-continued
B413
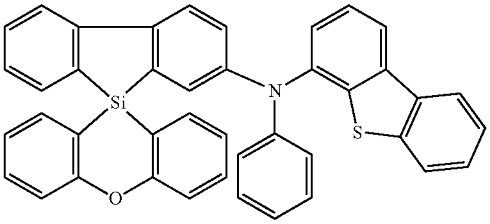
B414
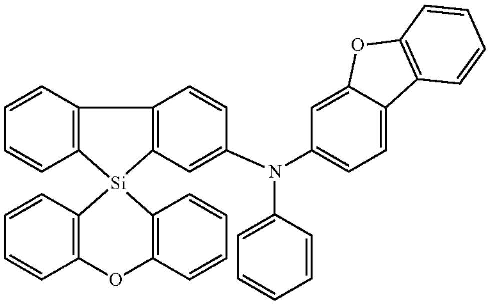
B415
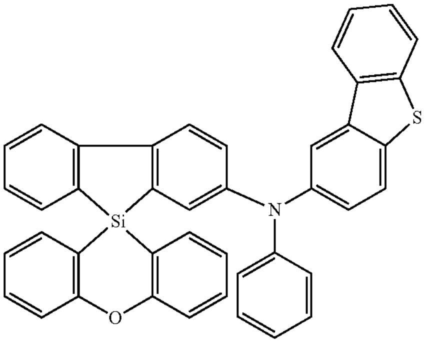
B416
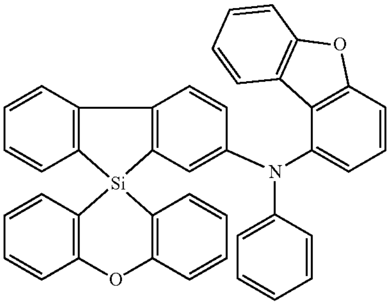
B417
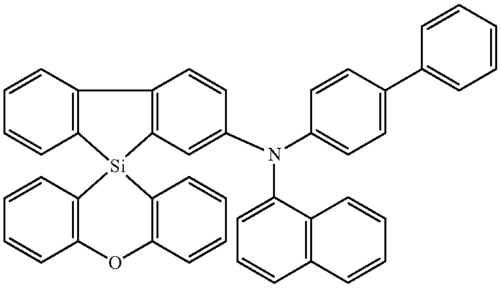
-continued
B418
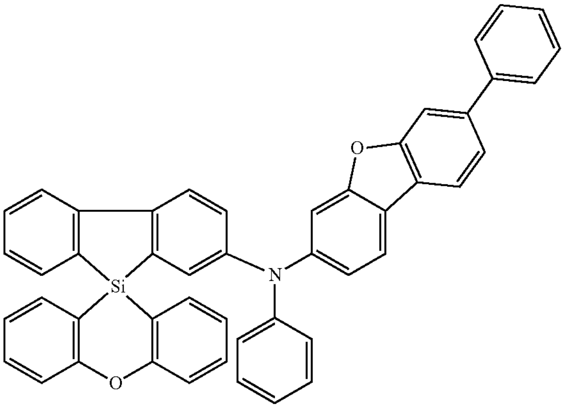
B419
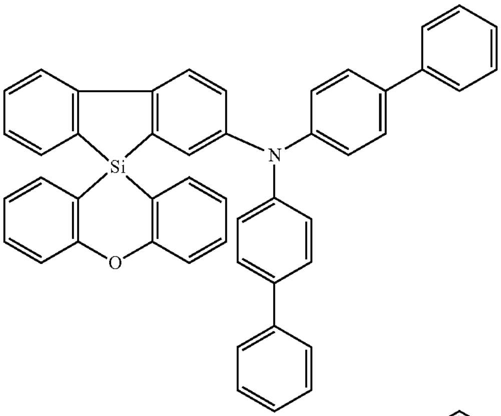
B420
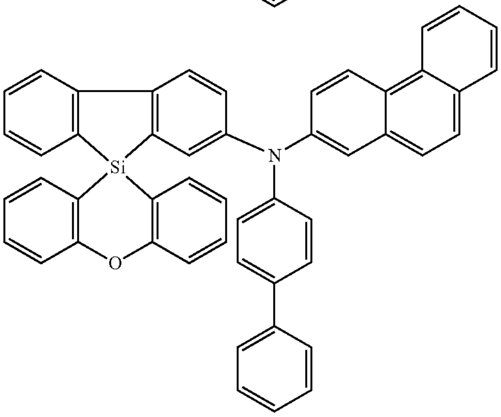
B421
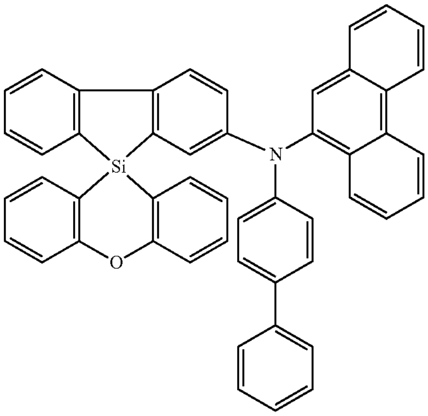

-continued
B422
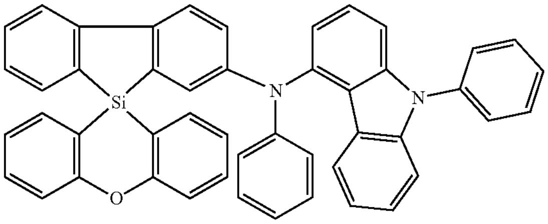
B423
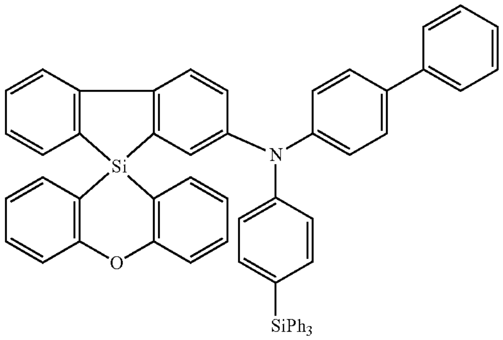
B424
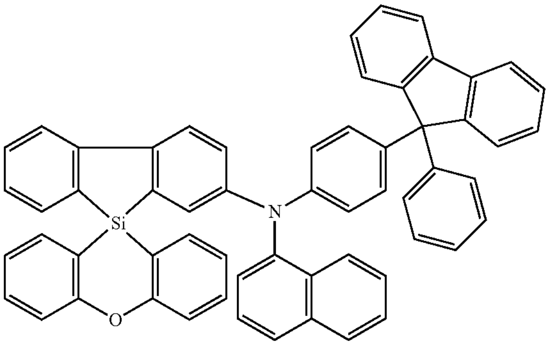
B425
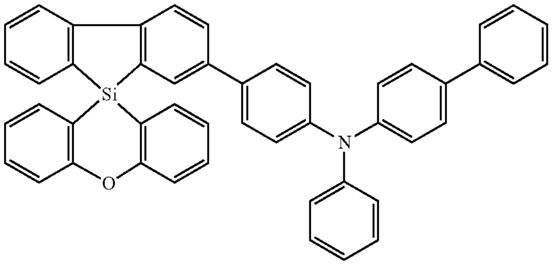
B426
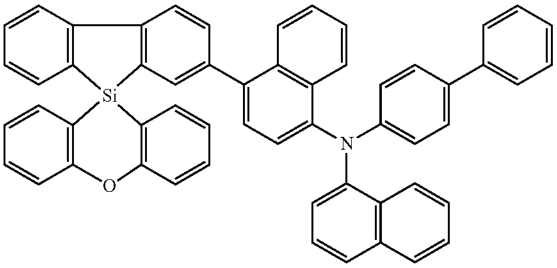
-continued
B427
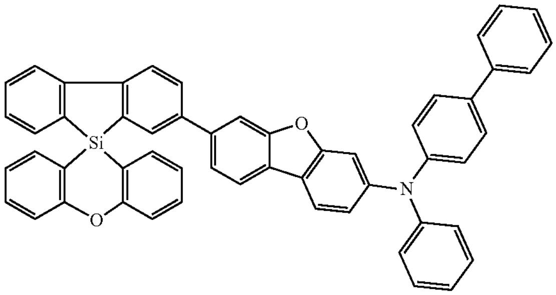
B428
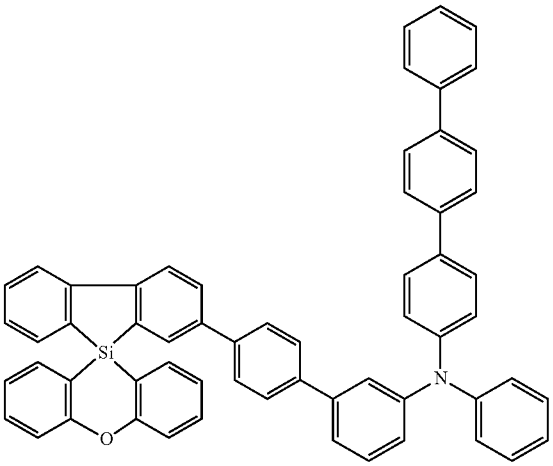
B429
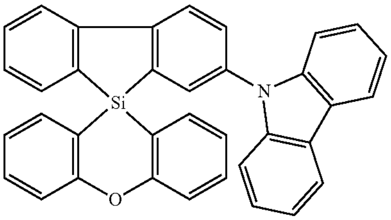
B430
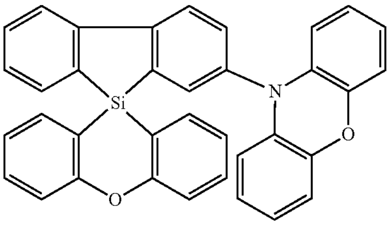
B431
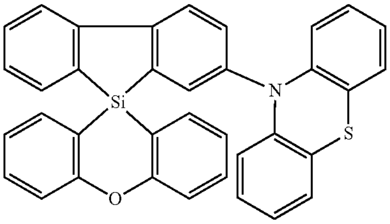

-continued
B432
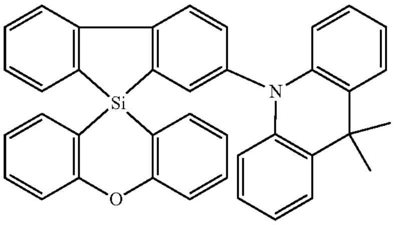
B433
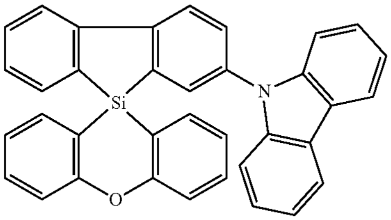
B434
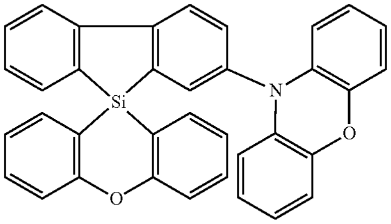
B435
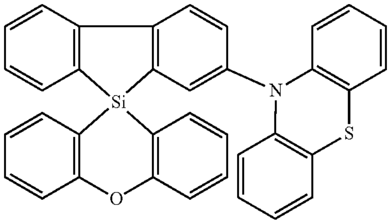
B436
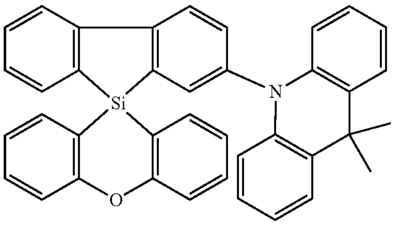
B437
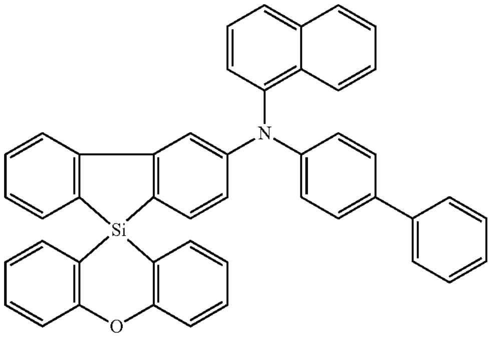
-continued
B438
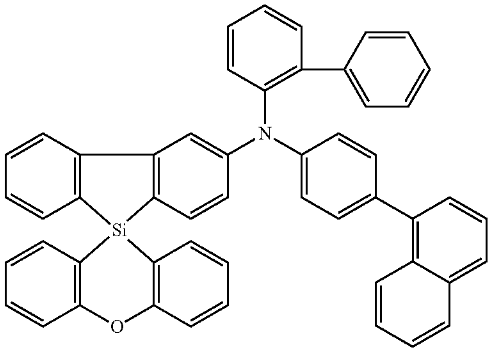
B349
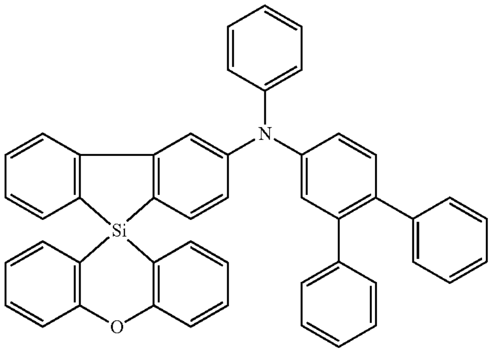
B440
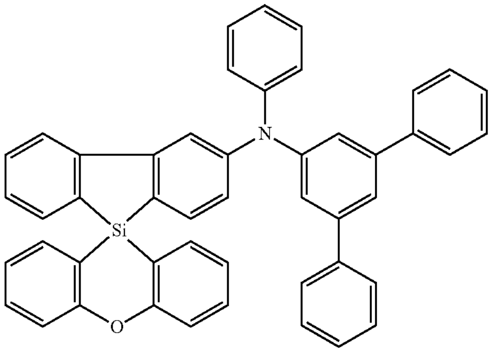
B441
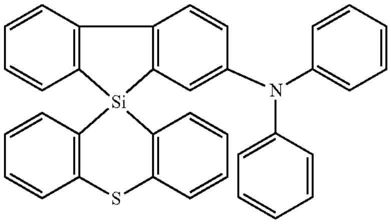
B442
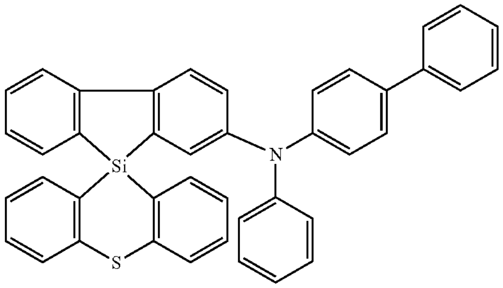

-continued
B443
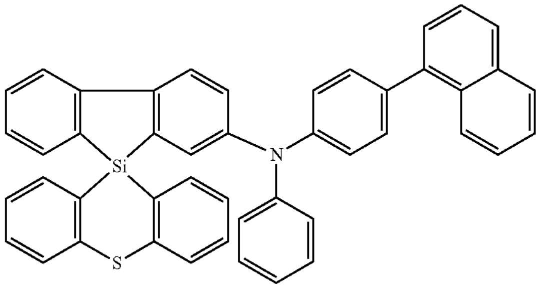
B444
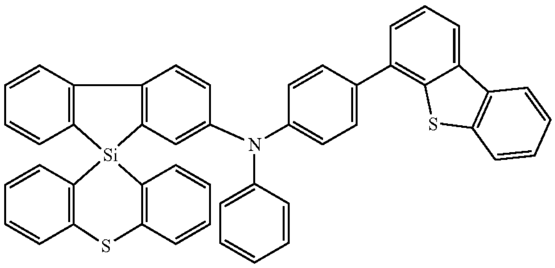
B445
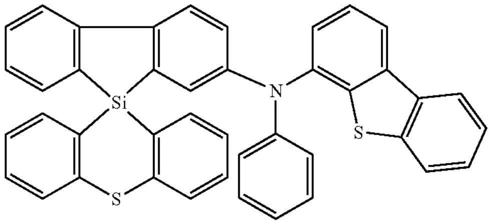
B446
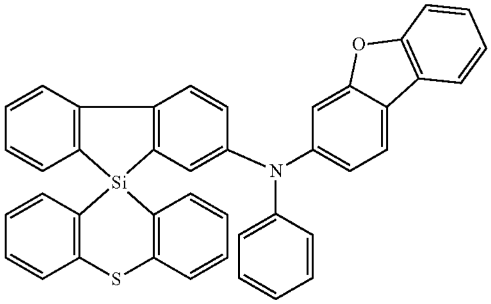
B447
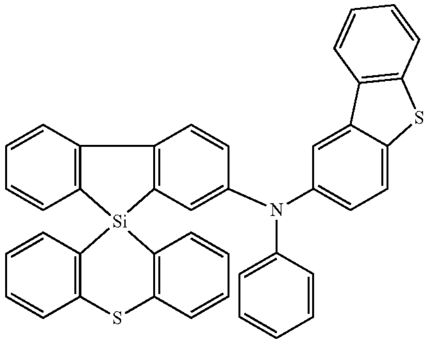
-continued
B448
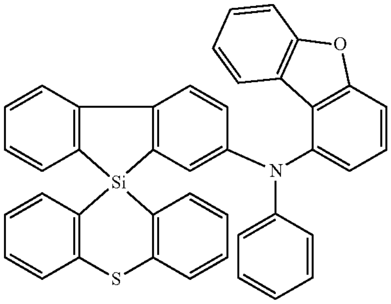
B449
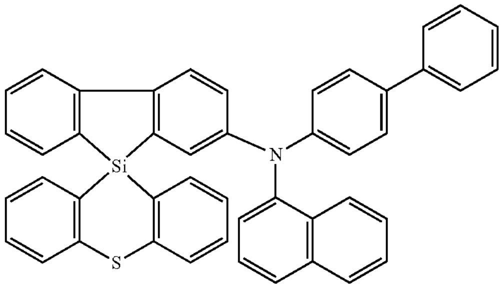
B450
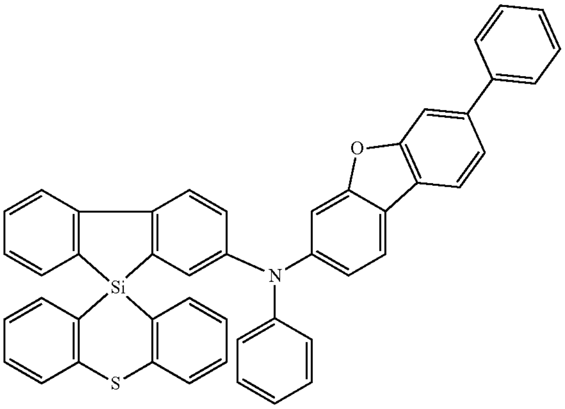
B451
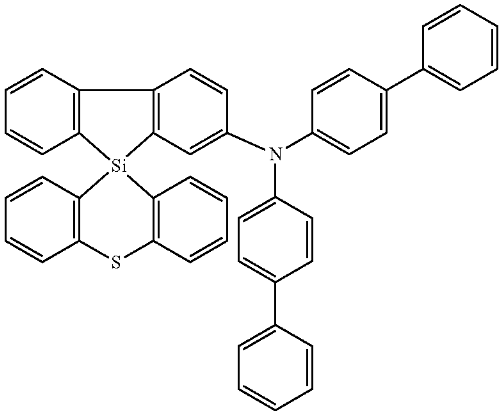

-continued
B452
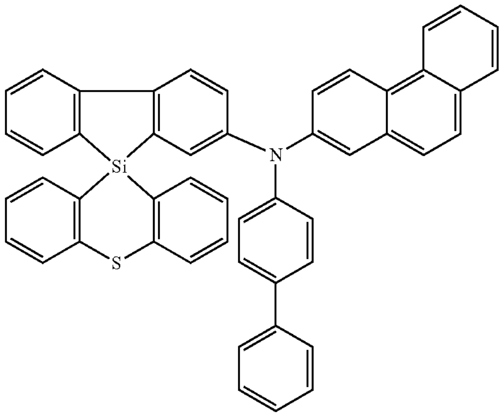
B453
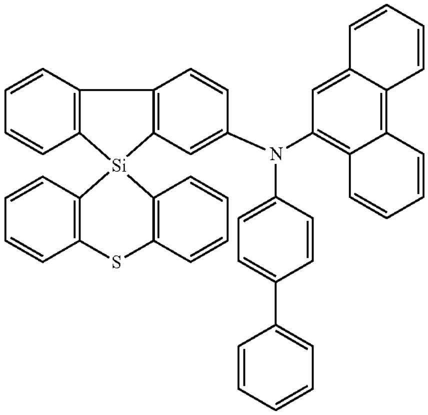
B454
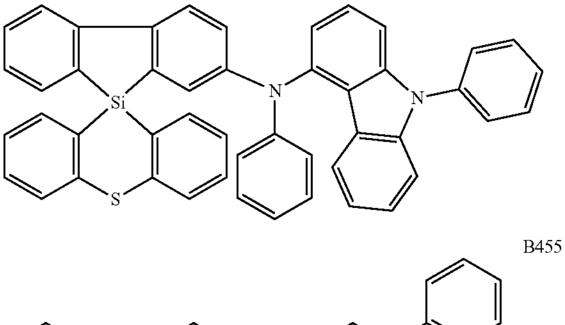
B455
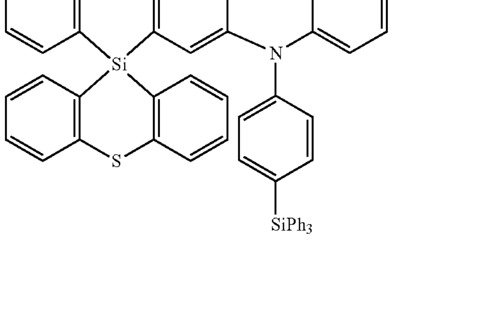
-continued
B456
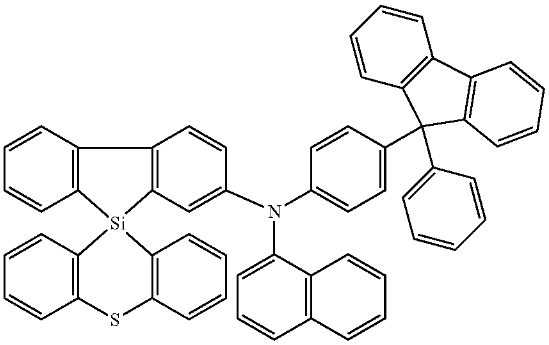
B457
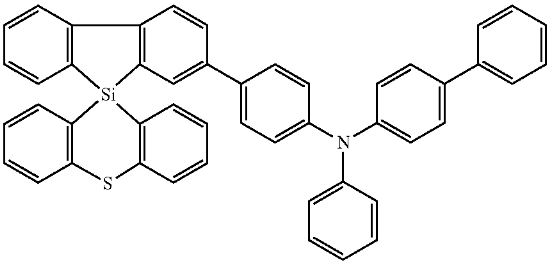
B458
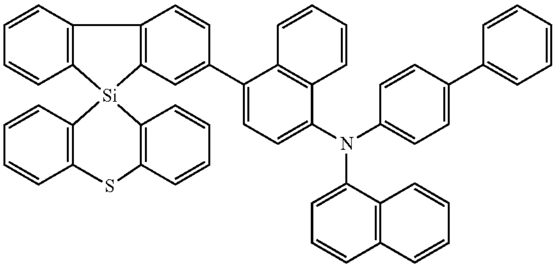
B459
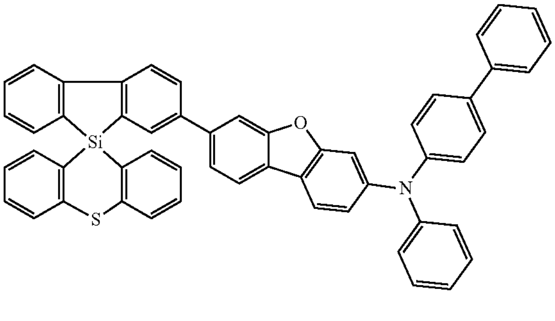

-continued
B460
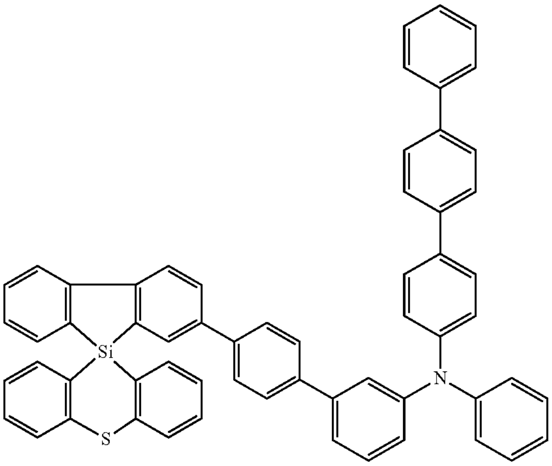
B461
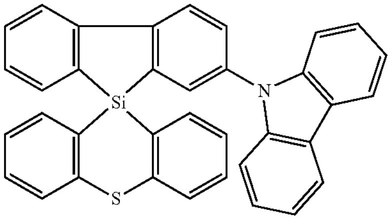
B462
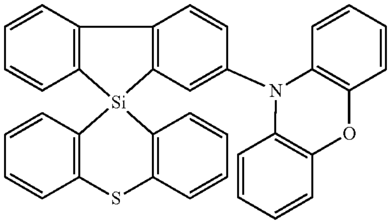
B463
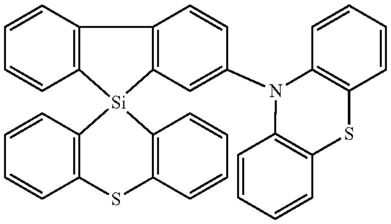
B464
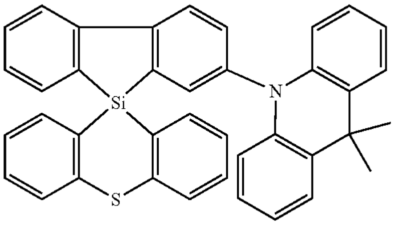
B465
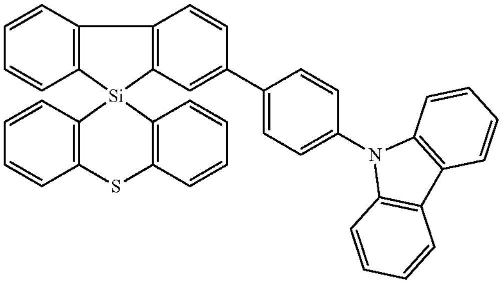
B466
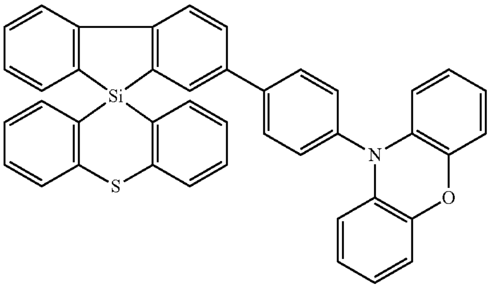
B467
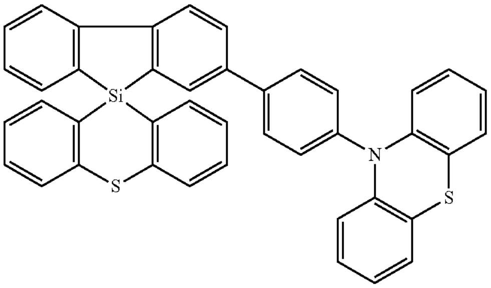
B468
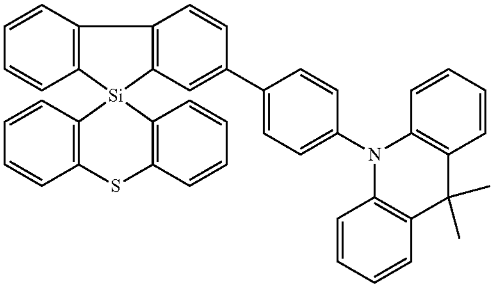
B469
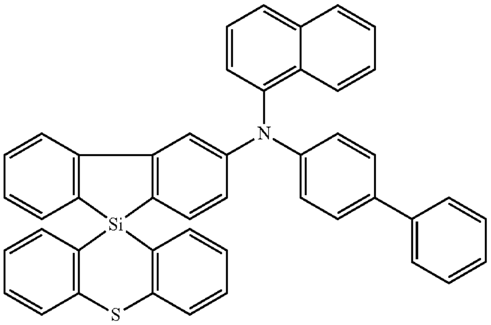

-continued

B470

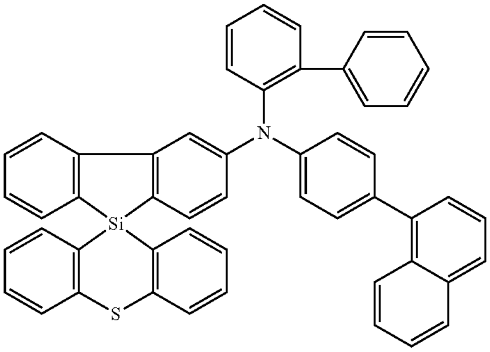

B471

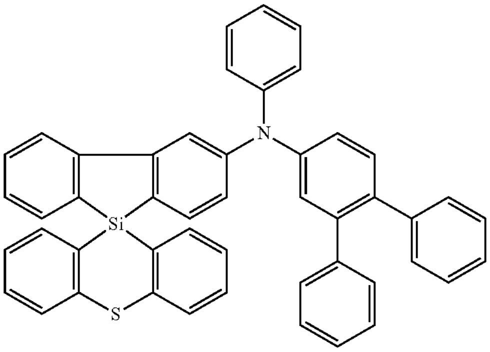

B472

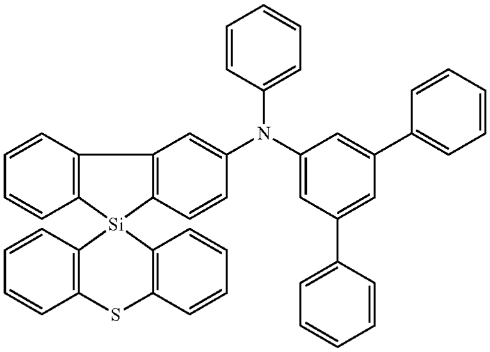

B473

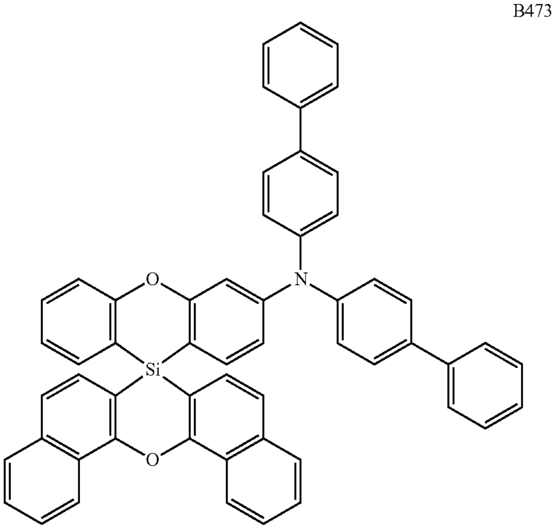

-continued

B474

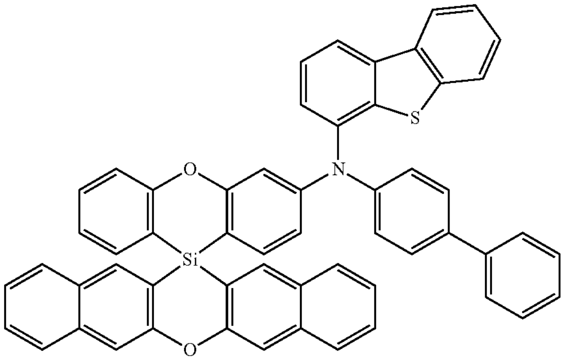

B475

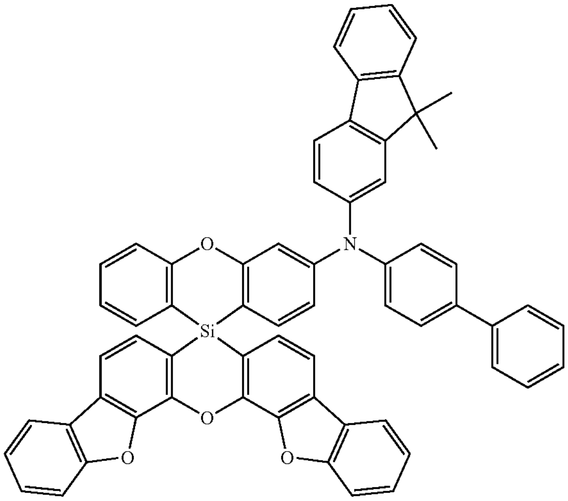

B476

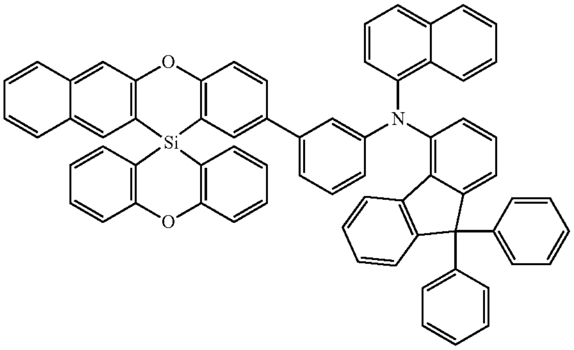

Referring to FIGS. 2 and 3 again, the hole transport region HTR may have a single layer formed utilizing a single material, a single layer formed utilizing a plurality of different materials, or a multilayer structure including a plurality of layers formed utilizing a plurality of different materials.

The hole transport region HTR may have a single layer structure of a hole injection layer HIL or a hole transport layer HTL, and may have a single layer structure formed utilizing a hole injection material and a hole transport material. Alternatively, the hole transport region HTR may have a single layer structure formed utilizing a plurality of different materials, or a structure laminated from the first electrode EL of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without being limited thereto.

The hole transport region HTR may be formed utilizing various suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PAN I/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] qunoxaline-2,3,6,7,10,11-hexacarbonitrile (HAT-CN), etc.

The hole transport layer HTL may include, for example, carbazole derivatives (such as N-phenyl carbazole and polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. When the hole transport region HTR includes both hole injection layer HIL and hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. When the thicknesses of the hole transport region HTR, the hole injection layer HIL and the hole transport layer HTL satisfy the above-described ranges, satisfactory hole transport properties may be obtained without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without being limited thereto. For example, non-limiting examples of the p-dopant may include quinone derivatives (such as tetracyanoquinodimethane (TCNQ) and 2,3,5,6-tetrafluoro-tetracyanoquinodimethane (F4-TCNQ)), metal oxides (such as tungsten oxide and molybdenum oxide), etc., without being limited thereto.

As described above, the hole transport region HTR may further include at least one of a hole buffer layer or an electron blocking layer in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be utilized as materials included in the hole buffer layer. The electron blocking layer is a layer preventing or reducing electron injection from the electron transport region ETR to the hole transport region HTR.

When the hole transport region HTR includes both hole injection layer HIL and hole transport layer HTL, and the aforementioned monoamine compound, the monoamine compound may be included in the hole transport layer HTL.

When the hole transport layer HTL is composed of a plurality of organic layers, the monoamine compound may be included in an organic layer which is adjacent to the emission layer EML.

When the hole transport region HTR includes a monoamine compound, the hole transport region HTR may further include a suitable (e.g., a known) material in addition to the monoamine compound.

The emission layer EML is provided on the hole transport region HTR. The emission layer EML may have a thickness of, for example, from about 100 Å to about 1,000 Å, or from about 100 Å to about 300 Å. The emission layer EML may have a single layer formed utilizing a single material, a single layer formed utilizing a plurality of different materials, or a multilayer structure having a plurality of layers formed utilizing a plurality of different materials.

The emission layer EML may include a condensed ring compound. The emission layer EML may include a host and a dopant, and the dopant may include a condensed ring compound. The dopant may be a phosphorescence dopant or a fluorescence dopant. The dopant may be a thermally activated delayed fluorescence dopant, and the condensed ring compound may be a thermally activated delayed fluorescence dopant.

The emission layer EML may be a layer which further includes a suitable (e.g., a known) material in addition to the condensed ring compound, or may not include the condensed ring compound.

The host may be any suitable materials commonly utilized, without specific limitation, and may include, for example, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TcTa), or 1,3,5-tris(N-phenylbenzimidazole-2-yl)benzene (TPBi). For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris (carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis (triphenylsilyl)benzene (UGH2), hexaphenylcyclotrisiloxane ($DPSiO_3$), octaphenylcyclotetra siloxane ($DPSiO_4$), 2,8-bis(diphenylphophoryl)dibenzofuran (PPF), etc., may be utilized as the host material.

For example, the emission layer EML may further include as the dopant, at least one of N, N, N',N'-tetraphenyl-pyrene-1,6-diamine (TDP), 4,4'-bis(2-(9-ethyl-9H-carbazol-3-yl)vinyl)-1,1'-biphenyl; 4,4'-bis(9-ethyl-3-carbazovinylene)-1,1'-biphenyl (BCzVBi), 10-phenyl-10H, 10'H-spiro[acridine-9, 9'-anthracene]-10'-one (ACRSA), 3,4,5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-9, 9-dimethyl-9,10-dihydroacridine]phenyl]sulfone (DMAC-DPS) or 2-phenoxazine-4,6-diphenyl-1,3,5-triazine (PSZ-TRZ). In addition, the emission layer EML may include as a suitable (e.g., a known) dopant materials, styryl derivatives (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBP)), and/or pyrene and derivatives thereof (for example, 1,1-dipyrene, 1,4-dipyrenylbenzene, and 1,4-bis(N,N-diphenylamino)pyrene).

The emission layer EML may be a blue emission layer which emits blue light. The emission layer EML may be an emission layer emitting light in a wavelength region of about 510 nm or less, or about 480 nm or less. The emission layer EML may be a fluorescence emission layer which radiates fluorescence.

The electron transport region ETR is provided on the emission layer EML. The electron transport region ETR may include at least one of a hole blocking layer, an electron transport layer ETL or an electron injection layer EIL, without being limited thereto.

The electron transport region ETR may have a single layer formed utilizing a single material, a single layer formed utilizing a plurality of different materials, or a multilayer structure having a plurality of layers formed utilizing a plurality of different materials.

For example, the electron transport region ETR may have a single layer structure of an electron injection layer EIL or an electron transport layer ETL, or a single layer structure formed utilizing an electron injection material and an electron transport material. Further, the electron transport region ETR may have a single layer structure having a plurality of different materials, or a structure laminated from the emission layer EML of electron transport layer ETL/electron injection layer EIL, or hole blocking layer/electron transport layer ETL/electron injection layer EIL, without being limited thereto. The thickness of the electron transport region ETR may be, for example, from about 1,000 Å to about 1,500 Å.

The electron transport region ETR may be formed utilizing various suitable methods such as a vacuum deposition method, a spin coating method, a cast method, a Langmuir-Blodgett (LB) method, an inkjet printing method, a laser printing method, and/or a laser induced thermal imaging (LITI) method.

When the electron transport region ETR includes an electron transport layer ETL, the electron transport region ETR may include an anthracene-based compound. The electron transport region may include, for example, without being limited thereto, tris(8-hydroxyquinolinato)aluminum ($Alq_3$), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl) anthracene (ADN), and a mixture thereof. The thickness of the electron transport layer ETL may be from about 100 Å to about 1,000 Å, for example, from about 150 Å to about 500 Å. When the thickness of the electron transport layer ETL satisfies the above-described ranges, satisfactory electron transport properties may be obtained without substantial increase of a driving voltage.

When the electron transport region ETR includes the electron injection layer EIL, the electron transport region ETR may use LiF, lithium quinolate (LiQ), $Li_2O$, BaO, NaCl, CsF, a metal in lanthanoides (such as Yb), or a metal halide (such as RbCl, and RbI). However, an embodiment of the inventive concept is not limited thereto. The electron injection layer EIL may also be formed utilizing a mixture material of an electron transport material and an insulating organo metal salt. The organo metal salt may be a material having an energy band gap of about 4 eV or more. In one embodiment, the organo metal salt may include, for example, metal acetates, metal benzoates, metal acetoacetates, metal acetylacetonates, or metal stearates. The thickness of the electron injection layer EIL may be from about 1 Å to about 100 Å, for example, from 3 Å to about 90 Å. When the thickness of the electron injection layer EIL satisfies the above-described ranges, satisfactory electron injection properties may be obtained without substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

A second electrode EL2 is provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed utilizing the above-described materials and a transparent conductive layer formed utilizing ITO, IZO, ZnO, ITZO, etc.

Though not shown, the second electrode EL2 may be connected with an auxiliary electrode. When the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EU may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

When the organic electroluminescence device 10 is a top emission type (i.e., a top emission device), the first electrode EL1 may be a reflective electrode and the second electrode EL2 may be a transmissive electrode or a transflective electrode. When the organic electroluminescence device 10 is a bottom emission type (i.e., a bottom emission device), the first electrode EL1 may be a transmissive electrode or a transflective electrode and the second electrode EL2 may be a reflective electrode.

The organic electroluminescence device 10 according to an embodiment of the inventive concept utilizes the aforementioned monoamine compound as a material of an organic material layer, and thus, the emission efficiency and life (i.e., lifespan) thereof may be increased.

An embodiment of the inventive concept provides a monoamine compound represented by the following Formula 1:

[Formula 1]

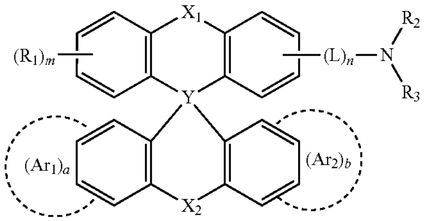

In Formula 1, Y is C or Si; when Y is C, $X_1$ and $X_2$ are each independently 0, S, or $SiR_4R_5$, and $X_1$ and $X_2$ are different from each other; and when Y is Si, $X_1$ and $X_2$ are each independently O, S, $SiR_4R_5$, or a direct linkage, and a case where both $X_1$ and $X_2$ are direct linkages is excluded.

In Formula 1, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring. In addition, L is a direct linkage, a substituted or unsubstituted arylene group having 6 to 30 carbon atoms, or a substituted or unsubstituted heteroarylene group having 2 to 30 carbon atoms for forming a ring.

In Formula 1, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, a, b and n are each independently 0 or 1, and m is an integer of 0 to 4.

The same explanation on the monoamine compound in the explanation of the organic electroluminescence device of an embodiment described above may be applied to the monoamine compound of the current embodiment, represented by Formula 1.

The monoamine compound according to an embodiment may be any one selected from the compounds represented in Compound Group 1 and Compound Group 2 above.

Hereinafter, the inventive concept will be explained in more detail with reference to example (e.g., particular) embodiments and comparative embodiments. The following embodiments are only illustrations to assist the understanding of the inventive concept, and the scope of the inventive concept is not limited thereto.

Synthesis Examples

The monoamine compounds according to exemplary embodiments of the inventive concept may be synthesized, for example, as follows. However, the synthetic method of the monoamine compound according to an embodiment of the inventive concept is not limited thereto.

1. Synthesis of Compound A12

Compound A12 according to an embodiment of the inventive concept may be synthesized, for example, as follows.

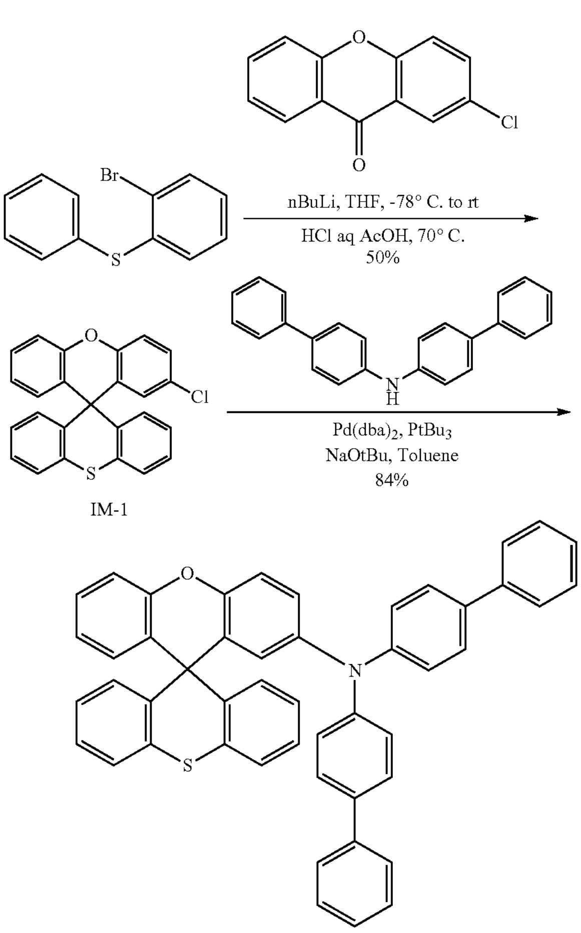

IM-1

A12

(Synthesis of Intermediate IM-1)

Under an argon (Ar) atmosphere, to a 500 ml, three-neck flask, 15.00 g (56.6 mmol) of 2-bromophenyl phenyl sulfide and 189 ml (0.3 M) of THF were added, and while stirring at about −78° C., 38.9 ml (1.1 equiv) of n-BuLi/n-hexane solution of 1.6 mol/L was added thereto dropwise. After stirring for about 1 hour at the same temperature, a THF solution (15.6 ml, 1 mol/L) of 14.35 g (1.1 equiv, 62.2 mmol) of 2-chloro-9H-xanthen-9-one was added thereto dropwise and stirred for about 30 minutes at the same temperature, followed by elevating the temperature to room temperature and stirring additionally for about 2 hours. After checking (e.g., detecting) the disappearance of the raw materials, 32.4 ml (10 equiv) of AcOH and the same amount of 32.4 ml of hydrochloric acid were added and then, heated to and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-1 (11.28 g, yield 50%).

Intermediate IM-1 was identified by measuring FAB-MS (i.e., measuring utilizing Fast Atom Bombardment-Mass Spectrometry) and observing a mass number of m/z=398 as a molecular ion peak.

(Synthesis of Compound A12)

Under an Ar atmosphere, to a 500 ml, three-neck flask, 5.00 g (16.7 mmol) of IM-1, 20.29 g (0.03 equiv, 0.5 mmol) of Pd(dba), 3.22 g (2 equiv, 33.5 mmol) of NaOtBu, 84 ml of toluene, 5.91 g (1.1 equiv, 18.4 mmol) of bis(4-biphenyl) amine, and 0.34 g (0.1 equiv, 1.7 mmol) of t-Bu3P were added in order (e.g., sequentially), followed by heating and refluxing for about 6 hours. After cooling in the air to room temperature, water was added to the reaction product, and an organic layer (e.g., a first organic layer) was separately taken (e.g., separated from a first aqueous layer). Toluene was added to an aqueous layer (e.g., added to the first aqueous layer), and an organic layer (e.g., a second organic layer) was extracted further. The organic layers (e.g., the first and second organic layers) were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A12 (9.61 g, yield 84%) as a white solid.

Compound A12 was identified by measuring FAB-MS and observing a mass number of m/z=683 as a molecular ion peak.

2. Synthesis of Compound A24

Compound A24 according to an embodiment of the inventive concept, may be synthesized, for example, as follows.

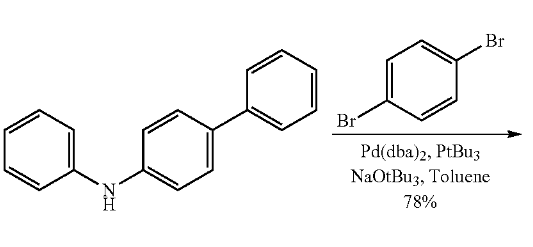

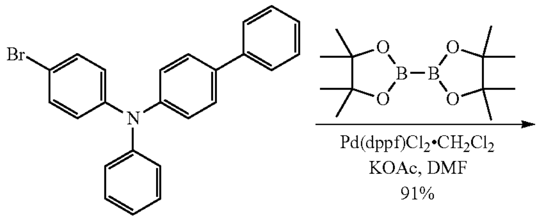

IM-2

-continued

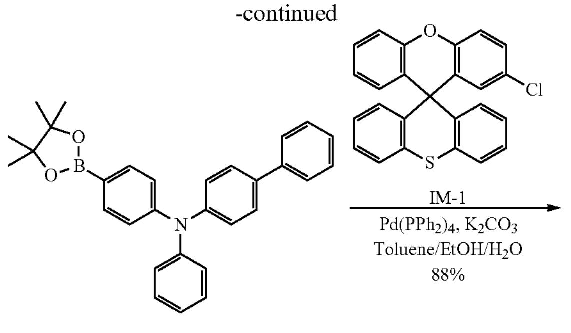

IM-3

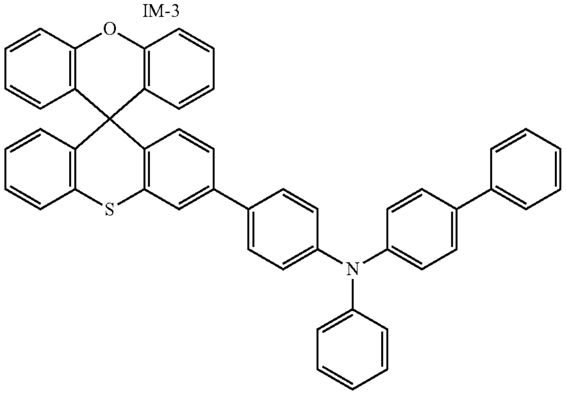

A24

(Synthesis of Intermediate IM-2)

Under an Ar atmosphere, to a 300 ml, three-neck flask, 10.40 g (42.4 mmol) of N-phenyl-4-biphenylaniline, 073 g (0.03 equiv, 1.3 mmol) of $Pd(dba)_2$, 4.07 g (1 equiv, 42.4 mmol) of NaOtBu, 212 ml of toluene, 10.00 g (1.0 equiv, 42.4 mmol) of 1,4-dibromobenzene, and 0.86 g (0.1 equiv, 4.23 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-2 (14.25 g, yield 78%).

Intermediate IM-2 was identified by measuring FAB-MS and observing a mass number of m/z=400 as a molecular ion peak.

(Synthesis of Intermediate IM-3)

Under an Ar atmosphere, to a 300 ml, three-neck flask, 10.00 g (25.0 mmol) of IM-2, 2.04 g (0.1 equiv, 2.5 mmol) of a $Pd(dppf)Cl_2.CH_2Cl_2$ complex, 4.90 g (2 equiv, 50.0 mmol) of KOAc, and 7.61 g (1.2 equiv, 30.0 mmol) of bis(pinacolato)diboron were added in order (e.g., sequentially), followed by heating and refluxing for about 5 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-3 (10.17 g, yield 91%).

Intermediate IM-3 was identified by measuring FAB-MS and observing a mass number of m/z=447 as a molecular ion peak.

(Synthesis of Compound A24)

Under an Ar atmosphere, to a 300 ml, three-neck flask, 5.00 g (11.2 mmol) of IM-3, 4.90 g (1.1 equiv, 12.3 mmol) of IM-1, 4.63 g (3 equiv, 33.5 mmol) of $K_2CO_3$, 0.65 g (0.05 equiv, 0.6 mmol) of $Pd(PPh_3)_4$, and 78 ml of a mixture solution of toluene/EtOH/$H_2O$ (4/2/1) were added in order (e.g., sequentially), followed by heating and refluxing for about 5 hours. After cooling in the air to room temperature, the reaction product was extracted with toluene. An aqueous layer was removed, and an organic layer was washed with a saturated saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A24 (6.88 g, yield 88%) as a white solid.

Compound A24 was identified by measuring FAB-MS and observing a mass number of m/z=699 as a molecular ion peak.

3. Synthesis of Compound A39

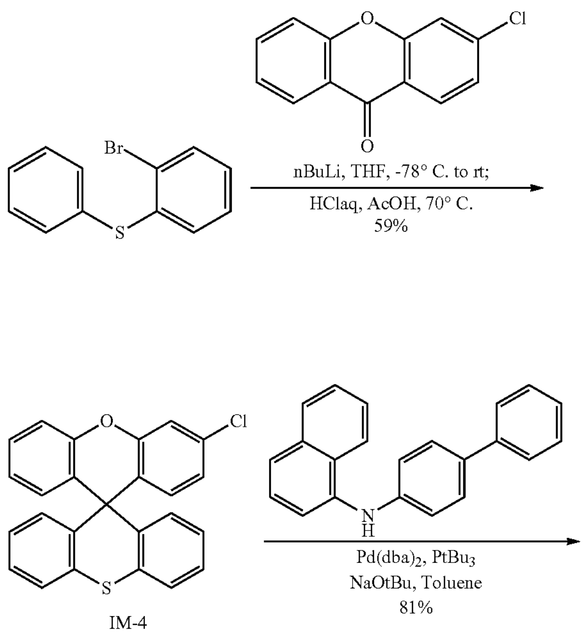

IM-4

-continued

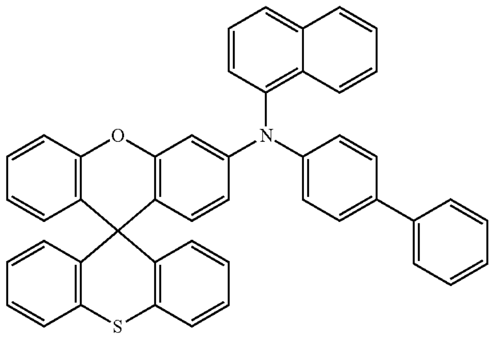

A39

(Synthesis of Intermediate IM-4)

Under an Ar atmosphere, to a 500 ml, three-neck flask, 15.00 g (56.6 mmol) of 2-bromophenyl phenyl sulfide and 189 ml (0.3 M) of THF were added, and while stirring at less than about −78° C., 38.9 ml (1.1 equiv) of n-BuLi/n-hexane solution of 1.6 mol/L was added thereto dropwise. After stirring for about 1 hour at the same temperature, a THF solution (15.6 ml, 1 mol/L) of 14.35 g (1.1 equiv, 62.2 mmol) of 2-chloro-9H-xanthen-9-one was added thereto dropwise and stirred for about 30 minutes at the same temperature, followed by elevating the temperature to room temperature and stirring additionally for about 2 hours. After checking the disappearance of the raw materials, 32.4 ml (10 equiv) of AcOH and the same amount of 32.4 ml of hydrochloric acid were added and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-4 (13.31 g, yield 59%).

Intermediate IM-4 was identified by measuring FAB-MS and observing a mass number of m/z=398 as a molecular ion peak.

(Synthesis of Compound A39)

Under an Ar atmosphere, to a 500 ml, three-neck flask, 5.00 g (16.7 mmol) of IM-4, 0.29 g (0.03 equiv, 0.5 mmol) of $Pd(dba)_2$, 3.22 g (2 equiv, 33.5 mmol) of NaOtBu, 84 ml of toluene, 5.44 g (1.1 equiv, 18.4 mmol) of N-(4-biphenylyl)-1-naphthylamine, and 0.34 g (0.1 equiv, 1.7 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A39 (8.91 g, yield 81%) as a white solid.

Compound A39 was identified by measuring FAB-MS and observing a mass number of m/z=657 as a molecular ion peak.

4. Synthesis of Compound A48
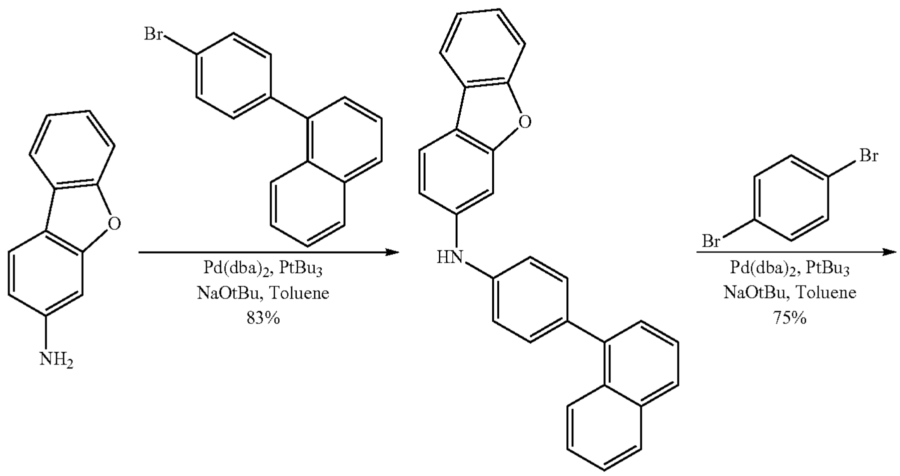
IM-5
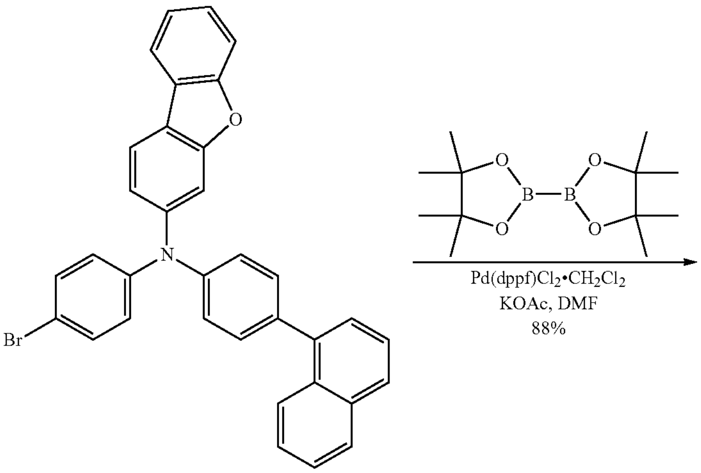
IM-6
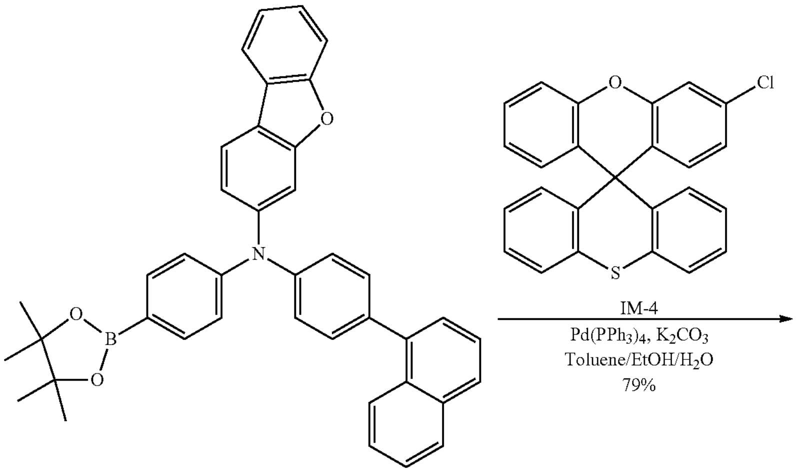
IM-7

-continued

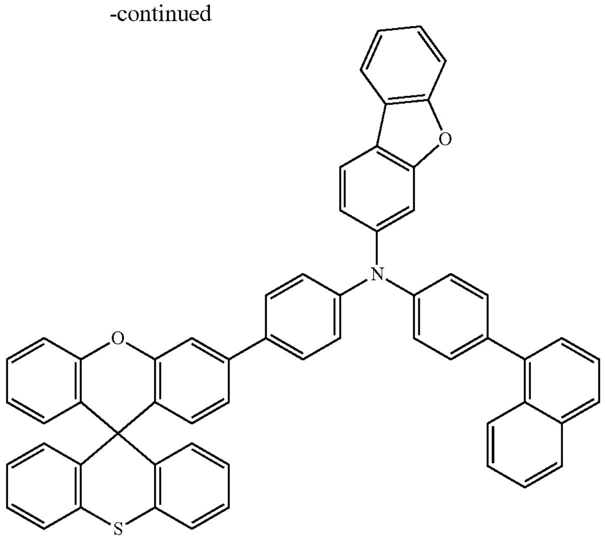

A48

(Synthesis of Intermediate IM-5)

Under an Ar atmosphere, to a 500 ml, three-neck flask, 10.00 g (54.6 mmol) of 3-dibenzofuranylamine, 0.94 g (0.03 equiv, 1.6 mmol) of $Pd(dba)_2$, 5.25 g (1 equiv, 54.6 mmol) of NaOtBu, 273 ml of toluene, 15.46 g (1.0 equiv, 54.6 mmol) of 1-(4-bromophenyl)naphthalene, and 1.10 g (0.1 equiv, 5.46 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-5 (12.93 g, yield 83%).

Intermediate IM-5 was identified by measuring FAB-MS and observing a mass number of m/z=285 as a molecular ion peak.

(Synthesis of Intermediate IM-6)

Under an Ar atmosphere, to a 300 ml, three-neck flask, 10.00 g (35.0 mmol) of IM-5, 0.60 g (0.03 equiv, 1.0 mmol) of $Pd(dba)_2$, 3.37 g (1 equiv, 35.0 mmol) of NaOtBu, 175 ml of toluene, 10.01 g (1.0 equiv, 35.0 mmol) of 1,4-dibromobenzene, and 0.71 g (0.1 equiv, 3.5 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-6 (14.20 g, yield 75%).

Intermediate IM-6 was identified by measuring FAB-MS and observing a mass number of m/z=540 as a molecular ion peak.

(Synthesis of Intermediate IM-7)

Under an Ar atmosphere, to a 300 ml, three-neck flask, 10.00 g (18.5 mmol) of IM-6, 1.51 g (0.1 equiv, 1.9 mmol) of a $Pd(dppf)Cl_2.CH_2Cl_2$ complex, 3.63 g (2 equiv, 37.0 mmol) of KOAc, and 5.64 g (1.2 equiv, 22.2 mmol) of bis(pinacolato)diboron were added in order (e.g., sequentially), followed by heating and refluxing for about 5 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-7 (9.57 g, yield 88%).

Intermediate IM-7 was identified by measuring FAB-MS and observing a mass number of m/z=587 as a molecular ion peak.

(Synthesis of Compound A48)

Under an Ar atmosphere, to a 200 ml, three-neck flask, 5.00 g (8.5 mmol) of IM-7, 3.73 g (1.1 equiv, 9.4 mmol) of IM-4, 3.53 g (3 equiv, 25.5 mmol) of $K_2CO_3$, 0.49 g (0.05 equiv, 0.4 mmol) of $Pd(PPh_3)_4$, and 60 ml of a mixture solution of toluene/EtOH/$H_2O$ (4/2/1) were added in order (e.g., sequentially), followed by heating and refluxing at about 80° C. for about 5 hours. After cooling in the air to room temperature, the reaction product was extracted with toluene. An aqueous layer was removed, and an organic layer was washed with a saturated saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A48 (5.54 g, yield 79%) as a white solid.

Compound A48 was identified by measuring FAB-MS and observing a mass number of m/z=824 as a molecular ion peak.

5. Synthesis of Compound A50

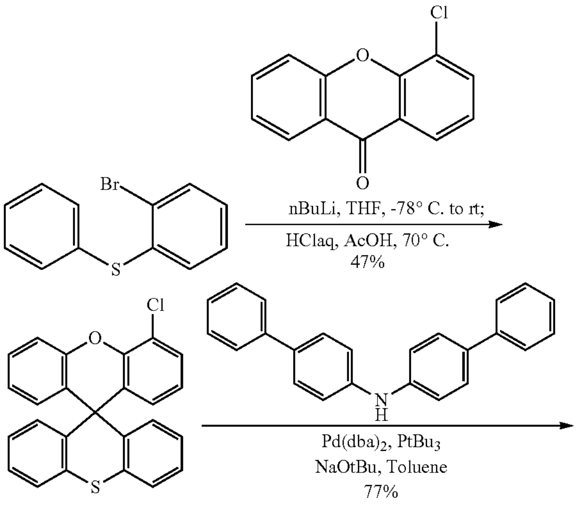

IM-8

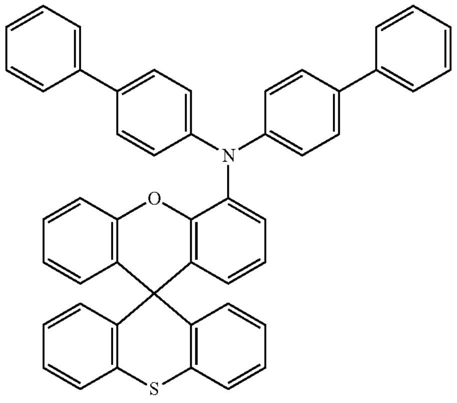

A50

(Synthesis of Intermediate IM-8)

Under an Ar atmosphere, to a 500 ml, three-neck flask, 15.00 g (56.6 mmol) of 2-bromophenyl phenyl sulfide and 189 ml (0.3 M) of THF were added, and while stirring at about −78° C., 38.9 ml (1.1 equiv) of n-BuLi/n-hexane solution of 1.6 mol/L was added thereto dropwise. After stirring for about 1 hour at the same temperature, a THF solution (15.6 ml, 1 mol/L) of 14.35 g (1.1 equiv, 62.2 mmol) of 1-chloro-9H-xanthen-9-one was added thereto dropwise and stirred for about 30 minutes at the same temperature, followed by elevating the temperature to room temperature and stirring additionally for about 2 hours. After checking the disappearance of the raw materials, 32.4 ml (10 equiv) of AcOH and the same amount of 32.4 ml of hydrochloric acid were added and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-8 (10.61 g, yield 47%).

Intermediate IM-8 was identified by measuring FAB-MS and observing a mass number of m/z=398 as a molecular ion peak.

(Synthesis of Compound A50)

Under an Ar atmosphere, to a 500 ml, three-neck flask, 5.00 g (16.7 mmol) of IM-8, 0.29 g (0.03 equiv, 0.5 mmol) of Pd(dba)$_2$, 3.22 g (2 equiv, 33.5 mmol) of NaOtBu, 84 ml of toluene, 5.91 g (1.1 equiv, 18.4 mmol) of bis(4-biphenyl) amine, and 0.34 g (0.1 equiv, 1.7 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A50 (8.81 g, yield 77%) as a white solid.

Compound A50 was identified by measuring FAB-MS and observing a mass number of m/z=683 as a molecular ion peak.

6. Synthesis of Compound A67

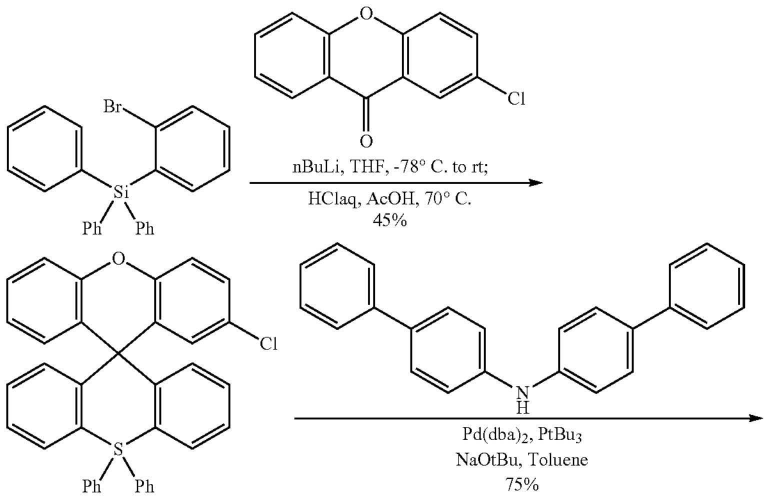

IM-9

-continued

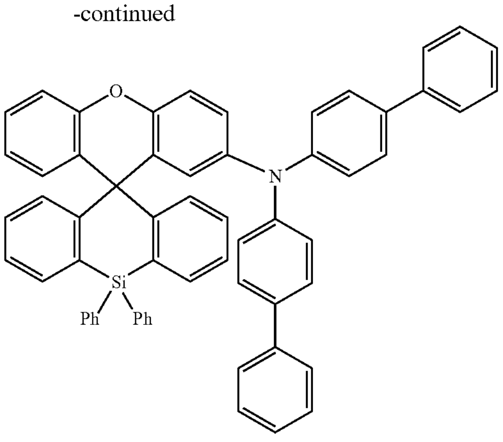

A67

(Synthesis of Intermediate IM-9)

Under an Ar atmosphere, to a 500 ml, three-neck flask, 15.00 g (36.1 mmol) of (2-bromophenyl)triphenylsilane and 120 ml (0.3 M) of THF were added, and while stirring at about −78° C., 24.8 ml (1.1 equiv) of n-BuLi/n-hexane solution of 1.6 mol/L was added thereto dropwise. After stirring for about 1 hour at the same temperature, a THF solution (16.6 ml, 1 mol/L) of 9.16 g (1.1 equiv, 9.2 mmol) of 3-chloro-9H-xanthen-9-one was added thereto dropwise and stirred for about 30 minutes at the same temperature, followed by elevating the temperature to room temperature and stirring additionally for about 2 hours. After checking the disappearance of the raw materials, 32.4 ml (10 equiv) of AcOH and the same amount of 32.4 ml of hydrochloric acid were added and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-9 (8.92 g, yield 45%).

Intermediate IM-9 was identified by measuring FAB-MS and observing a mass number of m/z=549 as a molecular ion peak.

(Synthesis of Compound A67)

Under an Ar atmosphere, to a 300 ml, three-neck flask, 5.00 g (9.1 mmol) of IM-9, 0.16 g (0.03 equiv, 0.3 mmol) of $Pd(dba)_2$, 1.75 g (2 equiv, 18.2 mmol) of NaOtBu, 46 ml of toluene, 3.22 g (1.1 equiv, 10.0 mmol) of bis(4-biphenylyl) amine, and 0.18 g (0.1 equiv, 0.9 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A67 (5.70 g, yield 75%) as a white solid.

Compound A67 was identified by measuring FAB-MS and observing a mass number of m/z=834 as a molecular ion peak.

7. Synthesis of Compound A111

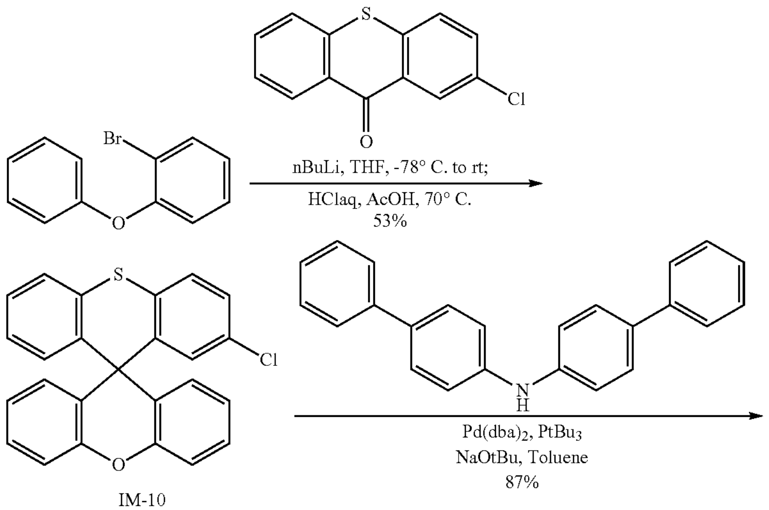

IM-10

-continued

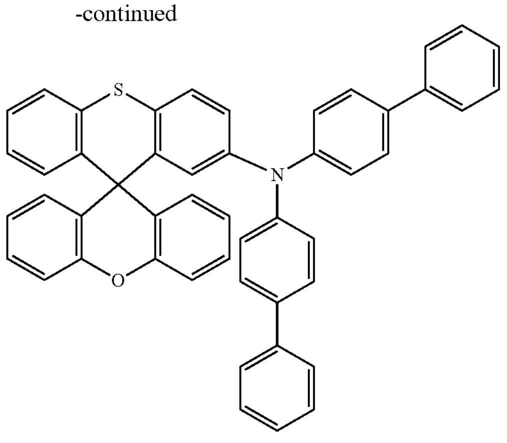

A111

(Synthesis of Intermediate IM-10)

Under an Ar atmosphere, to a 500 ml, three-neck flask, 15.00 g (60.2 mmol) of 2-bromophenyl phenyl ether and 200 ml (0.3 M) of THF were added, and while stirring at about −78° C., 41.4 ml (1.1 equiv) of n-BuLi/n-hexane solution of 1.6 mol/L was added thereto dropwise. After stirring for about 1 hour at the same temperature, a THF solution (16.6 ml, 1 mol/L) of 16.34 g (1.1 equiv, 66.2 mmol) of 3-chloro-9H-thioxanthen-9-one was added thereto dropwise and stirred for about 30 minutes at the same temperature, followed by elevating the temperature to room temperature and stirring additionally for about 2 hours. After checking the disappearance of the raw materials, 34.4 ml (10 equiv) of AcOH and the same amount of 34.4 ml of hydrochloric acid were added and then, heated to and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-10 (12.44 g, yield 53%).

Intermediate IM-10 was identified by measuring FAB-MS and observing a mass number of m/z=398 as a molecular ion peak.

(Synthesis of Compound A111)

Under an Ar atmosphere, to a 300 ml, three-neck flask, 5.00 g (12.8 mmol) of 1M-10, 0.22 g (0.03 equiv, 0.4 mmol) of $Pd(dba)_2$, 2.46 g (2 equiv, 25.6 mmol) of NaOtBu, 64 ml of toluene, 4.53 g (1.1 equiv, 14.1 mmol) of bis(4-biphenylyl)amine, and 0.26 g (0.1 equiv, 1.3 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A111 (7.63 g, yield 87%) as a white solid.

Compound A111 was identified by measuring FAB-MS and observing a mass number of m/z=683 as a molecular ion peak.

8. Synthesis of Compound A124

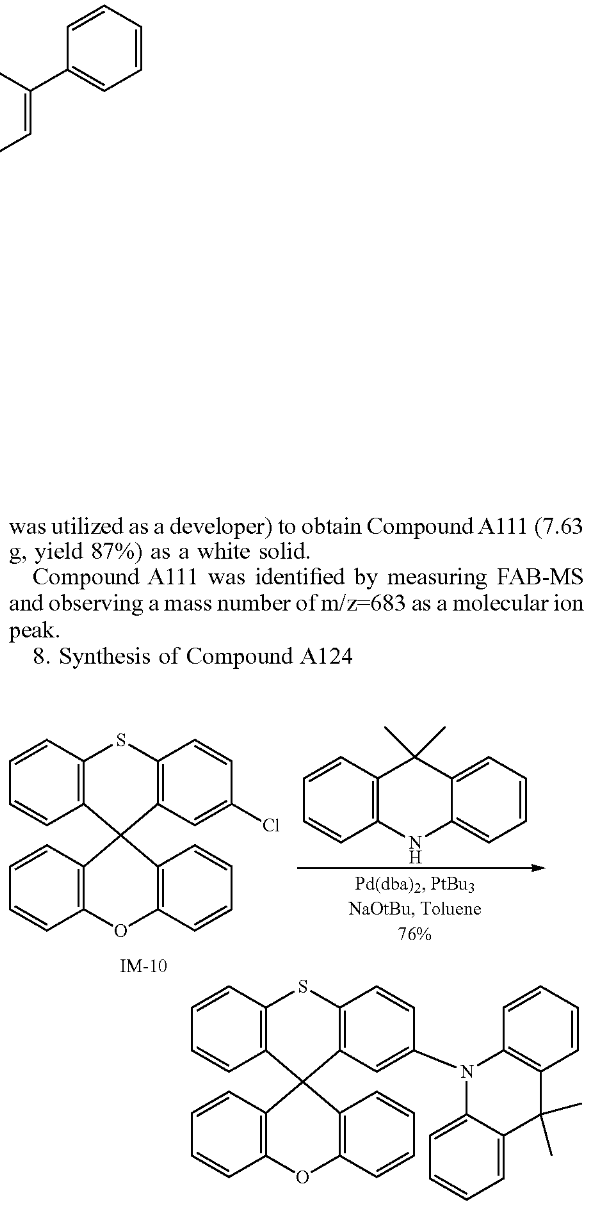

IM-10

A124

(Synthesis of Compound A124)

Under an Ar atmosphere, to a 200 ml, three-neck flask, 7.00 g (17.5 mmol) of 1M-10, 0.31 g (0.03 equiv, 0.5 mmol) of $Pd(dba)_2$, 3.37 g (2 equiv, 35.1 mmol) of NaOtBu, 88 ml of toluene, 4.04 g (1.1 equiv, 19.3 mmol) of 9,9-dimethyl-9,10-dihydroacridine, and 0.36 g (0.1 equiv, 1.8 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A124 (7.63 g, yield 76%) as a white solid.

Compound A124 was identified by measuring FAB-MS and observing a mass number of m/z=571 as a molecular ion peak.

9. Synthesis of Compound A177

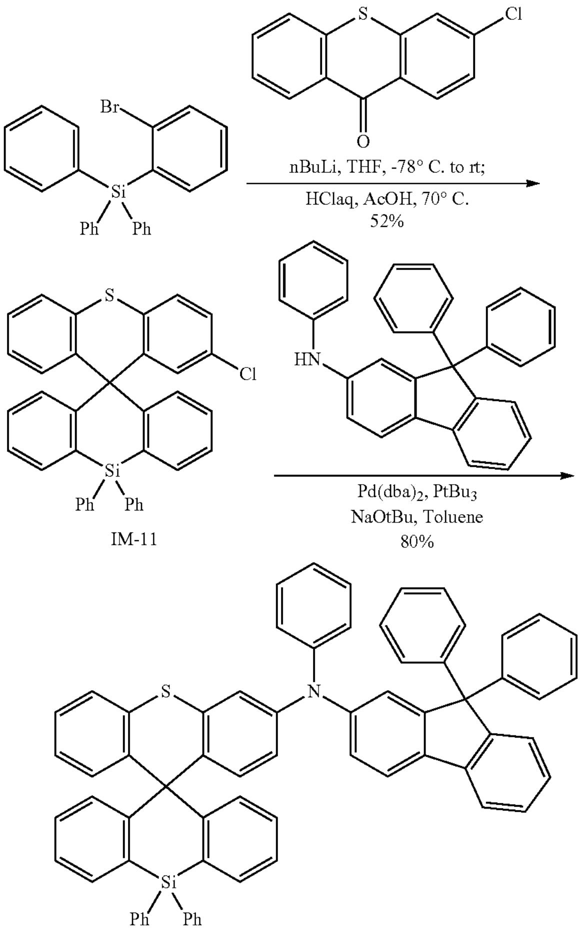

IM-11

A177

(Synthesis of Intermediate IM-11)

Under an Ar atmosphere, to a 500 ml, three-neck flask, 15.00 g (36.1 mmol) of (2-bromophenyl)triphenylsilane and 120 ml (0.3 M) of THF were added, and while stirring at about −78° C., 24.8 ml (1.1 equiv) of n-BuLi/n-hexane solution of 1.6 mol/L was added thereto dropwise. After stirring for about 1 hour at the same temperature, a THF solution (16.6 ml, 1 mol/L) of 9.80 g (1.1 equiv, 39.7 mmol) of 2-chloro-9H-thioxanthen-9-one was added thereto dropwise and stirred for about 30 minutes at the same temperature, followed by elevating the temperature to room temperature and stirring additionally for about 2 hours. After checking the disappearance of the raw materials, 20.5 ml (10 equiv) of AcOH and the same amount of 20.5 ml of hydrochloric acid were added and then, heated to and stirred at about 70° C. for about 1 hour. After cooling in the air to room temperature, the reaction product solution was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-11 (10.61 g, yield 52%).

Intermediate IM-11 was identified by measuring FAB-MS and observing a mass number of m/z=565 as a molecular ion peak.

(Synthesis of Compound A177)

Under an Ar atmosphere, to a 300 ml, three-neck flask, 5.00 g (8.8 mmol) of IM-11, 0.15 g (0.03 equiv, 0.3 mmol) of $Pd(dba)_2$, 1.70 g (2 equiv, 17.7 mmol) of NaOtBu, 44 ml of toluene, 3.99 g (1.1 equiv, 9.7 mmol) of N,9,9-triphenyl-9H-fluoren-2-amine, and 0.18 g (0.1 equiv, 0.9 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound A177 (6.64 g, yield 80%) as a white solid.

Compound A177 was identified by measuring FAB-MS and observing a mass number of m/z=938 as a molecular ion peak.

10. Synthesis of Compound B12

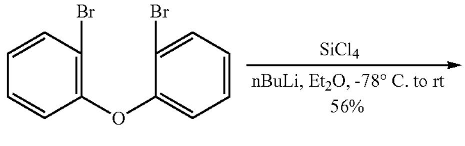

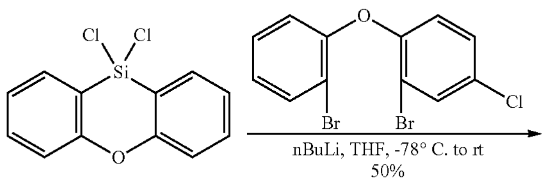

IM-12

-continued

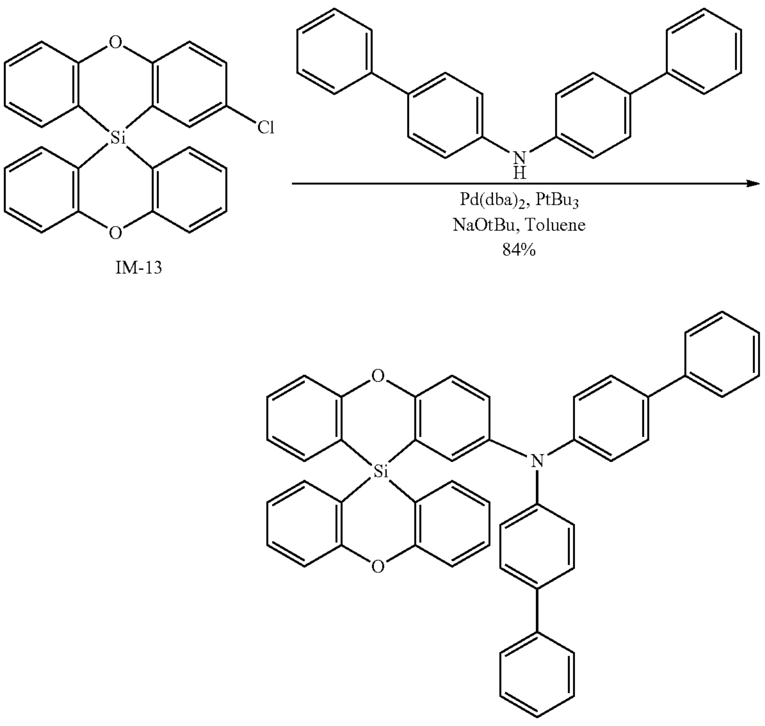

IM-13

B12

(Synthesis of Intermediate IM-12)

Under an Ar atmosphere, to a 500 ml, three-neck flask, 20.00 g (61.0 mmol) of bis(2-bromophenyl) ether and 203 ml (0.3 M) of diethyl ether were added, and while stirring at about −78° C., 83.8 ml (2.2 equiv) of n-BuLi/n-hexane solution of 1.6 mol/L was added thereto dropwise. After stirring for about 1 hour at the same temperature, a diethyl ether solution (17 ml, 1 mol/L) of 11.40 g (1.1 equiv, 67.1 mmol) of $SiCl_4$ was added thereto dropwise and stirred for about 30 minutes at the same temperature, followed by elevating the temperature to room temperature and stirring additionally for about 8 hours. A white solid precipitated under an argon atmosphere was separated by filtering, and a filtrate solution was distilled. The crude product IM-12 (9.12 g, yield 56%) in an oily phase was not separated further and utilized as it was in the next reaction.

Intermediate IM-12 was identified by measuring FAB-MS and observing a mass number of m/z=267 as a molecular ion peak.

(Synthesis of Intermediate IM-13)

Under an Ar atmosphere, to a 300 ml, three-neck flask, 10.00 g (27.6 mmol) of (2-bromophenyl) (2-bromo-4-chorophenyl) ether and 92 ml (0.3 M) of THF were added and while stirring at about −78° C., 37.9 ml (2.2 equiv) of n-BuLi/n-hexane solution of 1.6 mol/L was added thereto dropwise. After stirring for about 1 hour at the same temperature, a THF solution (8 ml, 1 mol/L) of 8.11 g (1.1 equiv, 30.3 mmol) of IM-12 was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-13 (5.50 g, yield 50%).

Intermediate IM-13 was identified by measuring FAB-MS and observing a mass number of m/z=398 as a molecular ion peak.

(Synthesis of Compound B12)

Under an Ar atmosphere, to a 300 ml, three-neck flask, 5.00 g (16.7 mmol) of IM-13, 0.29 g (0.03 equiv, 0.5 mmol) of Pd(dba)$_2$, 3.21 g (2 equiv, 33.5 mmol) of NaOtBu, 85 ml of toluene, 5.91 g (1.1 equiv, 18.4 mmol) of N-(4-biphenyl) aniline, and 0.34 g (0.1 equiv, 1.7 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B12 (9.61 g, yield 84%) as a white solid.

Compound B12 was identified by measuring FAB-MS and observing a mass number of m/z=683 as a molecular ion peak.

11. Synthesis of Compound B24

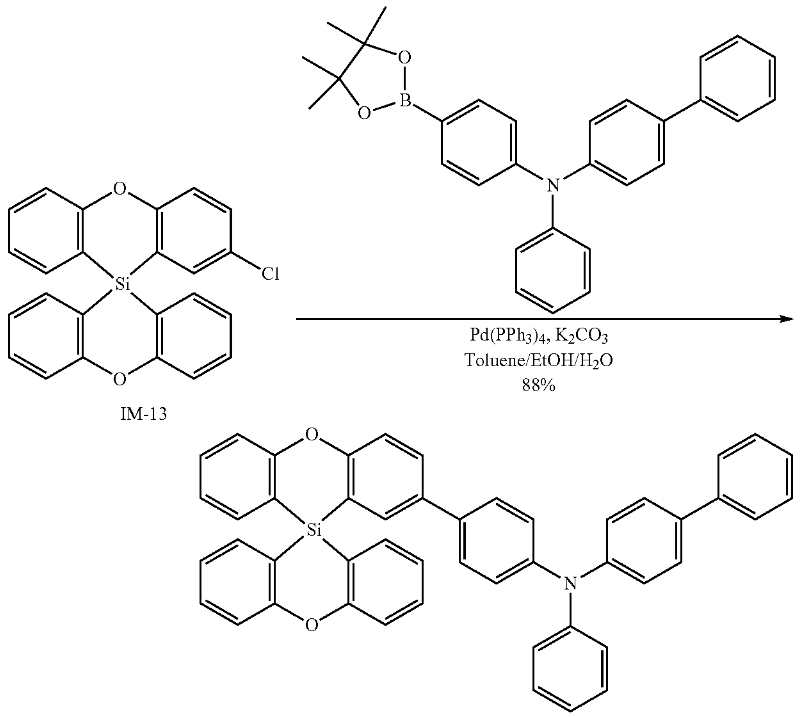

IM-13

B24

(Synthesis of Compound B24)

Under an Ar atmosphere, to a 300 ml, three-neck flask, 5.00 g (12.5 mmol) of IM-13, 7.16 g (1.1 equiv, 13.8 mmol) of N-phenyl-N-(4-(4,4,5,5-tetramethyl-1,3,2-dioxaborolan-2-yl)phenyl)-(1,1'-biphenyl)-4-am ine, 5.20 g (3 equiv, 37.6 mmol) of $K_2CO_3$, 0.72 g (0.05 equiv, 0.6 mmol) of $Pd(PPh_3)_4$, and 88 ml of a mixture solution of toluene/EtOH/$H_2O$ (4/2/1) were added in order (e.g., sequentially), followed by heating and stirring at about 80° C. for about 5 hours. After cooling in the air to room temperature, the reaction product was extracted with toluene. An aqueous layer was removed, and an organic layer was washed with a saturated saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B24 (7.54 g, yield 88%) as a white solid.

Compound B24 was identified by measuring FAB-MS and observing a mass number of m/z=683 as a molecular ion peak.

12. Synthesis of Compound B58

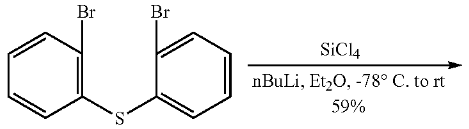

-continued

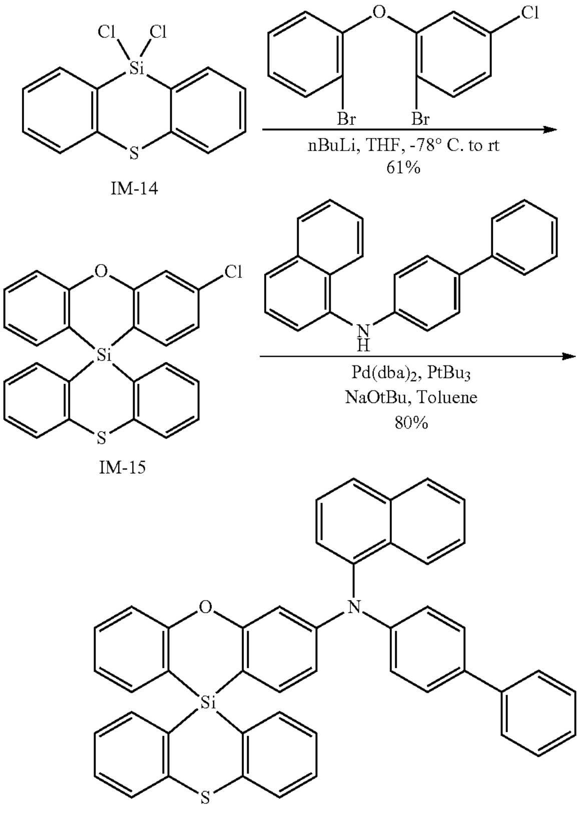

IM-14

IM-15

B58

(Synthesis of Intermediate IM-14)

Under an Ar atmosphere, to a 500 ml, three-neck flask, 20.00 g (58.1 mmol) of bis(2-bromophenyl) sulfide and 194 ml (0.3 M) of diethyl ether were added, and while stirring at about −78° C., 79.9 ml (2.2 equiv) of n-BuLi/n-hexane solution of 1.6 mol/L was added thereto dropwise. After stirring for about 1 hour at the same temperature, a diethyl ether solution (16 ml, 1 mol/L) of 10.86 g (1.1 equiv, 63.9 mmol) of $SiCl_4$ was added thereto dropwise and stirred for about 30 minutes at the same temperature, followed by elevating the temperature to room temperature and stirring additionally for about 8 hours. A white solid precipitated under an argon atmosphere was separated by filtering, and a filtrate solution was distilled. The crude product IM-14 (9.71 g, yield 59%) in an oily phase was not separated further and utilized as it was in the next reaction.

Intermediate IM-14 was identified by measuring FAB-MS and observing a mass number of m/z=283 as a molecular ion peak.

(Synthesis of Intermediate IM-15)

Under an Ar atmosphere, to a 300 ml, three-neck flask, 10.00 g (27.6 mmol) of (2-bromophenyl) (2-bromo-4-chorophenyl) ether and 92 ml (0.3 M) of THF were added and while stirring at about −78° C., 37.9 ml (2.2 equiv) of n-BuLi/n-hexane solution of 1.6 mol/L was added thereto dropwise. After stirring for about 1 hour at the same temperature, a THF solution (8 ml, 1 mol/L) of 8.60 g (1.1 equiv, 30.3 mmol) of IM-14 was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-15 (6.98 g, yield 61%).

Intermediate IM-15 was identified by measuring FAB-MS and observing a mass number of m/z=414 as a molecular ion peak.

(Synthesis of Compound B58)

Under an Ar atmosphere, to a 300 ml, three-neck flask, 5.00 g (12.0 mmol) of IM-15, 0.21 g (0.03 equiv, 0.4 mmol) of $Pd(dba)_2$, 2.32 g (2 equiv, 24.1 mmol) of NaOtBu, 60 ml of toluene, 3.91 g (1.1 equiv, 13.3 mmol) of N-(4-biphenylyl)-1-naphthylamine, and 0.24 g (0.1 equiv, 1.2 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B58 (6.50 g, yield 80%) as a white solid.

Compound B58 was identified by measuring FAB-MS and observing a mass number of m/z=673 as a molecular ion peak.

13. Synthesis of Compound B138

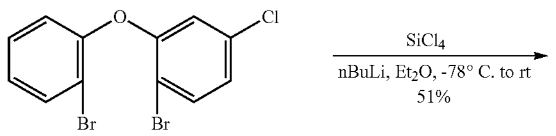

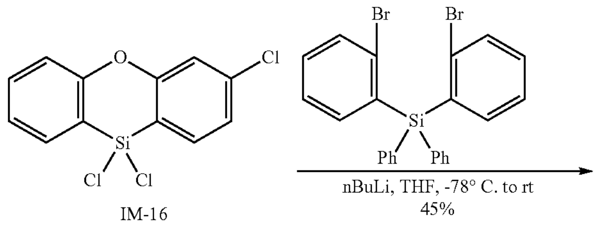

IM-16

-continued

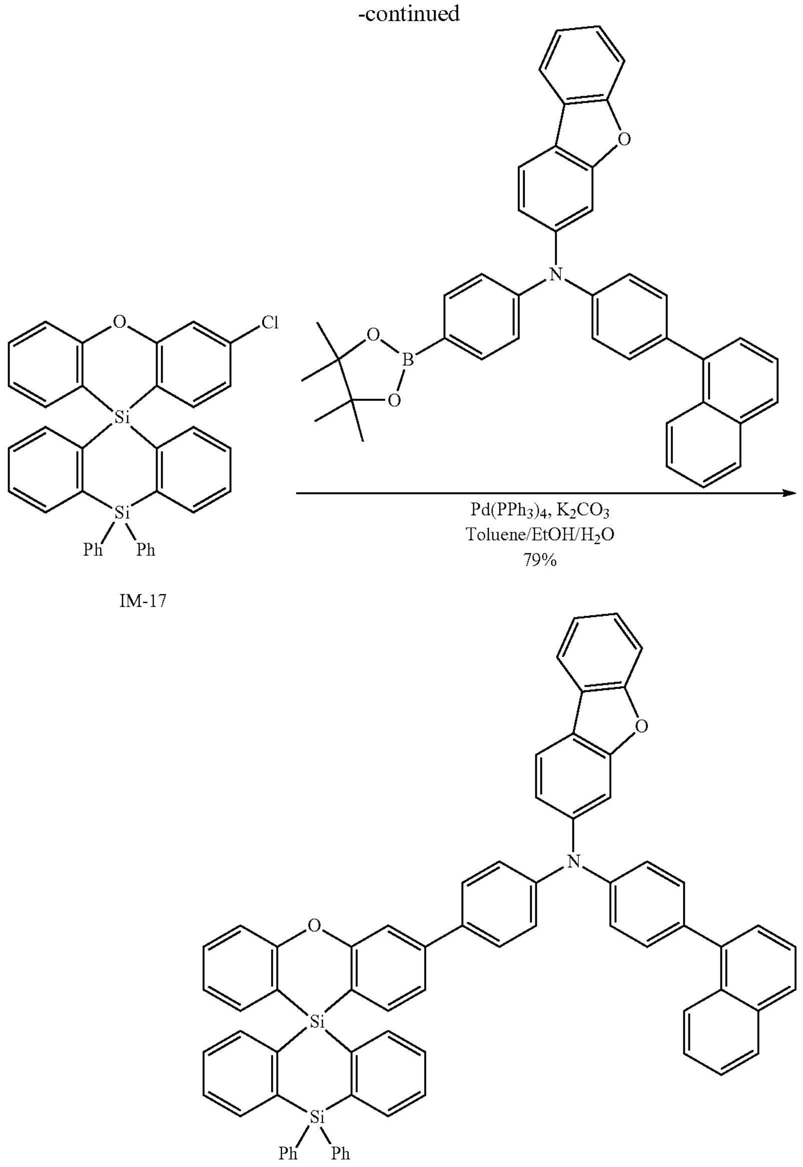

IM-17

B138

(Synthesis of Intermediate IM-16)

Under an Ar atmosphere, to a 500 ml, three-neck flask, 20.00 g (55.2 mmol) of (2-bromophenyl) (2-bromo-5-chlorophenyl) ether and 184 ml (0.3 M) of diethyl ether were added, and while stirring at about −78° C., 75.9 ml (2.2 equiv) of n-BuLi/n-hexane solution of 1.6 mol/L was added thereto dropwise. After stirring for about 1 hour at the same temperature, a diethyl ether solution (15 ml, 1 mol/L) of 10.31 g (1.1 equiv, 60.7 mmol) of $SiCl_4$ was added thereto dropwise and stirred for about 30 minutes at the same temperature, followed by elevating the temperature to room temperature and stirring additionally for about 8 hours. A white solid precipitated under an argon atmosphere was separated by filtering, and a filtrate solution was distilled. The crude product IM-16 (8.49 g, yield 51%) in an oily phase was not separated further and utilized as it was in the next reaction.

Intermediate IM-16 was identified by measuring FAB-MS and observing a mass number of m/z=301 as a molecular ion peak.

(Synthesis of Intermediate IM-17)

Under an Ar atmosphere, to a 300 ml, three-neck flask, 10.00 g (20.2 mmol) of bis(2-bromophenyl)diphenylsilane and 67 ml (0.3 M) of THF were added and while stirring at about −78° C., 27.8 ml (2.2 equiv) of n-BuLi/n-hexane solution of 1.6 mol/L was added thereto dropwise. After stirring for about 1 hour at the same temperature, a THF solution (6 ml, 1 mol/L) of 6.71 g (1.1 equiv, 22.3 mmol) of IM-16 was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-17 (5.15 g, yield 45%).

Intermediate IM-17 was identified by measuring FAB-MS and observing a mass number of m/z=565 as a molecular ion peak.

(Synthesis of Compound B138)

Under an Ar atmosphere, to a 300 ml, three-neck flask, 5.00 g (8.8 mmol) of IM-17, 5.72 g (1.1 equiv, 9.7 mmol) of N-[4-(naphthalen-1-yl)phenyl]-N-[4-(4,4,5,5-tetramethyl-1,3,2-dioxaborolan-2-yl)phenyl]-dibenzofuran-3-amine, 3.67 g (3 equiv, 26.5 mmol) of $K_2CO_3$, 0.51 g (0.05 equiv, 0.4 mmol) of $Pd(PPh_3)_4$, and 62 ml of a mixture solution of toluene/EtOH/$H_2O$ (4/2/1) were added in order (e.g., sequentially), followed by heating at about 80° C. for about 5 hours. After cooling in the air to room temperature, the reaction product was extracted with toluene. An aqueous layer was removed, and an organic layer was washed with a saturated saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B138 (6.92 g, yield 79%) as a white solid.

Compound B138 was identified by measuring FAB-MS and observing a mass number of m/z=990 as a molecular ion peak.

14. Synthesis of Compound B185

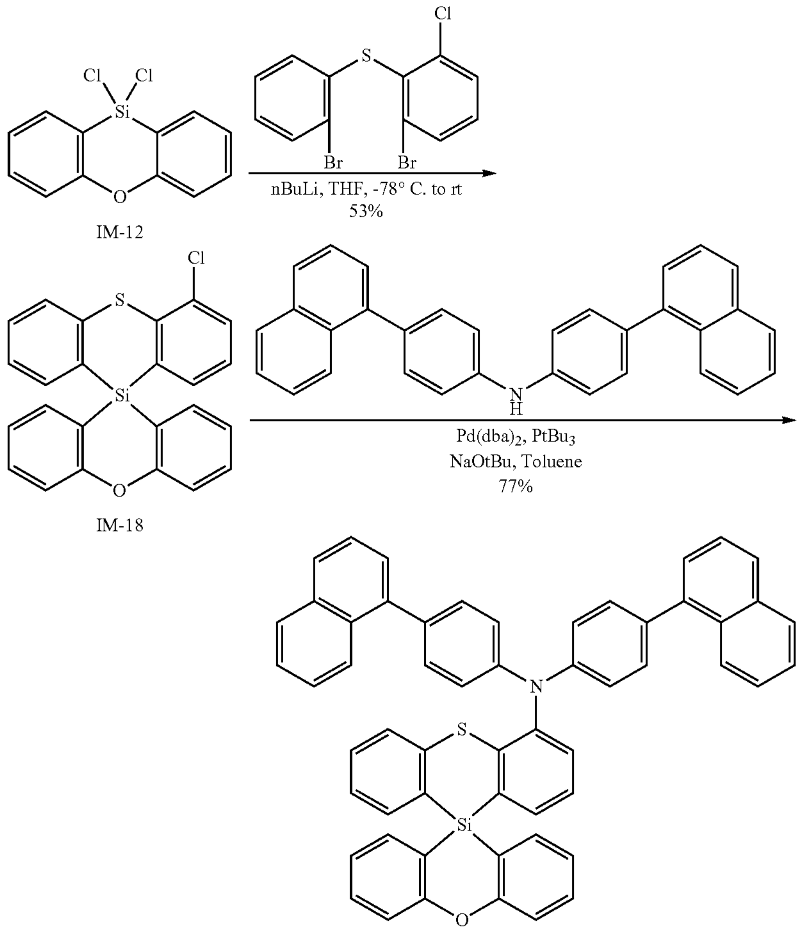

IM-12

IM-18

B185

(Synthesis of Intermediate IM-18)

Under an Ar atmosphere, to a 300 ml, three-neck flask, 10.00 g (26.4 mmol) of (2-bromophenyl) (2-bromo-6-chlorophenyl) sulfide and 88 ml (0.3 M) of THF were added and while stirring at about −78° C., 36.3 ml (2.2 equiv) of n-BuLi/n-hexane solution of 1.6 mol/L was added thereto dropwise. After stirring for about 1 hour at the same temperature, a THF solution (7 ml, 1 mol/L) of 7.76 g (1.1 equiv, 29.1 mmol) of IM-12 was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-18 (5.81 g, yield 53%).

Intermediate IM-18 was identified by measuring FAB-MS and observing a mass number of m/z=414 as a molecular ion peak.

(Synthesis of Compound B185)

Under an Ar atmosphere, to a 300 ml, three-neck flask, 5.00 g (12.0 mmol) of IM-18, 0.21 g (0.03 equiv, 0.4 mmol) of $Pd(dba)_2$, 2.31 g (2 equiv, 24.1 mmol) of NaOtBu, 60 ml of toluene, 5.59 g (1.1 equiv, 13.3 mmol) of bis[4-(naphthalen-1-yl)phenyl]amine, and 0.24 g (0.1 equiv, 1.2 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B185 (7.42 g, yield 77%) as a white solid.

Compound B185 was identified by measuring FAB-MS and observing a mass number of m/z=800 as a molecular ion peak.

15. Synthesis of Compound B200

(Synthesis of Intermediate IM-19)

Under an Ar atmosphere, to a 300 ml, three-neck flask, 10.00 g (26.4 mmol) of (2-bromophenyl) (2-bromo-6-chlorophenyl) sulfide and 88 ml (0.3 M) of THF were added and while stirring at about −78° C., 36.3 ml (2.2 equiv) of n-BuLi/n-hexane solution of 1.6 mol/L was added thereto dropwise. After stirring for about 1 hour at the same temperature, a THF solution (7 ml, 1 mol/L) of 8.23 g (1.1 equiv, 29.1 mmol) of IM-14 was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-19 (7.29 g, yield 64%).

Intermediate IM-19 was identified by measuring FAB-MS and observing a mass number of m/z=431 as a molecular ion peak.

(Synthesis of Compound B200)

Under an Ar atmosphere, to a 300 ml, three-neck flask, 5.00 g (11.6 mmol) of IM-19, 0.20 g (0.03 equiv, 0.3 mmol)

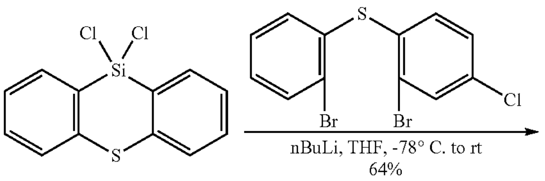

IM-14

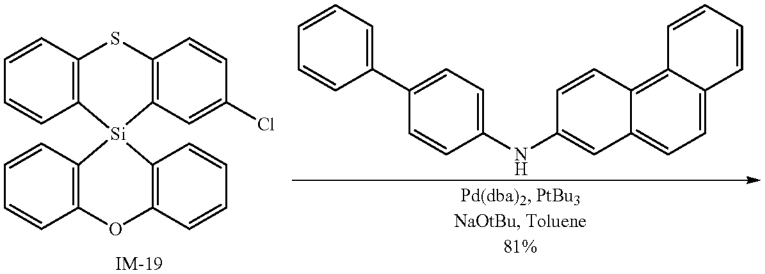

IM-19

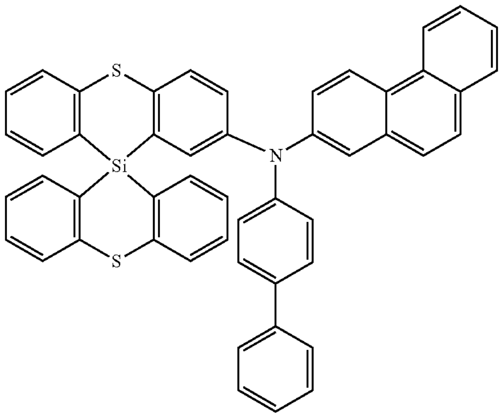

B200 of $Pd(dba)_2$, 2.23 g (2 equiv, 23.2 mmol) of NaOtBu, 58 ml of toluene, 4.41 g (1.1 equiv, 12.8 mmol) of N-[(1,1'-biphenyl)-4-yl]phenanthren-2-amine, and 0.23 g (0.1 equiv, 1.2 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B200 (6.95 g, yield 81%) as a white solid.

Compound B200 was identified by measuring FAB-MS and observing a mass number of m/z=740 as a molecular ion peak.

16. Synthesis of Compound B322

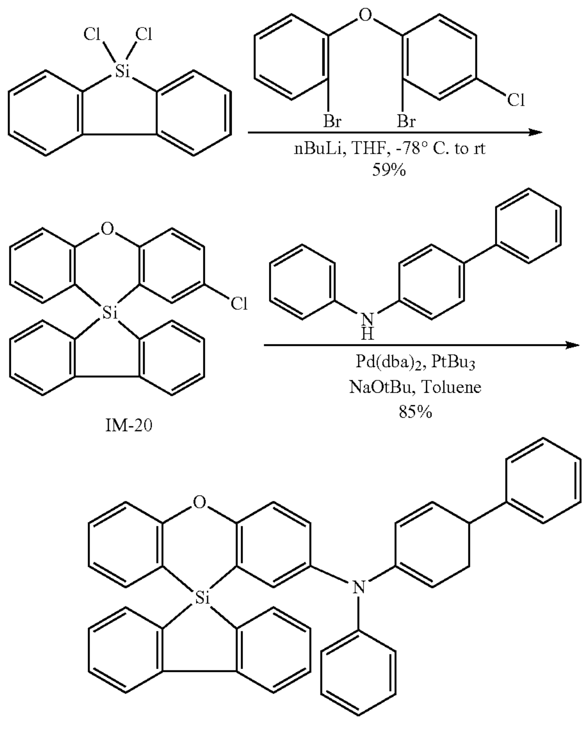

IM-20

B322

(Synthesis of Intermediate IM-20)

Under an Ar atmosphere, to a 300 ml, three-neck flask, 10.00 g (27.6 mmol) of (2-bromophenyl) (2-bromo-4-chlorophenyl) ether and 92 ml (0.3 M) of THF were added and while stirring at about −78° C., 37.9 ml (2.2 equiv) of n-BuLi/n-hexane solution of 1.6 mol/L was added thereto dropwise. After stirring for about 1 hour at the same temperature, a THF solution (8 ml, 1 mol/L) of 7.62 g (1.1 equiv, 30.3 mmol) of 5,5-dichloro-5H-dibenzosilole was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-20 (6.23 g, yield 59%).

Intermediate IM-20 was identified by measuring FAB-MS and observing a mass number of m/z=382 as a molecular ion peak.

(Synthesis of Compound B322)

Under an Ar atmosphere, to a 300 ml, three-neck flask, 5.00 g (13.1 mmol) of IM-20, 0.23 g (0.03 equiv, 0.4 mmol) of $Pd(dba)_2$, 2.51 g (2 equiv, 26.1 mmol) of NaOtBu, 65 ml of toluene, 3.52 g (1.1 equiv, 14.4 mmol) of N-phenyl-1,1'-biphenyl-4-amine, and 0.26 g (0.1 equiv, 1.3 mmol) of t-Bu3P were added in order (e.g., sequentially), followed by heating and refluxing for about 6 hours. After cooling in the air to room temperature, water was added to the reaction product, and an organic layer was separately taken. Toluene was added to an aqueous layer, and an organic layer was extracted further. The organic layers were collected and washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B322 (6.57 g, yield 85%) as a white solid.

Compound B322 was identified by measuring FAB-MS and observing a mass number of m/z=591 as a molecular ion peak.

17. Synthesis of Compound B465

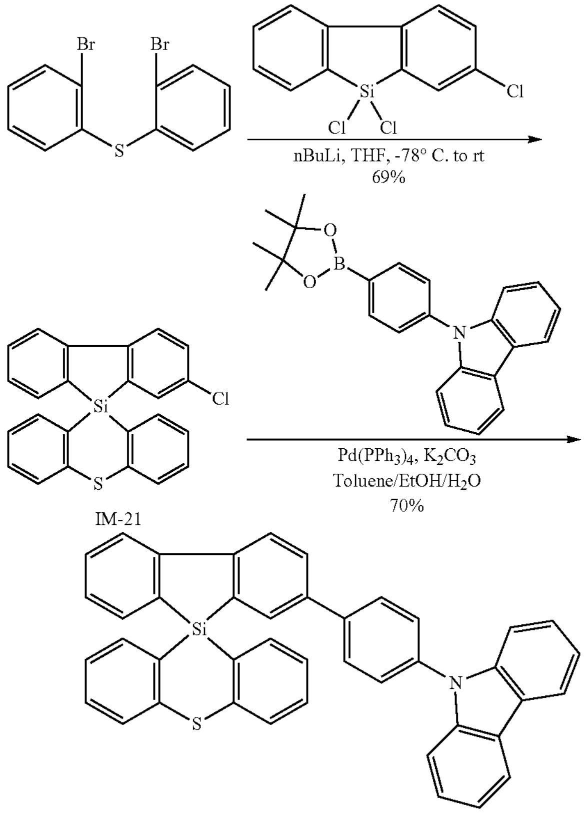

IM-21

B465

(Synthesis of Intermediate IM-21)

Under an Ar atmosphere, to a 300 ml, three-neck flask, 10.00 g (29.1 mmol) of bis(2-bromophenyl) sulfide and 97 ml (0.3 M) of THF were added and while stirring at about −78° C., 40.0 ml (2.2 equiv) of n-BuLi/n-hexane solution of 1.6 mol/L was added thereto dropwise. After stirring for about 1 hour at the same temperature, a THF solution (8 ml, 1 mol/L) of 9.12 g (1.1 equiv, 32.0 mmol) of 3,5,5-trichloro-5H-dibenzosilole was added thereto dropwise and stirred for about 30 minutes at the same temperature, followed by elevating the temperature to room temperature and stirring additionally for about 8 hours. After cooling rapidly utilizing an aqueous saturated ammonium chloride solution, the reaction product was extracted with toluene. An aqueous layer was removed, and an organic layer was washed with an aqueous sodium bicarbonate solution and a saturated saline solution in order (e.g., sequentially) and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Intermediate IM-21 (8.00 g, yield 69%).

Intermediate IM-21 was identified by measuring FAB-MS and observing a mass number of m/z=398 as a molecular ion peak.

(Synthesis of Compound B465)

Under an Ar atmosphere, to a 300 ml, three-neck flask, 5.00 g (12.5 mmol) of IM-21, 5.09 g (1.1 equiv, 13.8 mmol) of 9-[4-(4,4,5,5-tetramethyl-1,3,2-dioxaborolan-2-yl)phenyl]-9H-carbazole, 5.19 g (3 equiv, 37.6 mmol) of $K_2CO_3$, 0.72 g (0.05 equiv, 0.6 mmol) of $Pd(PPh_3)_4$, and 88 ml of a mixture solution of toluene/EtOH/$H_2O$ (4/2/1) were added in order (e.g., sequentially), followed by heating and stirring at about 80° C. for about 5 hours. After cooling in the air to room temperature, the reaction product was extracted with toluene. An aqueous layer was removed, and an organic layer was washed with a saline solution and dried with $MgSO_4$. $MgSO_4$ was filtered out and the organic layer was concentrated and then, the crude product thus obtained was separated by silica gel column chromatography (a mixture solvent of hexane and toluene was utilized as a developer) to obtain Compound B465 (6.45 g, yield 70%) as a white solid.

Compound B465 was identified by measuring FAB-MS and observing a mass number of m/z=605 as a molecular ion peak.

The above-described synthetic examples are exemplary embodiments, and reaction conditions may be changed as necessary. In addition, the compound according to an embodiment of the inventive concept may be synthesized so as to have diverse substituents by utilizing suitable methods and materials (e.g, those well-known in the art). By introducing diverse substituents in the core structure represented by Formula 1, appropriate properties for an organic electroluminescence device may be achieved.

(Device Manufacturing Example 1)

Organic electroluminescence devices of Examples 1 to 9 were manufactured utilizing each of Compounds A12, A24, A39, A48, A50, A67, A111, A124 and A177 respectively as materials for their hole transport layers.

Example Compounds

A12

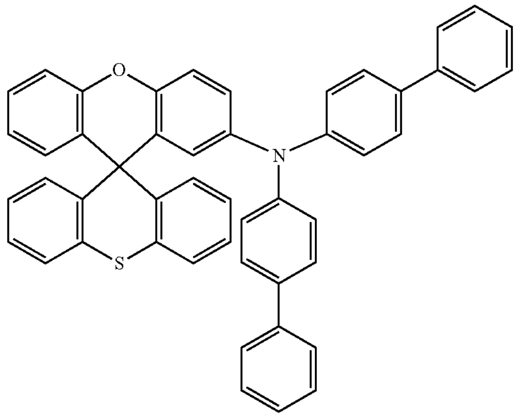

A24

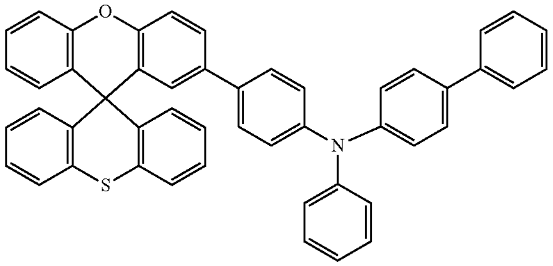

A39

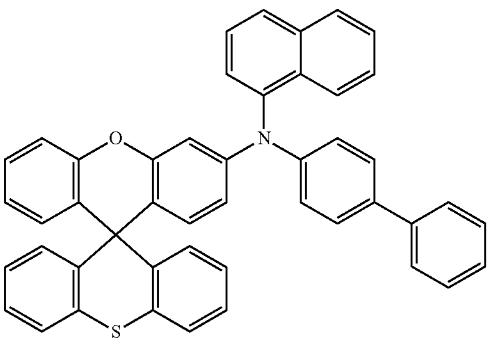

A48

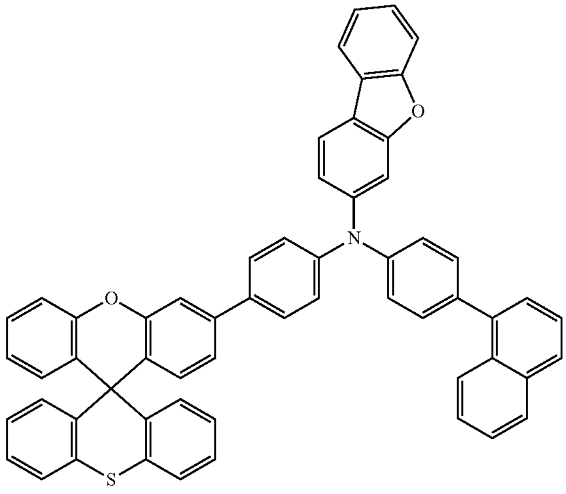

A50
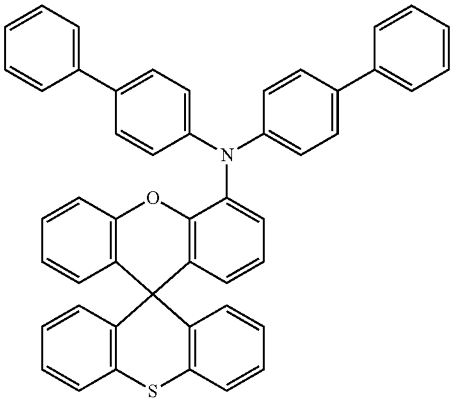
A67
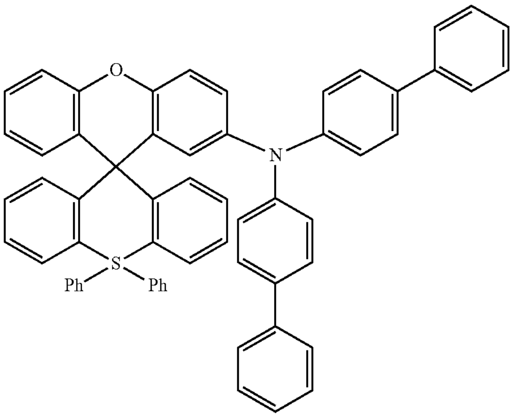
A111
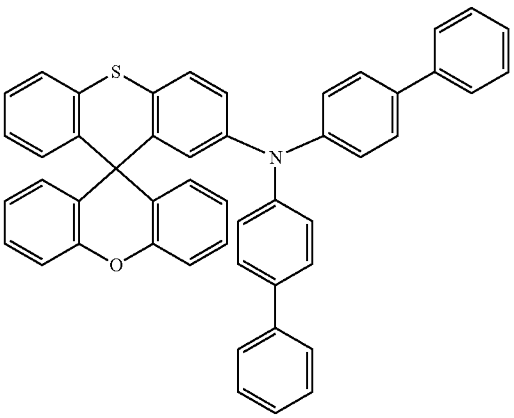
A124
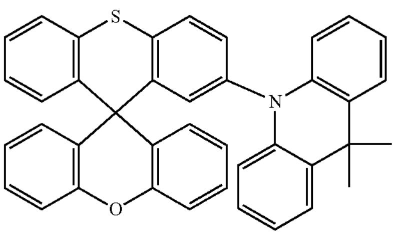
A177
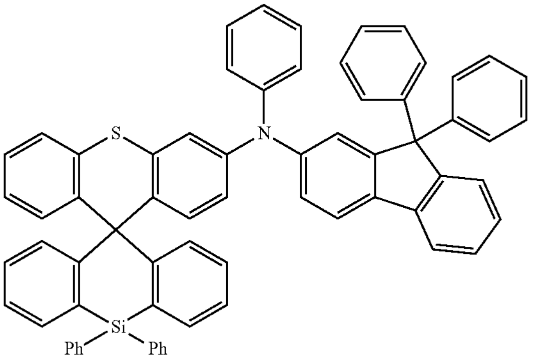
Utilizing known compounds below respectively as materials for their hole transport layers, organic electroluminescence devices of Comparative Examples 1 to 6 were manufactured.
[Comparative Compounds]
R1
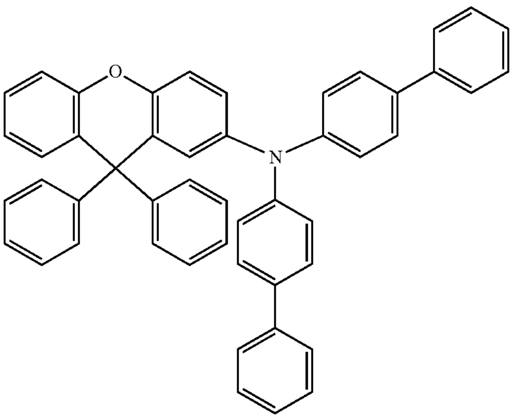
R2
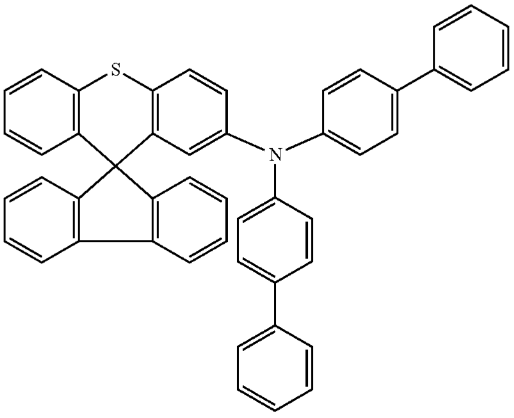

-continued

R3

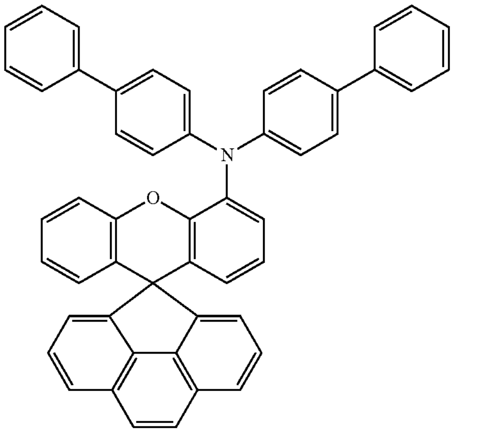

R4

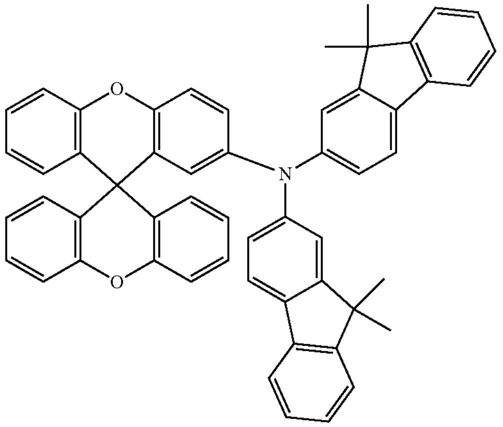

R5

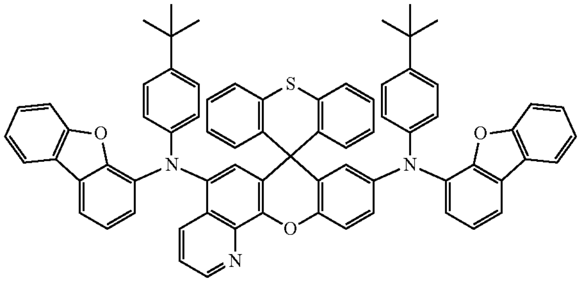

R6

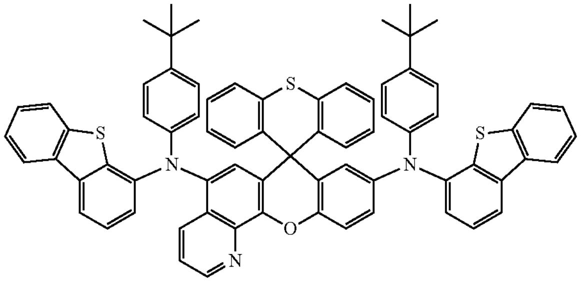

Organic electroluminescence devices of Examples 1 to 9 and Comparative Examples 1 to 6 were each manufactured as follows.

An ITO glass substrate (product of Corning Inc.,) on which an ITO layer was formed to a thickness of about 1,500 Å was cut into a size of 50 mm×50 mm×0.7 mm, and washed by ultrasonic waves utilizing isopropyl alcohol and pure water each for about 5 minutes. The ITO glass substrate was exposed to ultraviolet rays for about 30 minutes and washed by exposing to ozone, and then, installed in a vacuum deposition apparatus.

On the substrate, 1-TNATA was deposited in vacuum to a thickness of about 600 Å to form a hole injection layer, and then, a respective example compound or comparative compound described above was deposited in vacuum to a thickness of about 300 Å to form a hole transport layer.

On the hole transport layer, a blue fluorescence host, 9,10-di-naphthalene-2-yl-anthracene (hereinafter, ADN), and a compound as a blue fluorescence dopant, 2,5,8,11-tetra-t-butylperylene (TBP), were co-deposited in a weight ratio of 97:3 to a thickness of about 250 Å to form an emission layer.

Then, on the emission layer, $Alq_3$ was deposited as an electron transport layer to a thickness of about 250 Å, and on the electron transport layer, an alkali metal halide, LiF, was deposited to a thickness of about 10 Å to form an electron injection layer, and A1 was deposited in vacuum to a thickness of about 1,000 Å (second electrode) to form an LiF/Al electrode. An organic electroluminescence device was thereby manufactured.

The driving voltage, efficiency and half-life of each of the organic electroluminescence devices according to Examples 1 to 9 and Comparative Examples 1 to 6 are listed in Table 1 below.

TABLE 1

| Device manufacturing example | Hole transport layer | Voltage (V) | Efficiency (cd/A) | Life LT50 (h) |
|---|---|---|---|---|
| Example 1 | Example Compound A12 | 5.7 | 7.8 | 2100 |
| Example 2 | Example Compound A24 | 5.8 | 7.7 | 2200 |
| Example 3 | Example Compound A39 | 5.6 | 8.1 | 2000 |
| Example 4 | Example Compound A48 | 5.7 | 8.0 | 2050 |
| Example 5 | Example Compound A50 | 5.6 | 8.3 | 1950 |
| Example 6 | Example Compound A67 | 5.8 | 7.9 | 2000 |
| Example 7 | Example Compound A111 | 5.8 | 7.8 | 2100 |
| Example 8 | Example Compound A124 | 6.0 | 8.0 | 2000 |
| Example 9 | Example Compound A177 | 5.9 | 8.1 | 2050 |
| Comparative Example 1 | Comparative Compound R1 | 6.2 | 6.2 | 1200 |
| Comparative Example 2 | Comparative Compound R2 | 6.0 | 6.2 | 1550 |
| Comparative Example 3 | Comparative Compound R3 | 6.0 | 6.4 | 1600 |
| Comparative Example 4 | Comparative Compound R4 | 6.0 | 6.7 | 1850 |
| Comparative Example 5 | Comparative Compound R5 | 6.1 | 6.5 | 1800 |
| Comparative Example 6 | Comparative Compound R6 | 6.1 | 6.6 | 1800 |

The resultant emission efficiency is a value measured at 10 mA/$cm^2$, and the half-life refers to the time taken for the luminance to decrease to half from an initial luminance of 1,000 cd/$cm^2$.

Referring to the results of Table 1, each of Examples 1 to 9 showed decreased driving voltage, increased life and improved efficiency when compared to each of Comparative Examples 1 to 6. The comparable (e.g., conventional) amine compound (e.g., compound R1 to R6) is known as a hole transportmaterial having strong electron tolerance and contributing to the increase of the life of a device. The monoamine compound of the inventive concept included a core structure with a spiro structure, and thermal stability was increased to achieve the increase of device life. In addition, the monoamine compound according to an embodiment included different heteroatoms in the spiro structure and an amine group was included only in one ring. Accordingly, the degree of molecular symmetry was reduced (e.g., degraded), crystallinity was reduced (e.g., degenerated) and layer quality was improved, thereby achieving high efficiency of a device.

In addition, each of the hole transport materials of Examples 1, 2, and 6 to 8 had a structure in which a heteroatom was positioned at para position with respect to the side chain of an amine group, and the life of the respective device was improved when compared to that of the comparative examples. It is thought that the HOMO conjugation system around a nitrogen atom was appropriately expanded to the heteroatom, and the stability in a radical state was improved, and the device life was improved.

Each of the hole transport materials of Examples 3 to 5 and 9 had a structure in which an amine group was substituted at carbon of position 3 or 4 of a spiro ring, and they were all found to have improved device life when compared to the comparative examples. If carbon at position 3 or 4 includes a substituent, the volume of a spiro structure is further increased, and the symmetry of the whole molecule may collapse to degrade the crystallinity, hole transport degree may be controlled, and recombination probability of holes and electrons in an emission layer may be improved, and device efficiency may be improved.

On the contrary, in the hole transport material of Comparative Example 1, a spiro bond was not formed by a monoamine compound having a xanthene ring, and carbon at position 4 might be easily decomposed under high temperature conditions. Accordingly, device efficiency and life of Comparative Example 1 were found to decrease when compared to the Examples.

Each of the hole transport materials of Comparative Examples 2 and 3 were monoamine compounds including a spiro ring, but the number of heteroatoms included in the spiro ring was smaller than that in the hole transport materials of the Examples, and their hole transport properties were all degraded. Accordingly, device efficiency and life of Comparative Examples 2 and 3 were found to decrease when compared to the Examples.

The hole transport material of Comparative Example 4 was a monoamine compound including a spiro ring, but all heteroatoms included in the spiro ring were the oxygen atoms and the degree of symmetry of the whole molecule was increased, and intermolecular interaction was increased and the distance between molecules was decreased. Therefore, the hole transport degree was decreased. Accordingly, device efficiency and life of Comparative Example 4 were found to decrease when compared to the examples.

The hole transport materials of Comparative Examples 5 and 6 were diamine compounds including a spiro ring and in each the degree of symmetry of the whole molecule was high, the change of energy level was large, and carrier balance was collapsed. Accordingly, device efficiency and life of Comparative Examples 5 and 6 were found to decrease when compared to the examples.

(Device Manufacturing Example 2)

Organic electroluminescence devices of Examples 10 to 17 were manufactured utilizing Compounds B12, B24, B58, B138, B185, B200, B322 and B465 respectively as materials of their hole transport layers.

Example Compound

B12

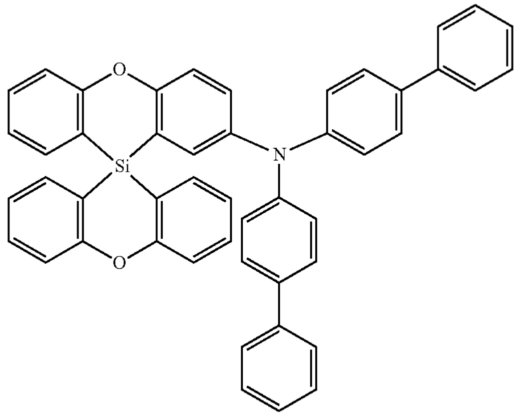

B24

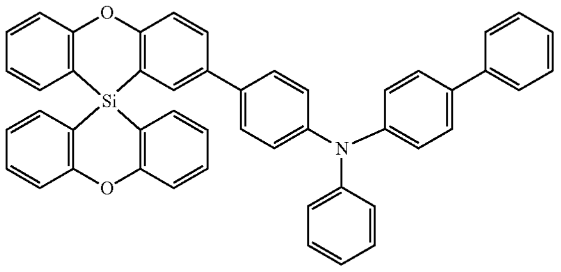

B58

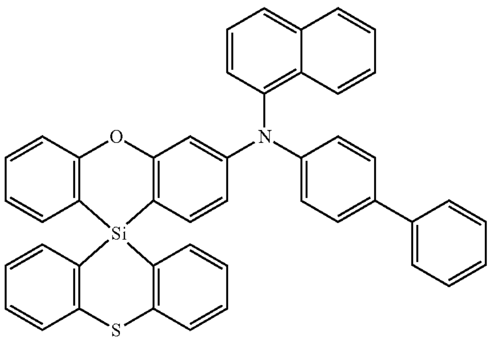

-continued
B138
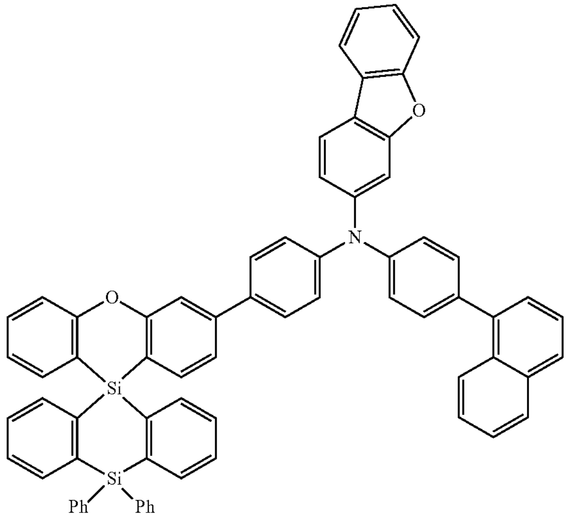 [SMILES: c1ccc2c(c1)Oc1cc(-c3ccc(N(c4ccc(-c5cccc6ccccc56)cc4)c4ccc5c(c4)oc4ccccc45)cc3)ccc1C21c2ccccc2Sc2ccccc21 ; "A48"]
B185
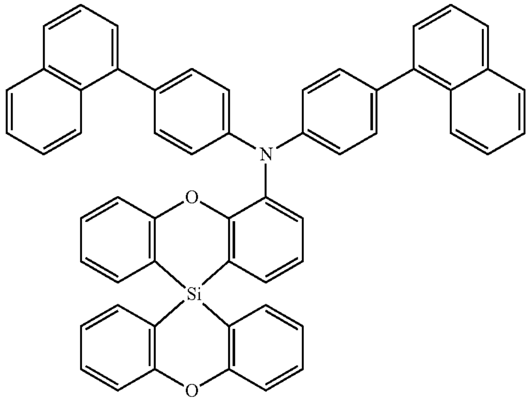
B200
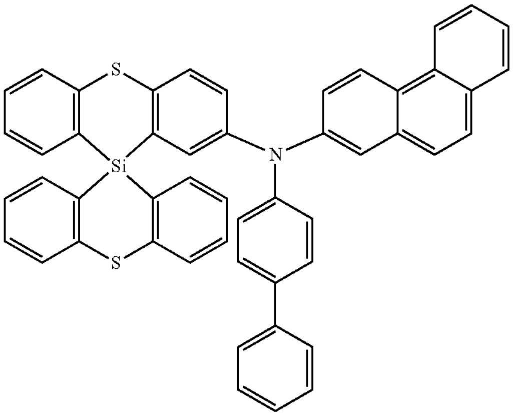
-continued
B322
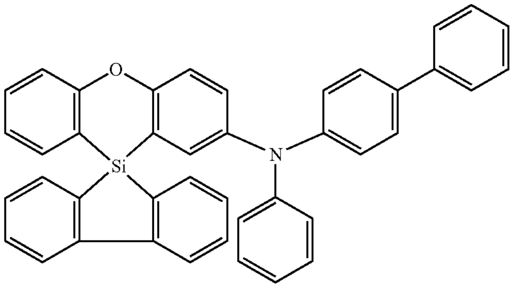
B465
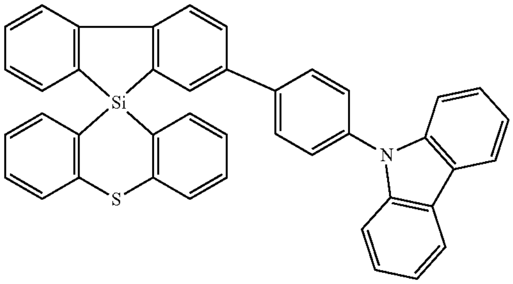
Organic electroluminescence devices of Comparative Examples 7 to 10 were manufactured utilizing materials below.
[Comparative Compound]
R7
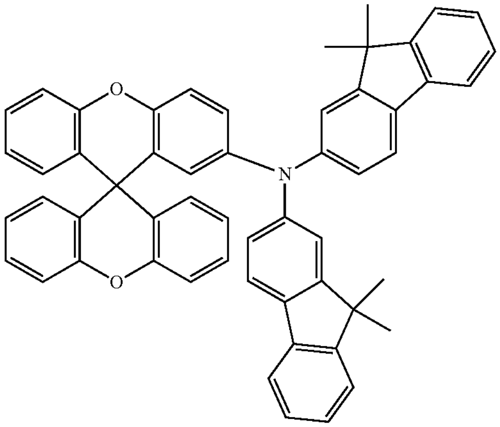

-continued

R8

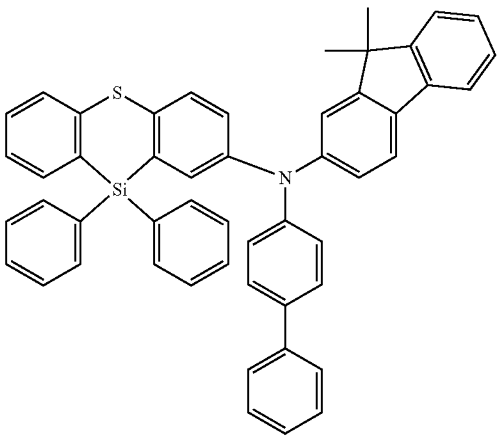

R9

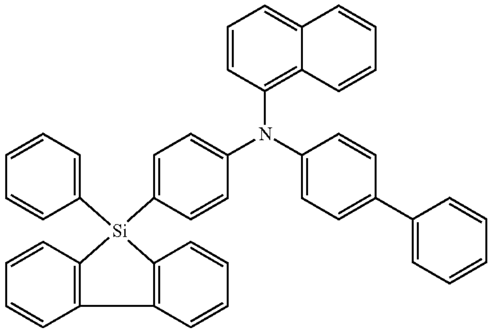

R10

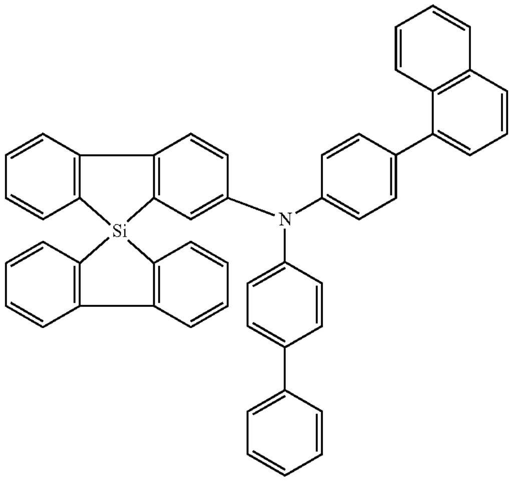

Organic electroluminescence devices of Examples 10 to 17 and Comparative Examples 7 to 10 were each manufactured according to the same method described in Device Manufacturing Example 1.

The driving voltage, efficiency and half-life of each of the organic electroluminescence devices according to Examples 10 to 17 and Comparative Examples 7 to 10 were measured by the same respective method described in Device Manufacturing Example 1 and are listed in Table 2 below.

TABLE 2

| Device manufacturing example | Hole transport layer | Voltage (V) | Efficiency (Cd/A) | Life LT50 (h) |
|---|---|---|---|---|
| Example 10 | Example Compound B12 | 5.7 | 7.7 | 2150 |
| Example 11 | Example Compound B24 | 5.8 | 7.7 | 2200 |
| Example 12 | Example Compound B58 | 5.6 | 8.0 | 1950 |
| Example 13 | Example Compound B138 | 5.7 | 7.9 | 2000 |
| Example 14 | Example Compound B185 | 5.6 | 8.2 | 1900 |
| Example 15 | Example Compound B200 | 5.8 | 7.8 | 2100 |
| Example 16 | Example Compound B322 | 6.5 | 7.9 | 2100 |
| Example 17 | Example Compound B465 | 5.9 | 7.8 | 2050 |
| Comparative Example 7 | Comparative Compound R7 | 6.0 | 6.7 | 1850 |
| Comparative Example 8 | Comparative Compound R8 | 6.0 | 6.8 | 1400 |
| Comparative Example 9 | Comparative Compound R9 | 6.0 | 6.7 | 1400 |
| Comparative Example 10 | Comparative Compound R10 | 6.0 | 6.6 | 1500 |

Referring to the results of Table 2, each of Examples 10 to 17 showed decreased driving voltage, increased life and improved efficiency when compared to each of Comparative Examples 7 to 10. The monoamine compound according to an embodiment of the inventive concept includes Si as the central atom of a spiro structure and has a twisted conformation, and thus, the volume of the molecule is increased, appropriate distance between molecules may be maintained, the degree of symmetry of the whole molecule is reduced (e.g., deteriorated), crystallinity may be reduced (e.g., degraded), layer quality may be improved, and a device with high efficiency may be achieved. In addition, each of the hole transport materials of Examples 10, 11, 15 and 16 had a structure in which a heteroatom is positioned at para position with respect to the side chain of an amine group, and the life of the devices was improved when compared to that of each of the Comparative Examples. It is thought that the HOMO conjugation system around a nitrogen atom was appropriately expanded to the heteroatom, and the stability in a radical state was improved, and the device life was improved.

The hole transport material of Example 17 had a structure in which an arylene group was positioned at para position with respect to the side chain of an amine group, and was found to show improved life when compared to the Comparative Examples. It is thought that HOMO conjugation system around a nitrogen atom was appropriately expanded to the heteroatom, and the stability in a radical state was improved, and the device life was improved.

Each of the hole transport materials of Examples 12 to 14 had a structure in which an amine group is substituted at carbon of position 3 or 4 of a spiro ring, and they were all found to have improved device life when compared to the Comparative Examples. In case where carbon at position 3 or 4 included a substituent, the volume of a compound having a spiro structure was further increased, and the symmetry of the whole molecule collapsed to degrade the crystallinity, the degree of hole transport property was controlled, and recombination probability of holes and electrons in an emission layer was improved, and device efficiency was improved.

Each of Examples 10 to 15, different from Examples 1 to 9, showed excellent emission efficiency and emission life irrespective of the kind of the heteroatom included in the spiro ring. In addition, as in each of Examples 16 and 17, in case where no heteroatom was included, excellent emission efficiency and emission life were achieved. Accordingly, as in Examples 10 to 17, in case where a hole transport material included Si as the central atom of the spiro structure, the heteroatom included in the spiro ring was not found to seriously affect device performance.

The hole transport material of Comparative Example 7 had a similar structure as the hole transport material of Example 10, but the central atom of the spiro ring was carbon. Because the radius of a carbon atom was smaller than that of a silicon atom, the volume of the whole molecule is smaller, and the distance between molecules was decreased, and thus, hole transport property may be degraded. Accordingly, device efficiency and life of Comparative Example 7 were deteriorated when compared to the Examples.

The hole transport materials of Comparative Examples 8 and 9 were monoamine compounds each including a cyclic silyl group, but did not form a spiro bond. Accordingly, decomposition between silicon and a side chain phenyl group may easily occur under high temperature conditions. As such, device efficiency and life of Comparative Examples 8 and 9 were found to decrease when compared to the Examples.

The hole transport material of Comparative Example 10 was a monoamine compound including a spiro ring, but in the spiro ring formed by two fluorenyl groups, large load was applied to the central atom of the spiro ring, and molecular stability was low. Thus, thermal decomposition was likely (e.g., liable) to occur under high temperature conditions. In addition, a heteroatom was not included, and carrier balance might collapse. Accordingly, device efficiency and life of Comparative Example 10 were found to decrease when compared to the Examples.

The organic electroluminescence device according to an embodiment of the inventive concept has excellent efficiency and long life. The organic electroluminescence device according to an embodiment of the inventive concept has an effect of a low driving voltage.

The organic electroluminescence device according to an embodiment of the inventive concept has excellent efficiency.

The organic electroluminescence device according to an embodiment of the inventive concept has long life.

The monoamine compound according to an embodiment of the inventive concept is applied to an organic electroluminescence device and may contribute to high efficiency and long life.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed, and equivalents thereof.

What is claimed is:

1. An organic electroluminescence device, comprising:

a first electrode;

a second electrode on the first electrode; and a plurality of organic material layers between the first electrode and the second electrode and comprising a hole transport region, wherein the hole transport region comprises an amine compound, the amine compound comprises a core structure comprising two condensed rings which are combined through sharing a central atom to form a spiro structure, each condensed ring having a condensed structure of three or more pentagonal or hexagonal rings, and when the central atom is carbon, each of the two condensed rings of the core structure comprises one of O, S, or $SiR_4R_5$, and the one of O, S, or $SiR_4R_5$ of one of the two condensed rings is different from the one of O, S, or $SiR_4R_5$ of the other one of the two condensed rings, and $R_4$ and $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring.

2. The organic electroluminescence device of claim 1, wherein the central atom of the spiro structure is carbon or silicon, and when the central atom is carbon, each condensed ring comprises a condensed structure of three or more hexagonal rings, and when the central atom is silicon, each condensed ring comprises a condensed structure of three or more pentagonal or hexagonal rings.

3. The organic electroluminescence device of claim 1, wherein the plurality of organic material layers comprise:

the hole transport region on the first electrode;

an emission layer on the hole transport region; and an electron transport region on the emission layer.

4. The organic electroluminescence device of claim 3, wherein the hole transport region comprises:

a hole injection layer; and a hole transport layer between the hole injection layer and the emission layer, wherein the hole transport layer comprises the amine compound.

5. The organic electroluminescence device of claim 4, wherein the hole transport layer comprises a plurality of organic layers, and an organic layer adjacent to the emission layer among the plurality of organic layers comprises the amine compound.

6. The organic electroluminescence device of claim 1, wherein the amine compound is represented by following Formula 1:

[Formula 1]

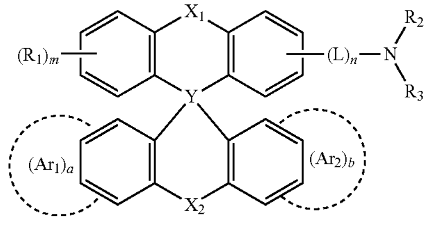

wherein in Formula 1,

Y is C or Si, when Y is C, $X_1$ and $X_2$ are each independently O, S, or $SiR_4R_5$, and $X_1$ and $X_2$ are different from each other, when Y is Si, $X_1$ and $X_2$ are each independently O, S, $SiR_4R_5$, or a direct linkage, and both $X_1$ and $X_2$ are direct linkages is excluded, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring, L is a direct linkage, a substituted or unsubstituted arylene group having 6 to 30 carbon atoms, or a substituted or unsubstituted heteroarylene group having 2 to 30 carbon atoms for forming a ring, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, a, b and n are each independently 0 or 1, and m is an integer of 0 to 4.

7. The organic electroluminescence device of claim 6, wherein the amine compound represented by Formula 1 is represented by following Formula 2 or Formula 3:

[Formula 2]

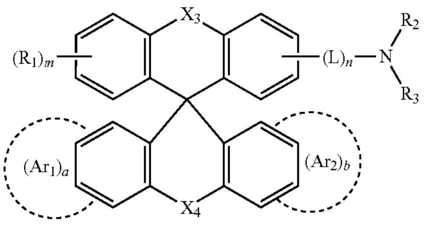

[Formula 3]

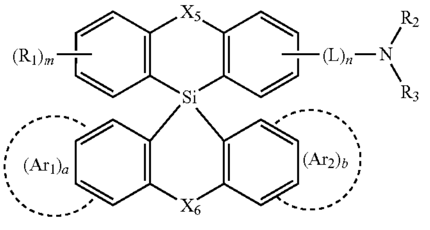

wherein in Formula 2, $X_3$ and $X_4$ are each independently O, S, or $SiR_4R_5$, and $X_3$ and $X_4$ are different from each other, wherein in Formula 3, $X_5$ and $X_6$ are each independently O, S, $SiR_4R_5$, or a direct linkage, and both $X_5$ and $X_6$ are direct linkages is excluded, and wherein in Formulae 2 and 3, $R_1$ to $R_5$, L, $Ar_1$, $Ar_2$, a, b, m and n are the same as respectively defined in association with Formula 1.

8. The organic electroluminescence device of claim 7, wherein the amine compound represented by Formula 2 is represented by any one of following Formulae 2-1 to 2-6:

[Formula 2-1]

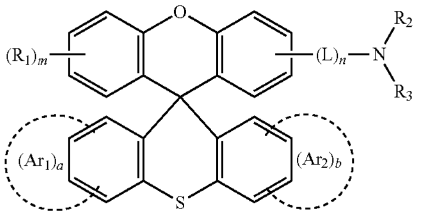

[Formula 2-2]

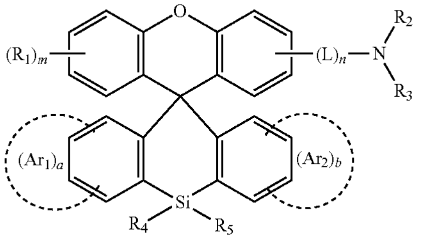

[Formula 2-3]

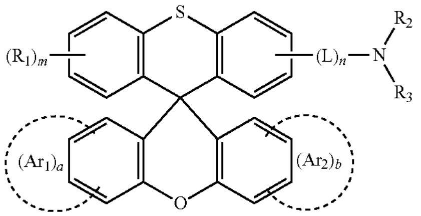

[Formula 2-4]

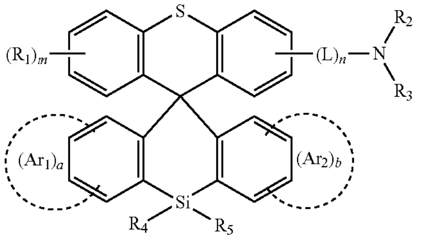

[Formula 2-5]

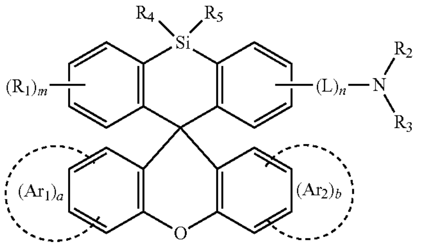

[Formula 2-6]

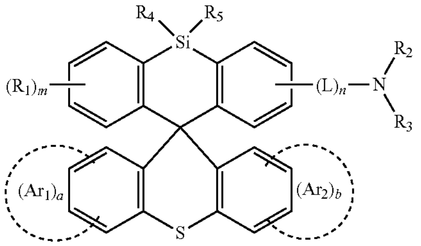

wherein in Formulae 2-1 to 2-6, $R_1$ to $R_5$, L, $Ar_1$, $Ar_2$, a, b, m and n are the same as respectively defined in association with Formula 1.

9. The organic electroluminescence device of claim 7, wherein the amine compound represented by Formula 3 is represented by any one of following Formulae 3-1 to 3-11:

[Formula 3-1]
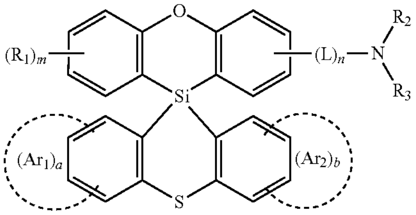
[Formula 3-2]
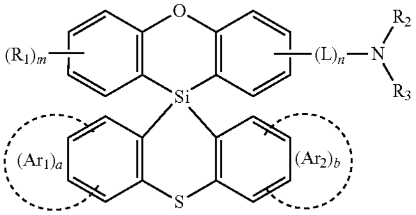
[Formula 3-3]
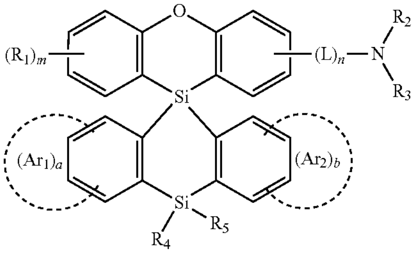
[Formula 3-4]
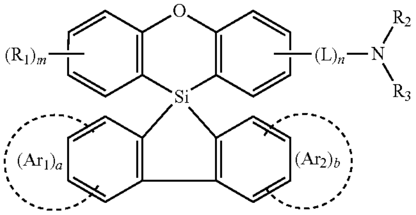
[Formula 3-5]
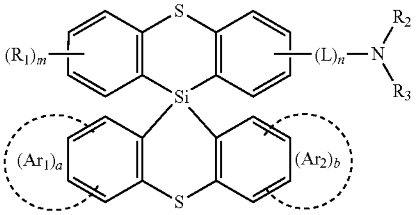
[Formula 3-6]
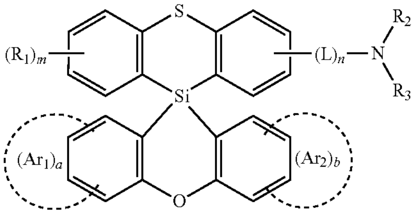
[Formula 3-7]
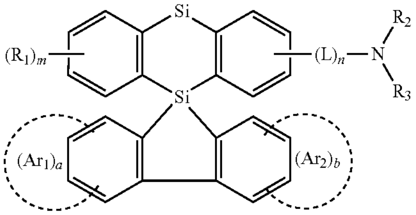
-continued
[Formula 3-8]
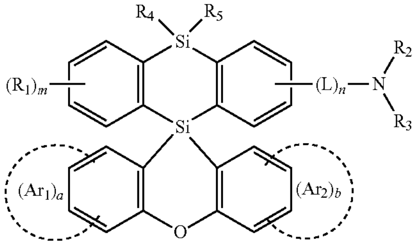
[Formula 3-9]
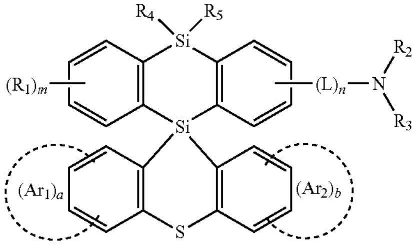
[Formula 3-10]
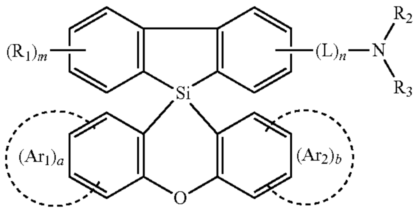
[Formula 3-11]
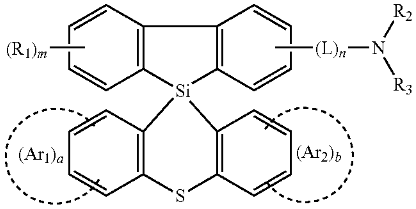
wherein in Formulae 3-1 to 3-11, $R_1$ to $R_5$, L, $Ar_1$, $Ar_2$, a, b, m and n are the same as respectively defined in association with Formula 1.
10. The organic electroluminescence device of claim 6, wherein L is a direct linkage or represented by any one of following Formulae L-1 to L-4:
L-1
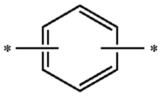
L-2
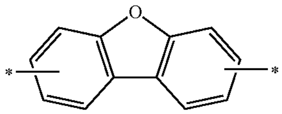
L-3
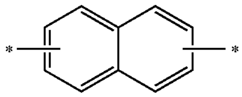
L-4
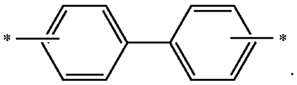

11. The organic electroluminescence device of claim 1, wherein the amine compound is any one selected from compounds represented in following Compound Group 1 and Compound group 2:
[Compound Group 1]
A1
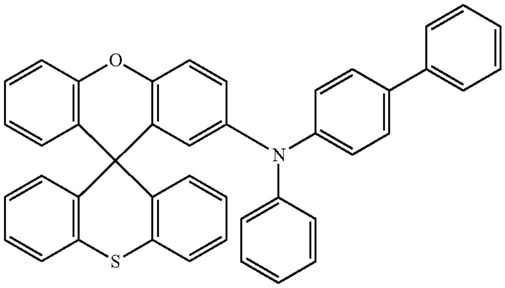
A2
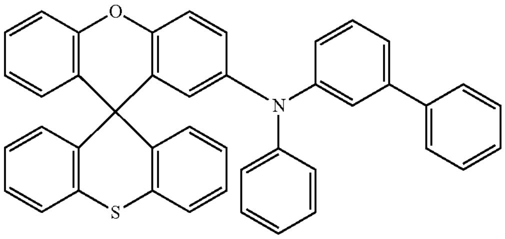
A3
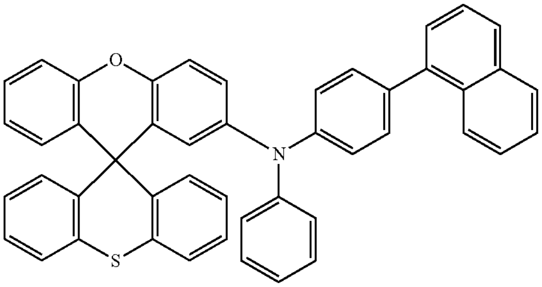
A4
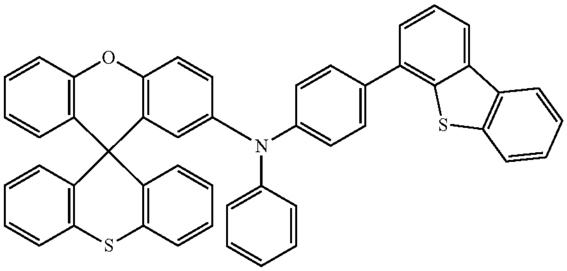
A5
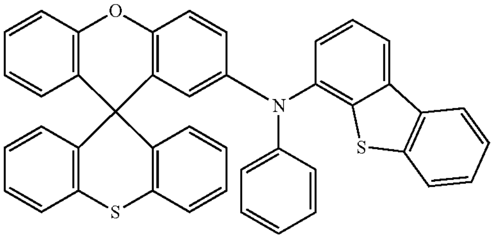
-continued
A6
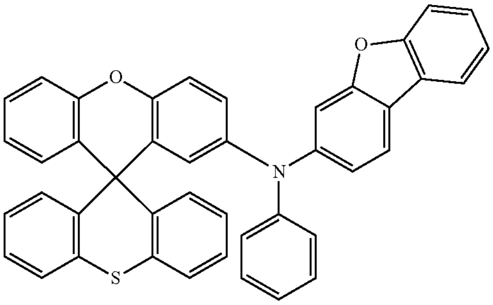
A7
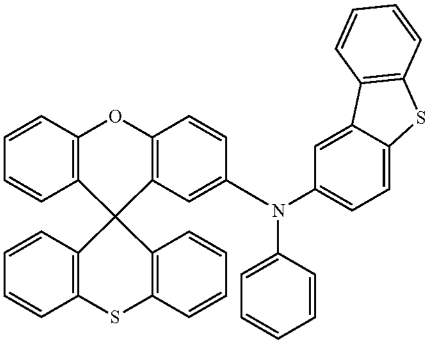
A8
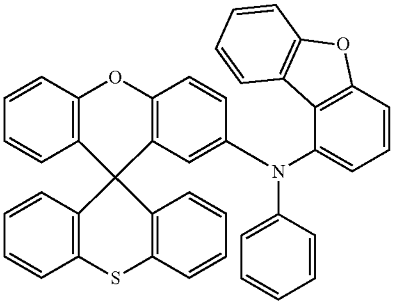
A9
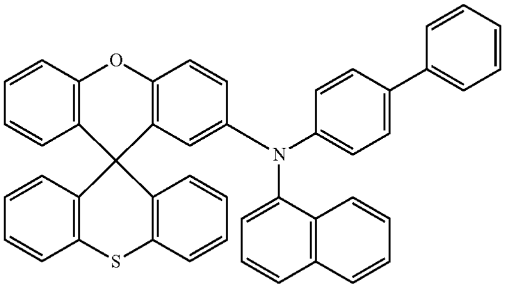

-continued
A10
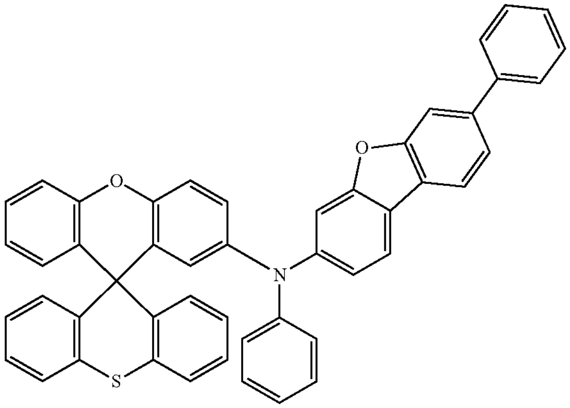
A11
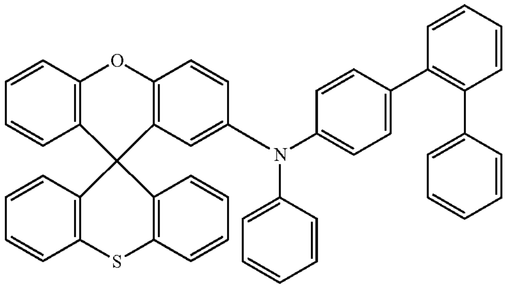
A12
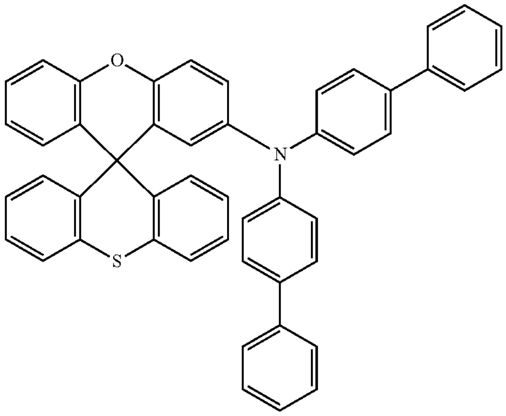
A13
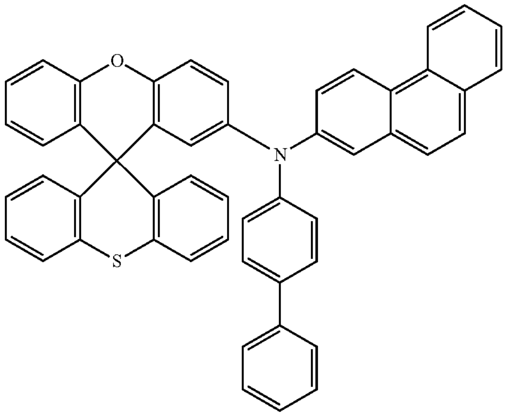
-continued
A14
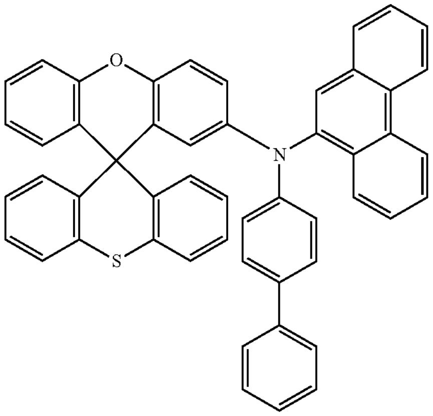
A15
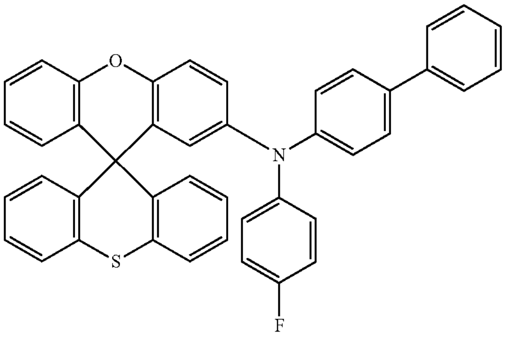
A16
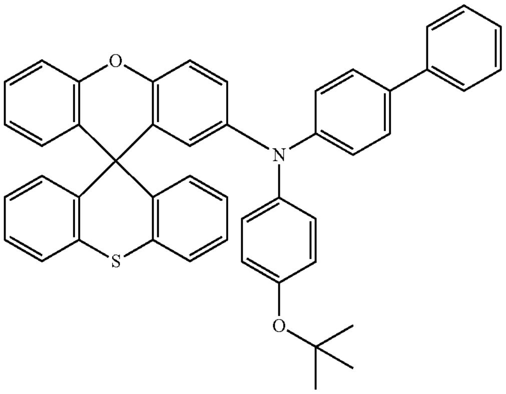
A17
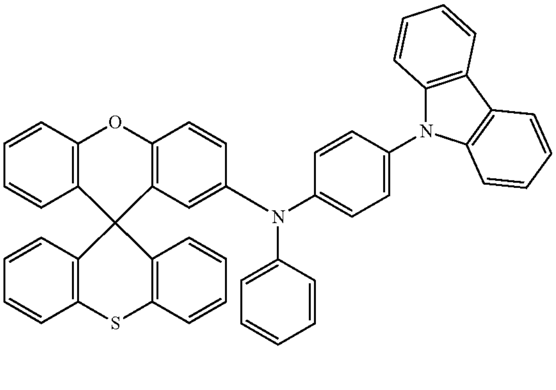

A18
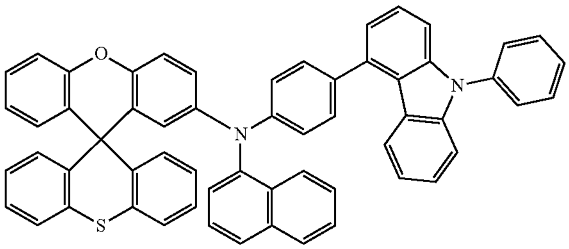
A19
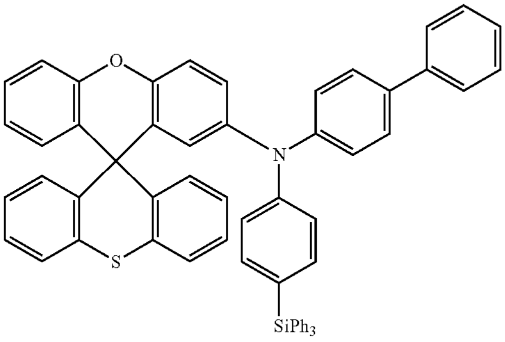
A20
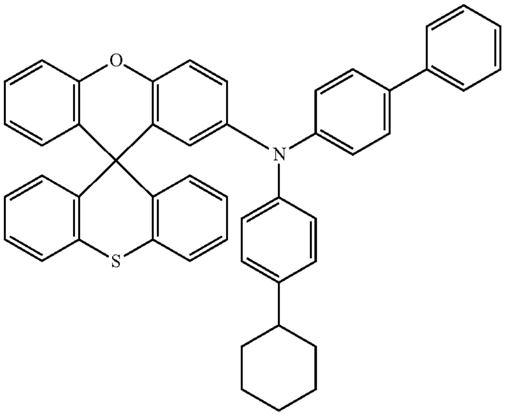
A21
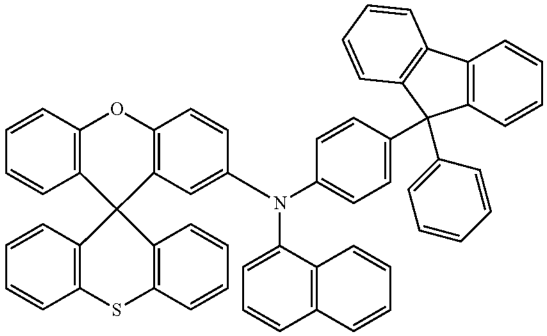
A22
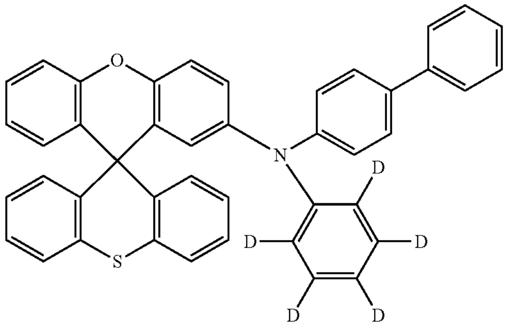
A23
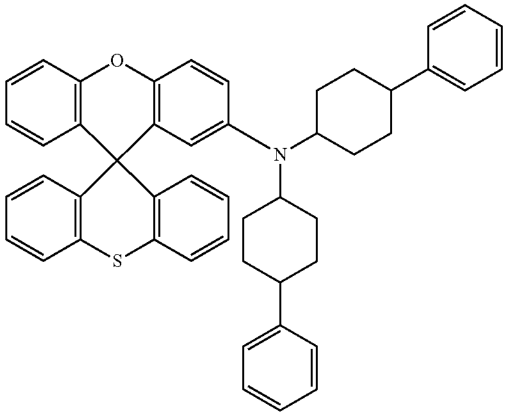
A24
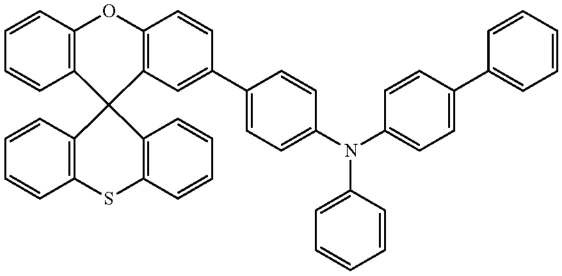
A25
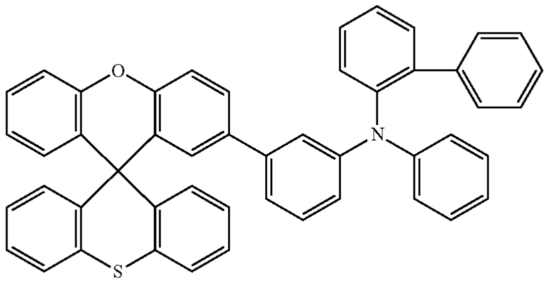

-continued
A26
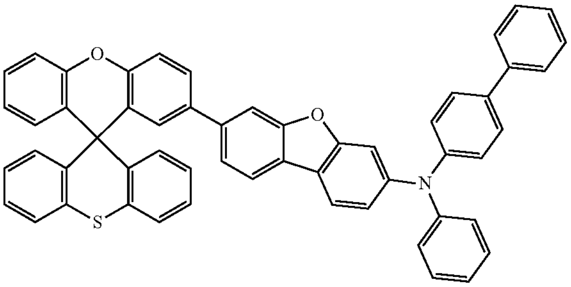
A27
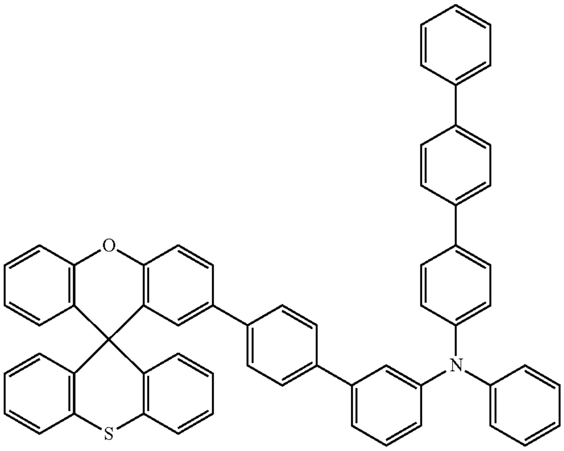
A28
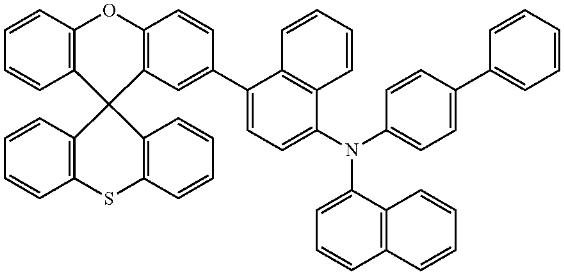
A29
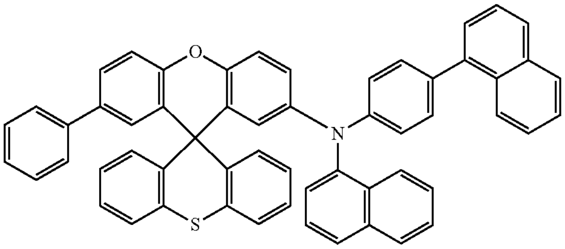
-continued
A30
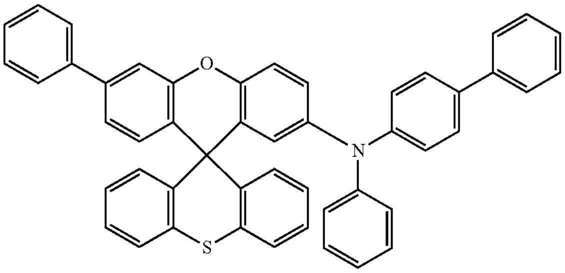
A31
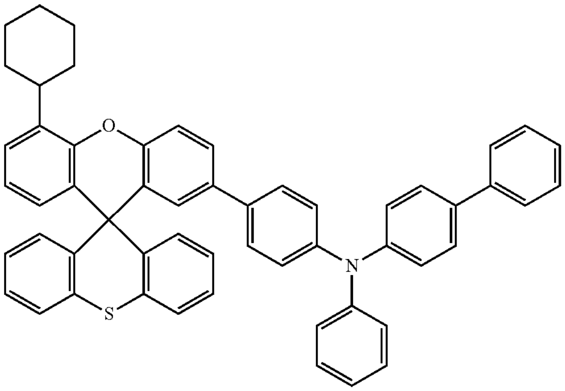
A32
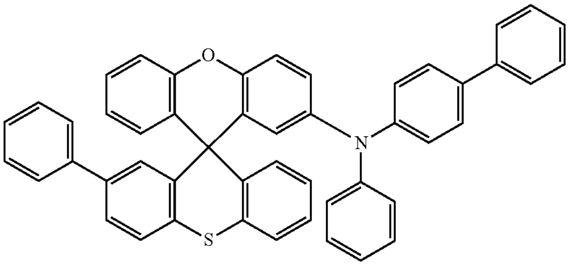
A33
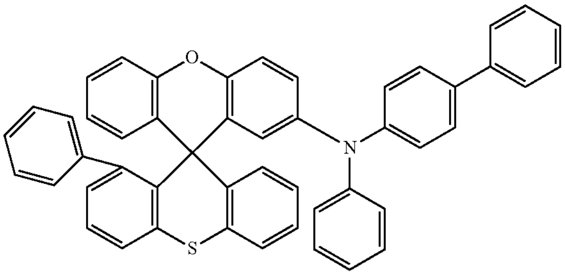
A34
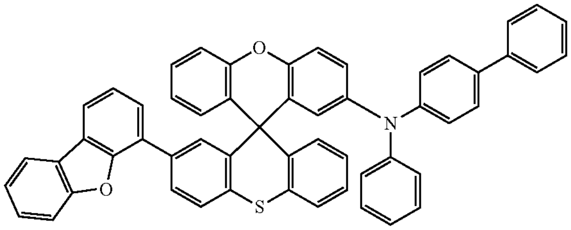

-continued
A35
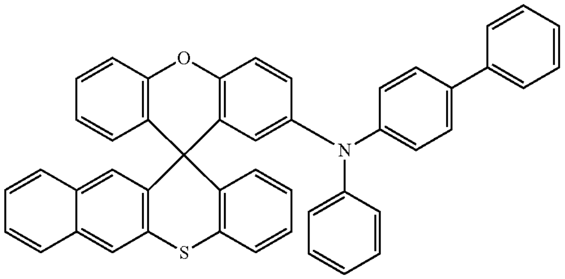
A36
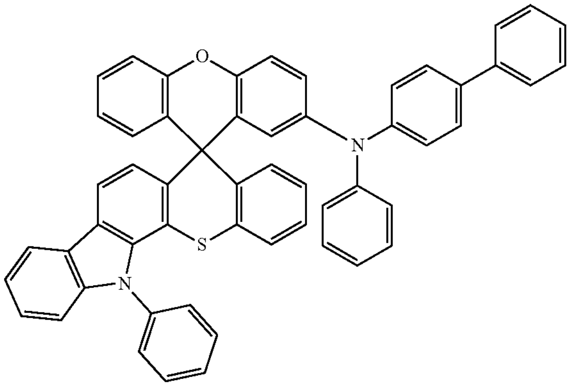
A37
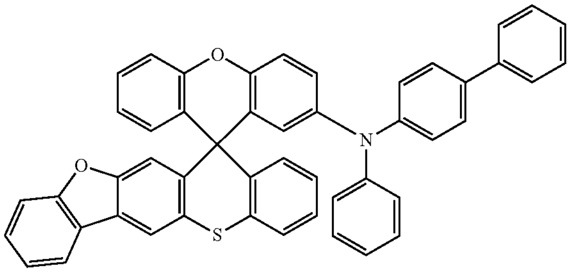
A38
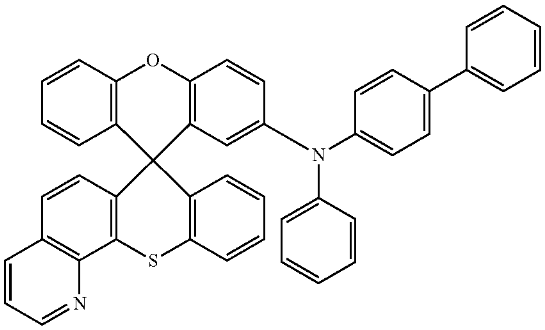
-continued
A39
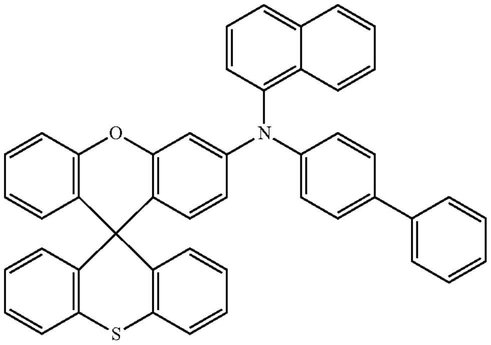
A40
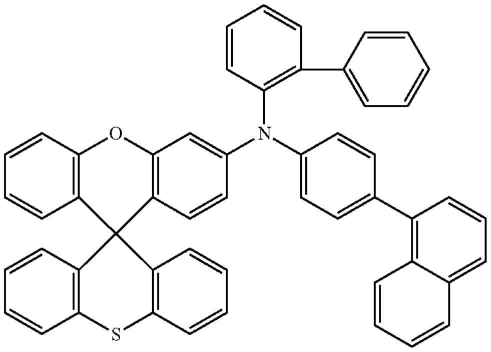
A41
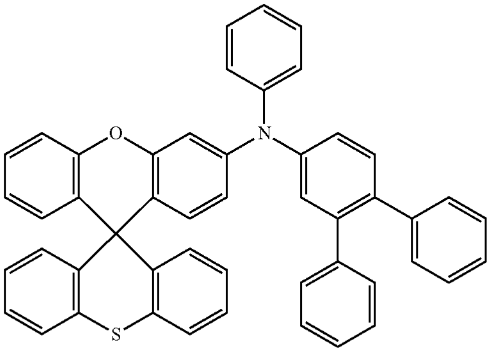
A42
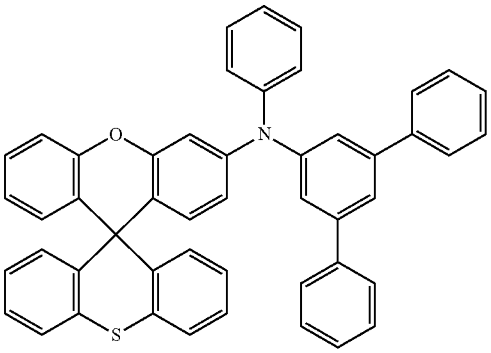

-continued
A43
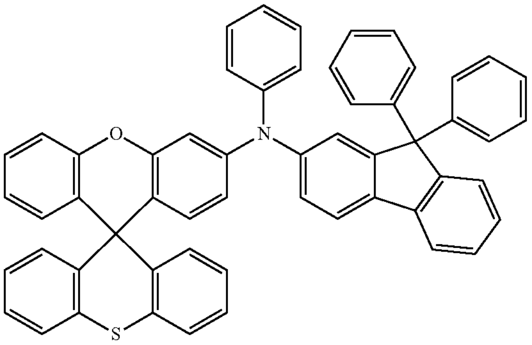
A44
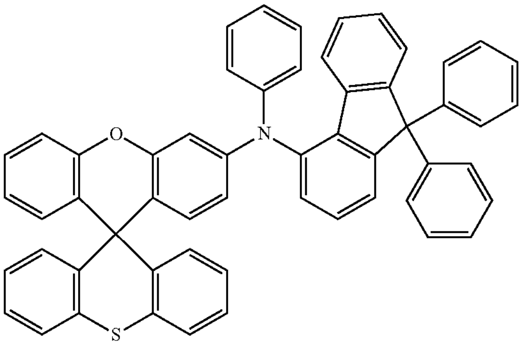
A45
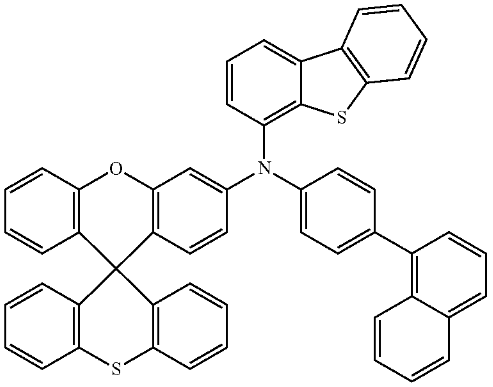
A46
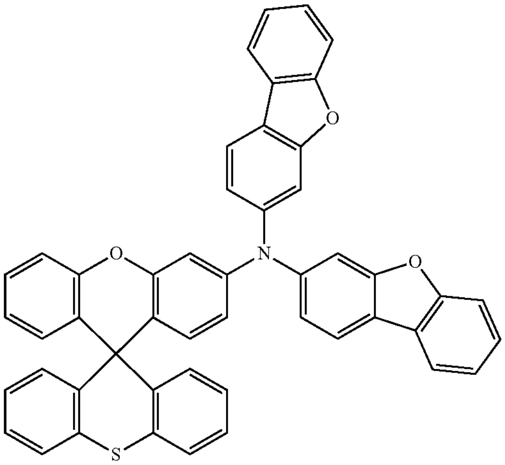
-continued
A47
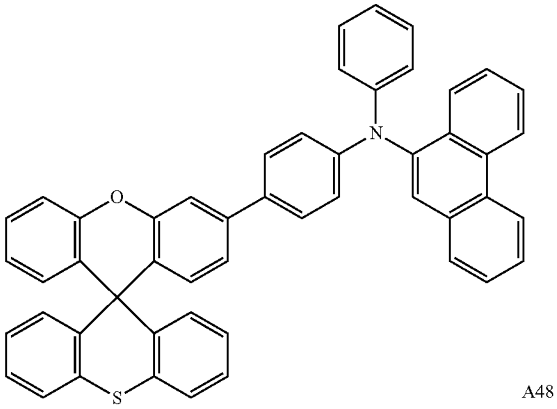
A48
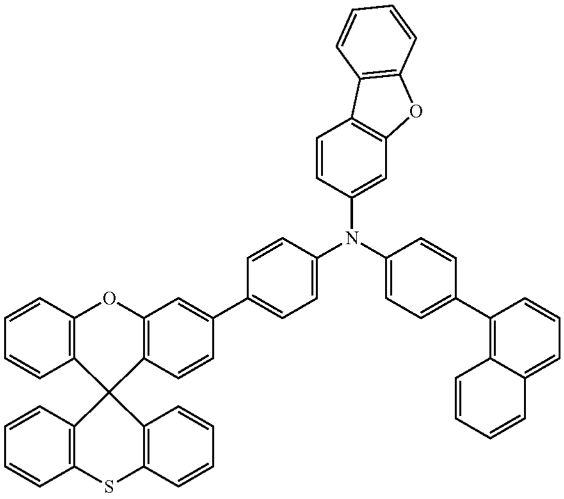
A49
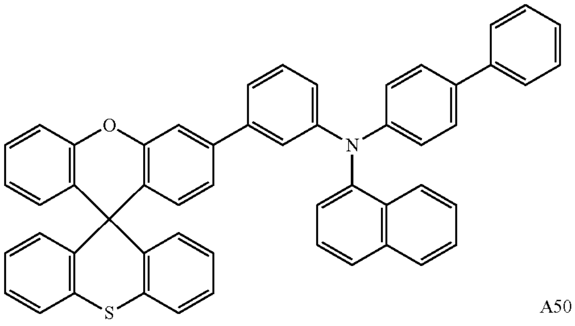
A50
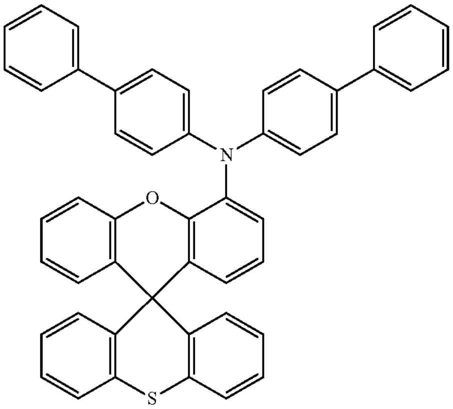

-continued
A51
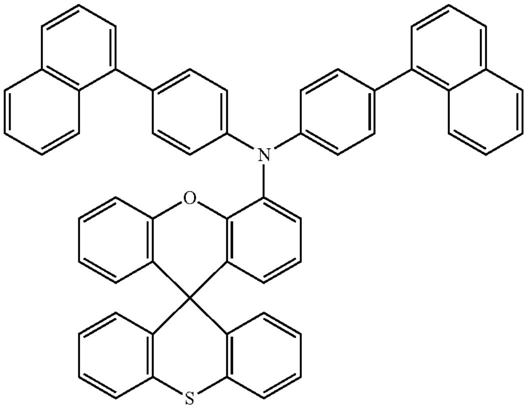
A52
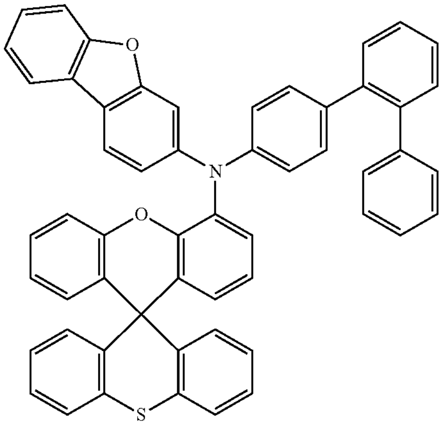
A53
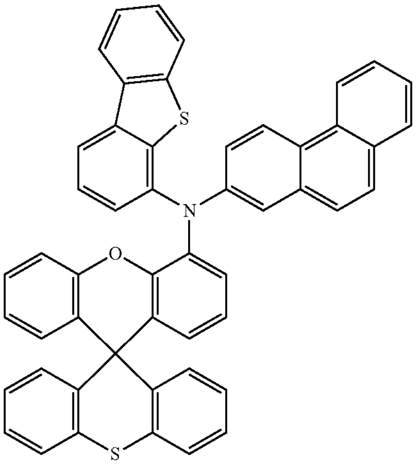
-continued
A54
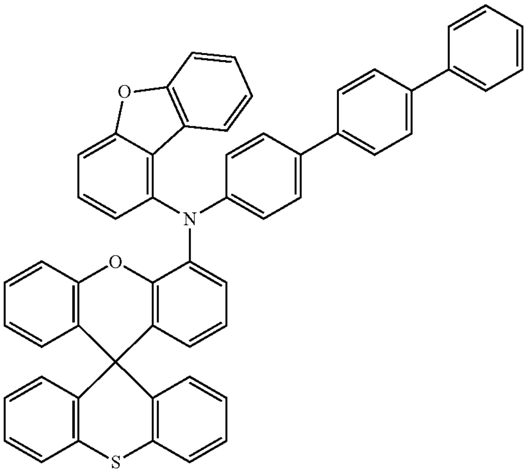
A55
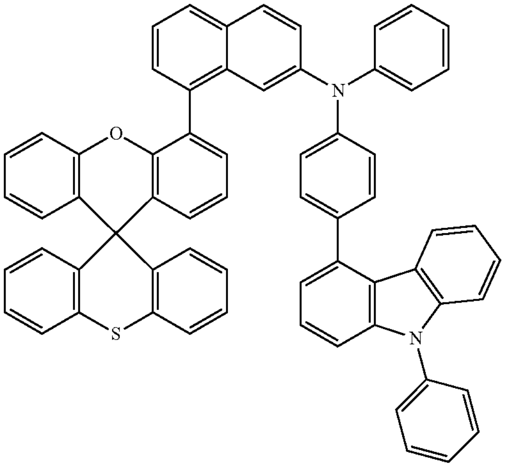
A56
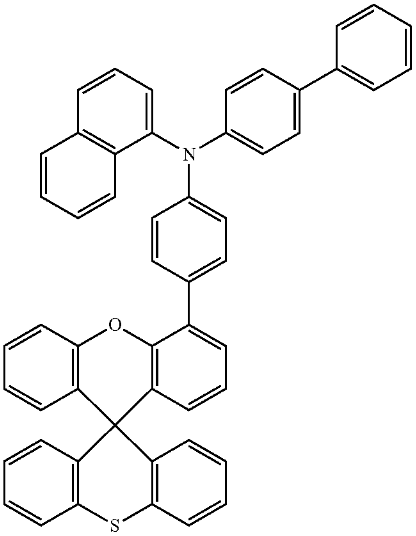

-continued
A57
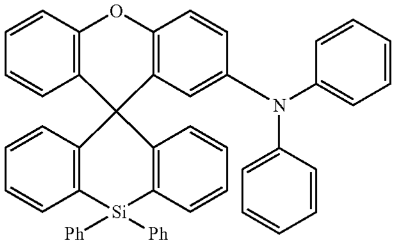
A58
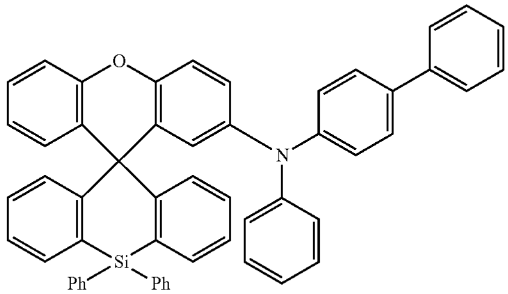
A59
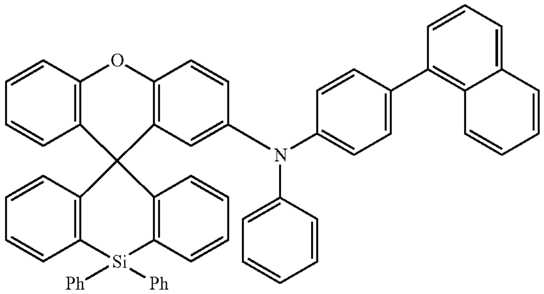
A60
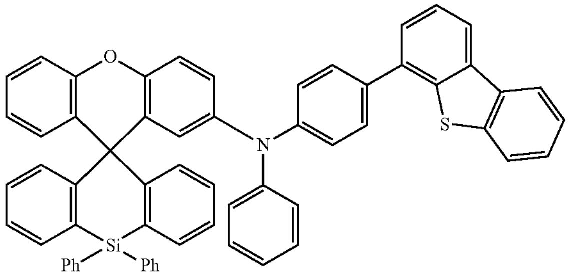
A61
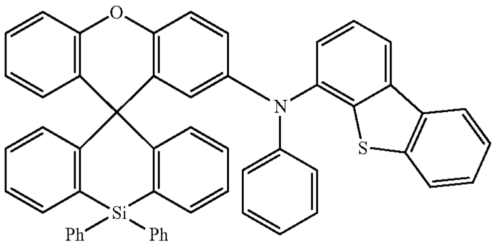
-continued
A62
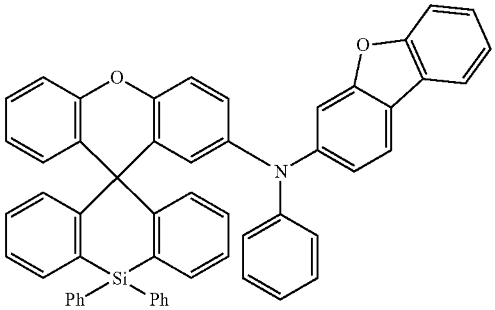
A63
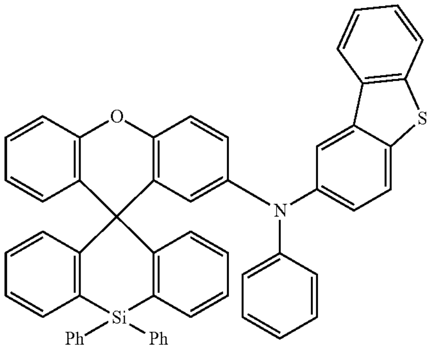
A64
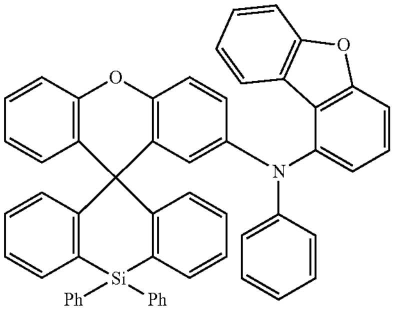
A65
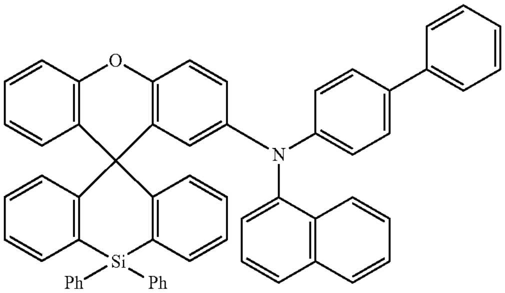

-continued
A66
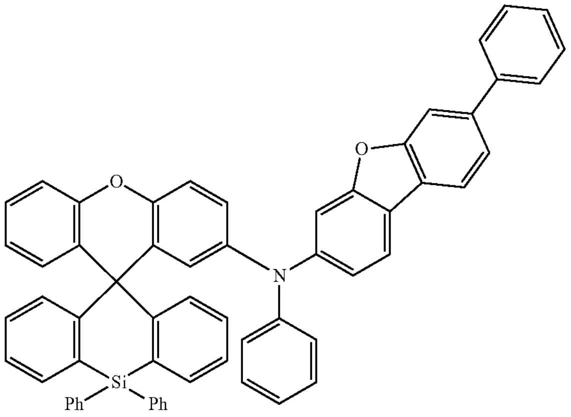
A67
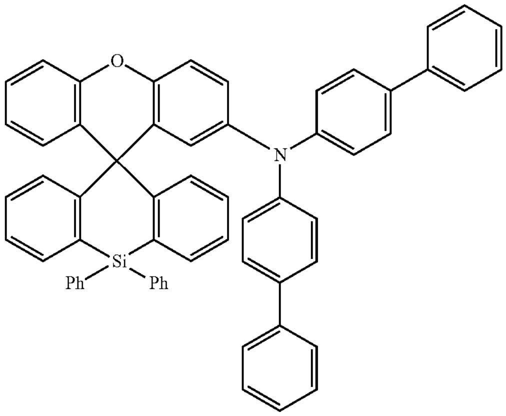
A68
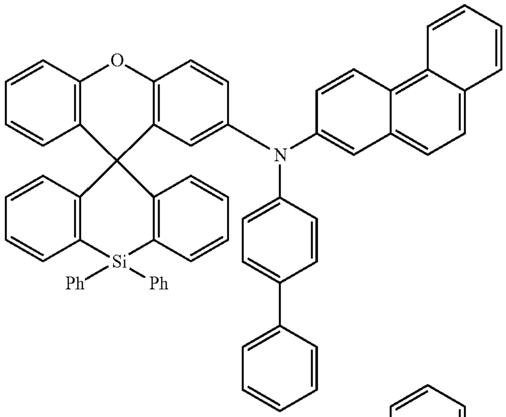
A69
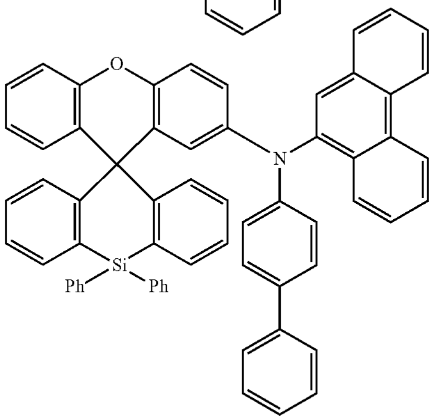
-continued
A70
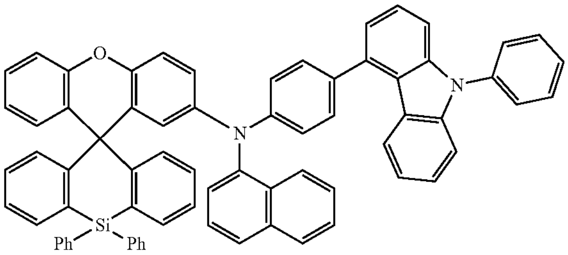
A71
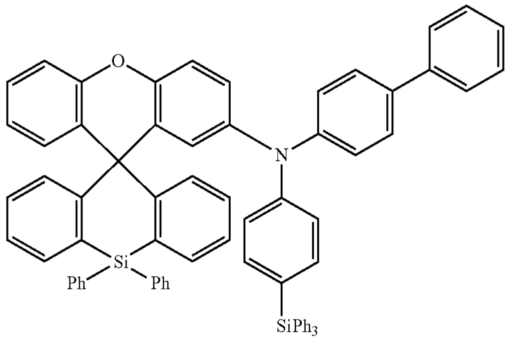
A72
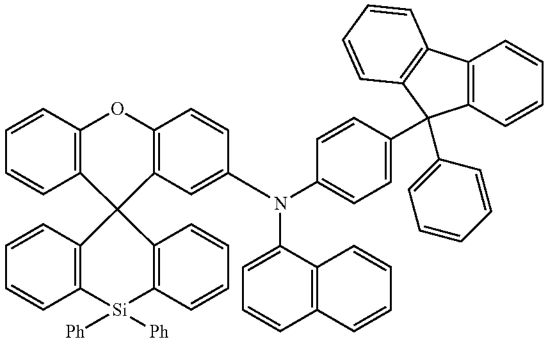
A73
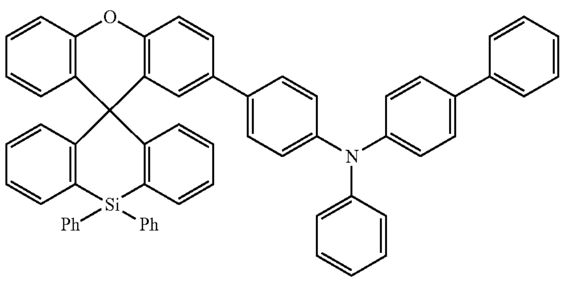
A74
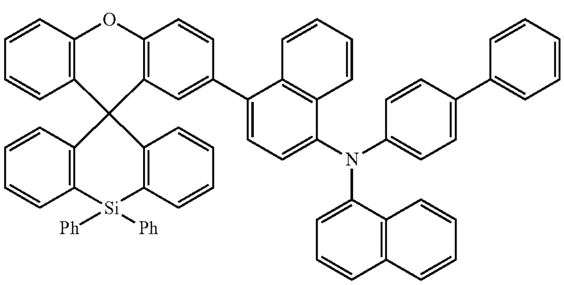

-continued
A75
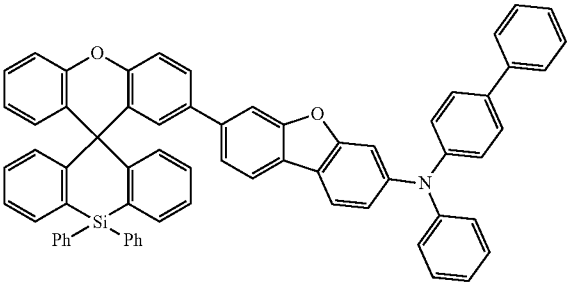
A76
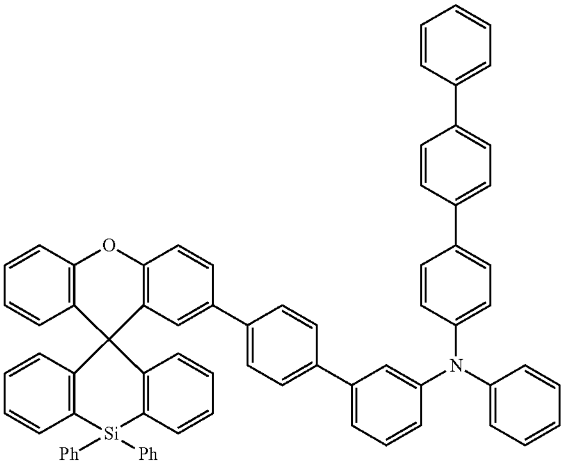
A77
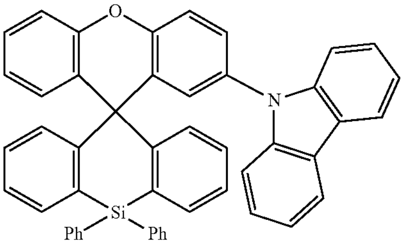
A78
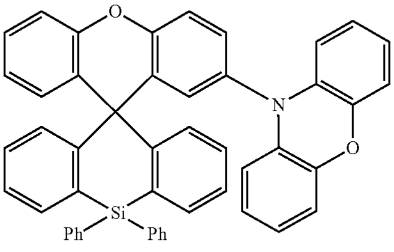
A79
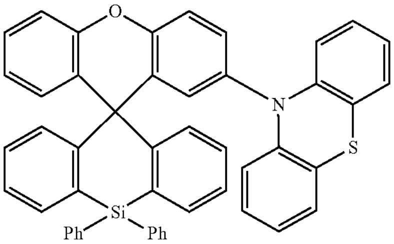
-continued
A80
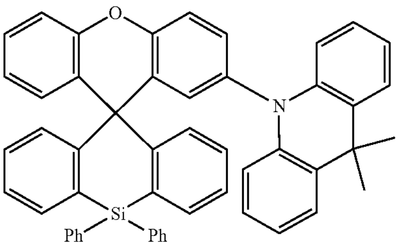
A81
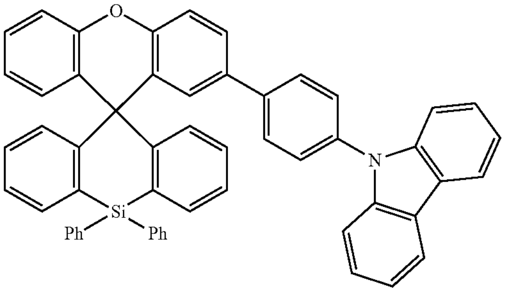
A82
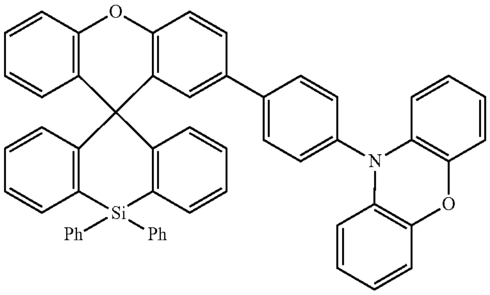
A83
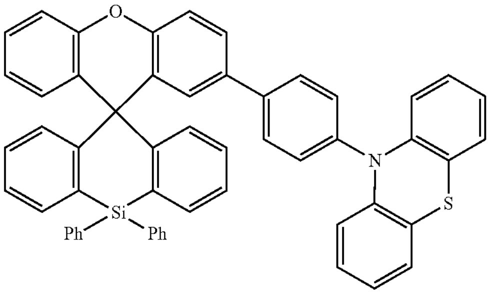
A84
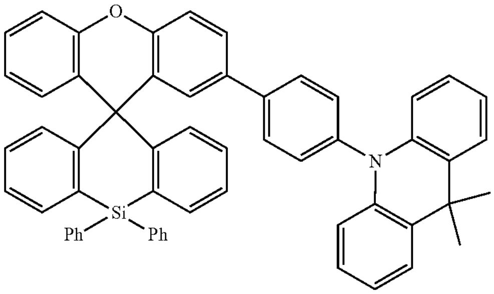

-continued
A85
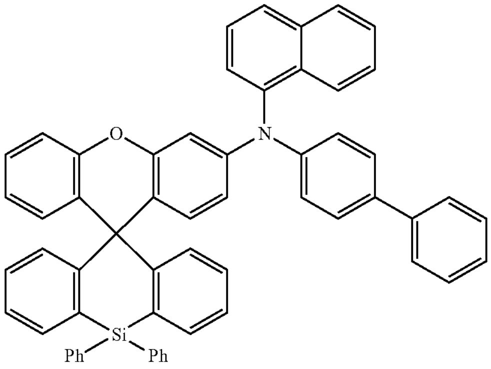
A86
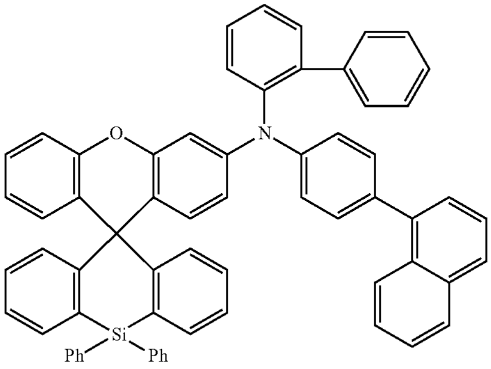
A87
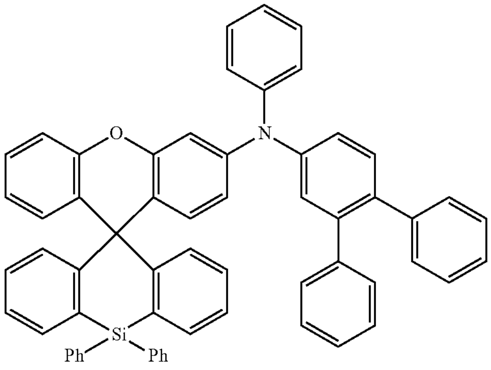
A88
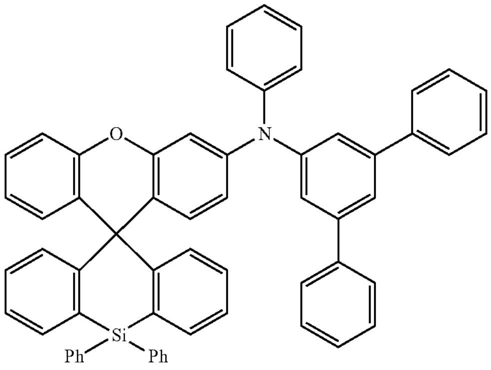
-continued
A89
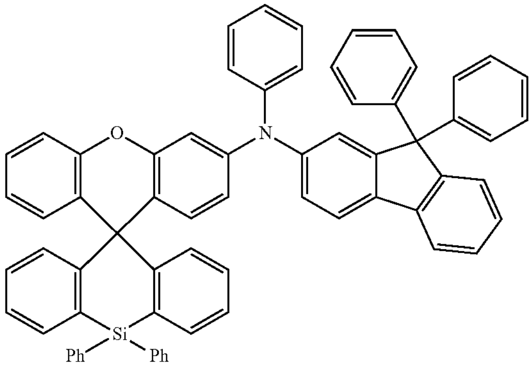
A90
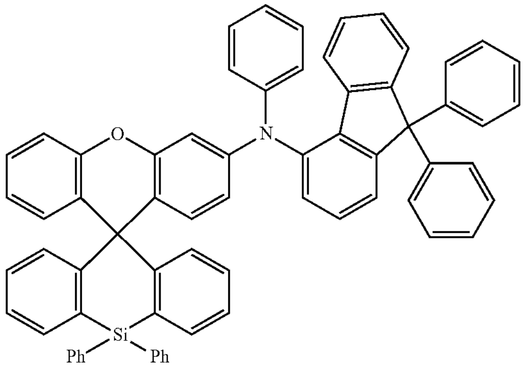
A91
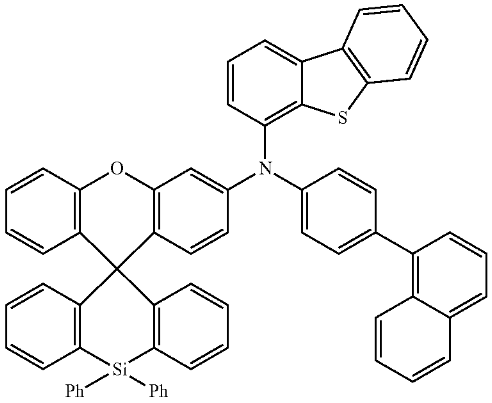
A92
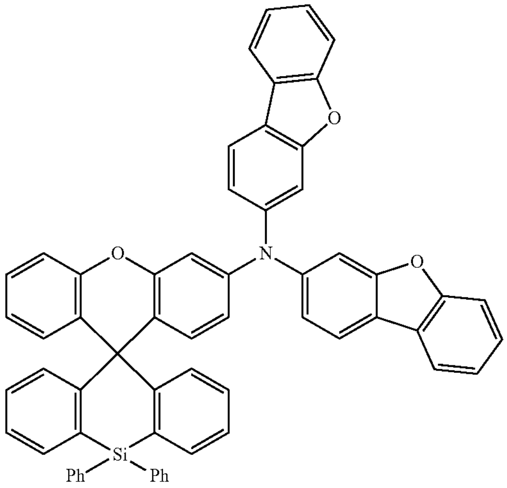

-continued
A93
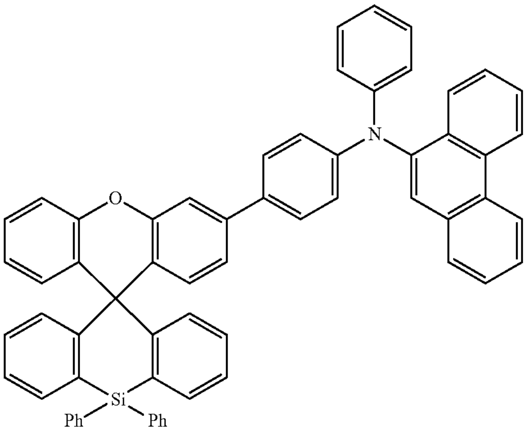
A94
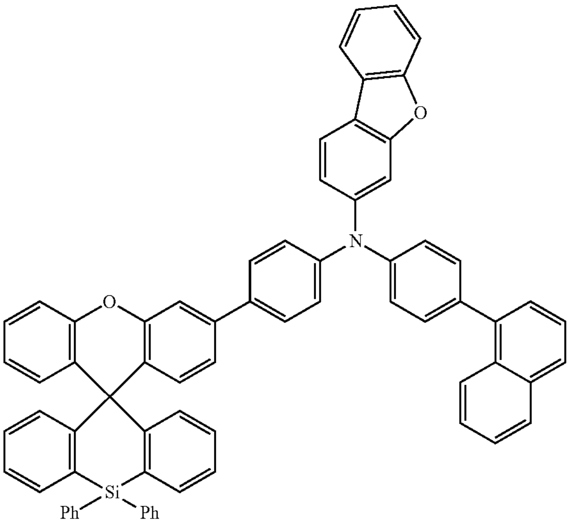
A95
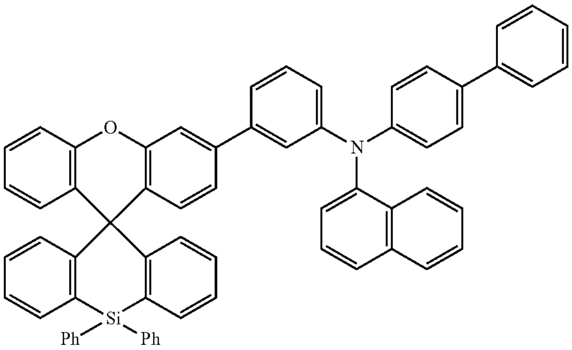
-continued
A96
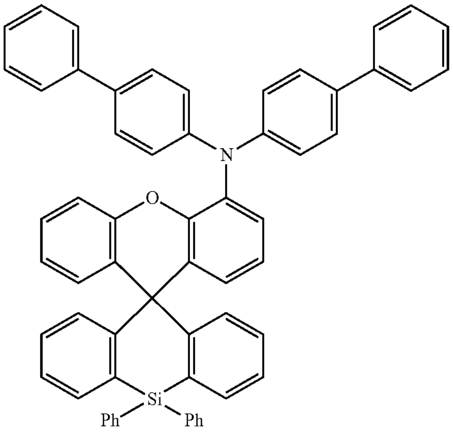
A97
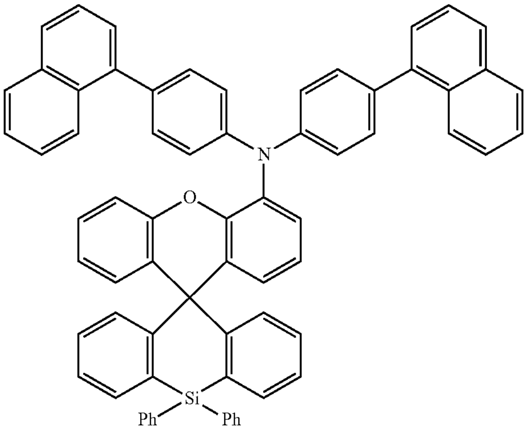
A98
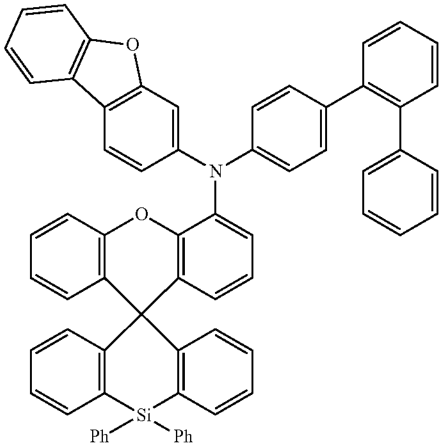

-continued
A99
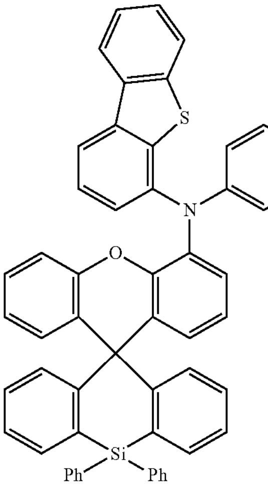
A100
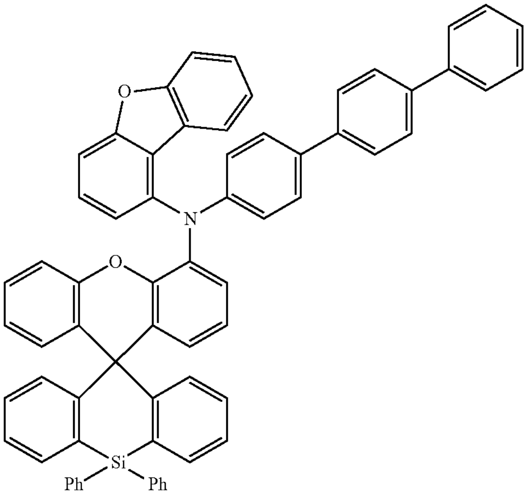
A101
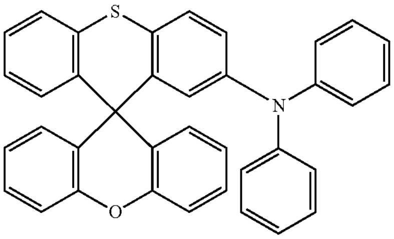
A102
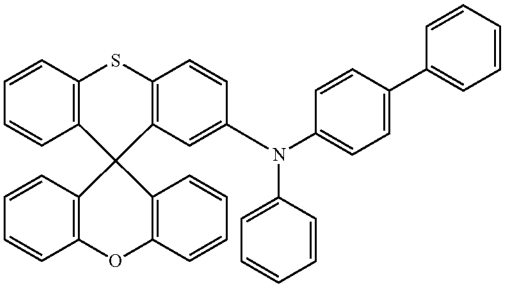
-continued
A103
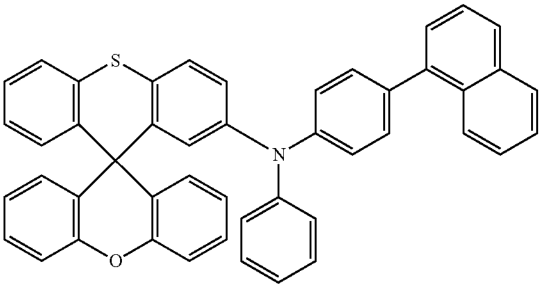
A104
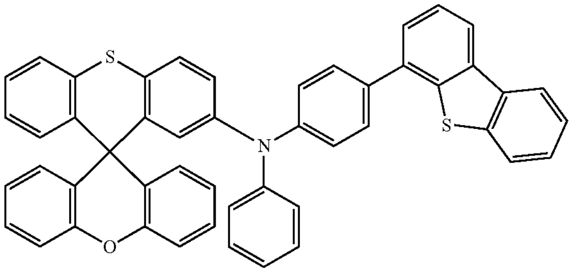
A105
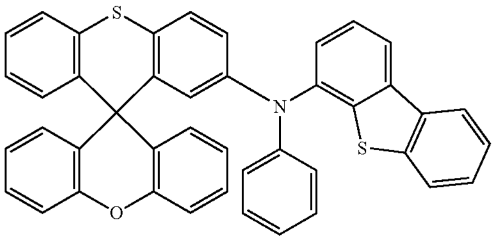
A106
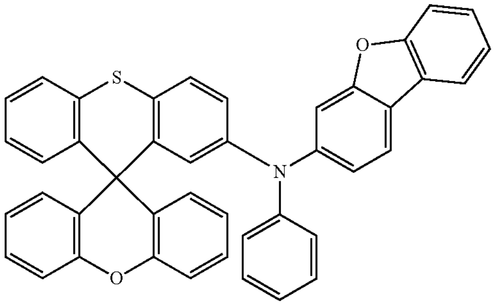
A107
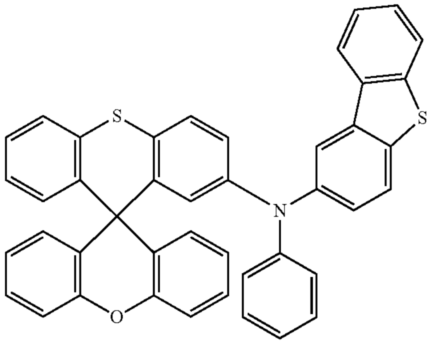

-continued
A108
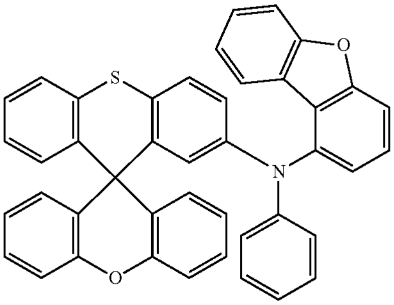
A109
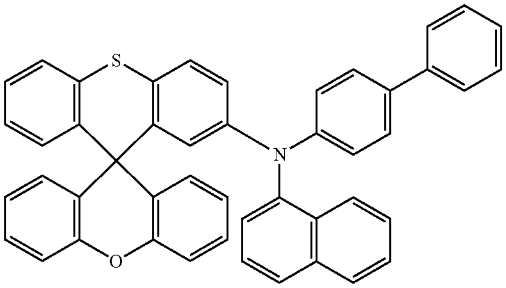
A110
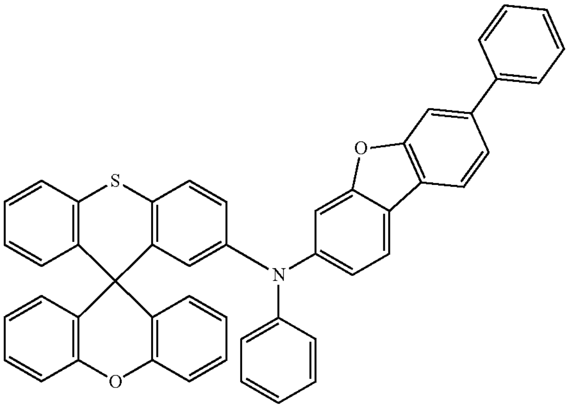
A111
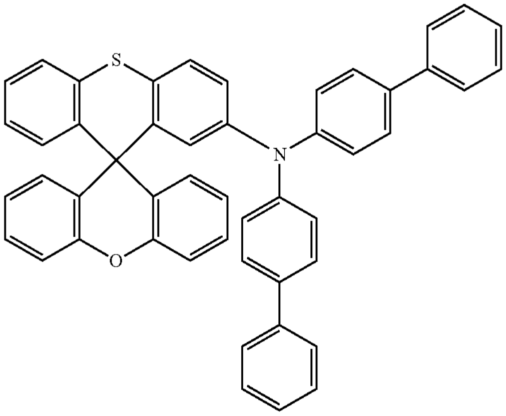
-continued
A112
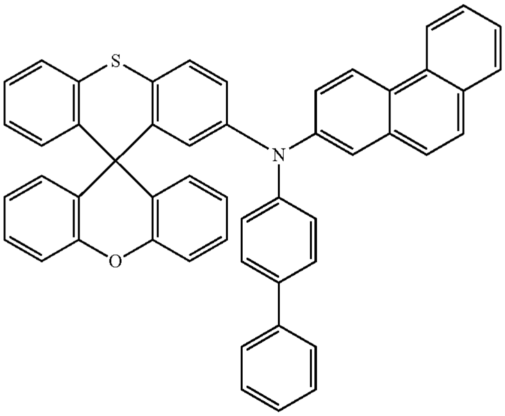
A113
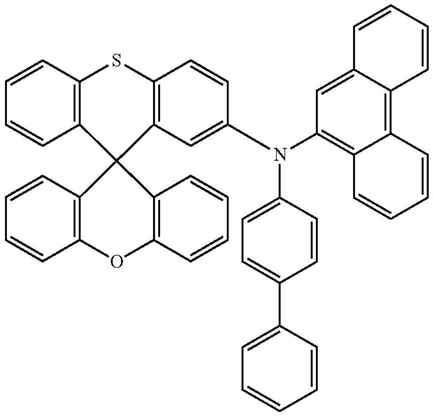
A114
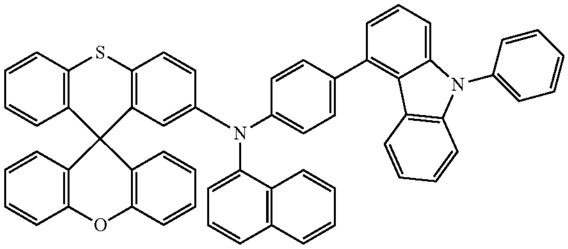
A115
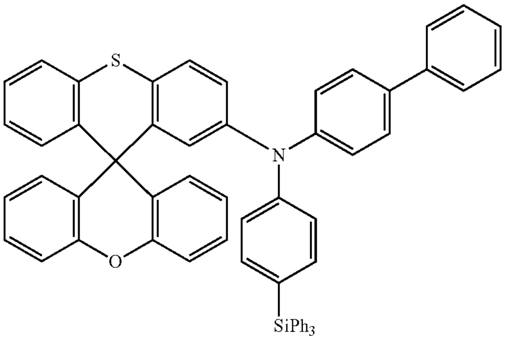

-continued
A116
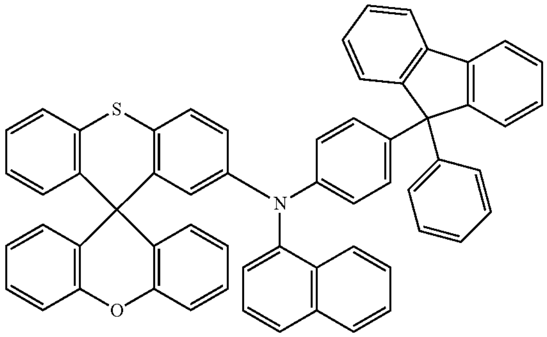
A117
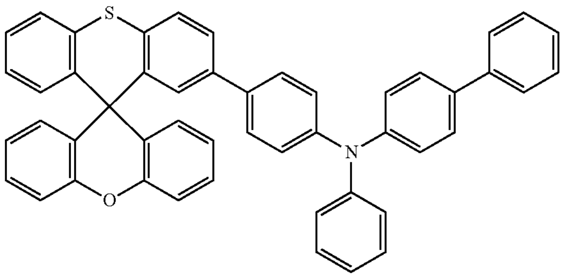
A118
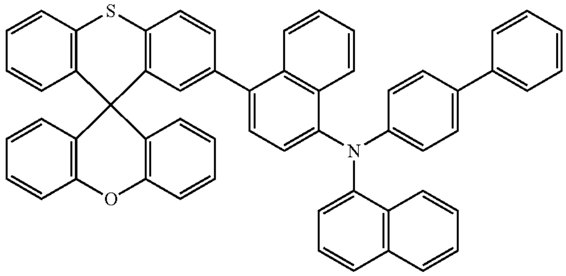
A119
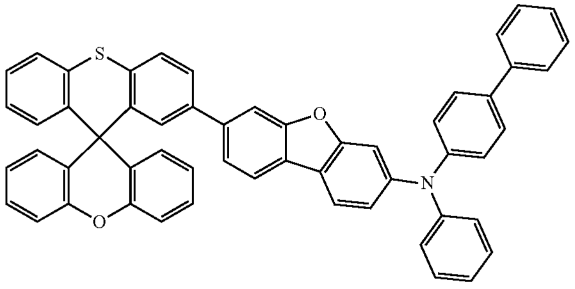
-continued
A120
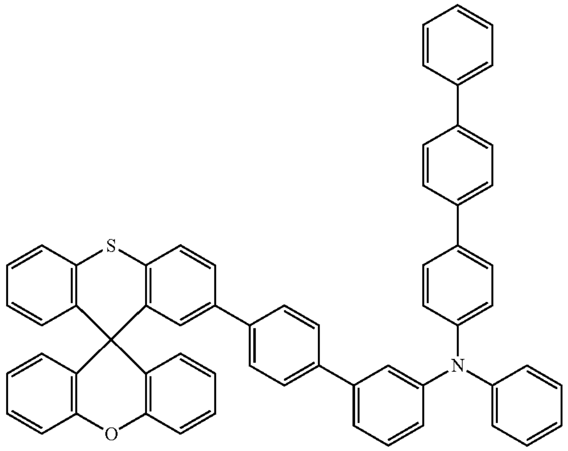
A121
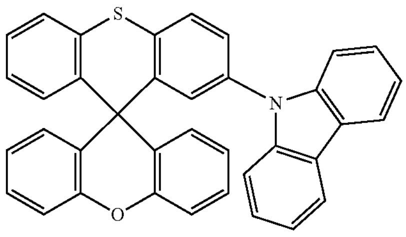
A122
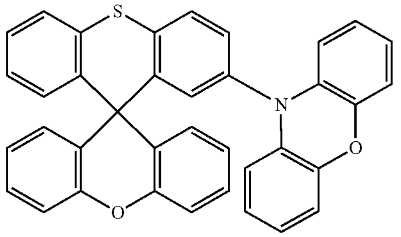
A123
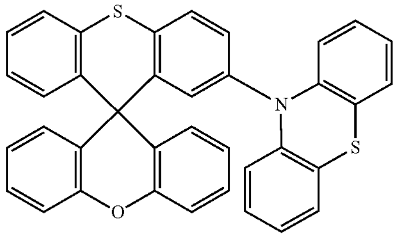
A124
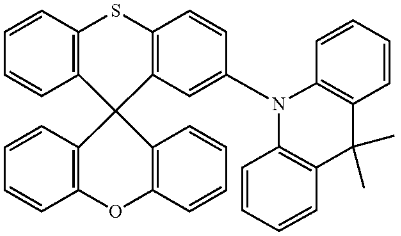

-continued
A125
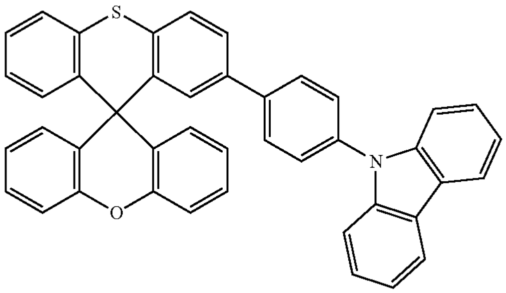
A126
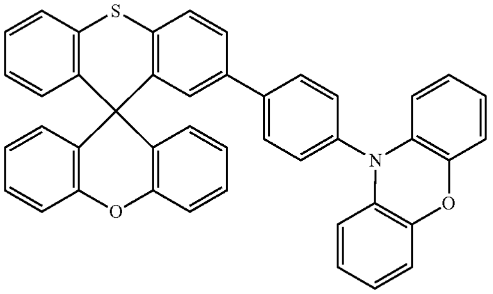
A127
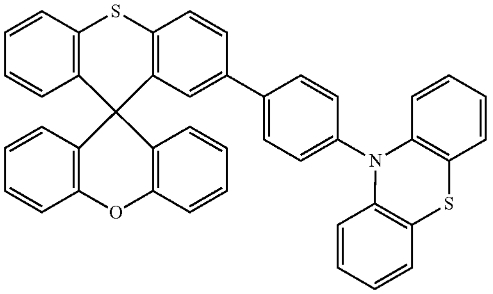
A128
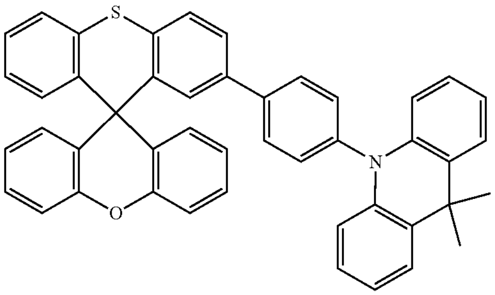
A129
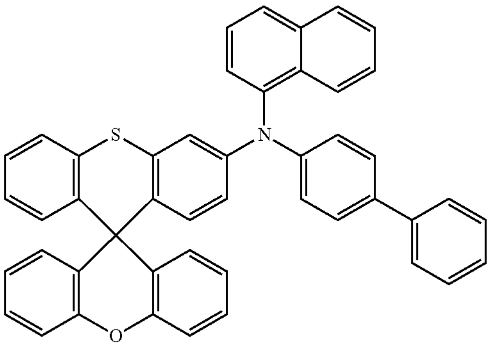
-continued
A130
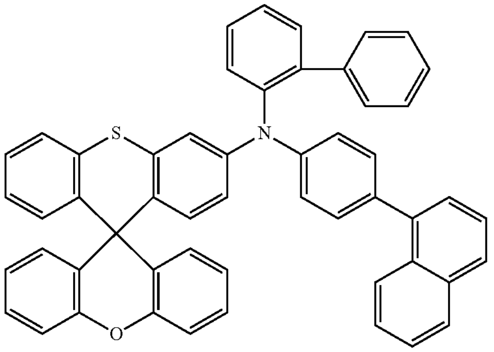
A131
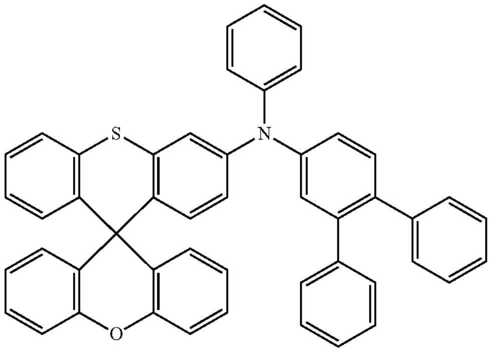
A132
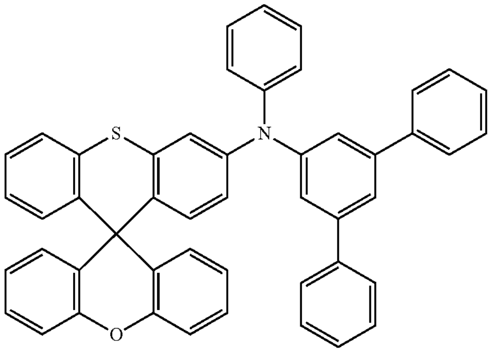
A133
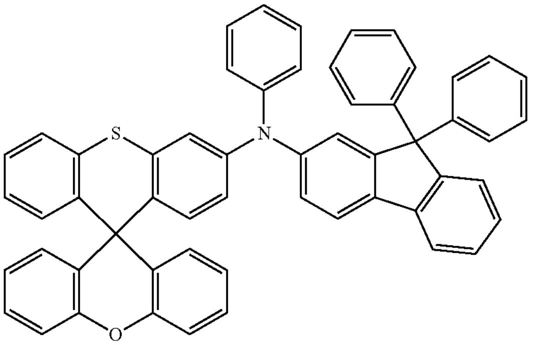

-continued
A134
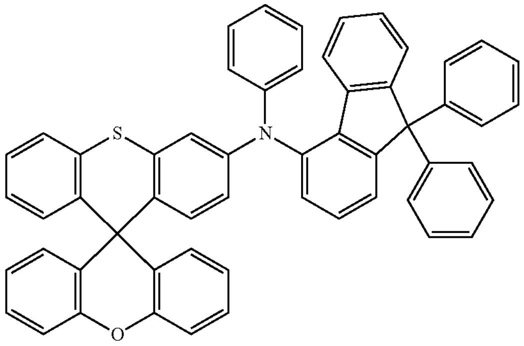
A135
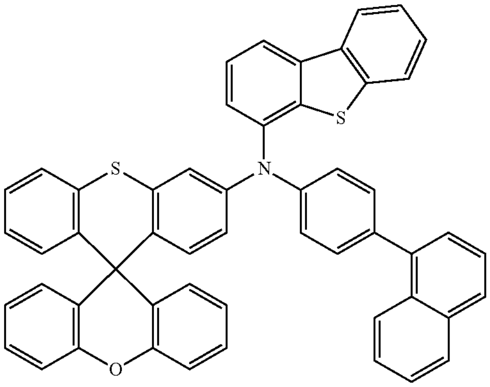
A136
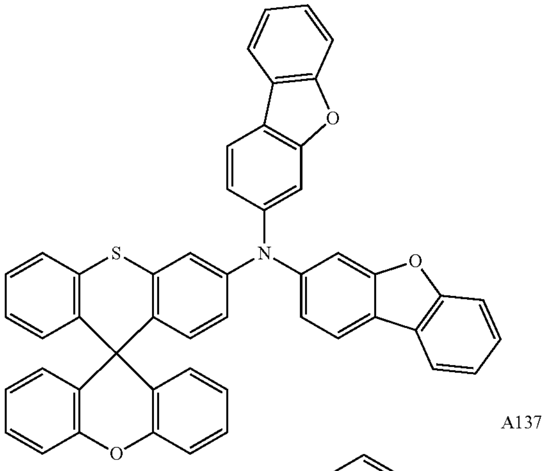
A137
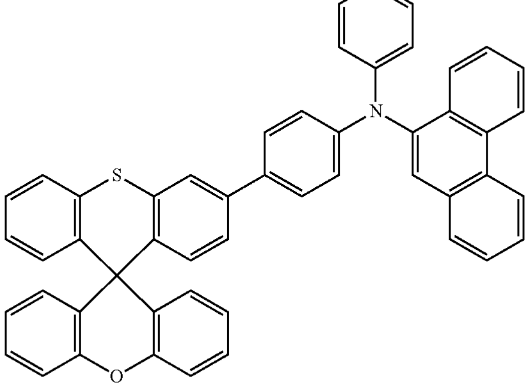
-continued
A138
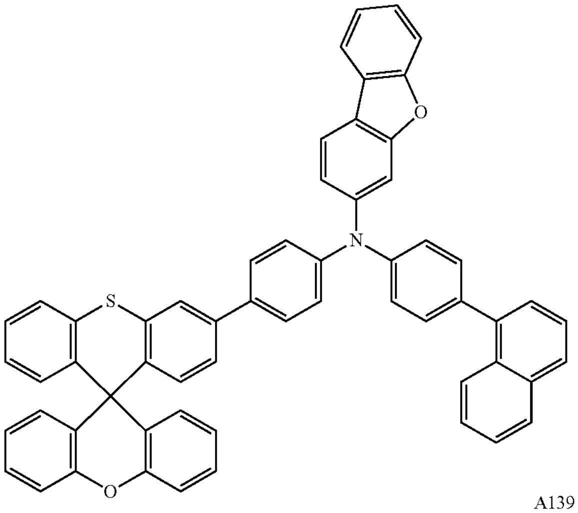
A139
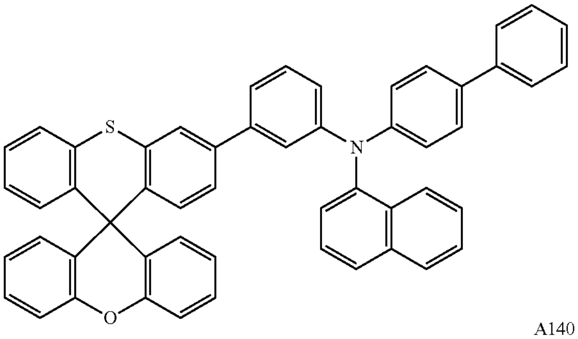
A140
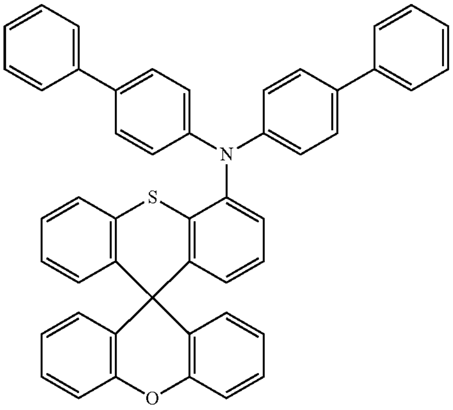
A141
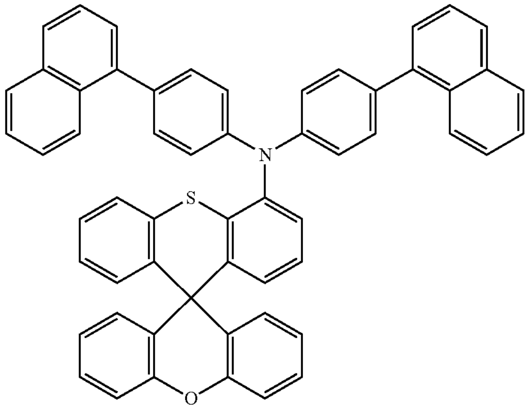

-continued
A142
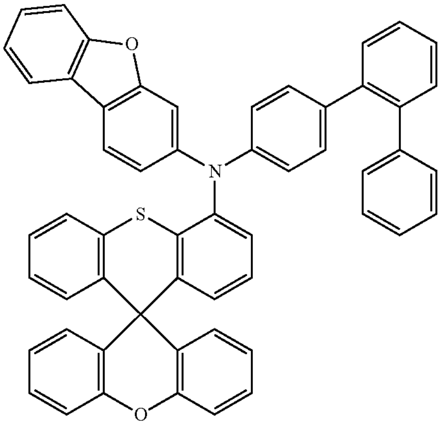
A143
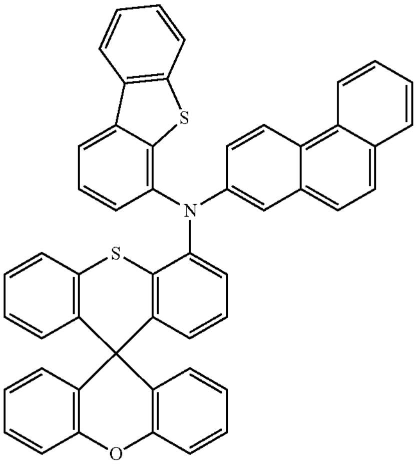
A144
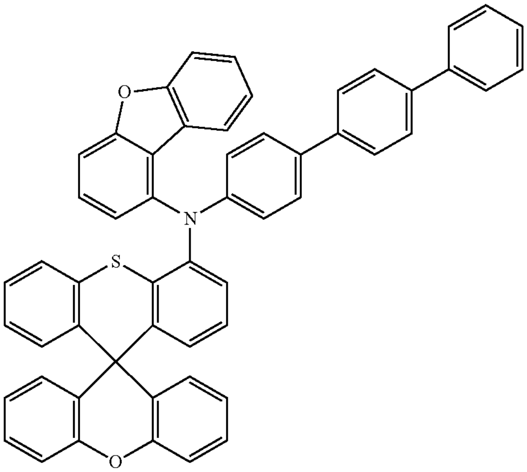
A145
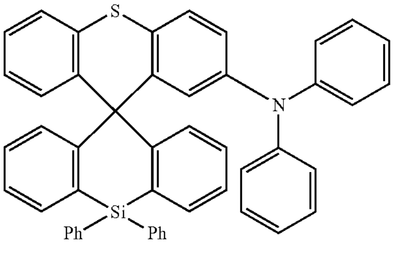
-continued
A146
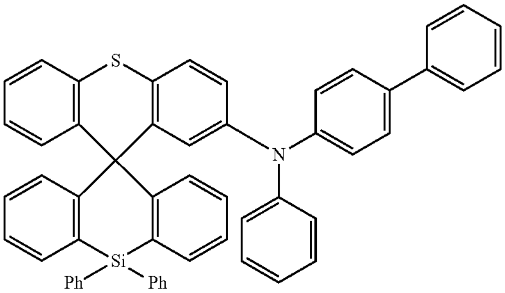
A147
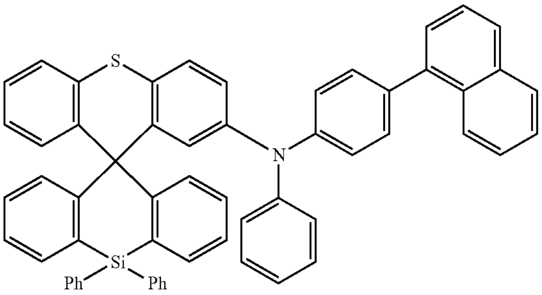
A148
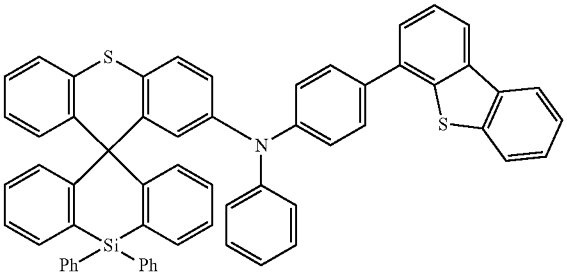
A149
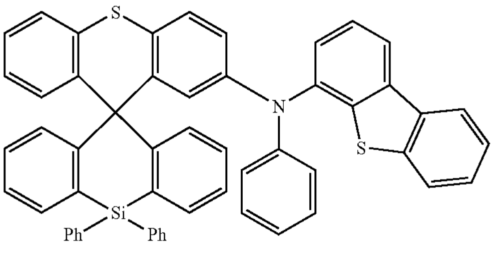
A150
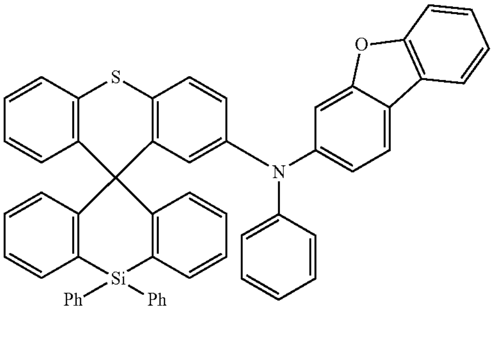

-continued
A151
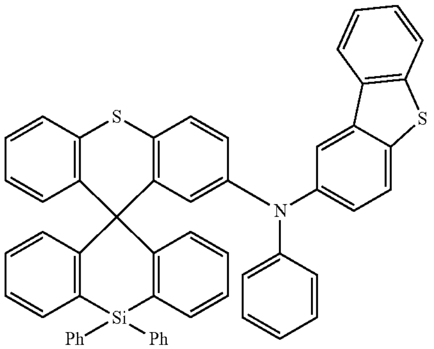
A152
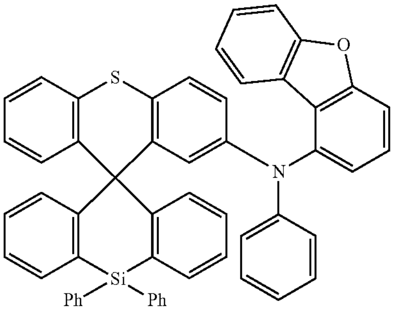
A153
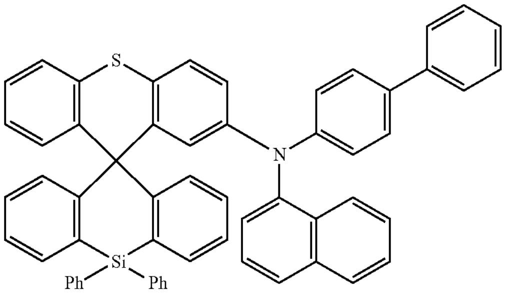
A154
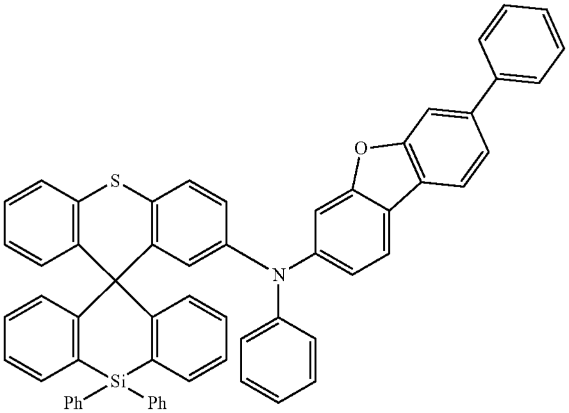
-continued
A155
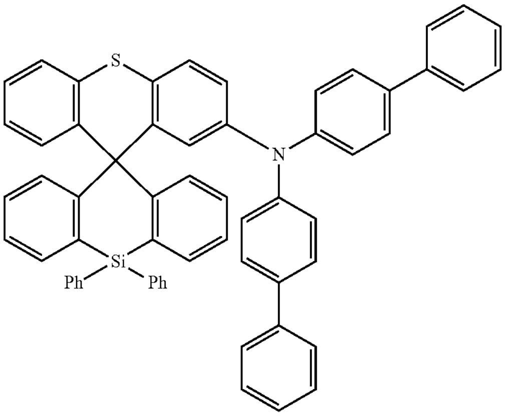
A156
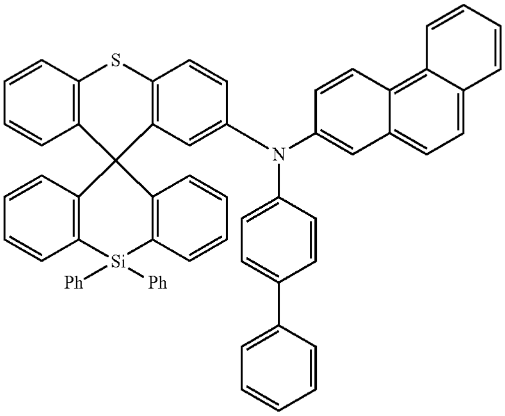
A157
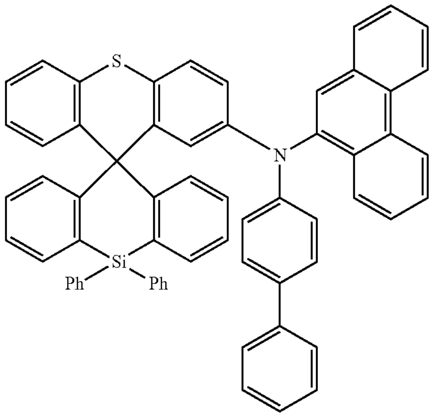
A158
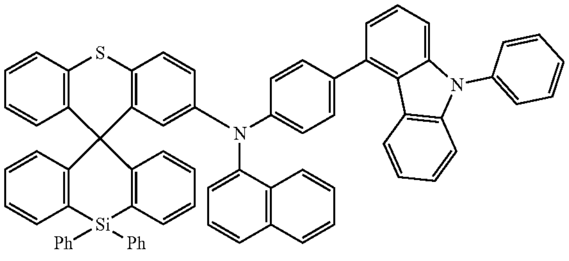

-continued
A159
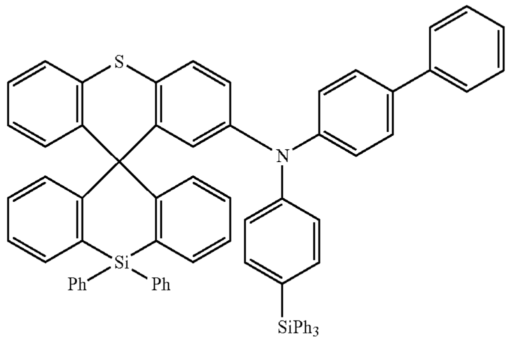
A160
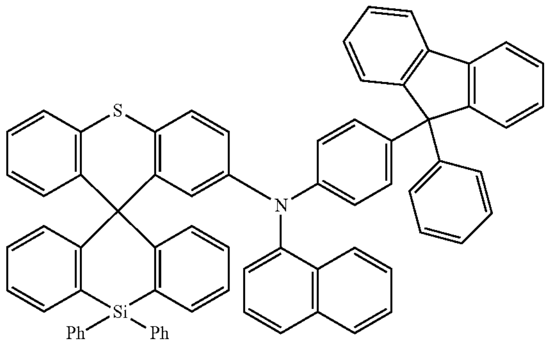
A161
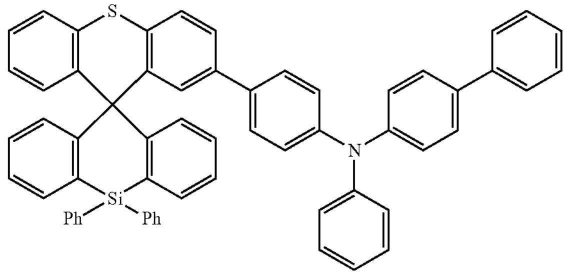
A162
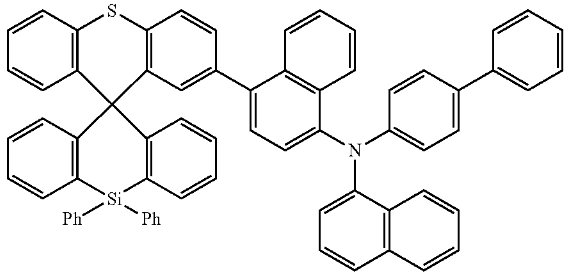
A163
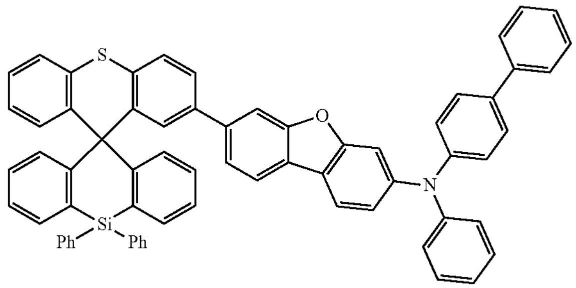
-continued
A164
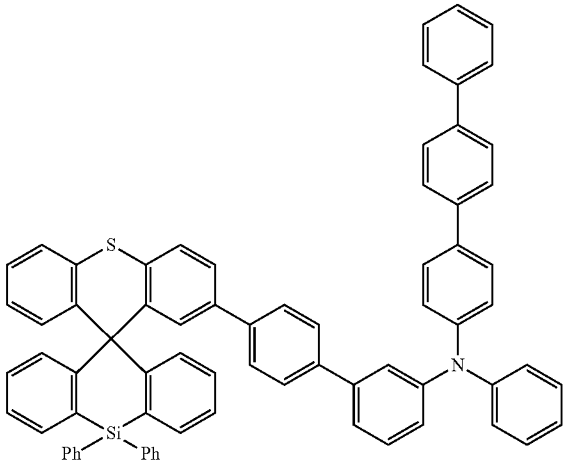
A165
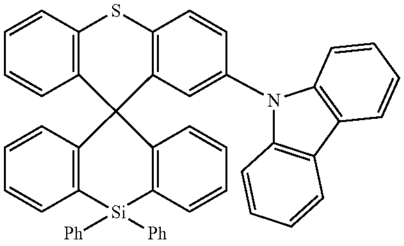
A166
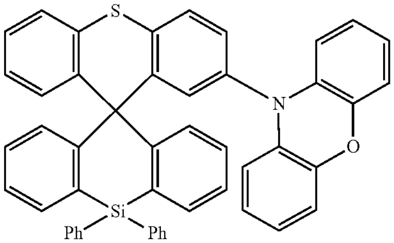
A167
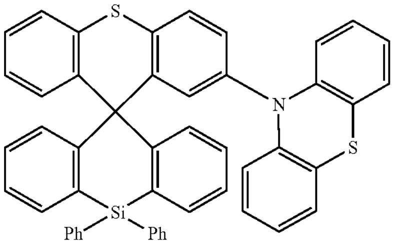
A168
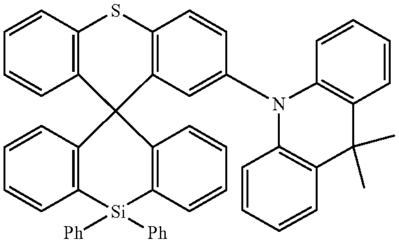

-continued
A169
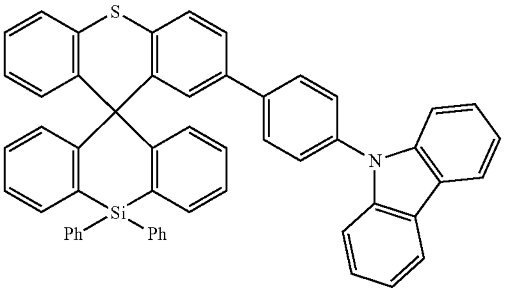
A170
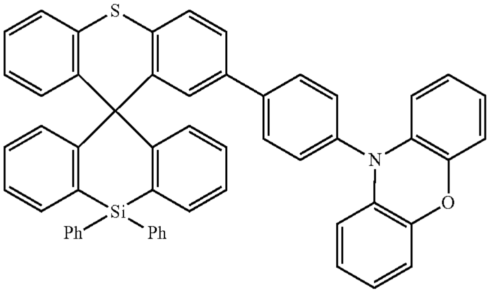
A171
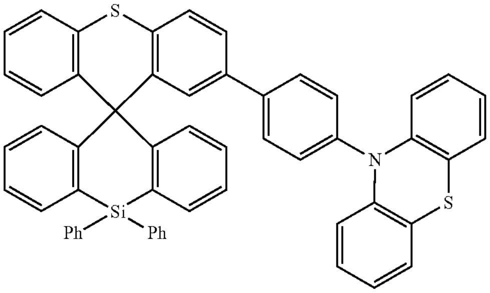
A172
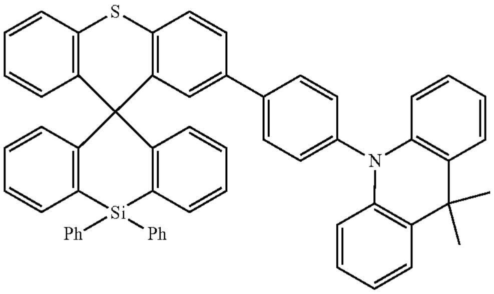
A173
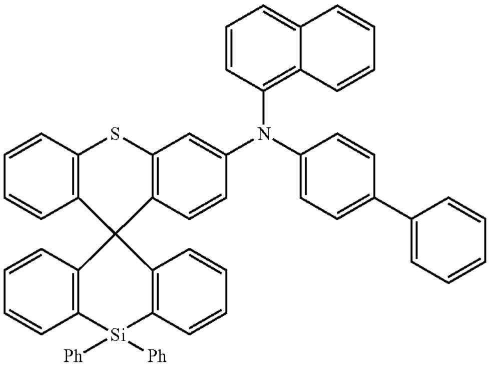
-continued
A174
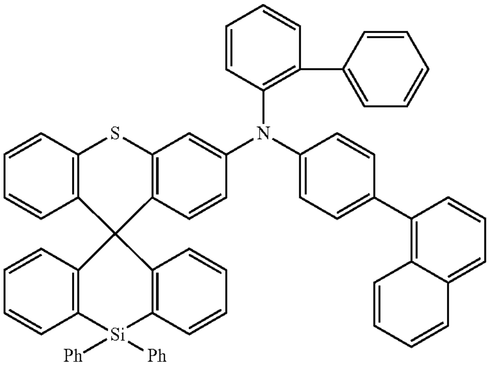
A175
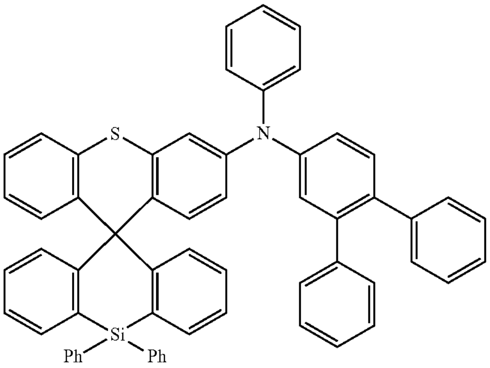
A176
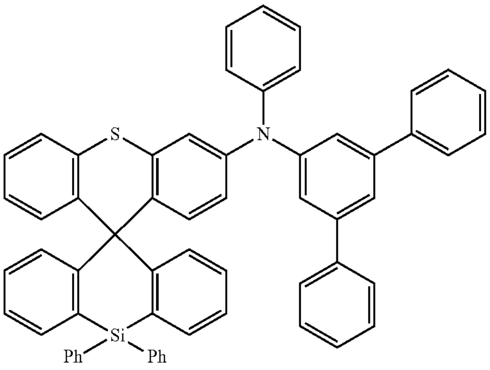
A177
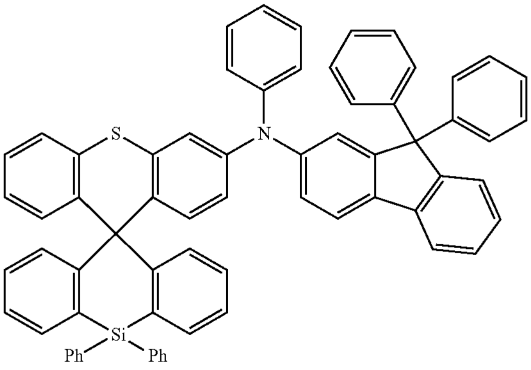

-continued
A178
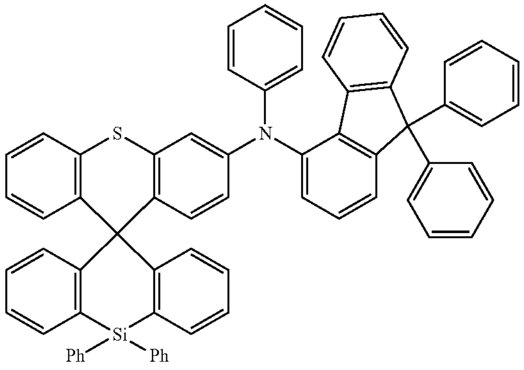
A179
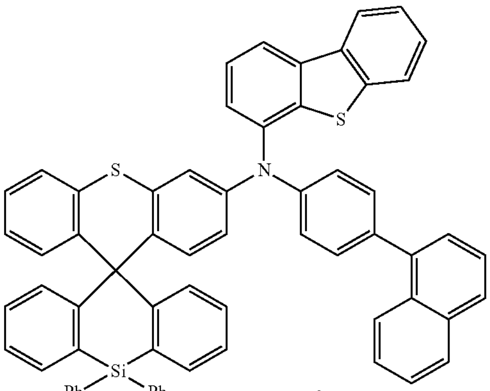
A180
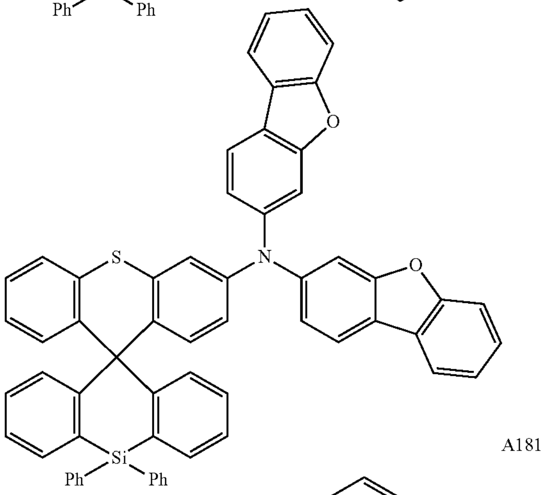
A181
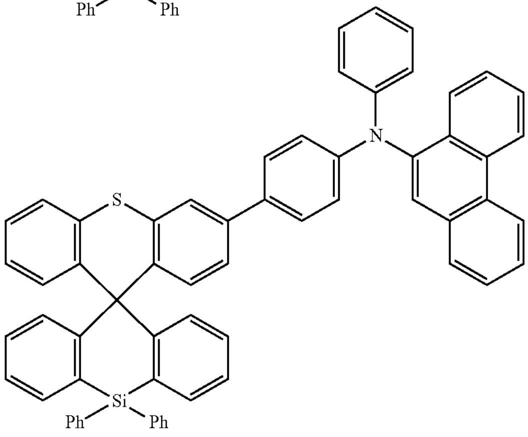
-continued
A182
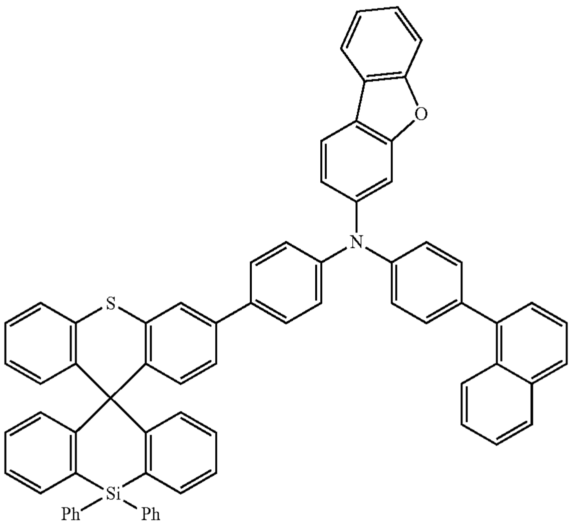
A183
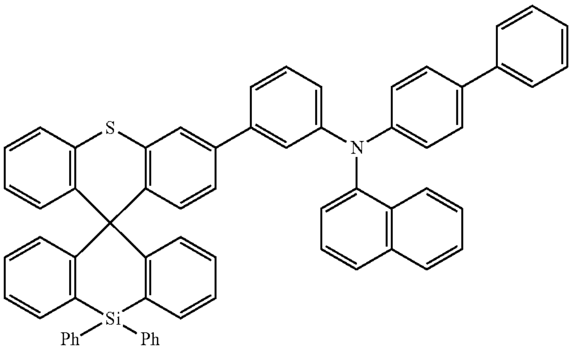
A184
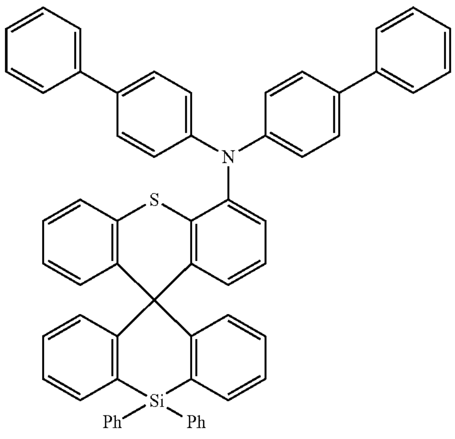

-continued
A185
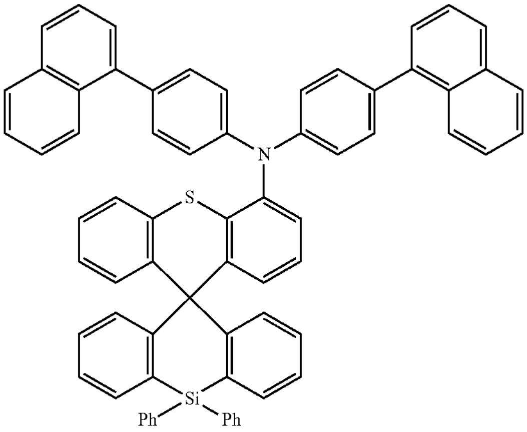
A186
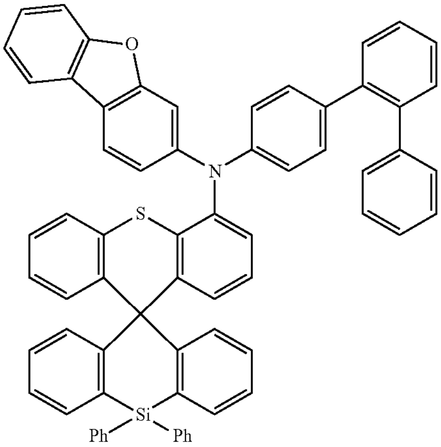
A187
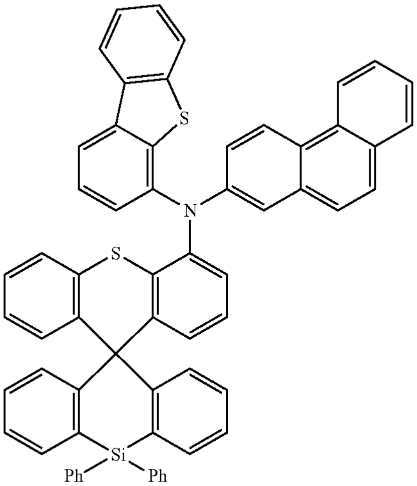
-continued
A188
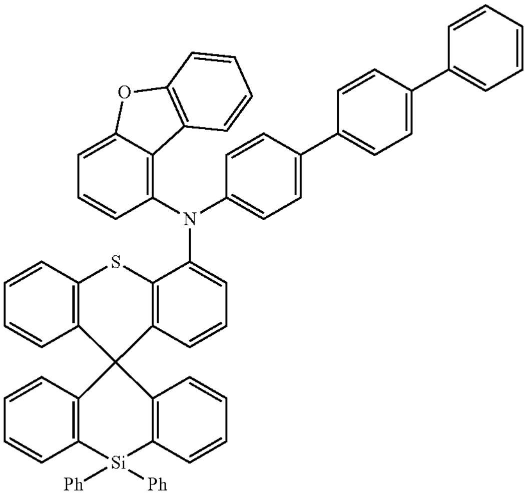
A189
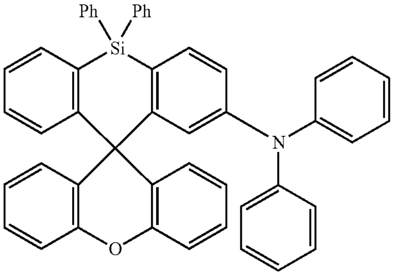
A190
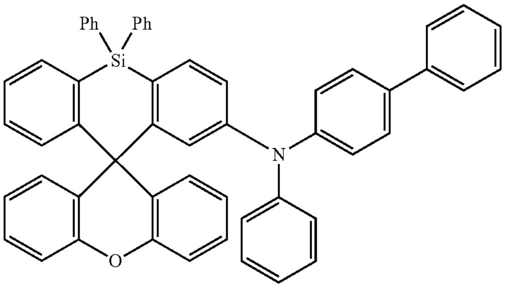
A191
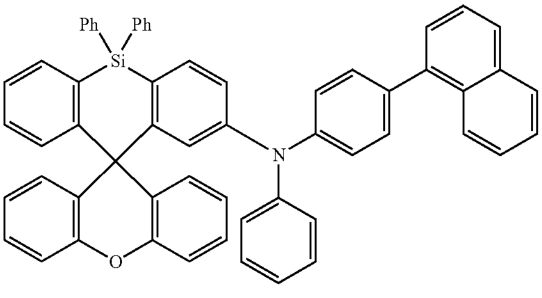

-continued
A192
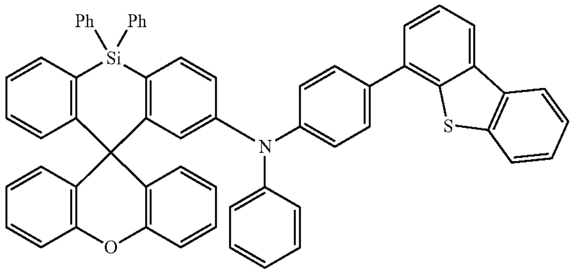
A193
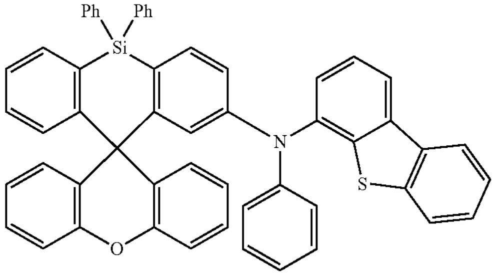
A194
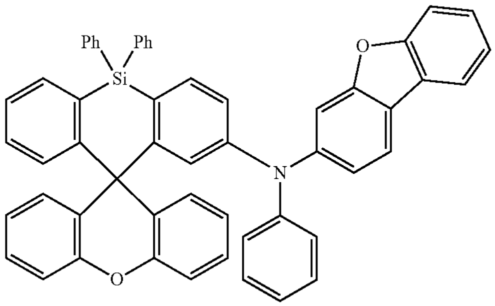
A195
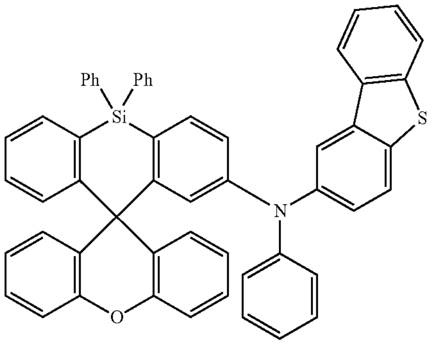
A196
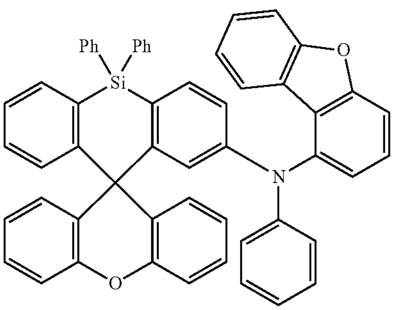
-continued
A197
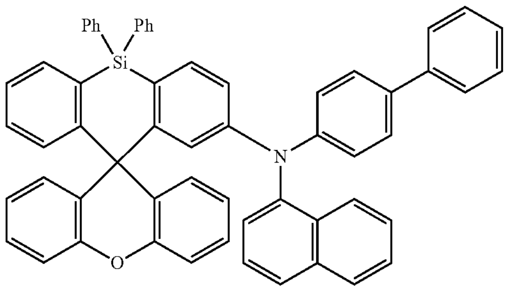
A198
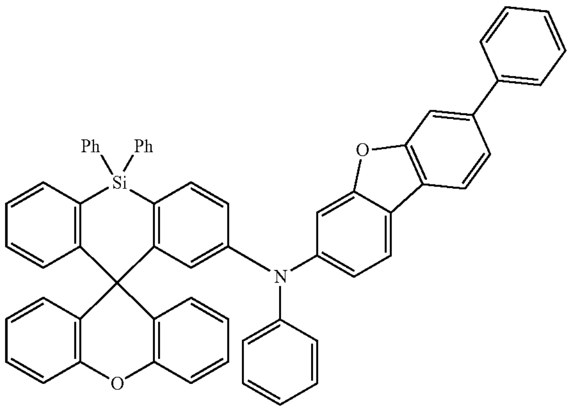
A199
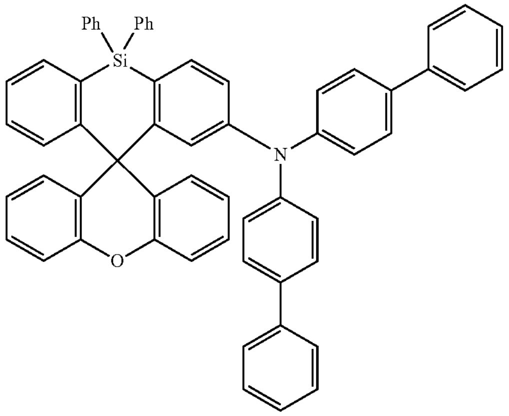
A200
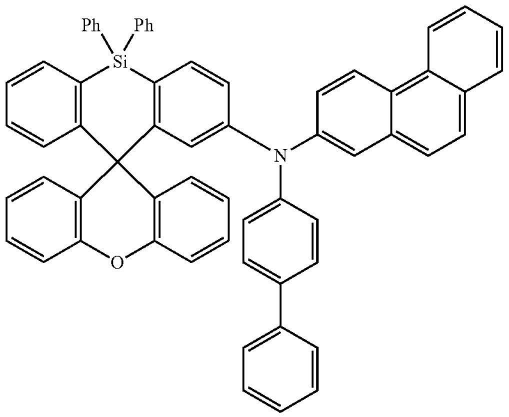

-continued
A201
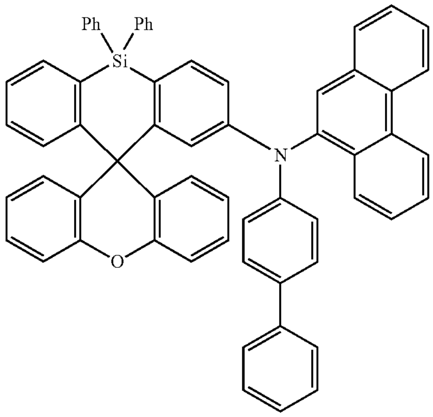
A202
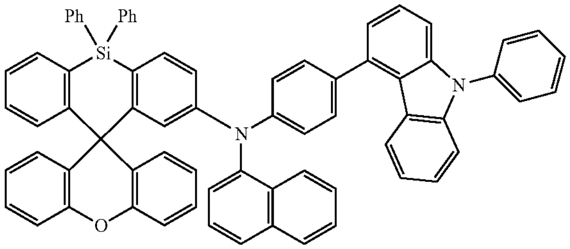
A203
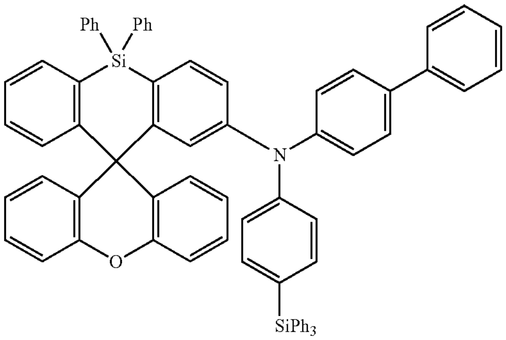
A204
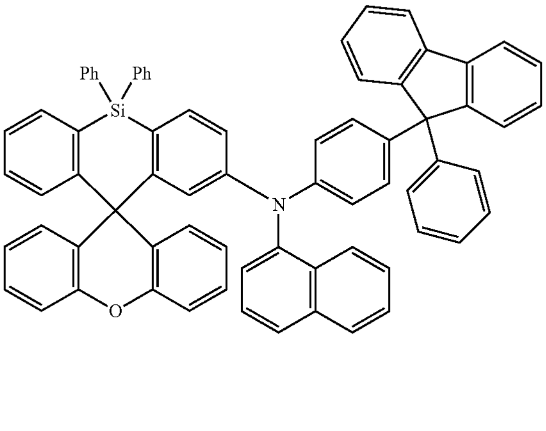
-continued
A205
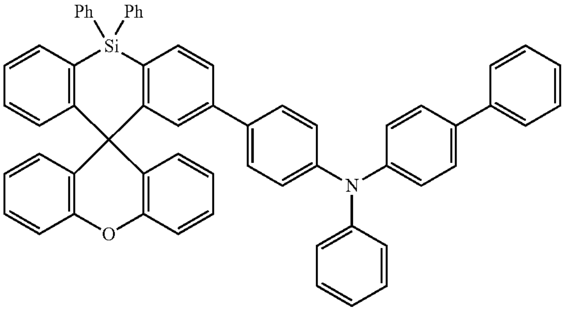
A206
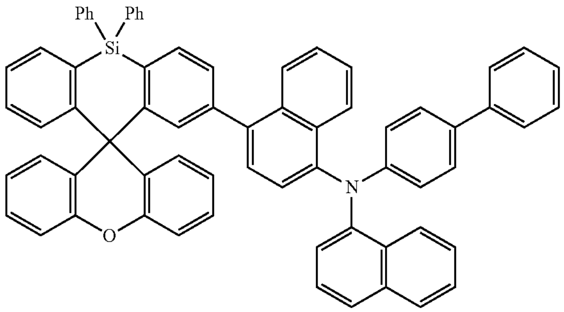
A207
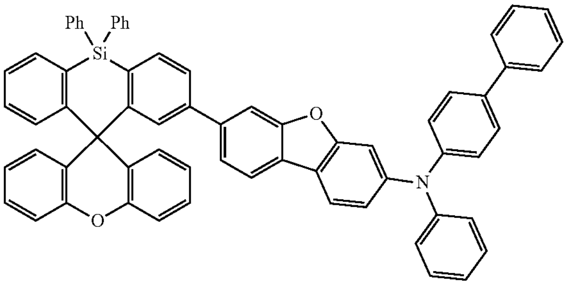
A208
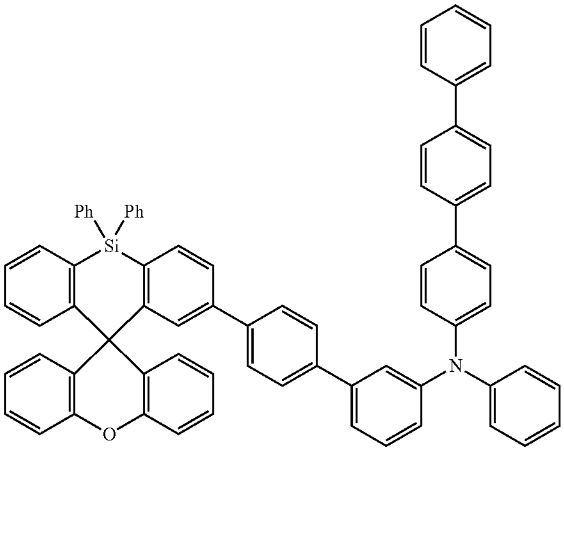

-continued
A209
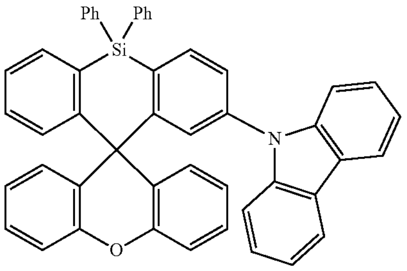
A210
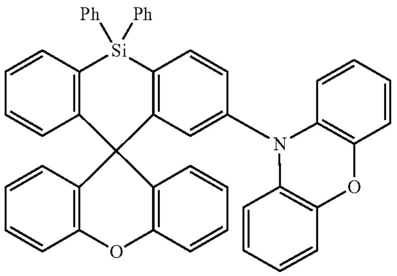
A211
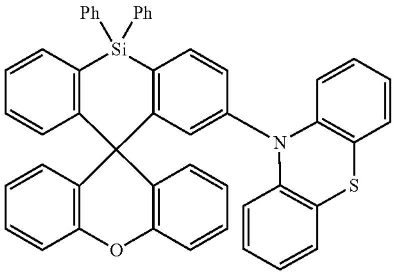
A212
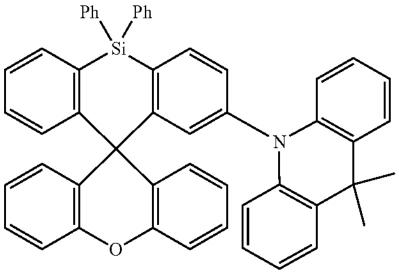
A213
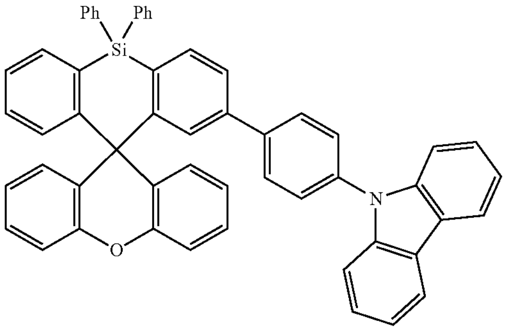
-continued
A214
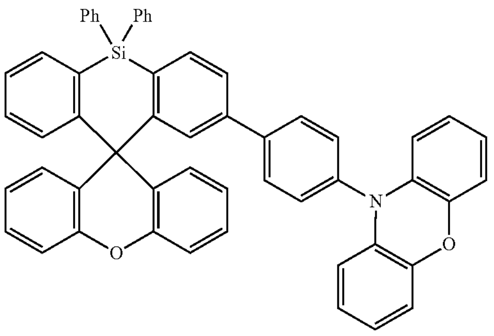
A215
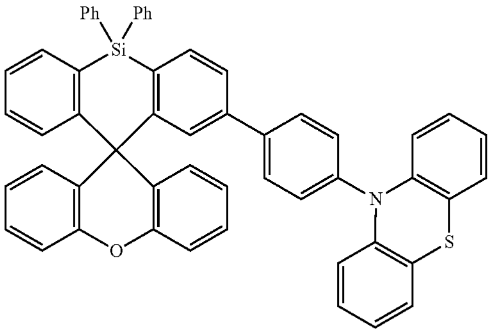
A216
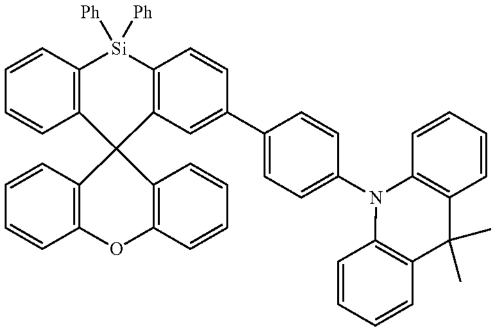
A217
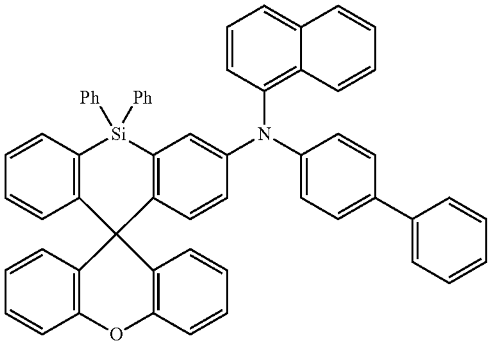

-continued
A218
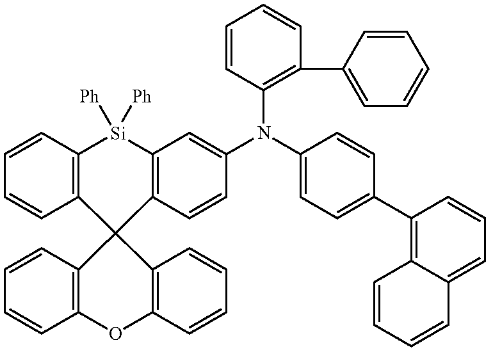
A219
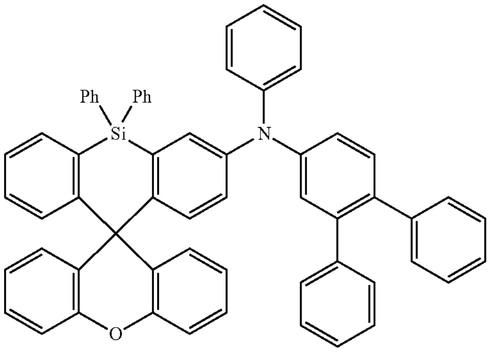
A220
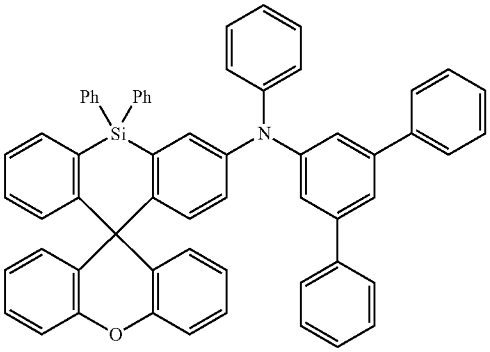
A221
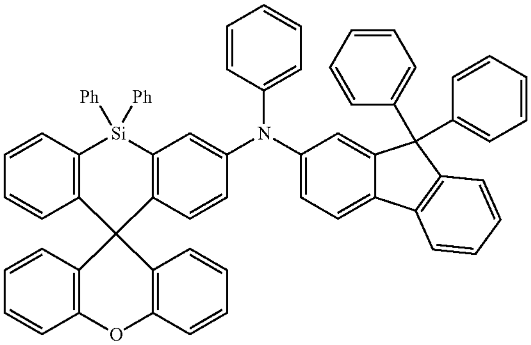
-continued
A222
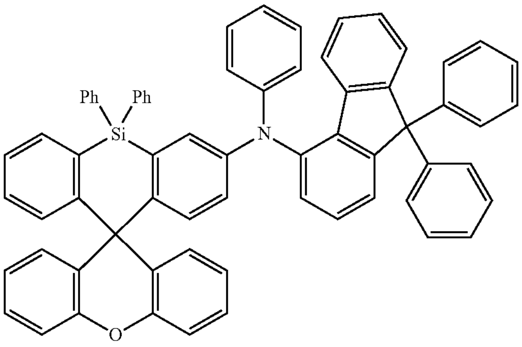
A223
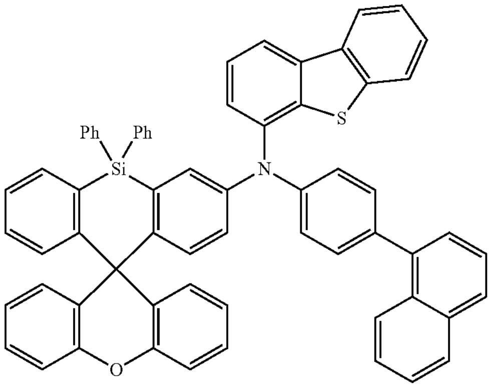
A224
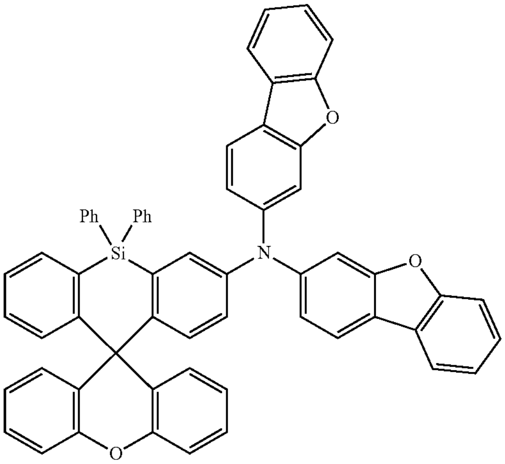

A225
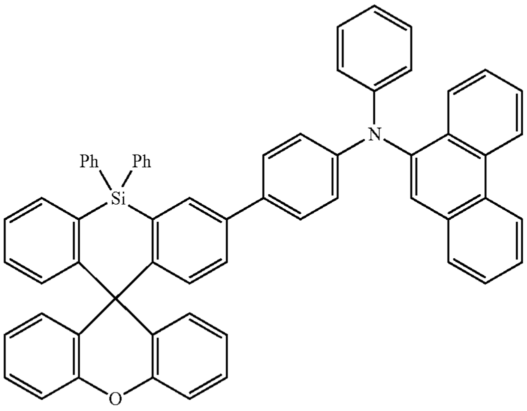
A226
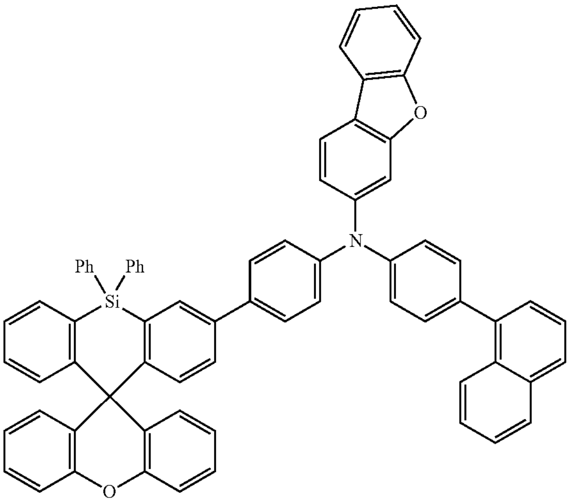
A227
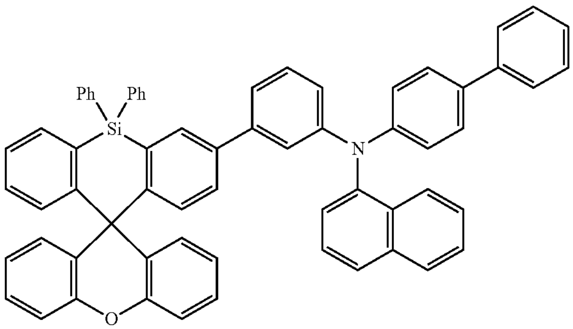
A228
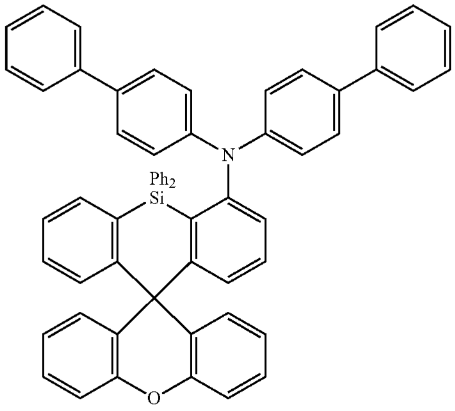
A229
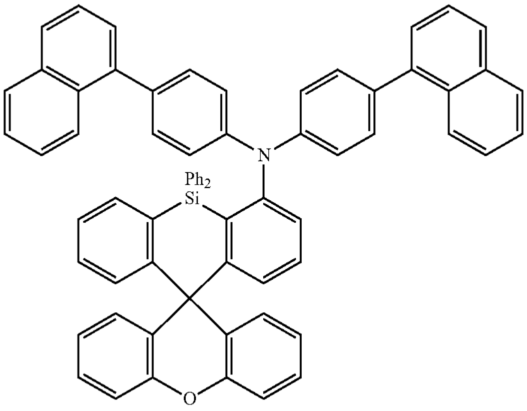
A230
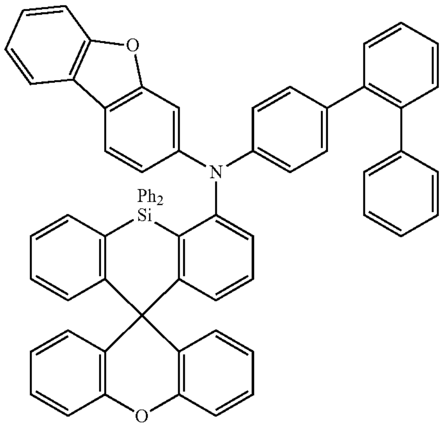

-continued
A231
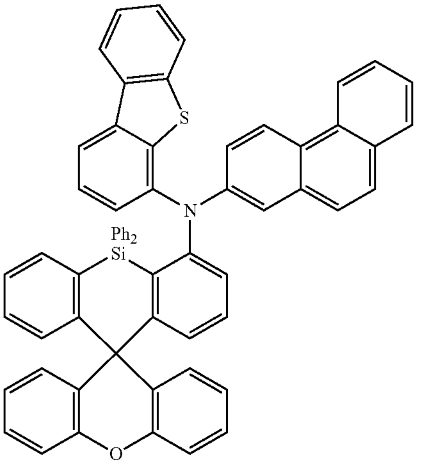
A232
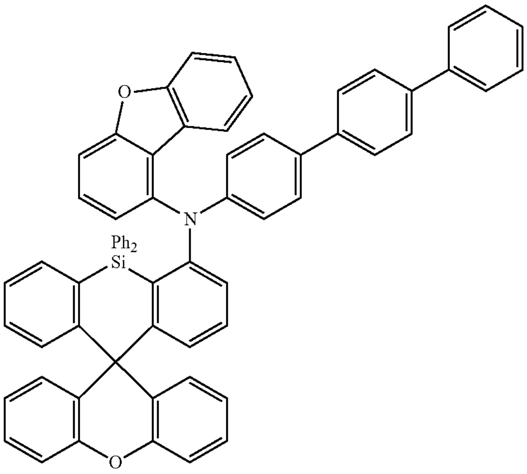
A233
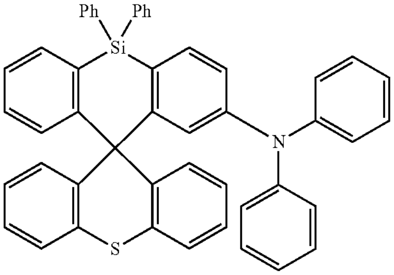
A234
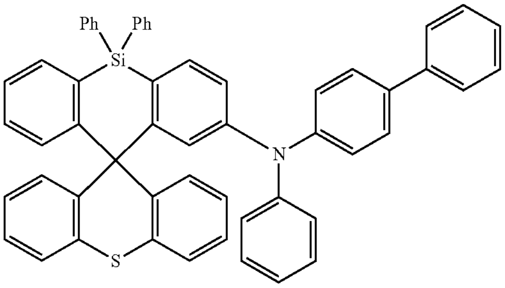
-continued
A235
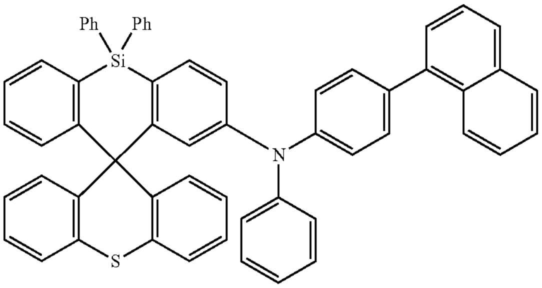
A236
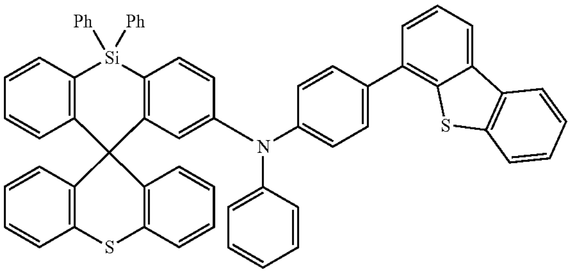
A237
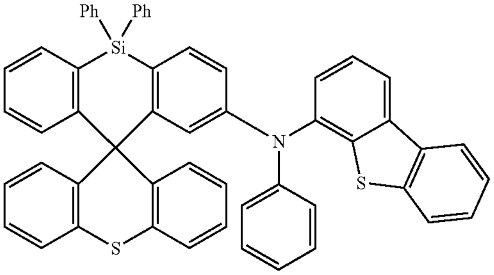
A238
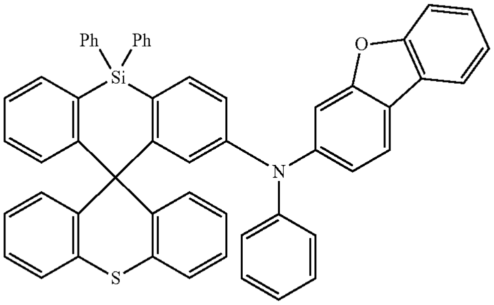
A239
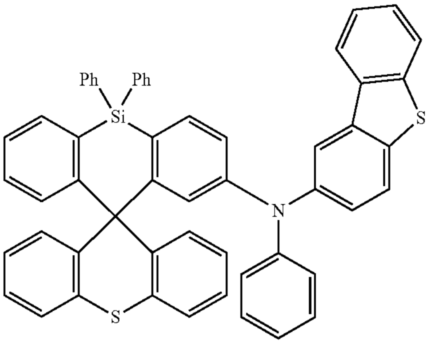

-continued
A240
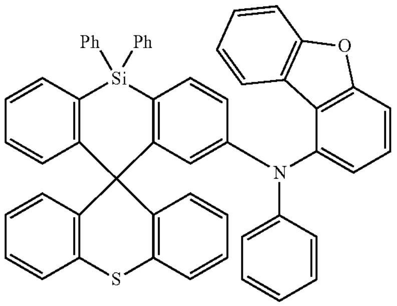
A241
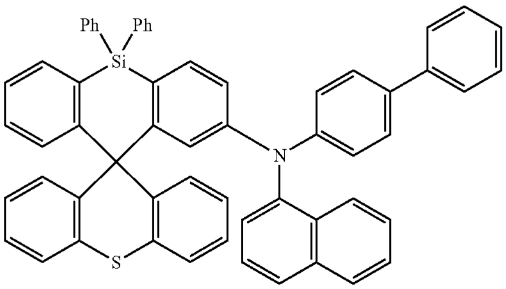
A242
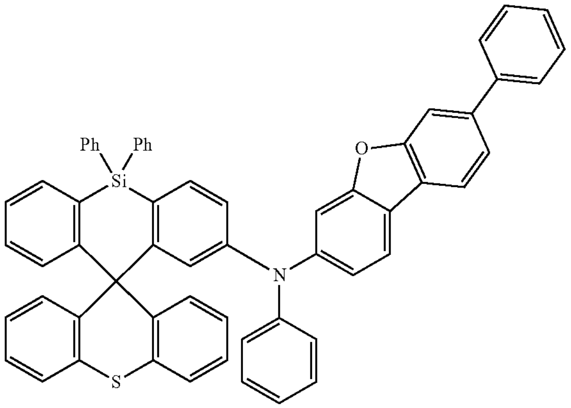
A243
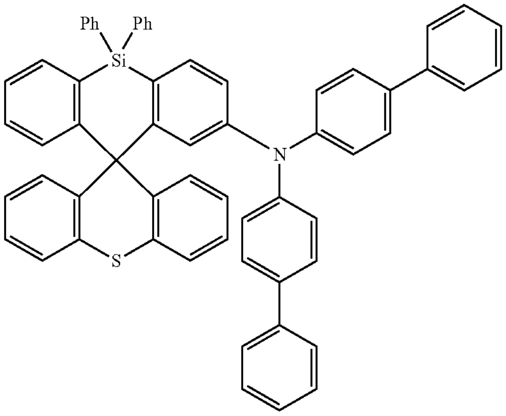
-continued
A244
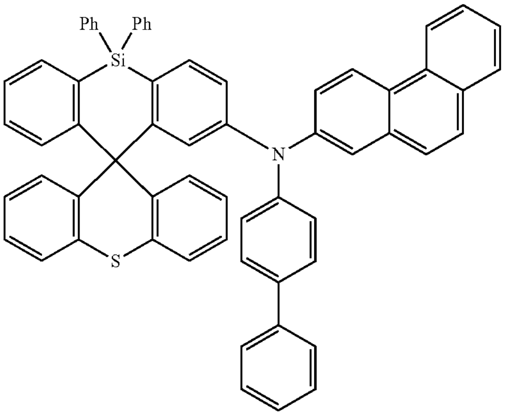
A245
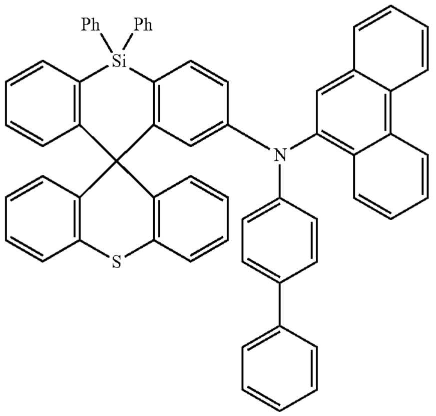
A246
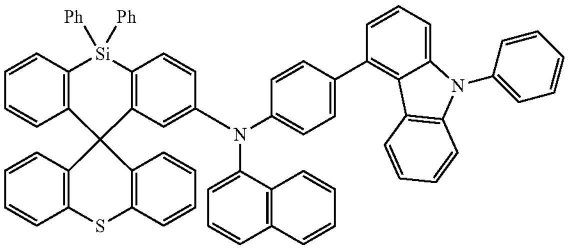
A247
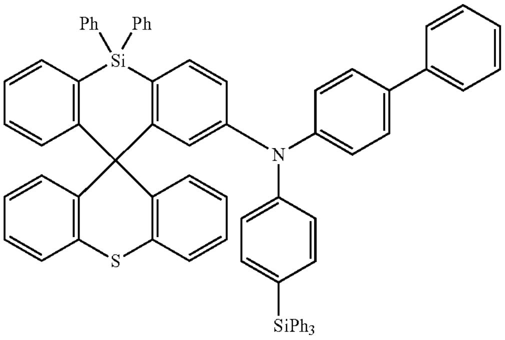

A248
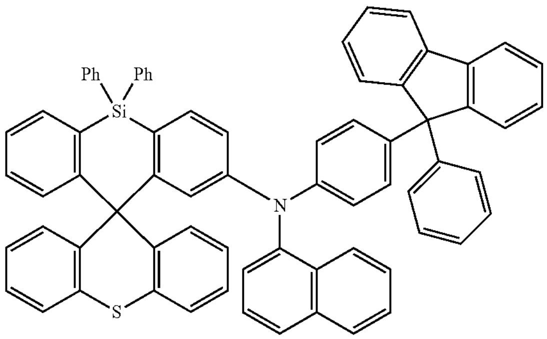
A249
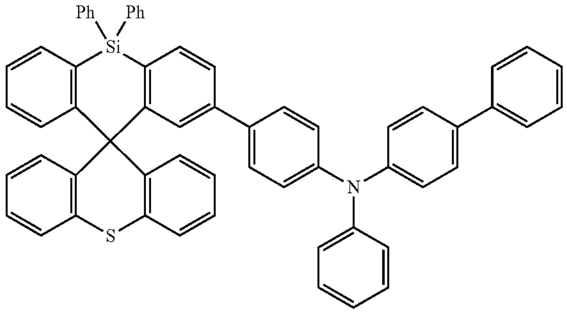
A250
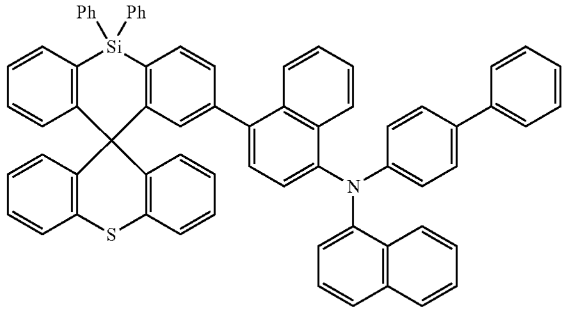
A251
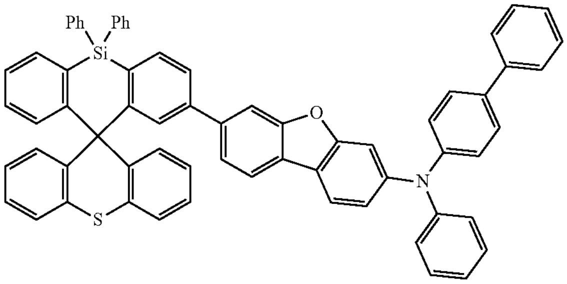
A252
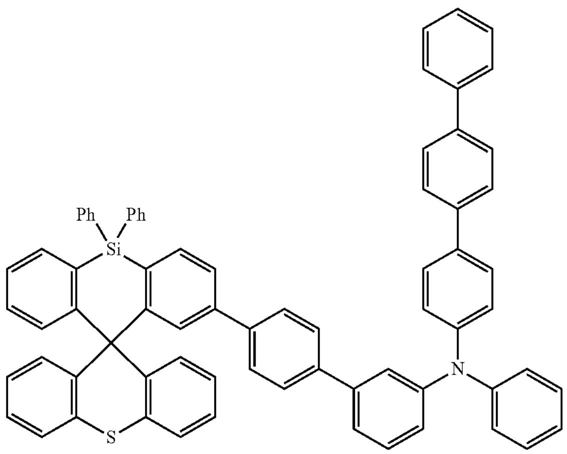
A253
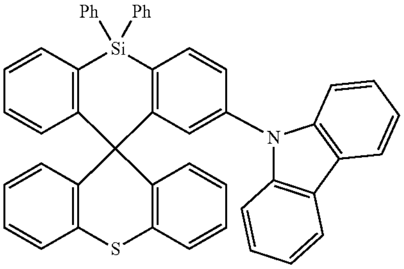
A254
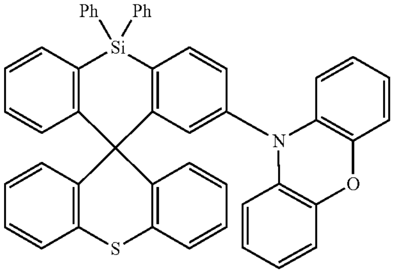
A255
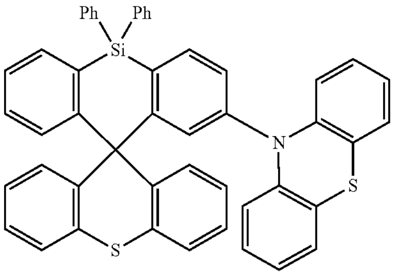
A256
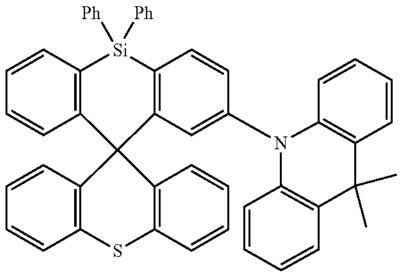

-continued
A257
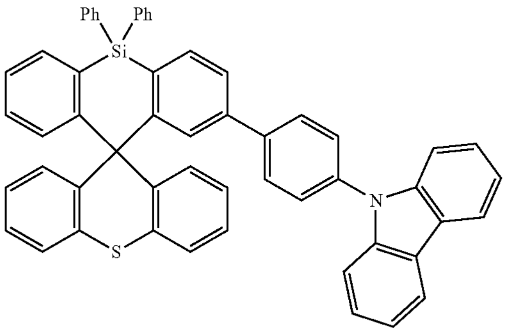
A258
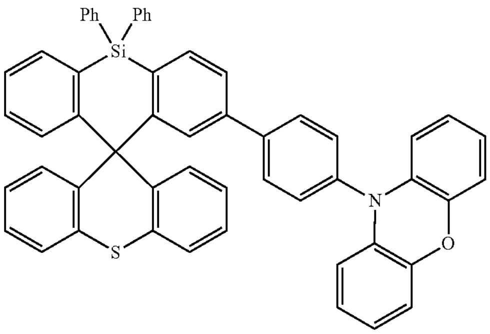
A259
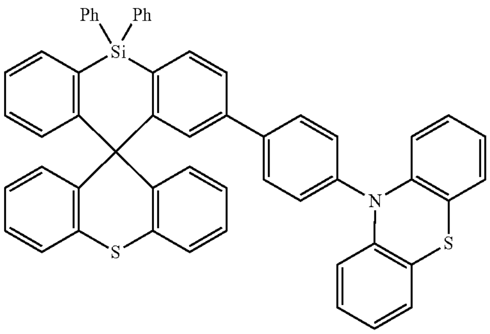
A260
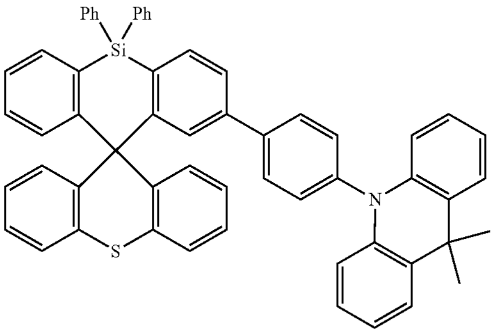
-continued
A261
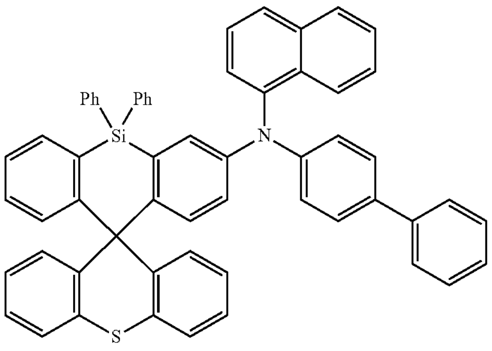
A262
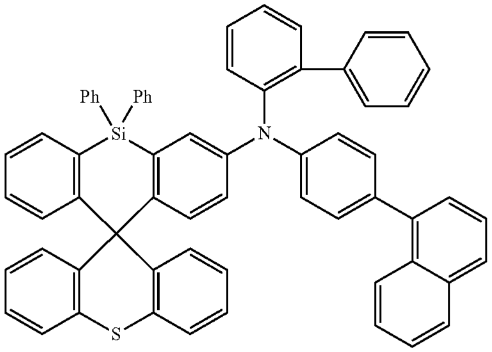
A263
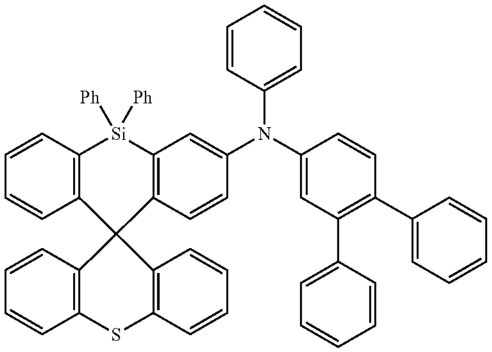
A264
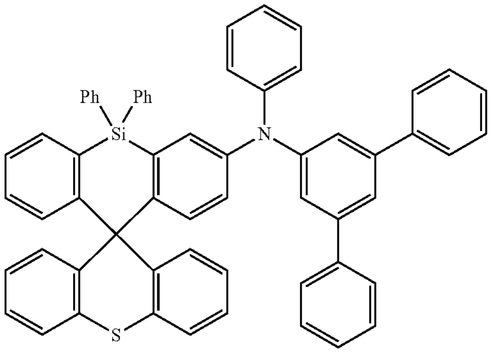

A265
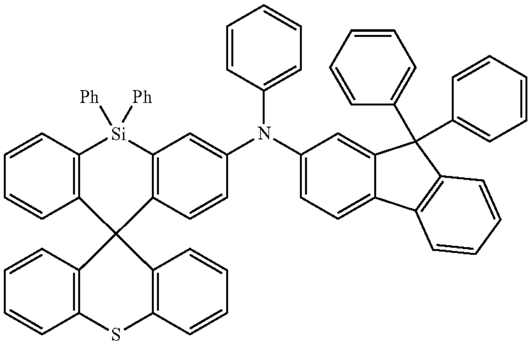
A266
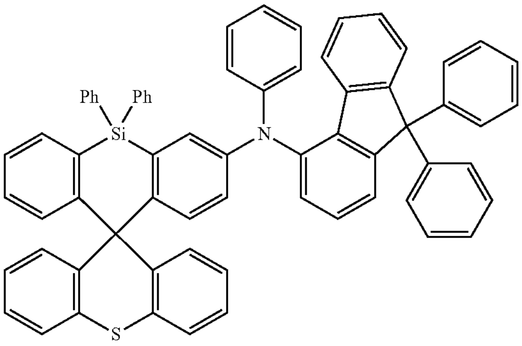
A267
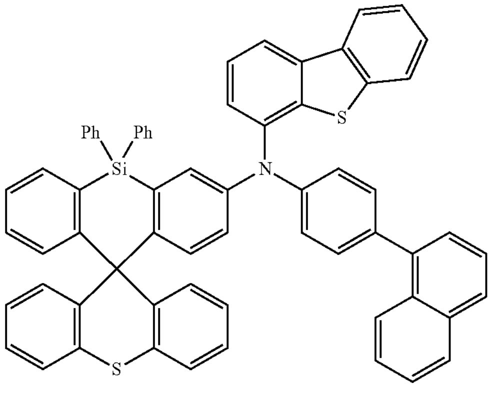
A268
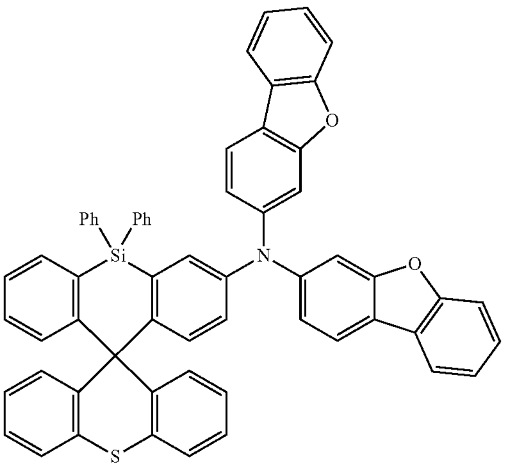
A269
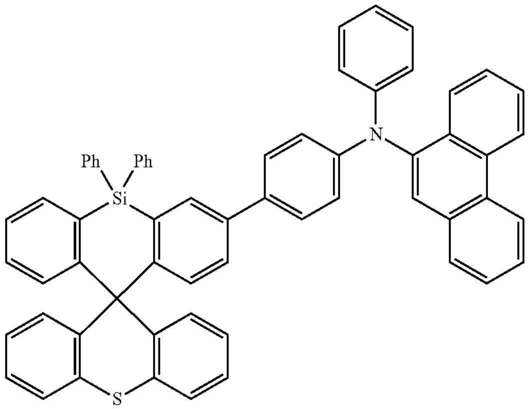
A270
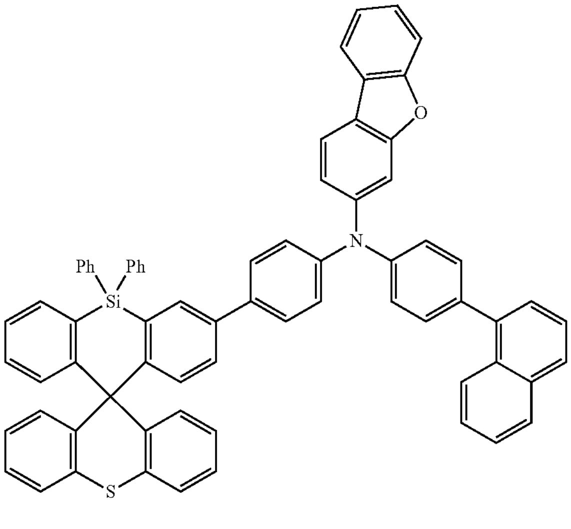
A271
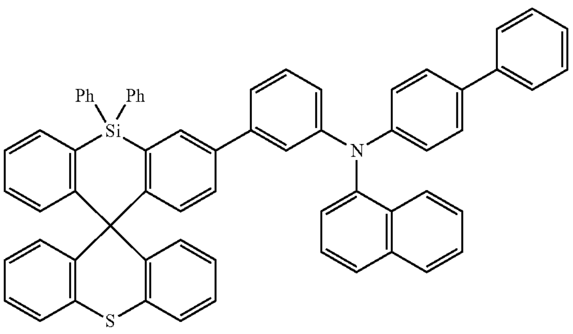

-continued
A272
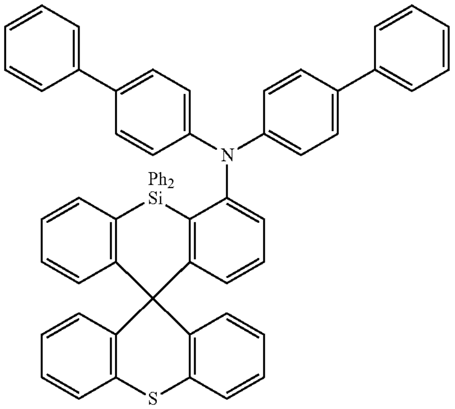
A273
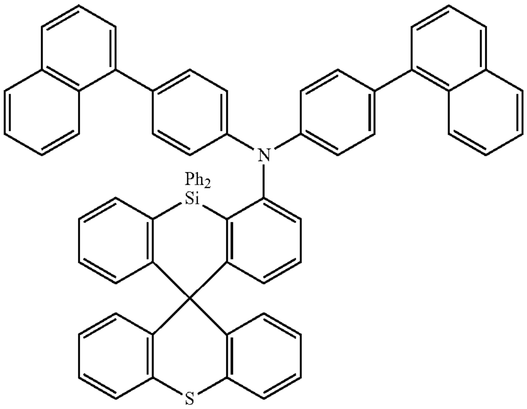
A274
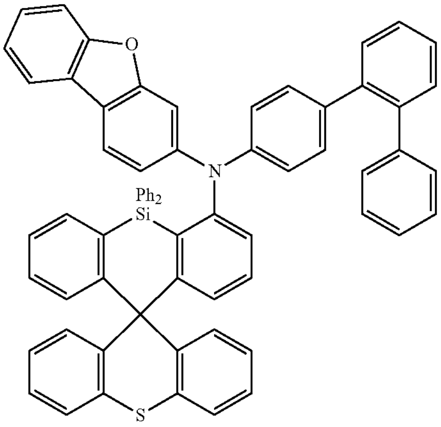
-continued
A275
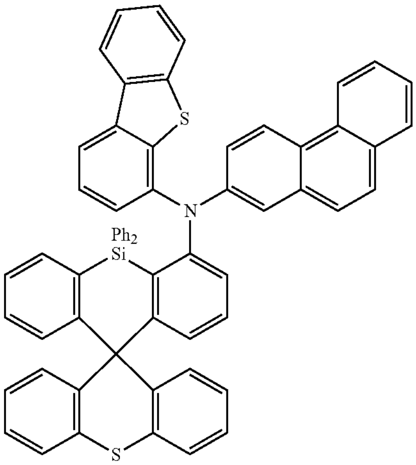
A276
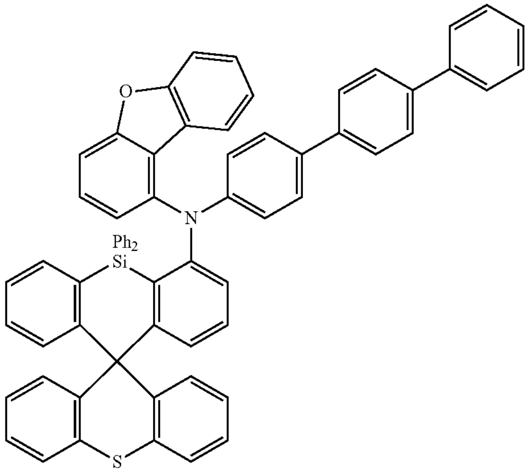
A277
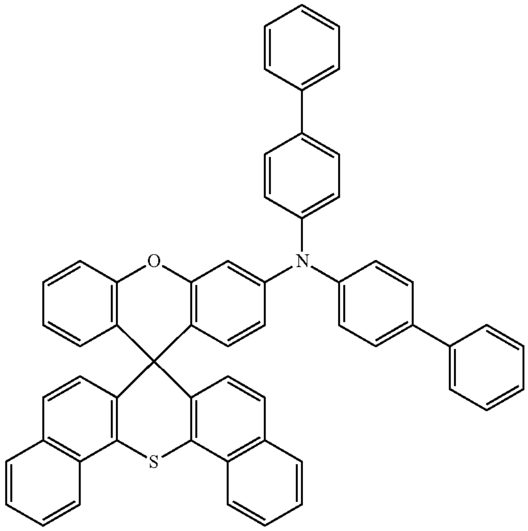

-continued
A278
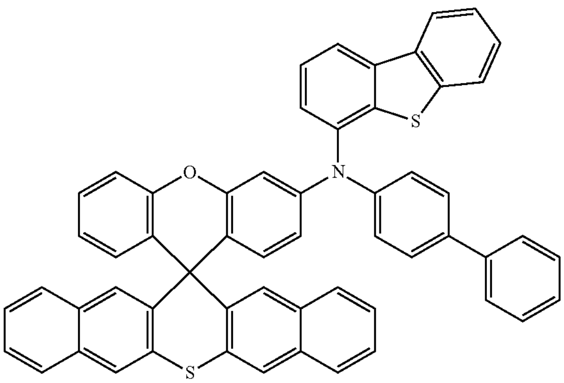
A279
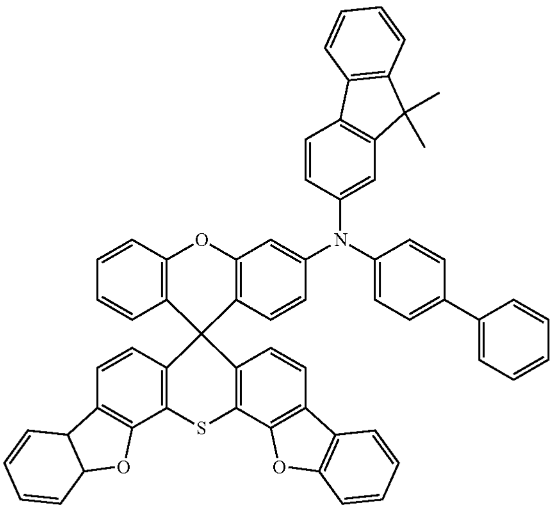
A280
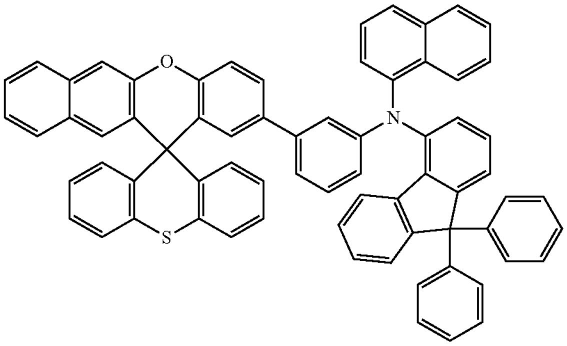
[Compound Group 2]
B1
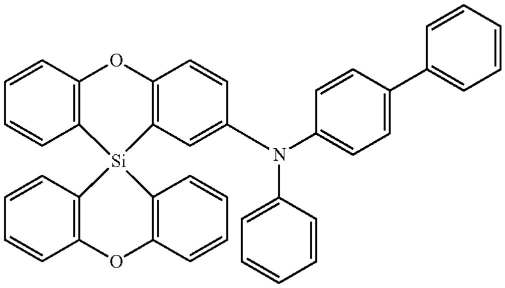
-continued
B2
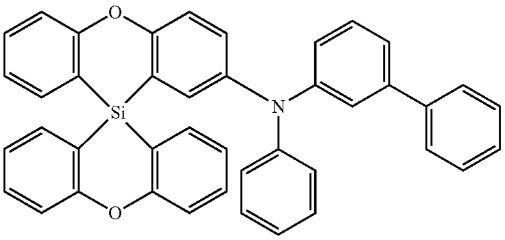
B3
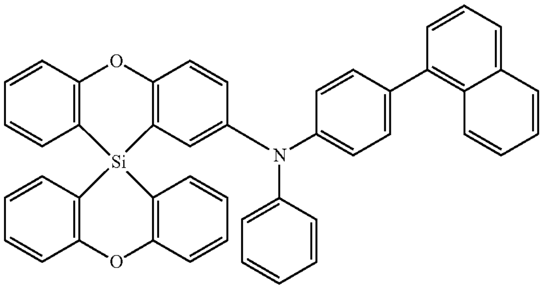
B4
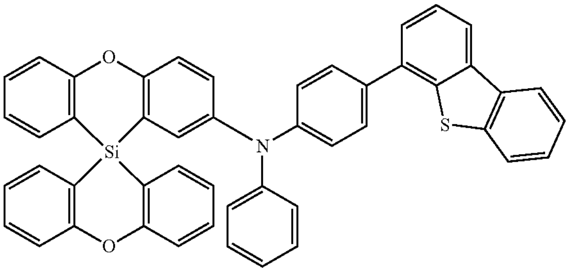
B5
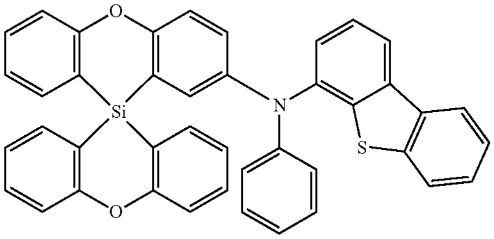
B6
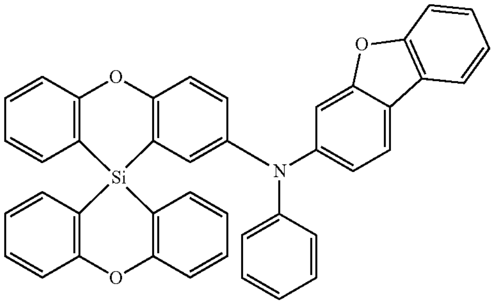

-continued
B7
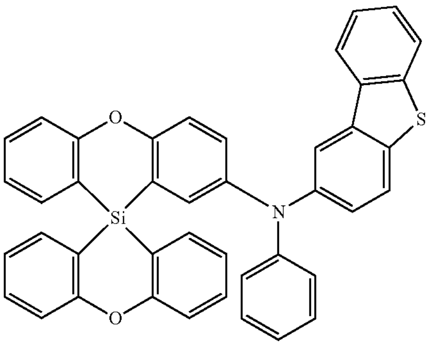
B8
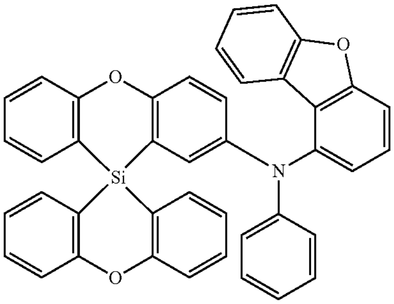
B9
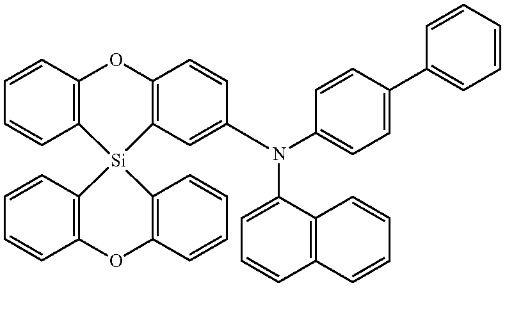
B10
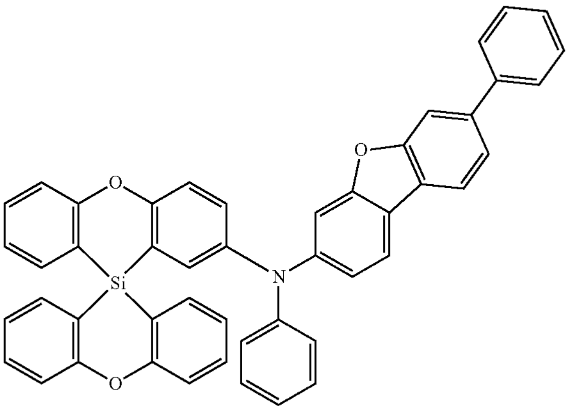
-continued
B11
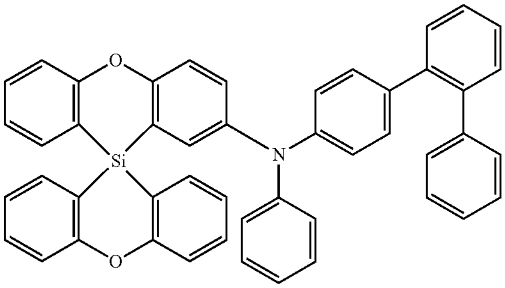
B12
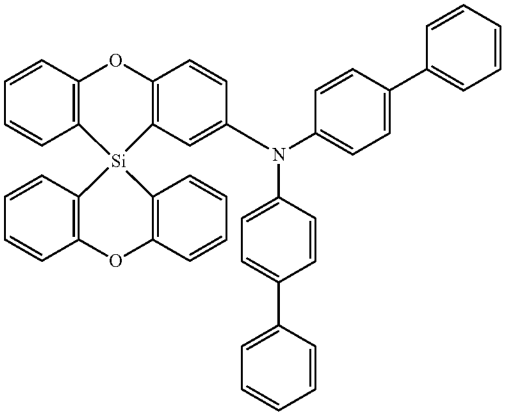
B13
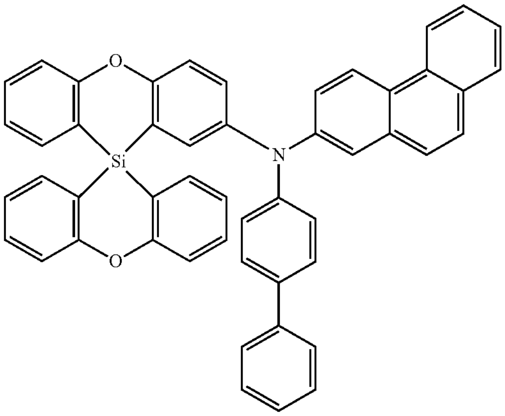
B14
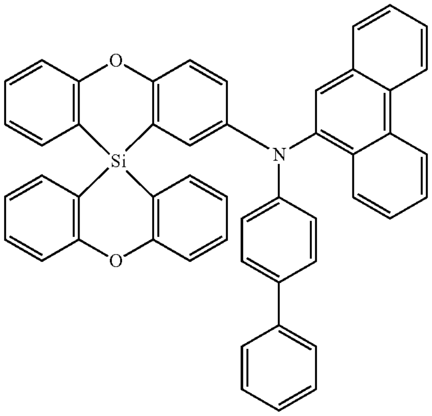

-continued
B15
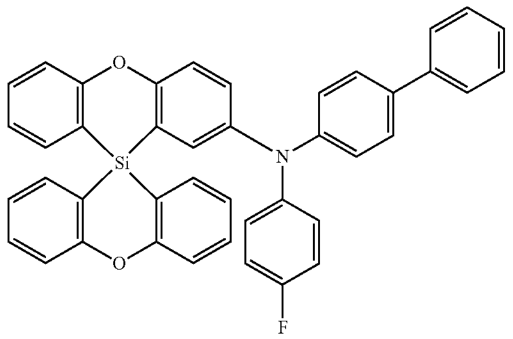
B16
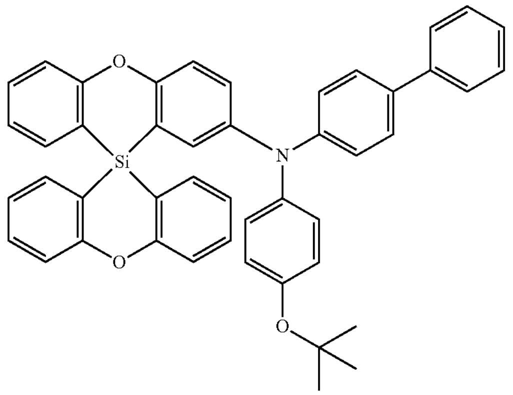
B17
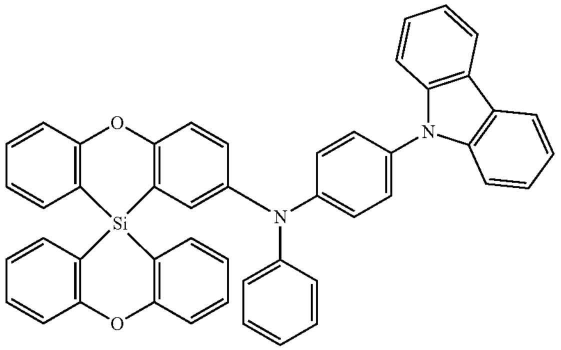
B18
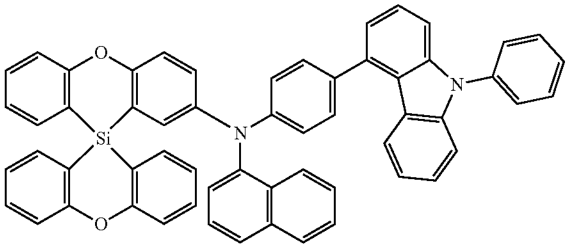
-continued
B19
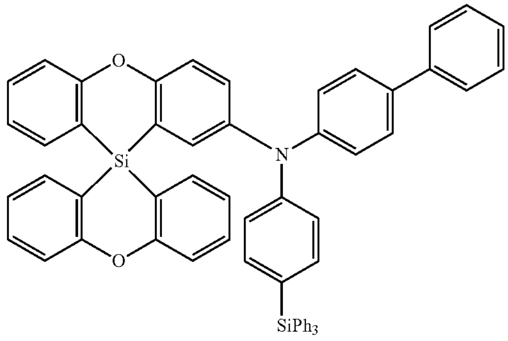
B20
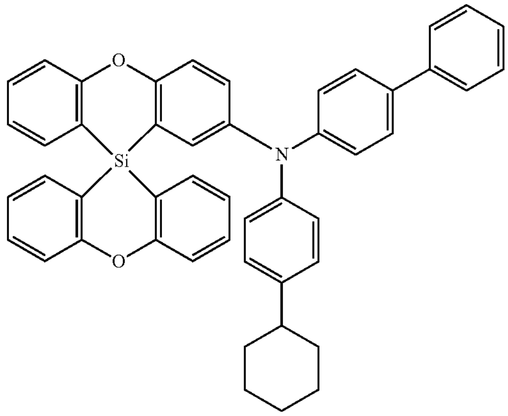
B21
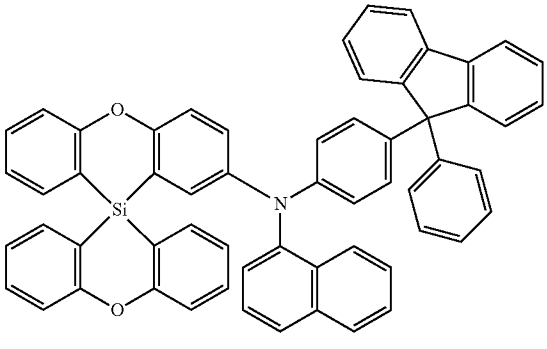
B22
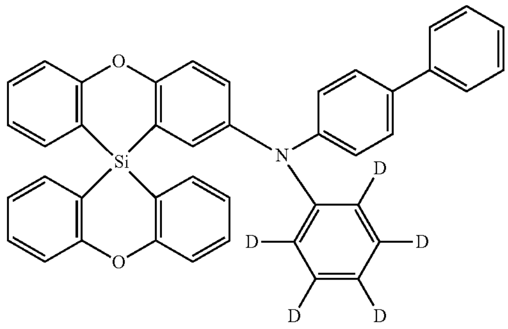

-continued
B23
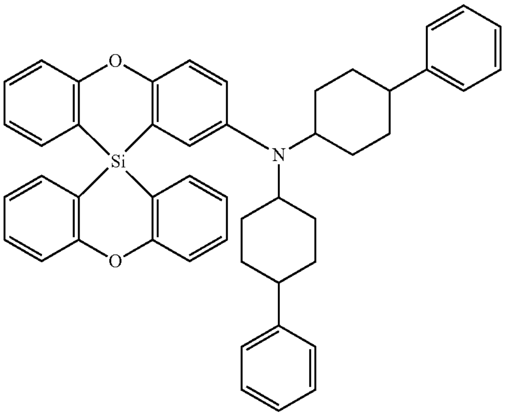
B24
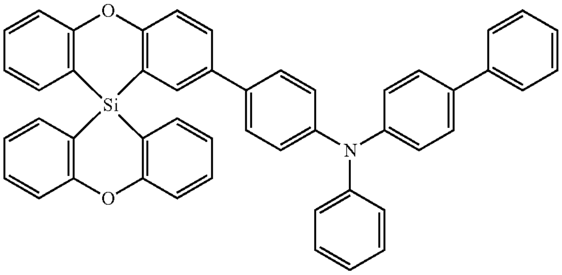
B25
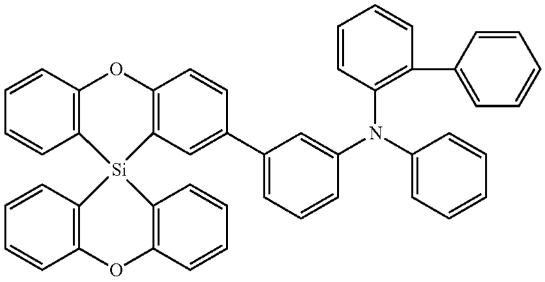
B26
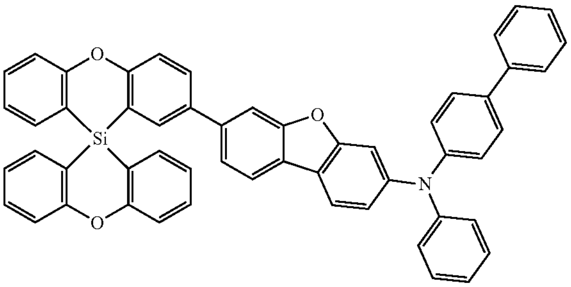
-continued
B27
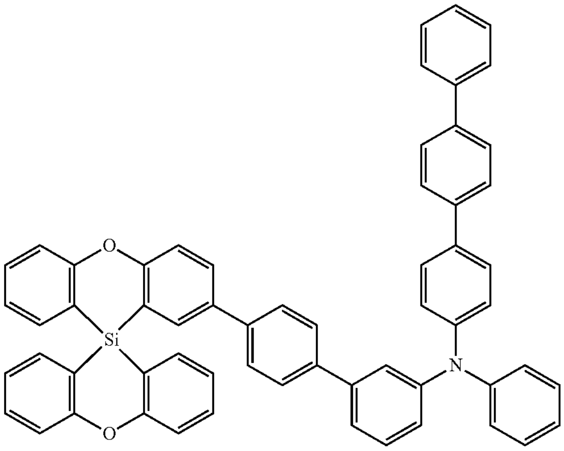
B28
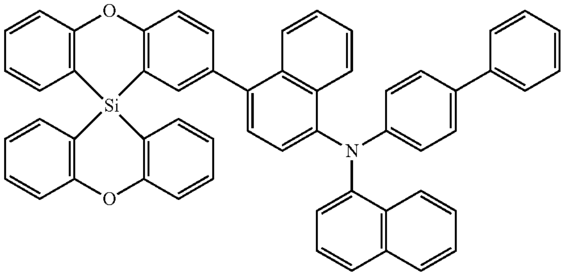
B29
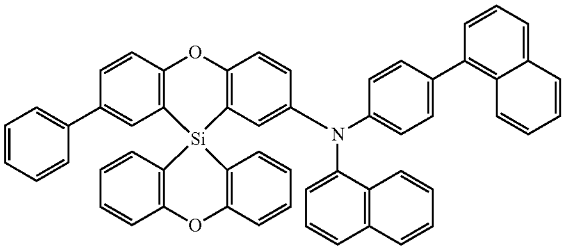
B30
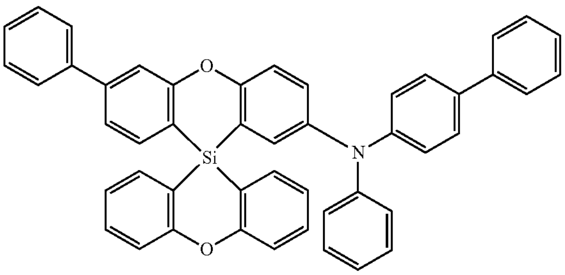

-continued
B31
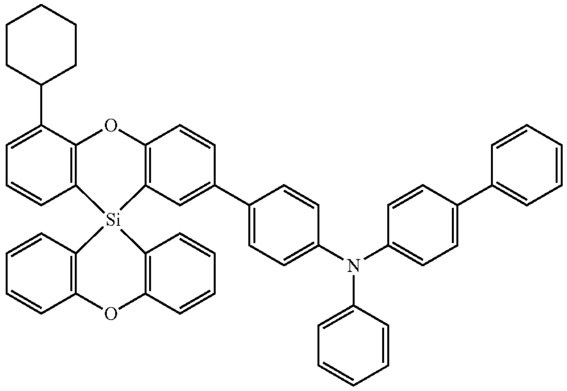
B32
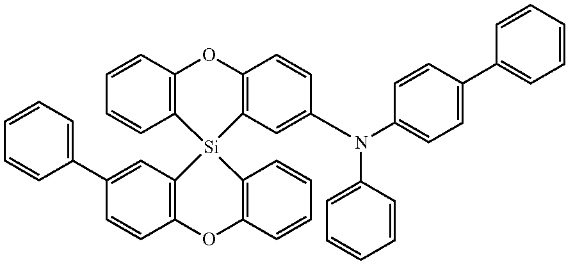
B33
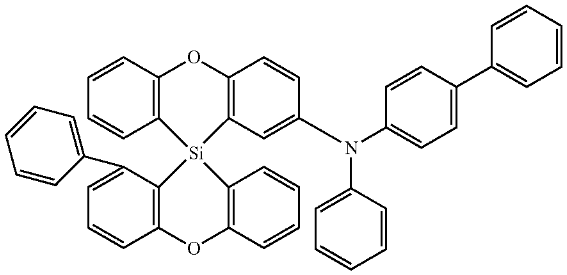
B34
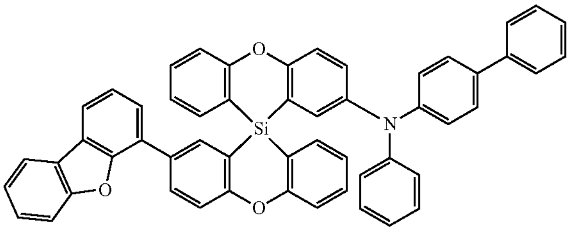
B35
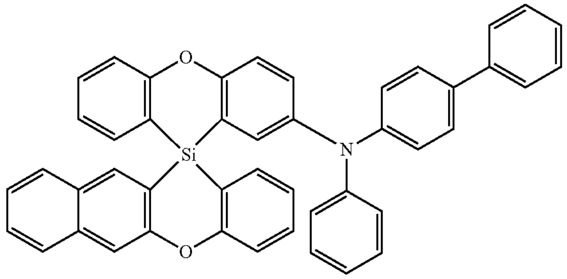
-continued
B36
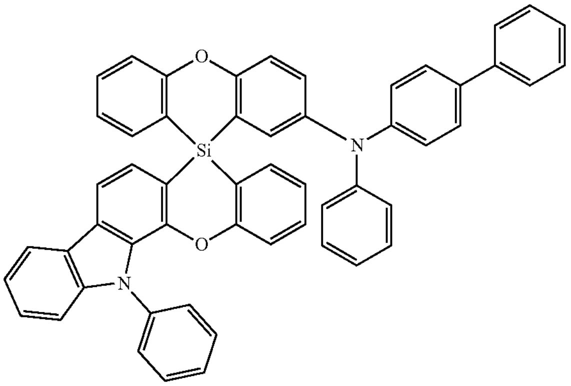
B37
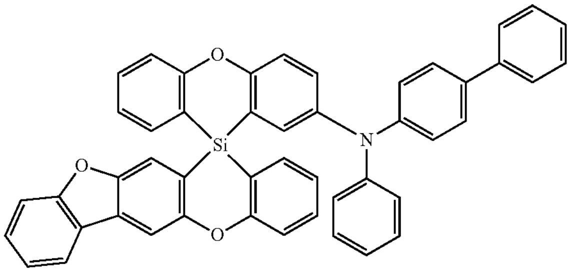
B38
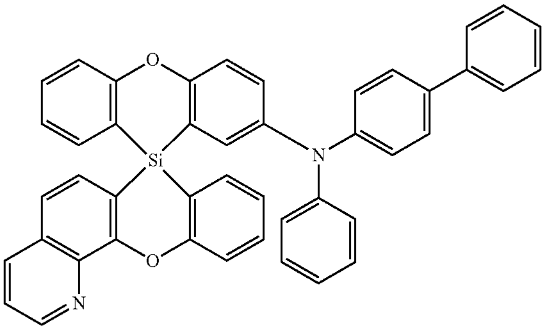
B39
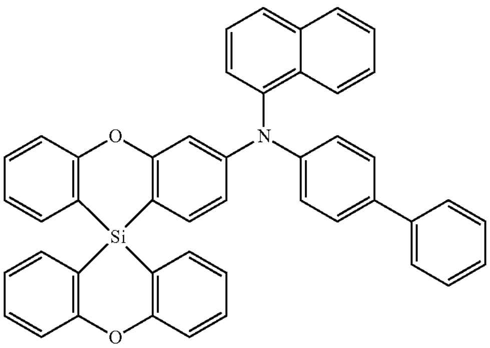

-continued
B40
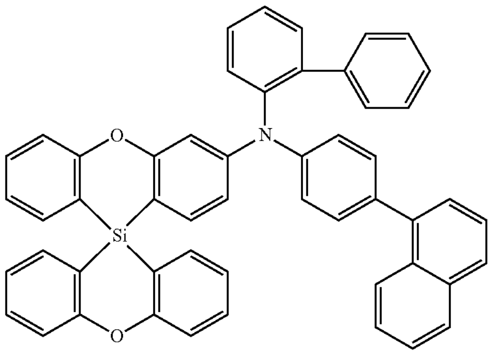
B41
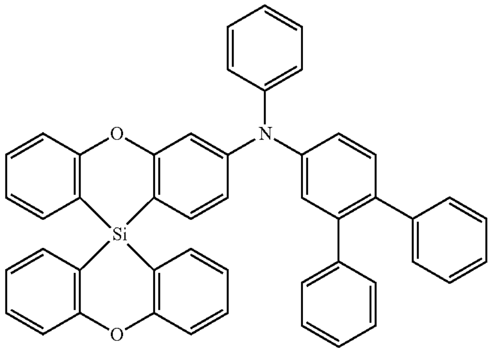
B42
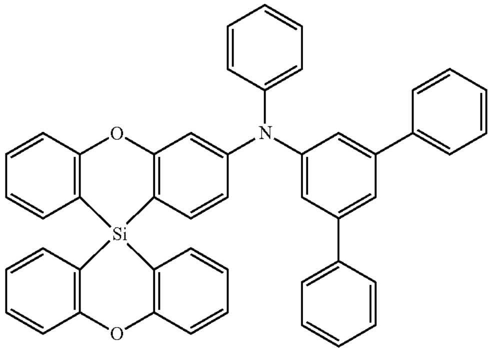
B43
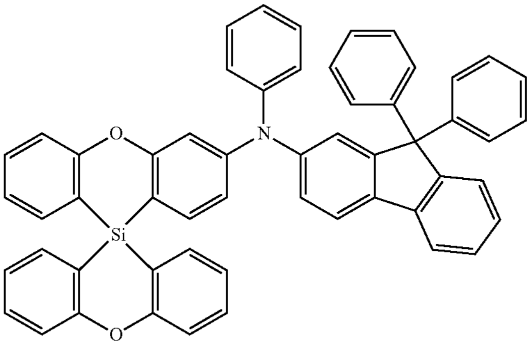
-continued
B44
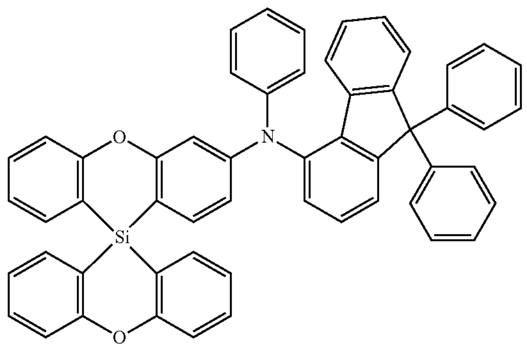
B45
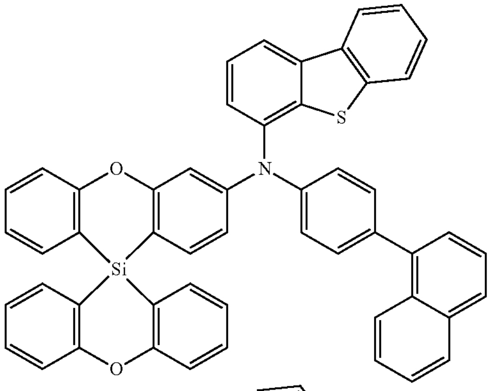
B46
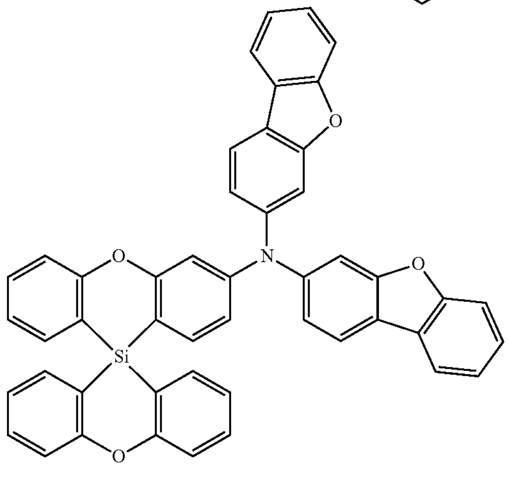
B47
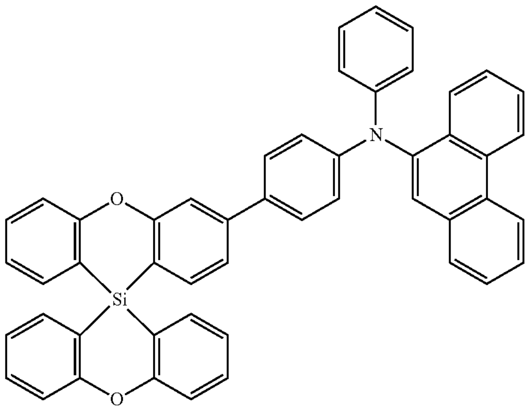

-continued
B48
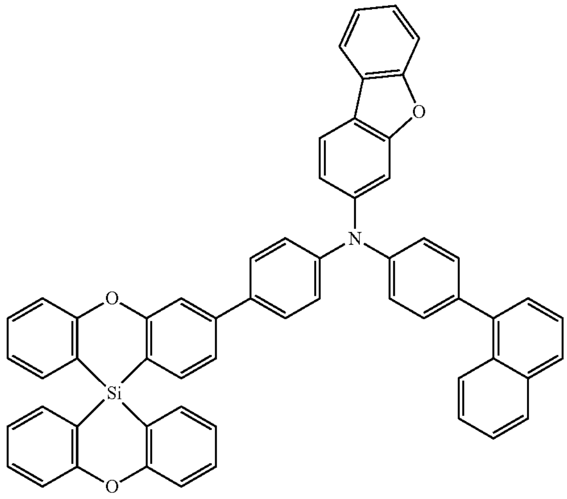
B49
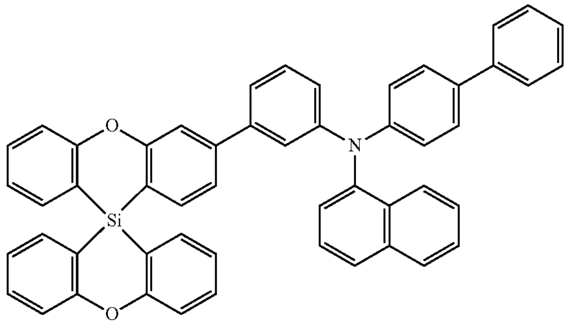
B50
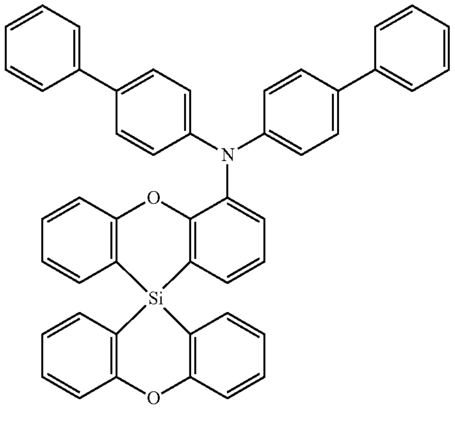
-continued
B51
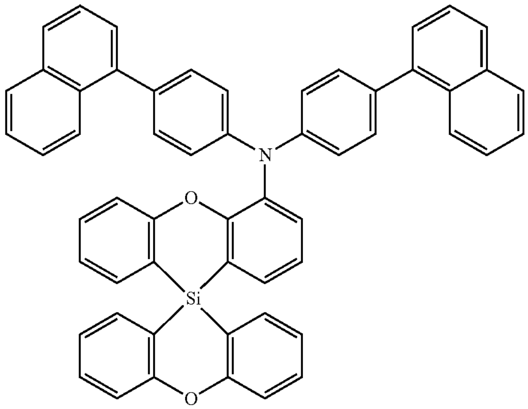
B52
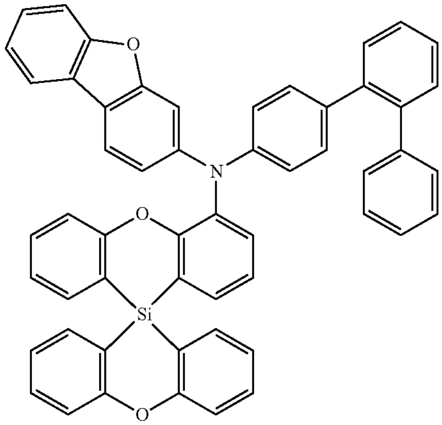
B53
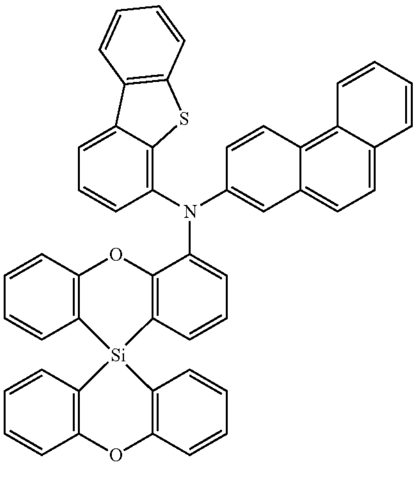

-continued
B54
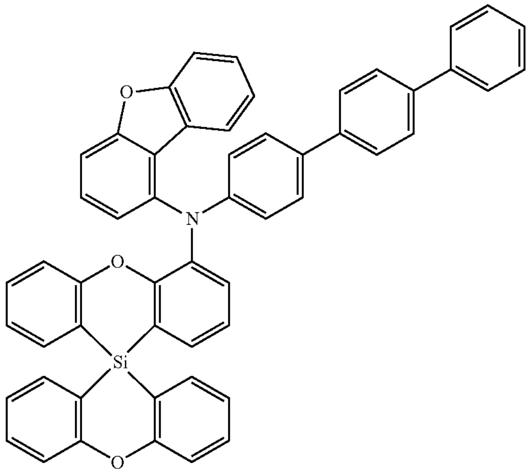
B55
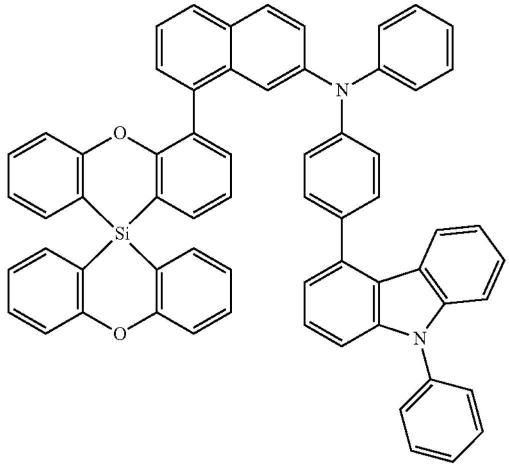
B56
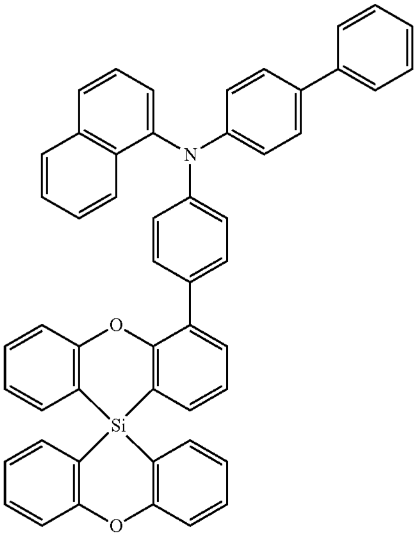
-continued
B57
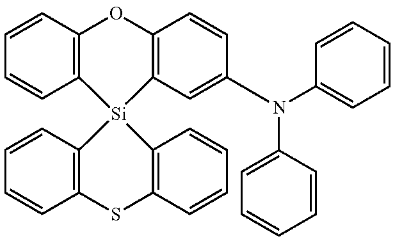
B58
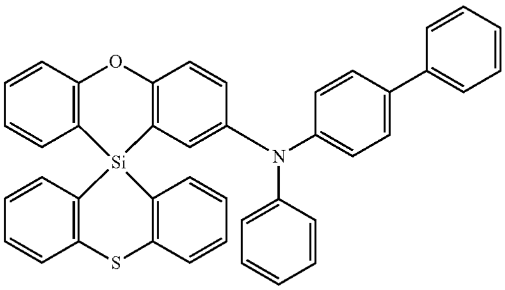
B59
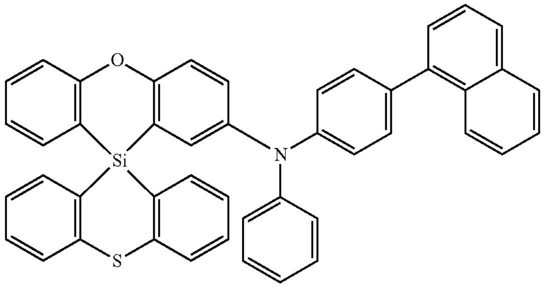
B60
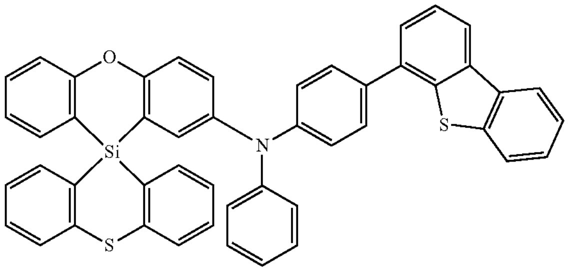
B61
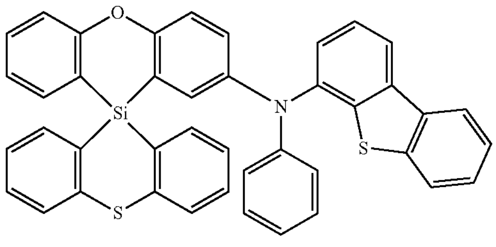

-continued
B62
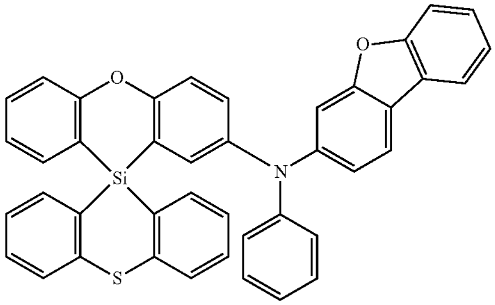
B63
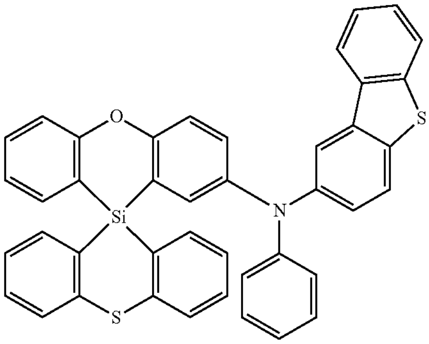
B64
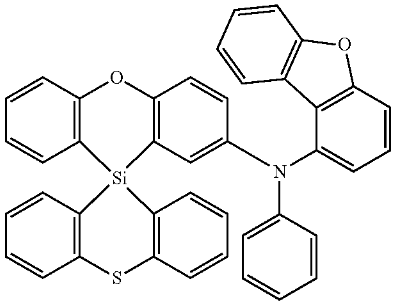
B65
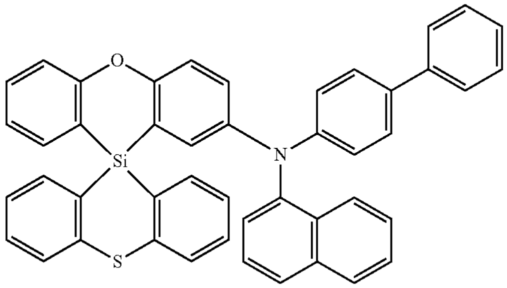
-continued
B66
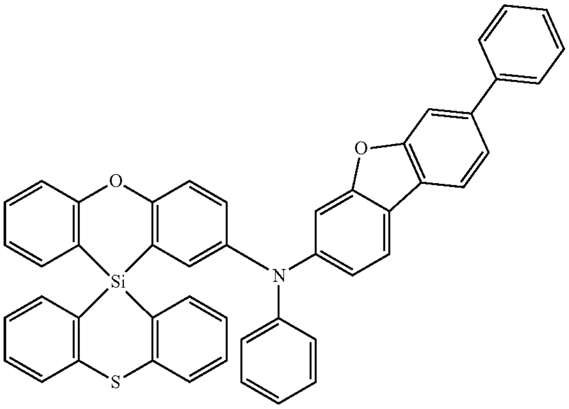
B67
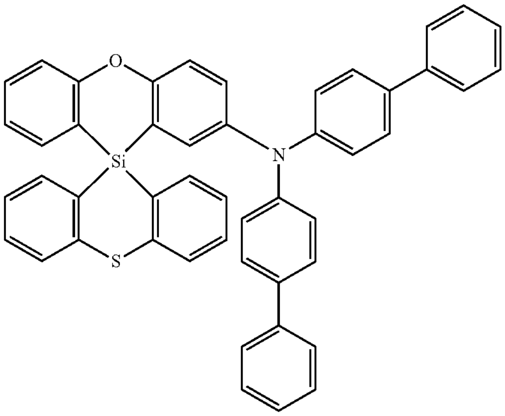
B68
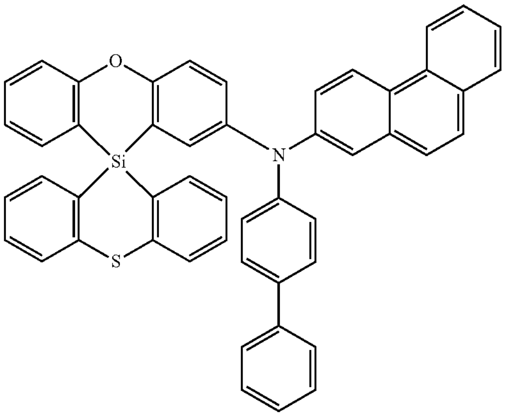

-continued
B69
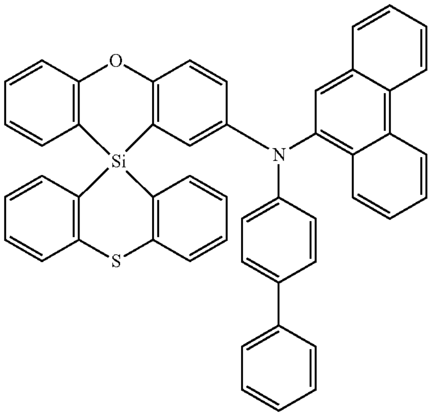
B70
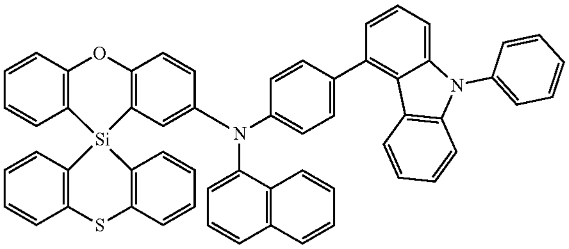
B71
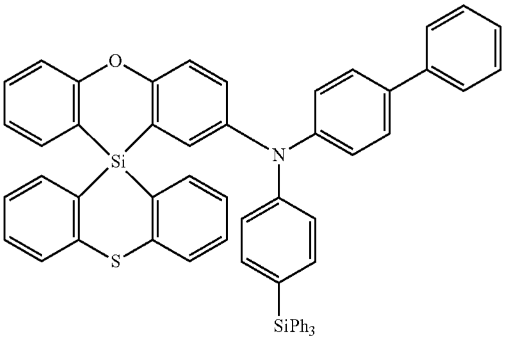
B72
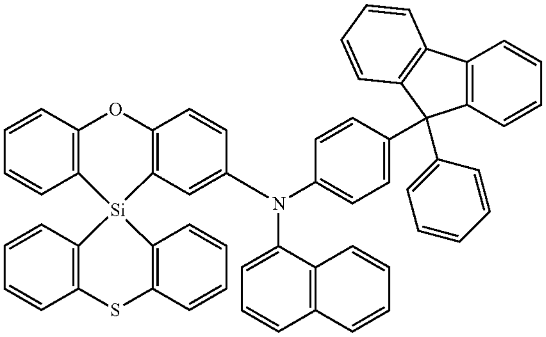
-continued
B73
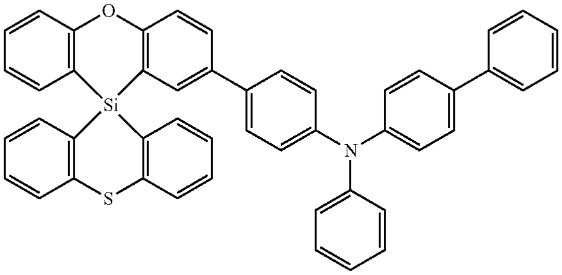
B74
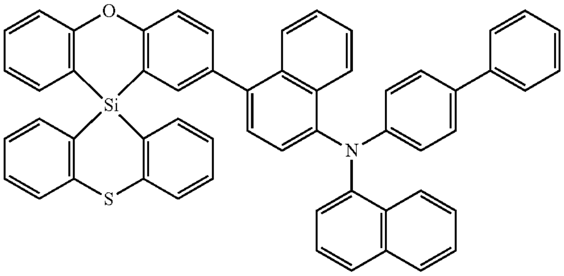
B75
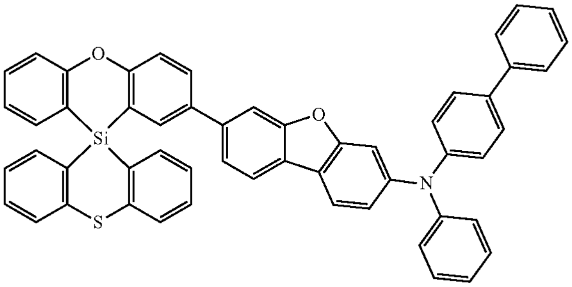
B76
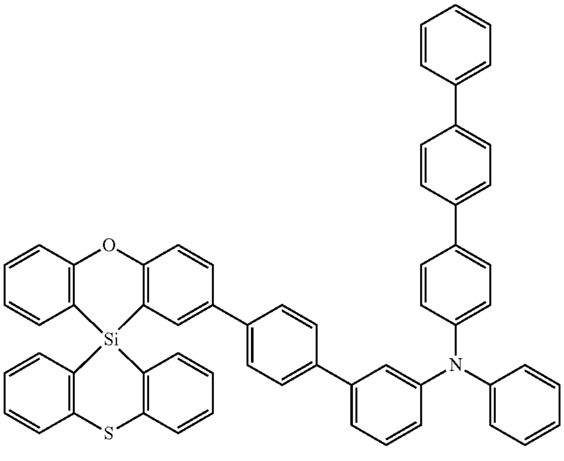
B77
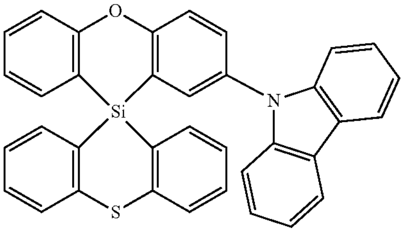

-continued
B78
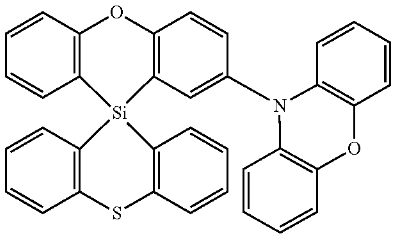
B79
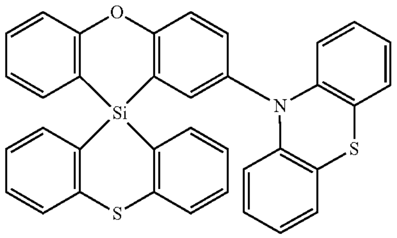
B80
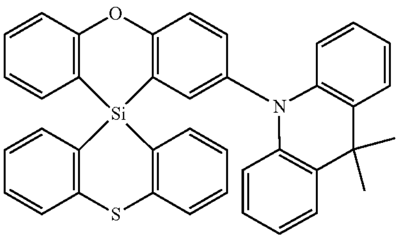
B81
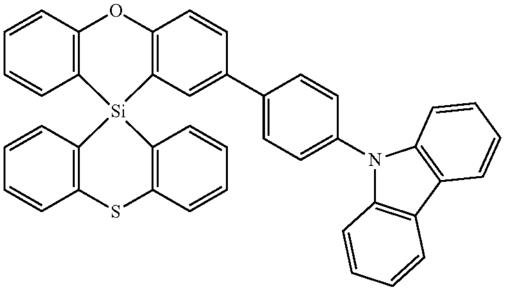
B82
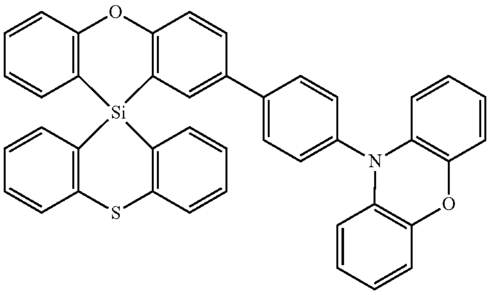
B83
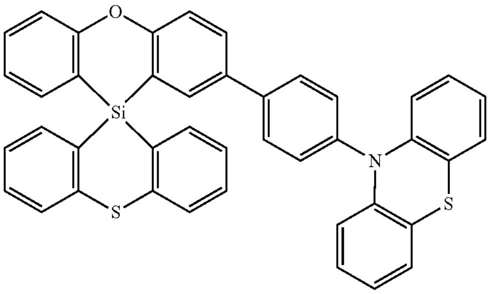
-continued
B84
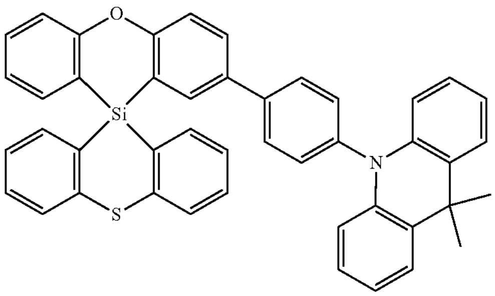
B85
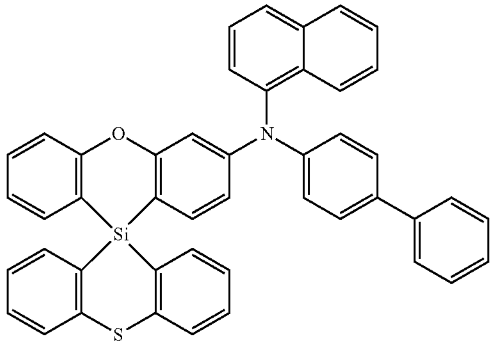
B86
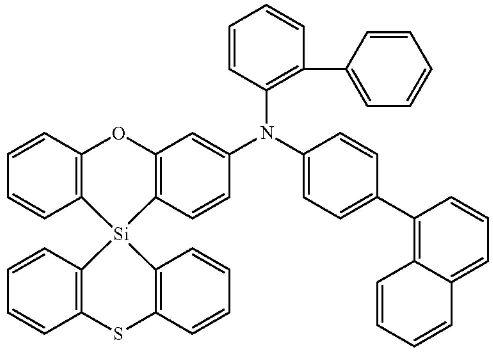
B87
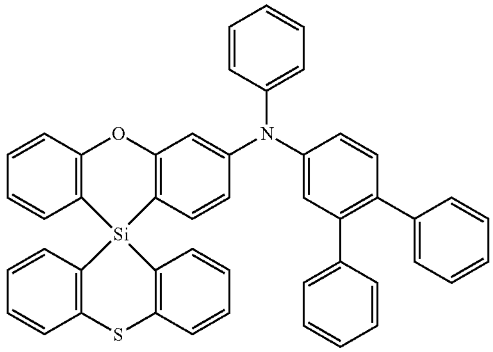

-continued
B88
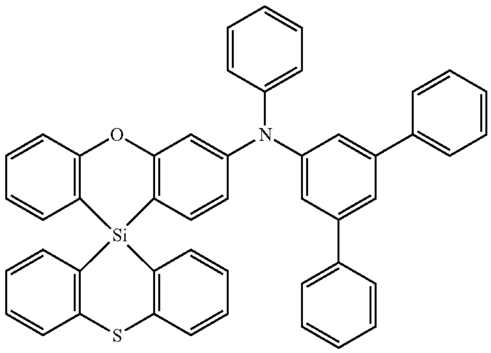
B89
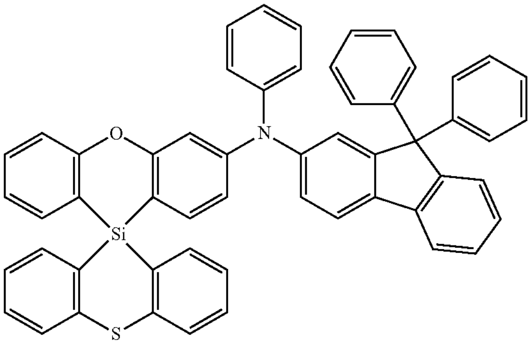
B90
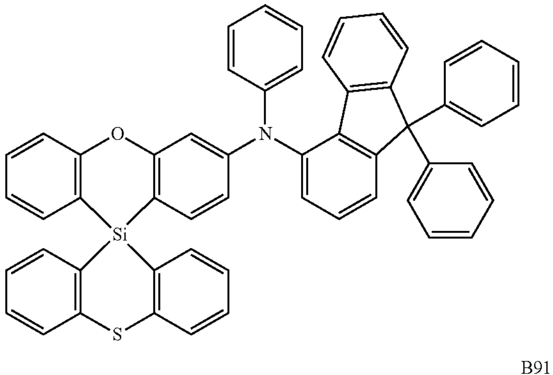
B91
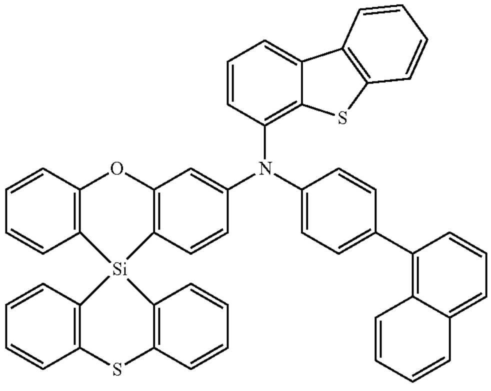
-continued
B92
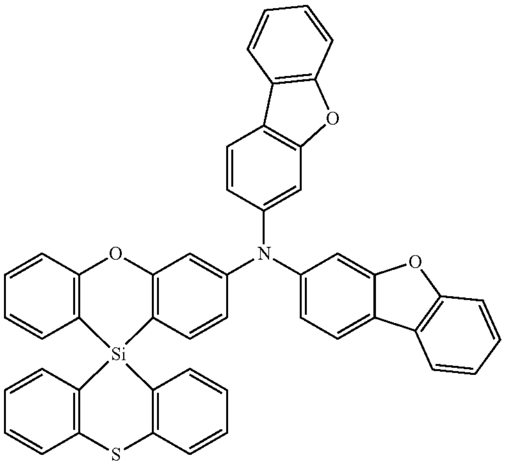
B93
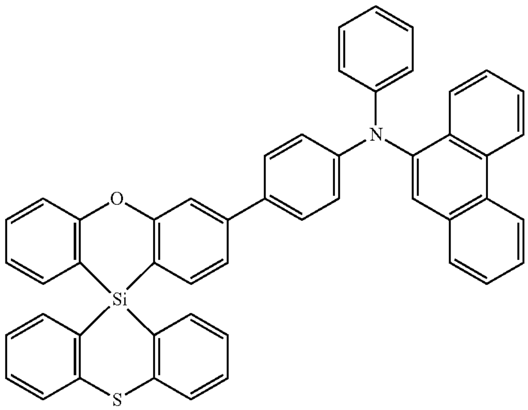
B94
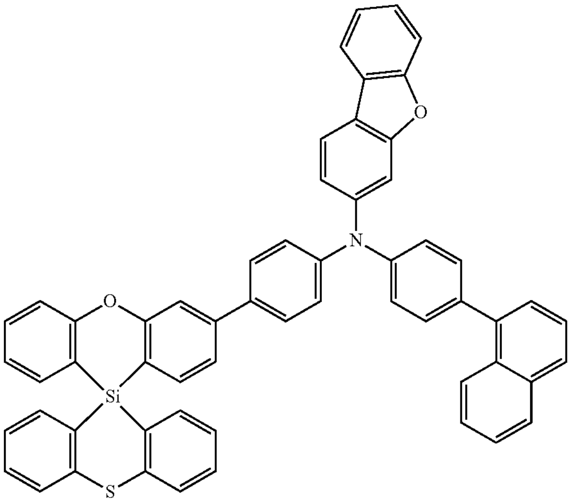

-continued
B95
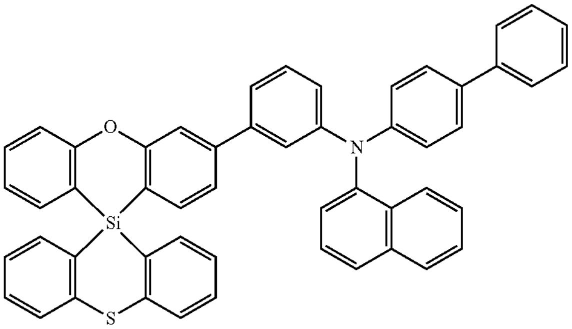
B96
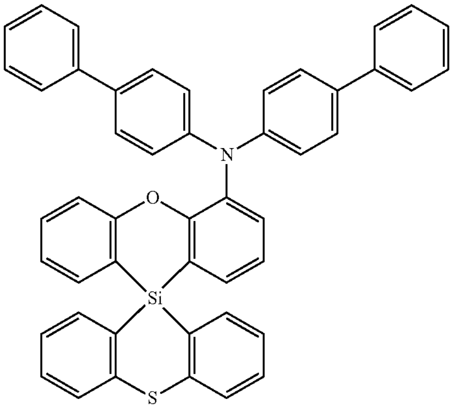
B97
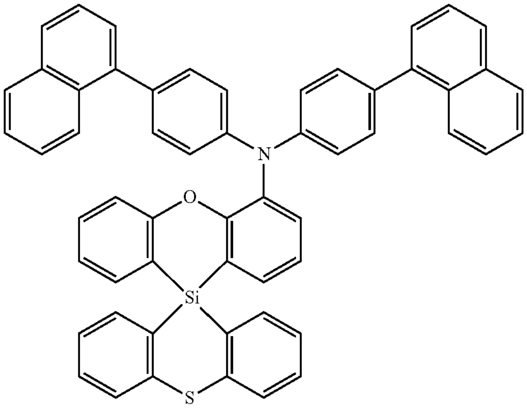
B98
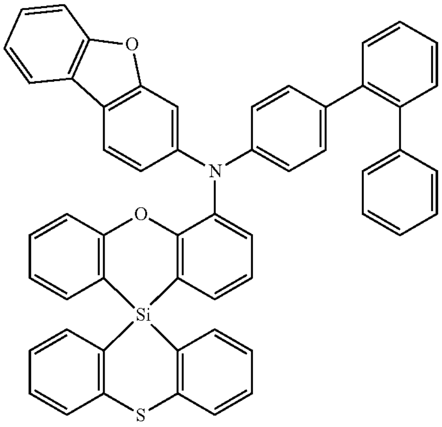
-continued
B99
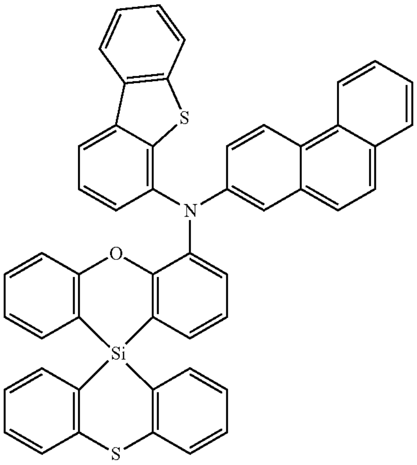
B100
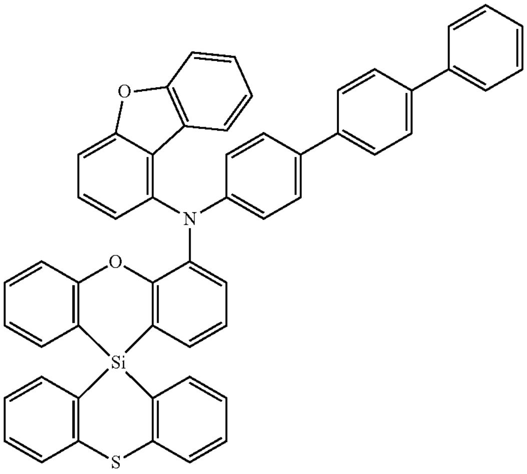
B101
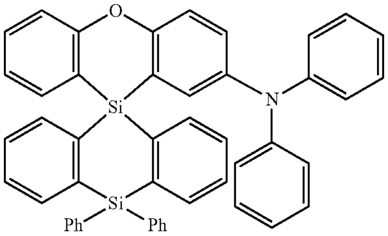
B102
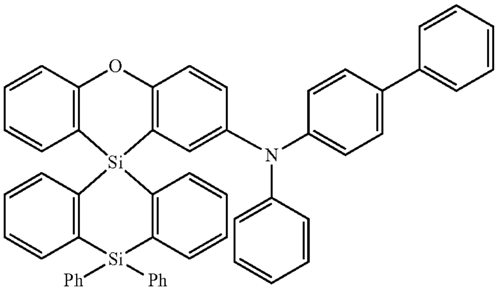

-continued
B103
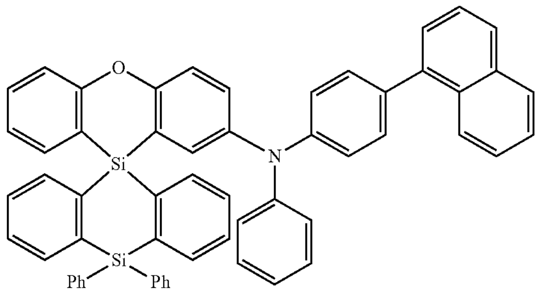
B104
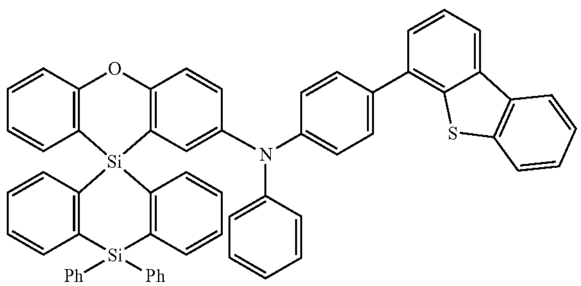
B105
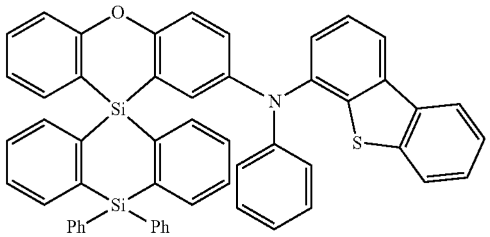
B106
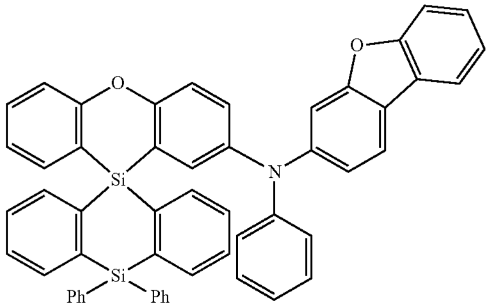
B107
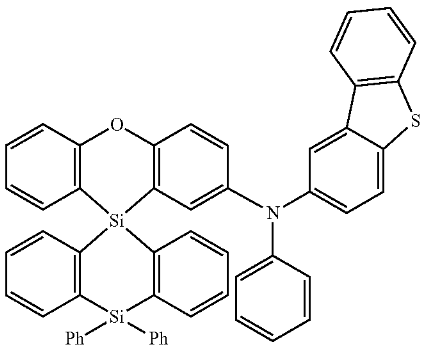
-continued
B108
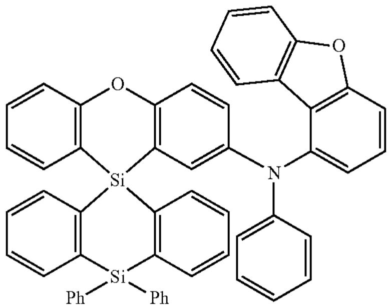
B109
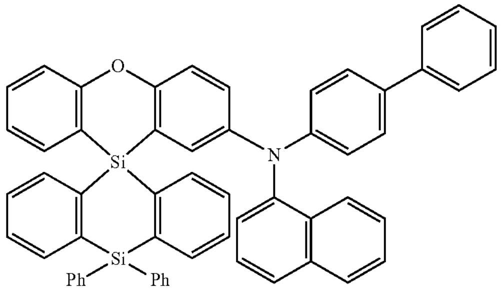
B110
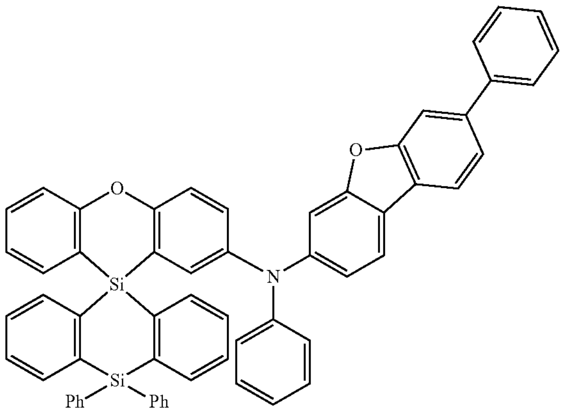
B111
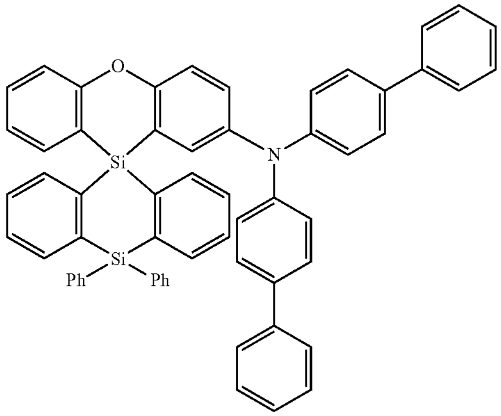

-continued
B112
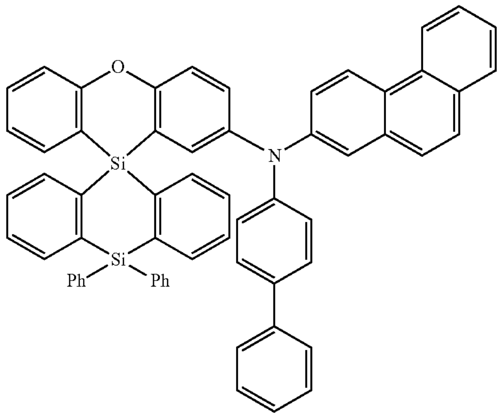
B113
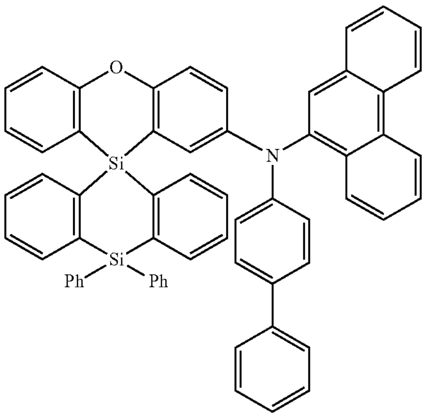
B114
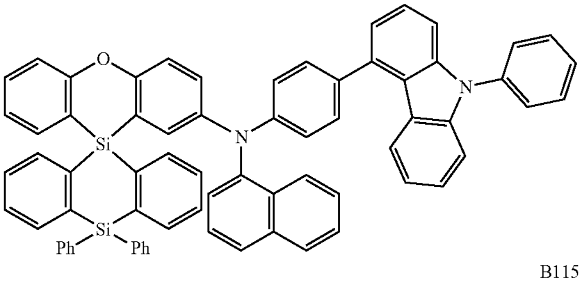
B115
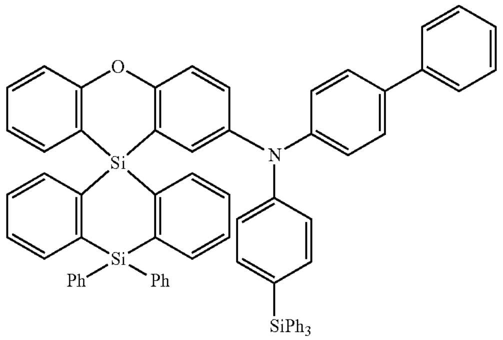
-continued
B116
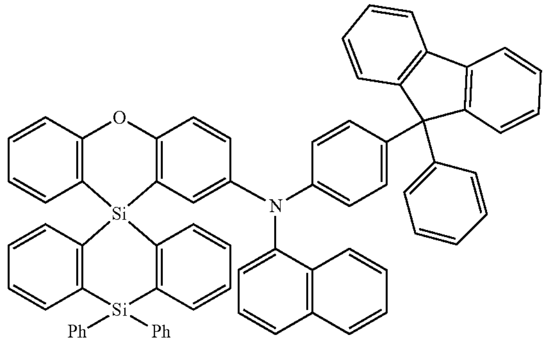
B117
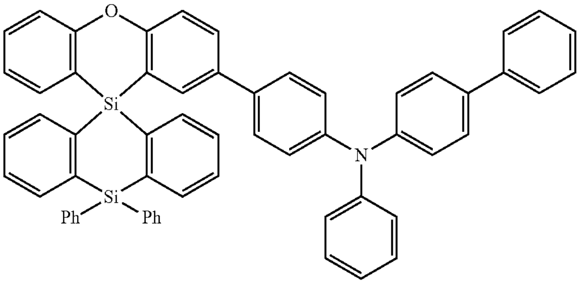
B118
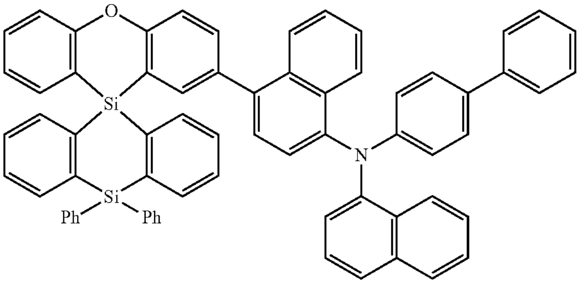
B119
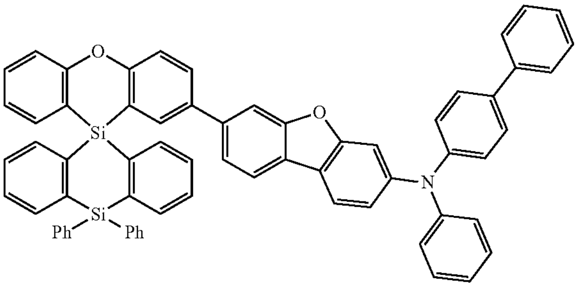

-continued
B120
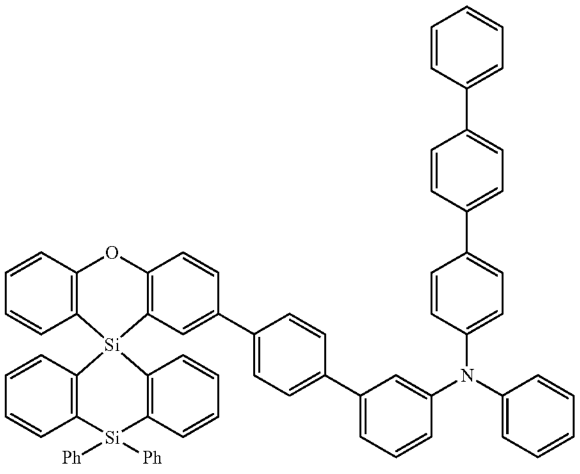
B121
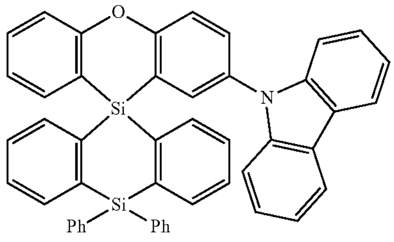
B122
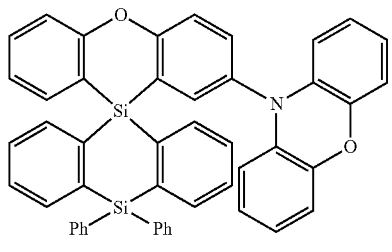
B123
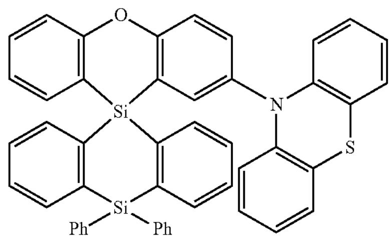
B124
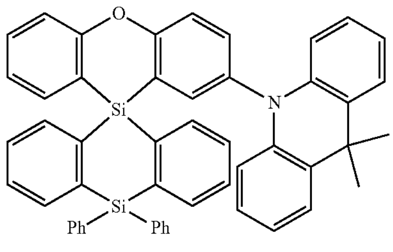
-continued
B125
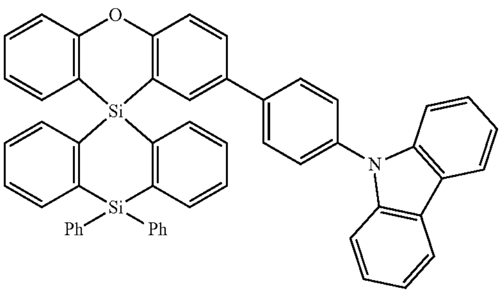
B126
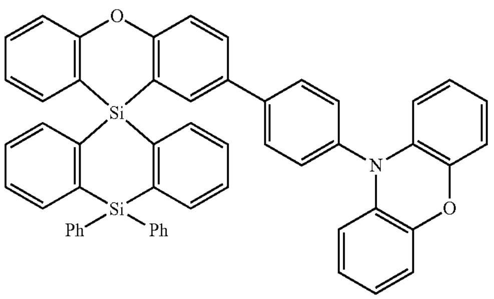
B127
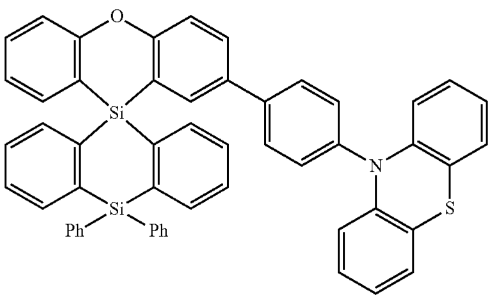
B128
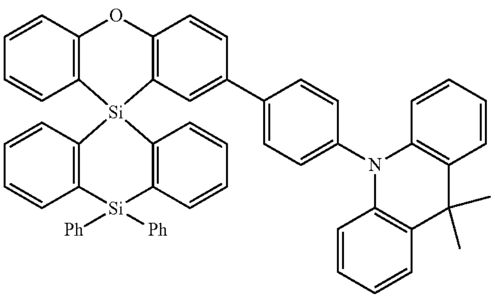
B129
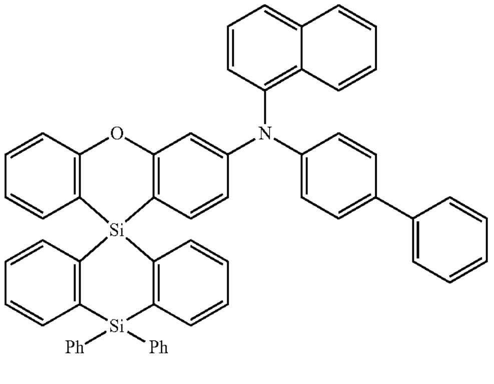

-continued
B130
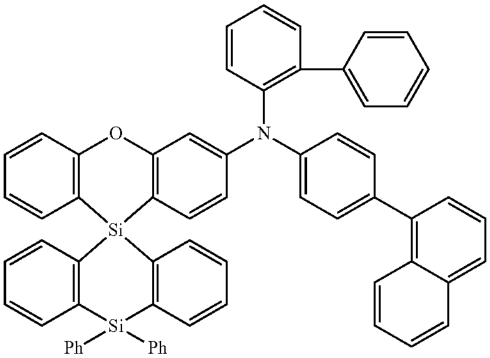
B131
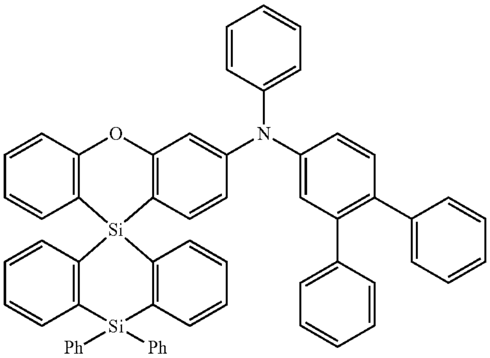
B132
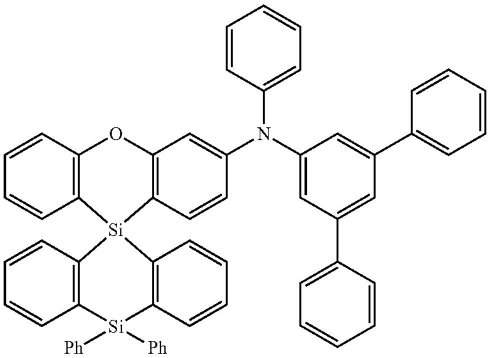
B133
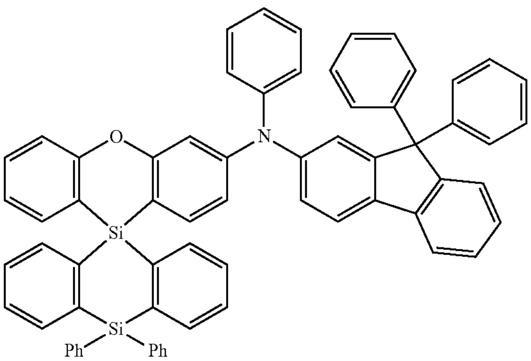
-continued
B134
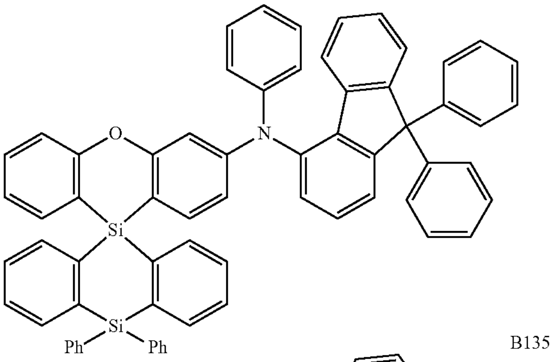
B135
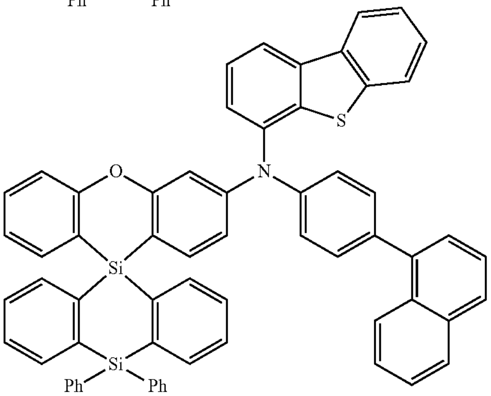
B136
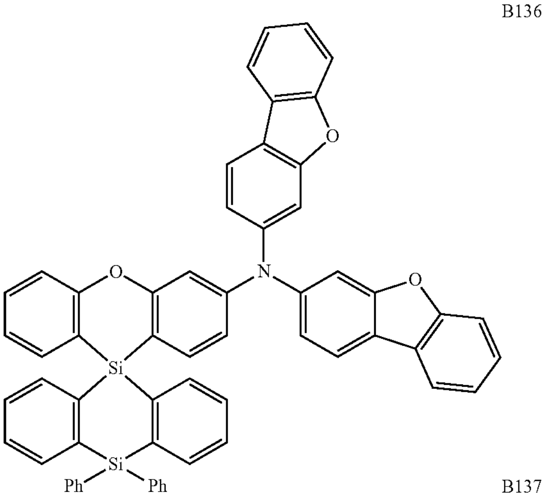
B137
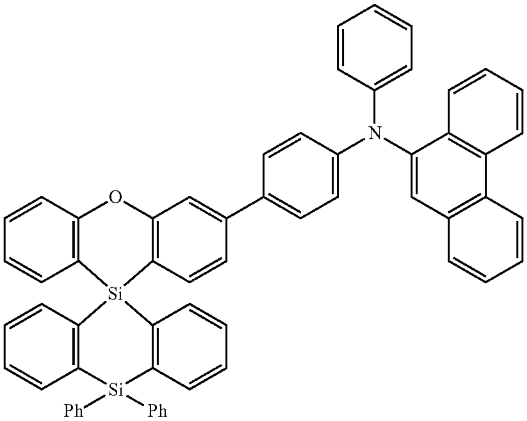

-continued
B138
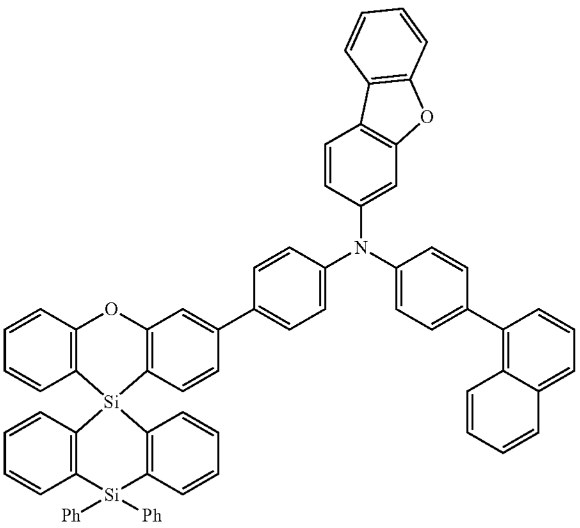
B139
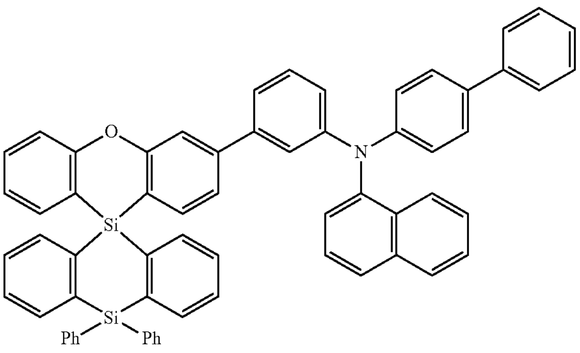
B140
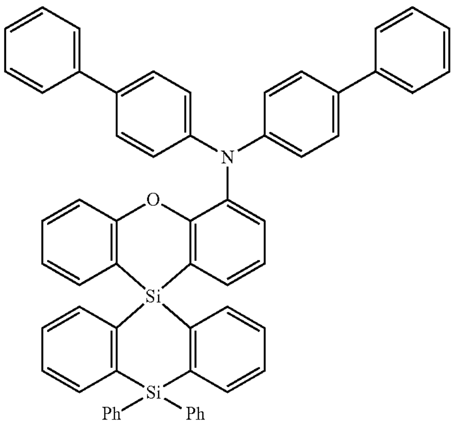
-continued
B141
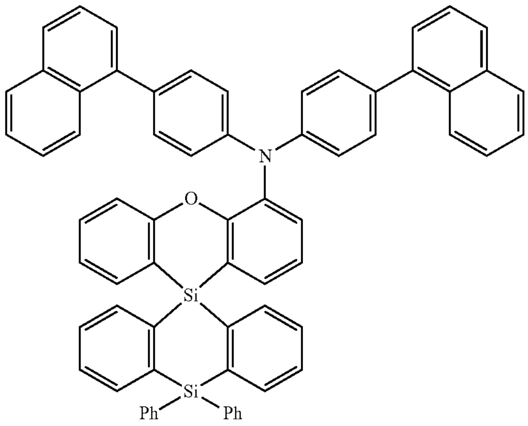
B142
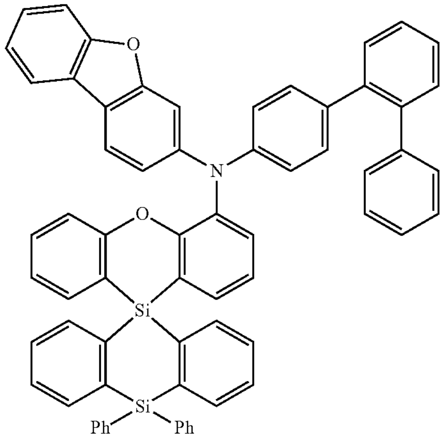
B143
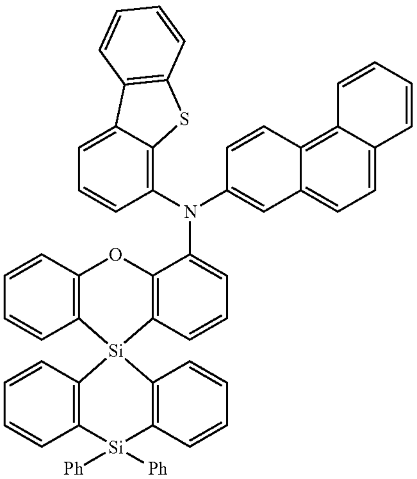

-continued
B144
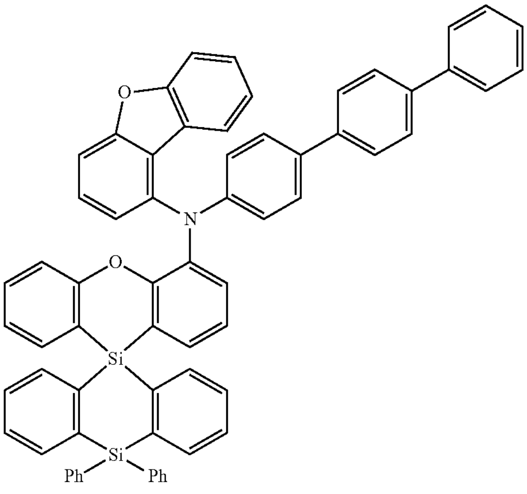
B145
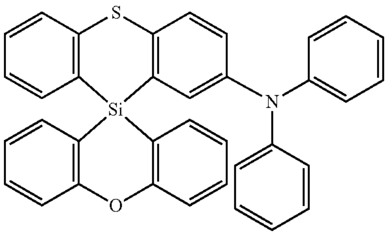
B146
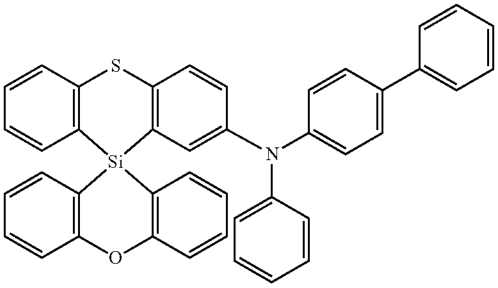
B147
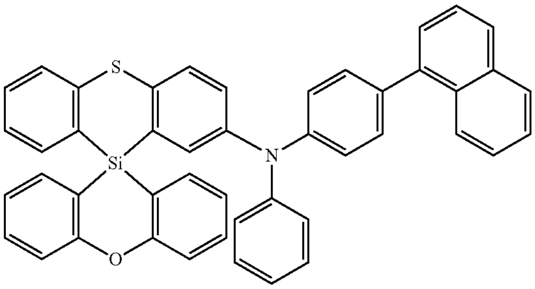
-continued
B148
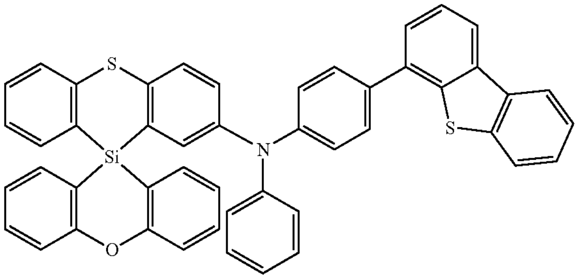
B149
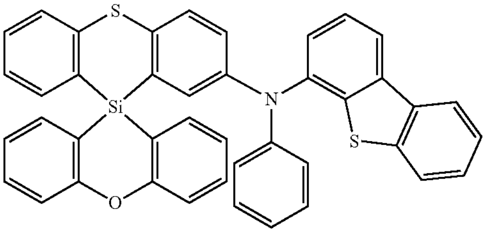
B150
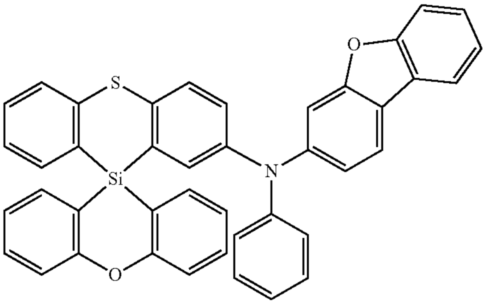
B151
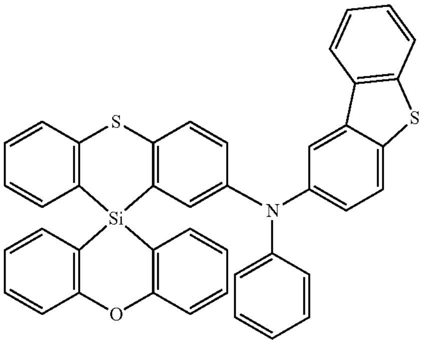
B152
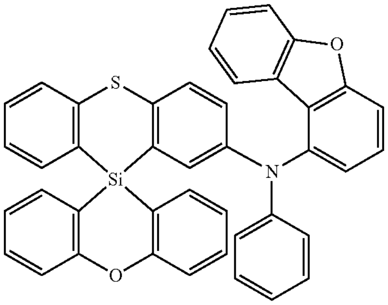

-continued
B153
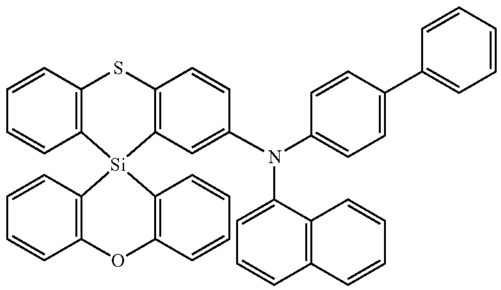
B154
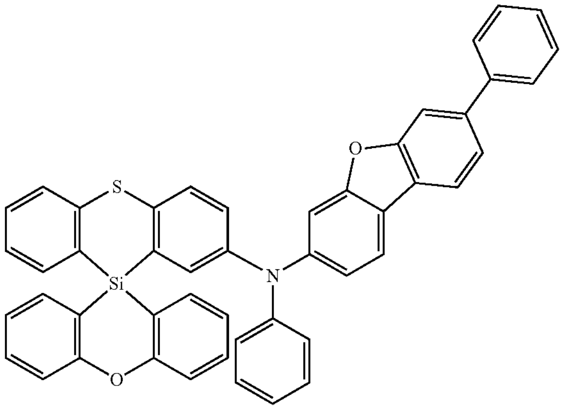
B155
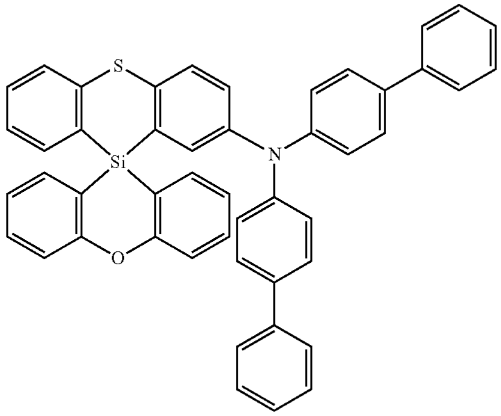
B156
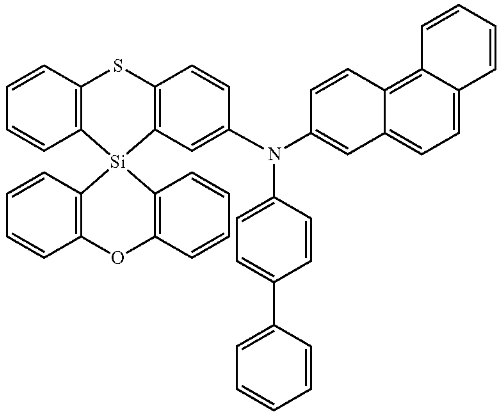
-continued
B157
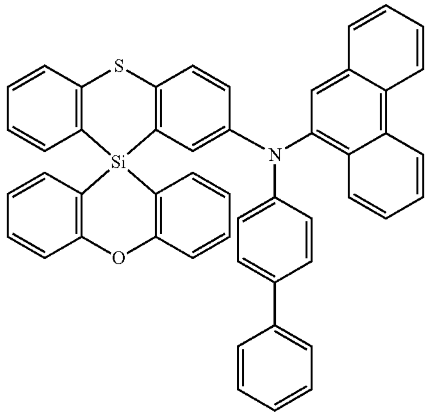
B158
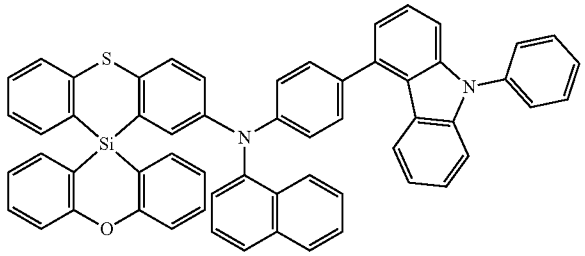
B159
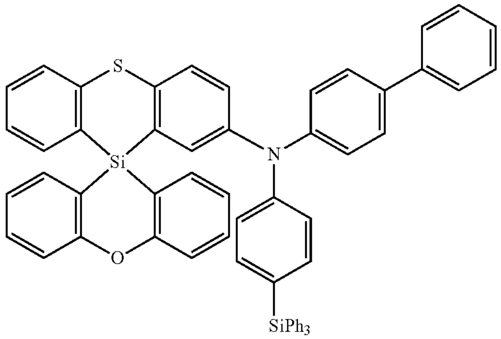
B160
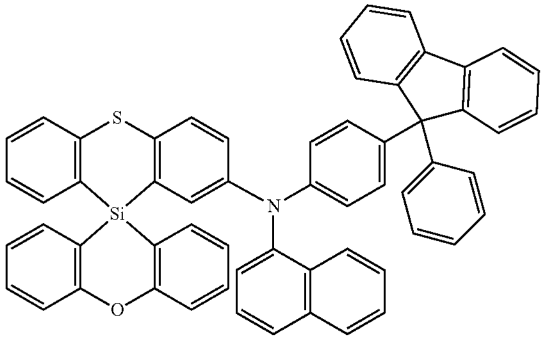

-continued
B161
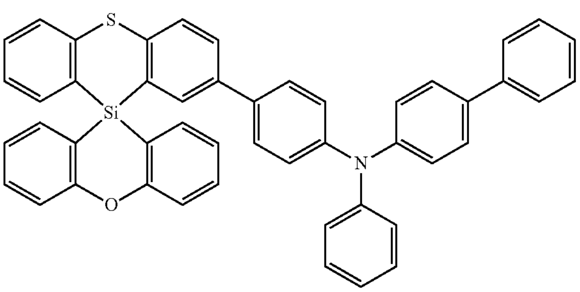
B162
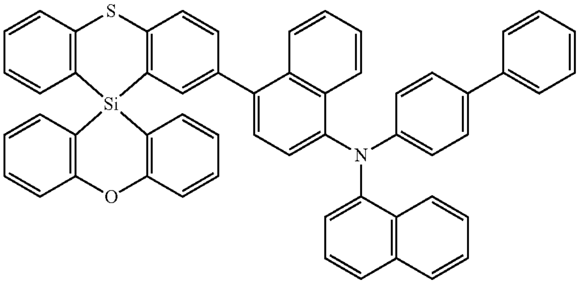
B163
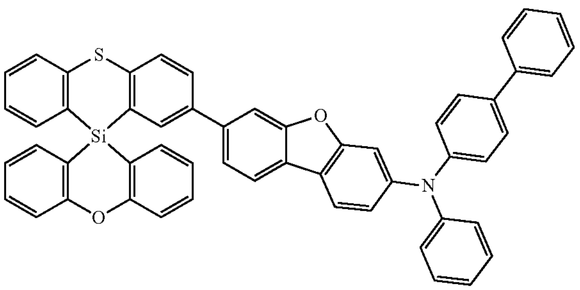
B164
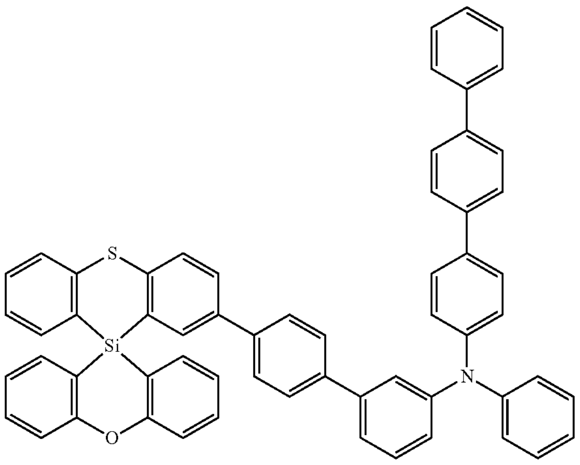
B165
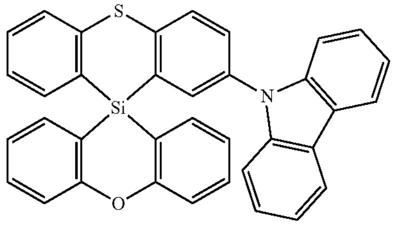
-continued
B166
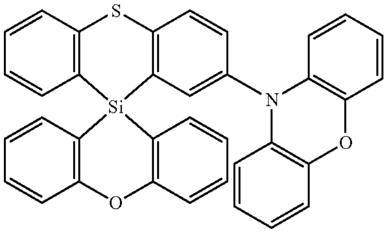
B167
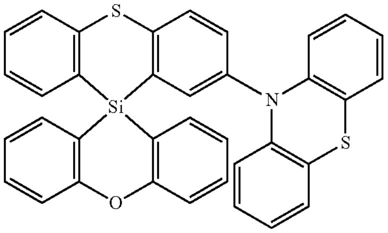
B168
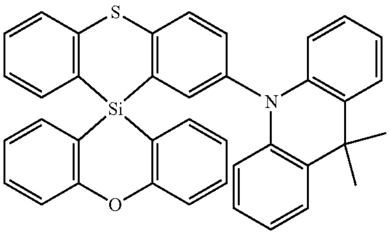
B169
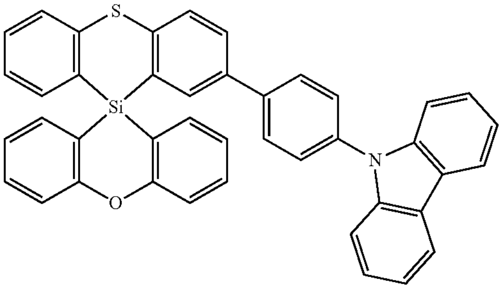
B170
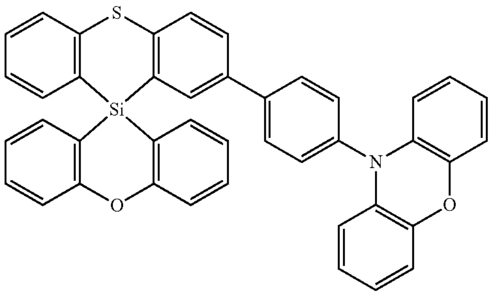
B171
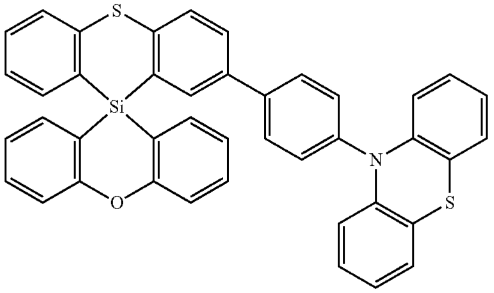

B172
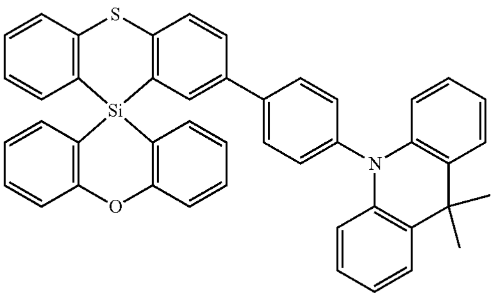
B173
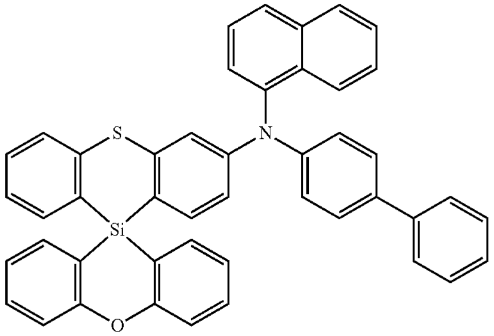
B174
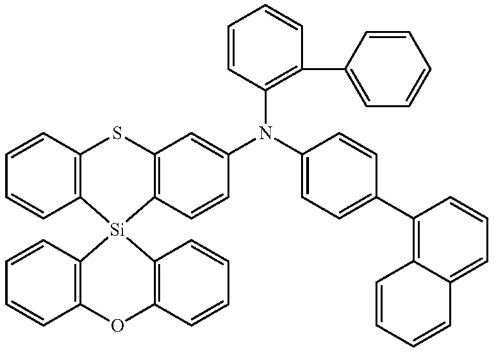
B175
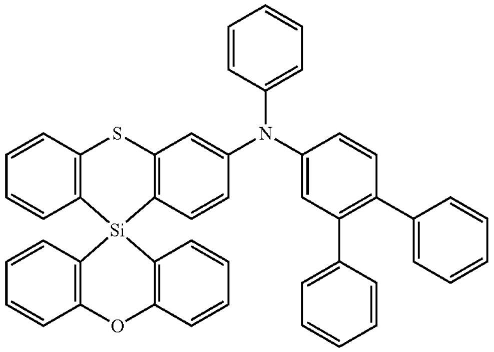
B176
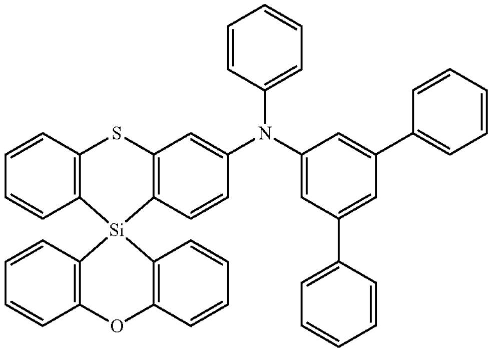
B177
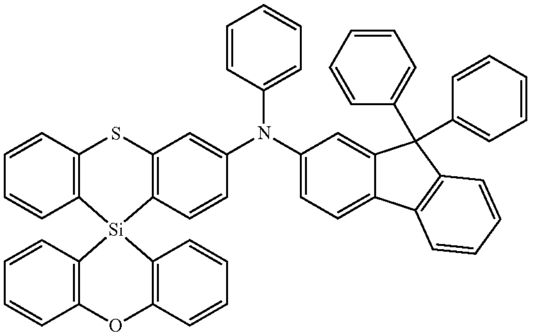
B178
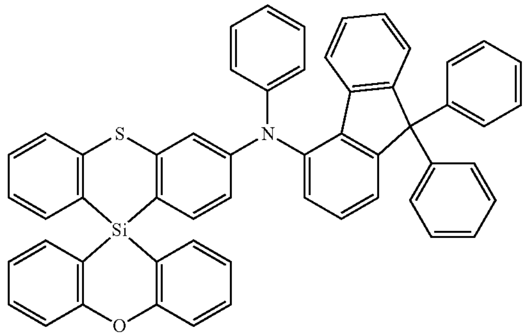
B179
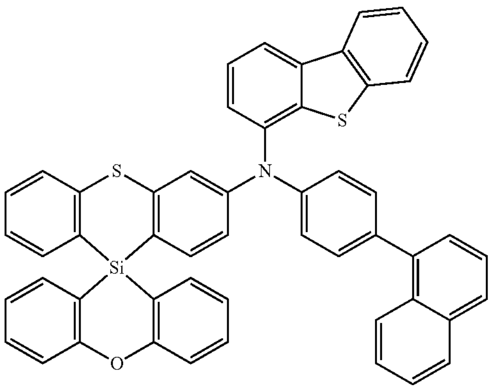

-continued
B180
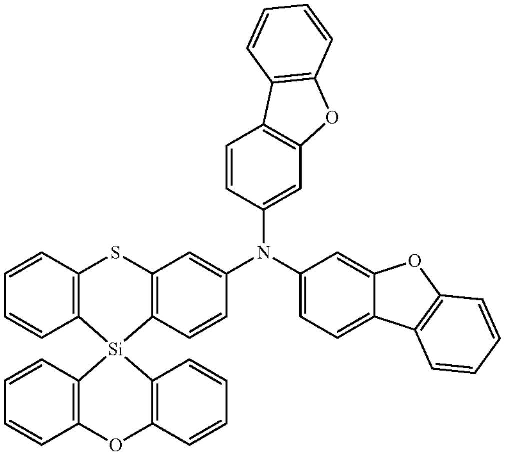
B181
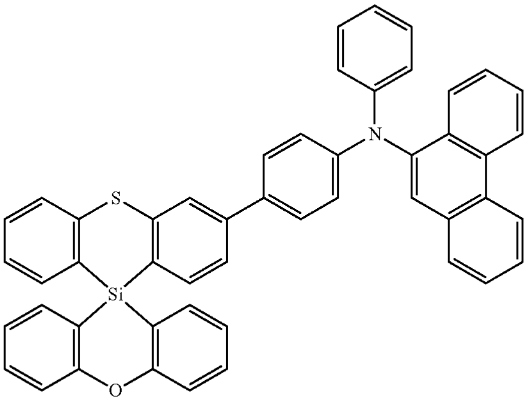
B182
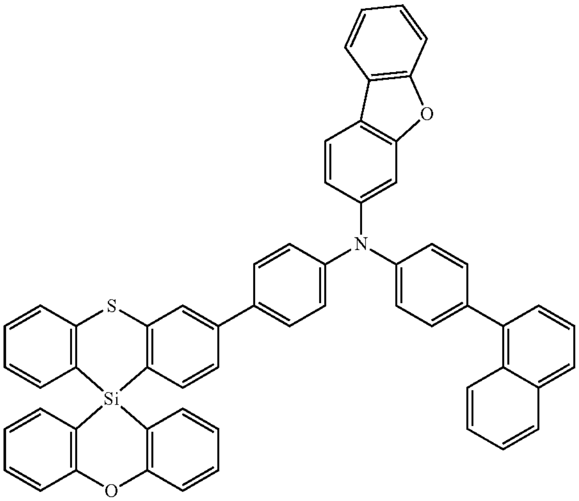
-continued
B183
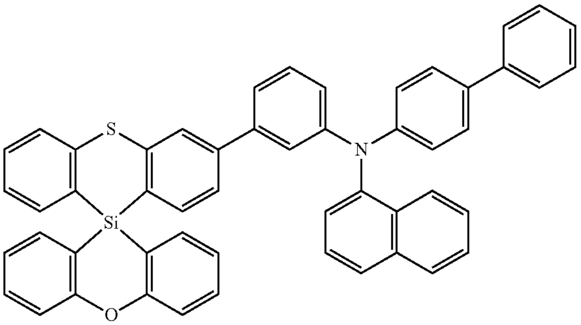
B184
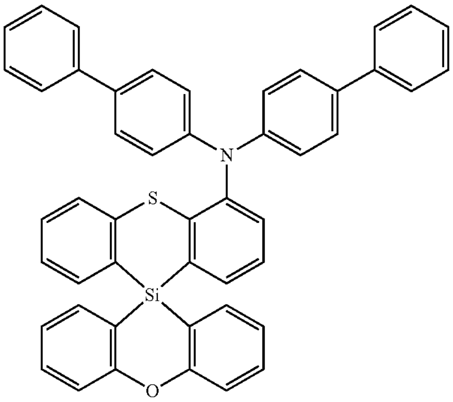
B185
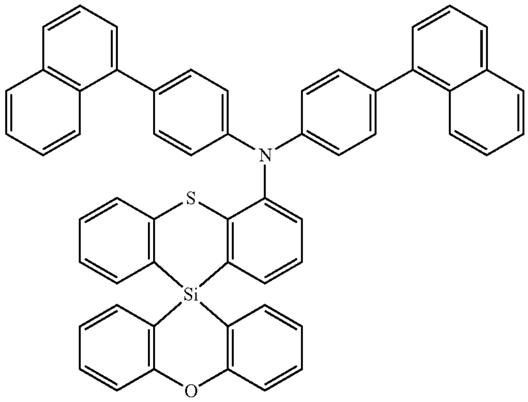
B186
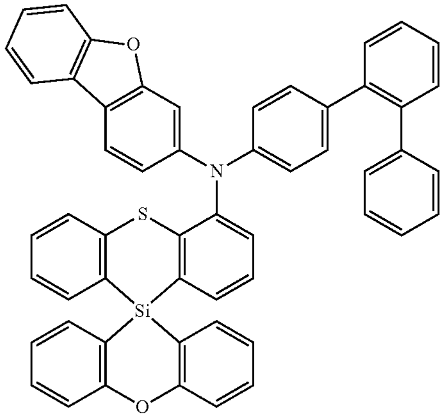

-continued
B187
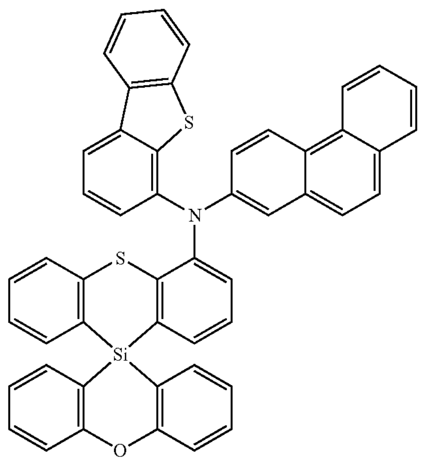
B188
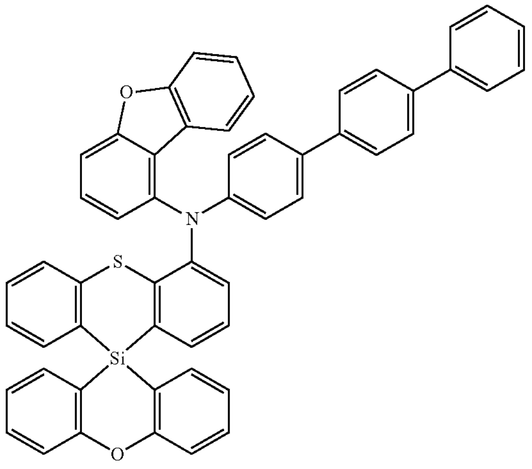
B189
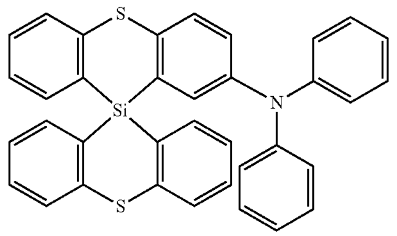
B190
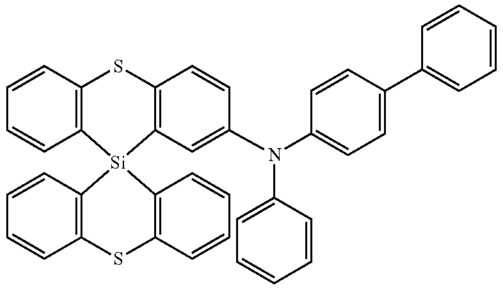
-continued
B191
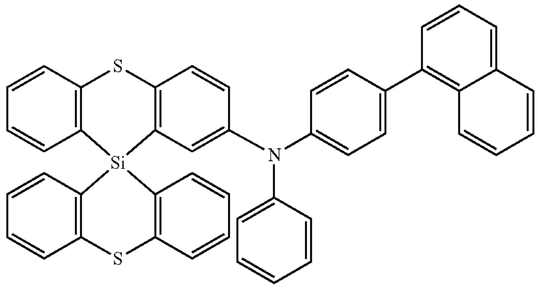
B192
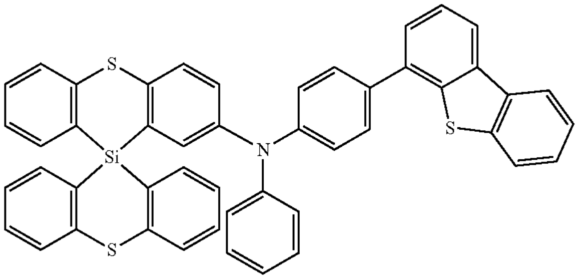
B193
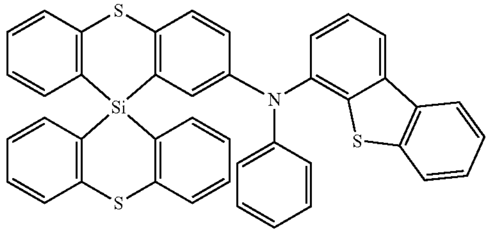
B194
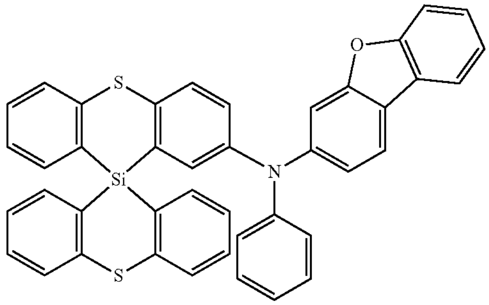
B195
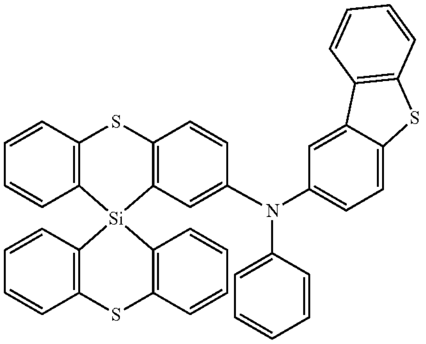

B196
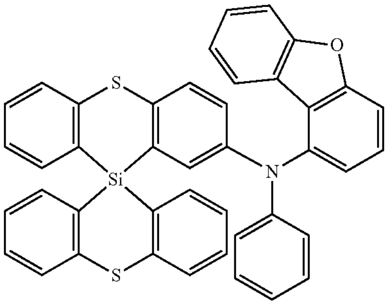
B197
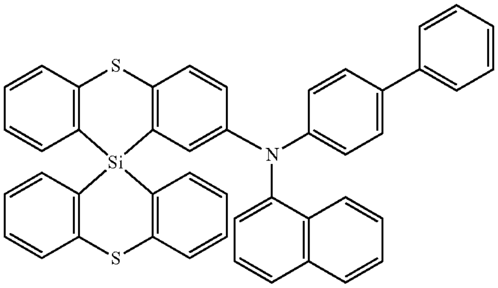
B198
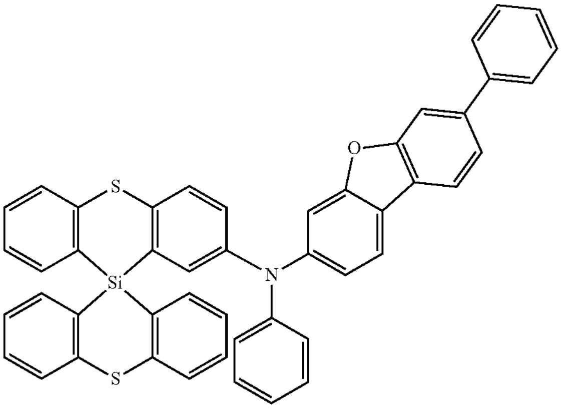
B199
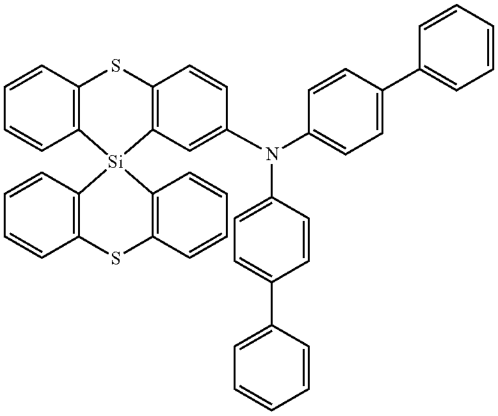
B200
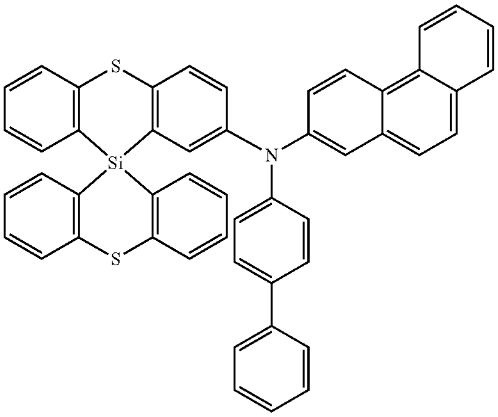
B201
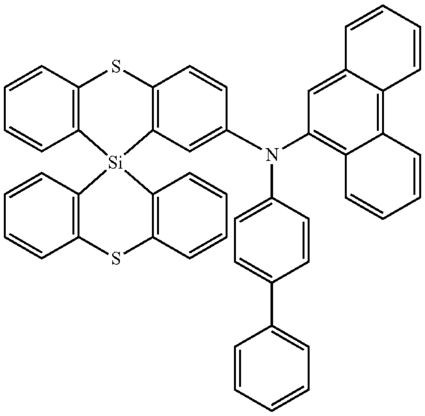
B202
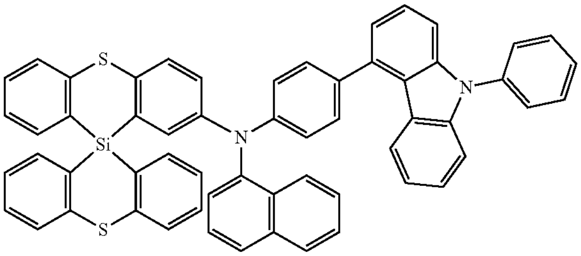
B203
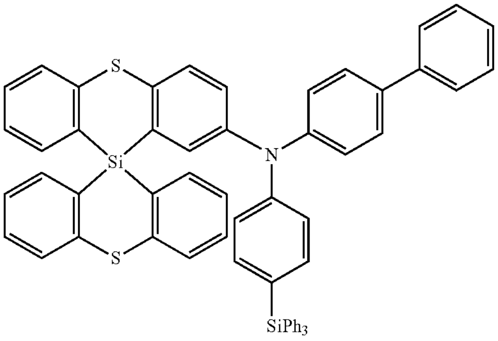

-continued
B204
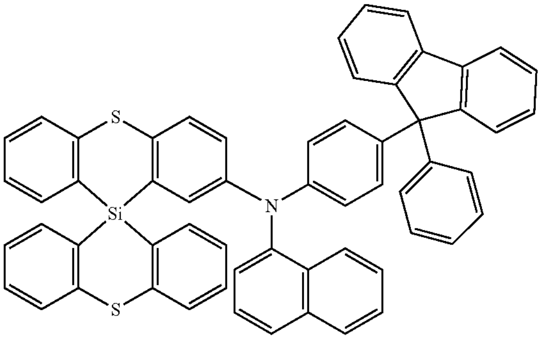
B205
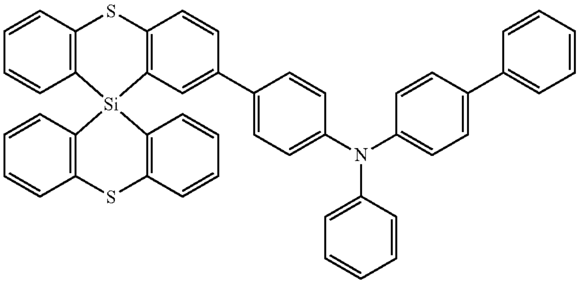
B206
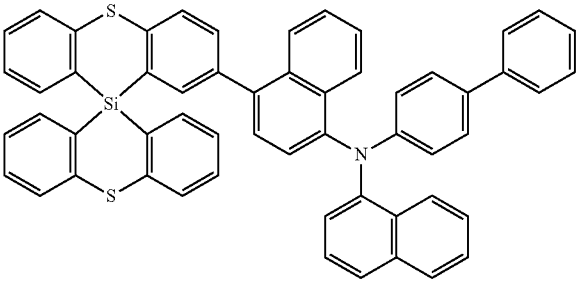
B207
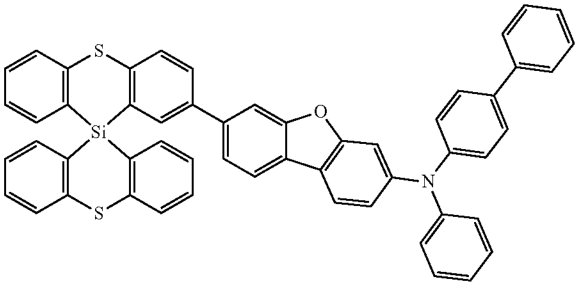
-continued
B208
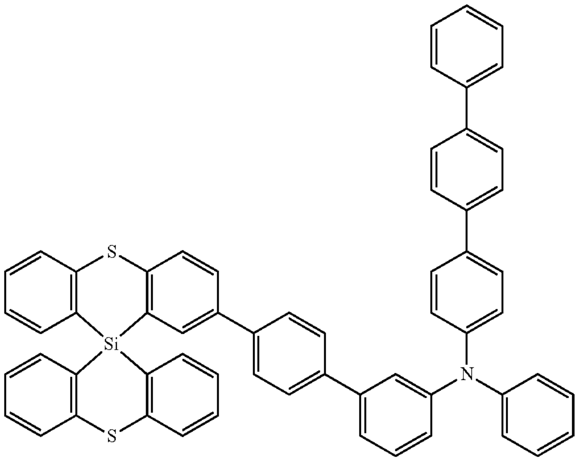
B209
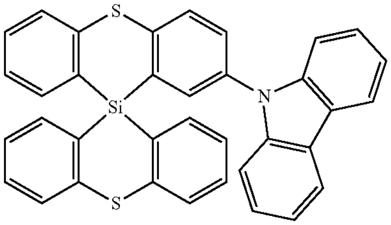
B210
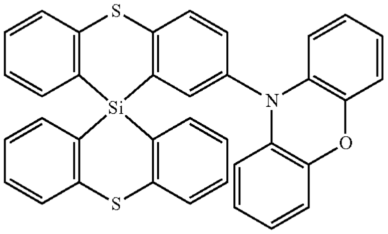
B211
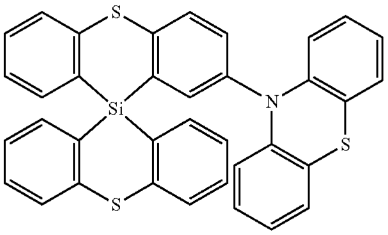
B212
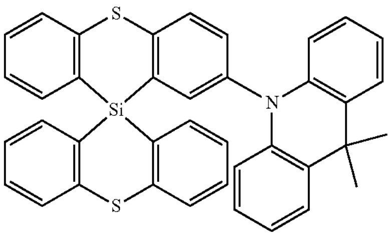

-continued
B213
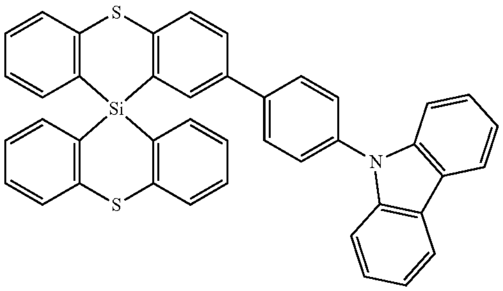
B214
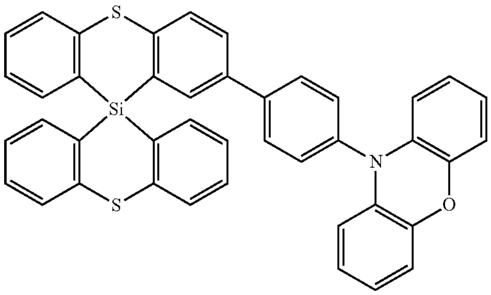
B215
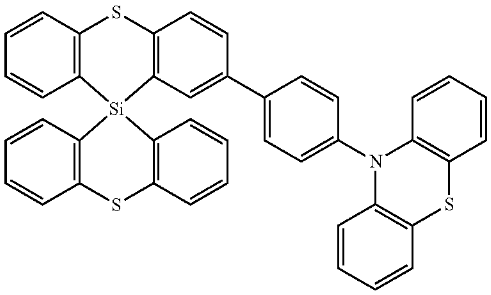
B216
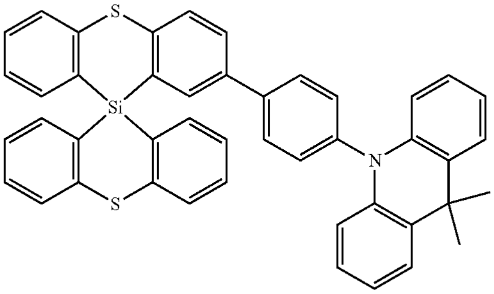
B217
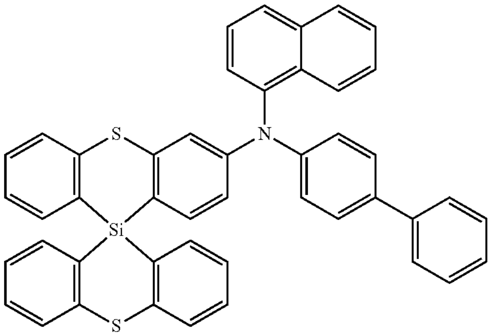
-continued
B218
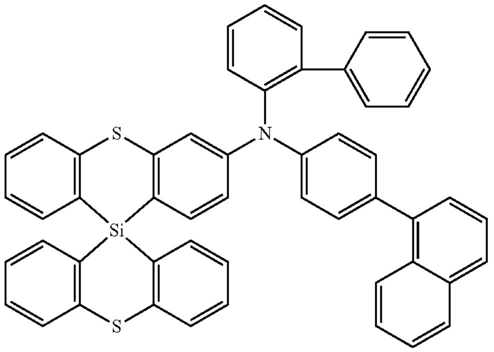
B219
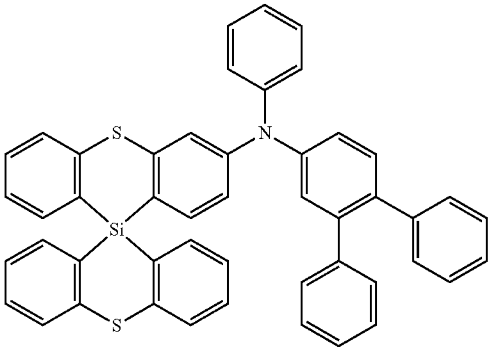
B220
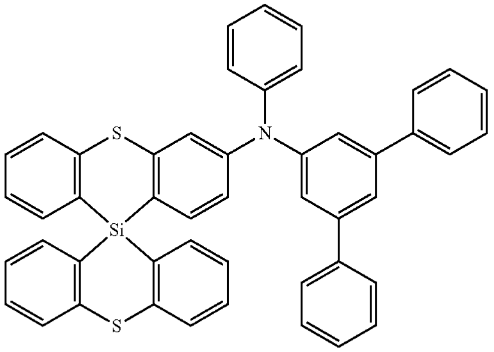
B221
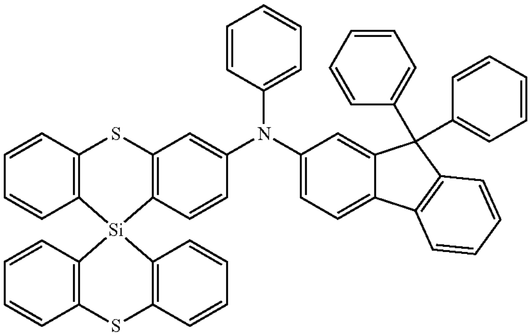

-continued
B222
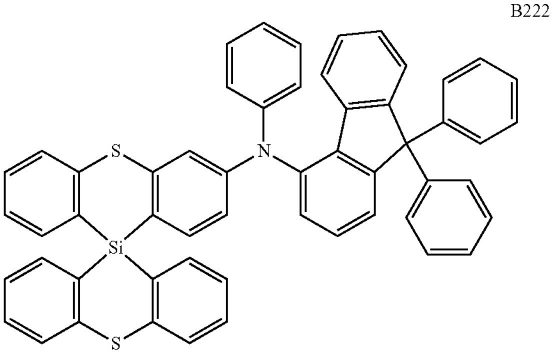
B223
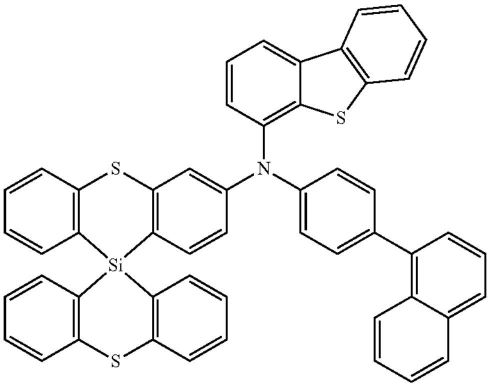
B224
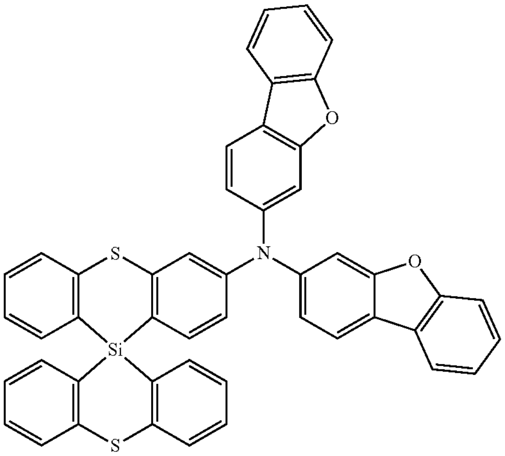
B225
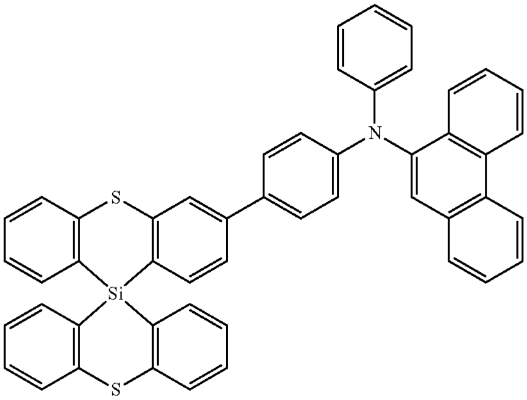
-continued
B226
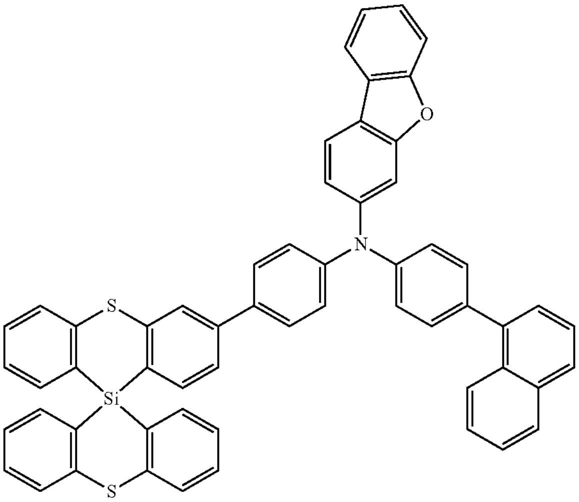
B227
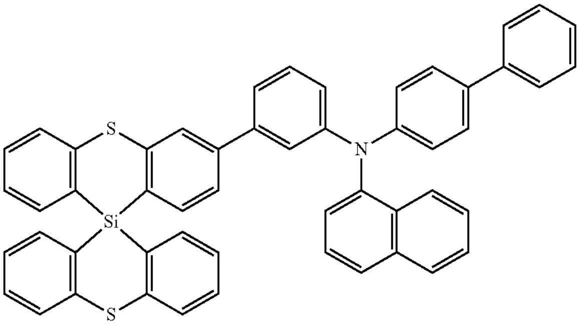
B228
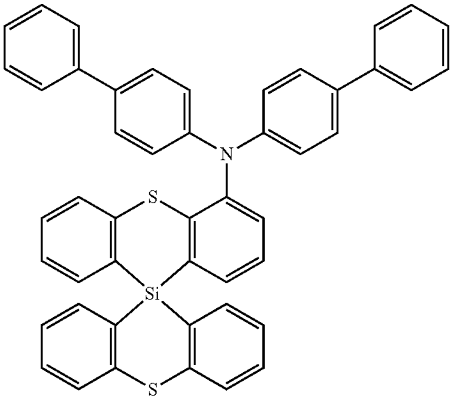

-continued
B229
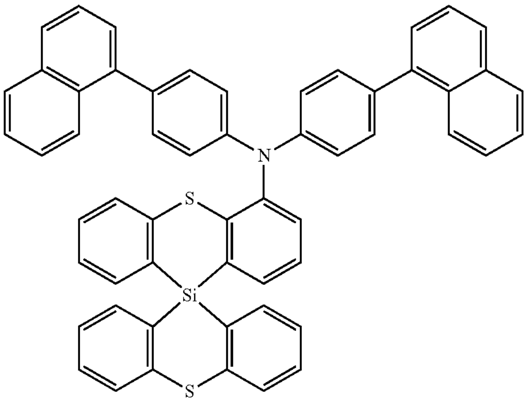
B230
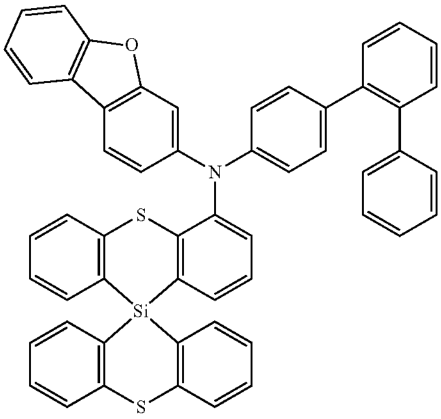
B231
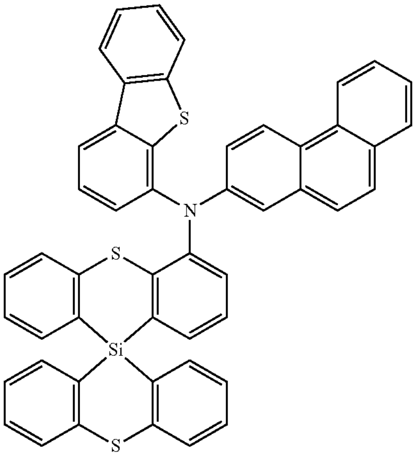
-continued
B232
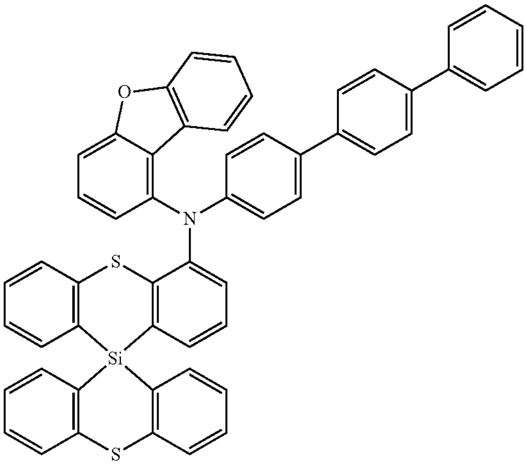
B233
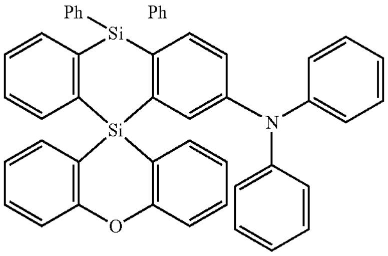
B234
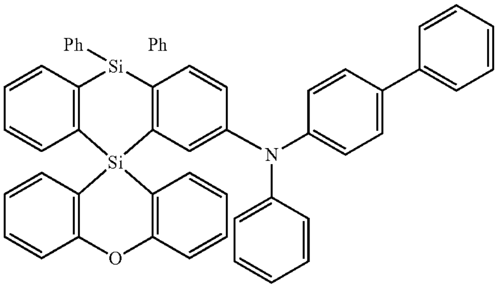
B235
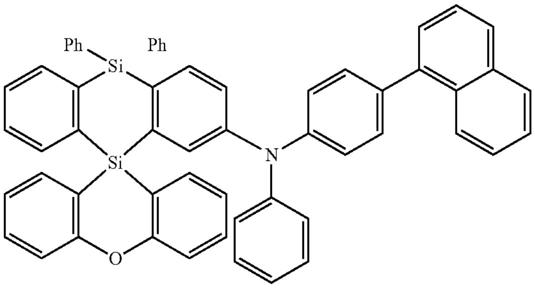

-continued
B236
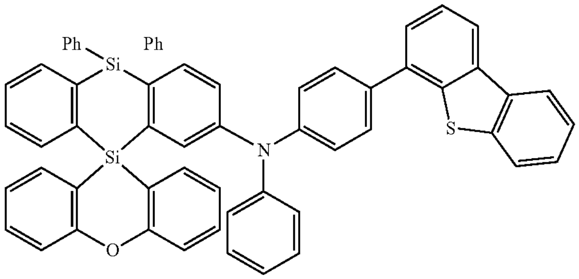
B237
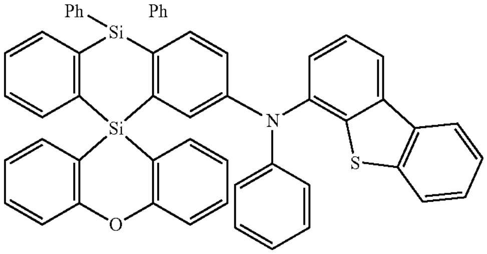
B238
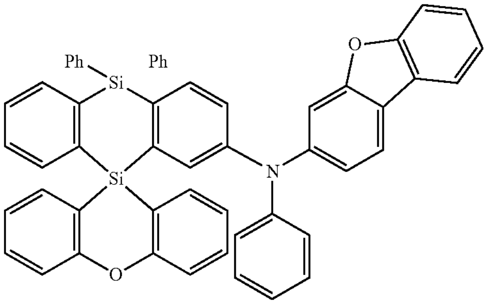
B239
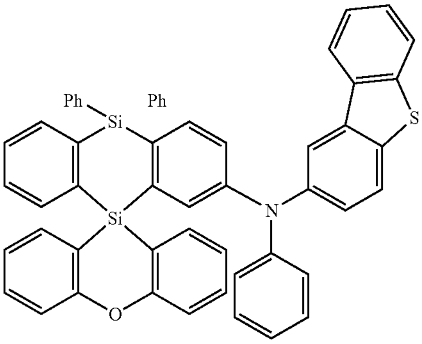
B240
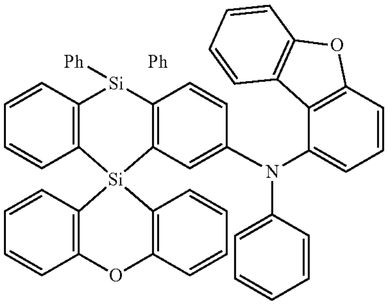
-continued
B241
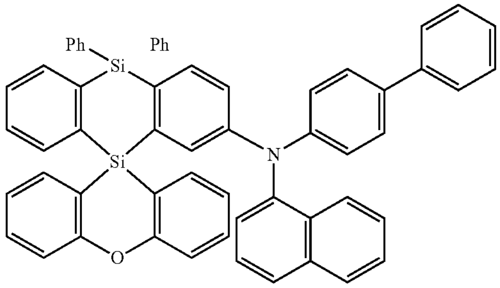
B242
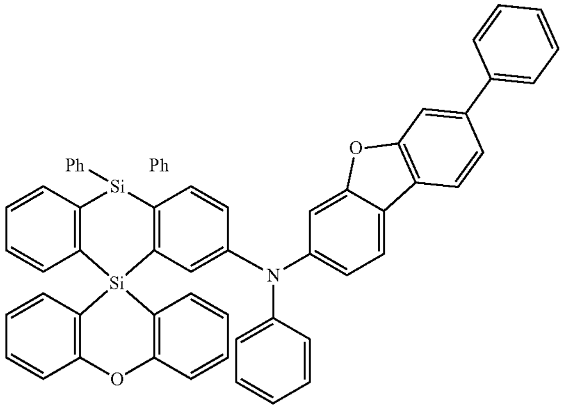
B243
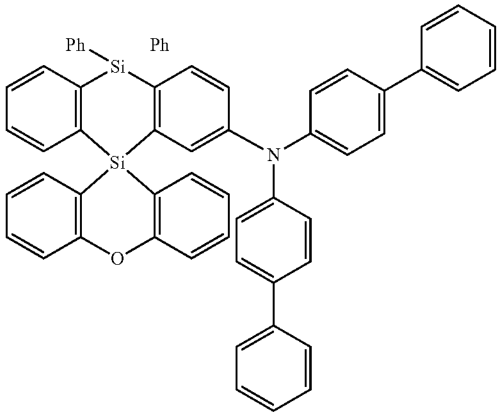
B244
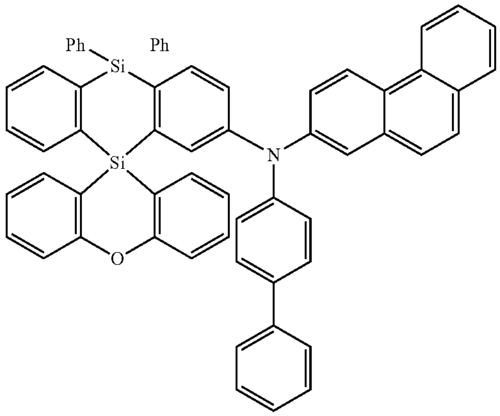

-continued
B245
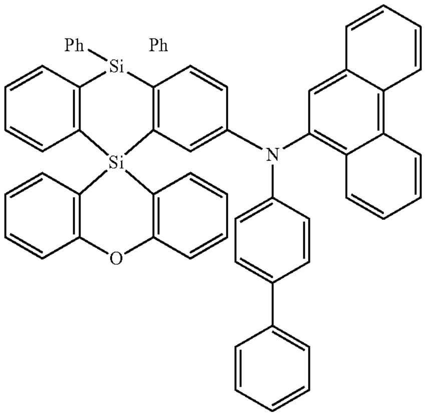
B246
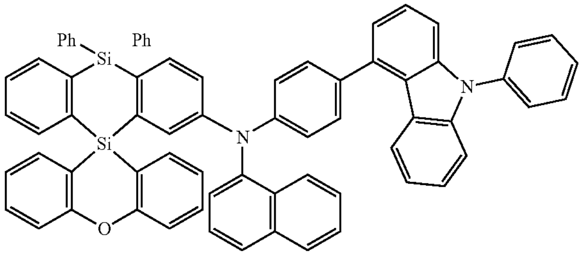
B247
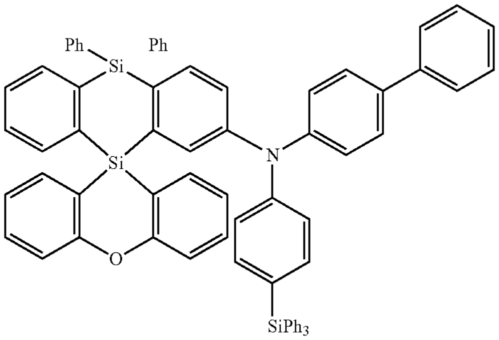
B248
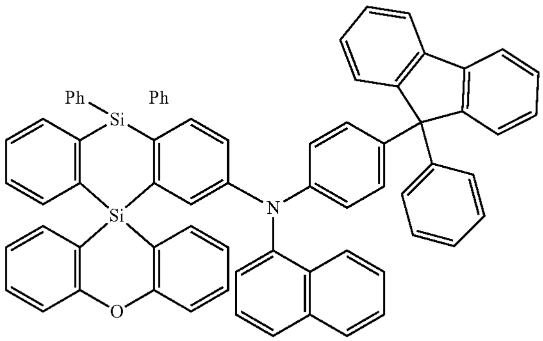
-continued
B249
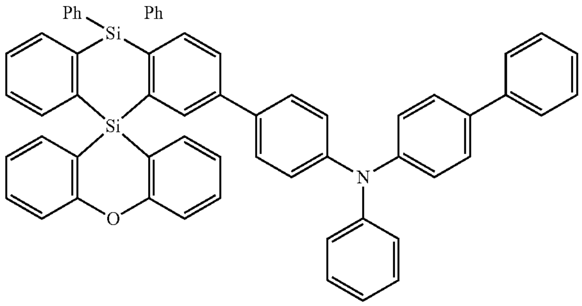
B250
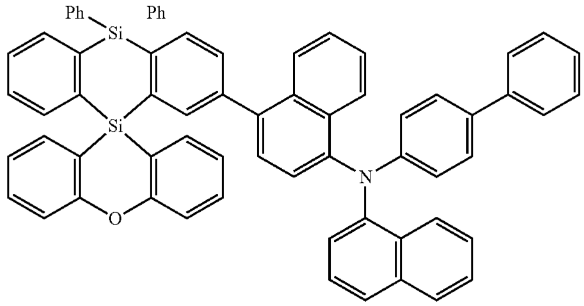
B251
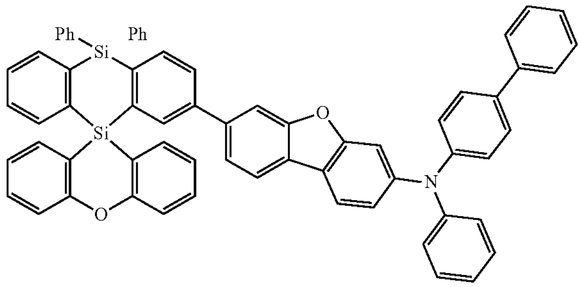
B252
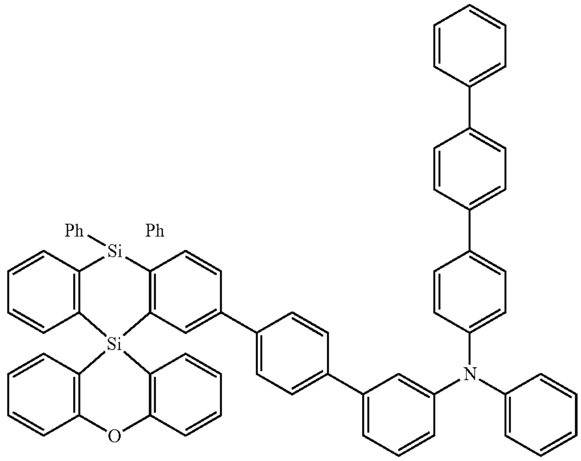

B253
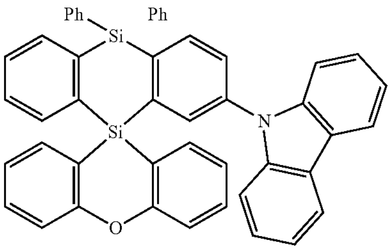
B254
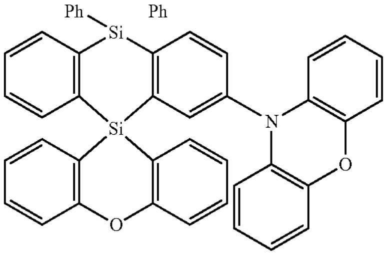
B255
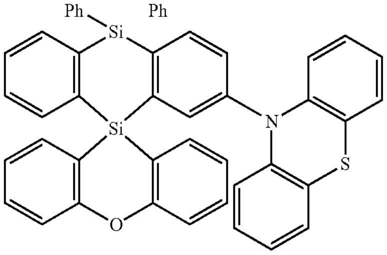
B256
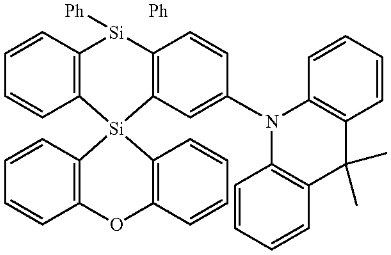
B257
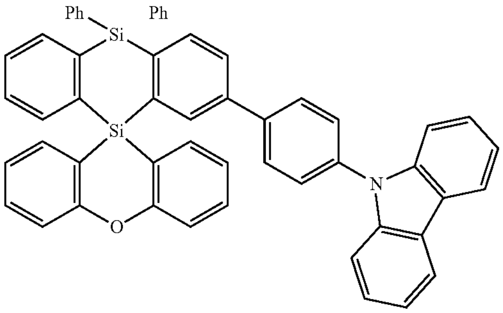
B258
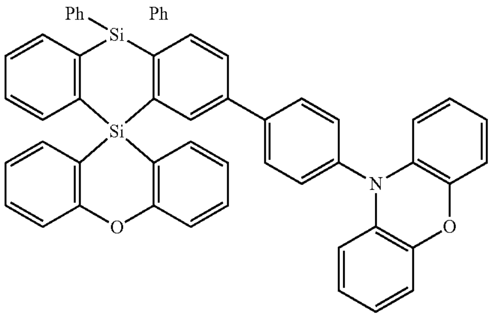
B259
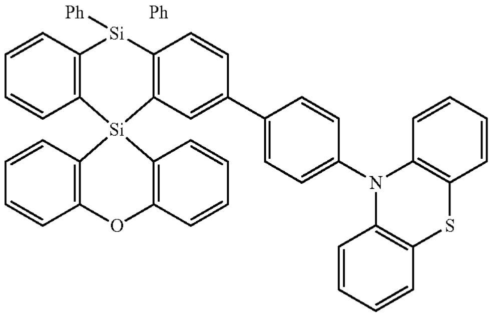
B260
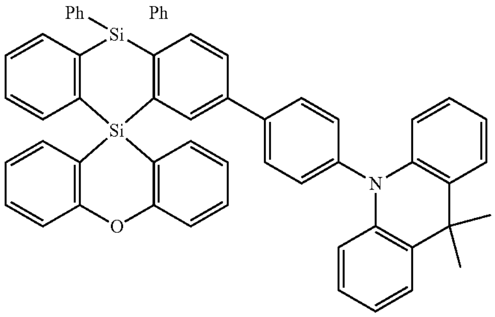
B261
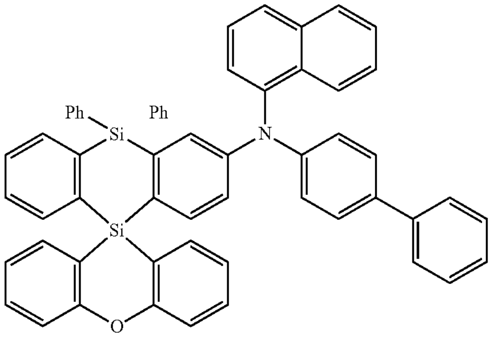

-continued
B262
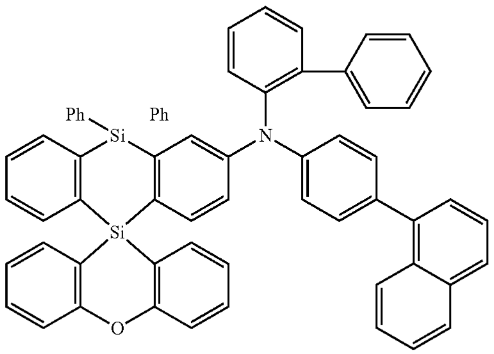
B263
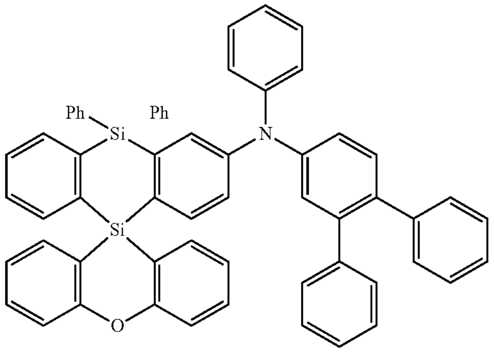
B264
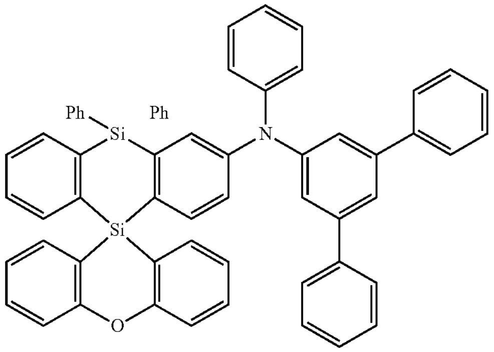
B265
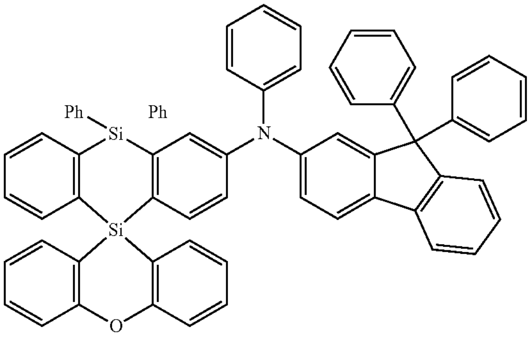
-continued
B266
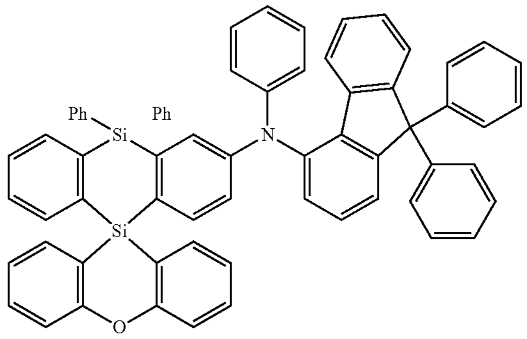
B267
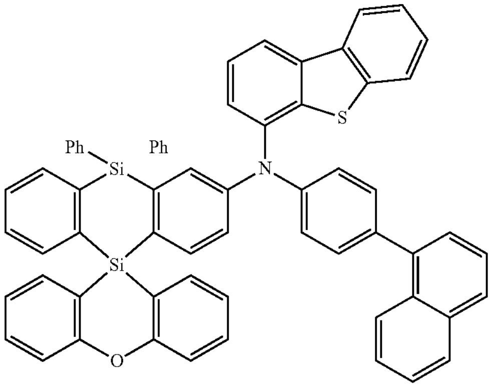
B268
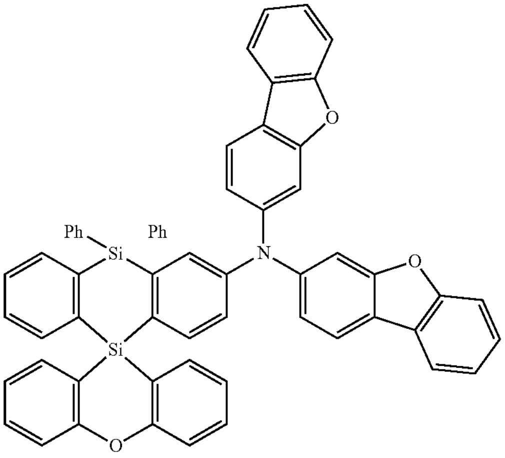
B269
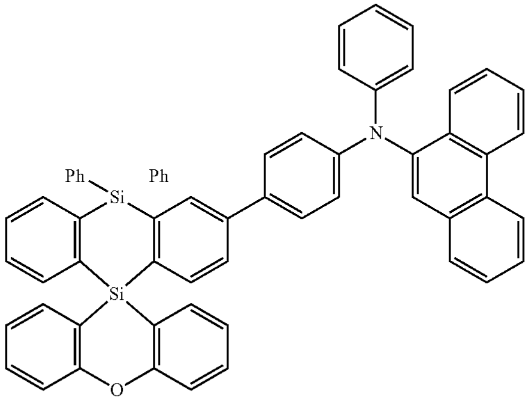

-continued
B270
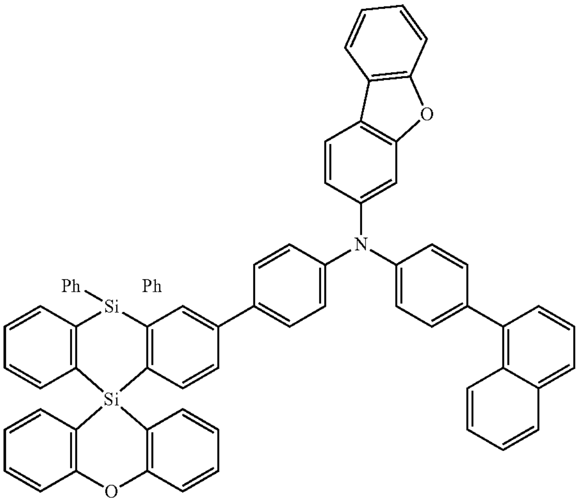
B271
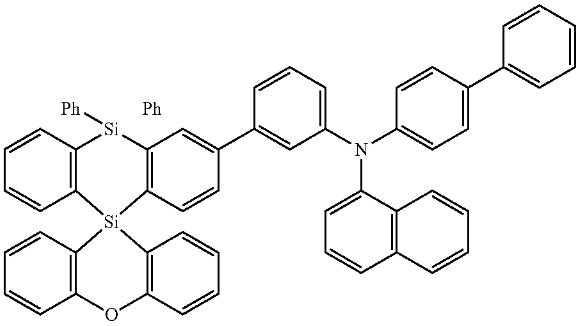
B272
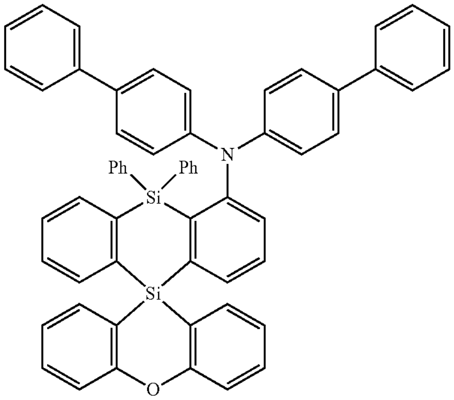
-continued
B273
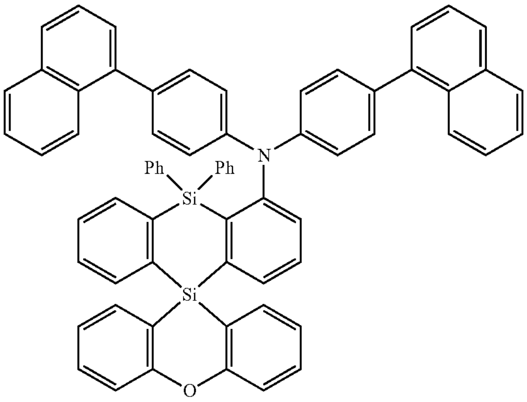
B274
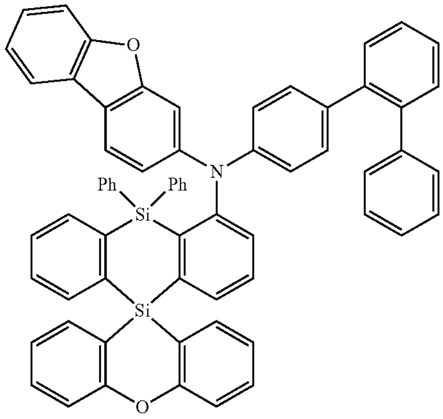
B275
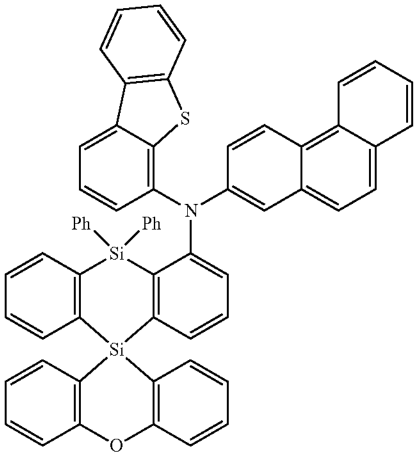

-continued
B276
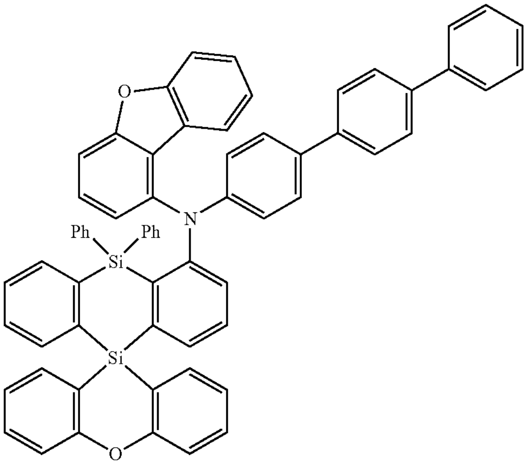
B277
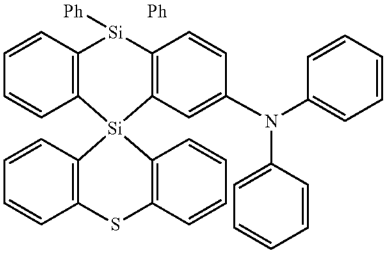
B278
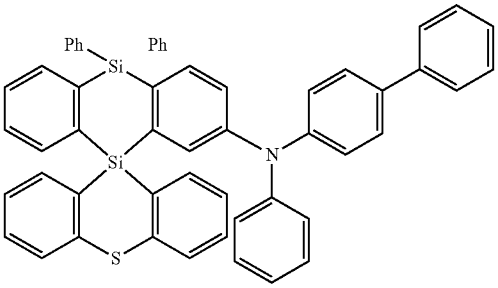
B279
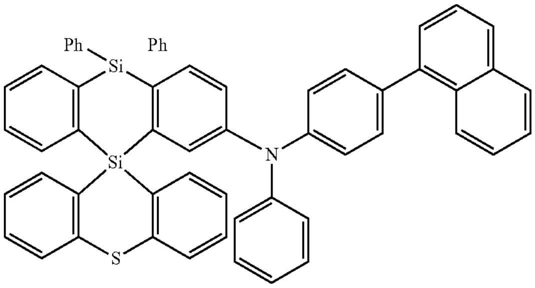
-continued
B280
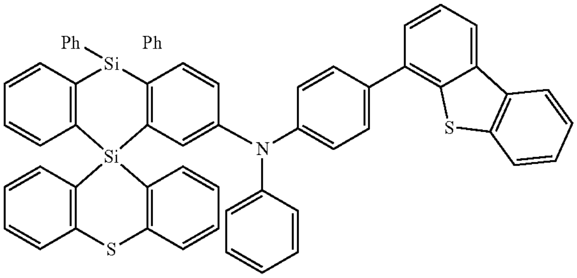
B281
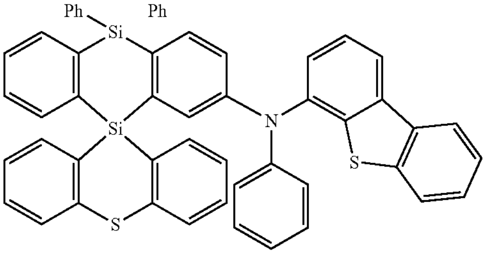
B282
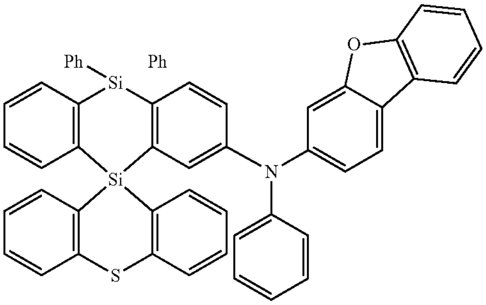
B283
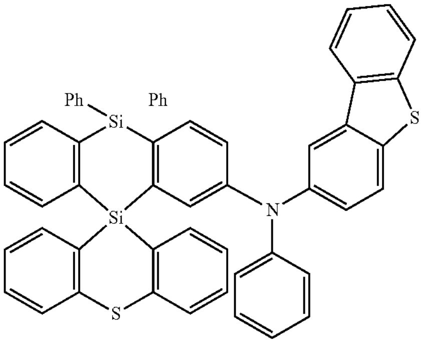
B284
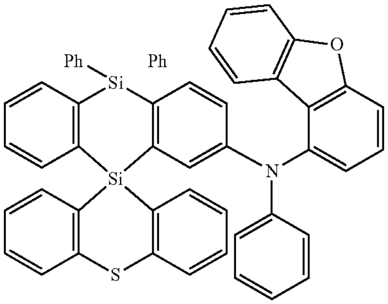

-continued
B285
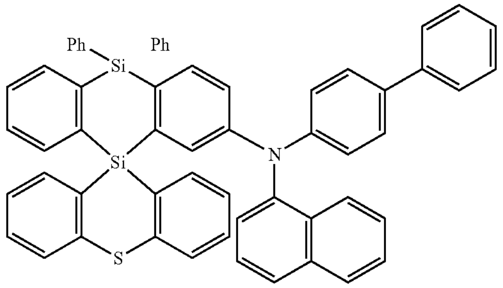
B286
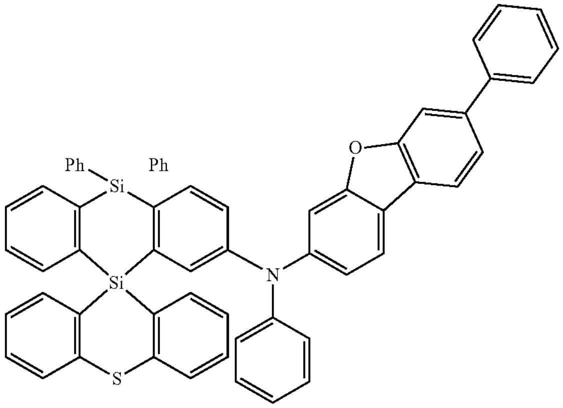
B287
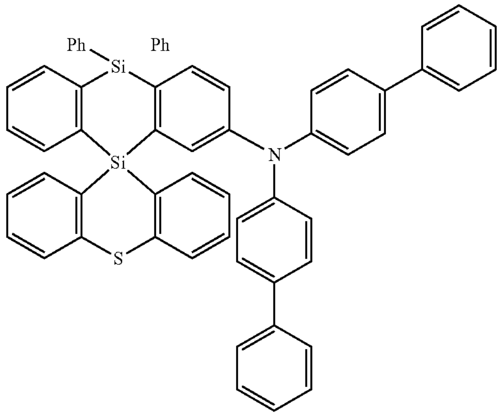
B288
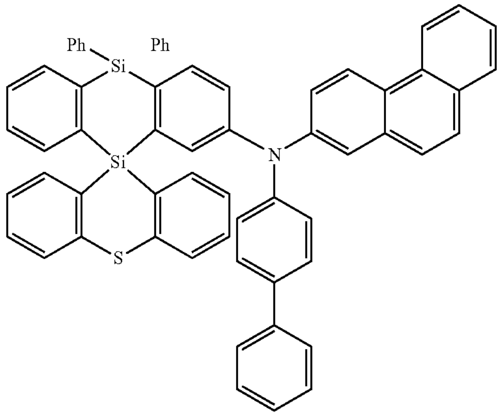
-continued
B289
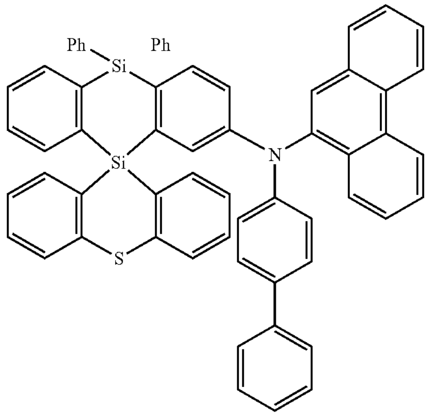
B290
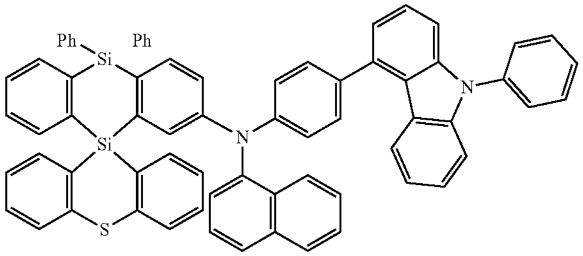
B291
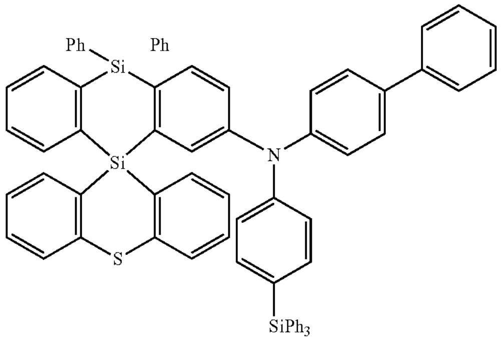
B292
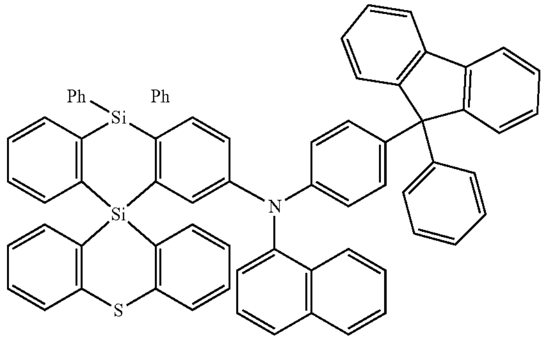

-continued
B293
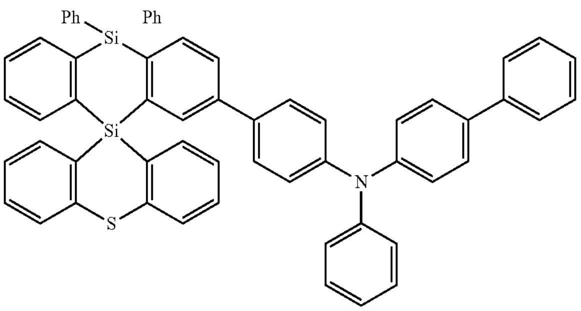
B294
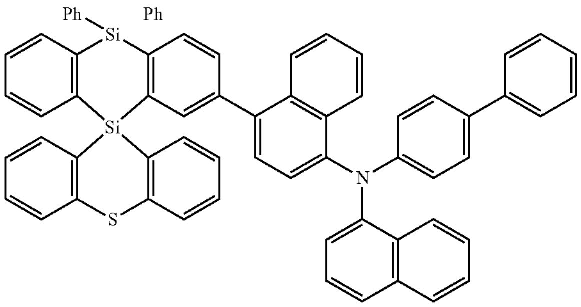
B295
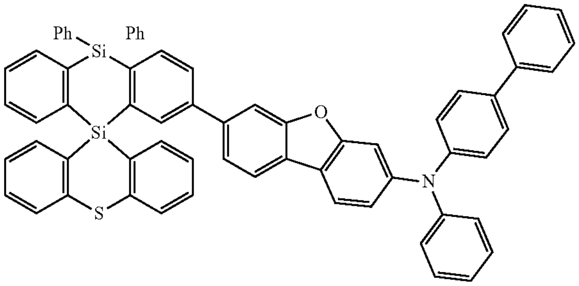
B296
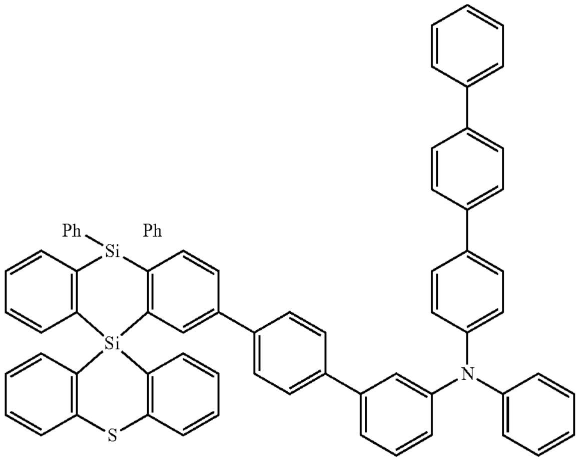
-continued
B297
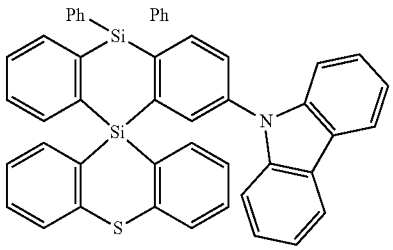
B298
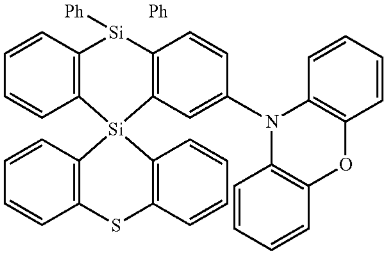
B299
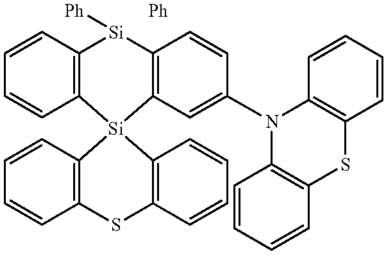
B300
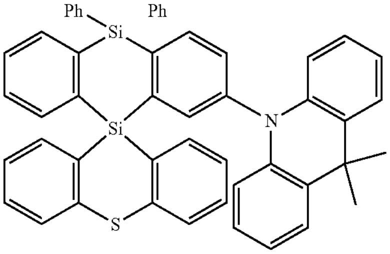
B301
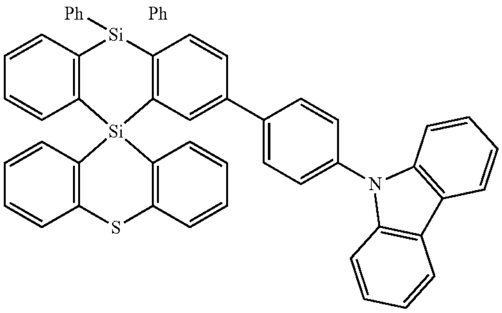

-continued
B302
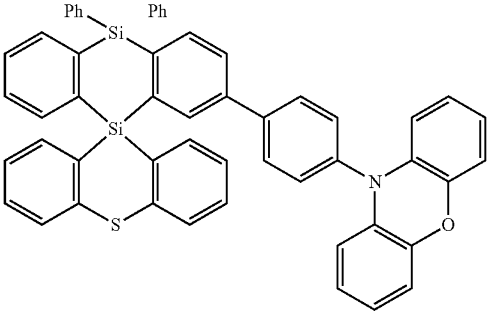
B303
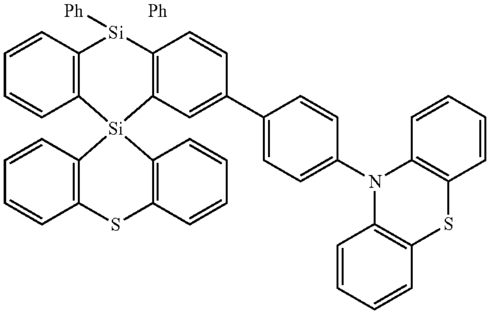
B304
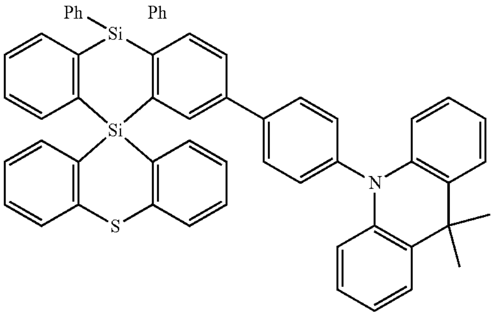
B305
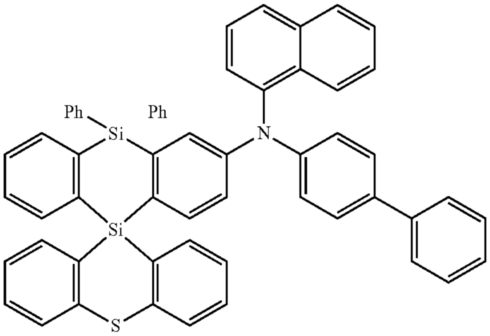
-continued
B306
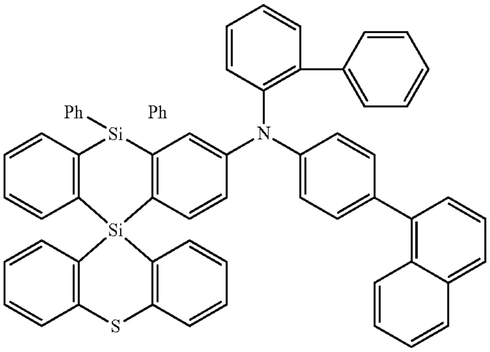
B307
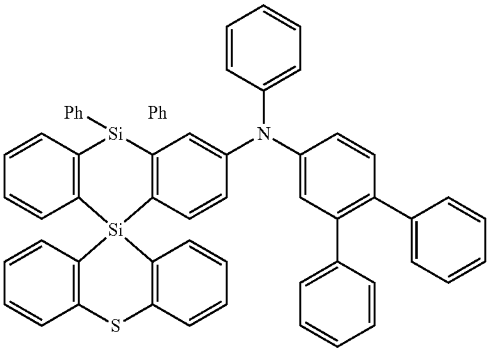
B308
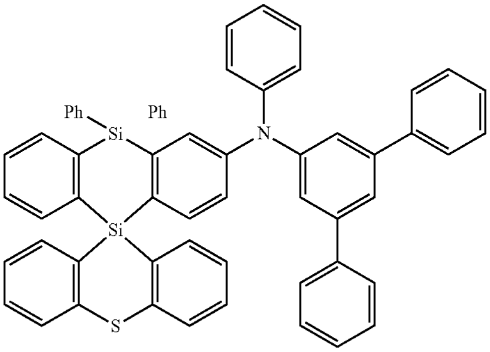
B309
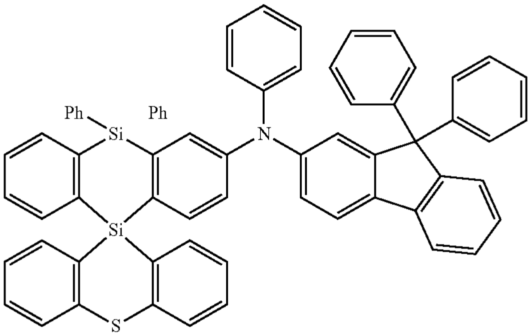

-continued
B310
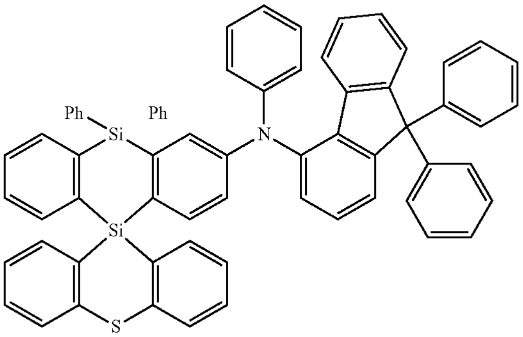
B311
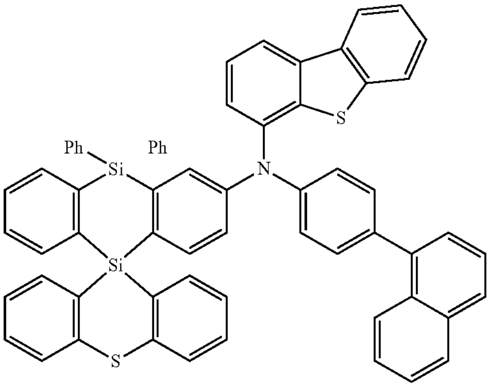
B312
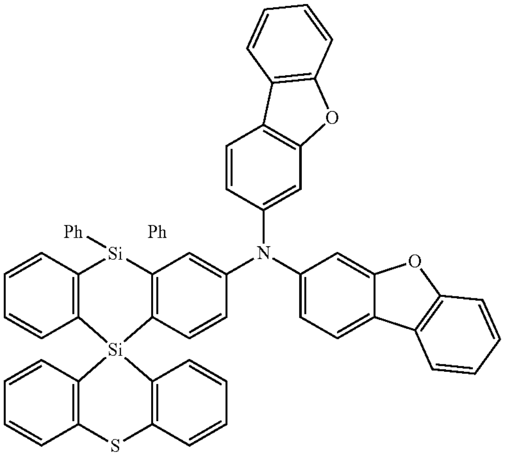
B313
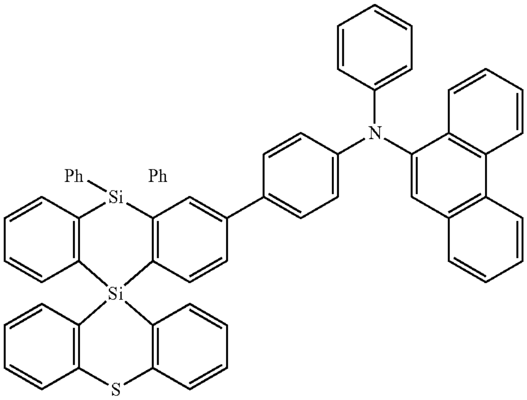
-continued
B314
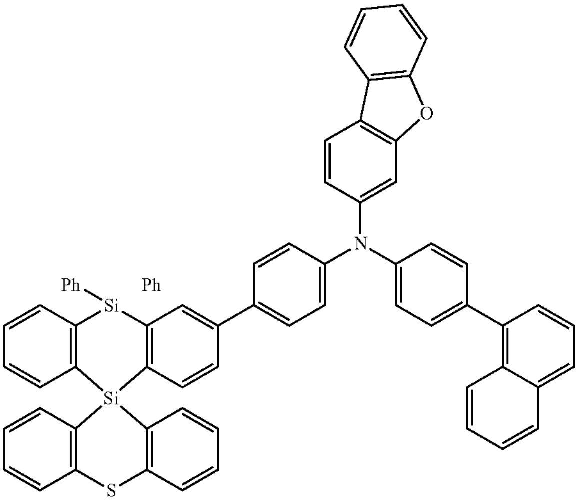
B315
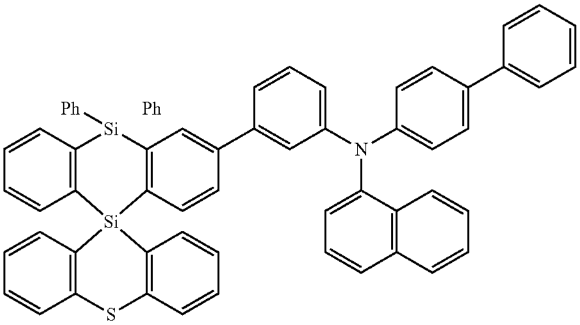
B316
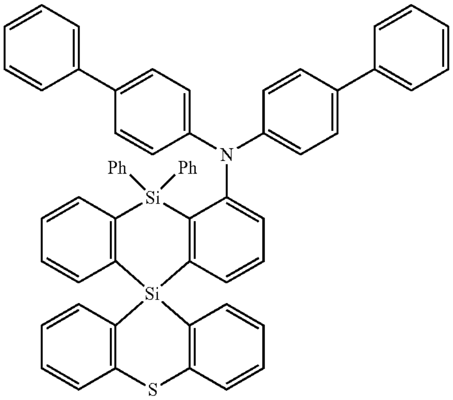

-continued
B317
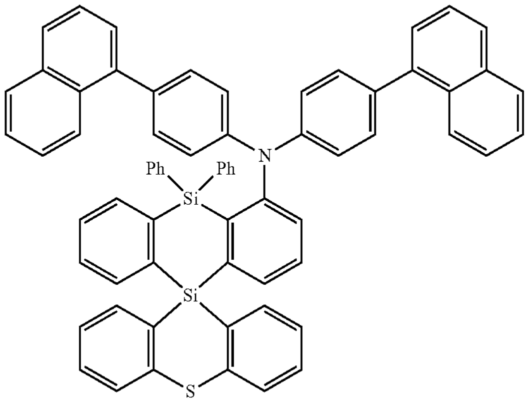
B318
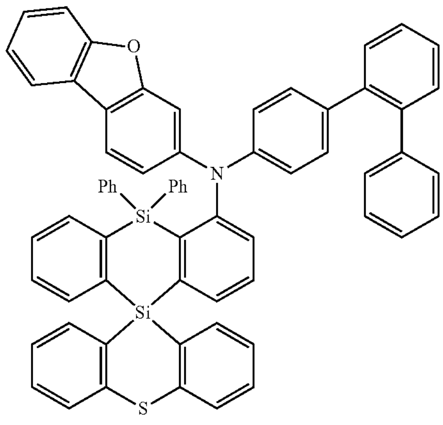
B319
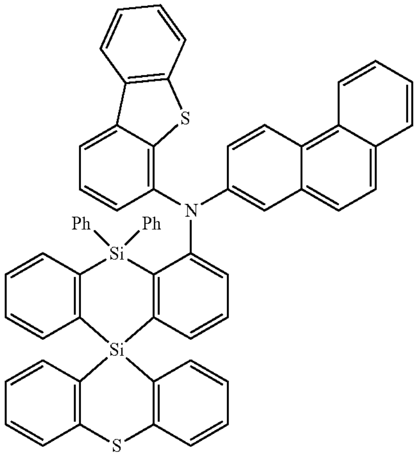
-continued
B320
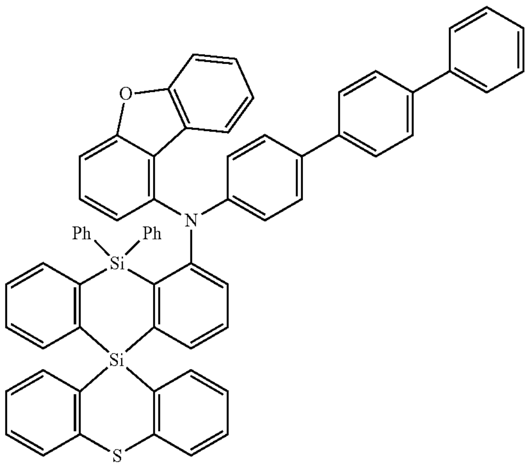
B321
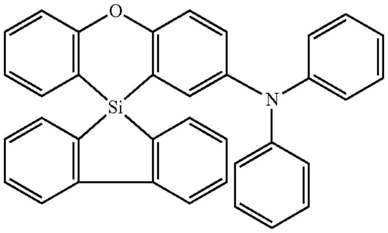
B322
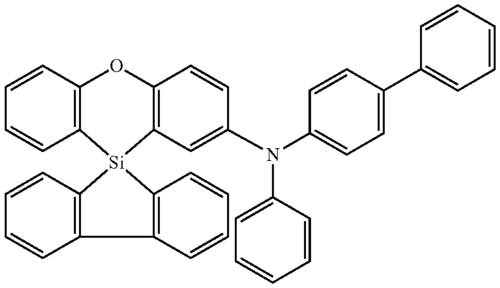
B323
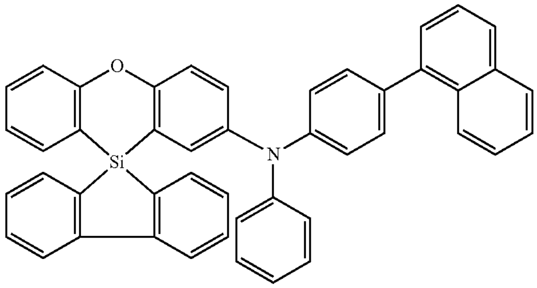
B324
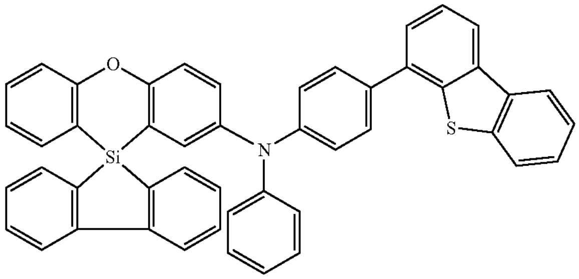

-continued
B325
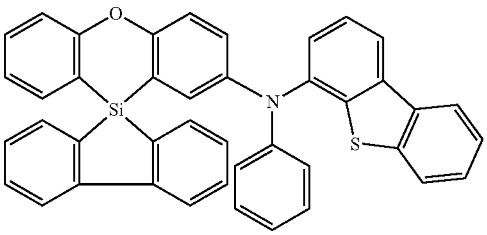
B326
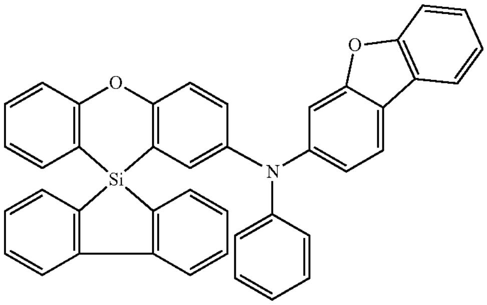
B327
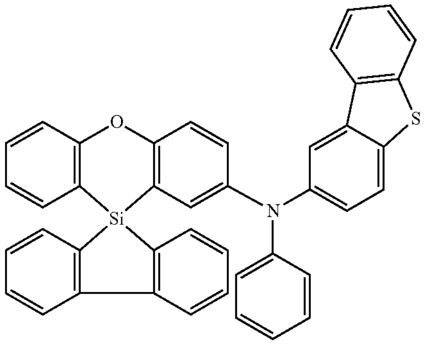
B328
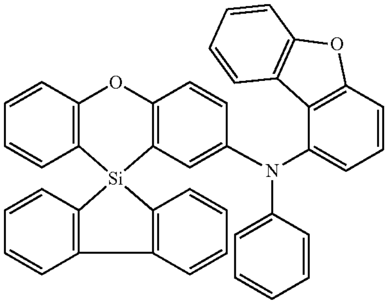
B329
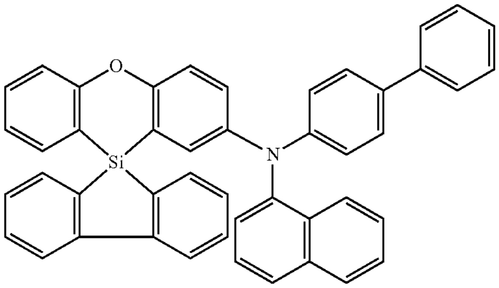
-continued
B330
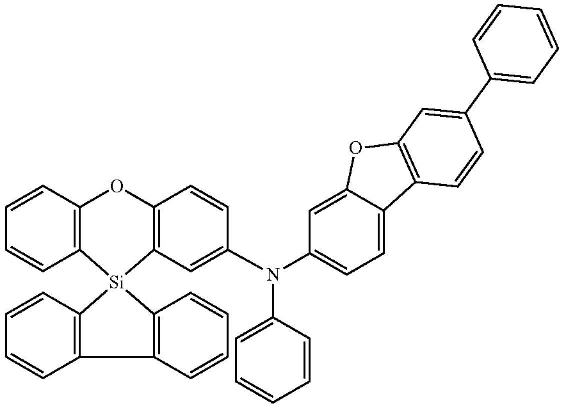
B331
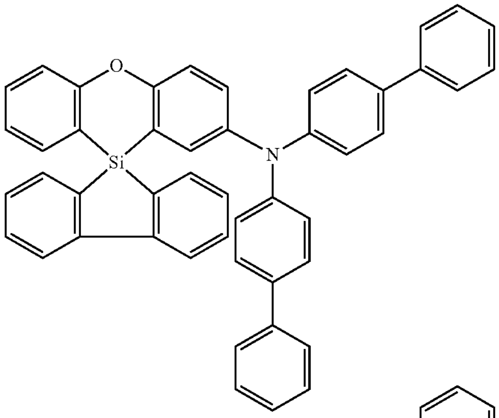
B332
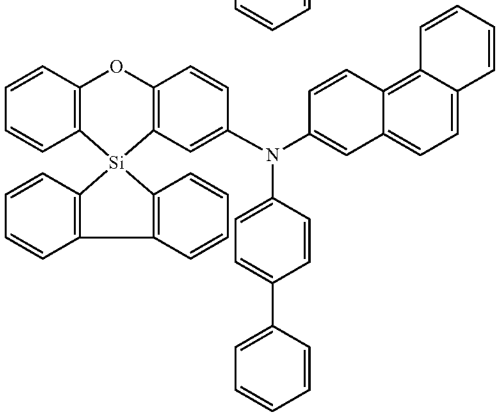
B333
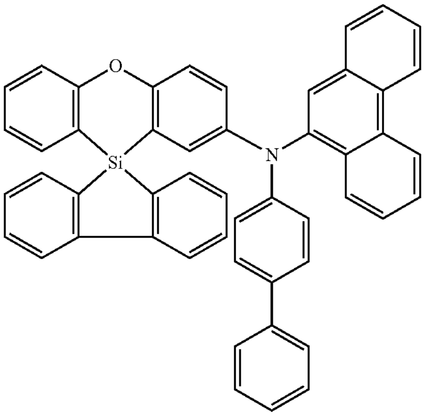

-continued
B334
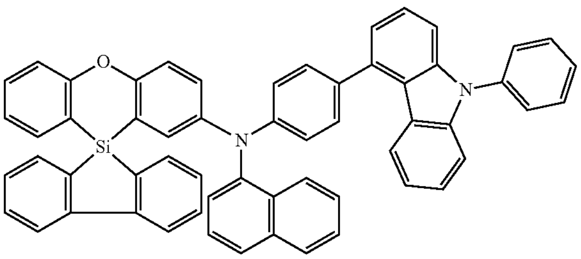
B335
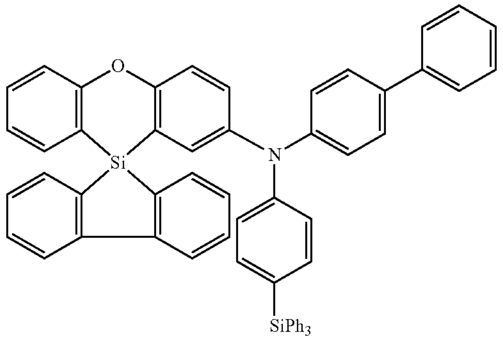
B336
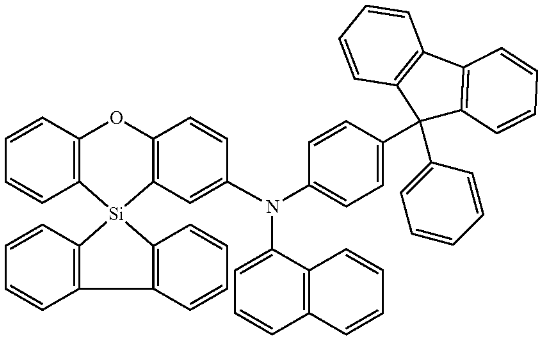
B337
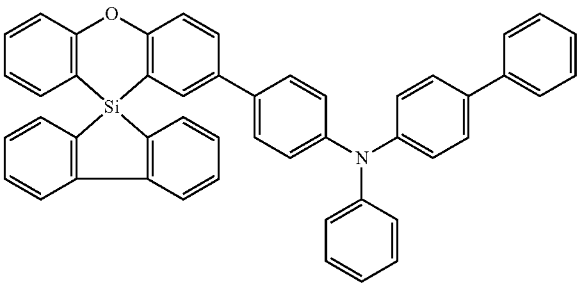
B338
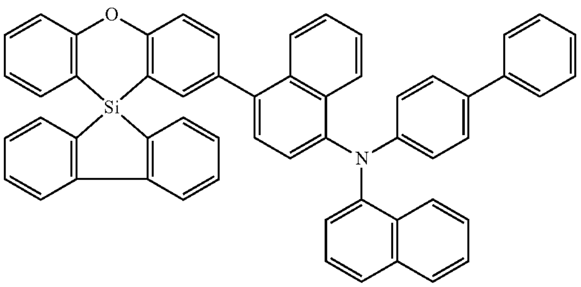
-continued
B339
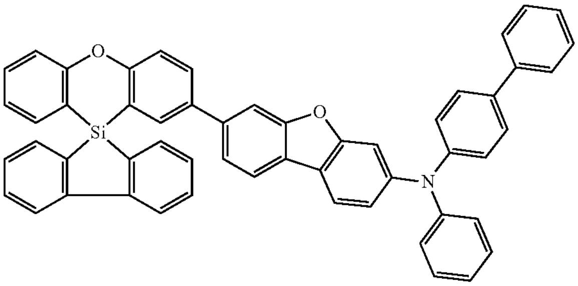
B340
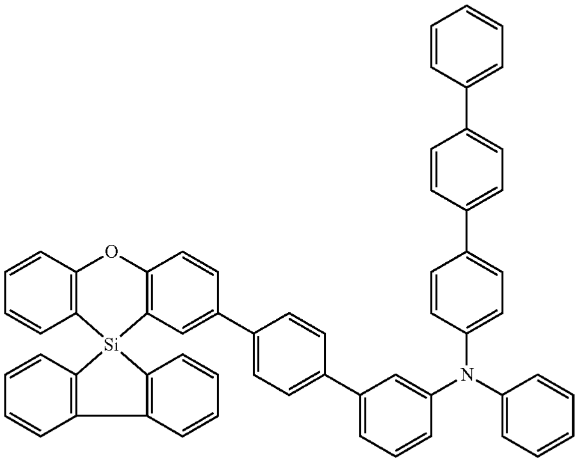
B341
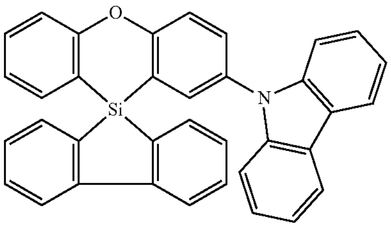
B342
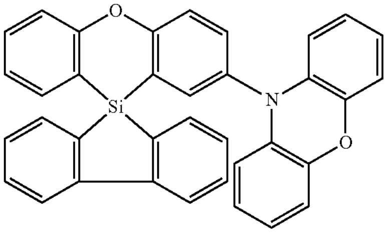
B343
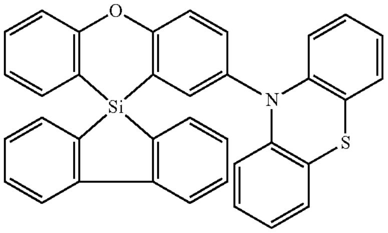

-continued
B344
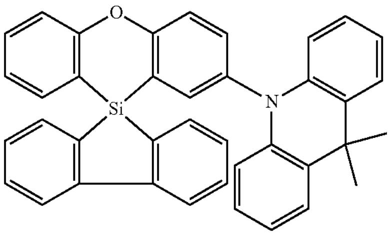
B345
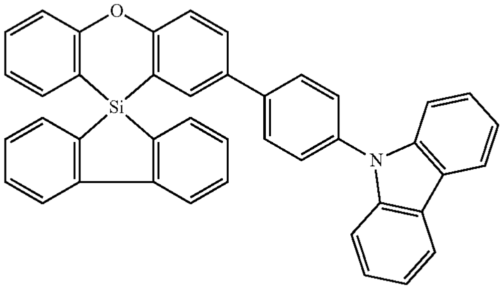
B346
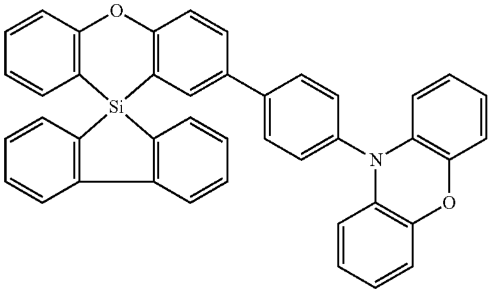
B347
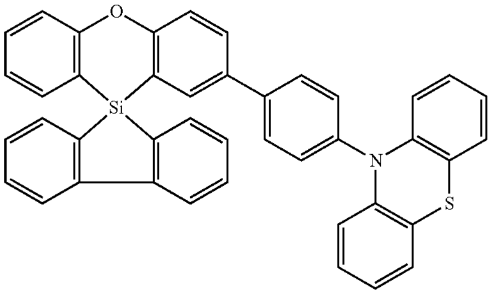
B348
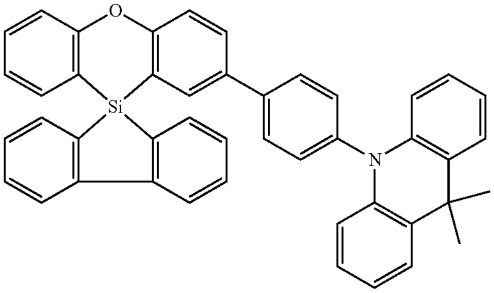
-continued
B349
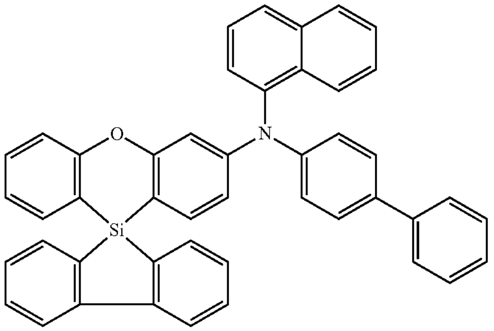
B350
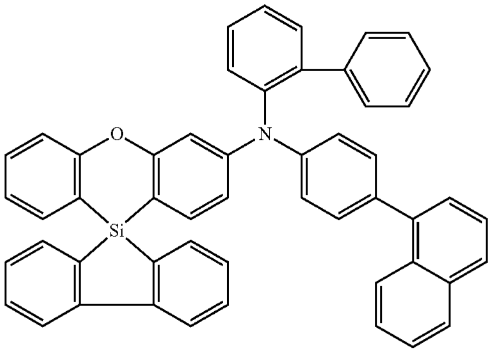
B351
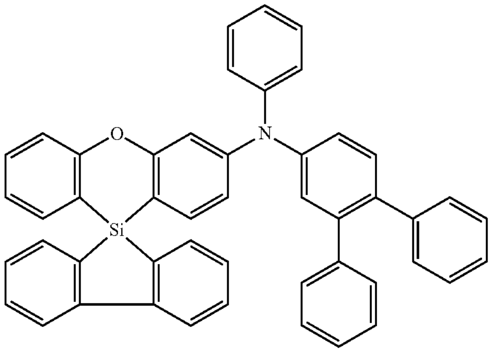
B352
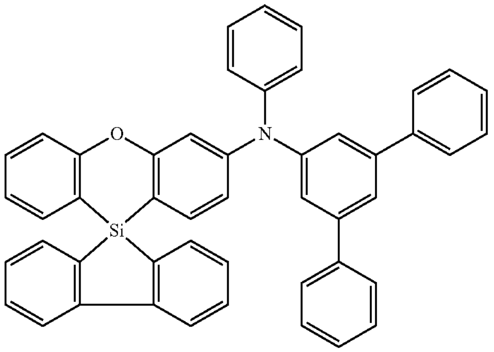

-continued
B353
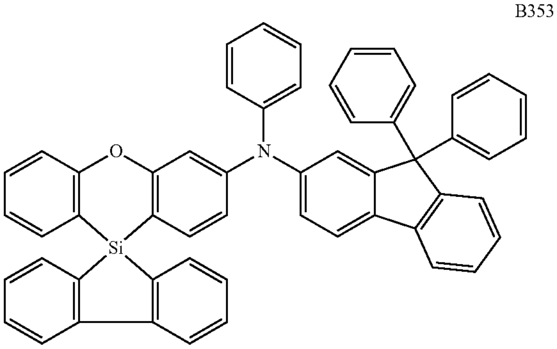
B354
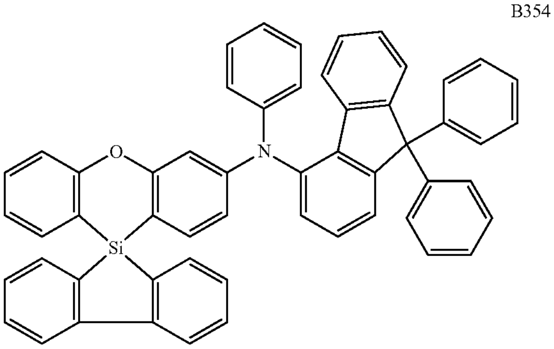
B355
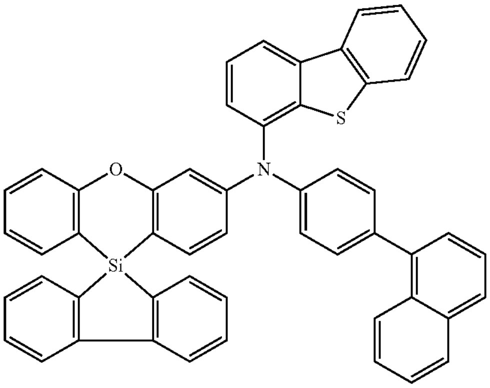
B356
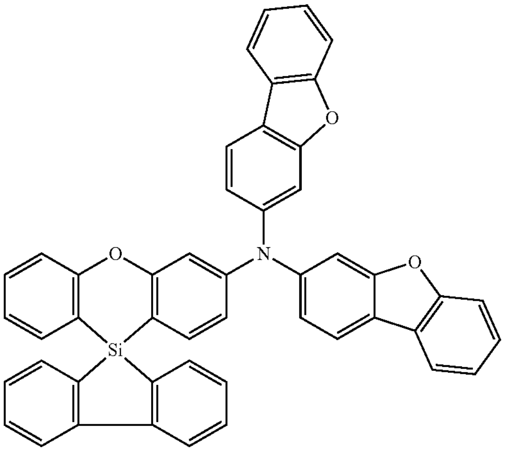
-continued
B357
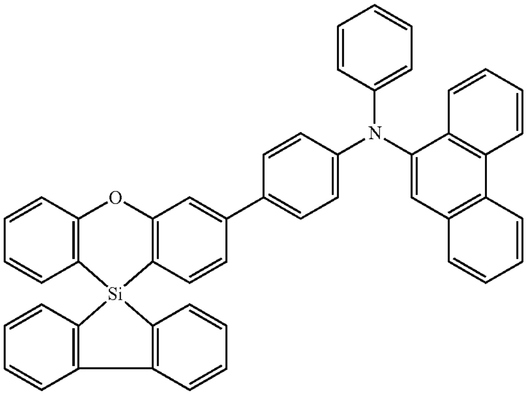
B358
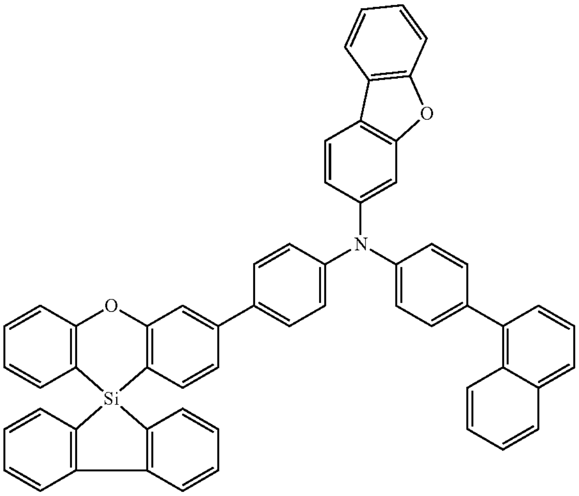
B359
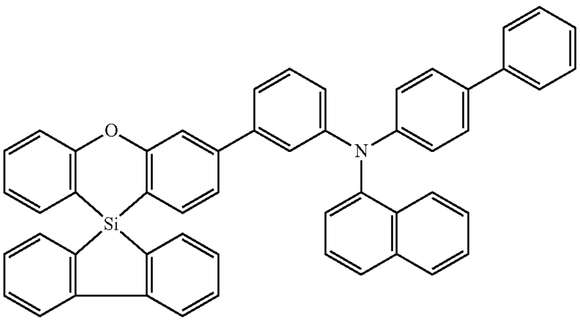

-continued
B360
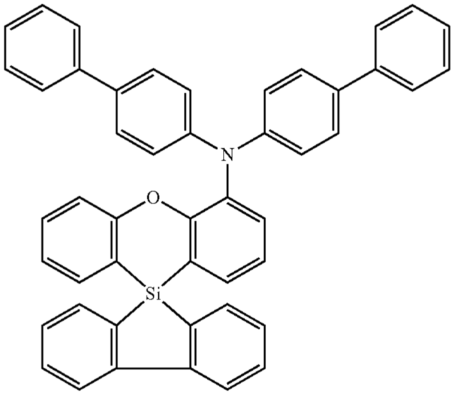
B361
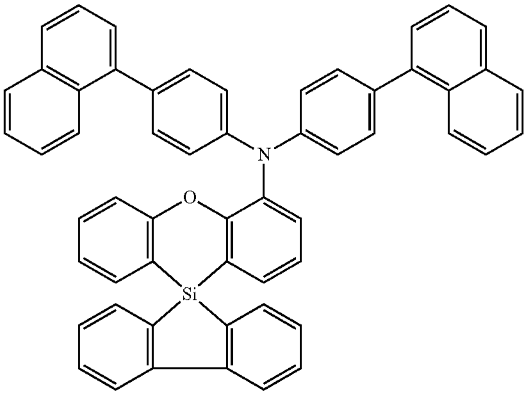
B362
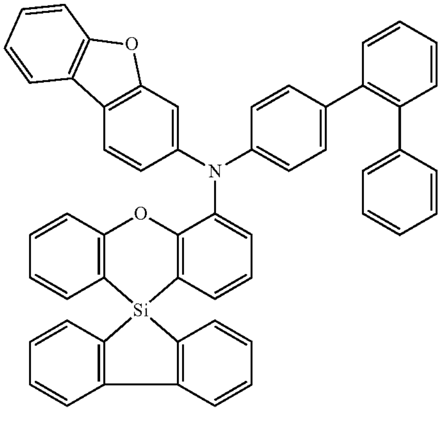
-continued
B363
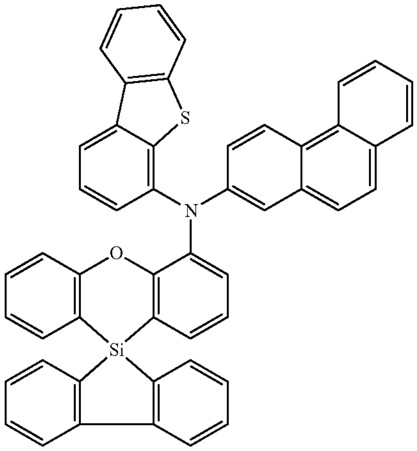
B364
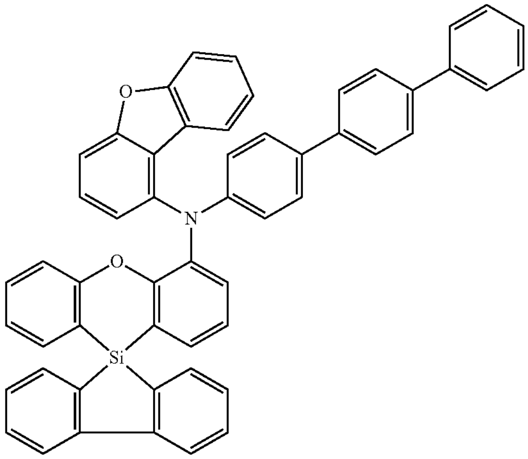
B365
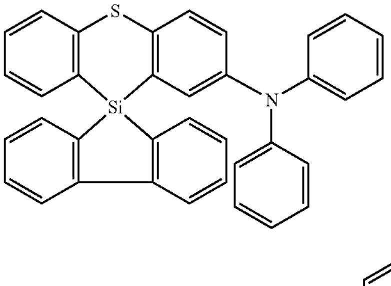
B366
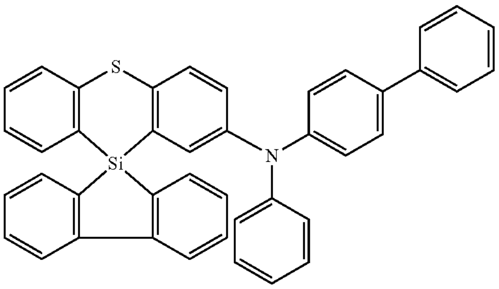

-continued
B367
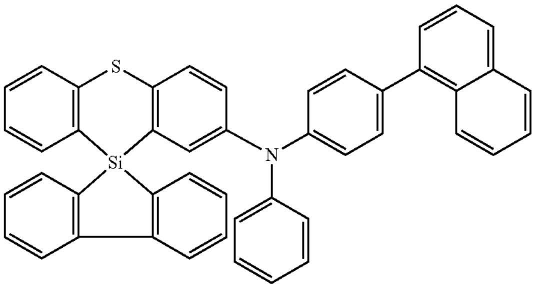
B368
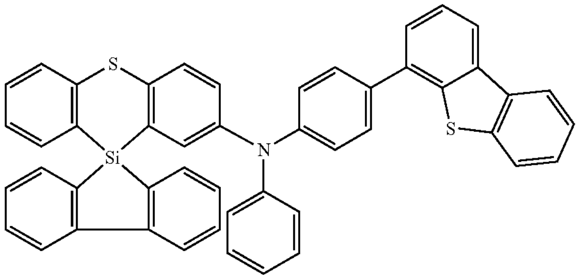
B369
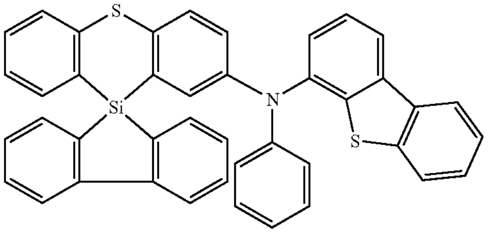
B370
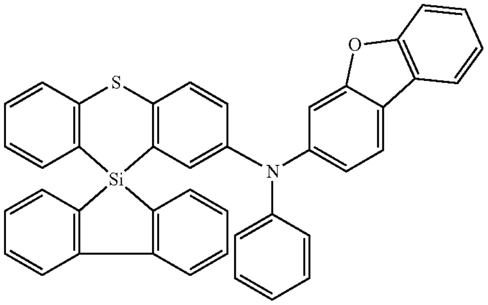
B371
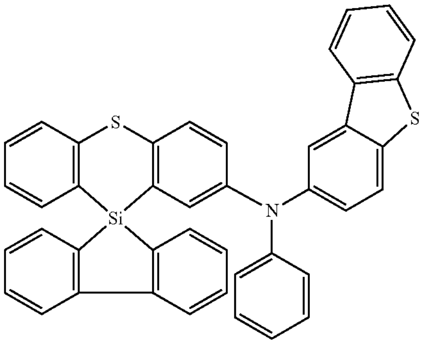
-continued
B372
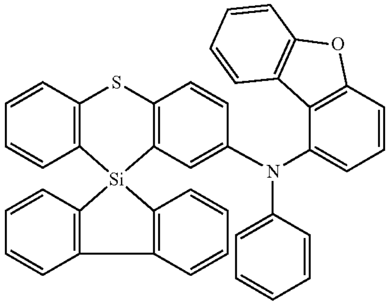
B373
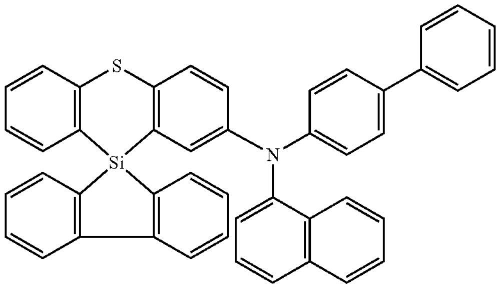
B374
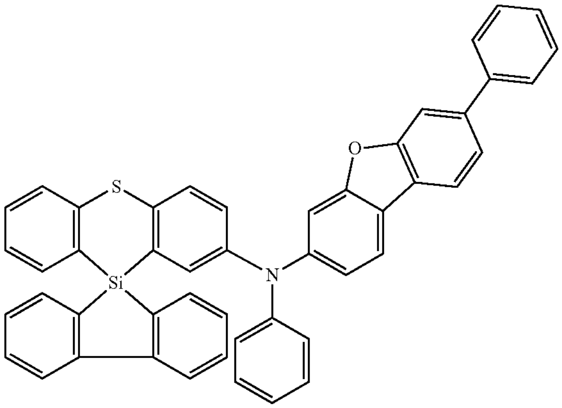
B375
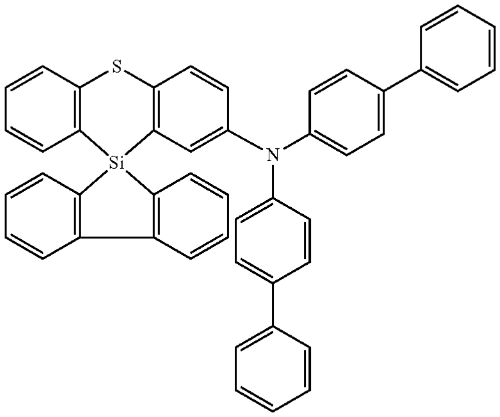

-continued
B376
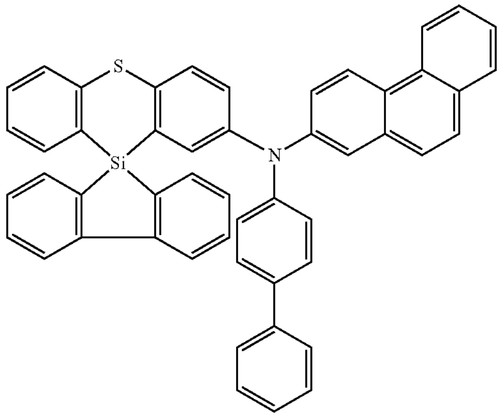
B377
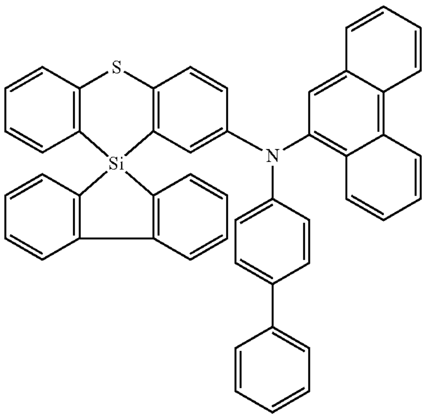
B378
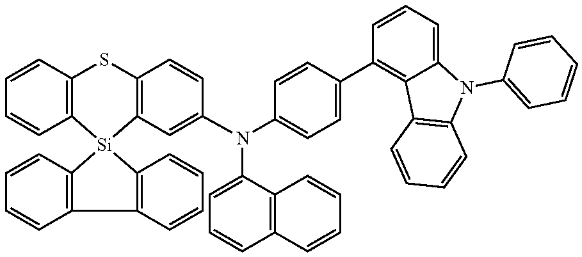
B379
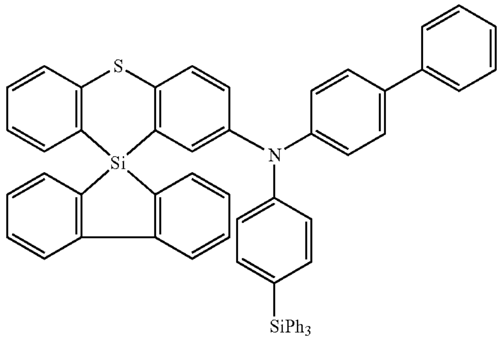
-continued
B380
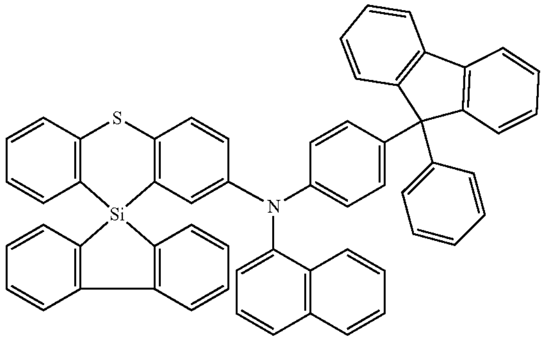
B381
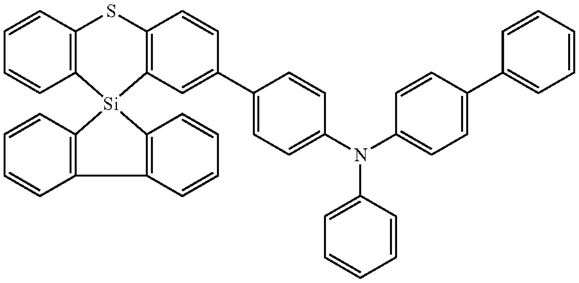
B382
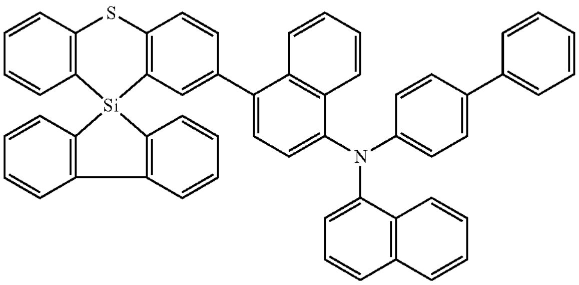
B383
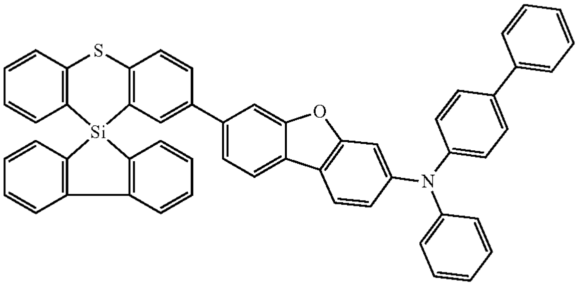

-continued
B384
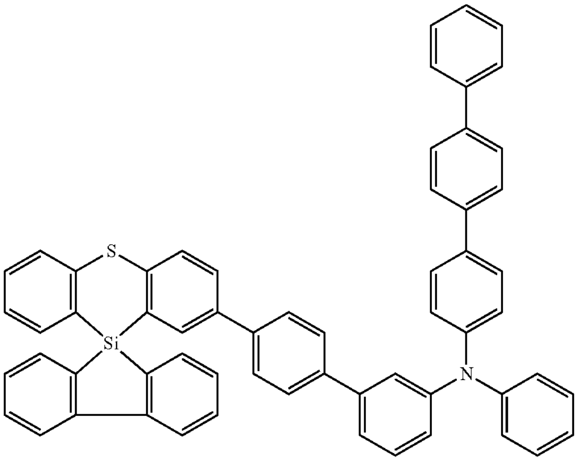
B385
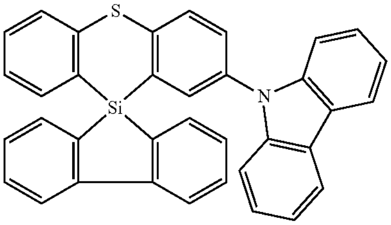
B386
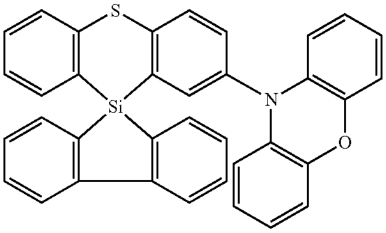
B387
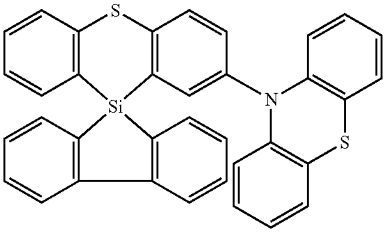
B388
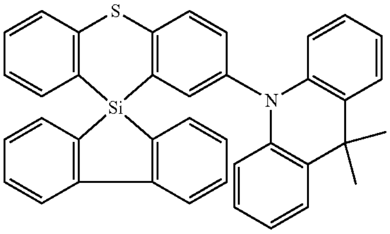
-continued
B389
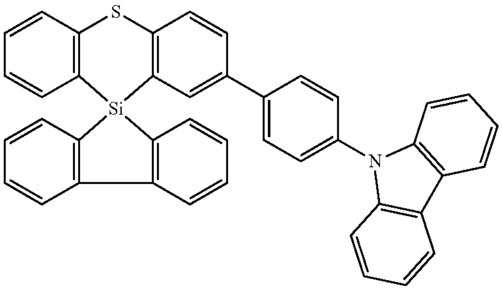
B390
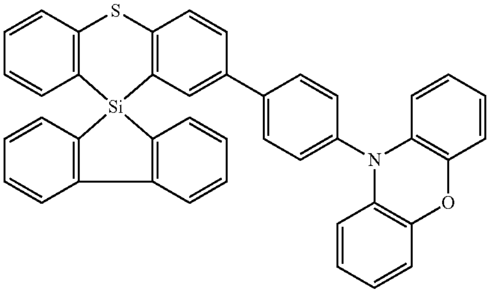
B391
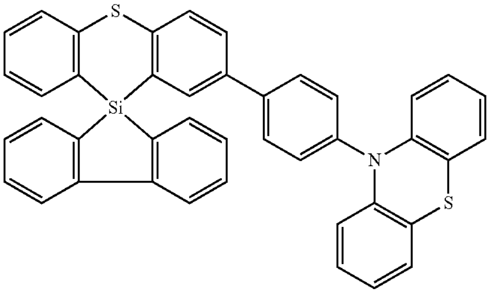
B392
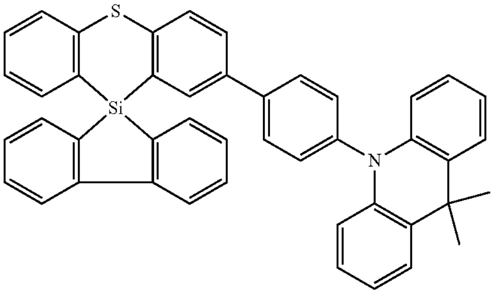
B393
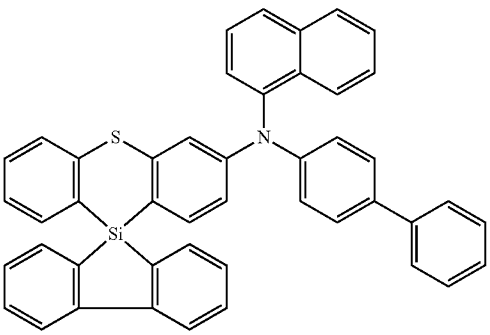

-continued
B394
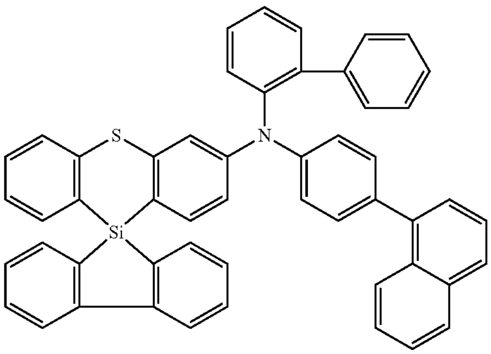
B395
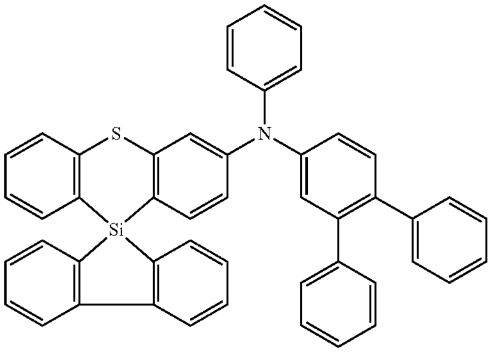
B396
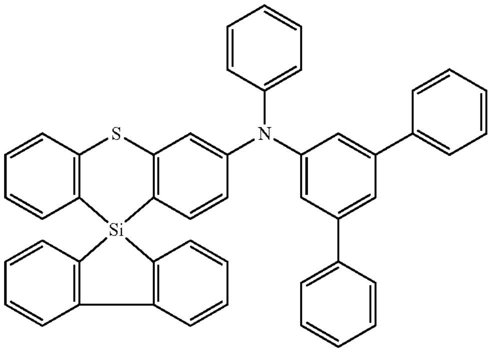
B397
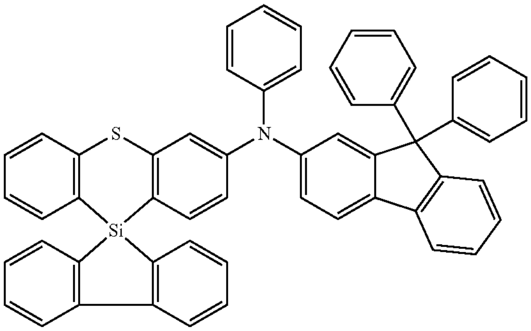
-continued
B398
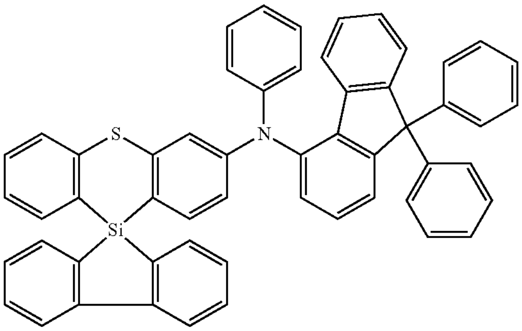
B399
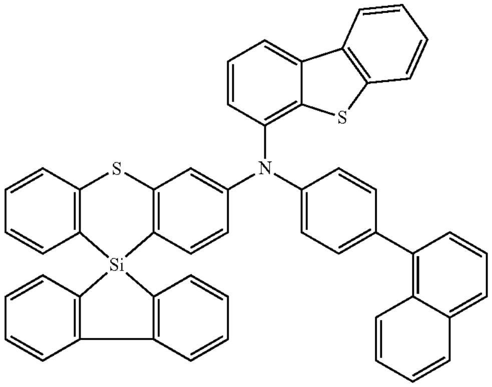
B400
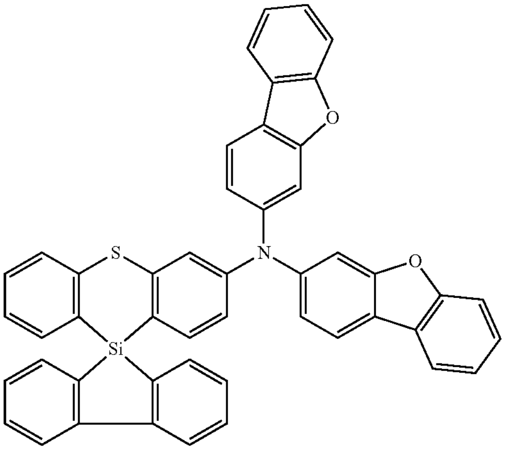
B401
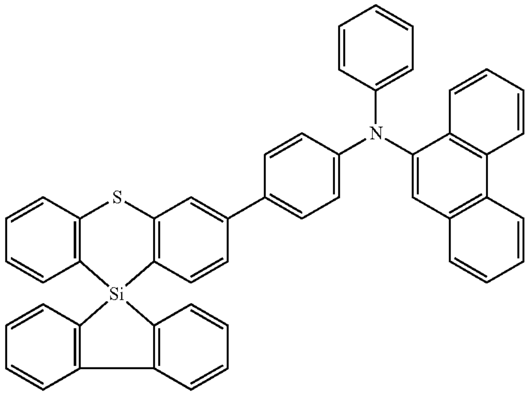

-continued
B402
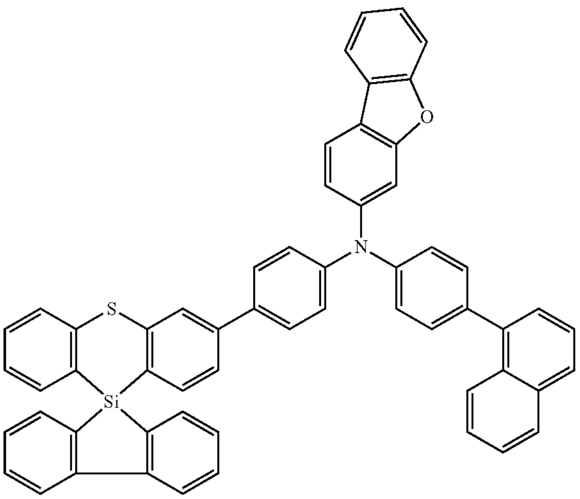
B403
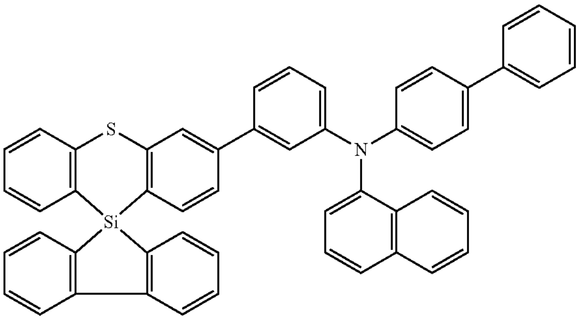
B404
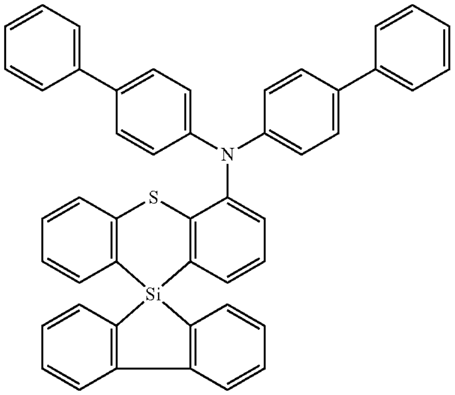
-continued
B405
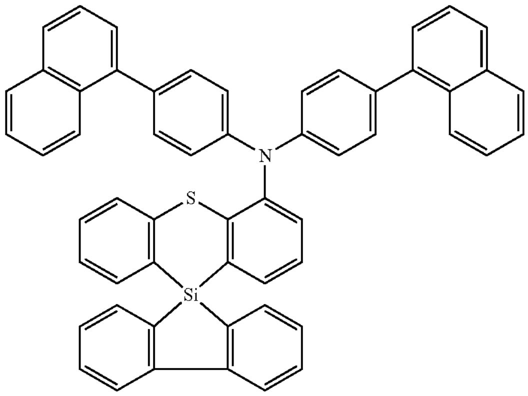
B406
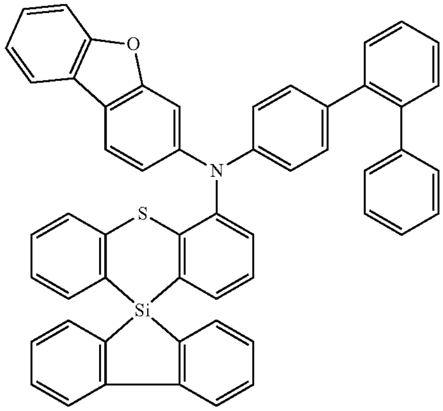
B407
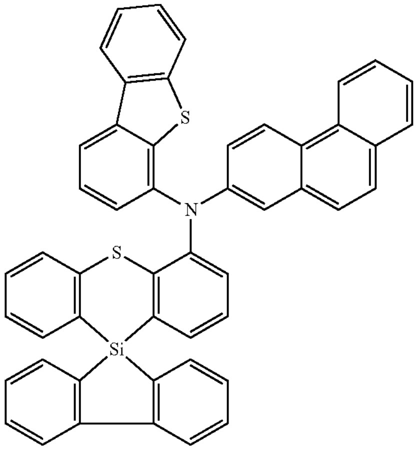

-continued
B408
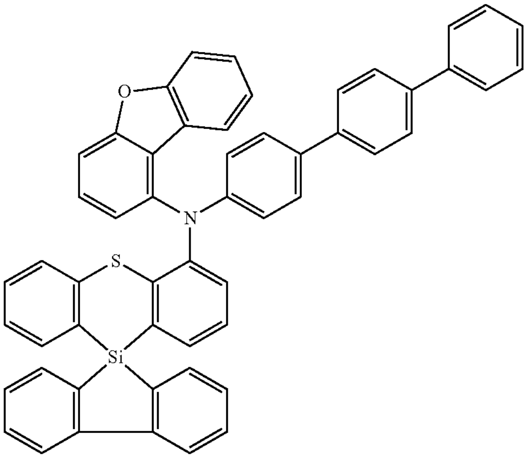
B409
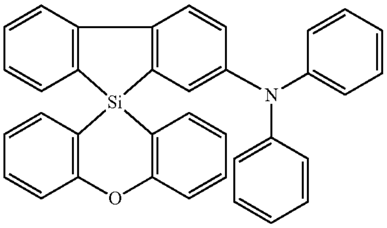
B410
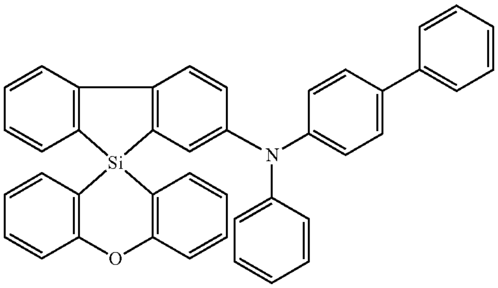
B411
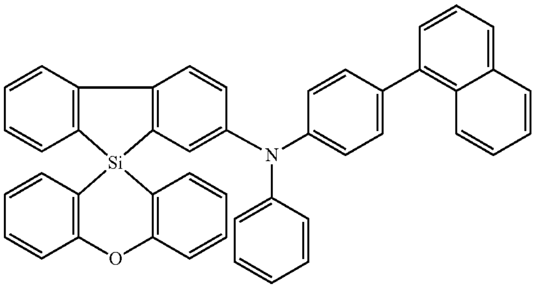
B412
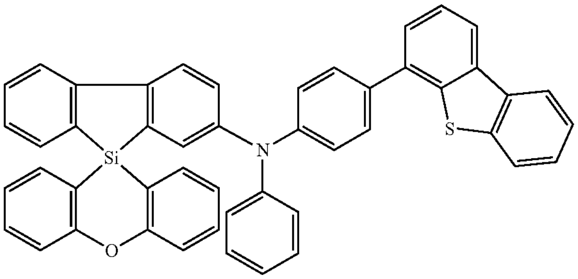
-continued
B413
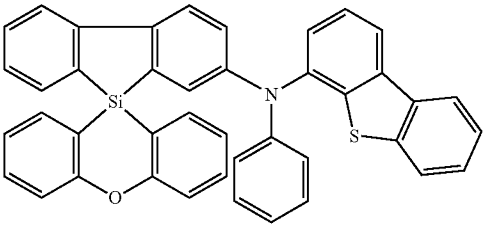
B414
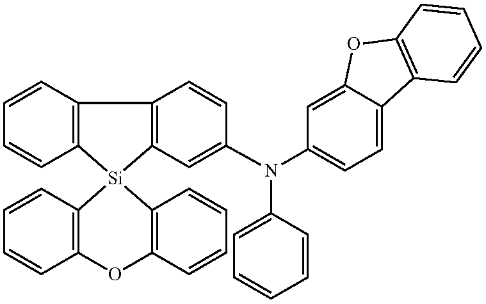
B415
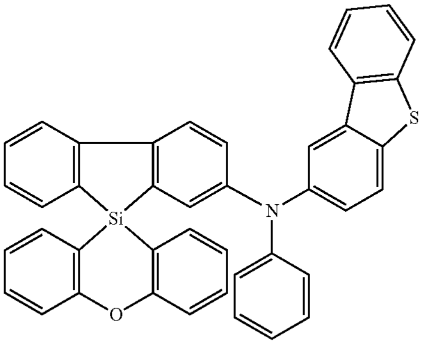
B416
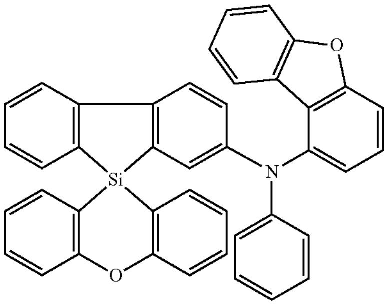
B417
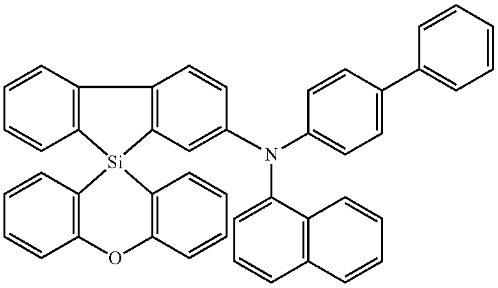

-continued
B418
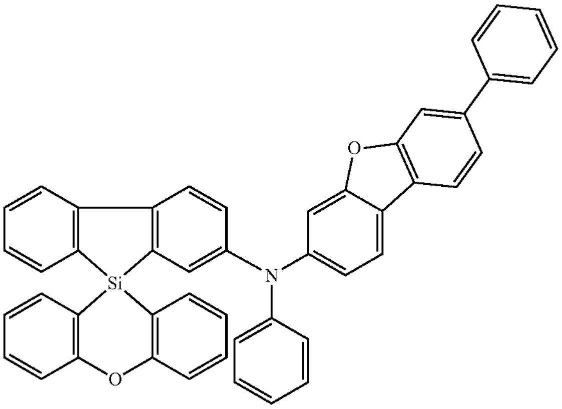
B419
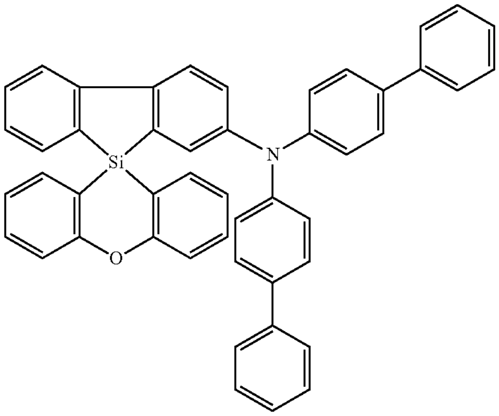
B420
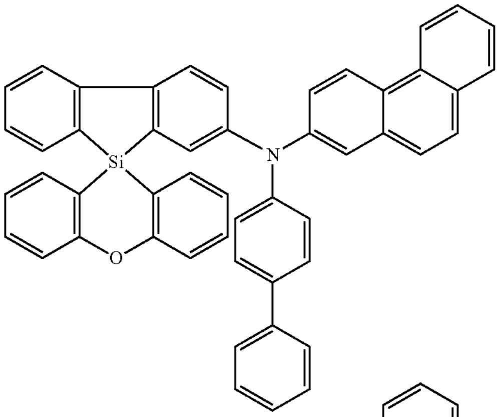
B421
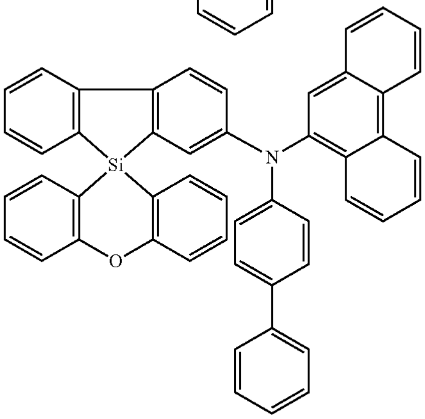
-continued
B422
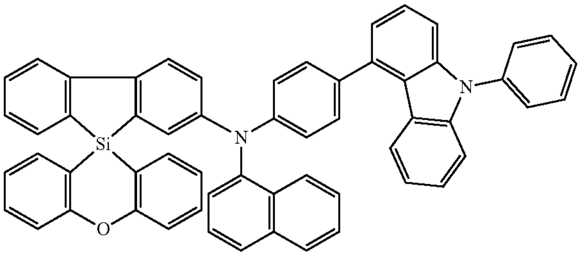
B423
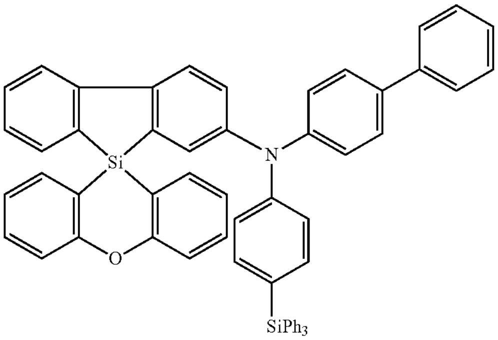
B424
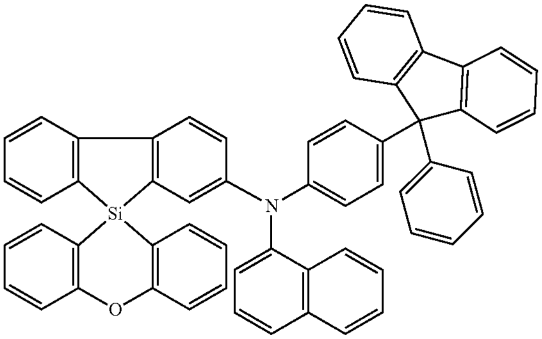
B425
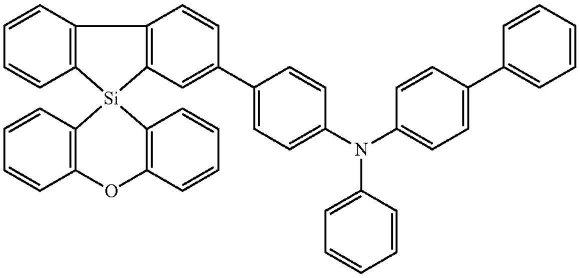
B426
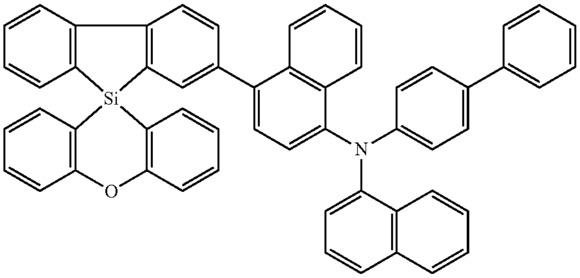

-continued
B427
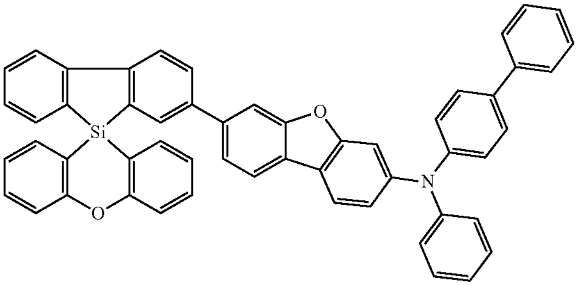
B428
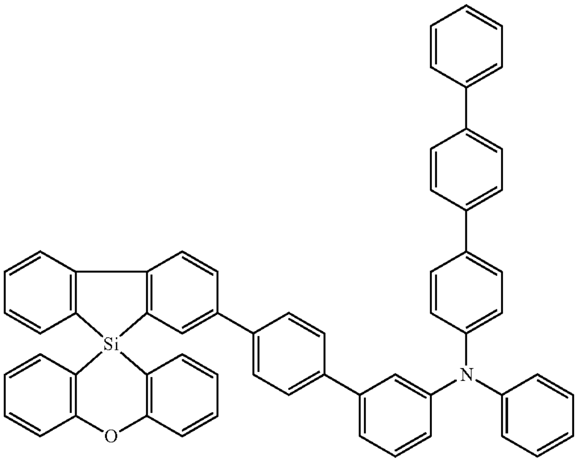
B429
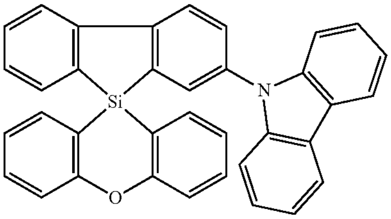
B430
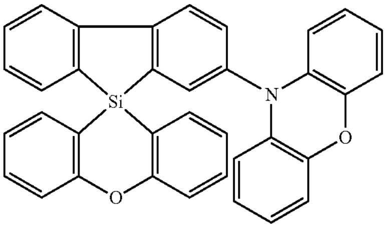
B431
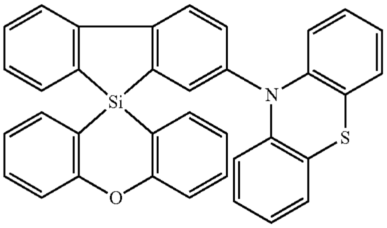
-continued
B432
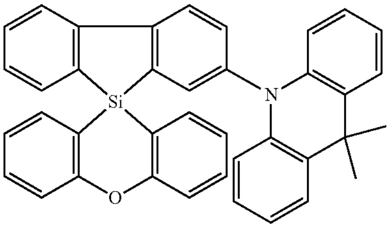
B433
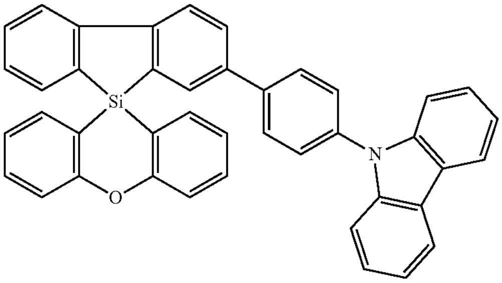
B434
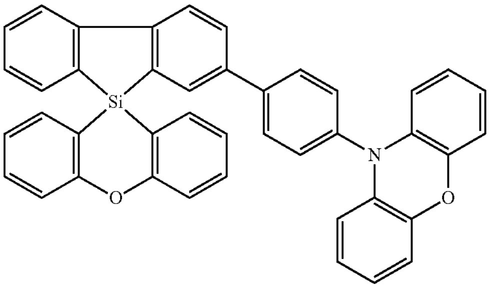
B345
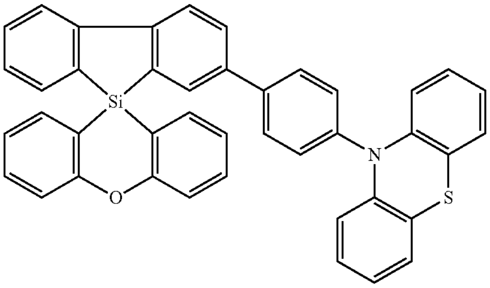
B436
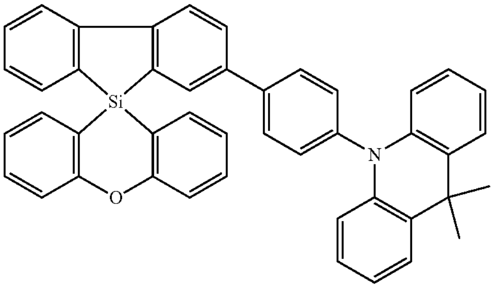

-continued
B437
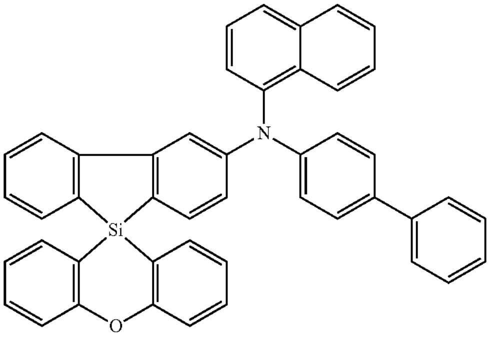
B438
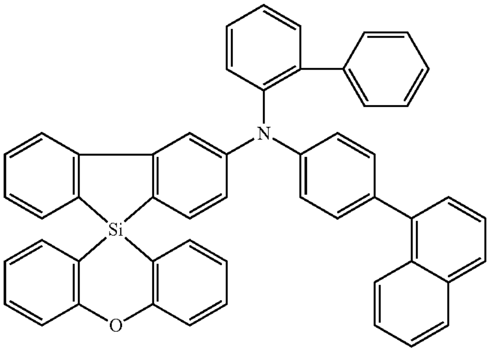
B439
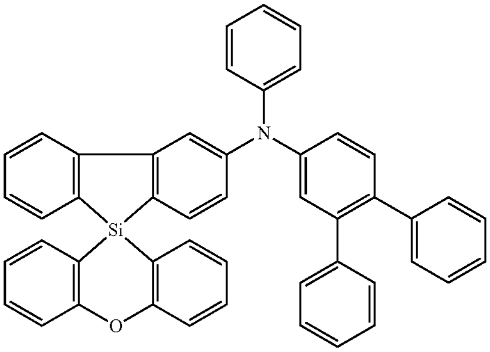
B440
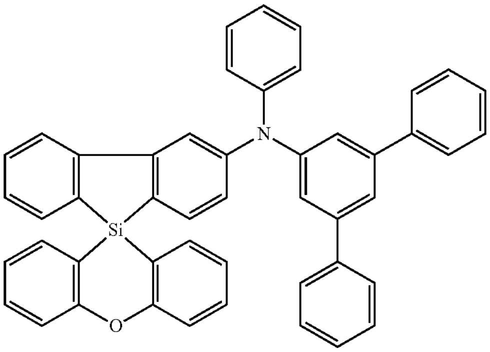
B441
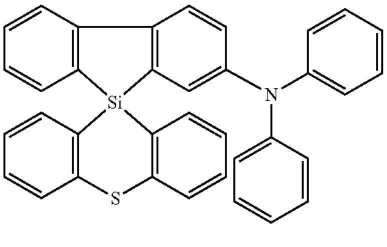
-continued
B442
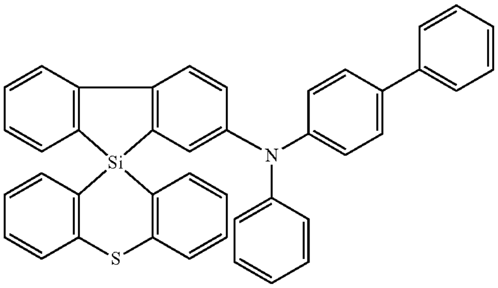
B443
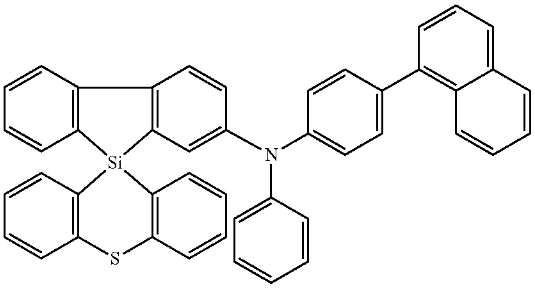
B444
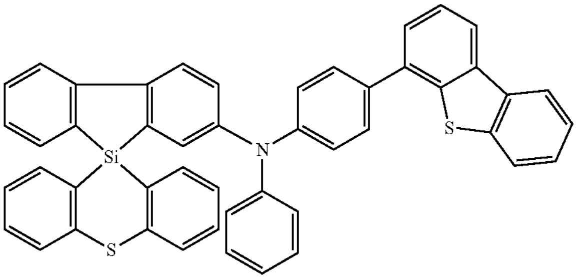
B445
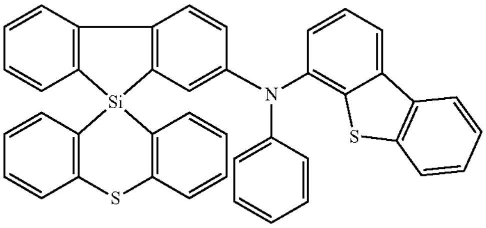
B446
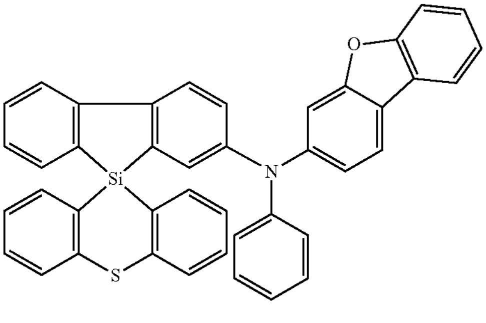

-continued
B447
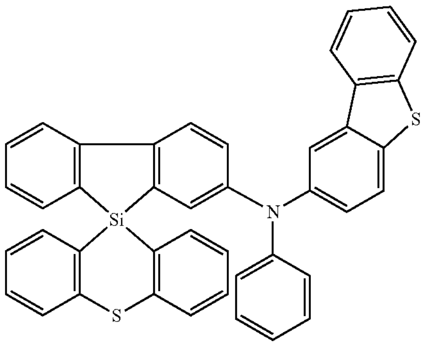
B448
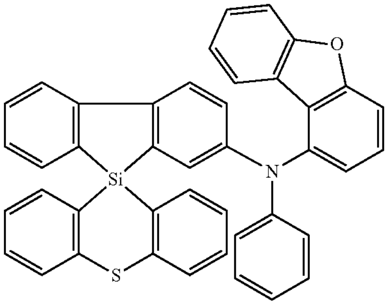
B449
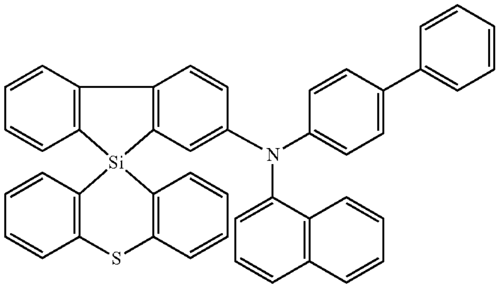
B450
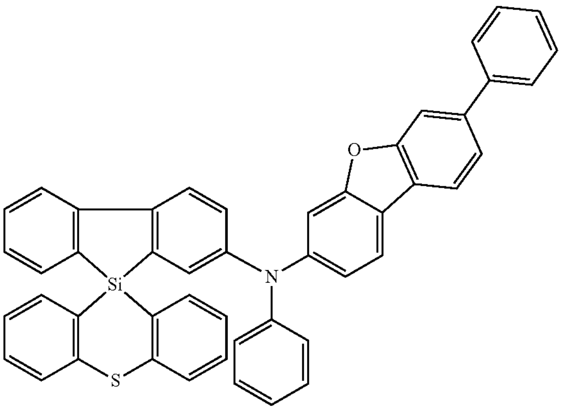
-continued
B451
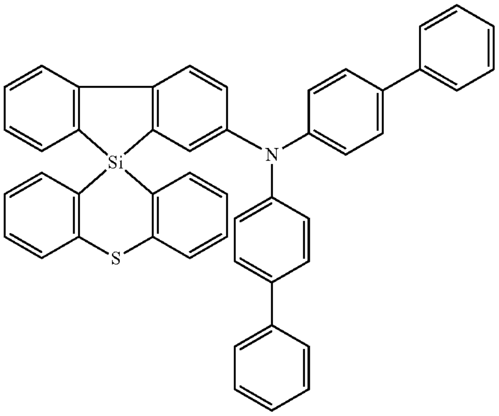
B452
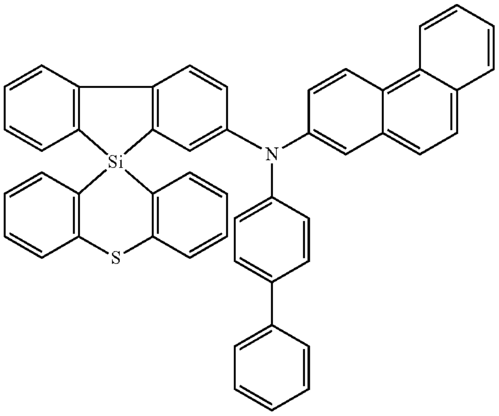
B453
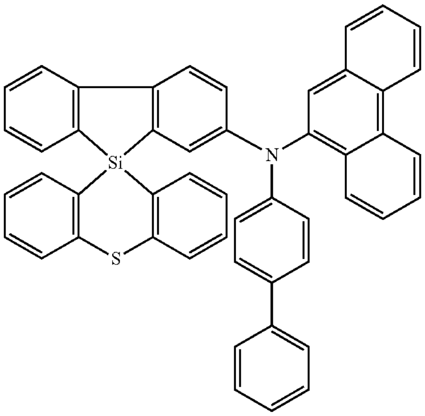
B454
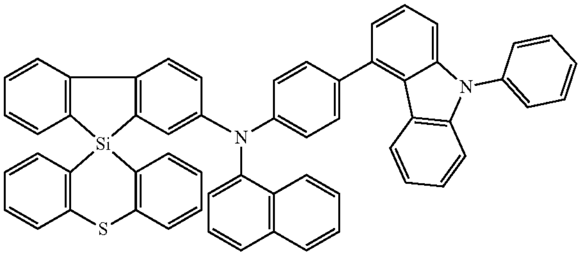

-continued
B455
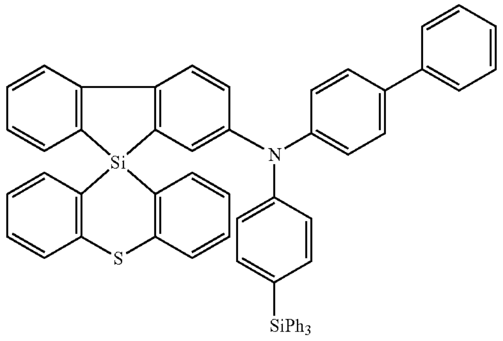
B456
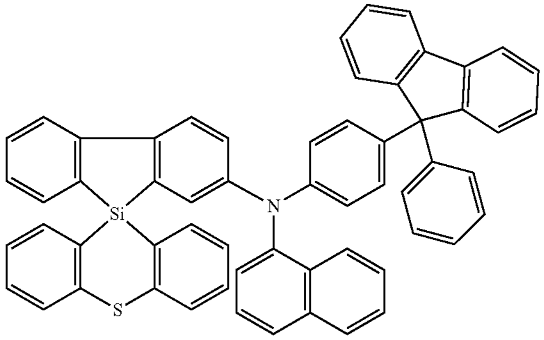
B457
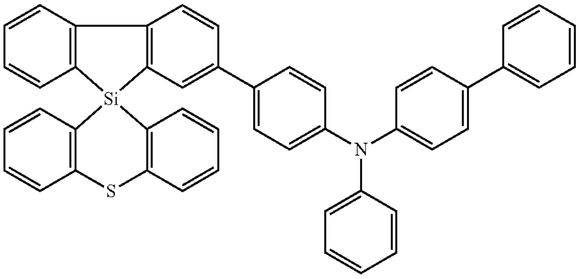
B458
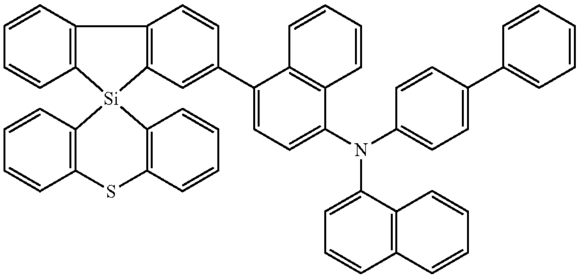
B459
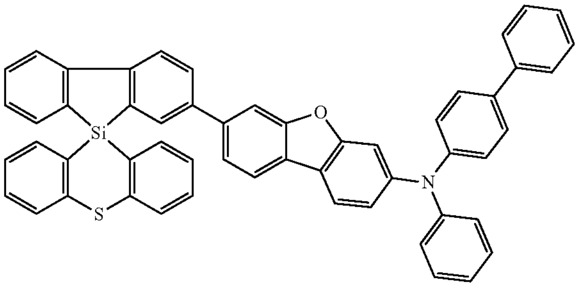
-continued
B460
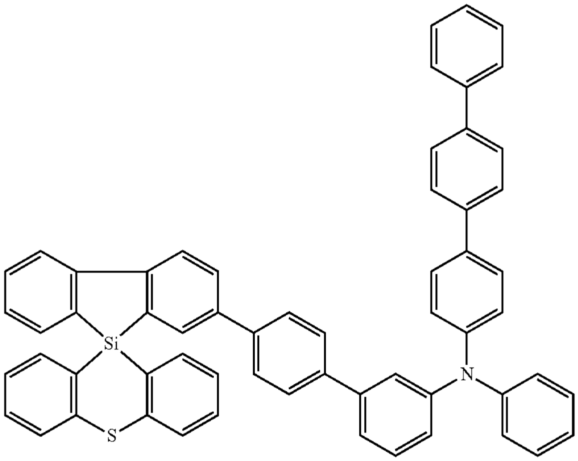
B461
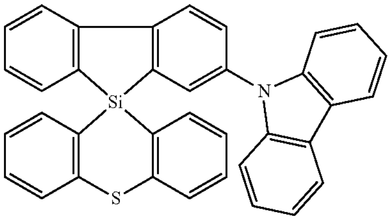
B462
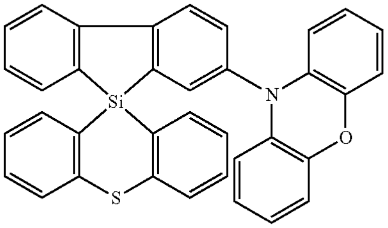
B463
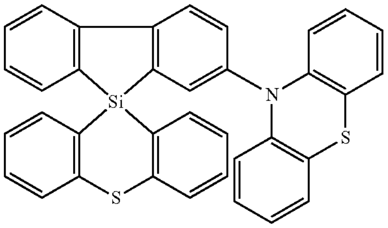
B464
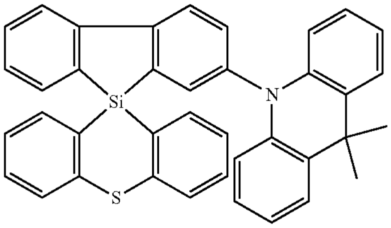

-continued
B465
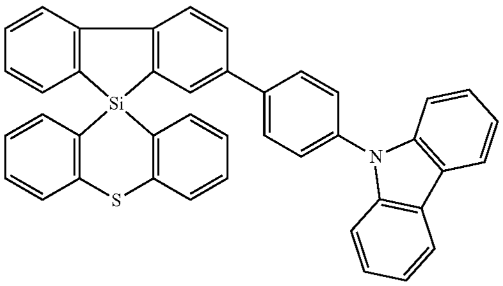
B466
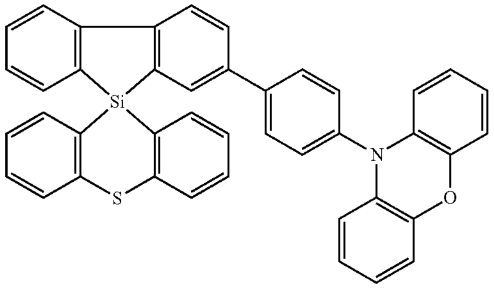
B367
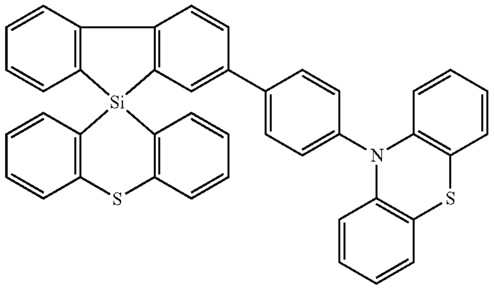
B468
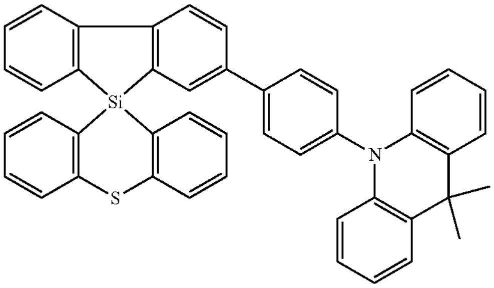
B469
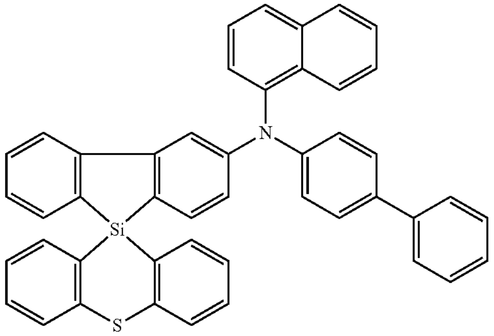
-continued
B470
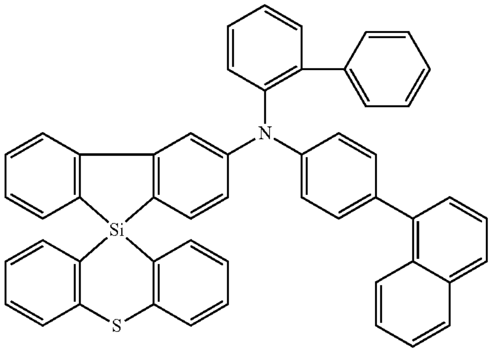
B471
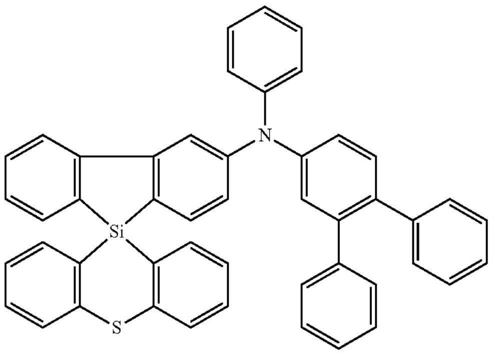
B472
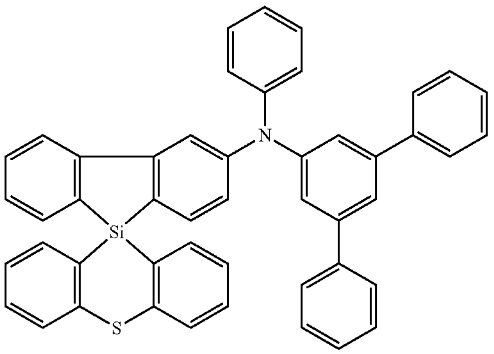
B473
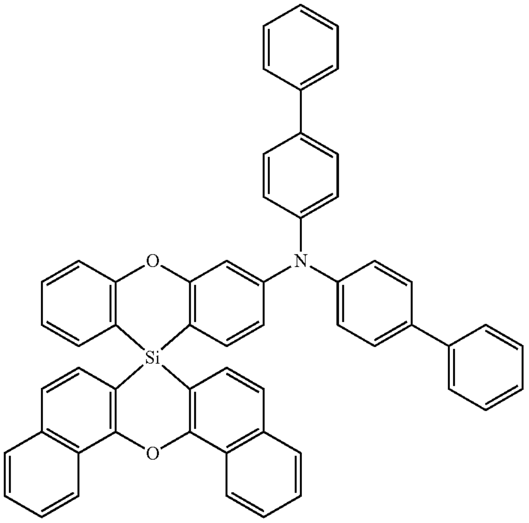

-continued

B474

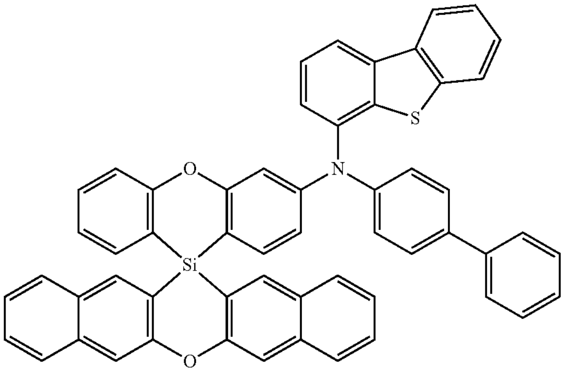

B475

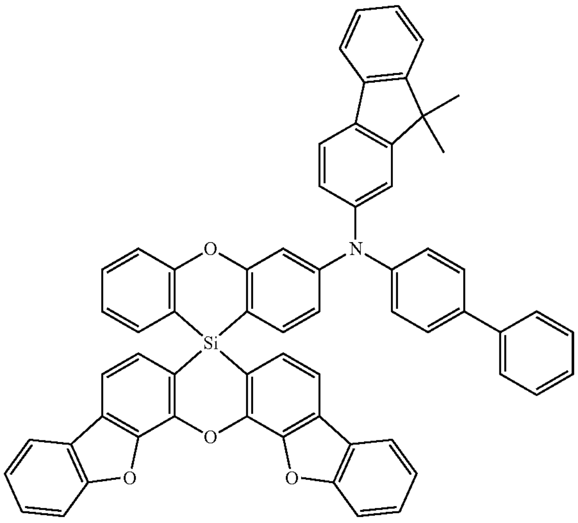

B476

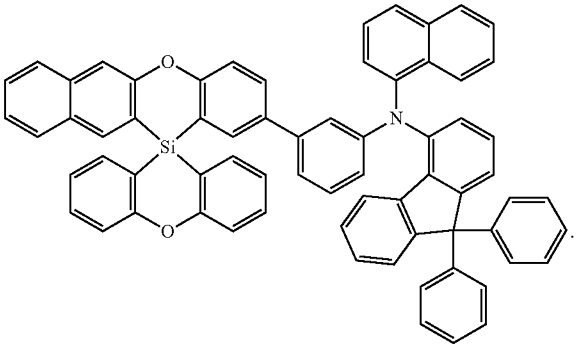

12. An organic electroluminescence device, comprising:

a first electrode;

a second electrode on the first electrode; and a plurality of organic material layers between the first electrode and the second electrode, wherein at least one organic material layer among the plurality of organic material layers comprises a monoamine compound represented by following Formula 1:

[Formula 1]

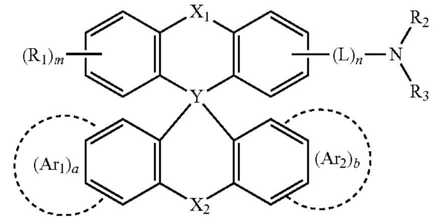

wherein in Formula 1,

Y is C or Si, when Y is C, $X_1$ and $X_2$ are each independently O, S, or $SiR_4R_5$, and $X_1$ and $X_2$ are different from each other, when Y is Si, $X_1$ and $X_2$ are each independently O, S, $SiR_4R_5$, or a direct linkage, and both $X_1$ and $X_2$ are direct linkages is excluded, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring, L is a direct linkage, a substituted or unsubstituted arylene group having 6 to 30 carbon atoms, or a substituted or unsubstituted heteroarylene group having 2 to 30 carbon atoms for forming a ring, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, a, b and n are each independently 0 or 1, and m is an integer of 0 to 4, wherein the organic material layers comprise:

a hole transport region on the first electrode;

an emission layer on the hole transport region; and an electron transport region on the emission layer, and wherein the hole transport region comprises the monoamine compound represented by Formula 1.

13. An amine compound represented by following Formula 1:

[Formula 1]

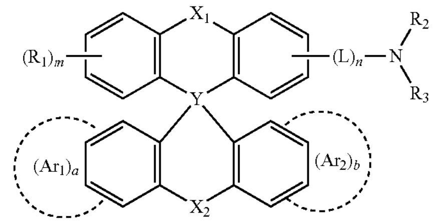

wherein in Formula 1,

Y is C or Si, when Y is C, $X_1$ and $X_2$ are each independently O, S, or $SiR_4R_5$, and $X_1$ and $X_2$ are different from each other, when Y is Si, $X_1$ and $X_2$ are each independently O, S, $SiR_4R_5$, or a direct linkage, and both $X_1$ and $X_2$ are direct linkages is excluded, $R_1$ to $R_5$ are each independently a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring, L is a direct linkage, a substituted or unsubstituted arylene group having 6 to 30 carbon atoms, or a substituted or unsubstituted heteroarylene group having 2 to 30 carbon atoms for forming a ring, $Ar_1$ and $Ar_2$ are each independently a substituted or unsubstituted hydrocarbon ring having 6 to 40 carbon atoms for forming a ring, or a substituted or unsubstituted heterocycle having 2 to 40 carbon atoms for forming a ring, a, b and n are each independently 0 or 1, and m is an integer of 0 to 4.

14. The amine compound of claim 13, wherein the monoamine compound represented by Formula 1 is represented by following Formula 2 or Formula 3:

[Formula 2]

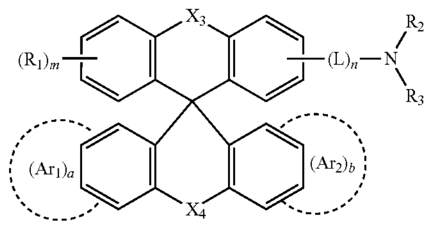

[Formula 3]

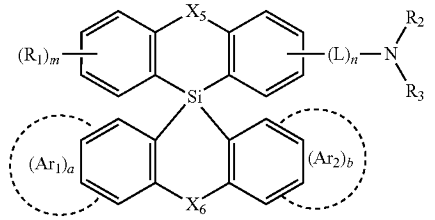

wherein in Formula 2, $X_3$ and $X_4$ are each independently O, S, or $SiR_4R_5$, and $X_3$ and $X_4$ are different from each other, wherein in Formula 3, $X_5$ and $X_6$ are each independently O, S, $SiR_4R_5$, or a direct linkage, and both $X_5$ and $X_6$ are direct linkages is excluded, and wherein in Formulae 2 and 3, $R_1$ to $R_5$, L, $Ar_1$, $Ar_2$, a, b, m and n are the same as respectively defined in association with Formula 1.

15. The amine compound of claim 14, wherein the amine compound represented by Formula 2 is represented by any one of following Formulae 2-1 to 2-6:

[Formula 2-1]

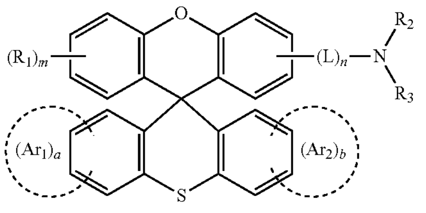

-continued

[Formula 2-2]

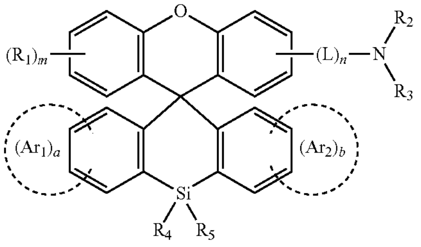

[Formula 2-3]

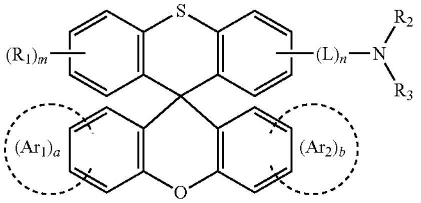

[Formula 2-4]

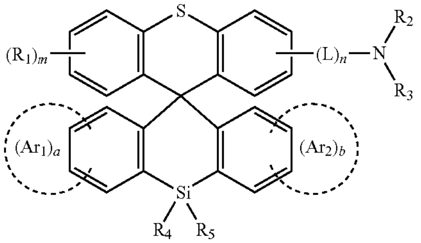

[Formula 2-5]

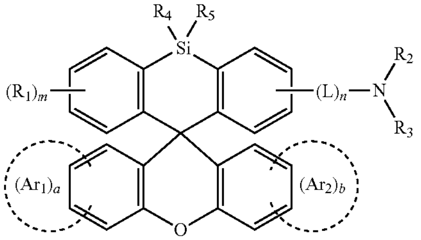

[Formula 2-6]

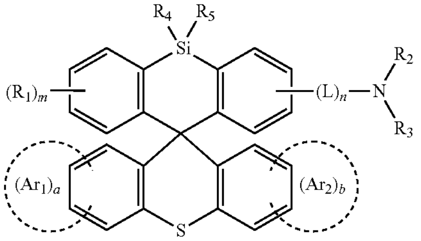

wherein in Formulae 2-1 to 2-6, $R_1$ to $R_5$, L, $Ar_1$, $Ar_2$, a, b, m and n are the same as respectively defined in association with Formula 1.

16. The amine compound of claim 14, wherein the amine compound represented by Formula 3 is represented by any one of following Formulae 3-1 to 3-11:

-continued
[Formula 3-1]
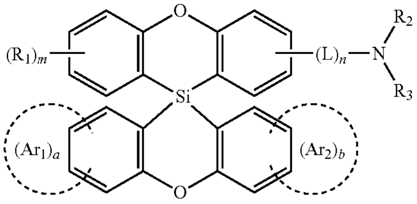
[Formula 3-2]
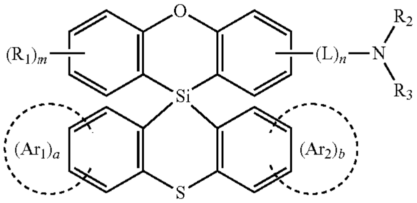
[Formula 3-3]
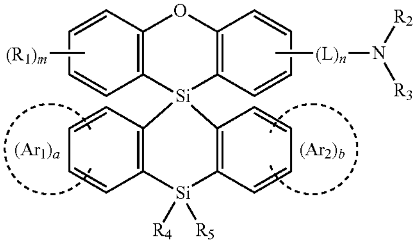
[Formula 3-4]
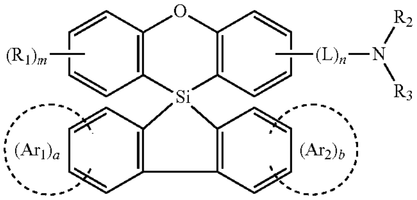
[Formula 3-5]
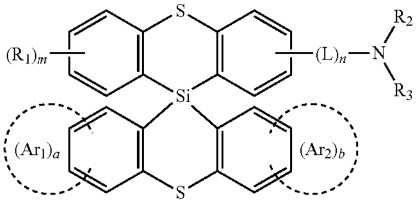
[Formula 3-6]
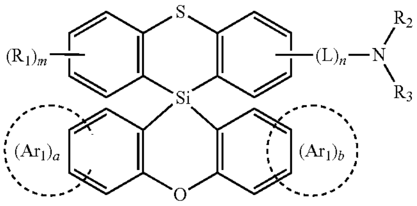
[Formula 3-7]
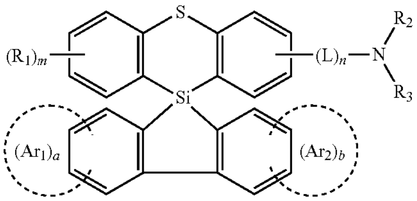
[Formula 3-8]
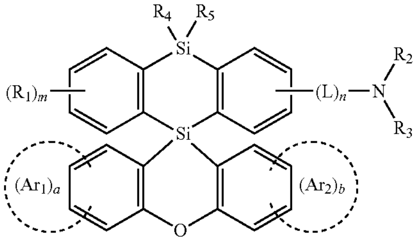
[Formula 3-9]
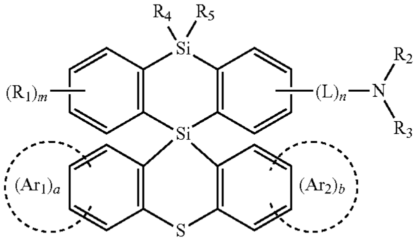
[Formula 3-10]
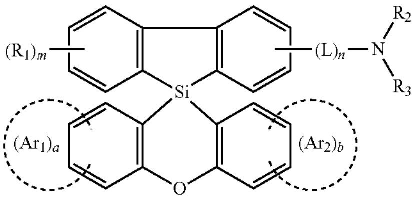
[Formula 3-11]
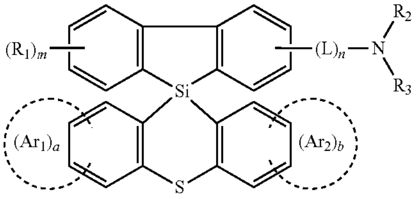
wherein in Formulae 3-1 to 3-11, $R_1$ to $R_5$, L, $Ar_1$, $Ar_2$, a, b, m and n are the same as respectively defined in association with Formula 1.
17. The amine compound of claim 13, wherein L is a direct linkage or represented by any one of following Formulae L-1 to L-4:
L-1
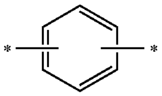
L-2
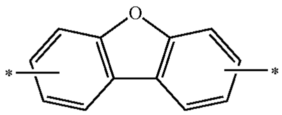
L-3
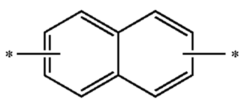
L-4
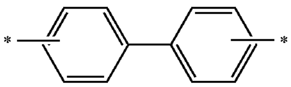
.

18. The amine compound of claim 13, wherein the amine compound represented by Formula 1 is a hole transport material.
19. The amine compound of claim 13, wherein the amine compound represented by Formula 1 is any one selected from compounds represented in following Compound Group 1 and Compound group 2:
[Compound Group 1]
A1
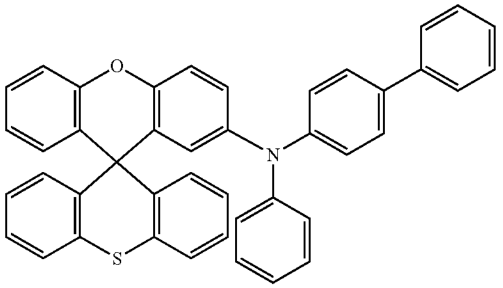
A2
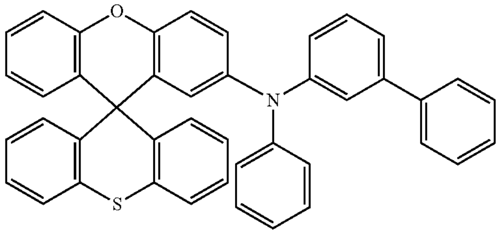
A3
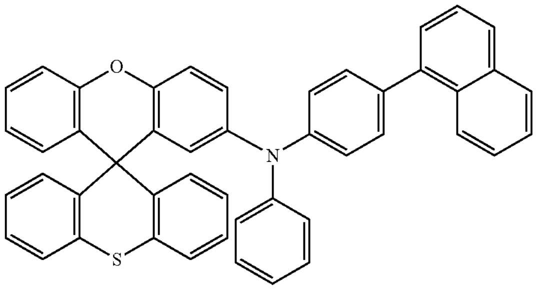
A4
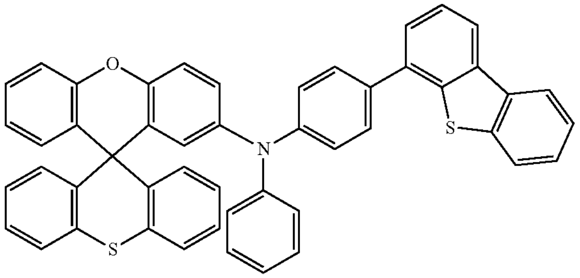
A5
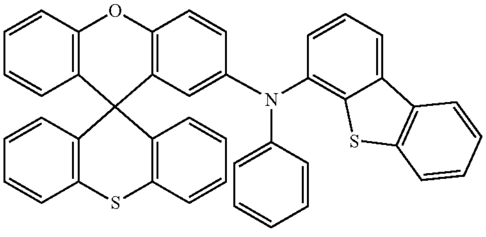
-continued
A6
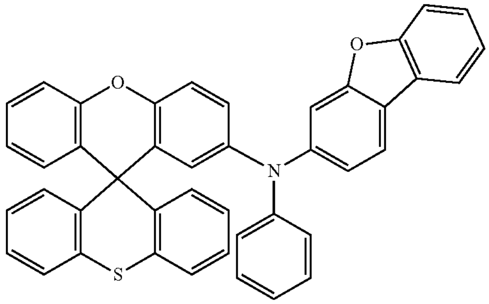
A7
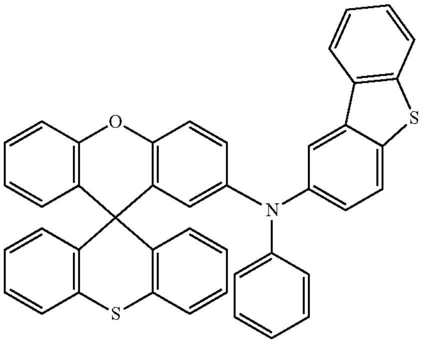
A8
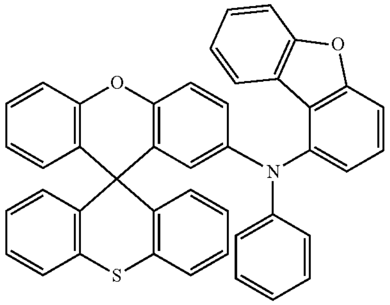
A9
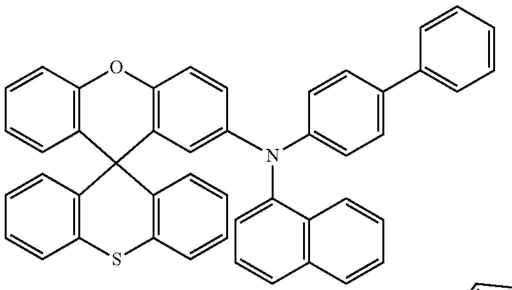
A10
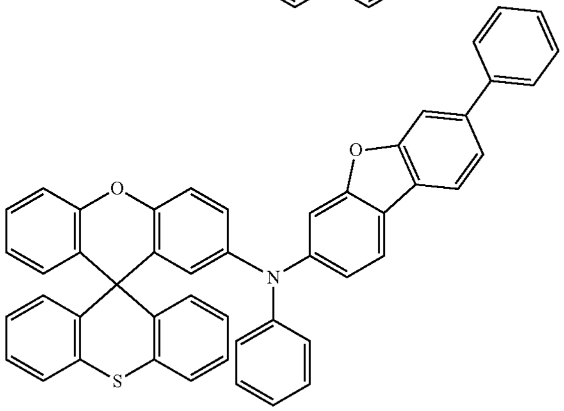

-continued
A11
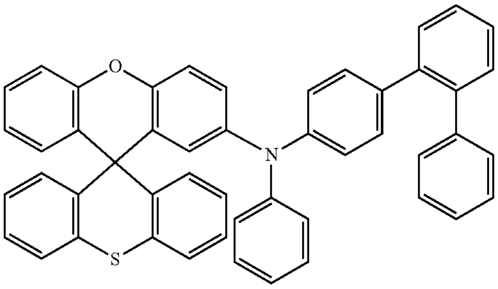
A12
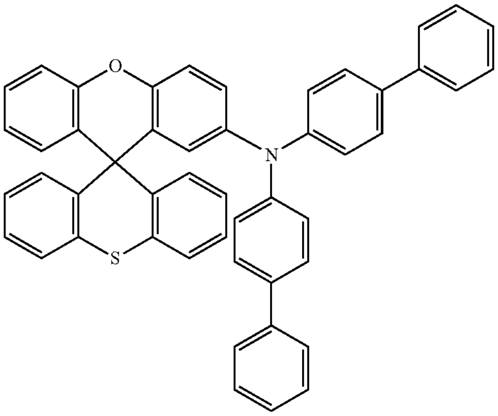
A13
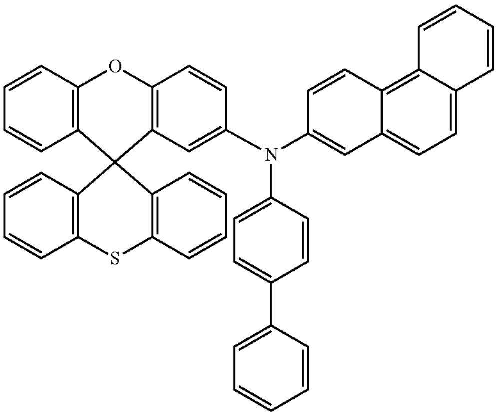
A14
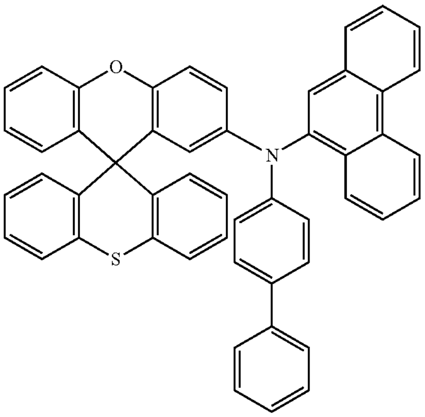
-continued
A15
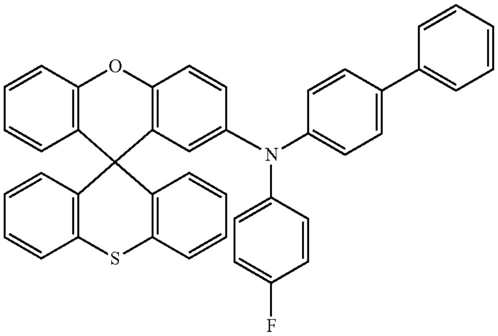
A16
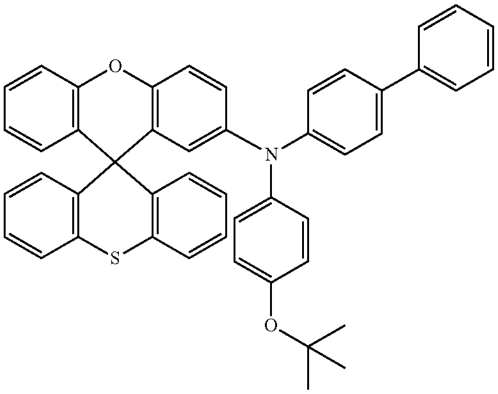
A17
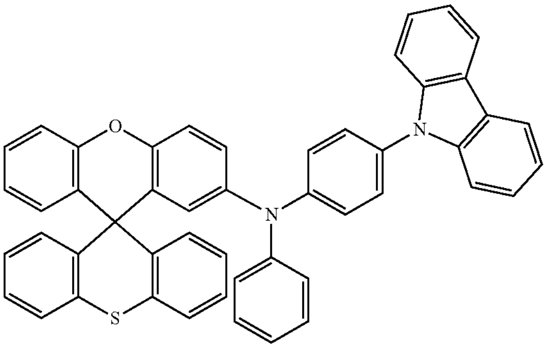
A18
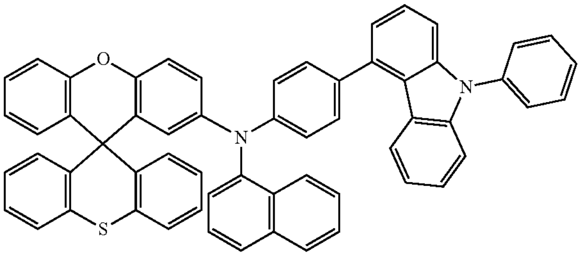

-continued
A19
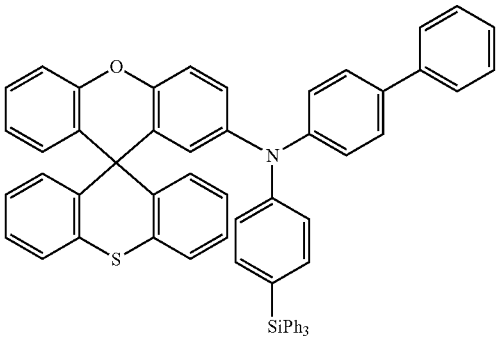
A20
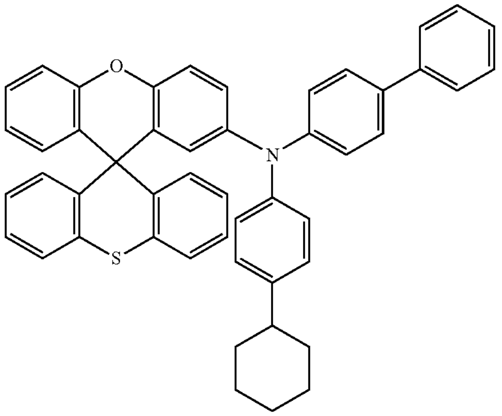
A21
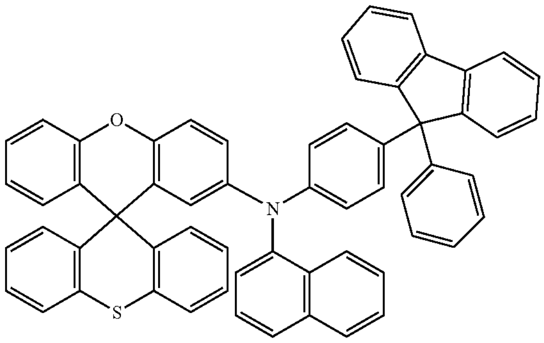
A22
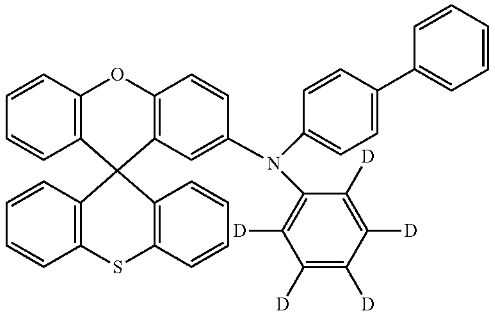
-continued
A23
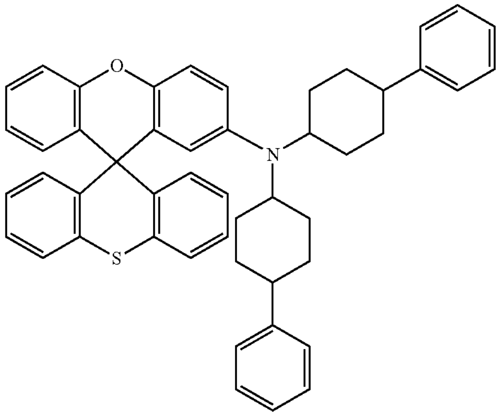
A24
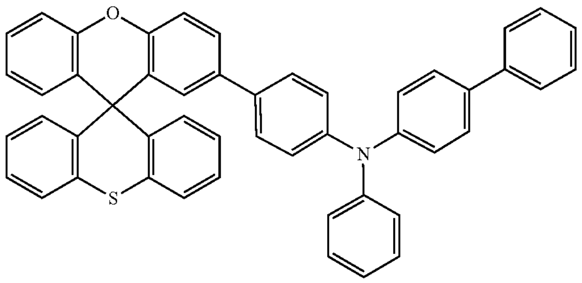
A25
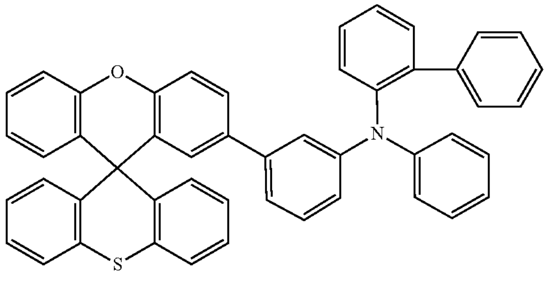
A26
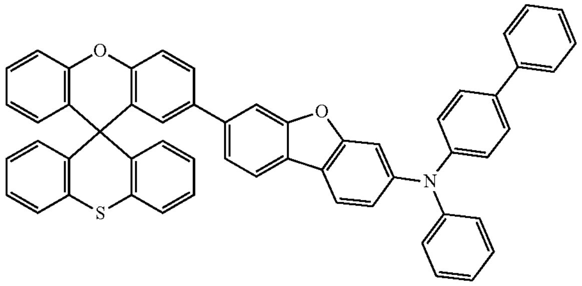

-continued
A27
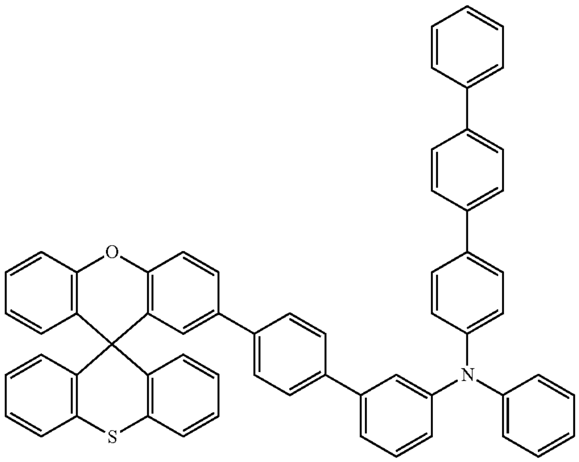
A28
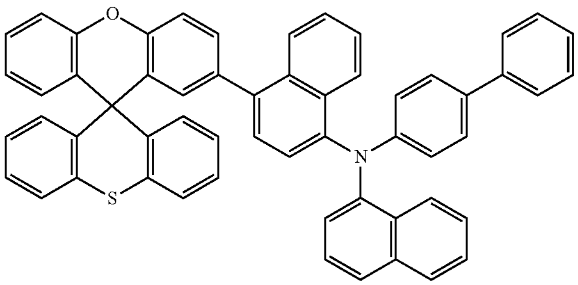
A29
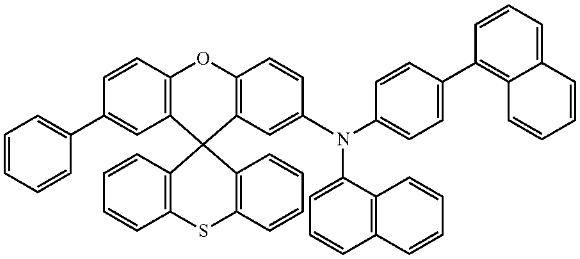
A30
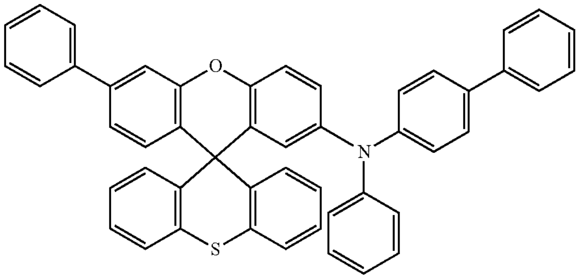
-continued
A31
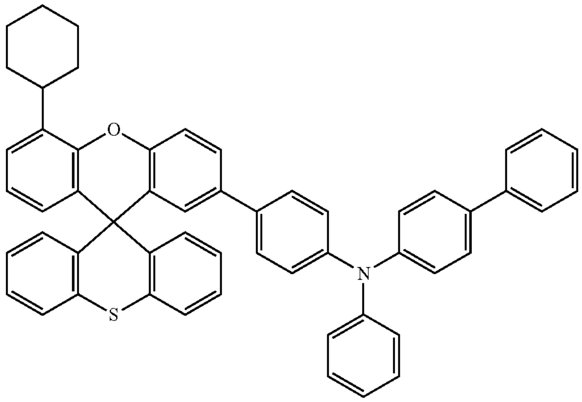
A32
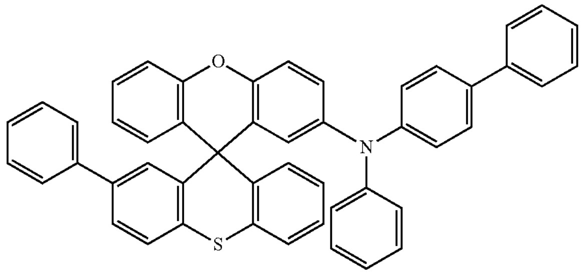
A33
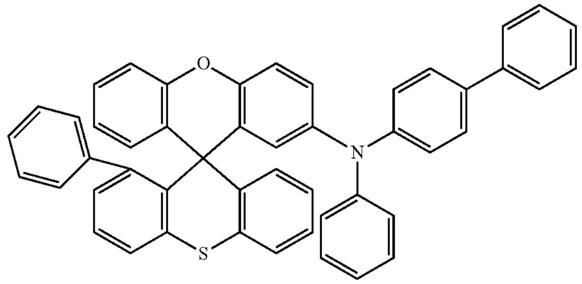
A34
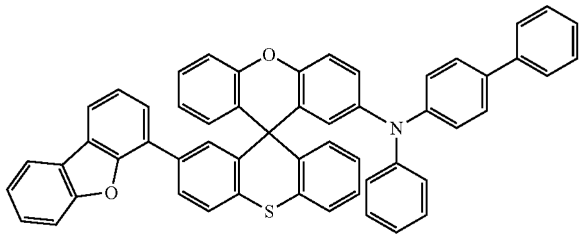
A35
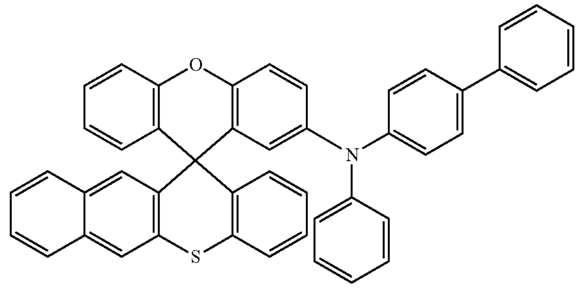

-continued
A36
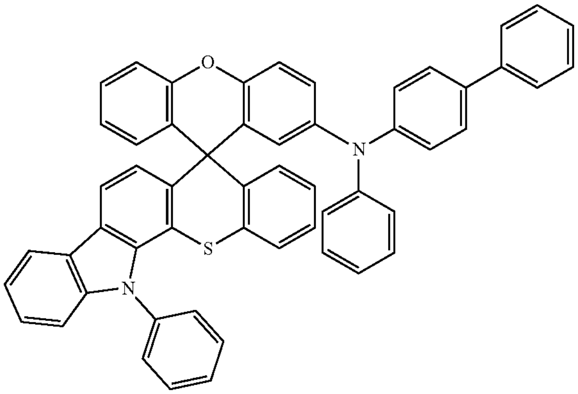
A37
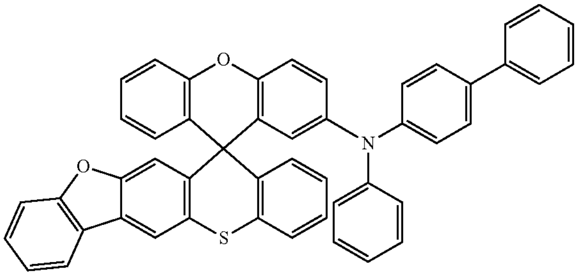
A38
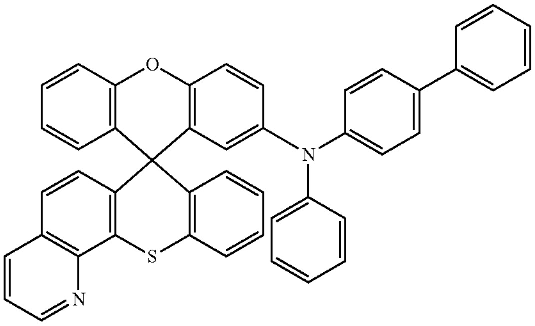
A39
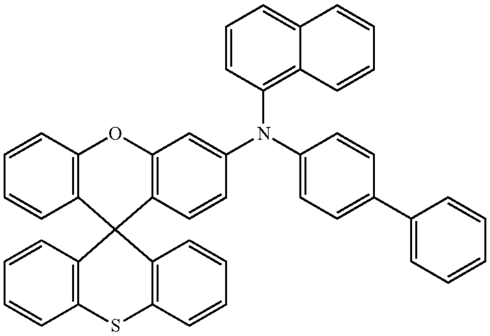
-continued
A40
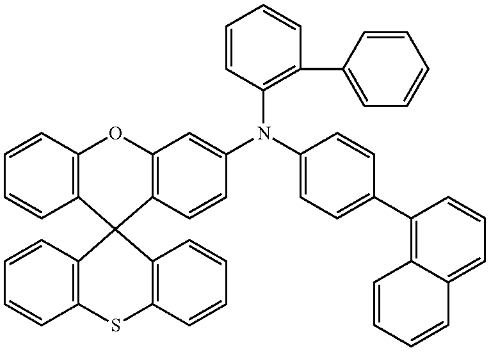
A41
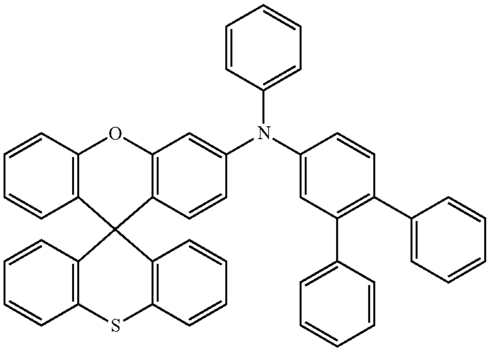
A42
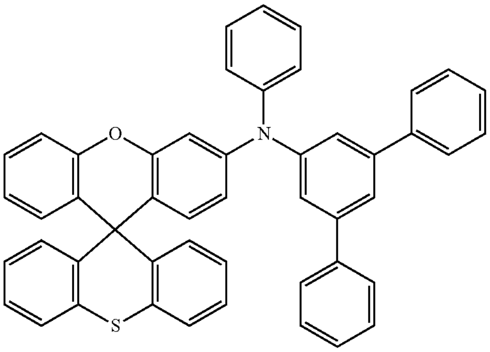
A43
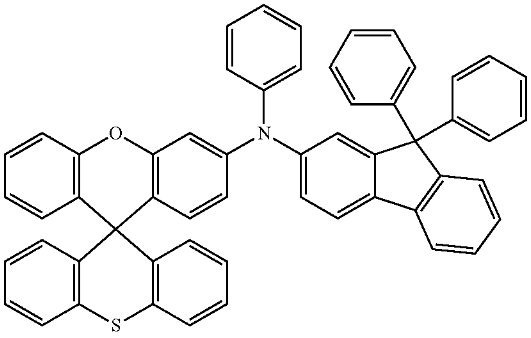

-continued
A44
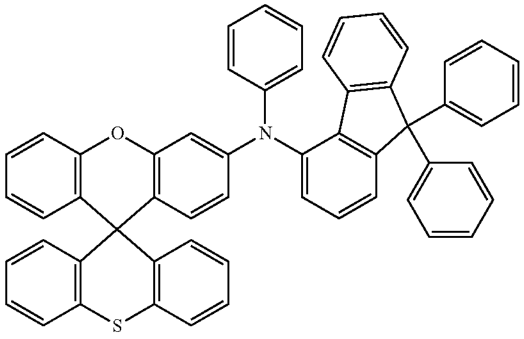
A45
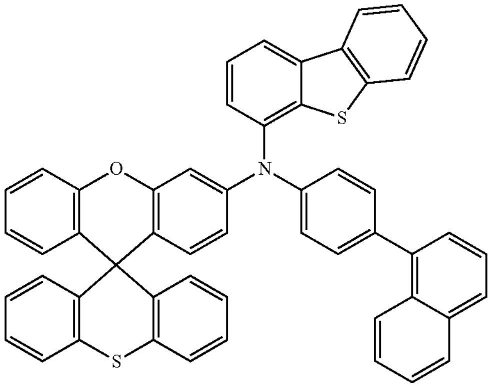
A46
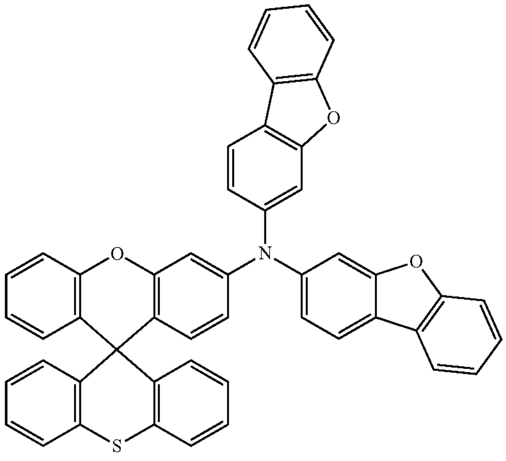
A47
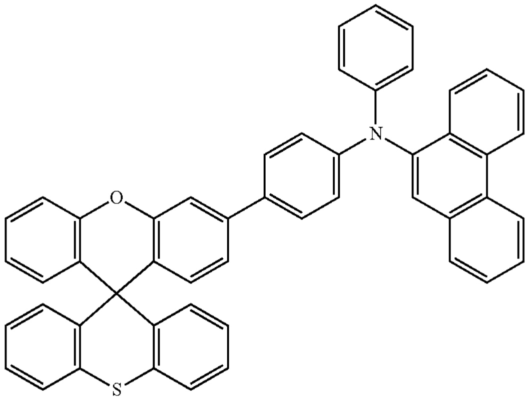
-continued
A48
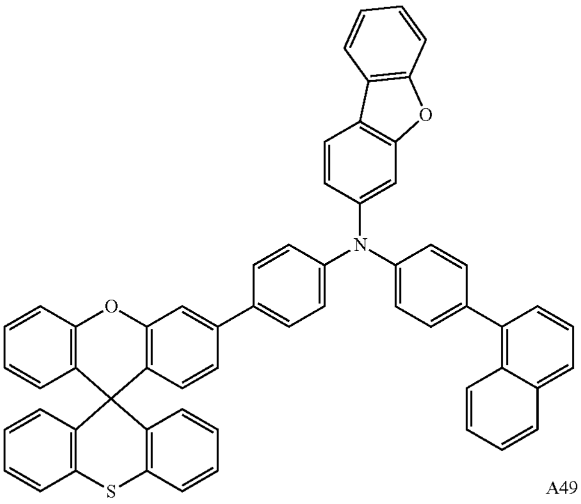
A49
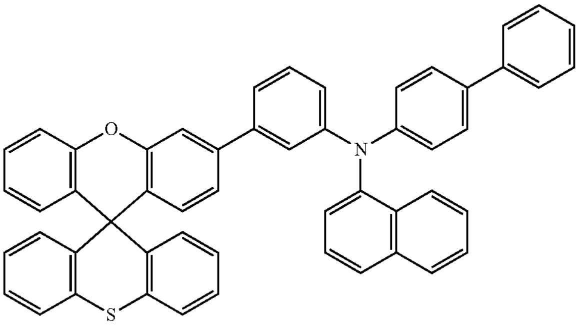
A50
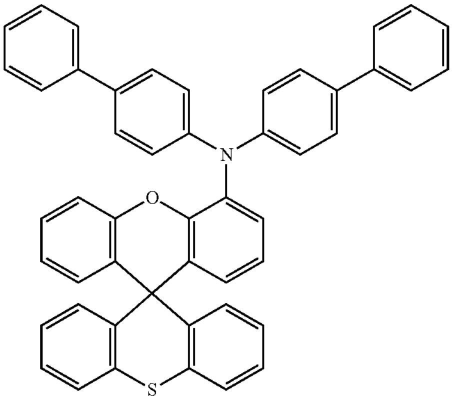
A51
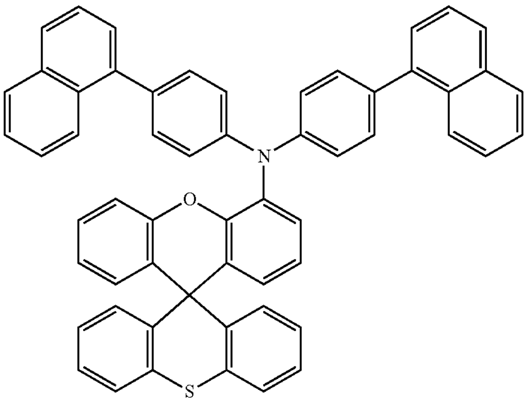

-continued
A52
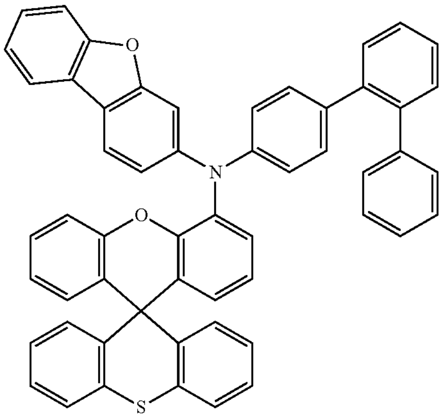
A53
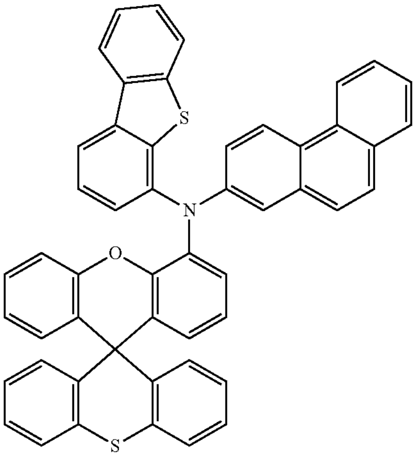
A54
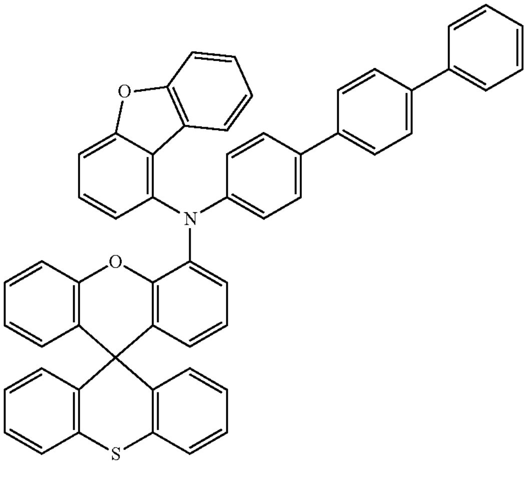
-continued
A55
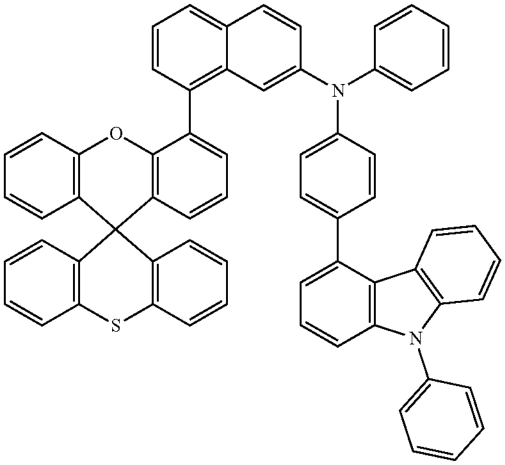
A56
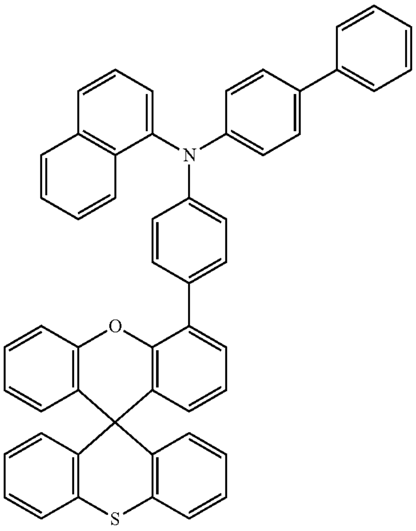
A57
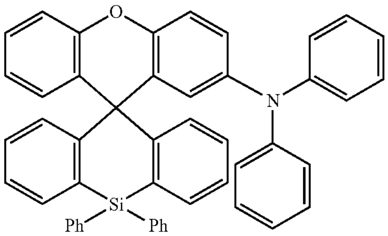
A58
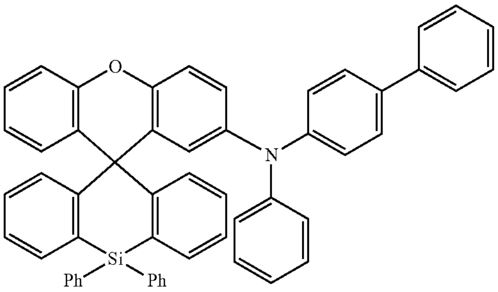

A59
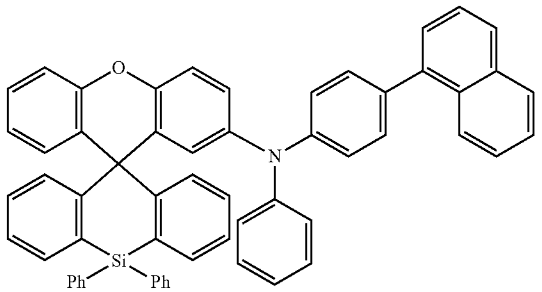
A60
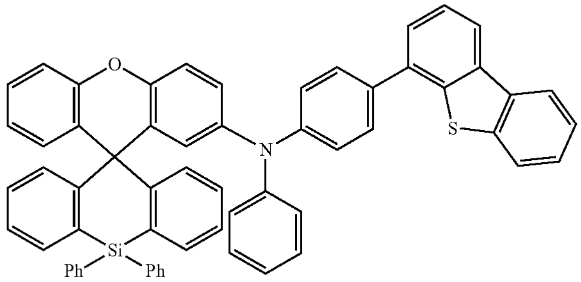
A61
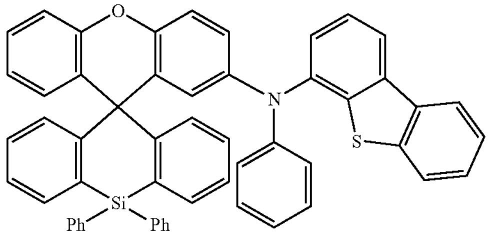
A62
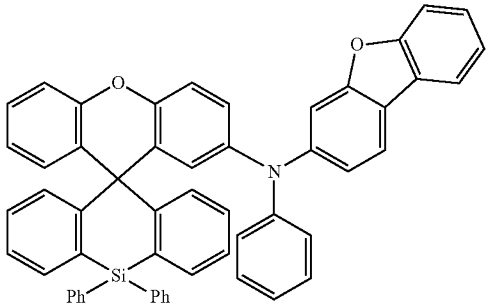
A63
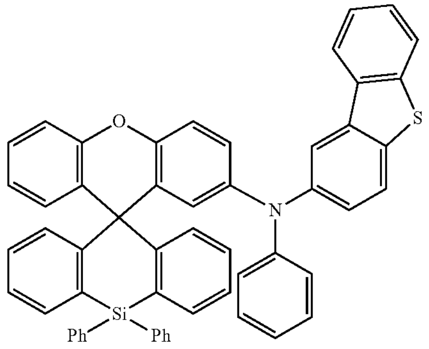
A64
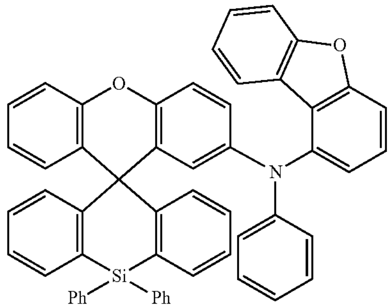
A65
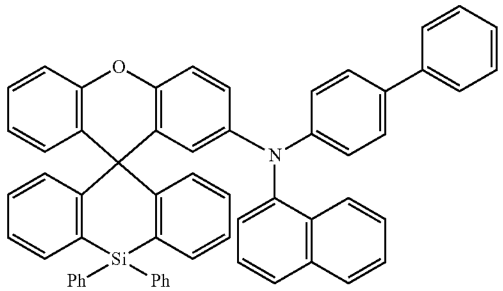
A66
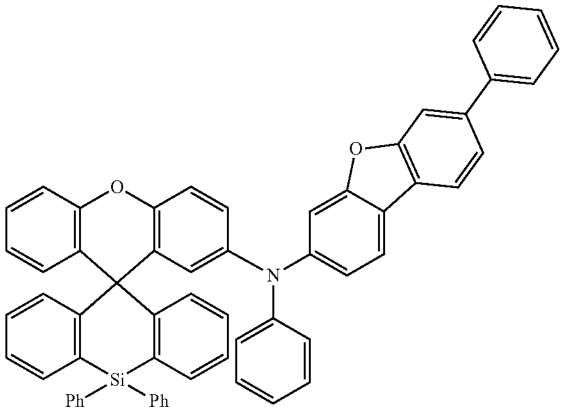
A67
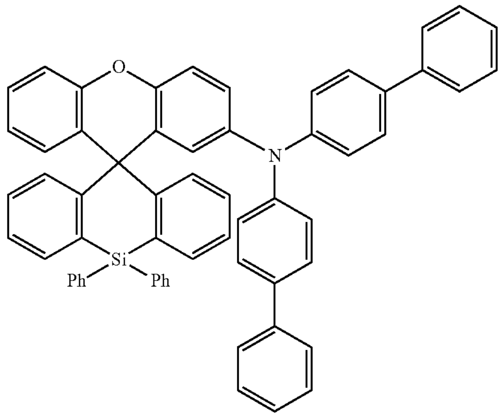

-continued
A68
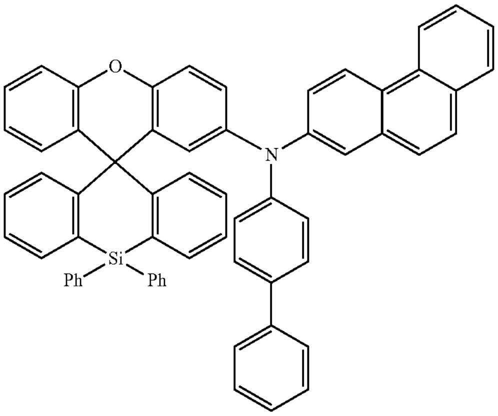
A69
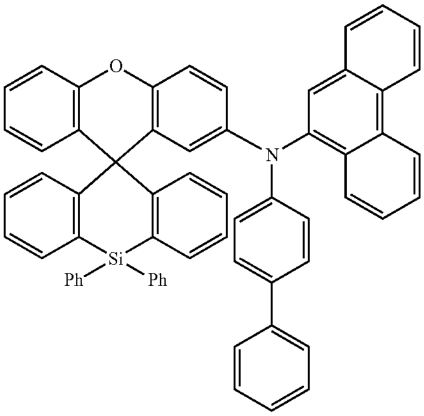
A70
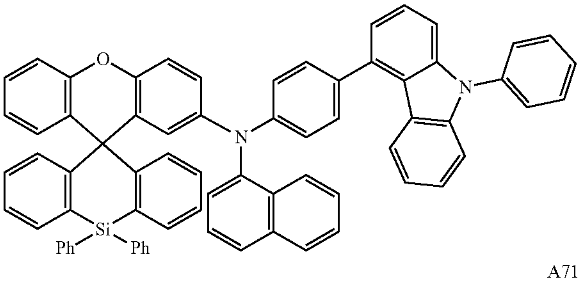
A71
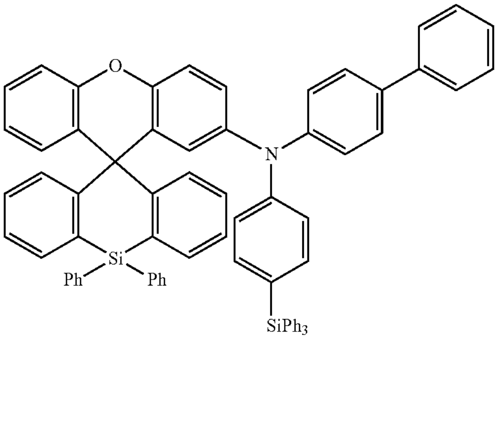
-continued
A72
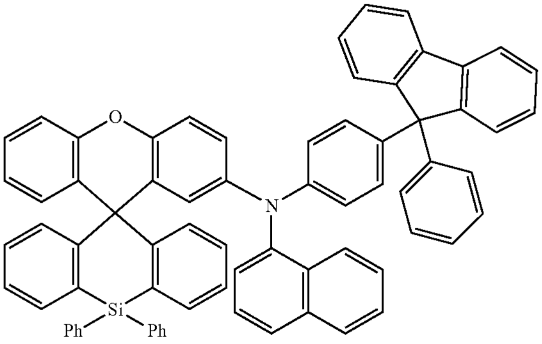
A73
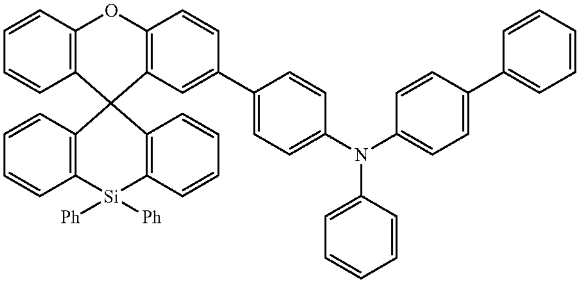
A74
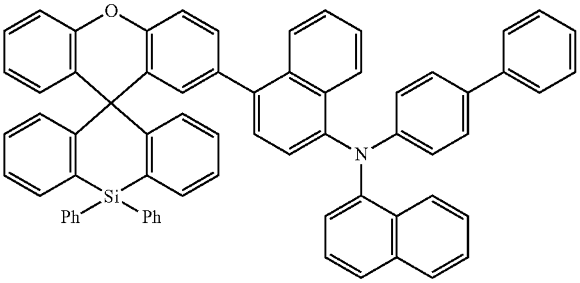
A75
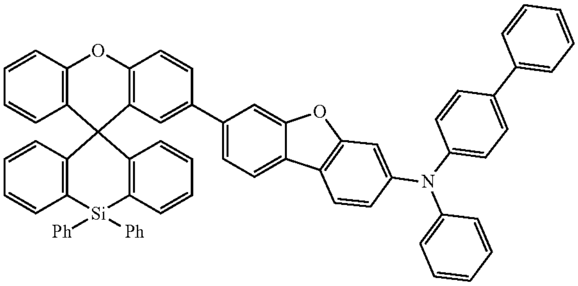

-continued
A76
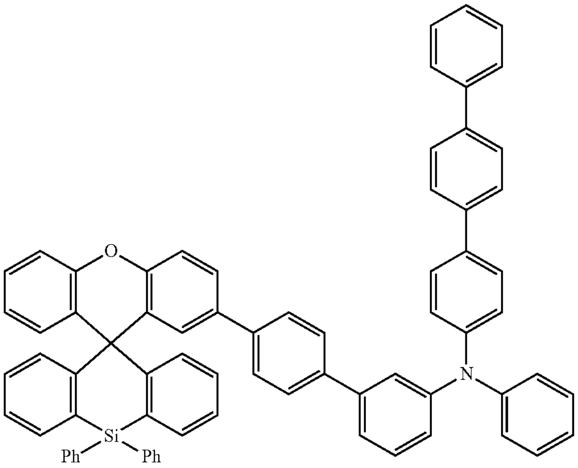
A77
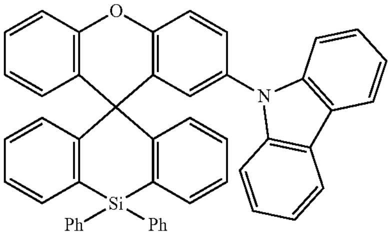
A78
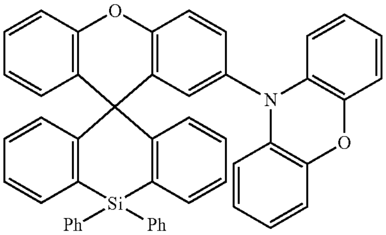
A79
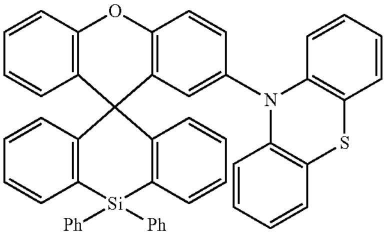
A80
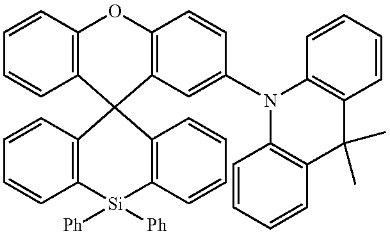
-continued
A81
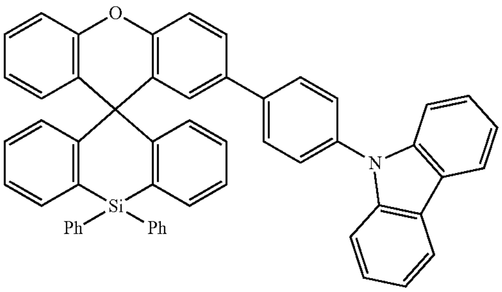
A82
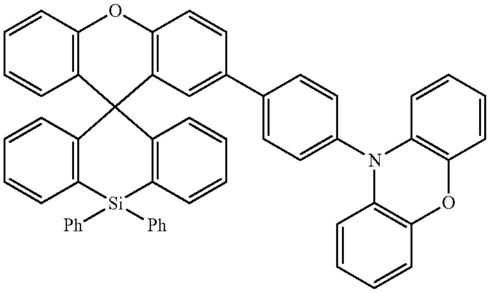
A83
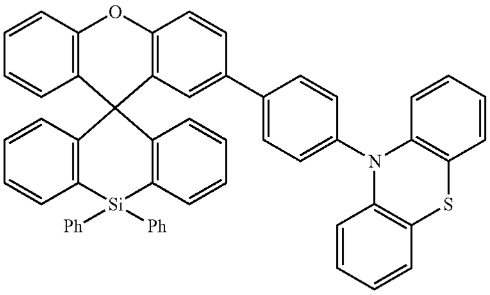
A84
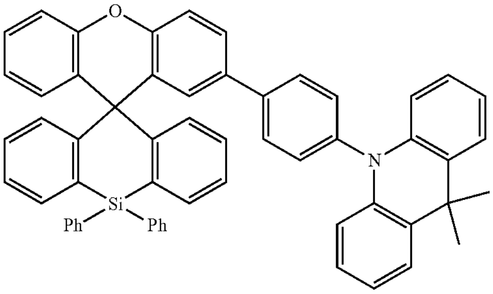
A85
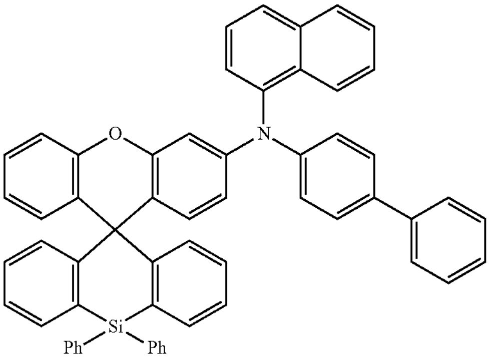

-continued
A86
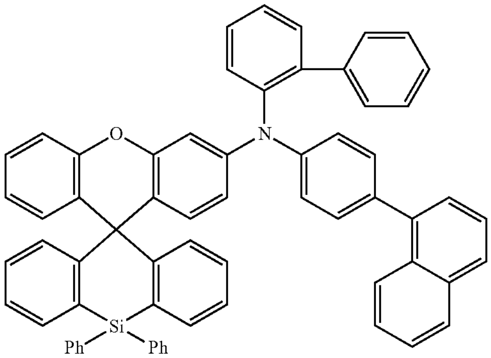
A87
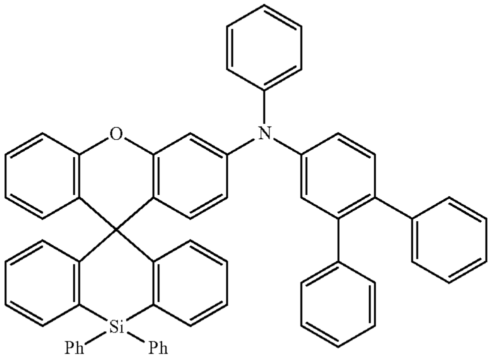
A88
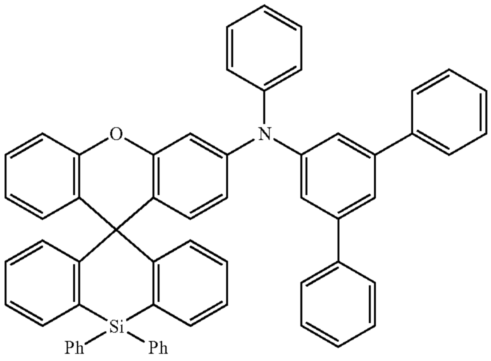
A89
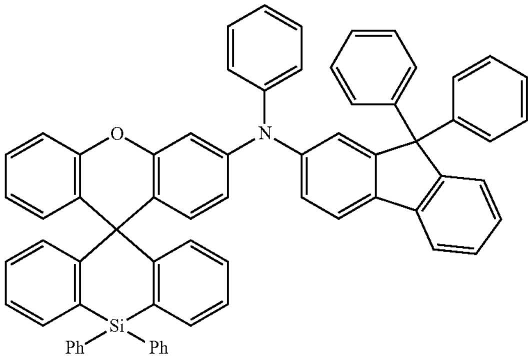
-continued
A90
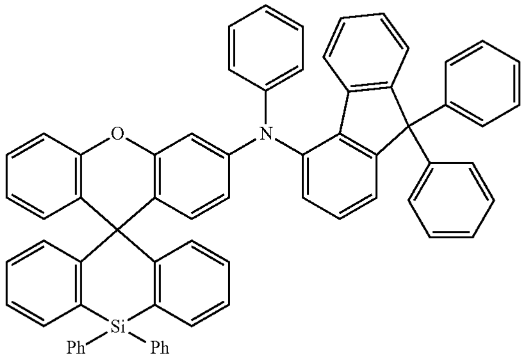
A91
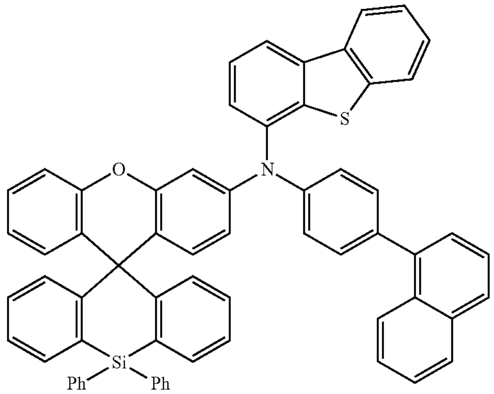
A92
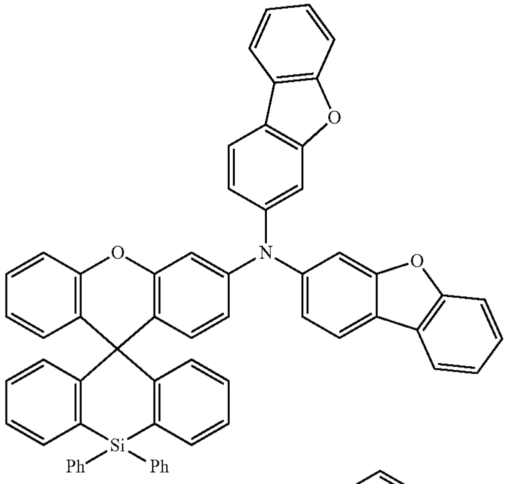
A93
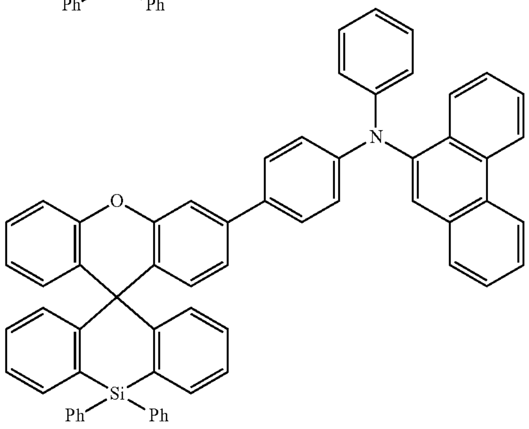

-continued
A94
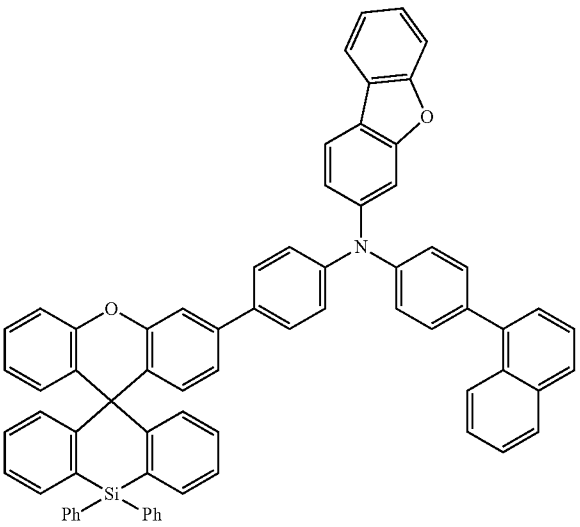
A95
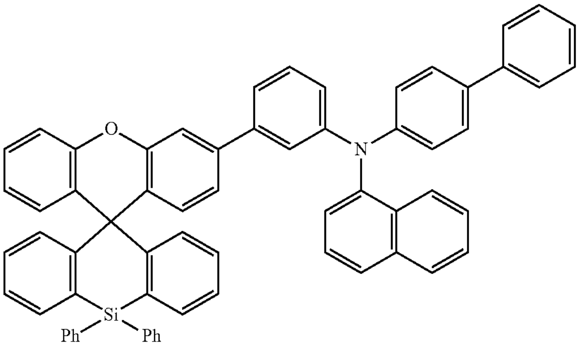
A96
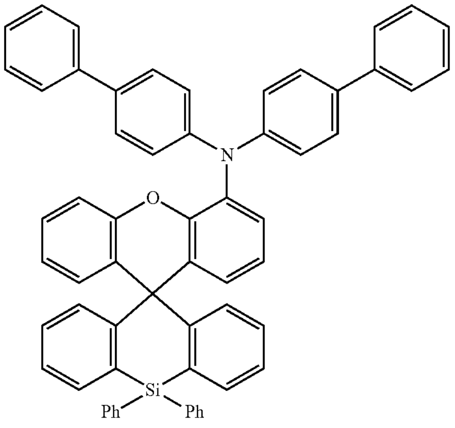
-continued
A97
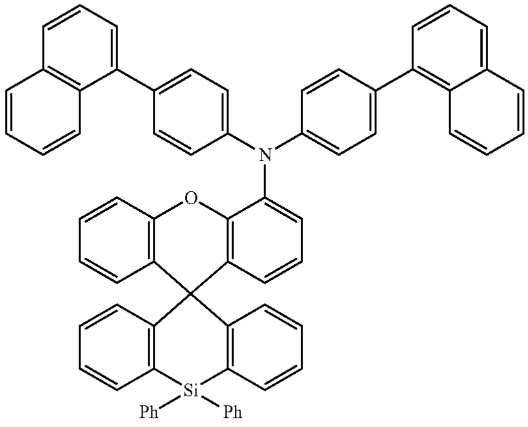
A98
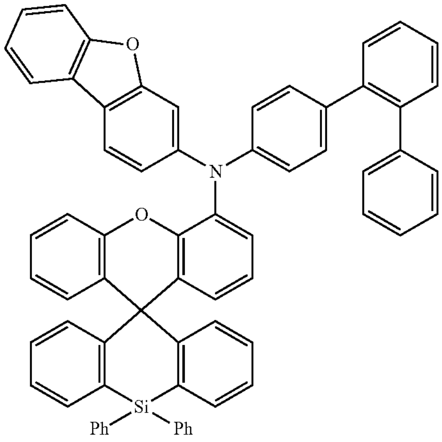
A99
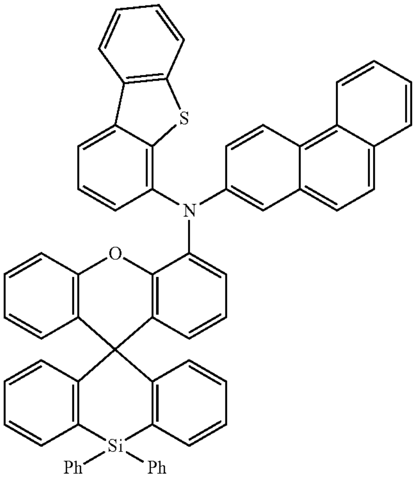

-continued
A100
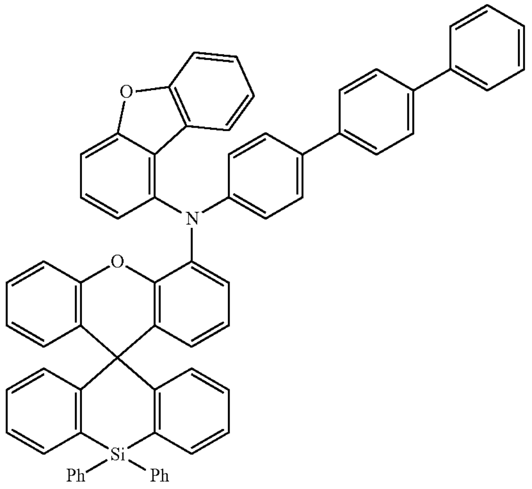
A101
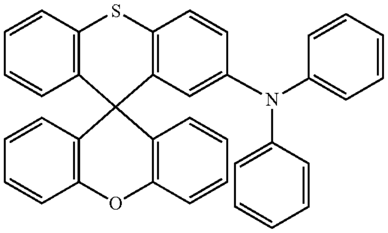
A102
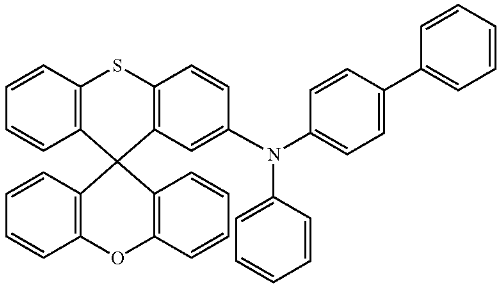
A103
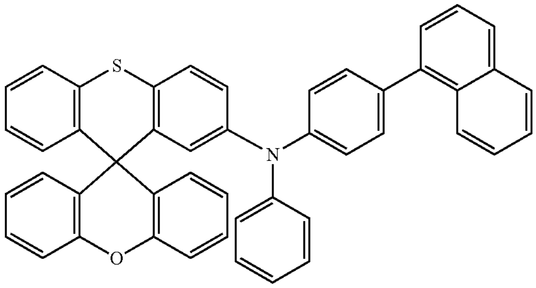
-continued
A104
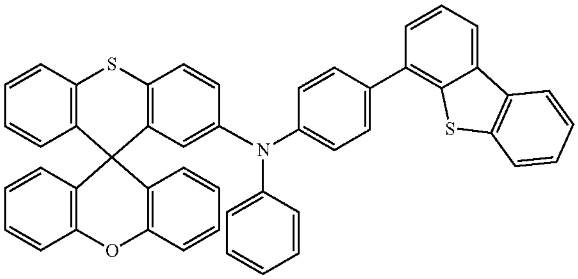
A105
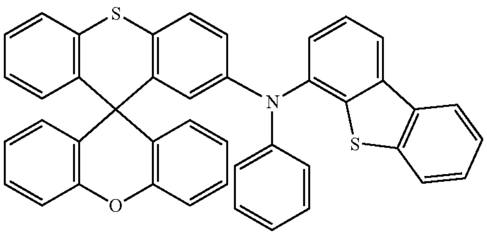
A106
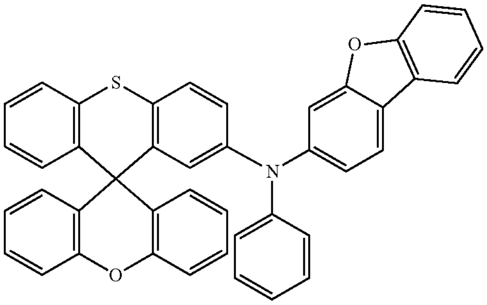
A107
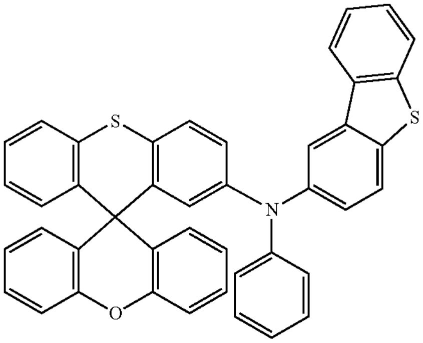
A108
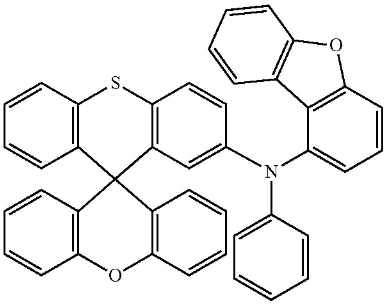

-continued
A109
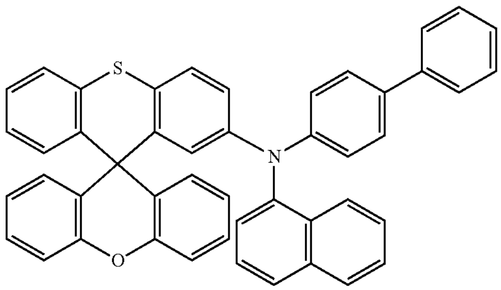
A110
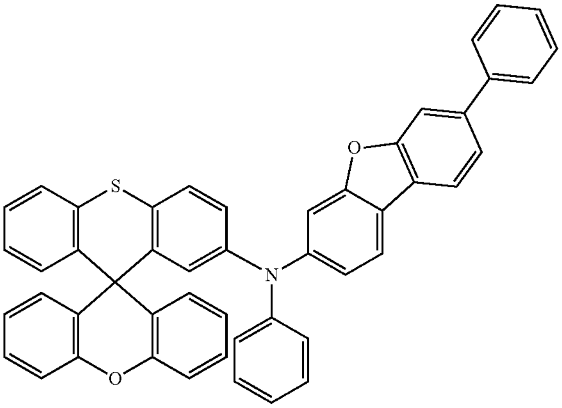
A111
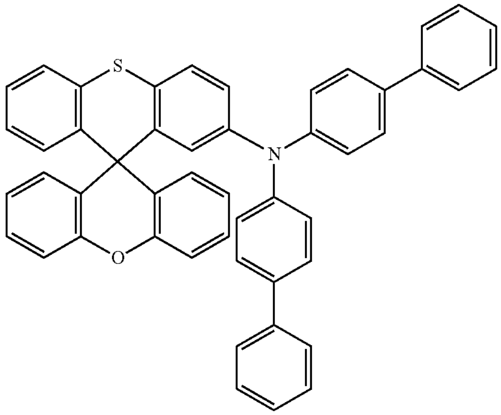
A112
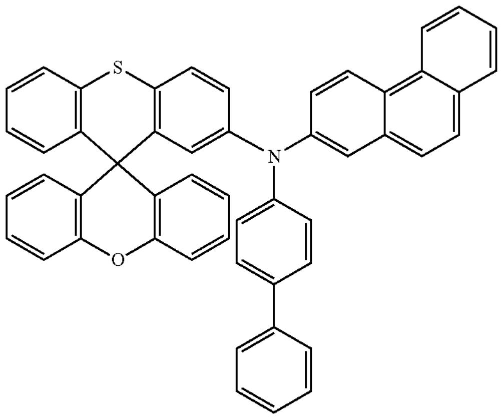
-continued
A113
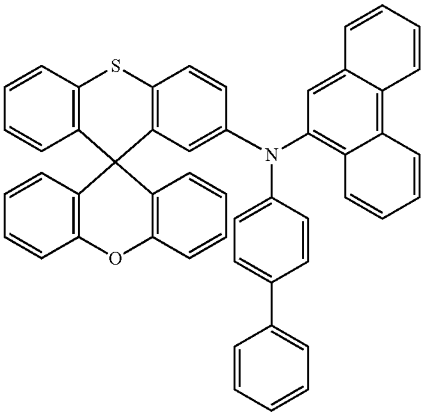
A114
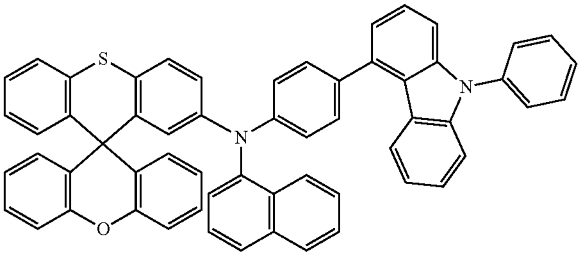
A115
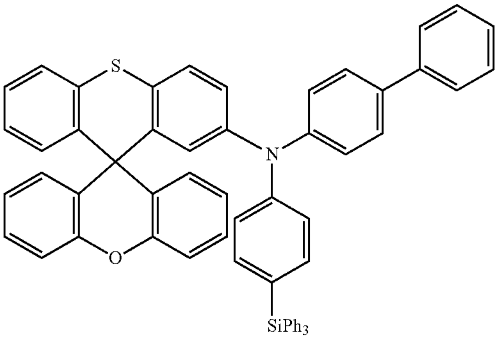
A116
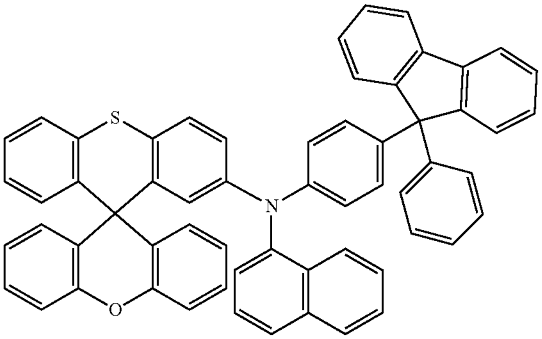

-continued
A117
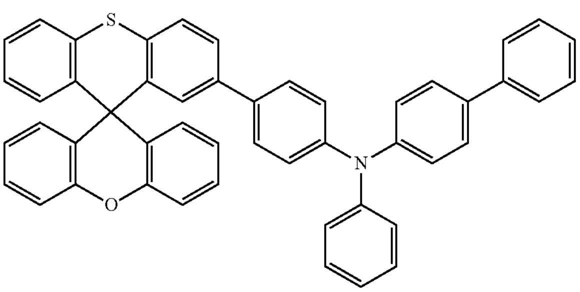
A118
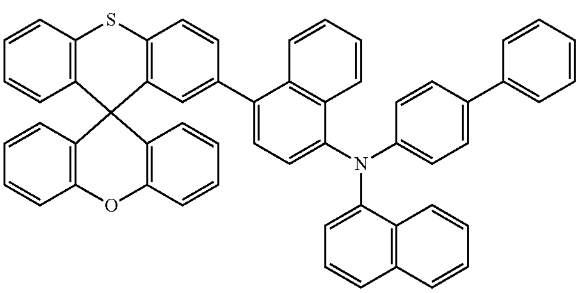
A119
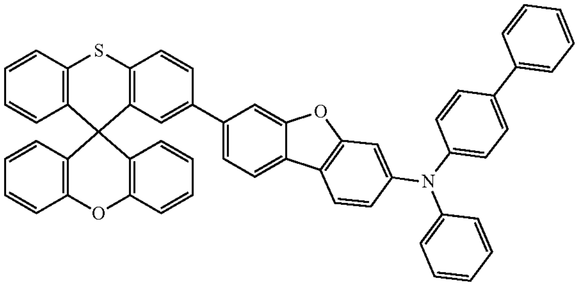
A120
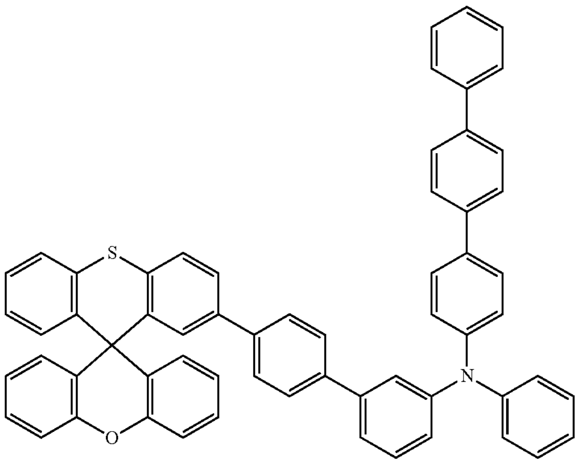
A121
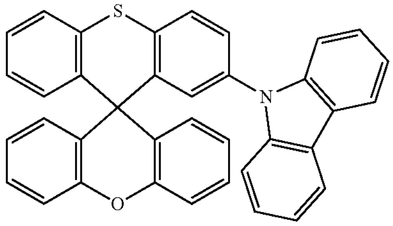
-continued
A122
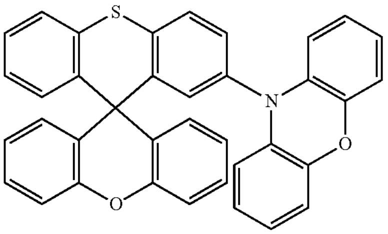
A123
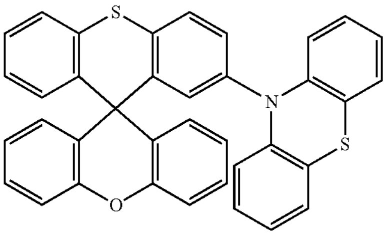
A124
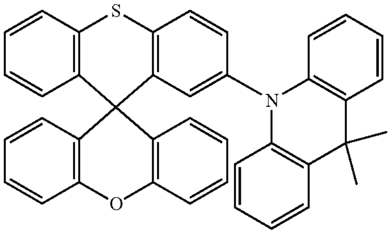
A125
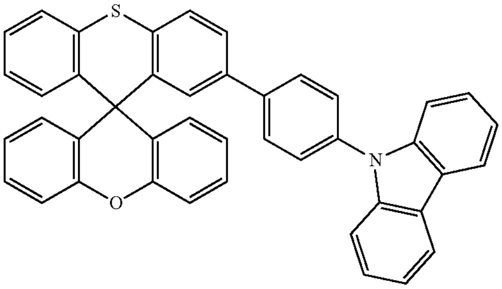
A126
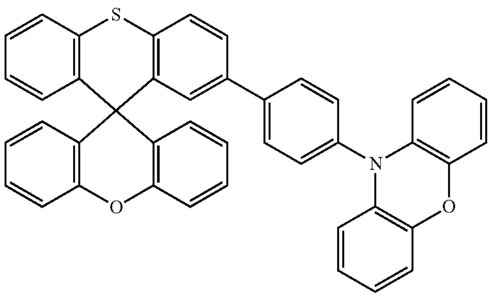
A127
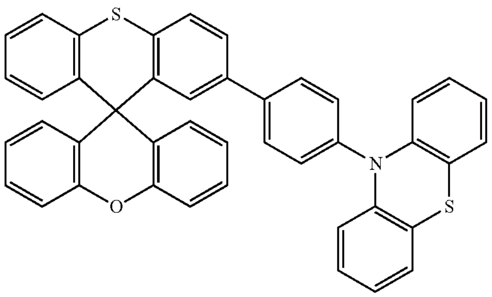

-continued
A128
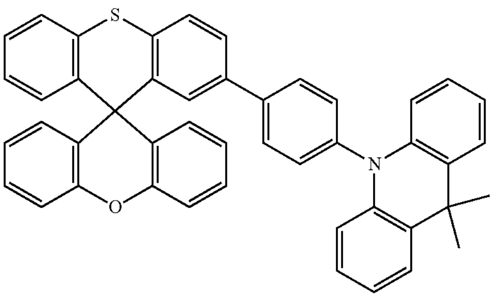
A129
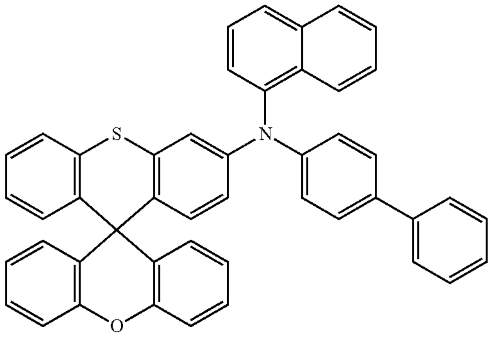
A130
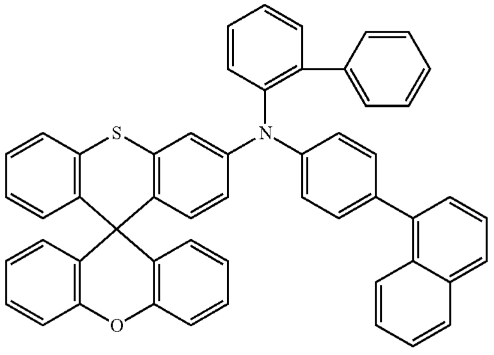
A131
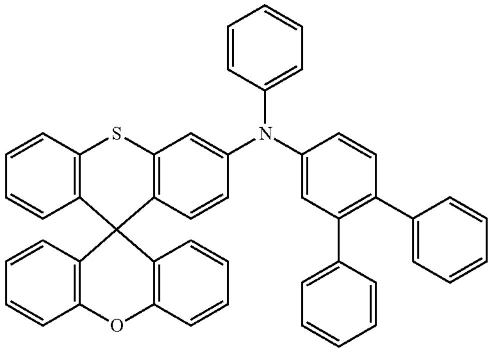
-continued
A132
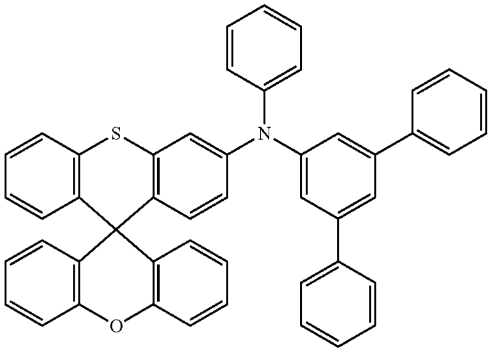
A133
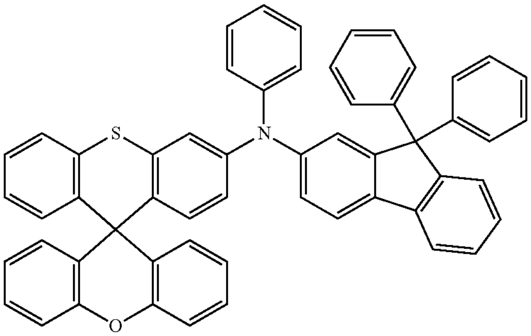
A134
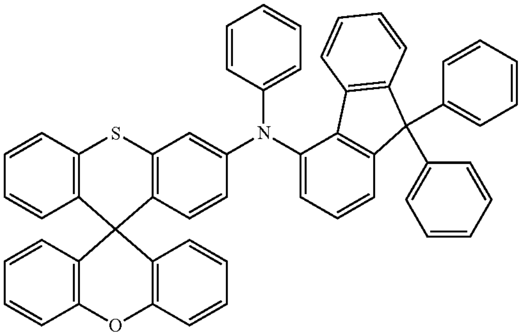
A135
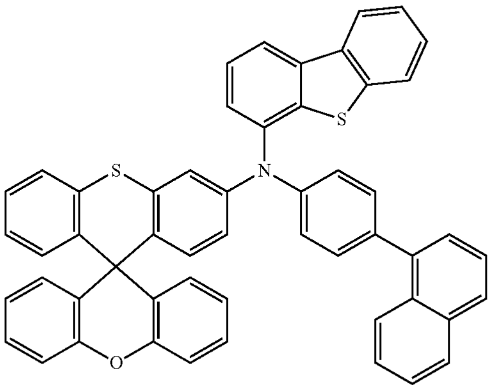

-continued
A136
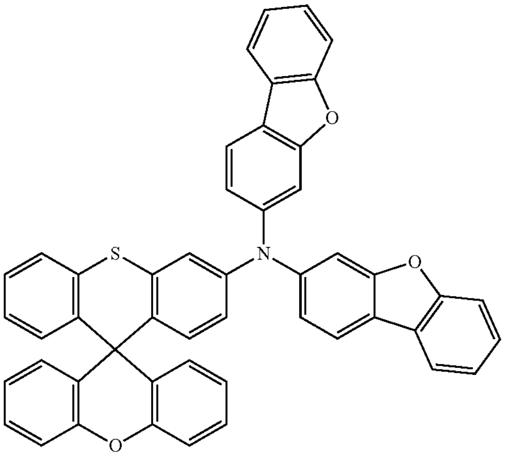
A137
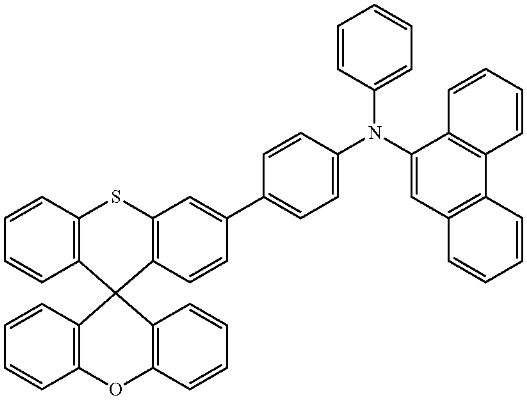
A138
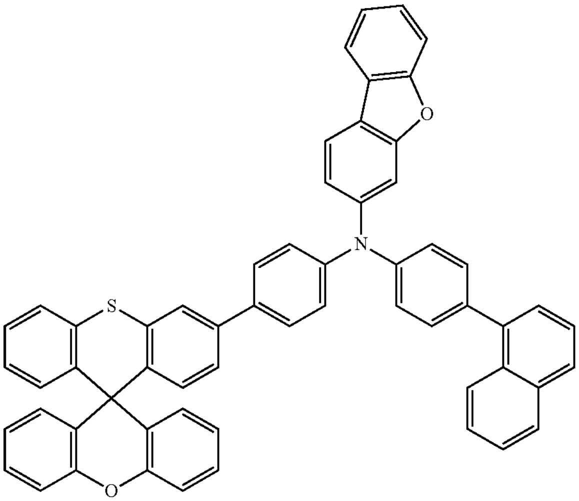
-continued
A139
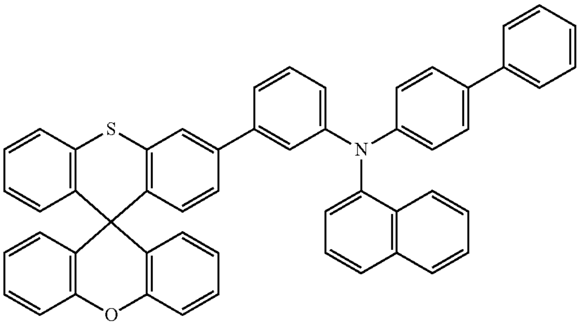
A140
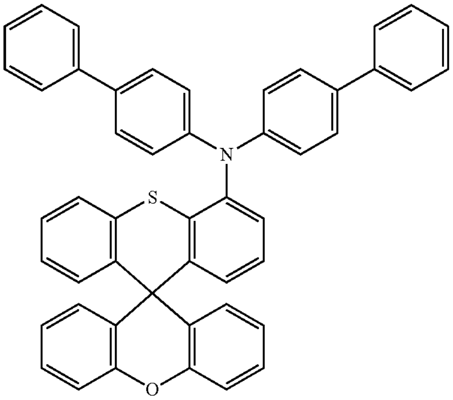
A141
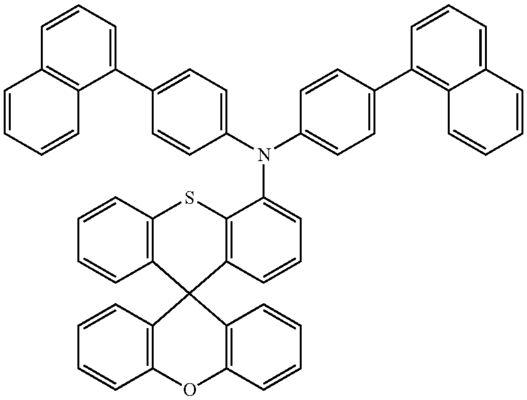
A142
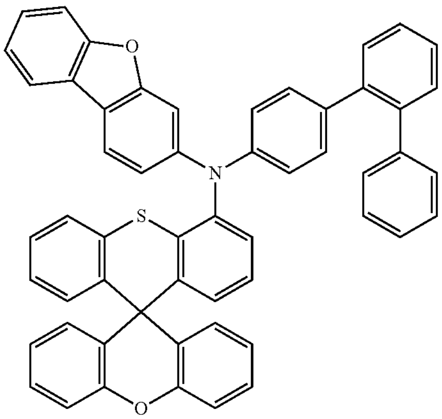

-continued
A143
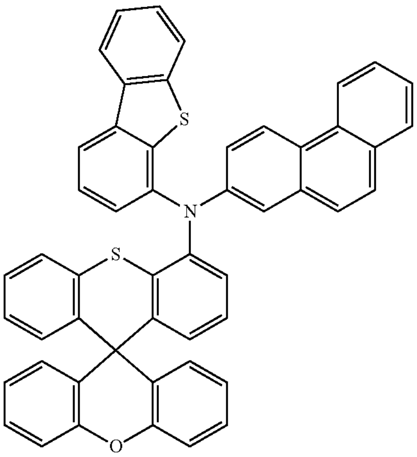
A144
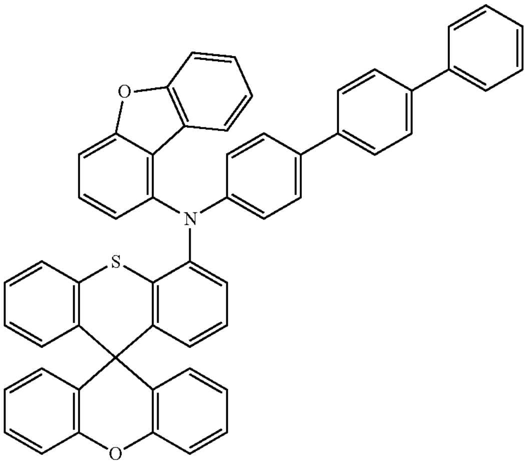
A145
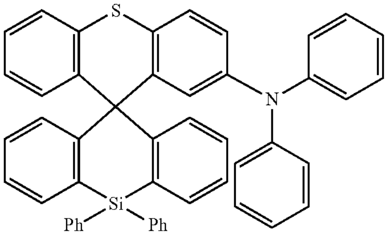
A146
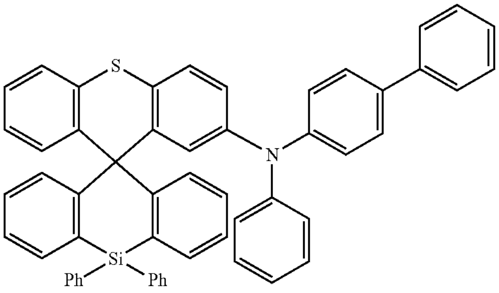
-continued
A147
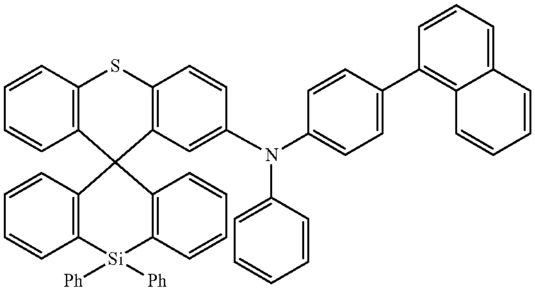
A148
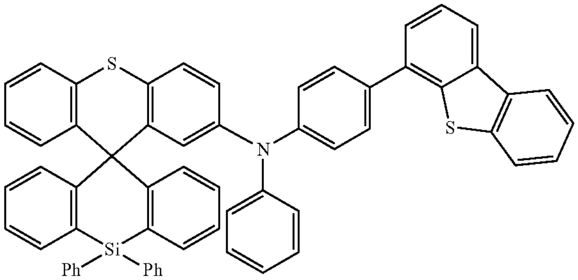
A149
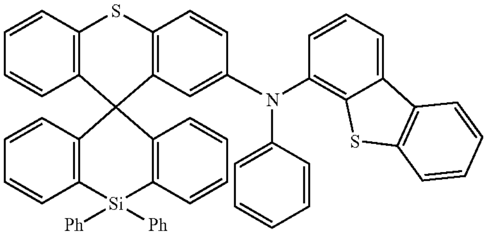
A150
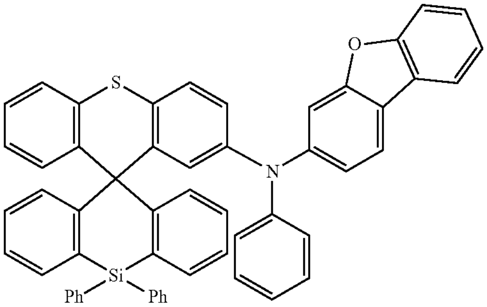
A151
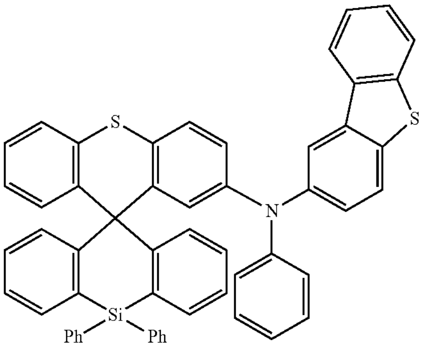

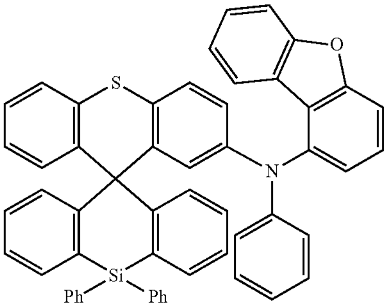
A152
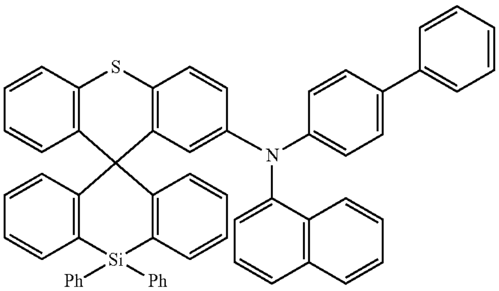
A153
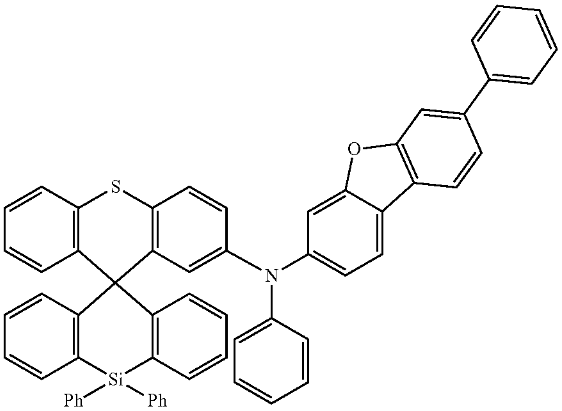
A154
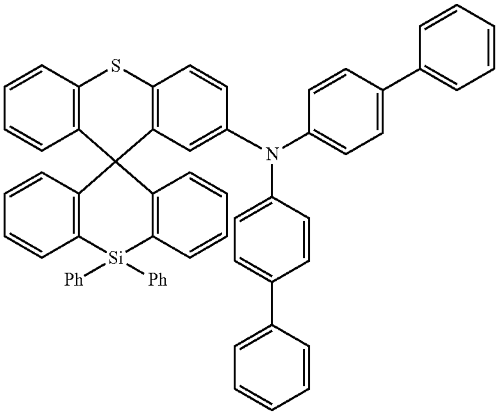
A155
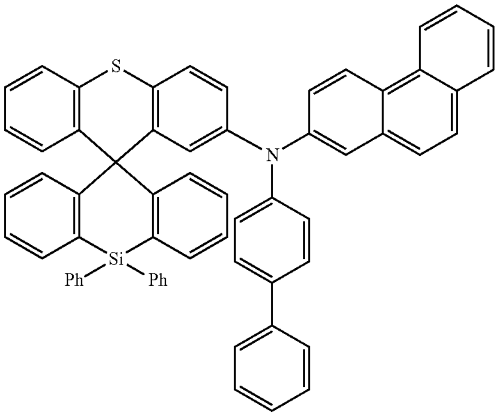
A156
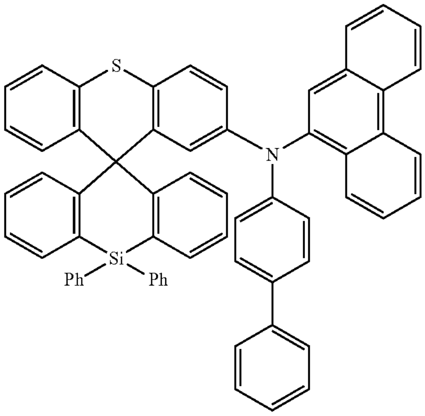
A157
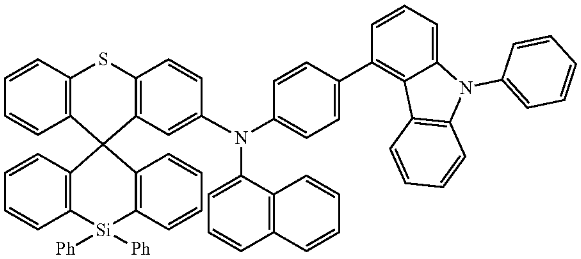
A158
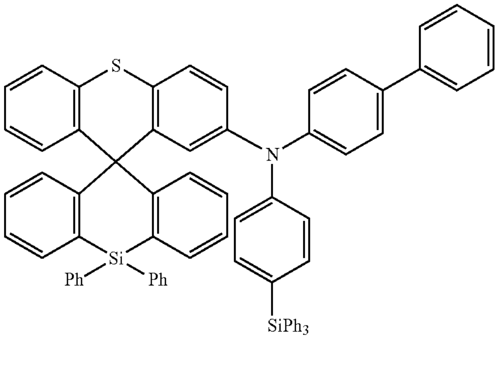
A159

-continued
A160
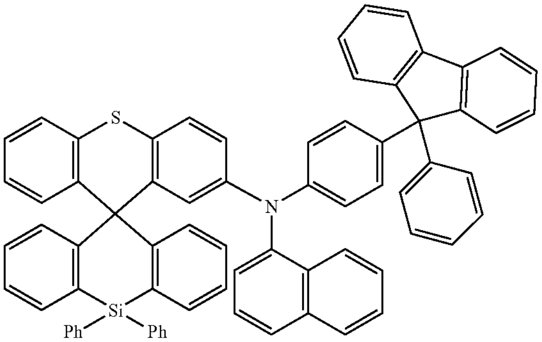
A161
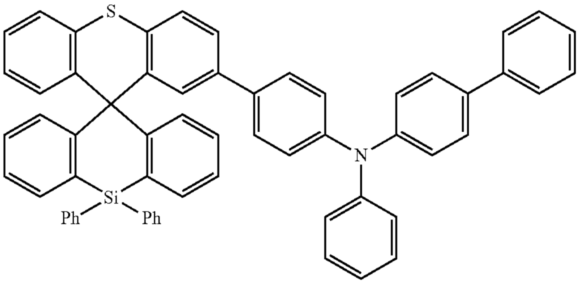
A162
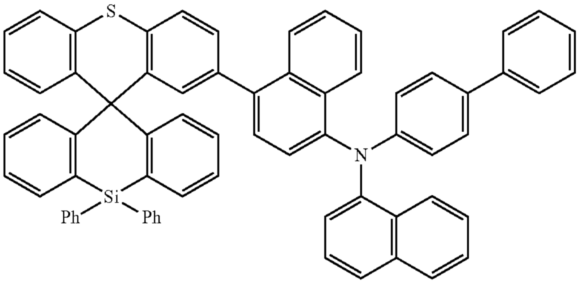
A163
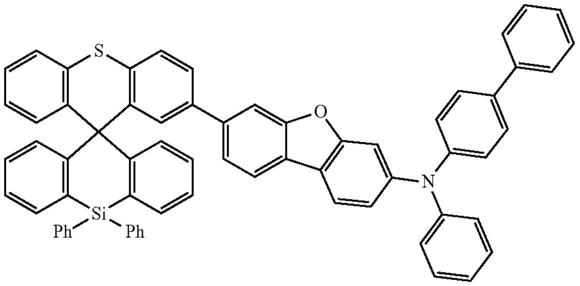
-continued
A164
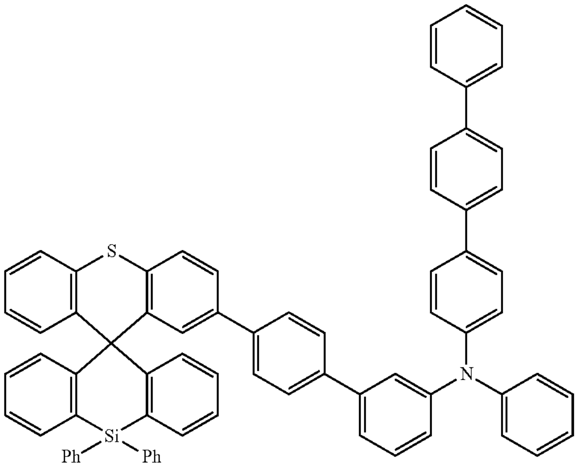
A165
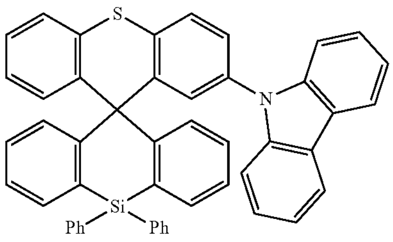
A166
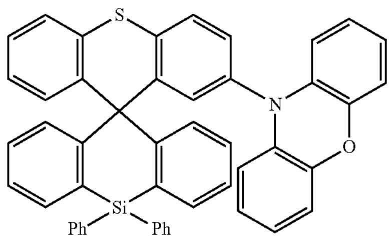
A167
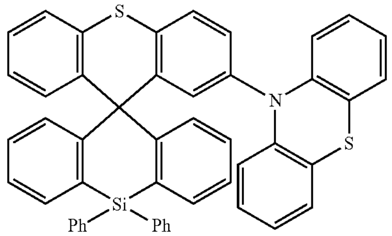
A168
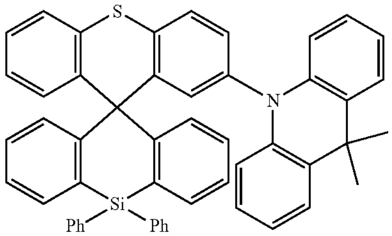

-continued
A169
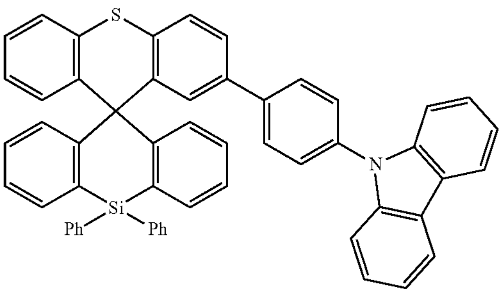
A170
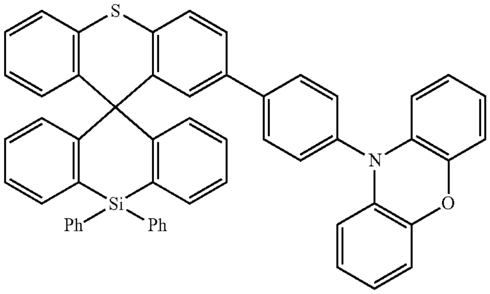
A171
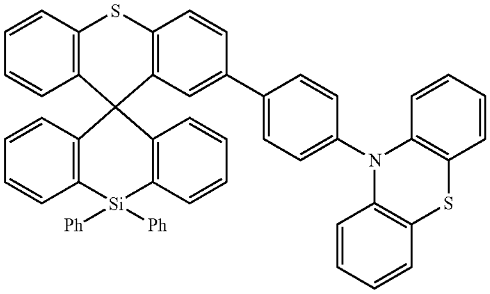
A172
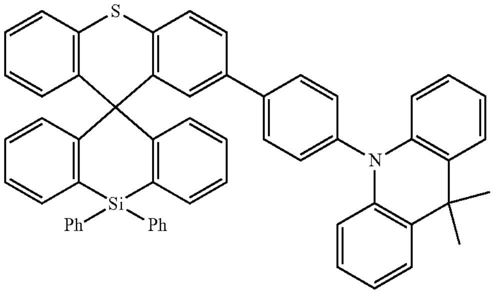
A173
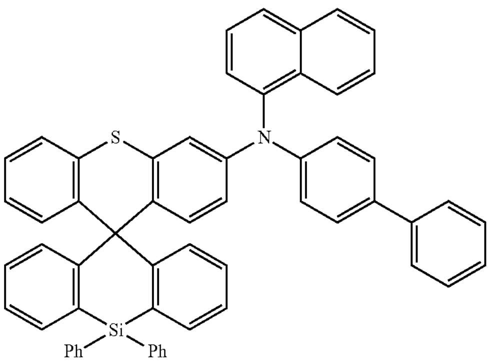
-continued
A174
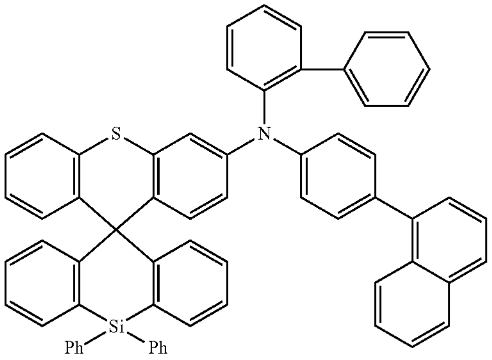
A175
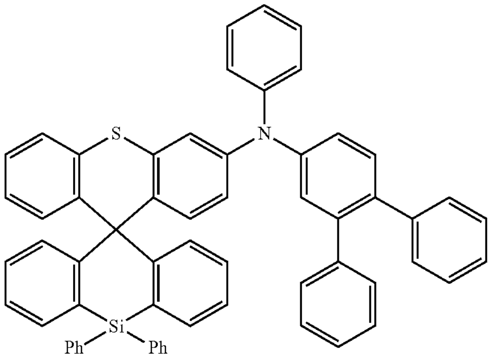
A176
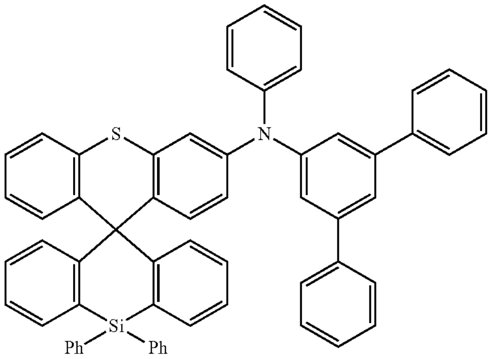
A177
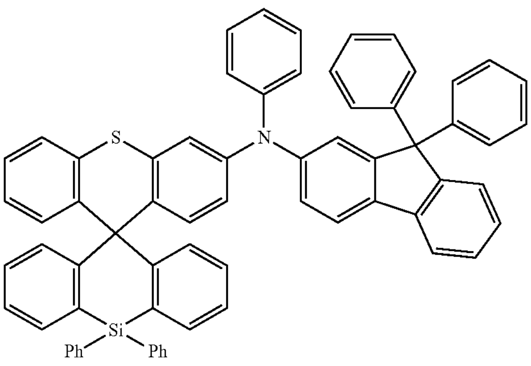

-continued
A178
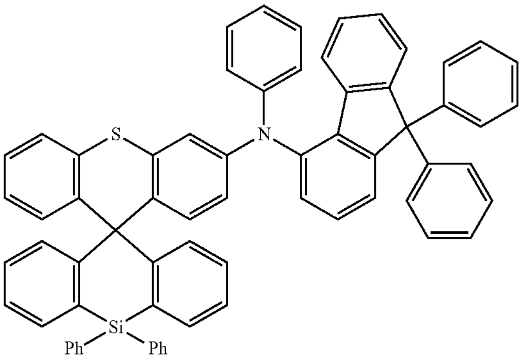
A179
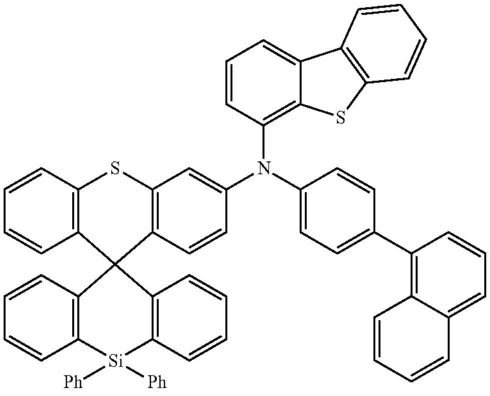
A180
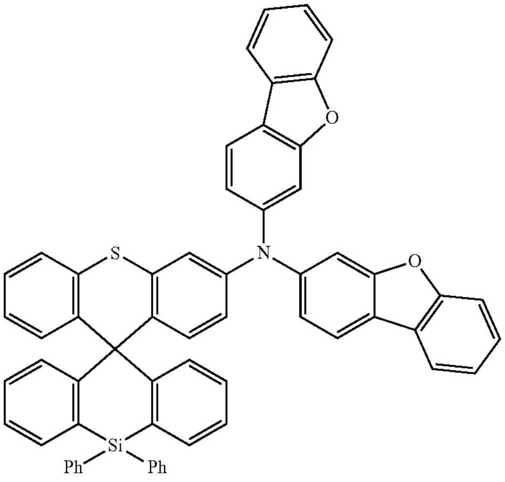
-continued
A181
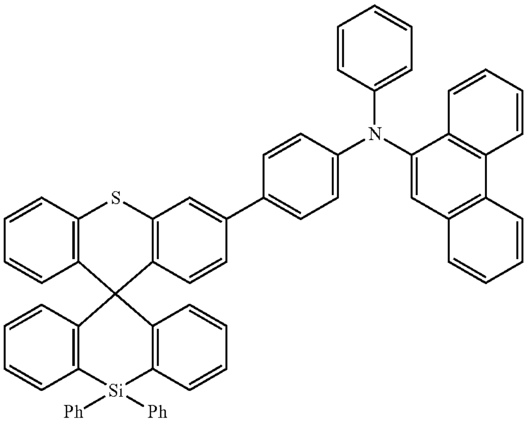
A182
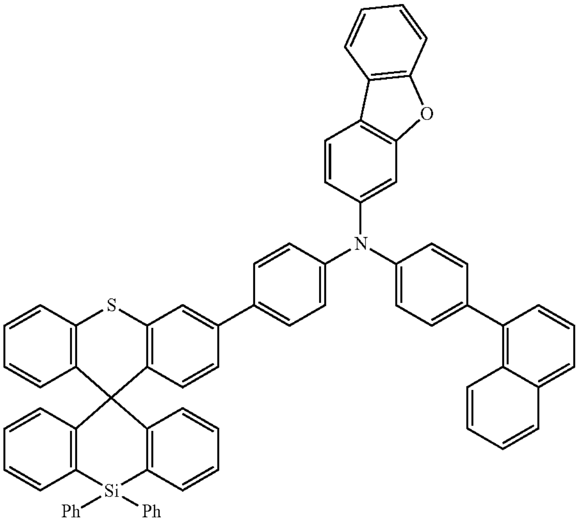
A183
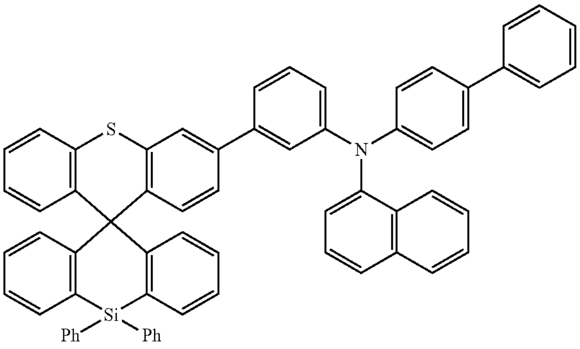

-continued
A184
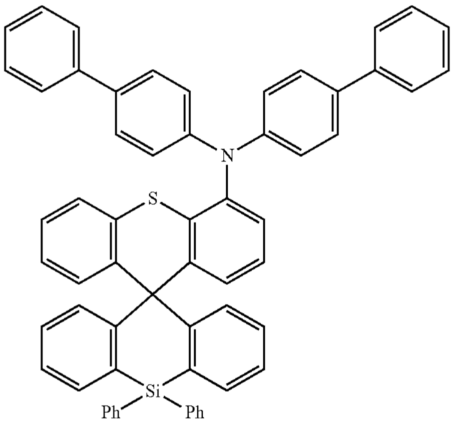
A185
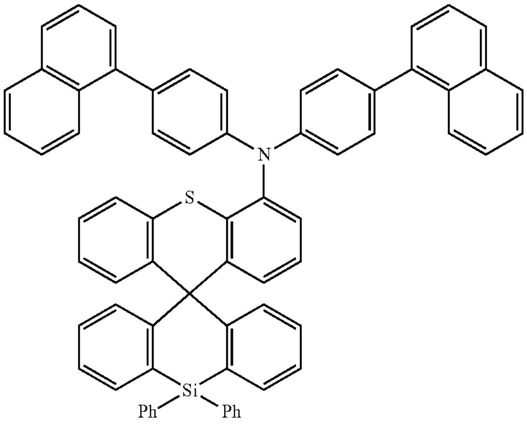
A186
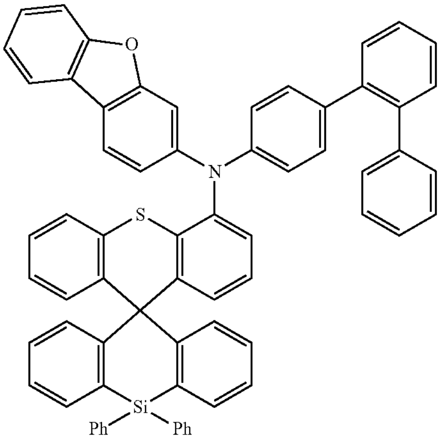
-continued
A187
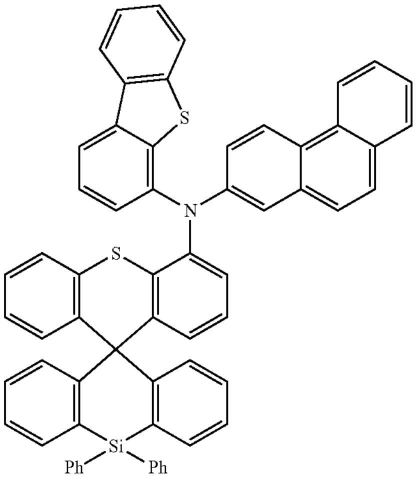
A188
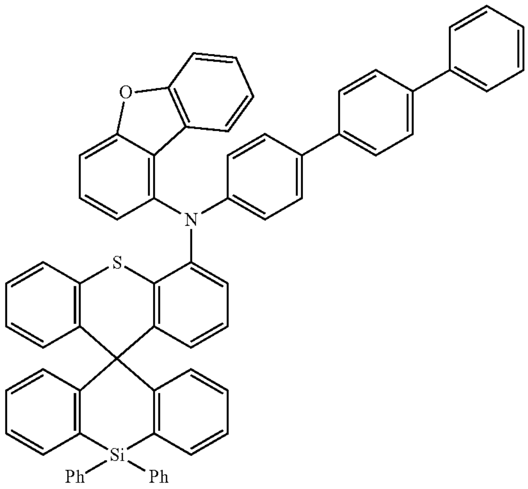
A189
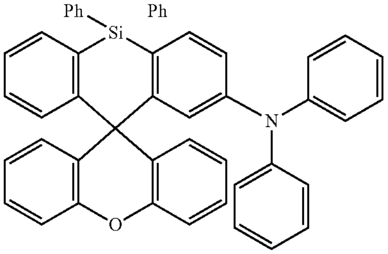
A190
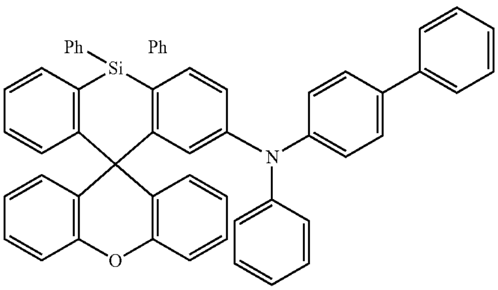

-continued
A191
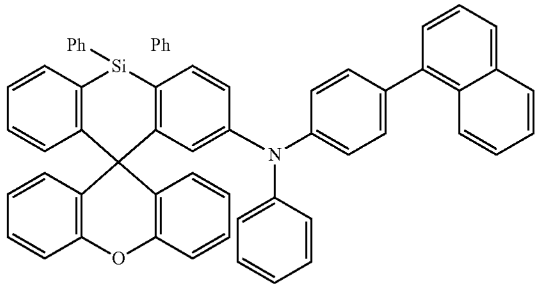
A192
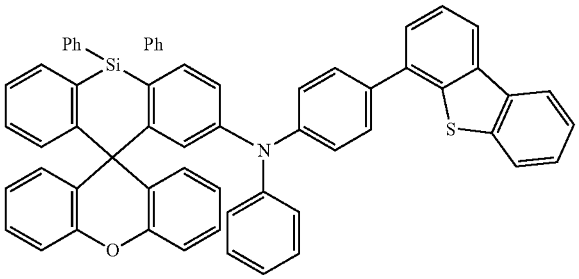
A193
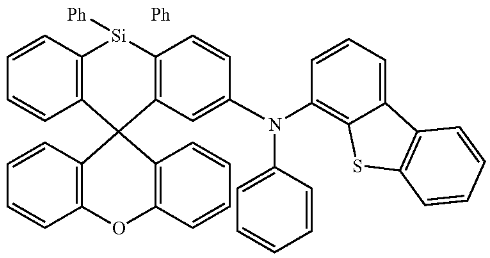
A194
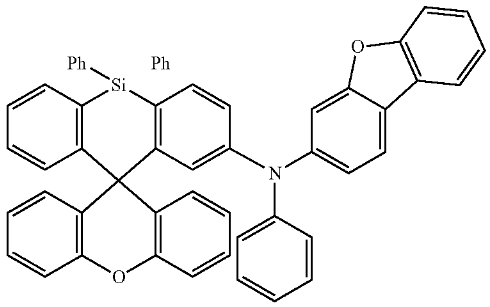
A195
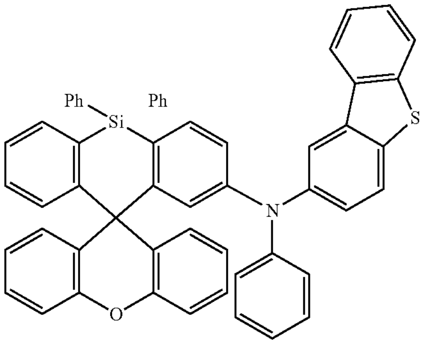
-continued
A196
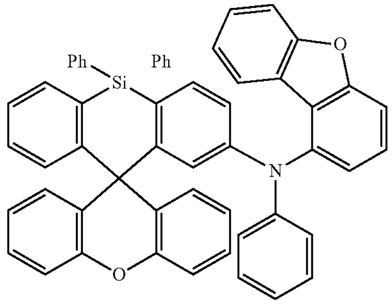
A197
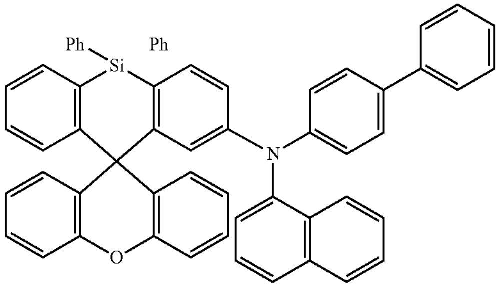
A198
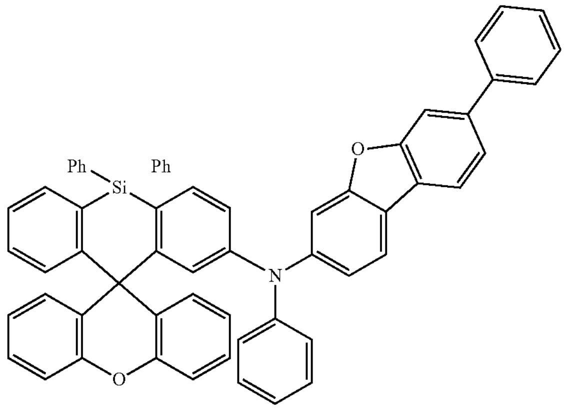
A199
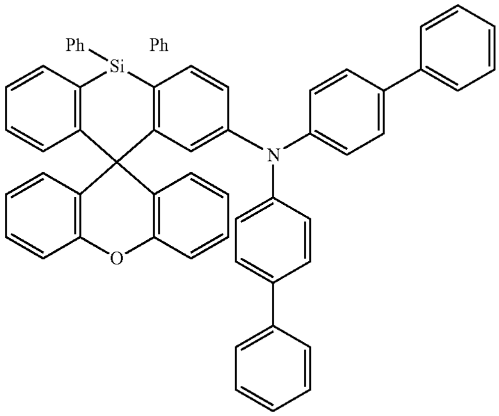

-continued
A200
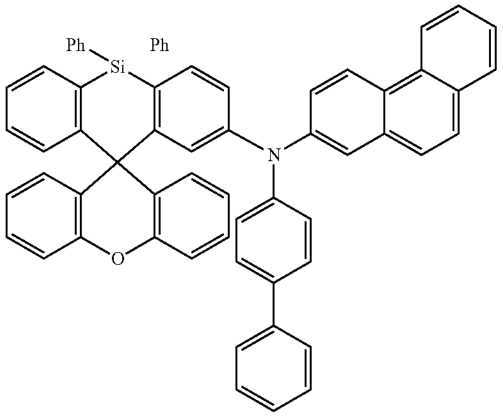
A201
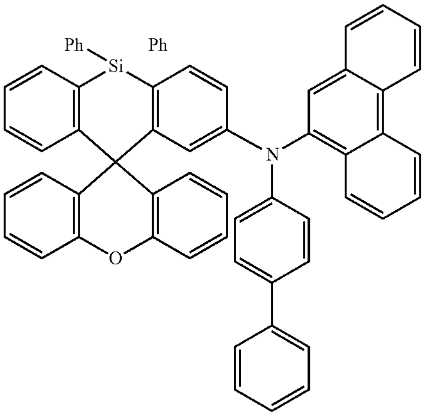
A202
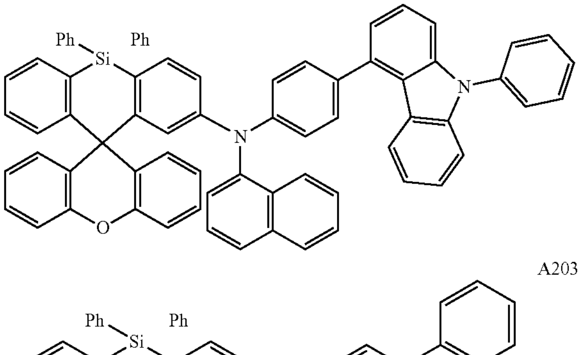
A203
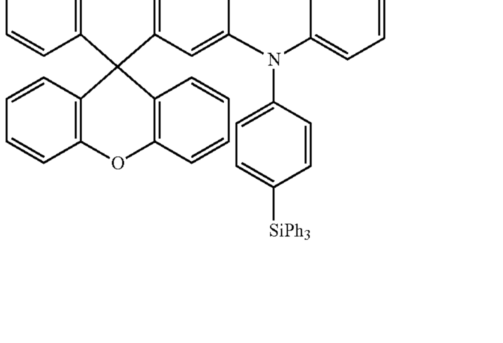
-continued
A204
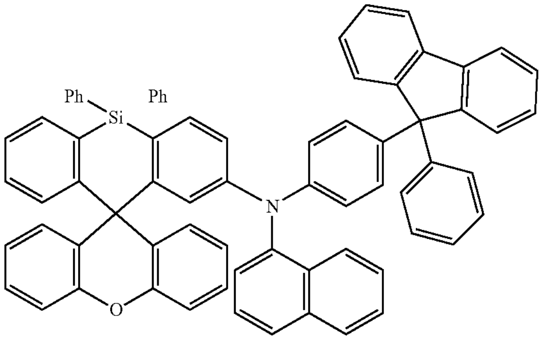
A205
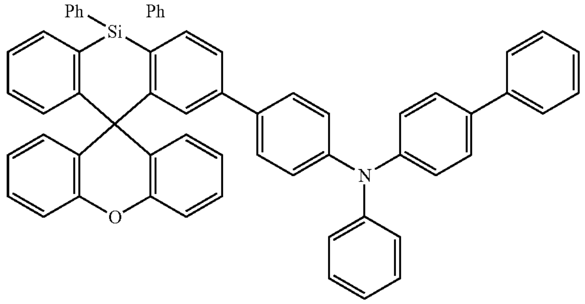
A206
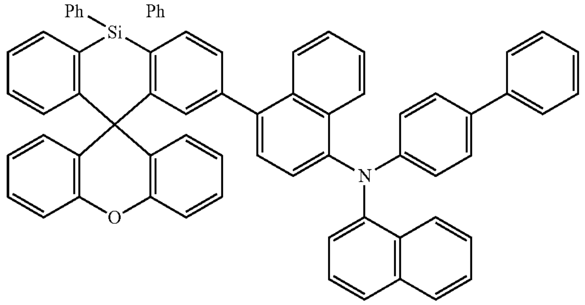
A207
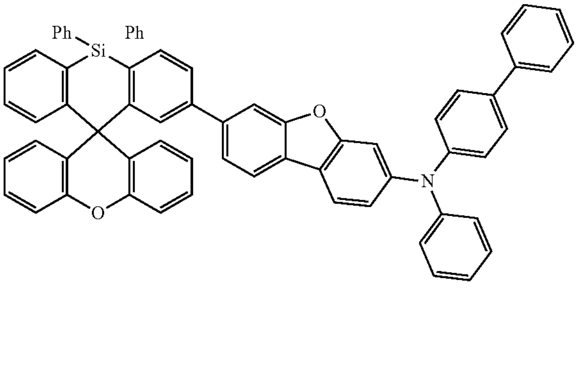

-continued
A208
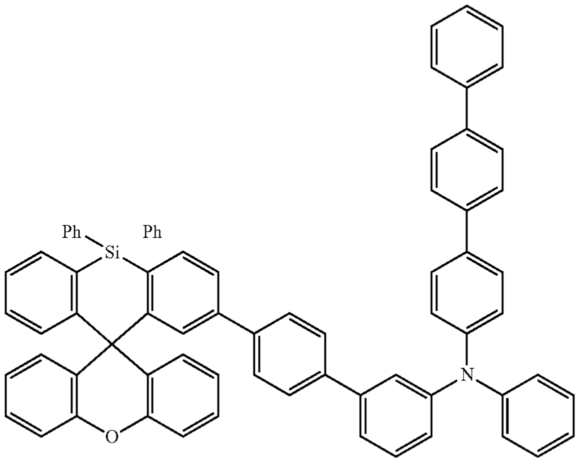
A209
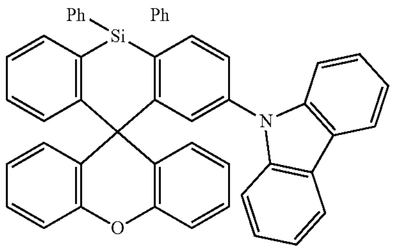
A210
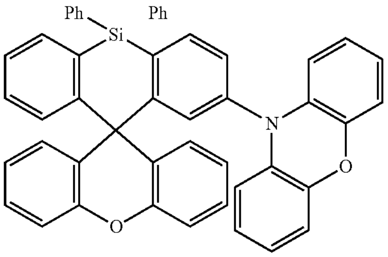
A211
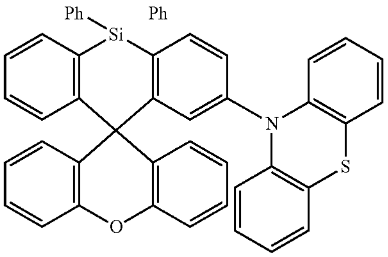
A212
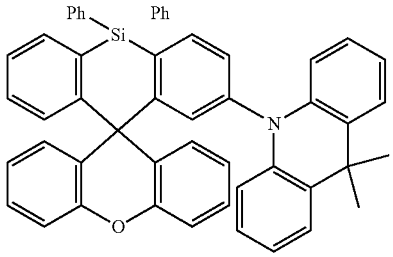
-continued
A213
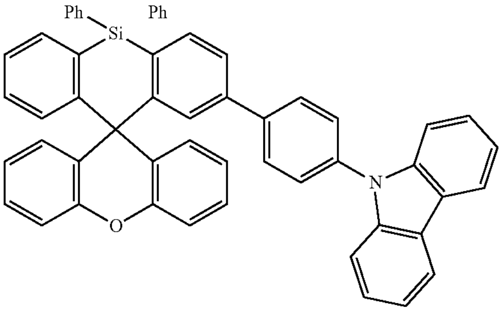
A214
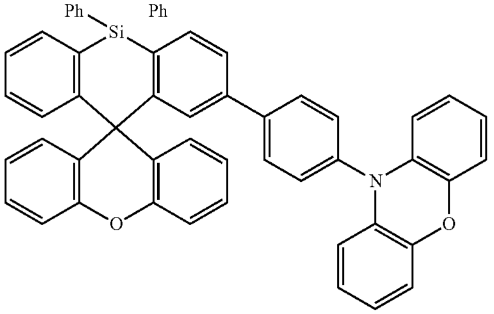
A215
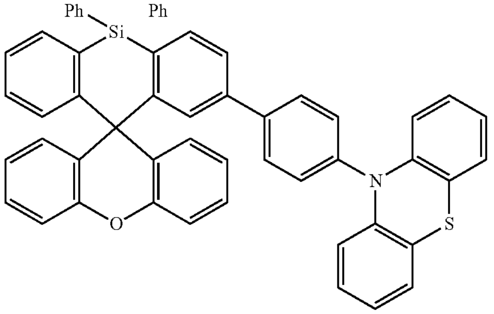
A216
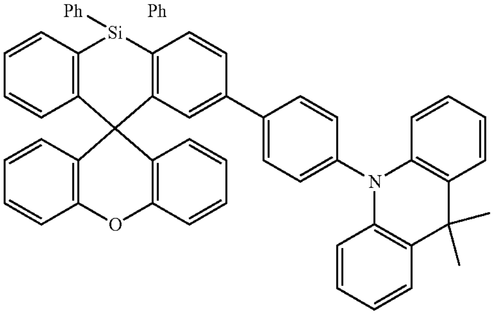
A217
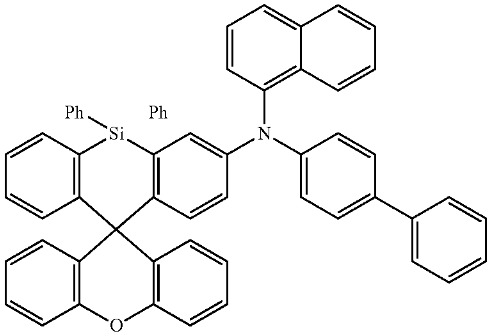

-continued
A218
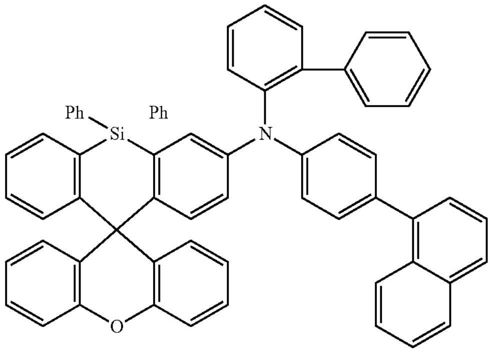
A219
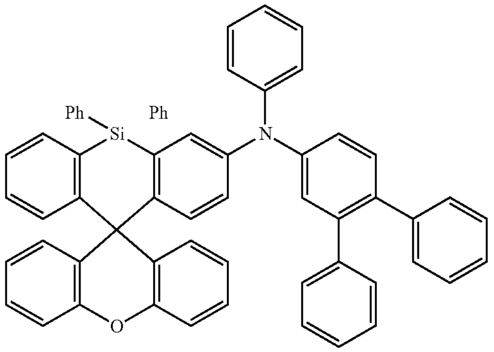
A220
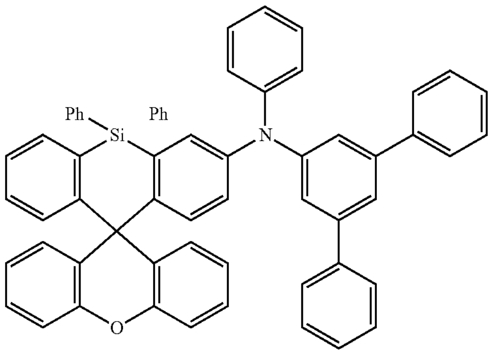
A221
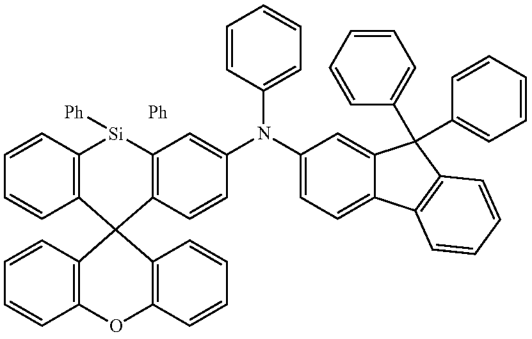
-continued
A222
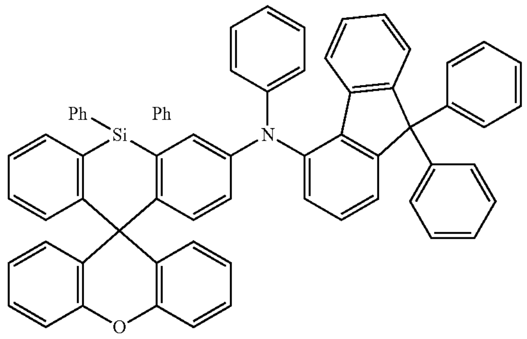
A223
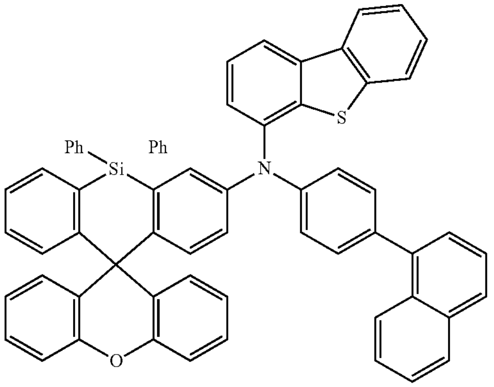
A224
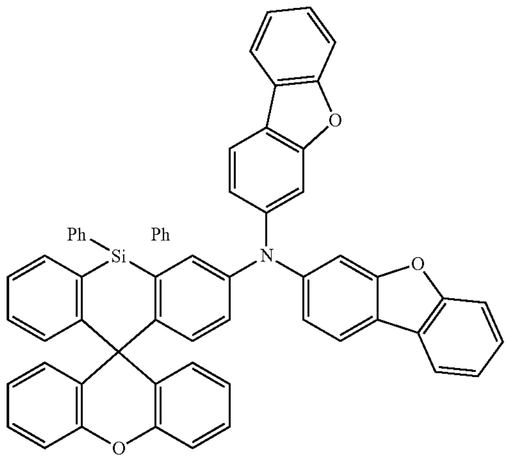
A225
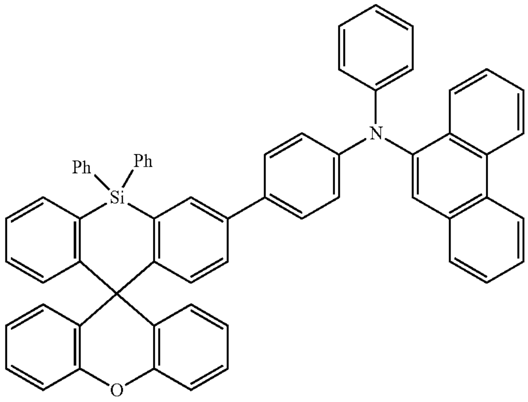

-continued
A226
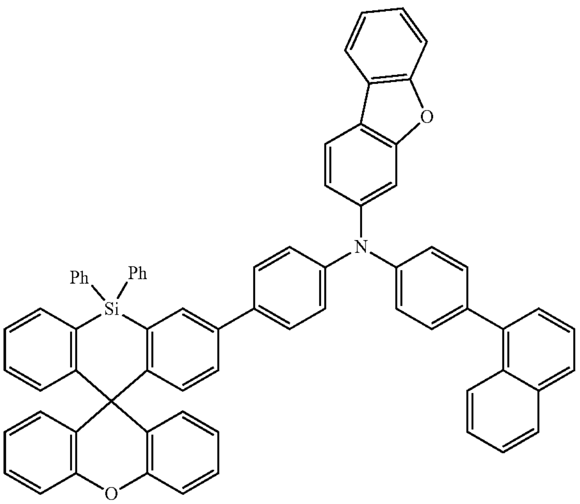
A227
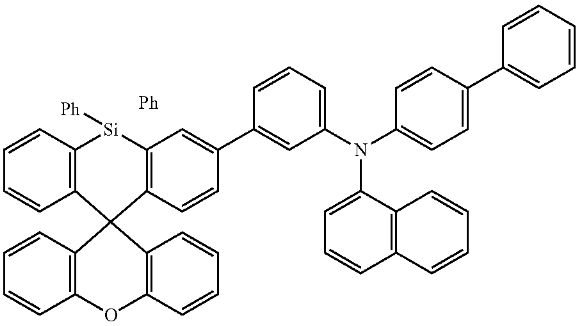
A228
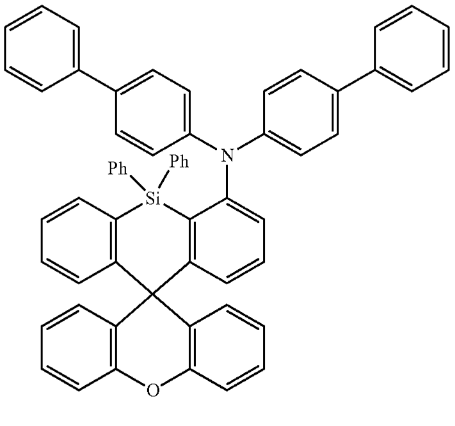
-continued
A229
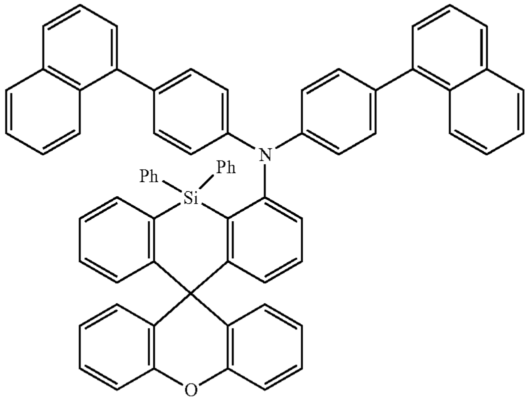
A230
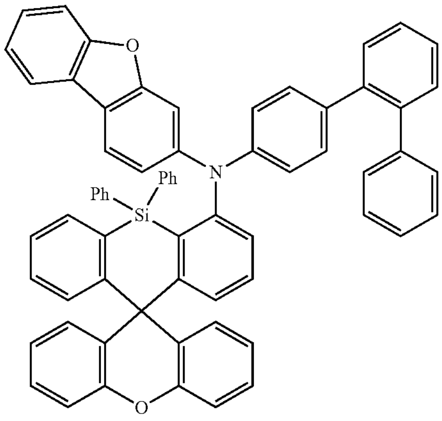
A231
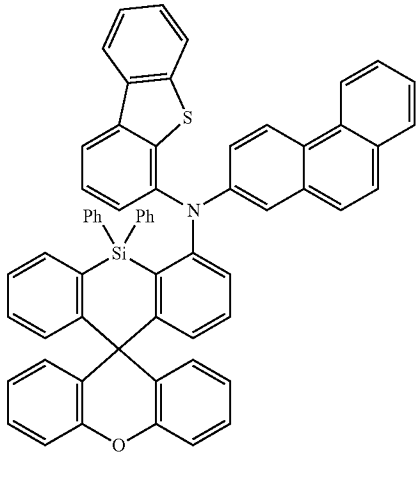

-continued
A232
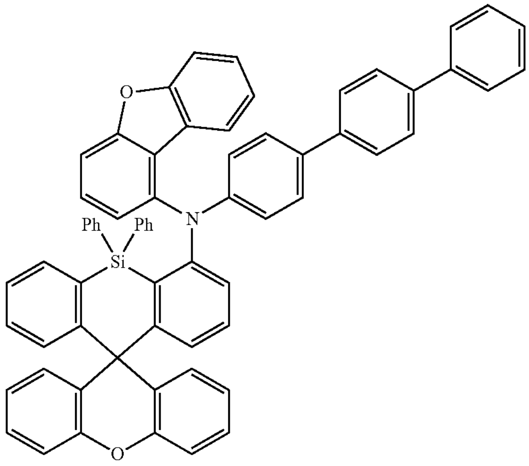
A233
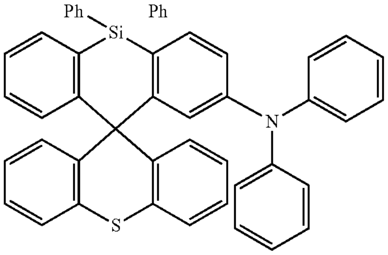
A234
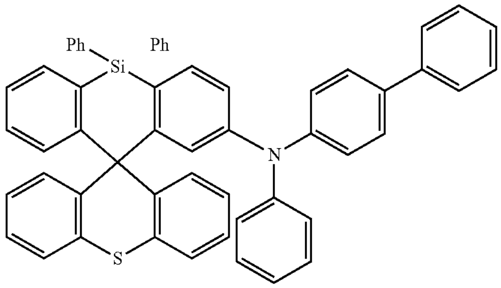
A235
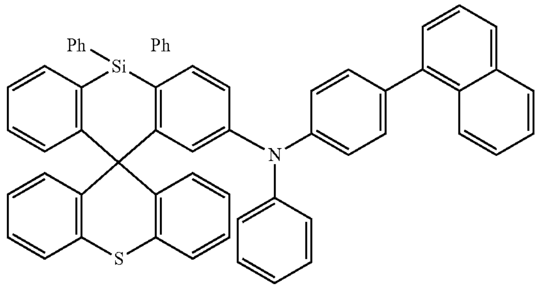
-continued
A236
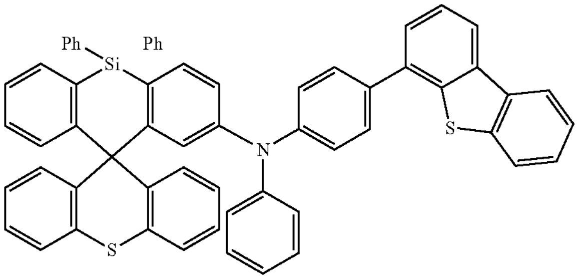
A237
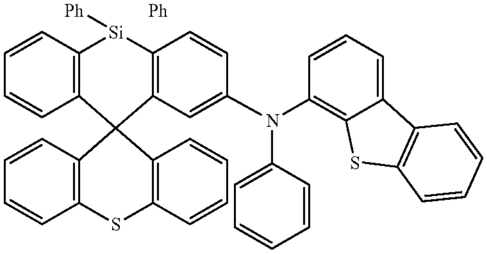
A238
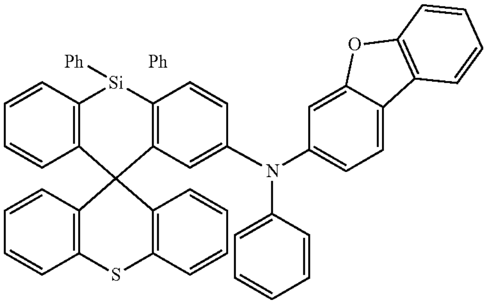
A239
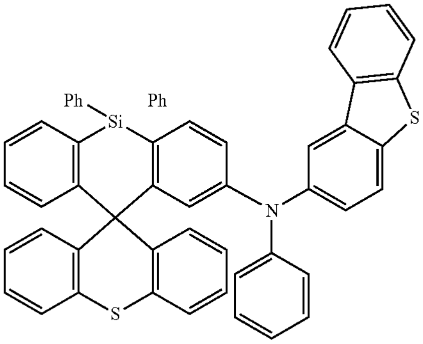
A240
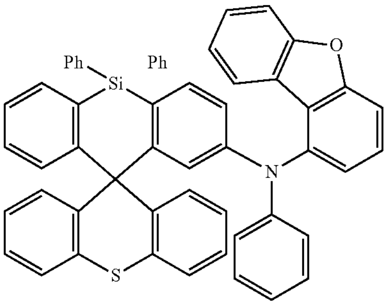

-continued
A241
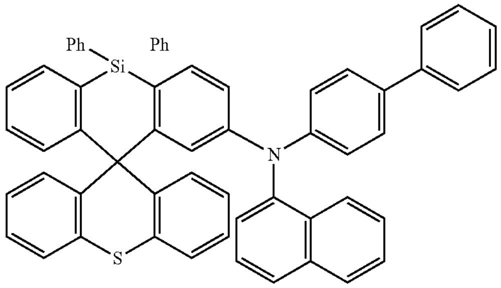
A242
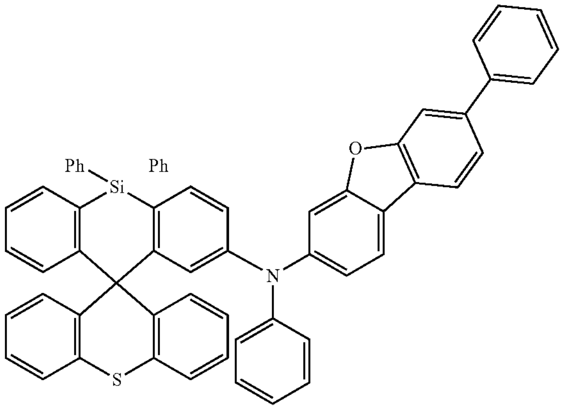
A243
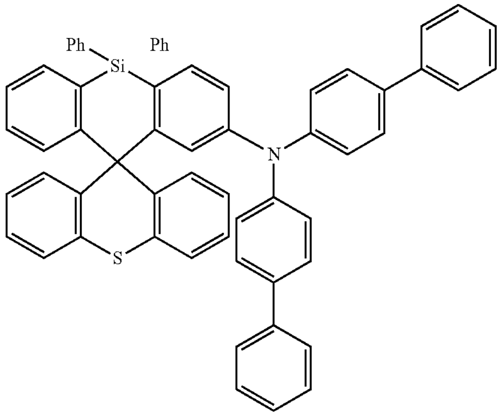
A244
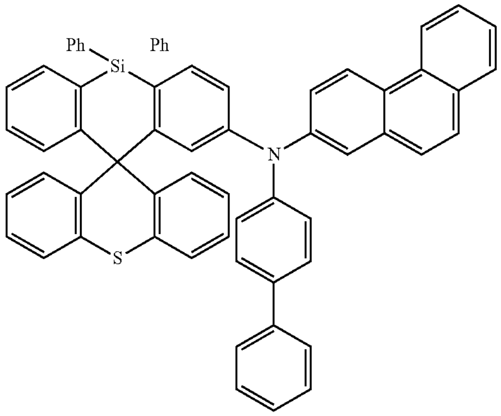
-continued
A245
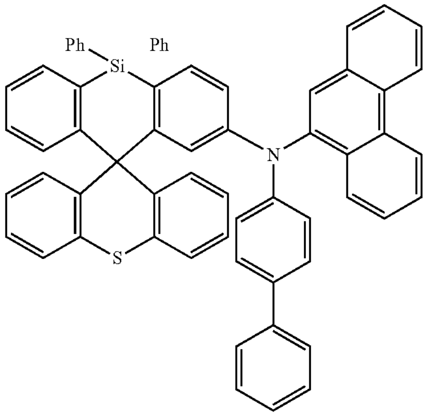
A246
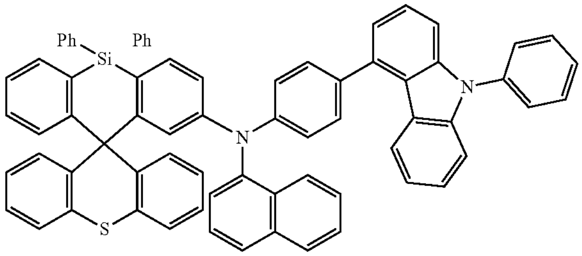
A247
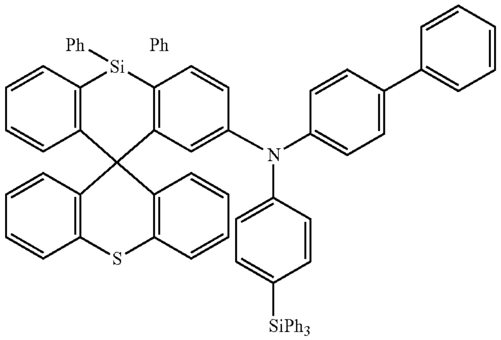
A248
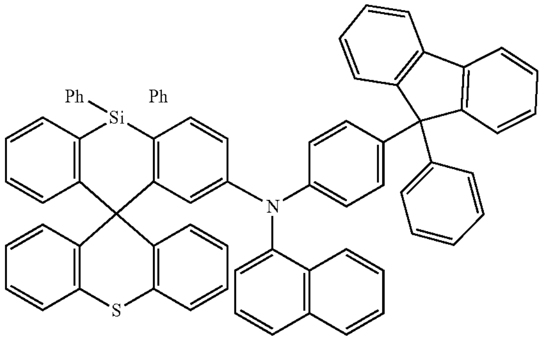

-continued
A249
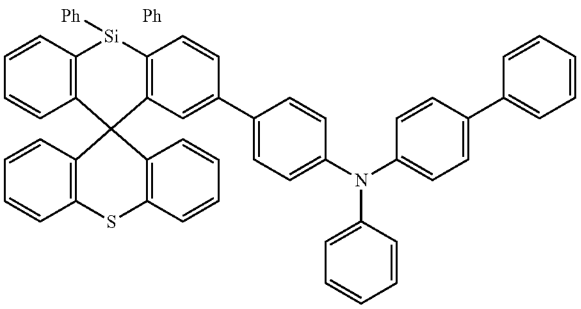
A250
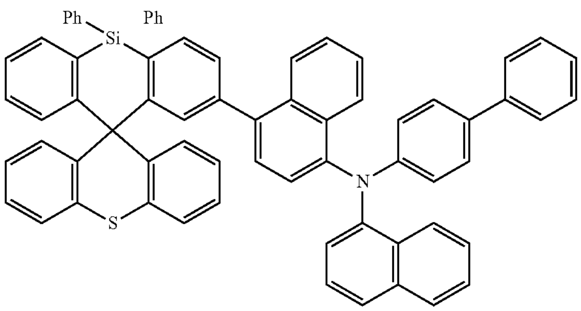
A251
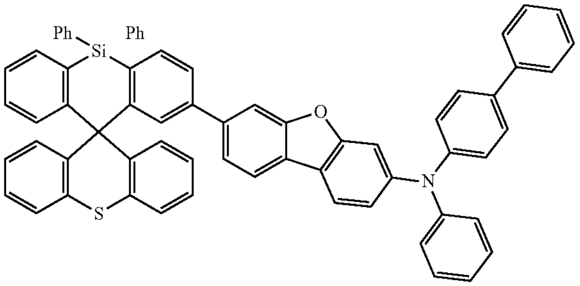
A252
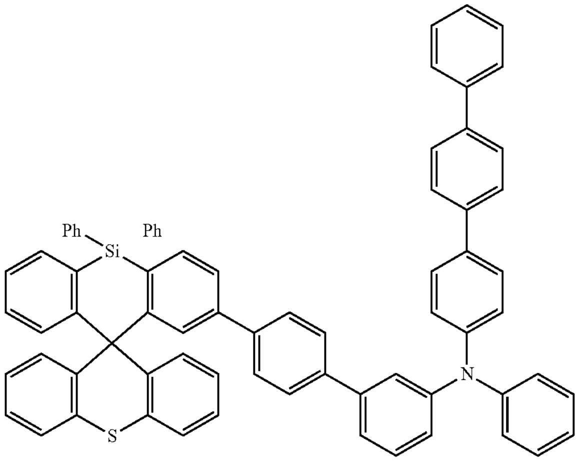
-continued
A253
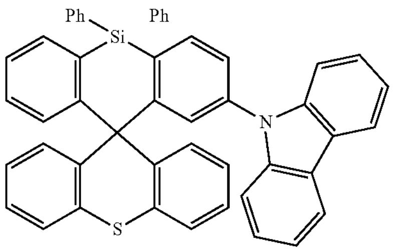
A254
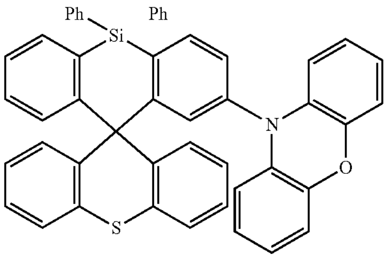
A255
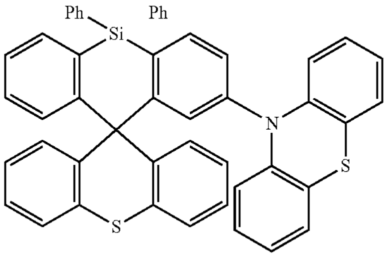
A256
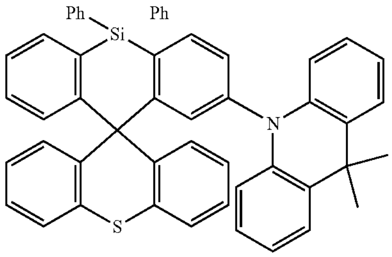
A257
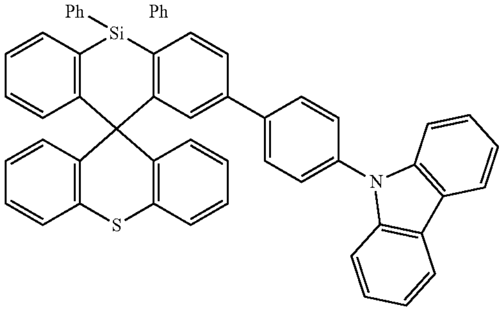

-continued
A258
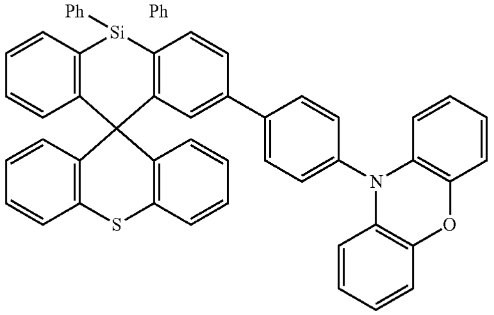
A259
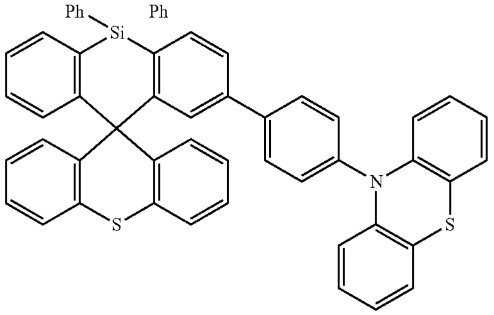
A260
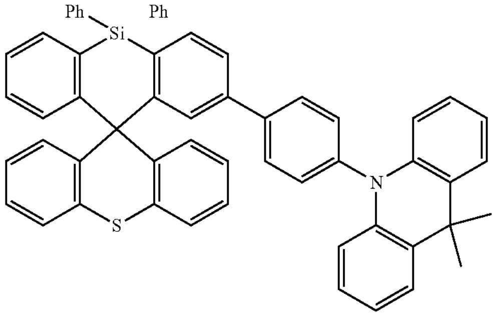
A261
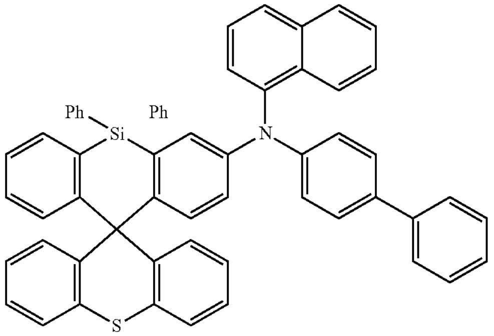
-continued
A262
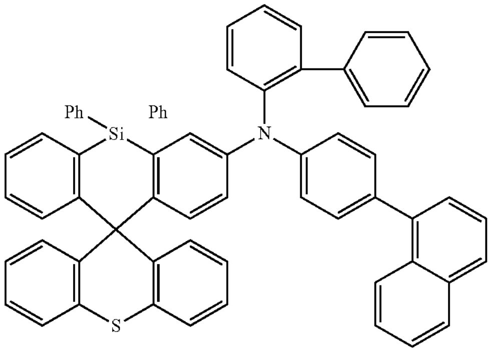
A263
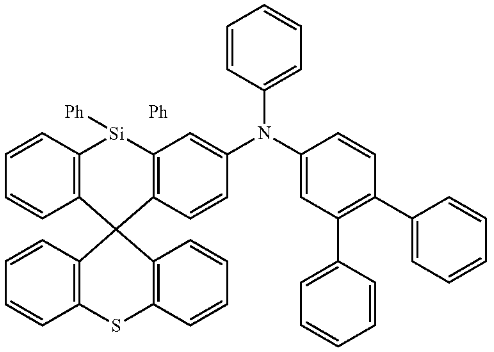
A264
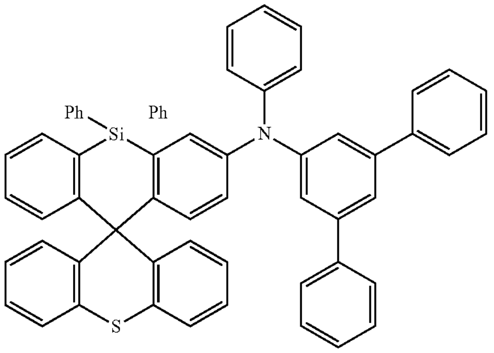
A265
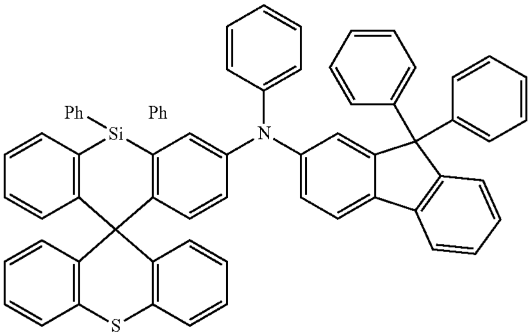

-continued
A266
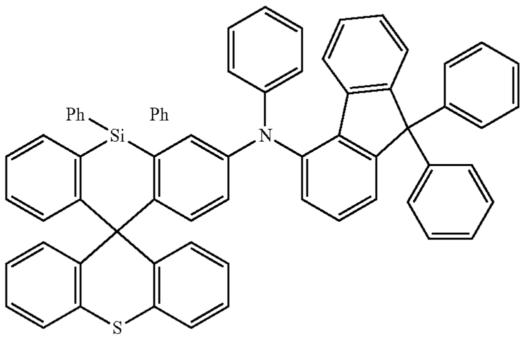
A267
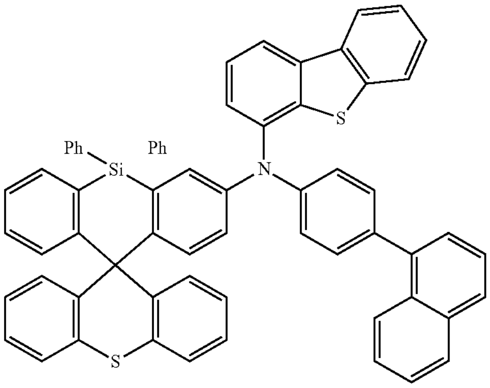
A268
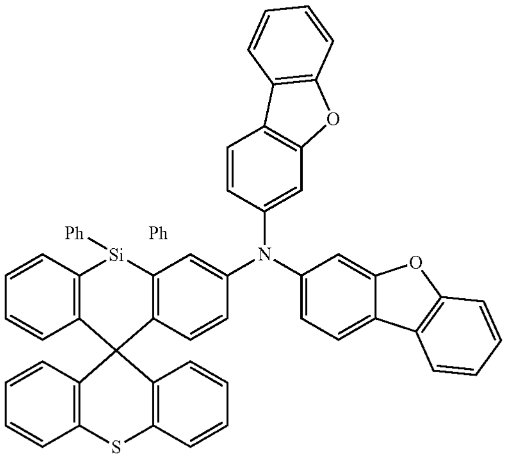
A269
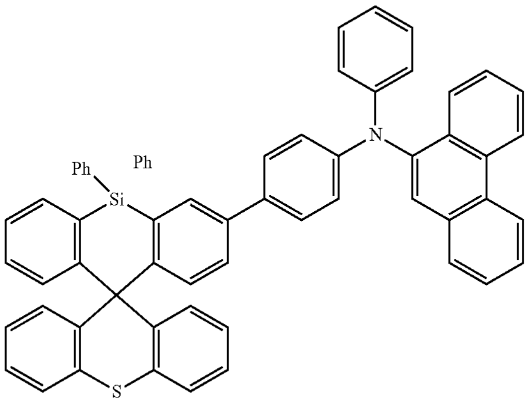
-continued
A270
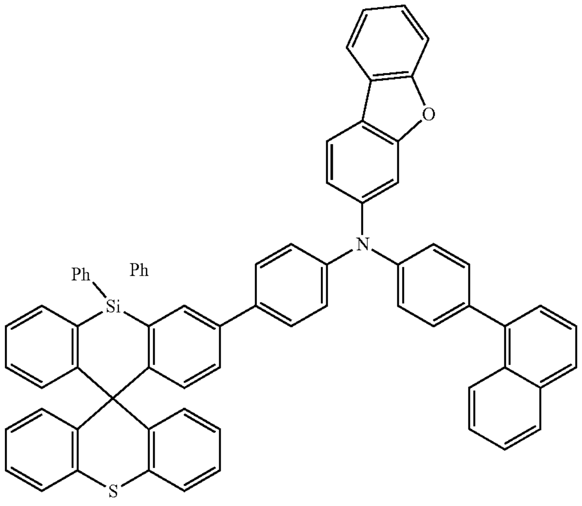
A271
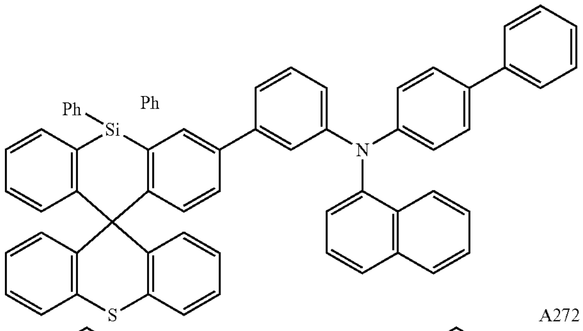
A272
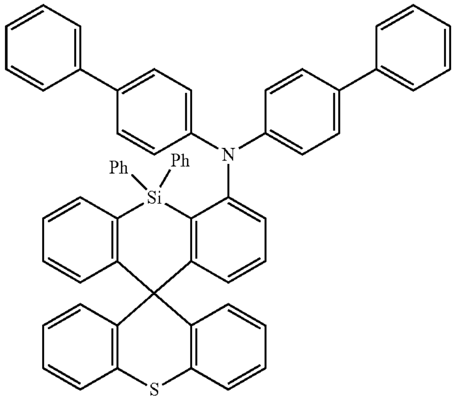
A273
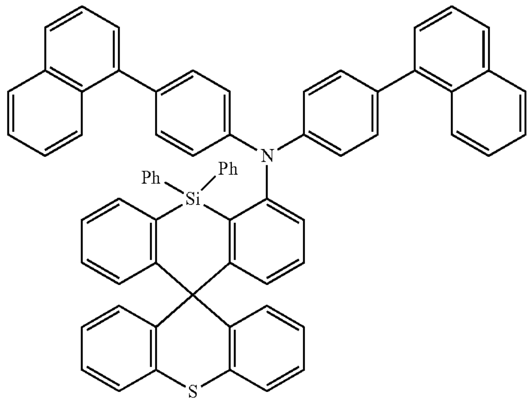

-continued
A274
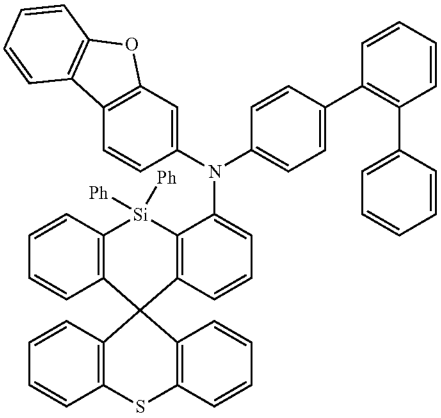
A275
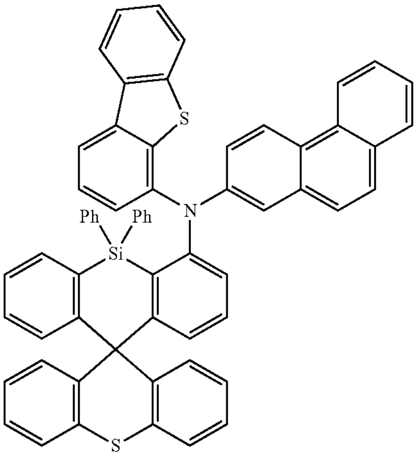
A276
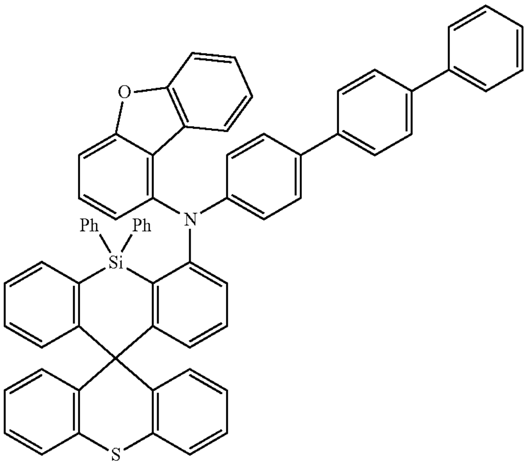
-continued
A277
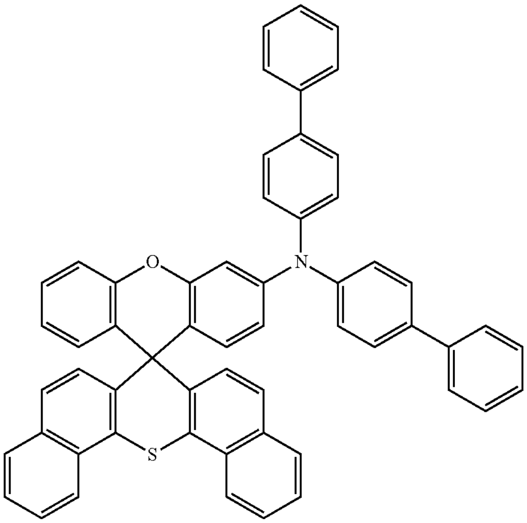
A278
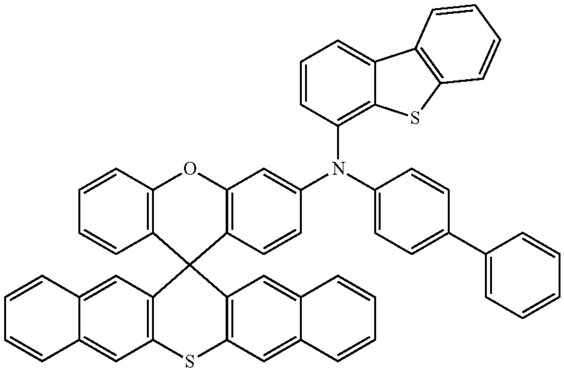
A279
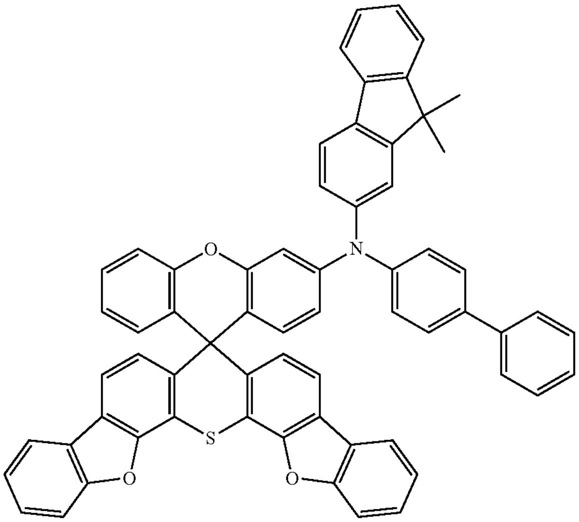

-continued
A280
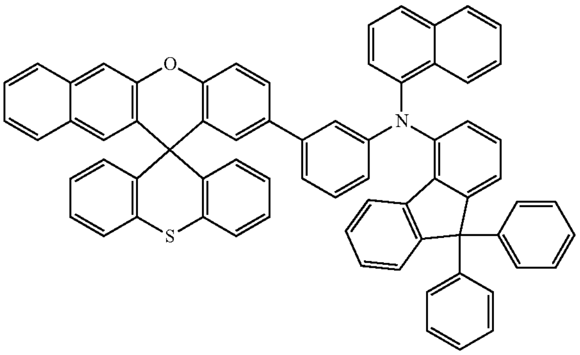
[Compound Group 2]
B1
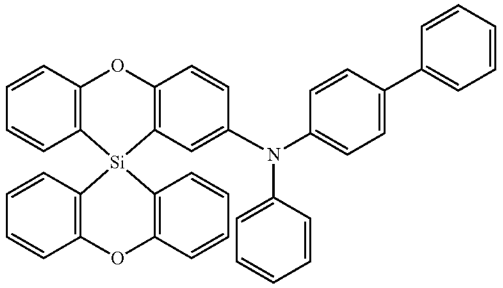
B2
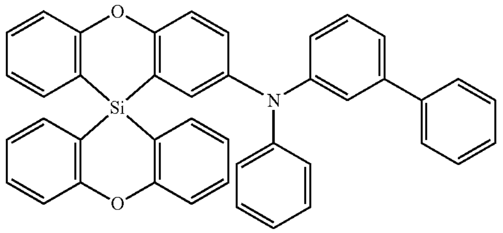
B3
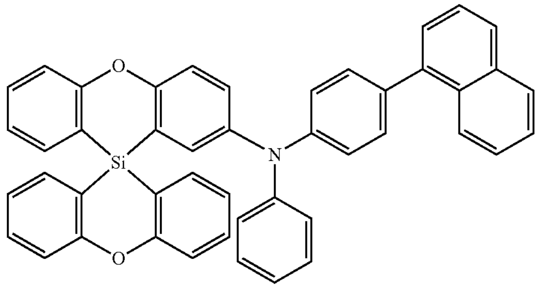
B4
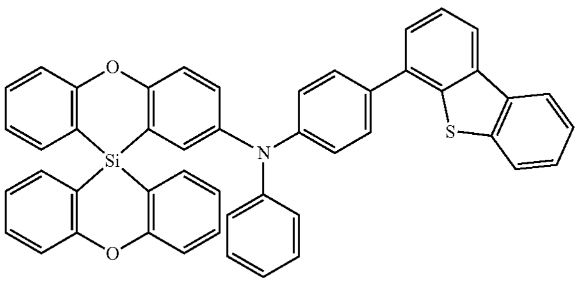
-continued
B5
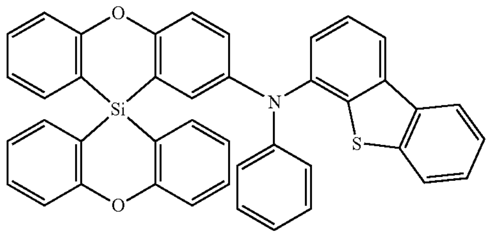
B6
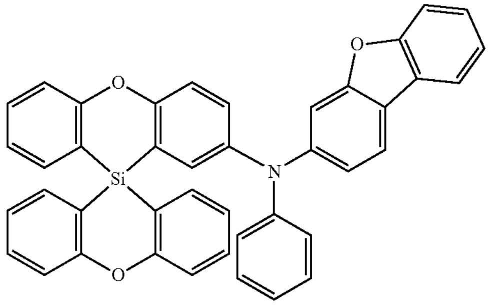
B7
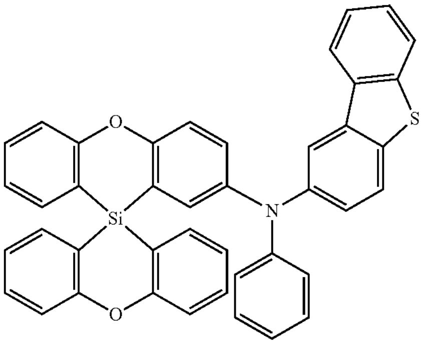
B8
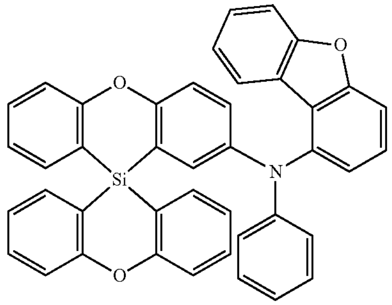
B9
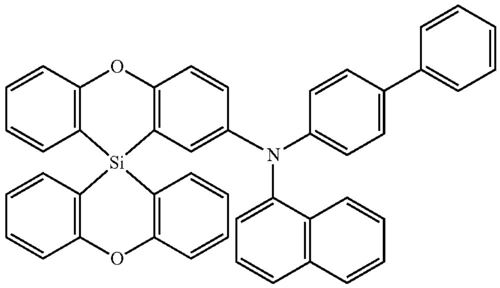

-continued
B10
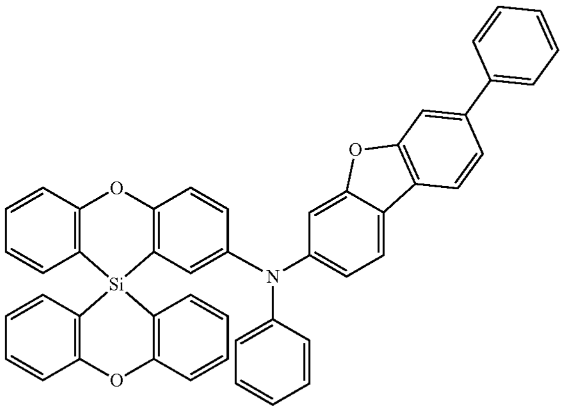
B11
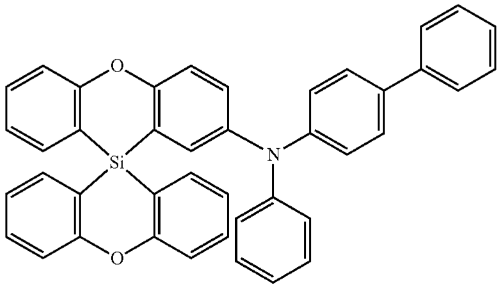
B12
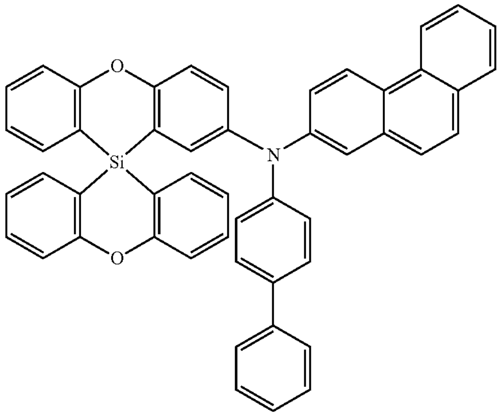
B13
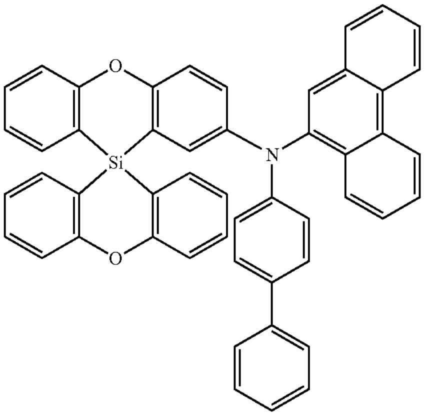
-continued
B14
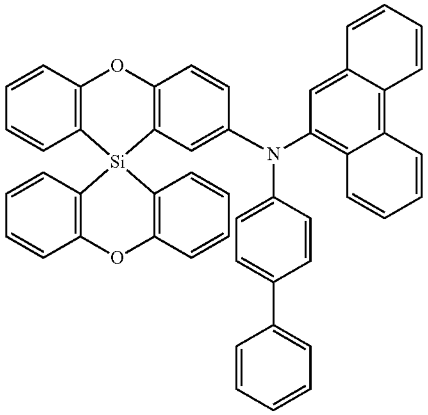
B15
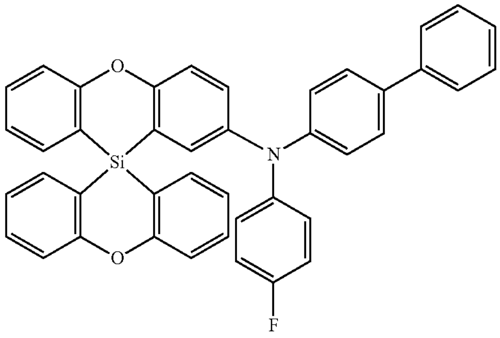
B16
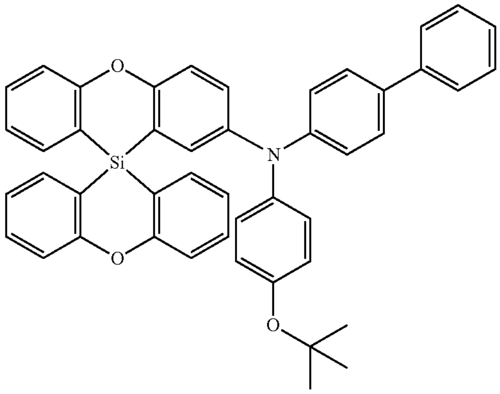
B17
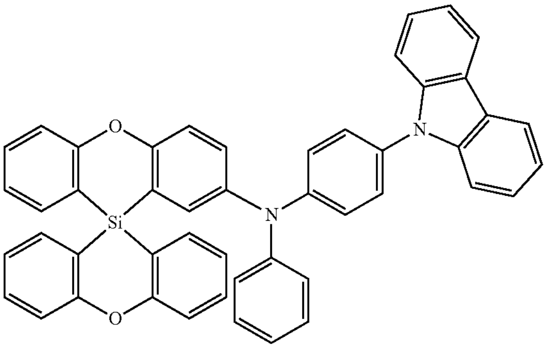

-continued
B18
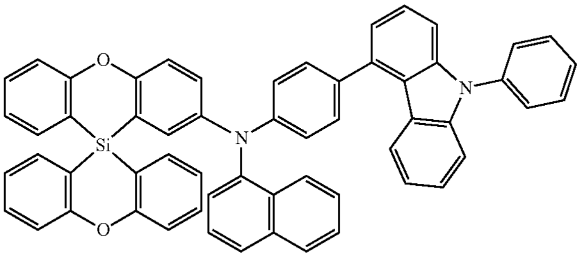
B19
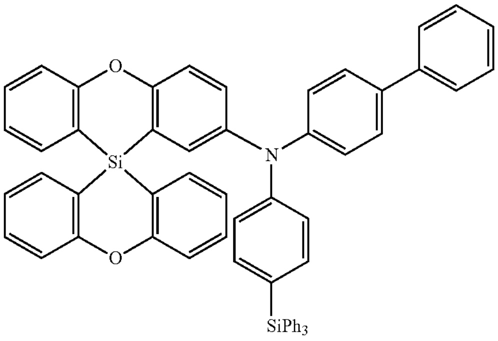
B20
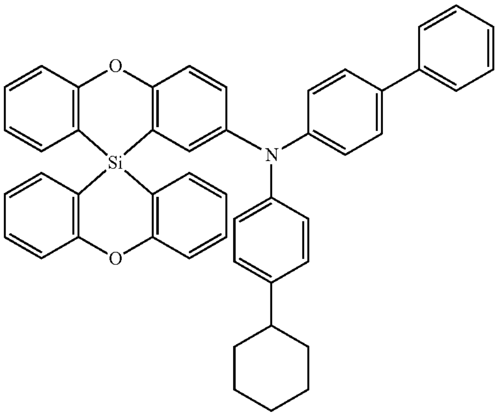
B21
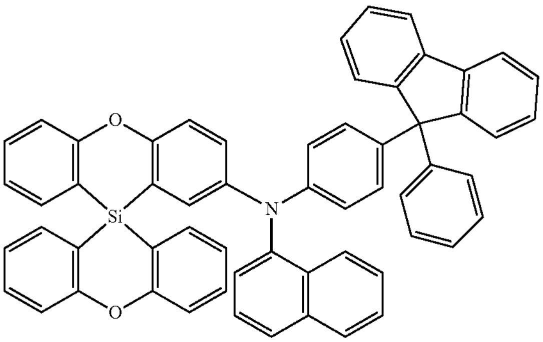
-continued
B22
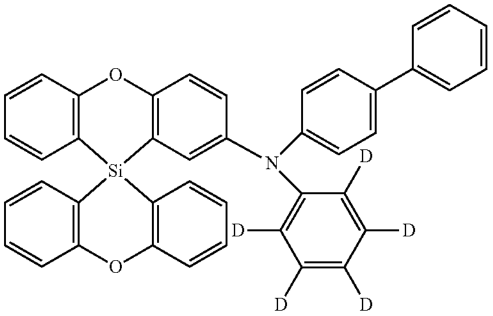
B23
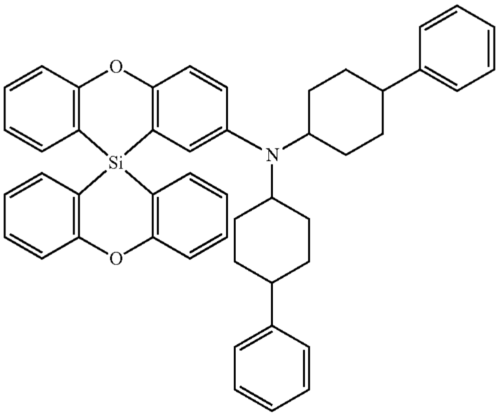
B24
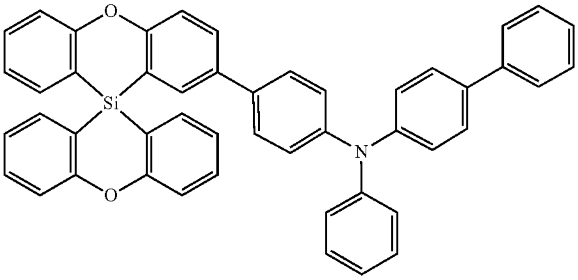
B25
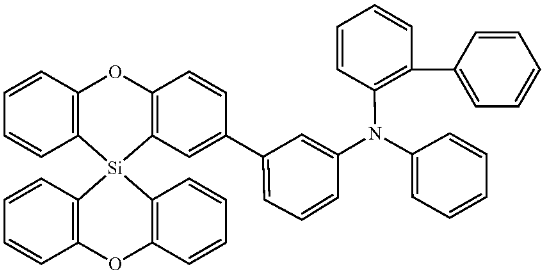

-continued
B26
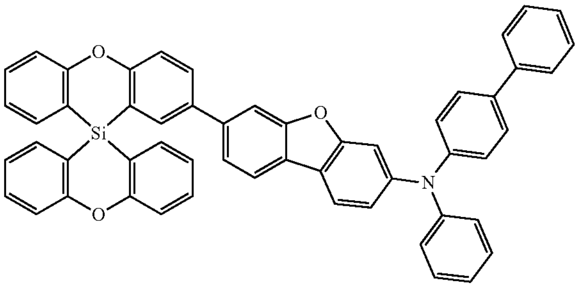
B27
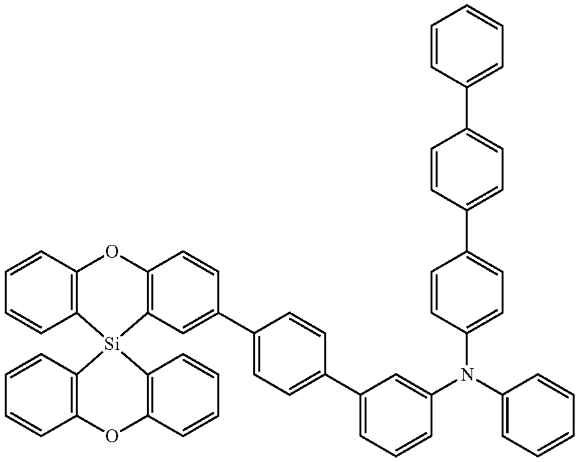
B28
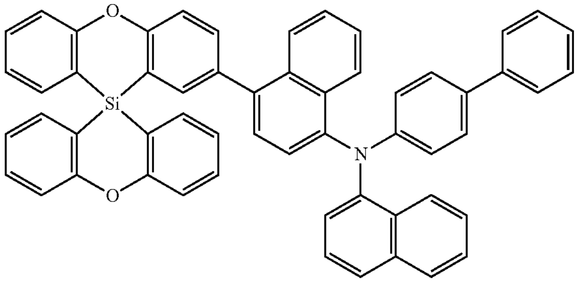
B29
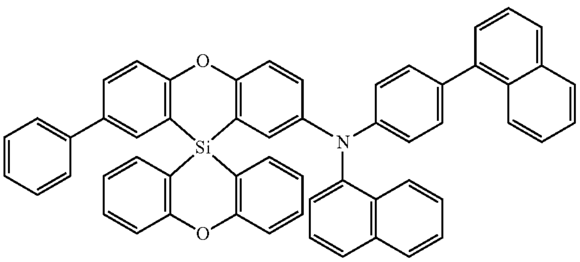
-continued
B30
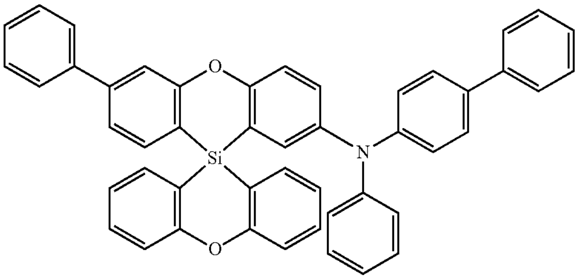
B31
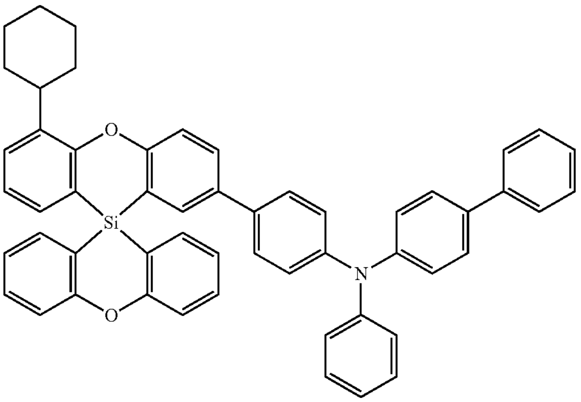
B32
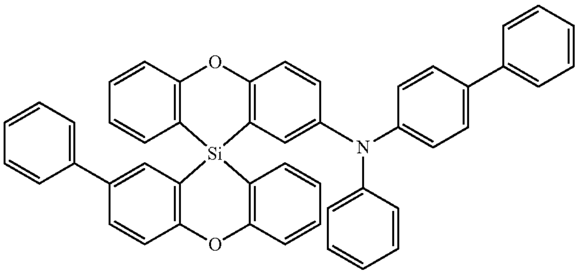
B33
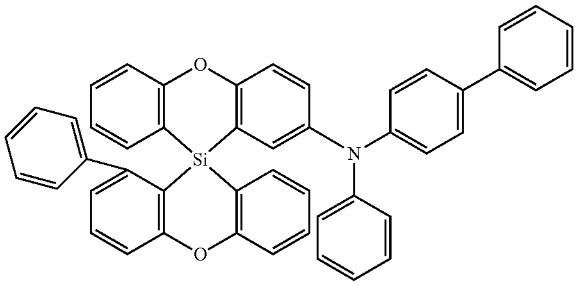
B34
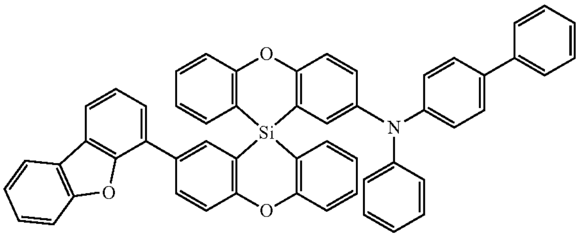

-continued
B35
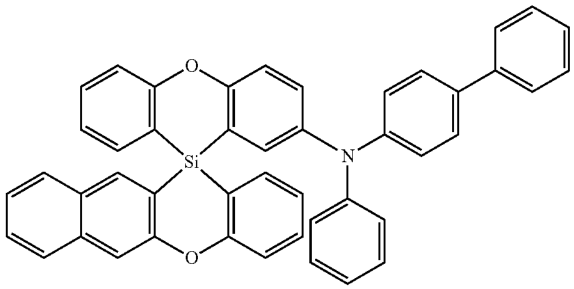
B36
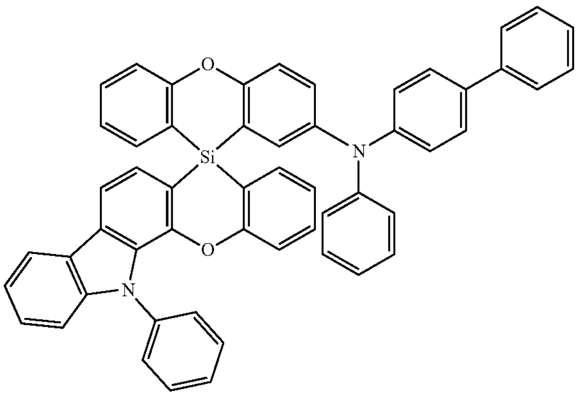
B37
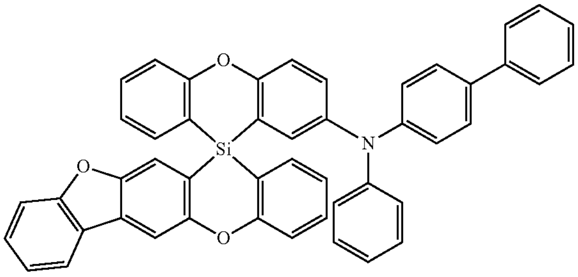
B38
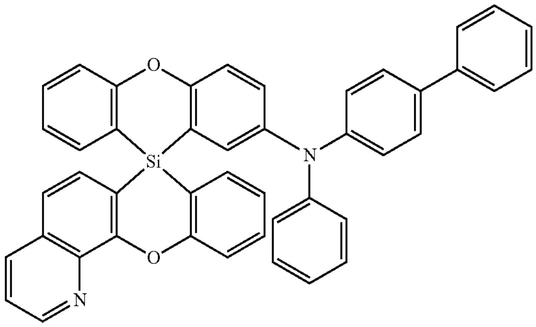
-continued
B39
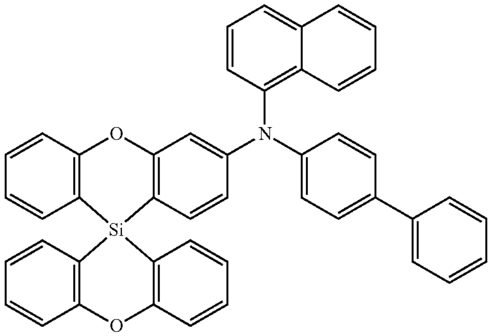
B40
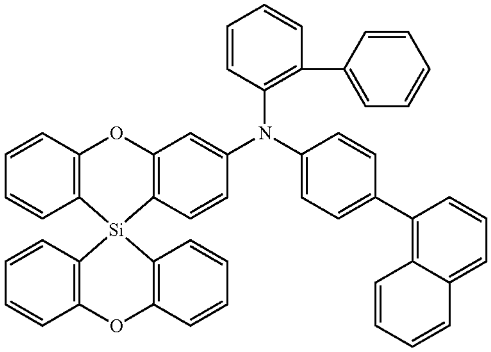
B41
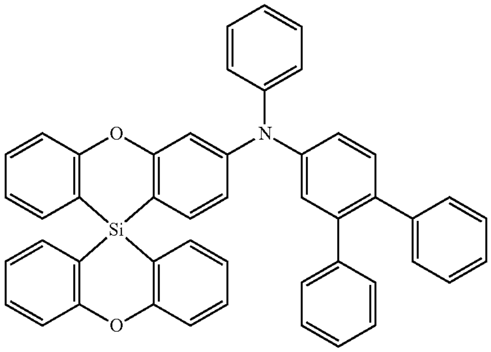
B42
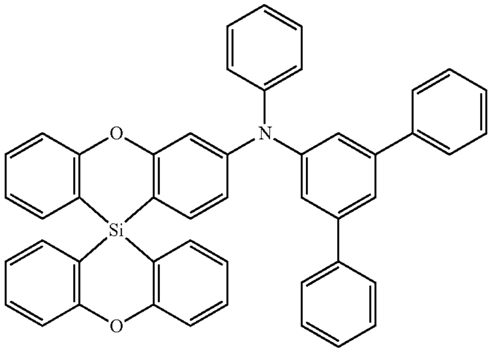

-continued
B43
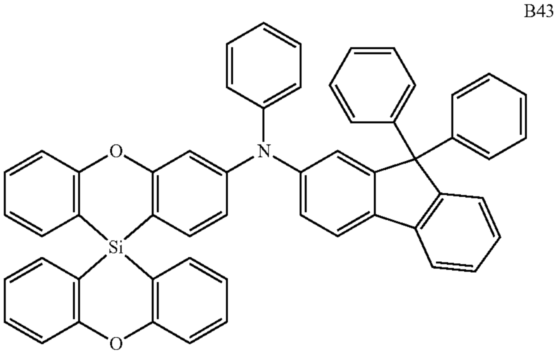
B44
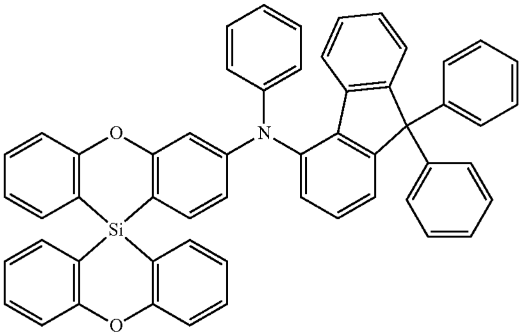
B45
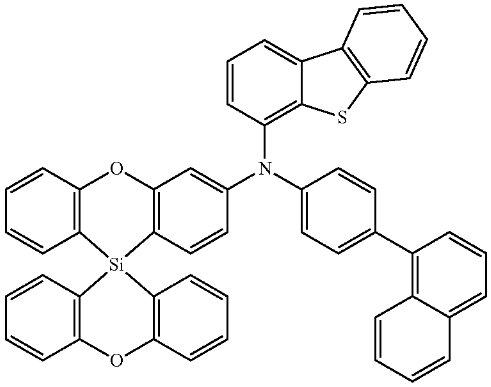
B46
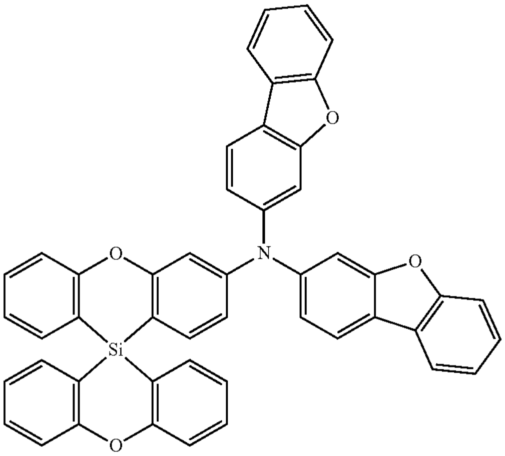
-continued
B47
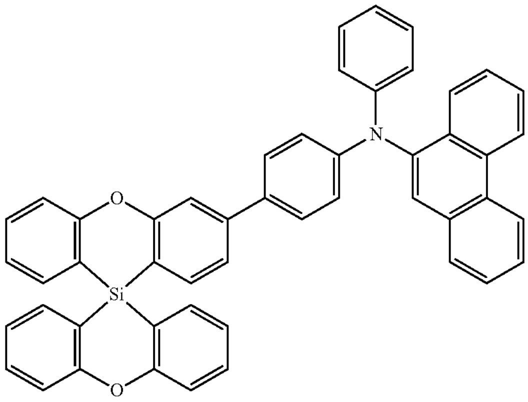
B48
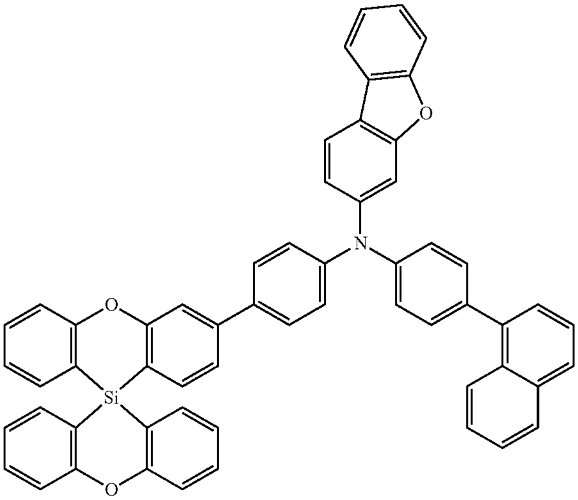
B49
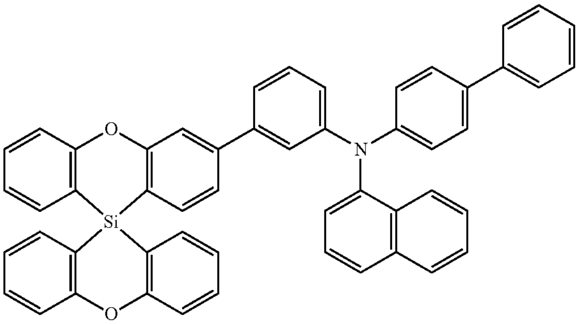

-continued
B50
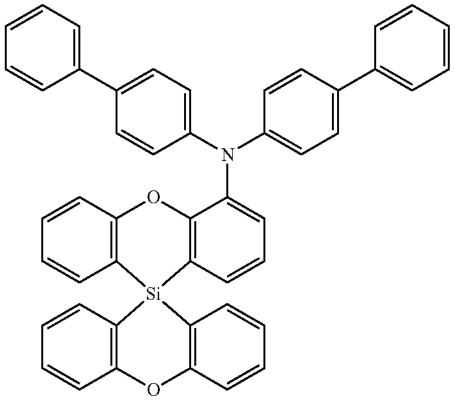
B51
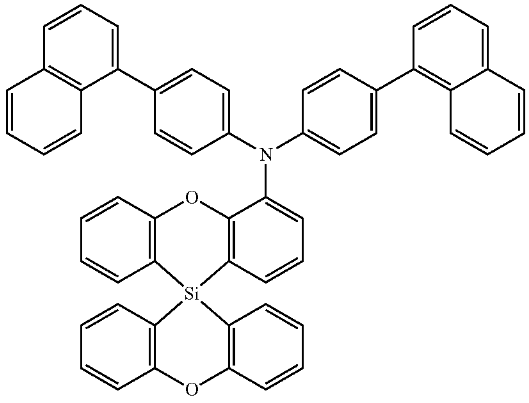
B52
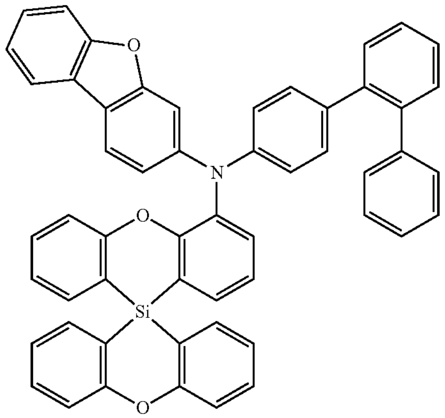
-continued
B53
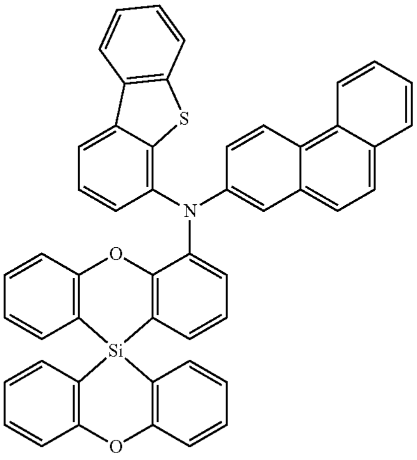
B54
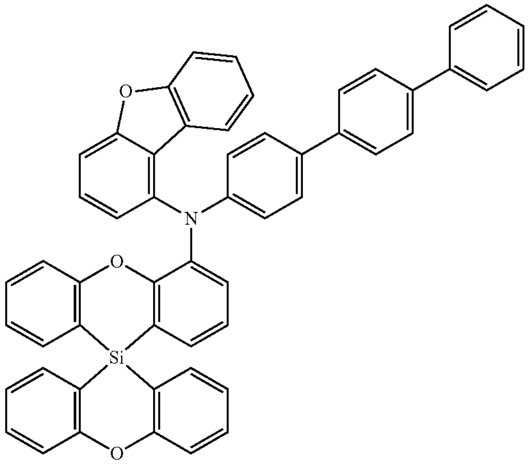
B55
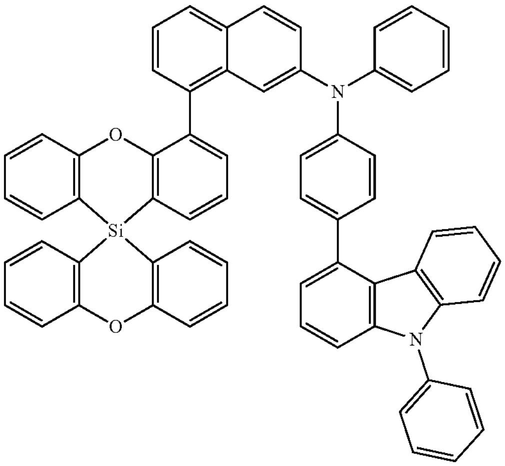

-continued
B56
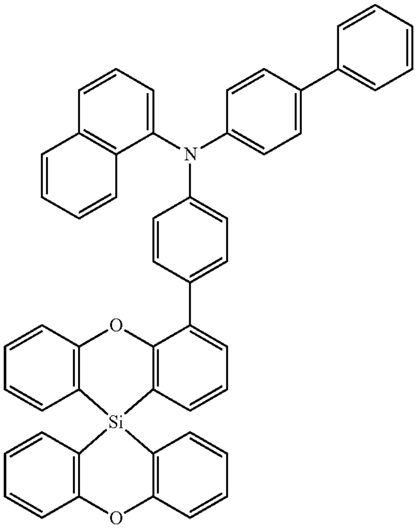
B57
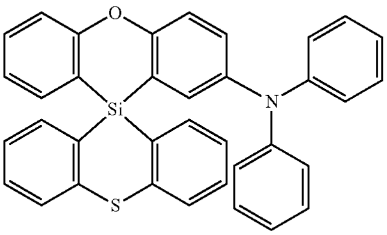
B58
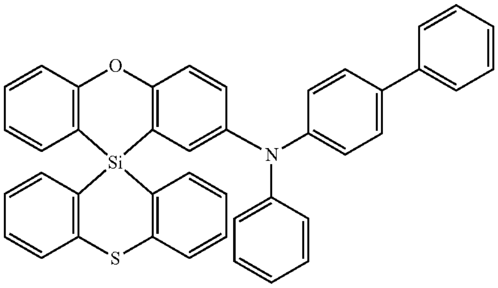
B59
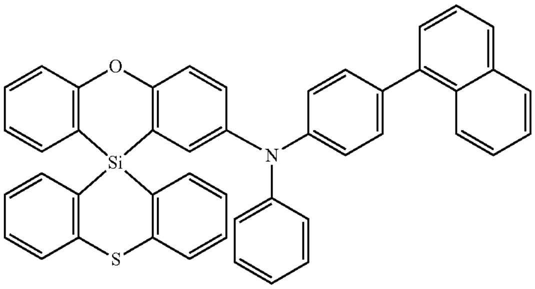
-continued
B60
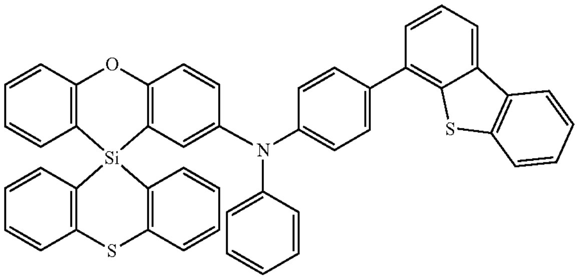
B61
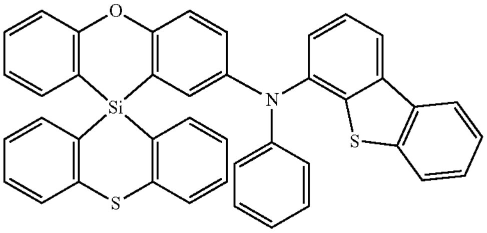
B62
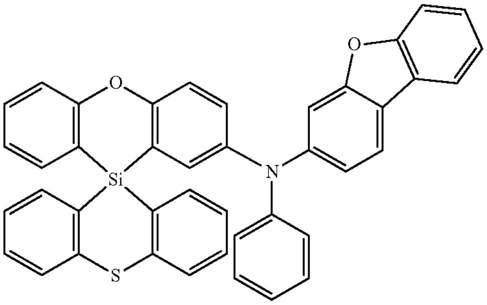
B63
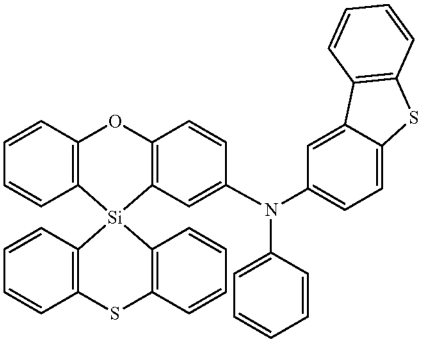
B64
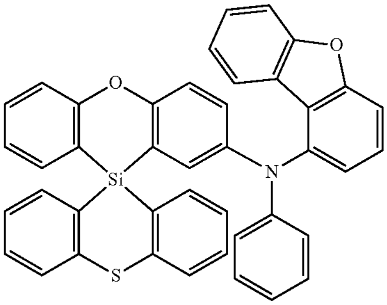

-continued
B65
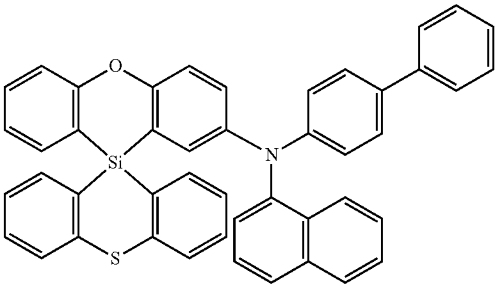
B66
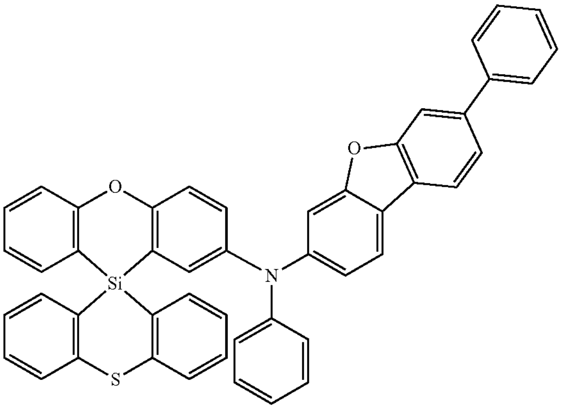
B67
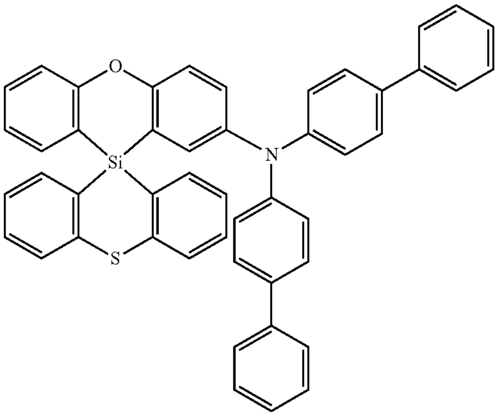
B68
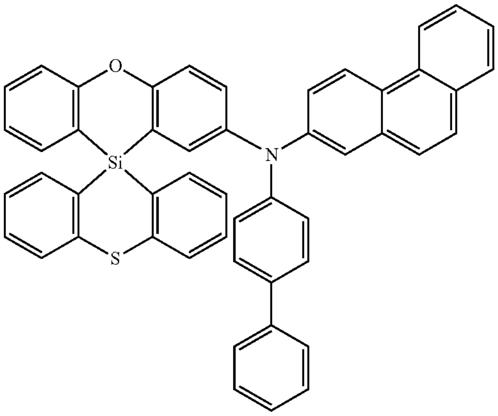
-continued
B69
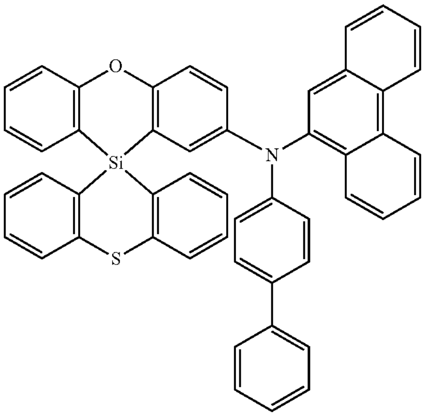
B70
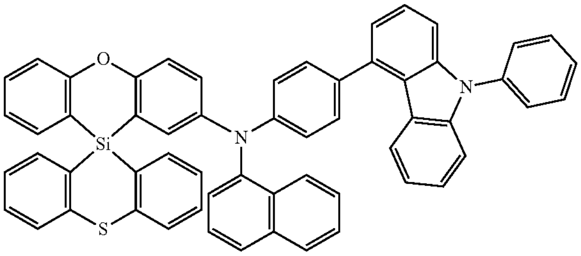
B71
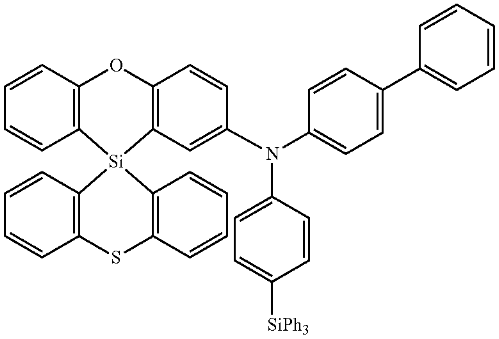
B72
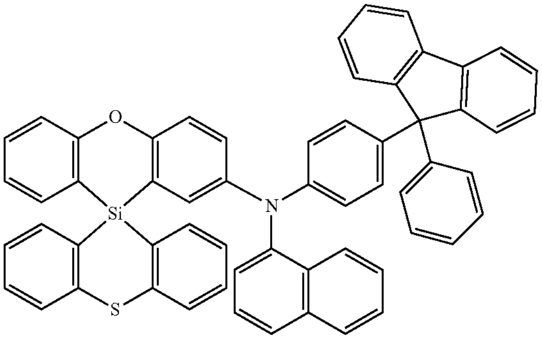

-continued
B73
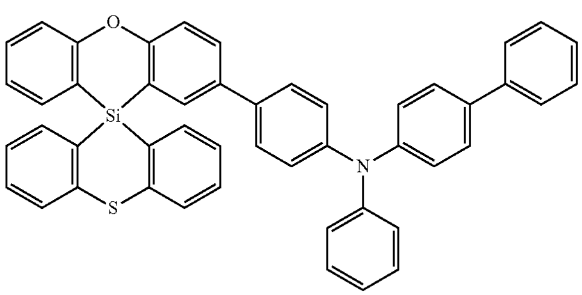
B74
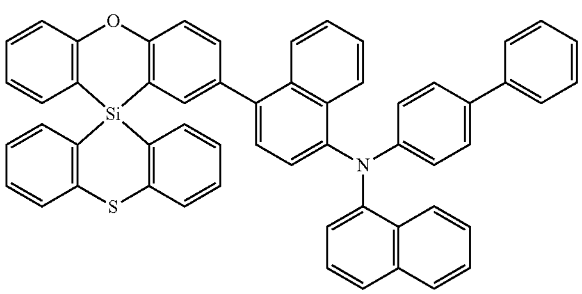
B75
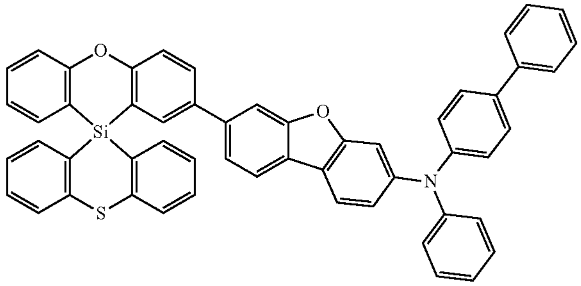
B76
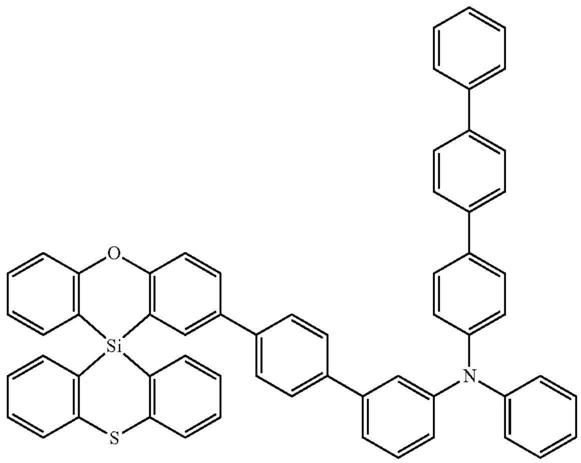
B77
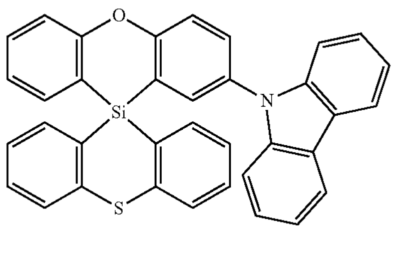
-continued
B78
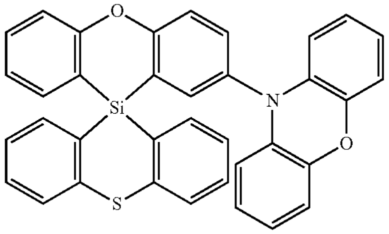
B79
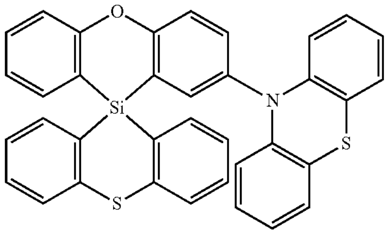
B80
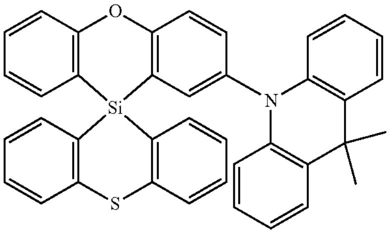
B81
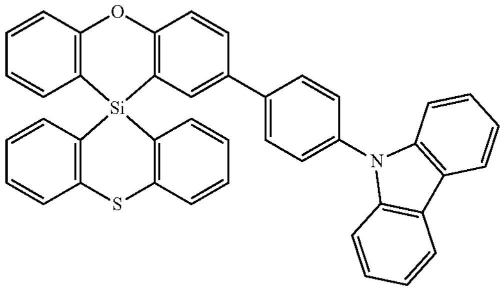
B82
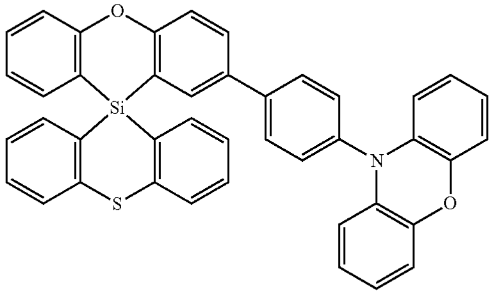
B83
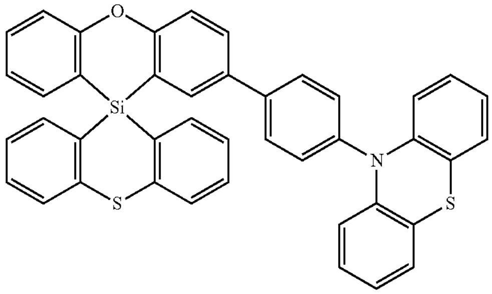

-continued
B84
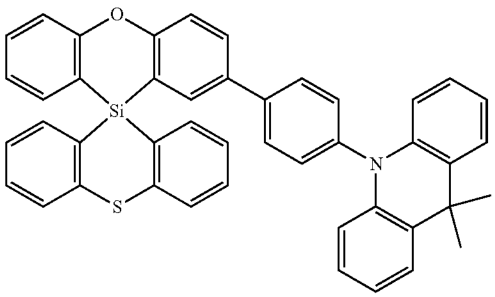
B85
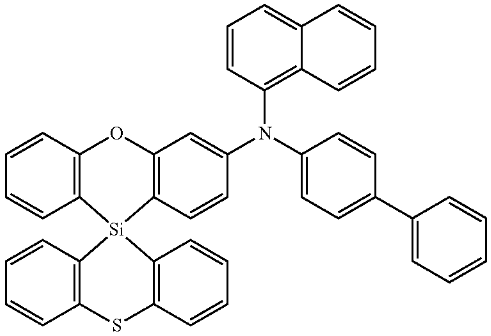
B86
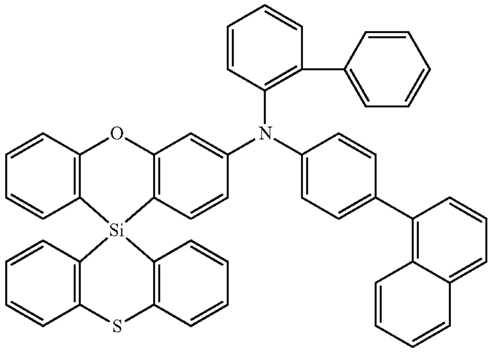
B87
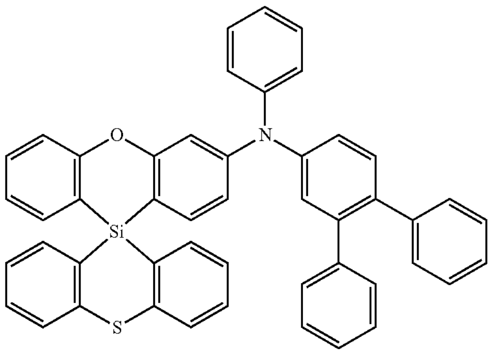
-continued
B88
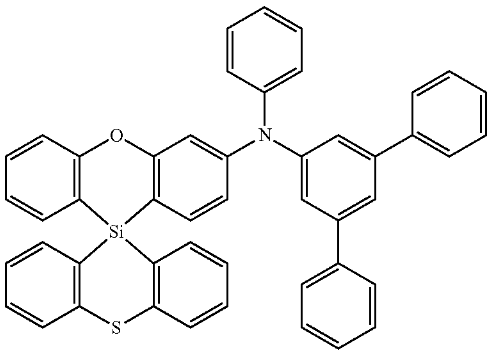
B89
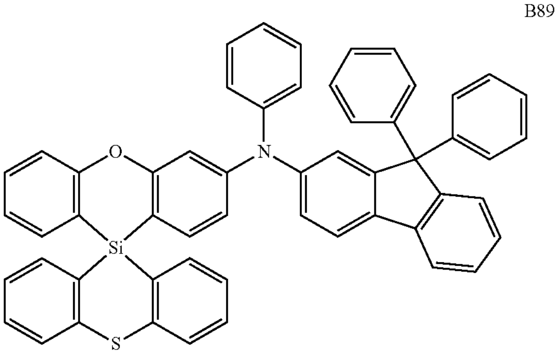
B90
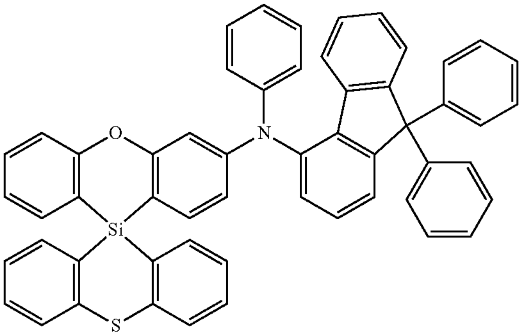
B91
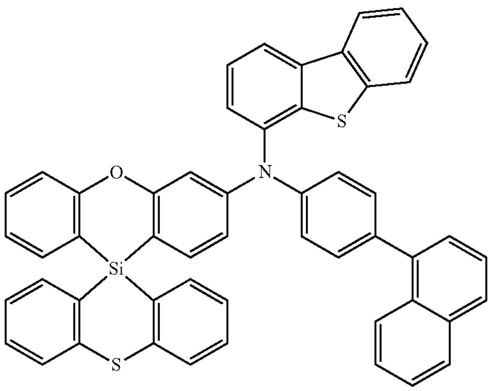

B92
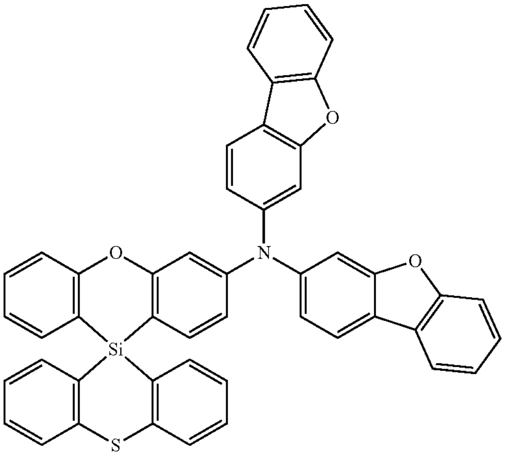
B93
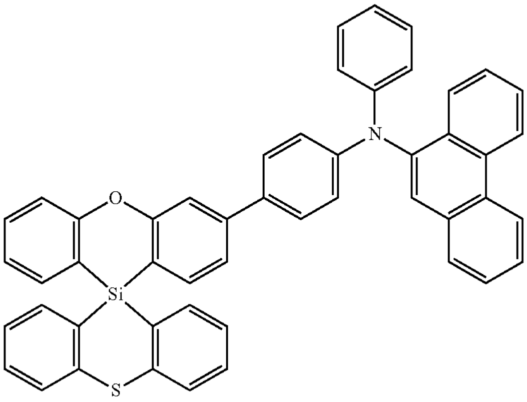
B94
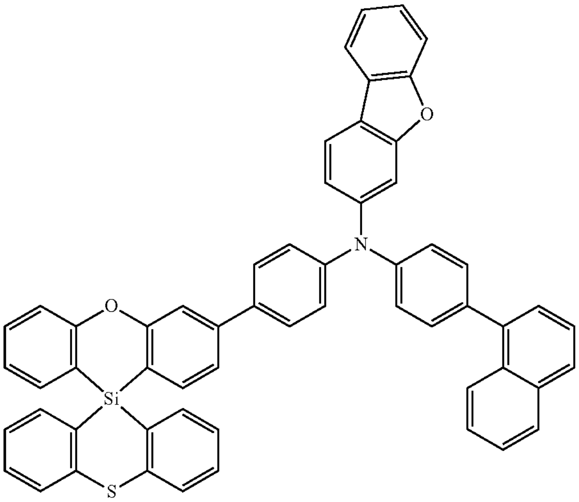
B95
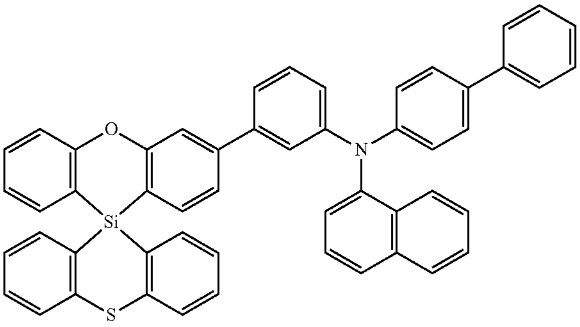
B96
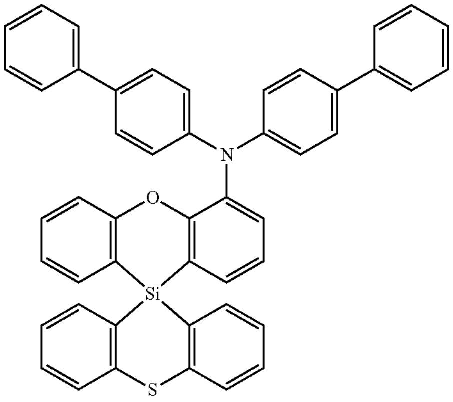
B97
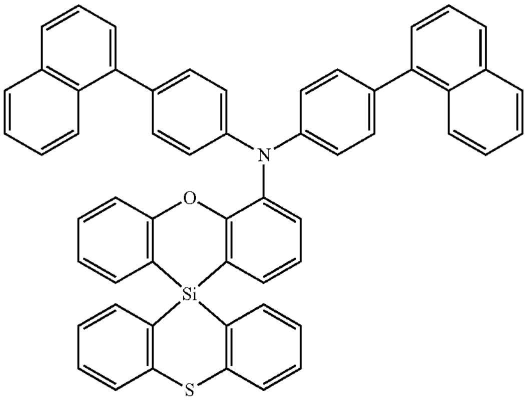
B98
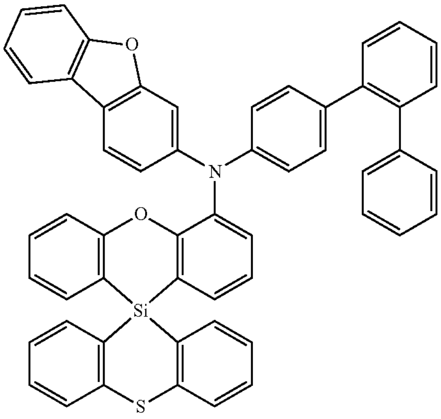

-continued
B99
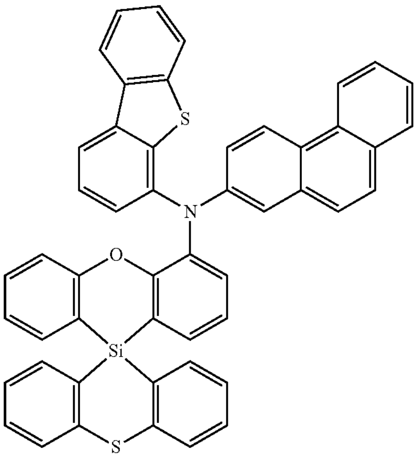
B100
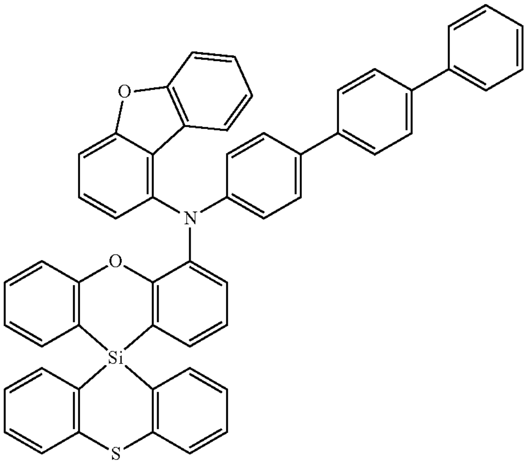
B101
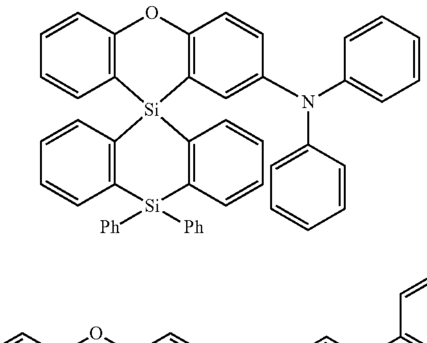
B102
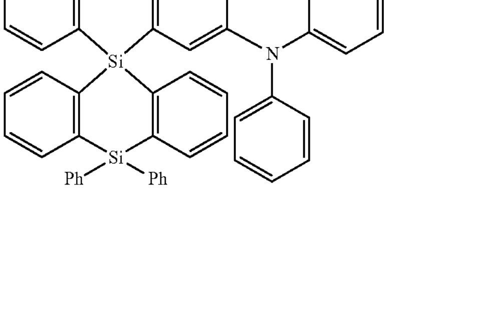
-continued
B103
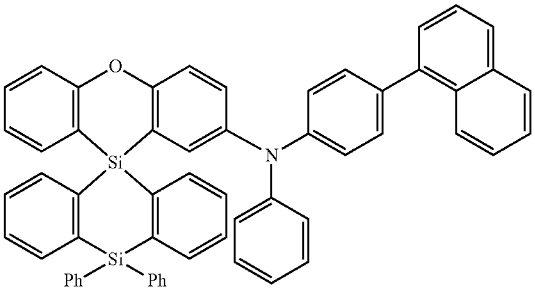
B104
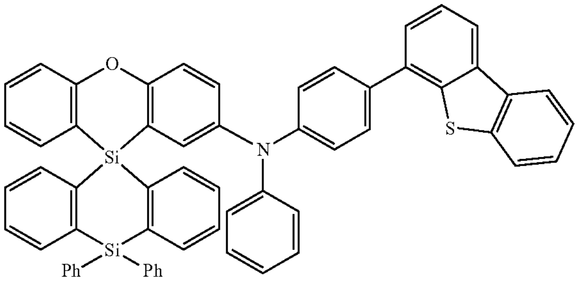
B105
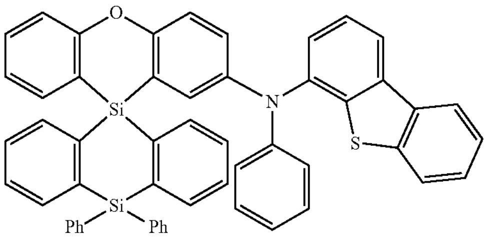
B106
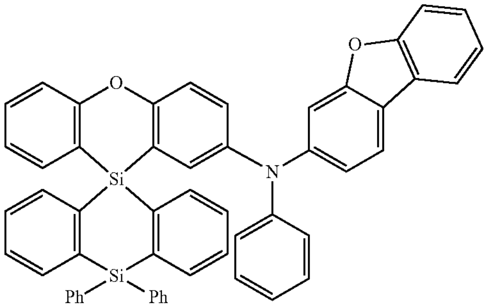
B107
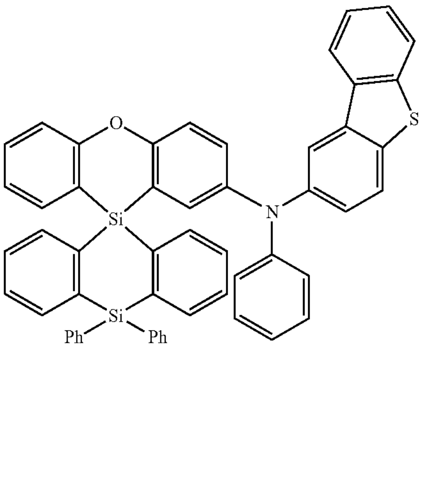

-continued
B108
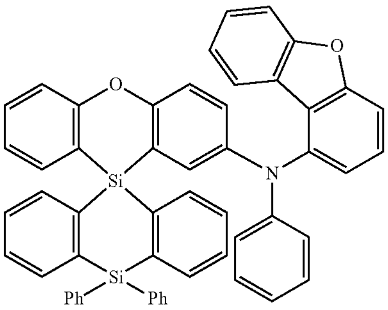
B109
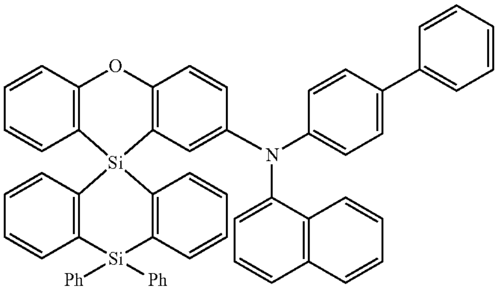
B110
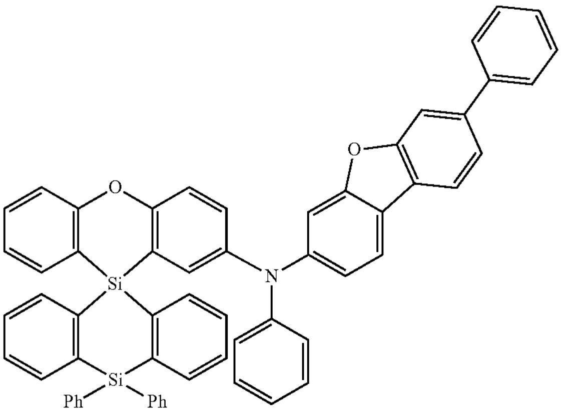
B111
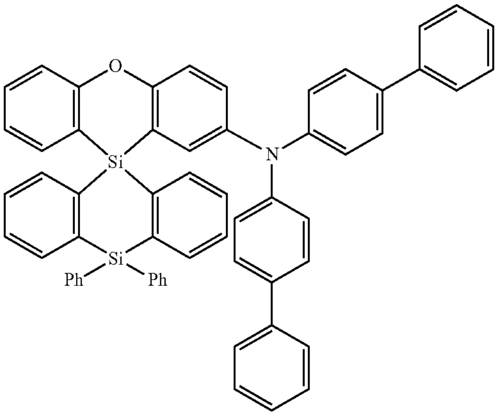
-continued
B112
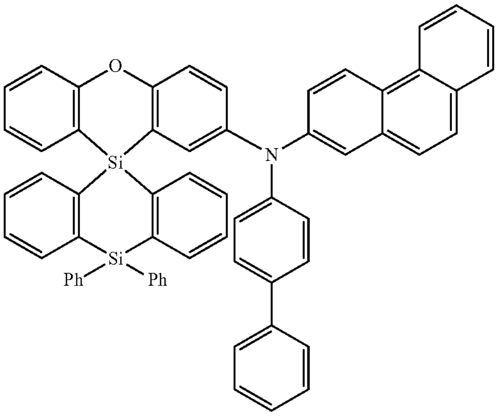
B113
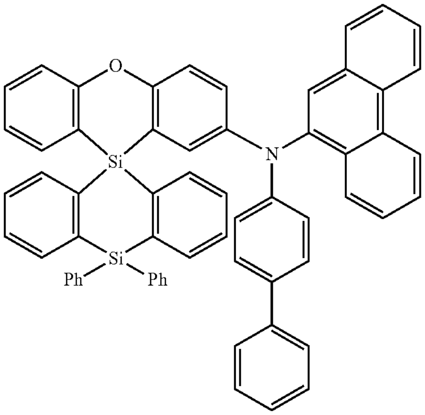
B114
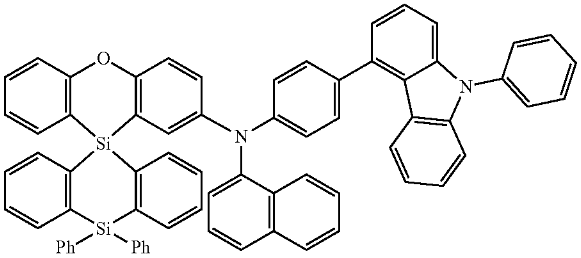
B115
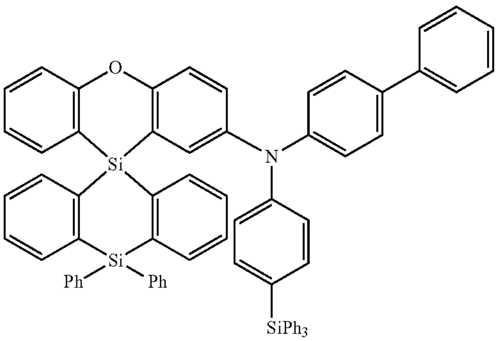

-continued
B116
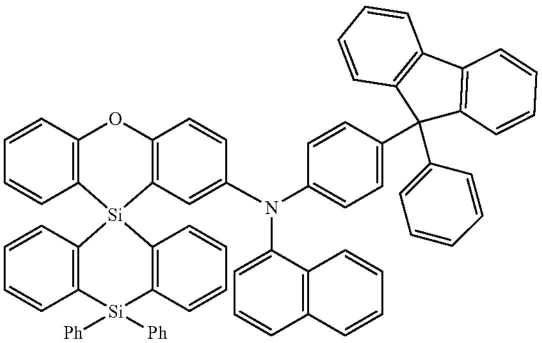
B117
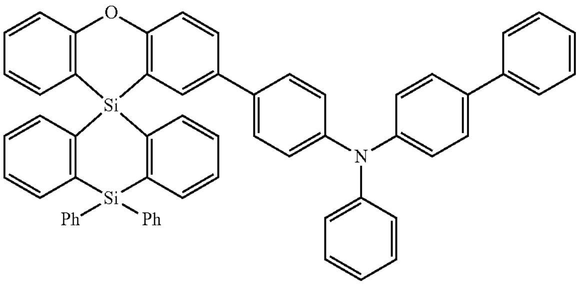
B118
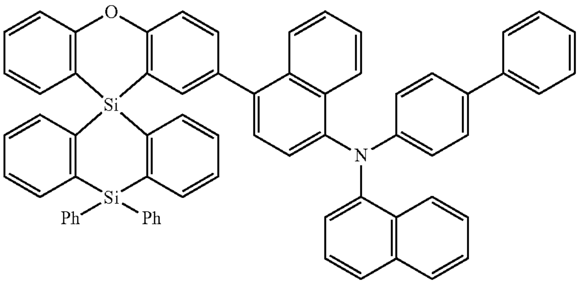
B119
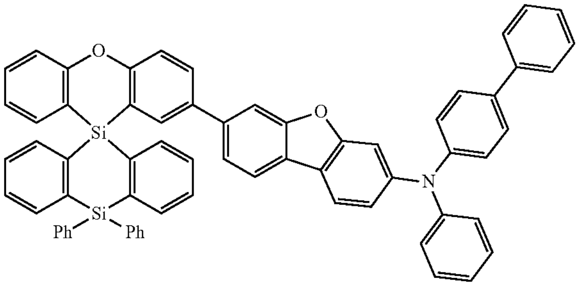
-continued
B120
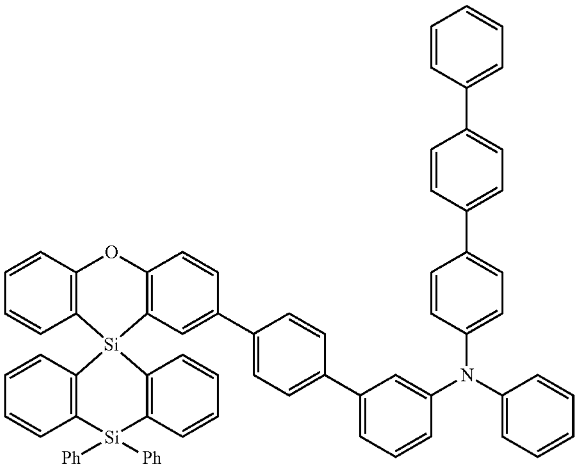
B121
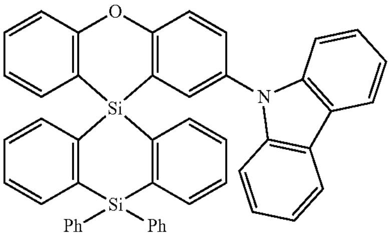
B122
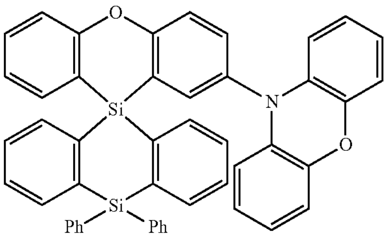
B123
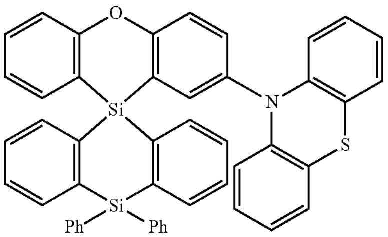
B124
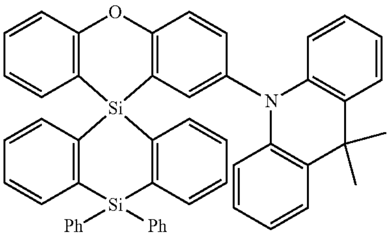

-continued
B125
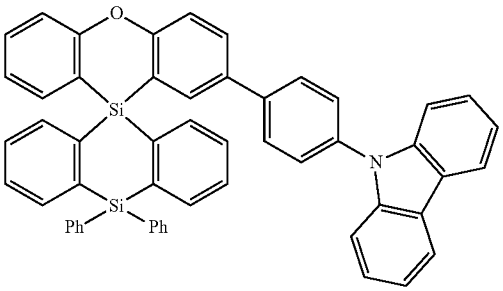
B126
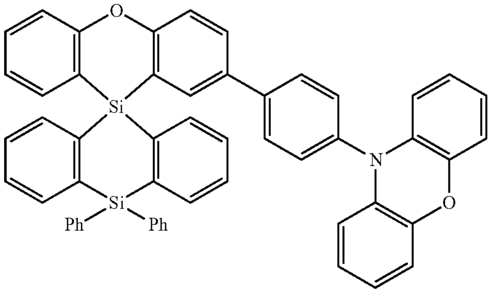
B127
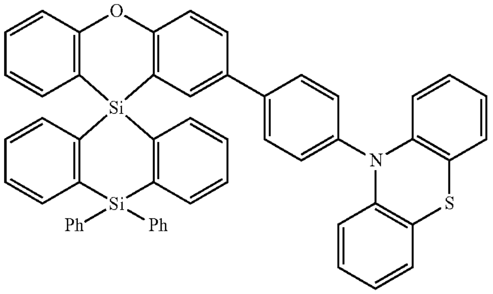
B128
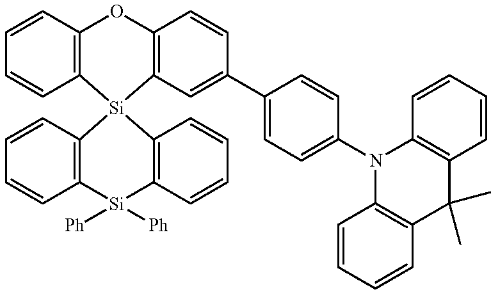
B129
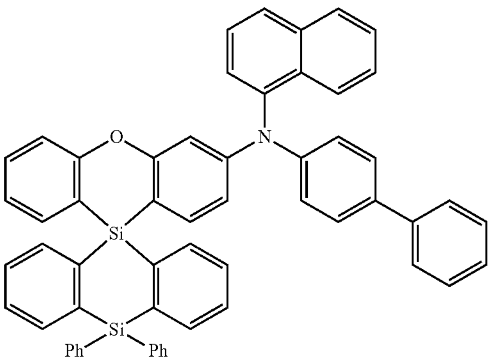
-continued
B130
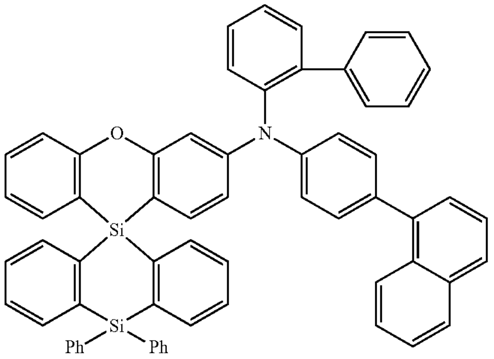
B131
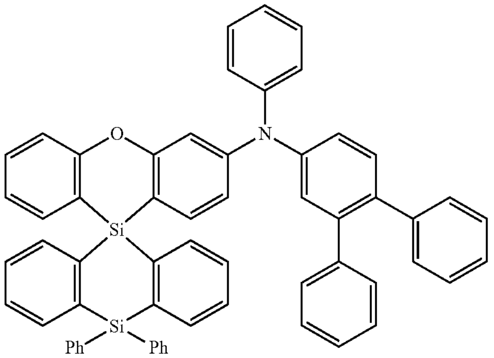
B132
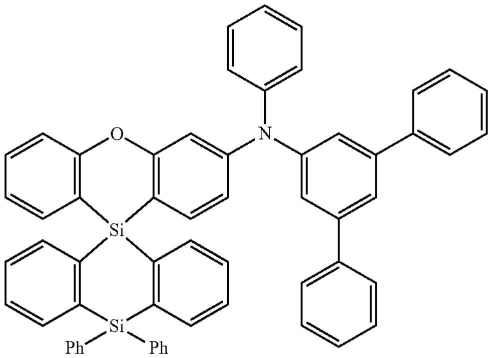
B133
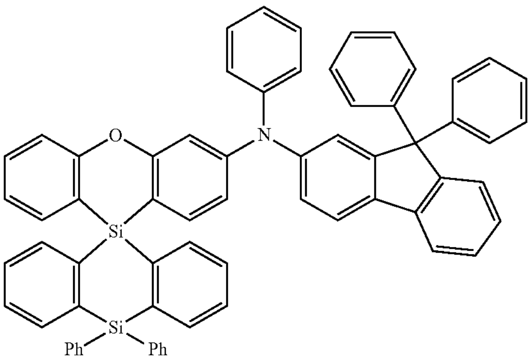

B134
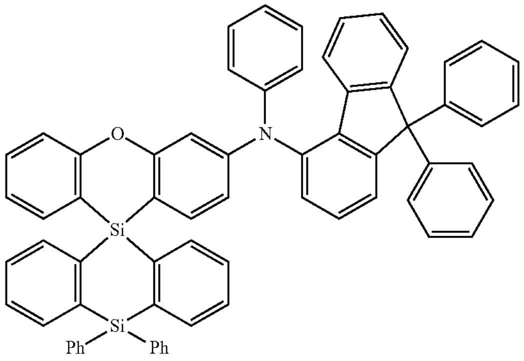
B135
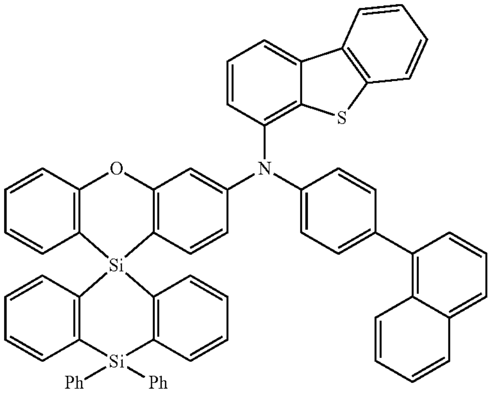
B136
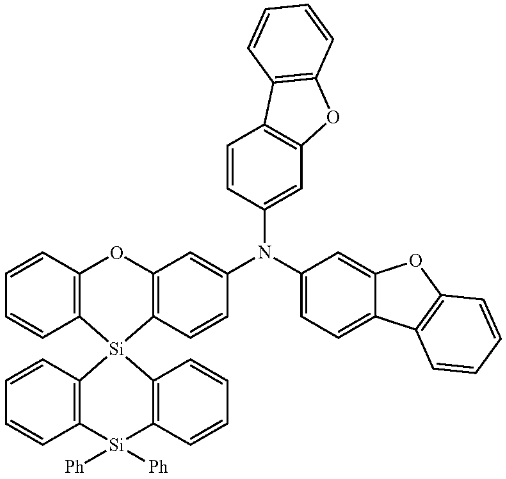
B137
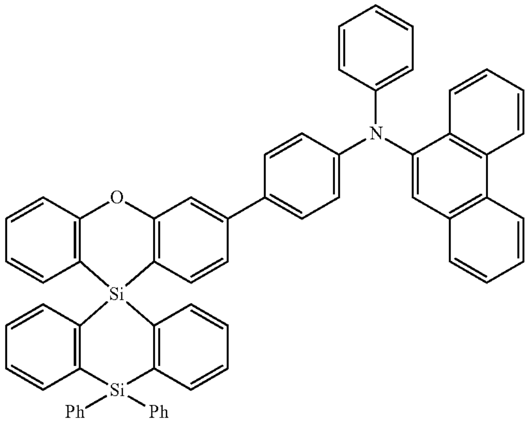
B138
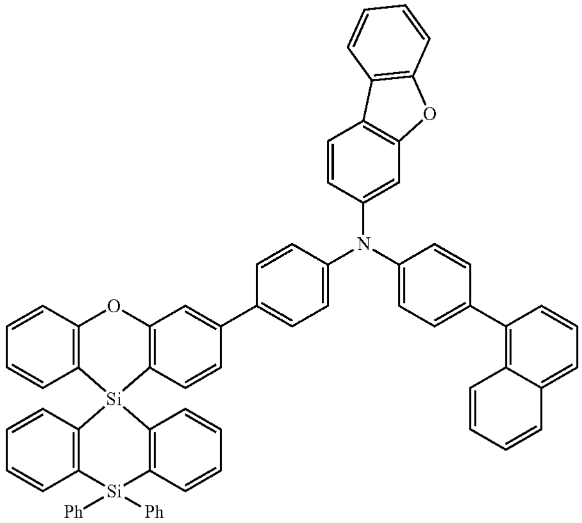
B139
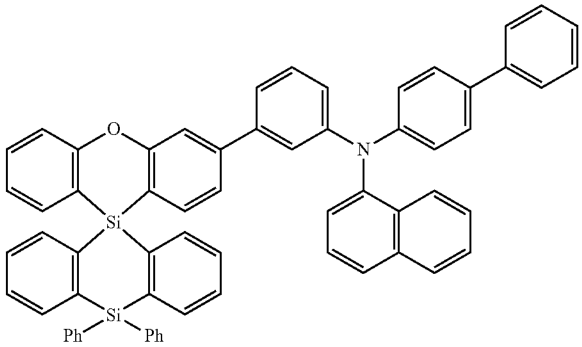

-continued
B140
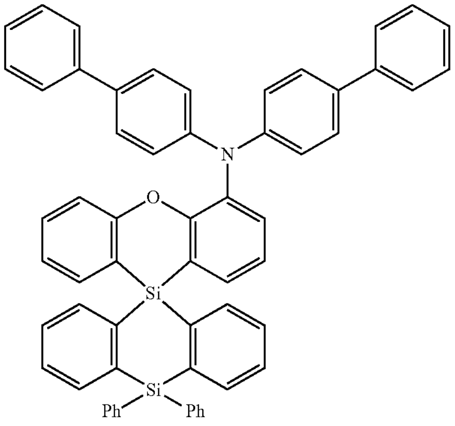
B141
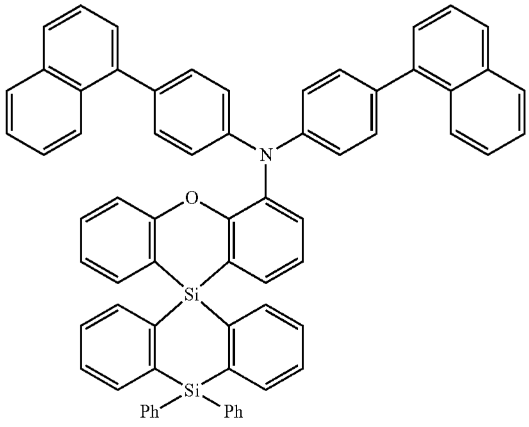
B142
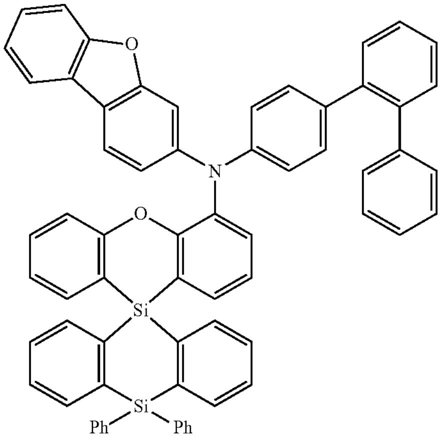
-continued
B143
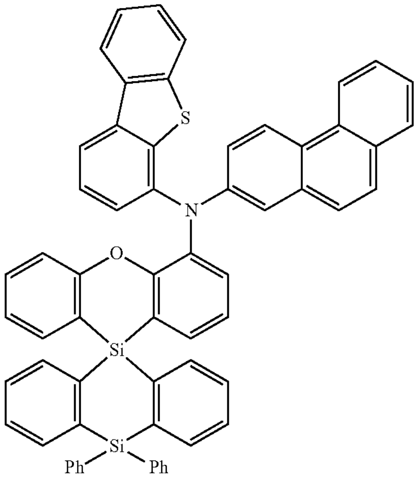
B144
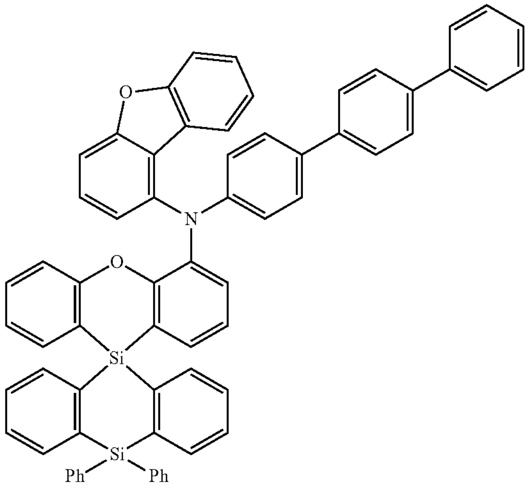
B145
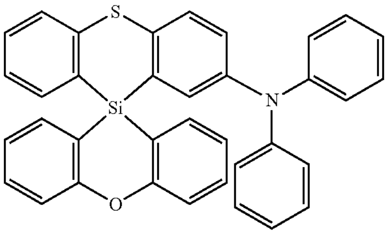
B146
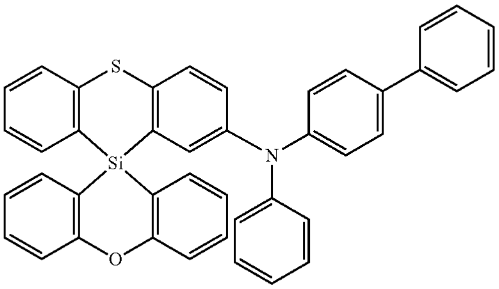

-continued
B147
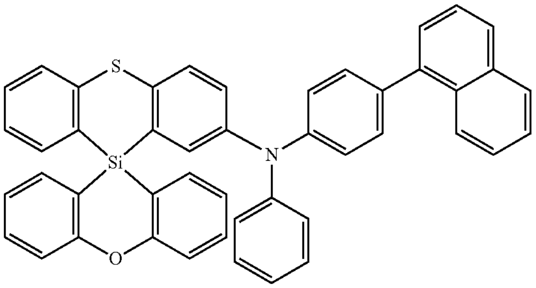
B148
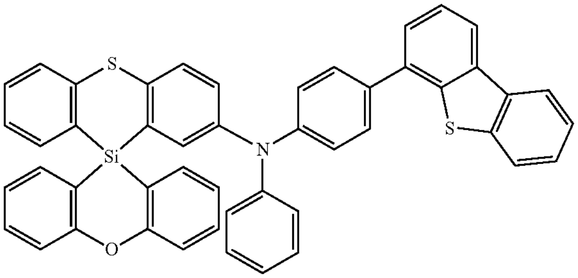
B149
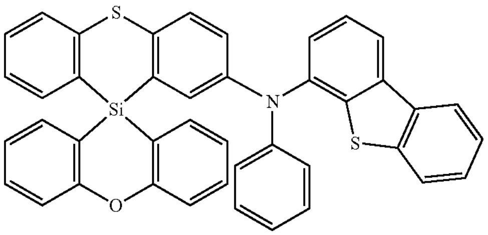
B150
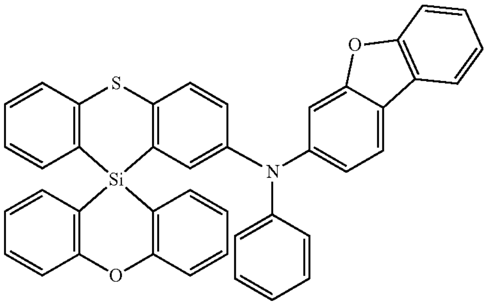
B151
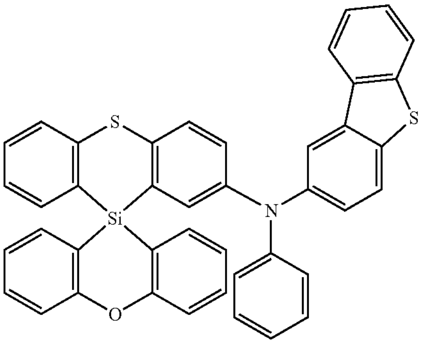
-continued
B152
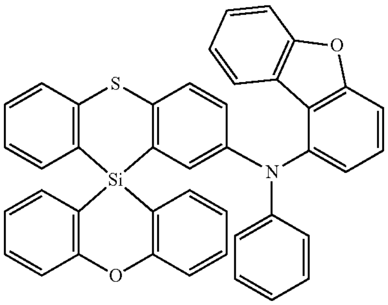
B153
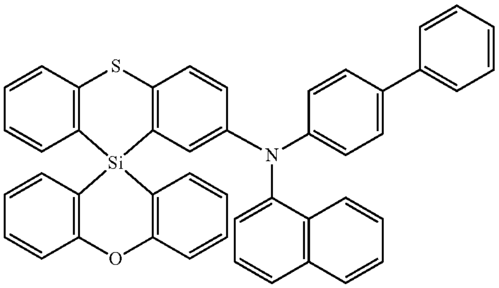
B154
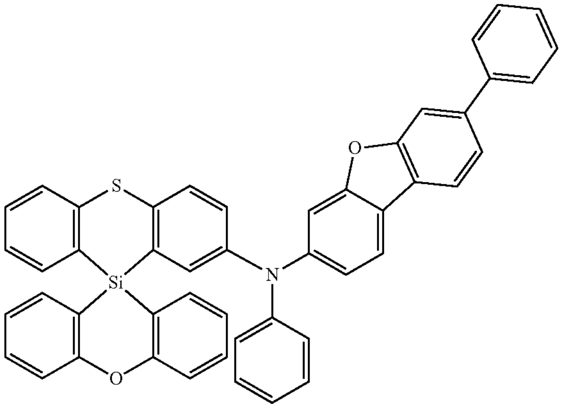
B155
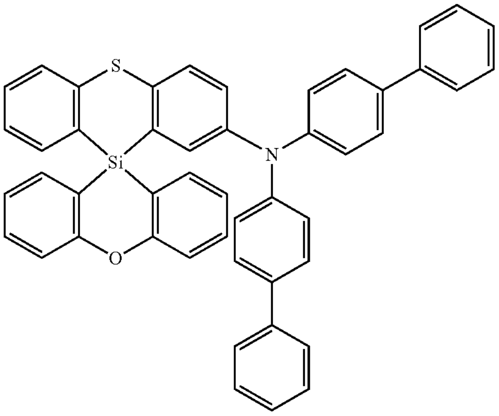

-continued
B156
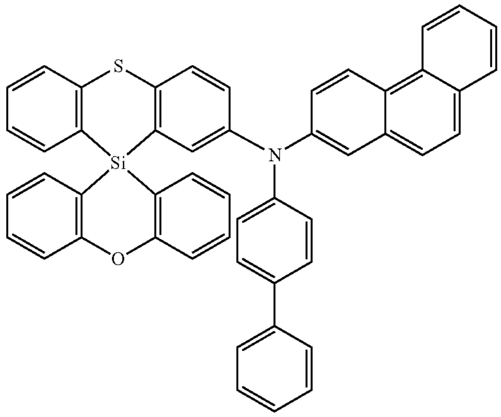
B157
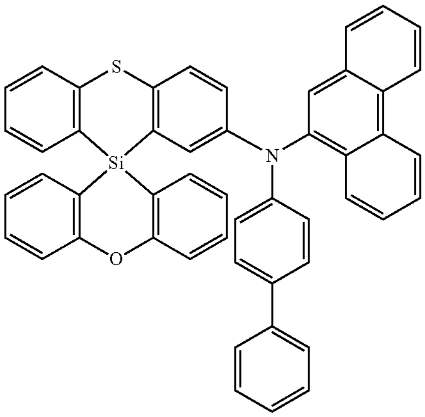
B158
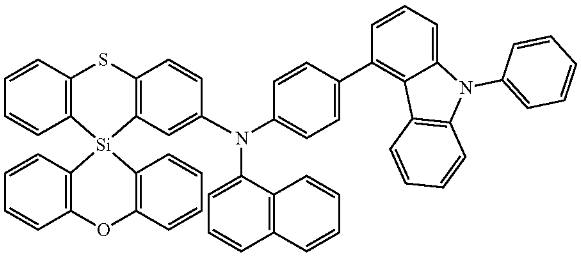
B159
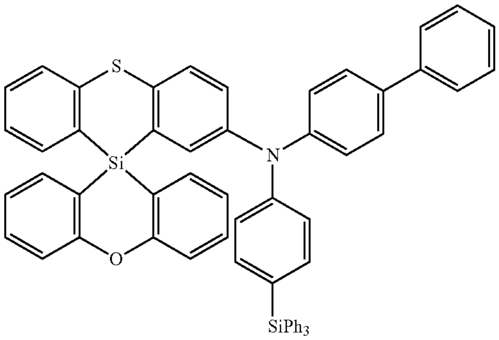
-continued
B160
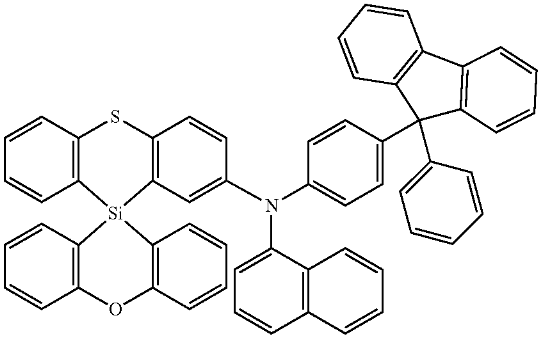
B161
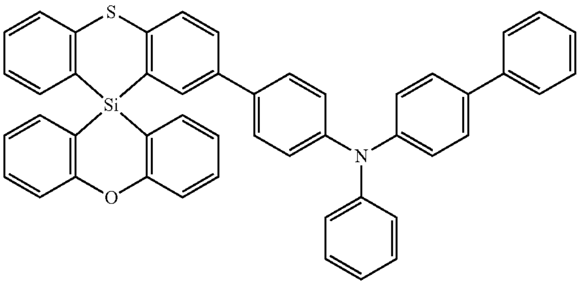
B162
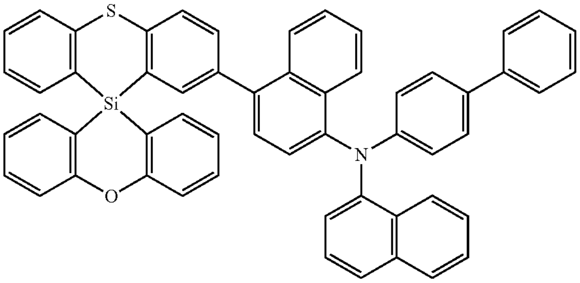
B163
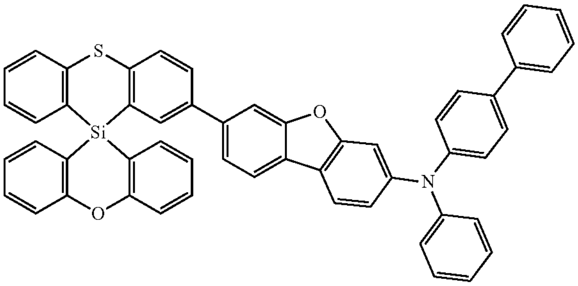

-continued
B164
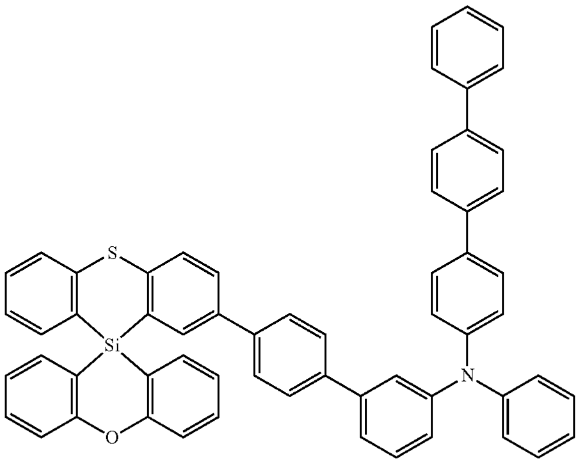
B165
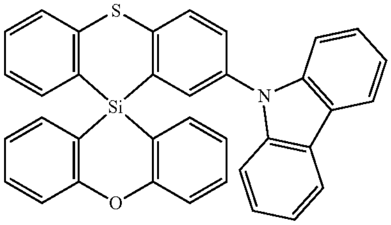
B166
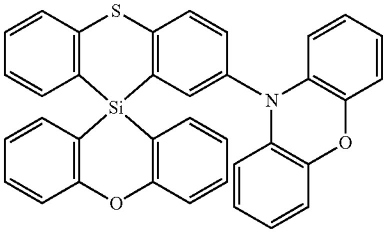
B167
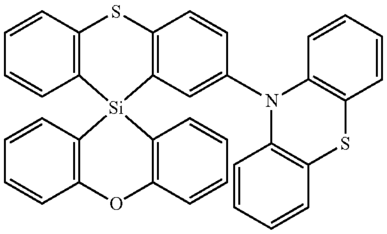
B168
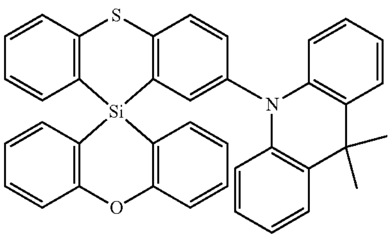
-continued
B169
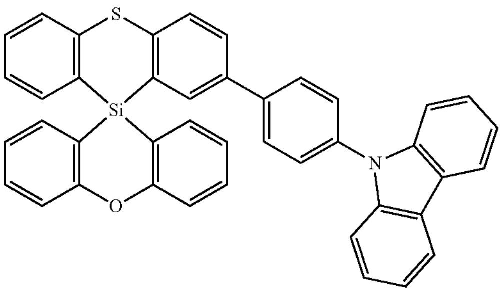
B170
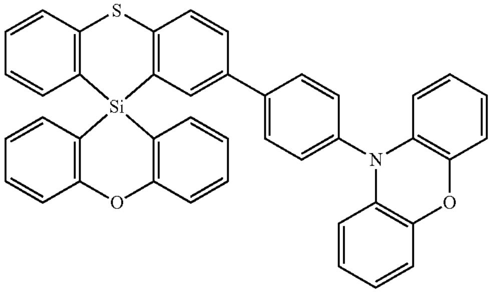
B171
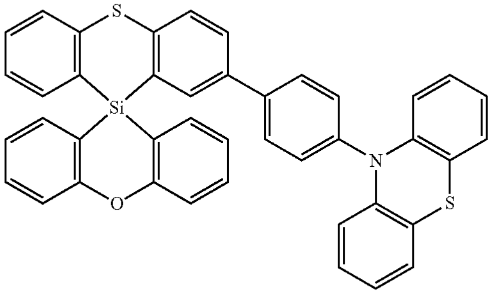
B172
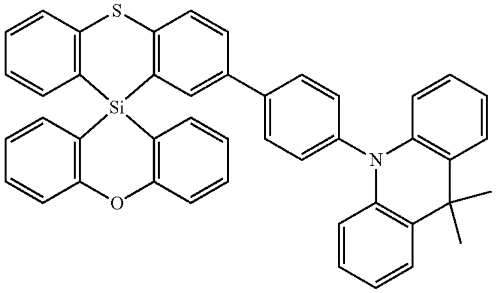
B173
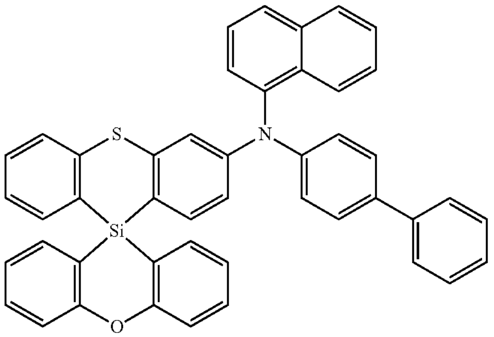

-continued
B174
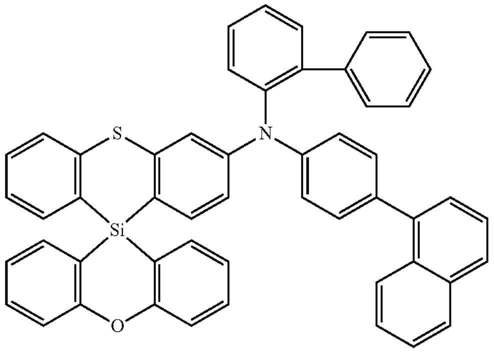
B175
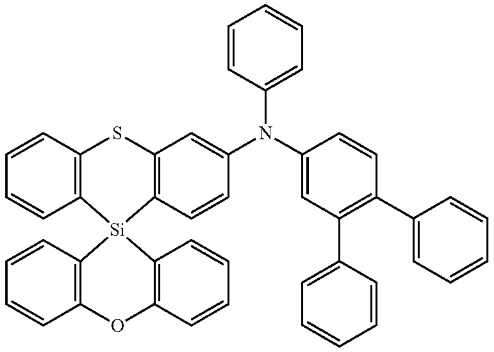
B176
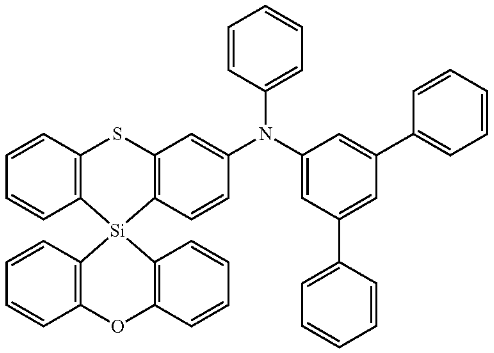
B177
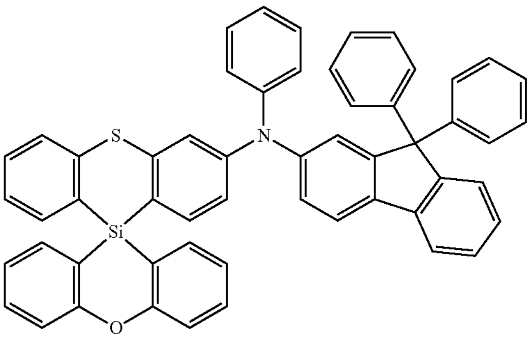
-continued
B178
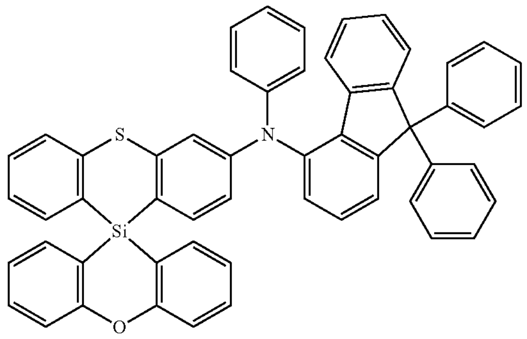
B179
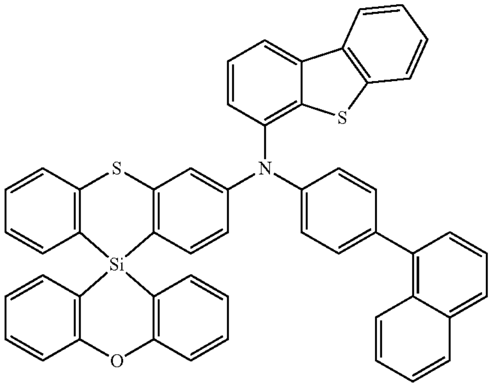
B180
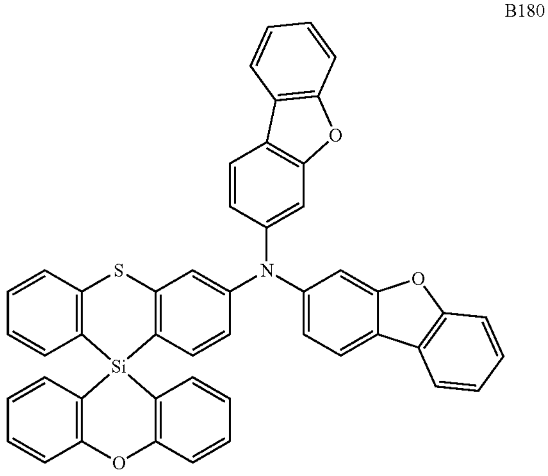
B181
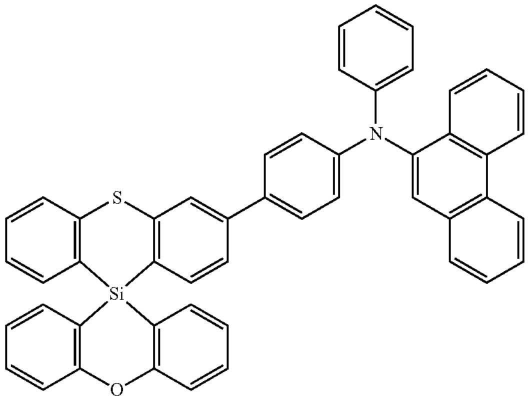

-continued
B182
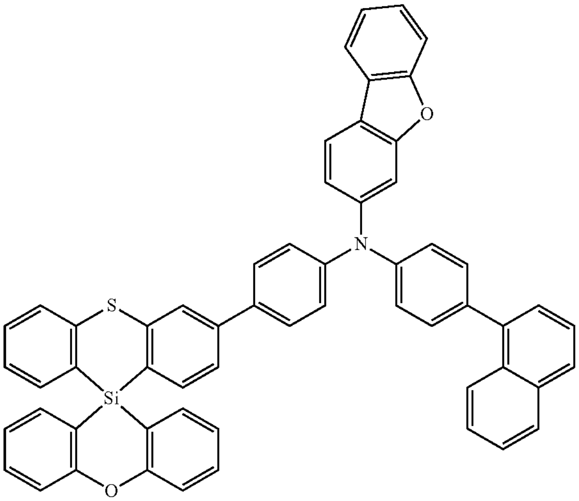
B183
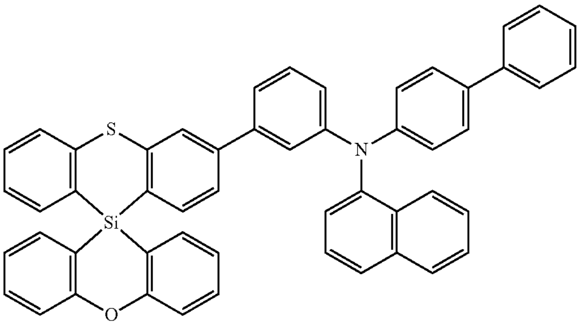
B184
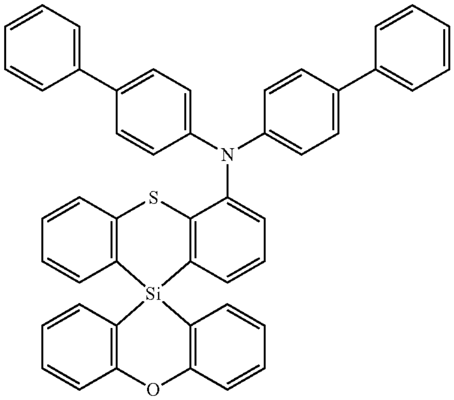
-continued
B185
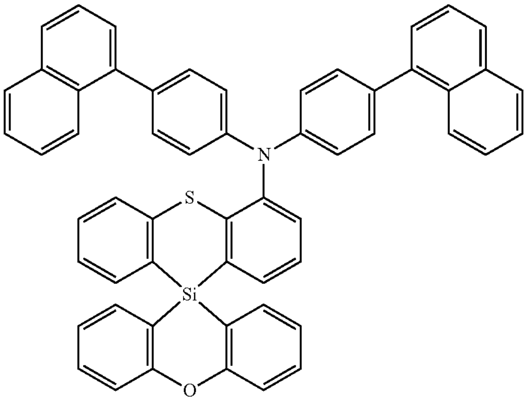
B186
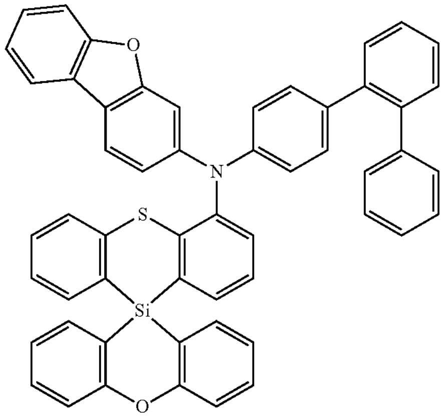
B187
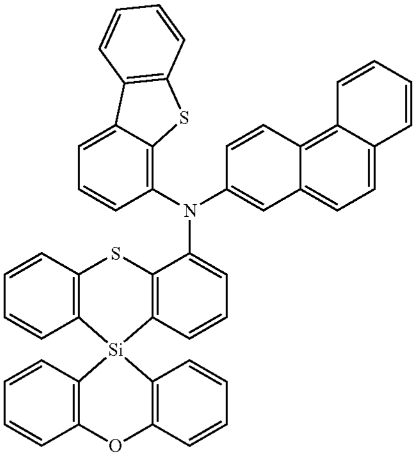

-continued
B188
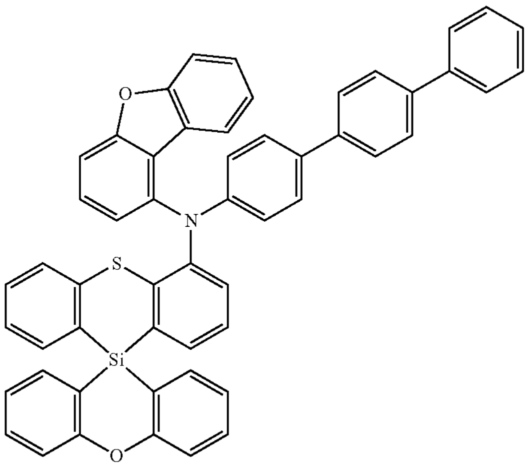
B189
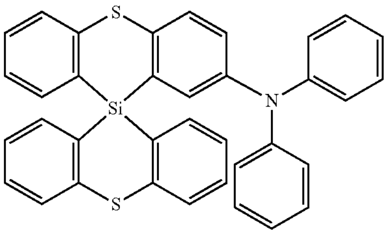
B190
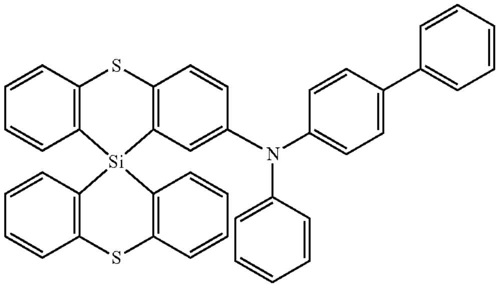
B191
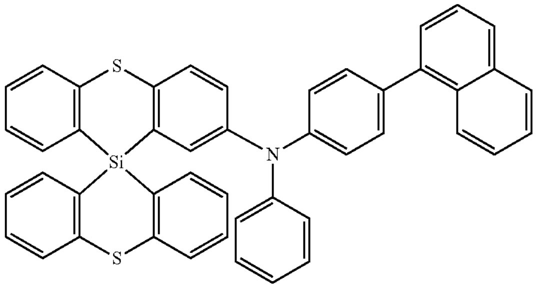
B192
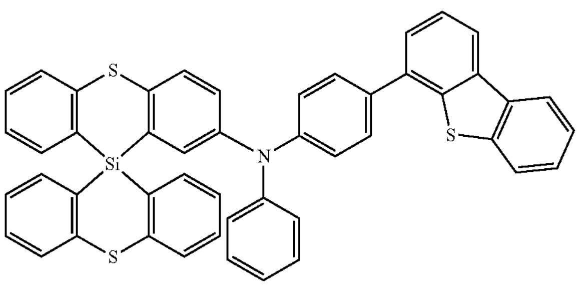
-continued
B193
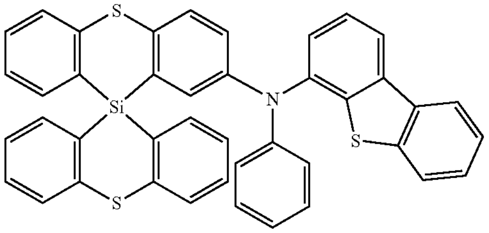
B194
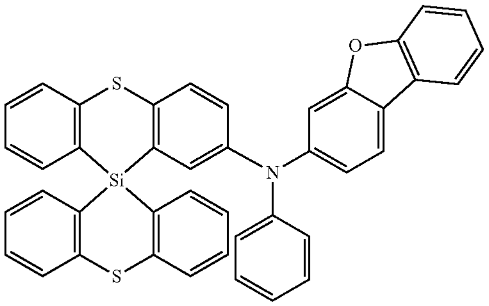
B195
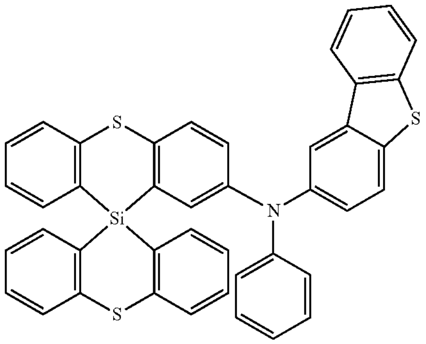
B196
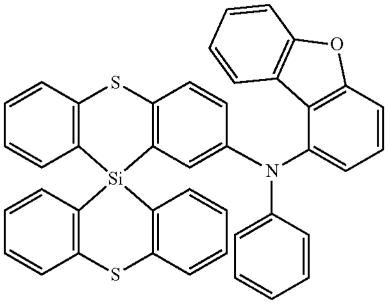
B197
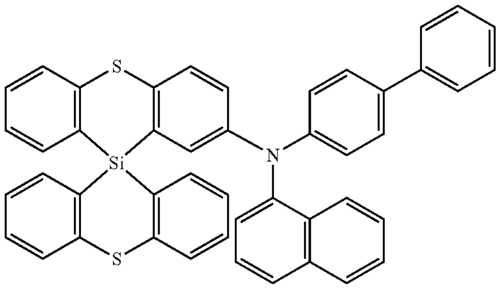

-continued
B198
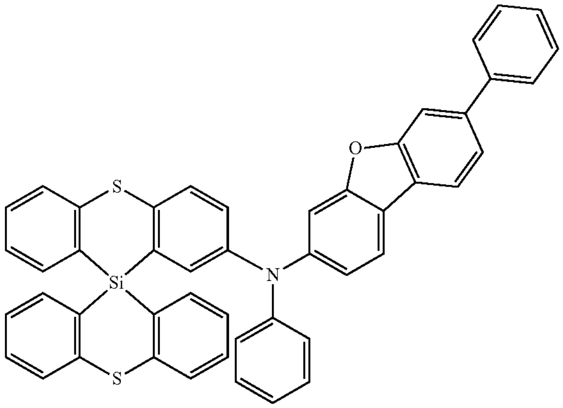
B199
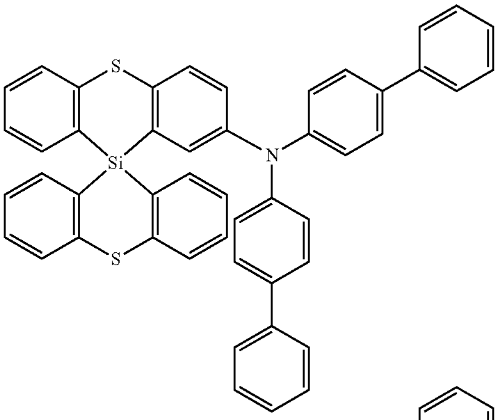
B200
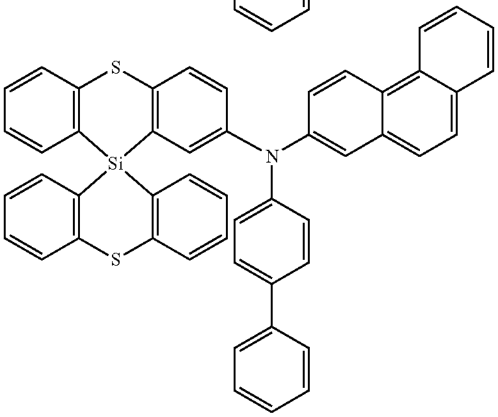
B201
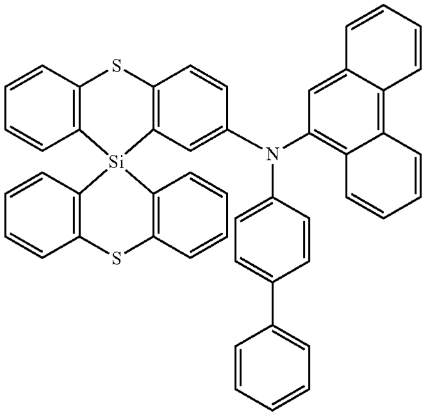
-continued
B202
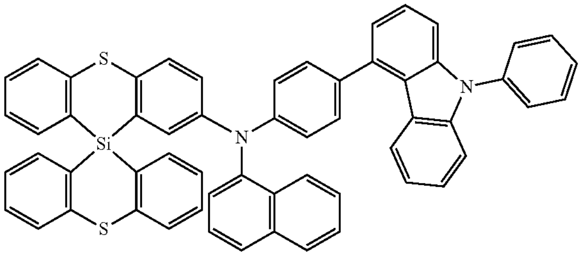
B203
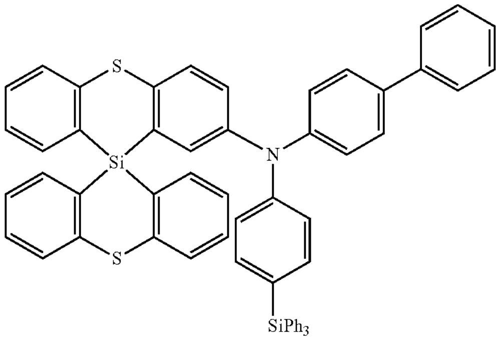
B204
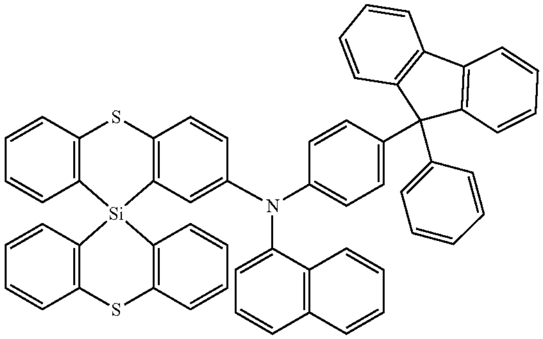
B205
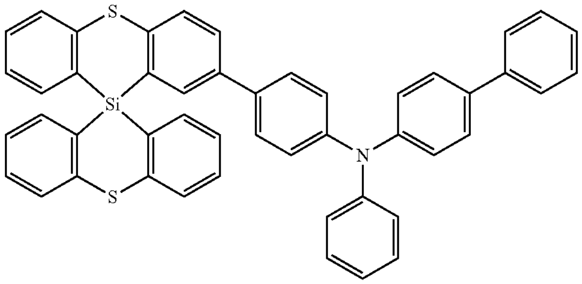
B206
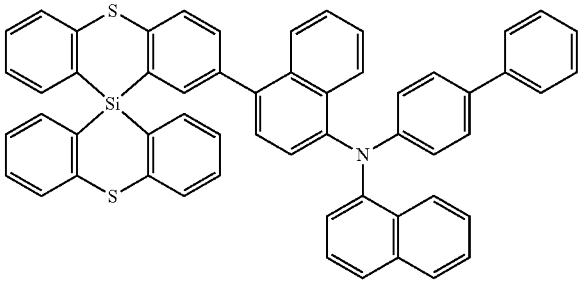

-continued
B207
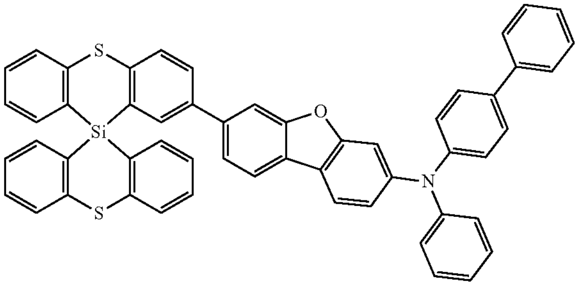
B208
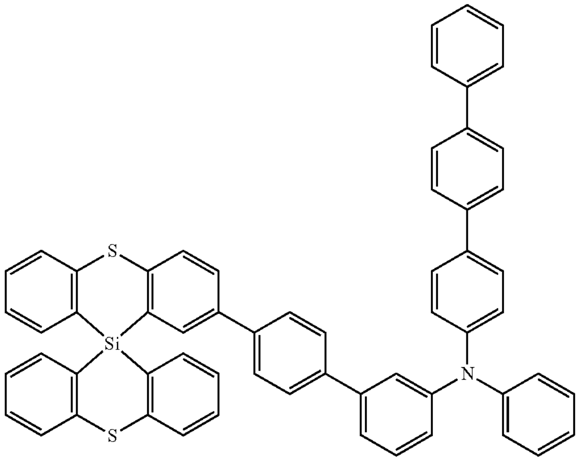
B209
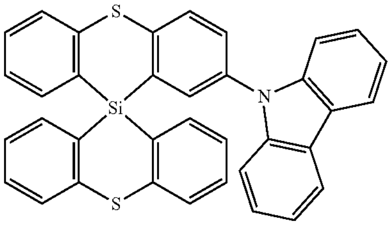
B210
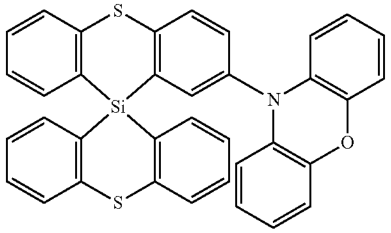
B211
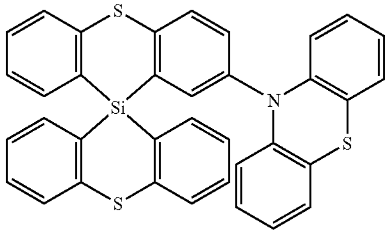
-continued
B212
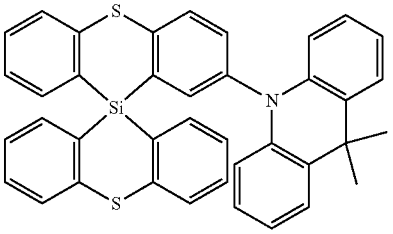
B213
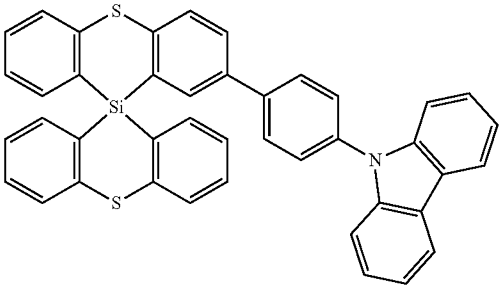
B214
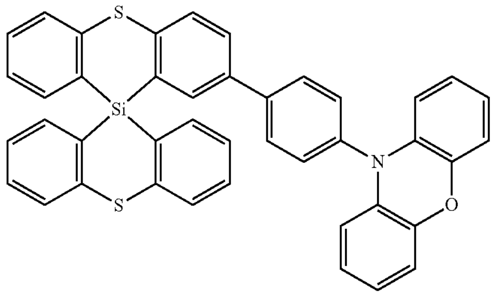
B215
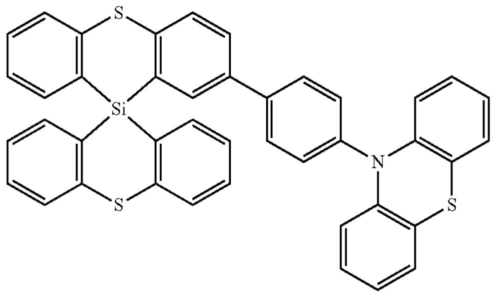
B216
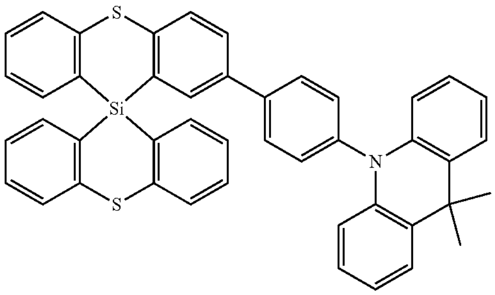

-continued
B217
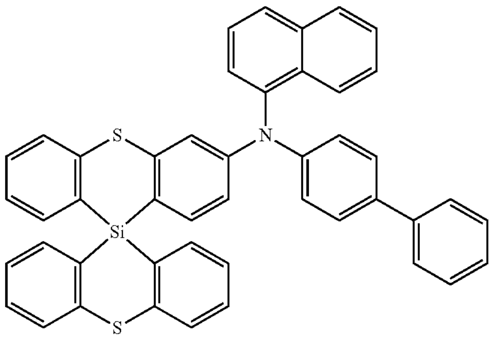
B218
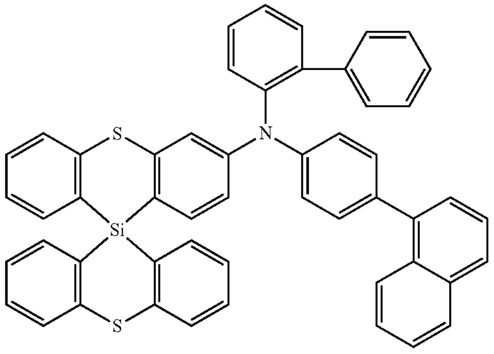
B219
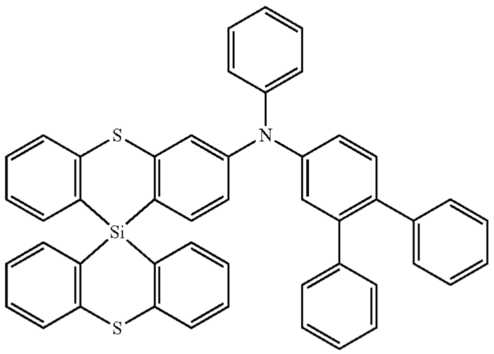
B220
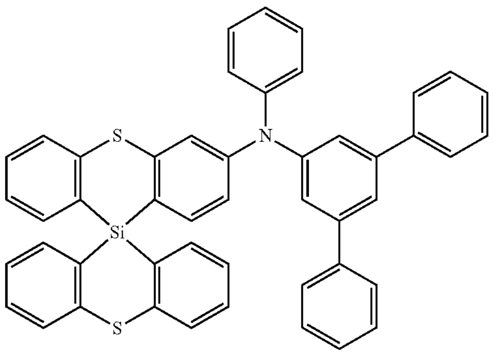
-continued
B221
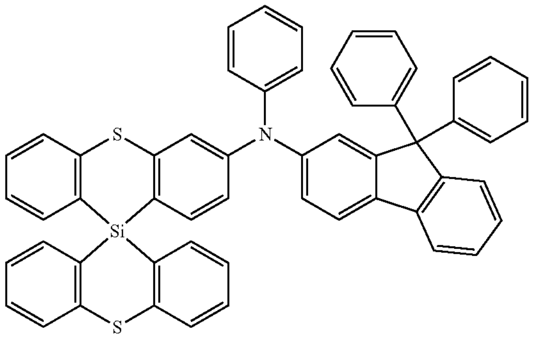
B222
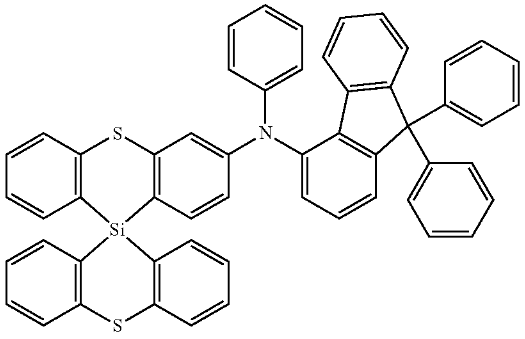
B223
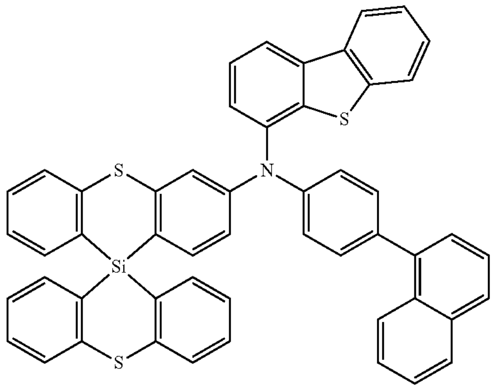
B224
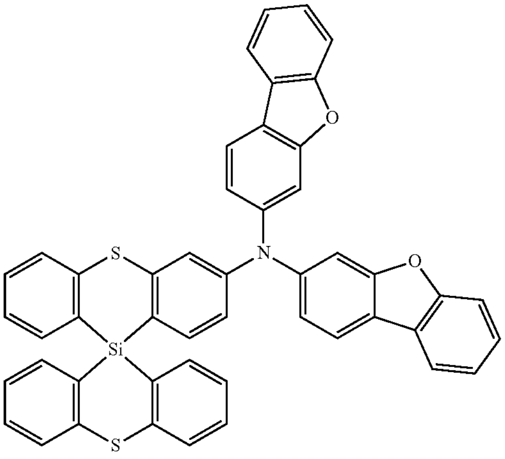

-continued
B225
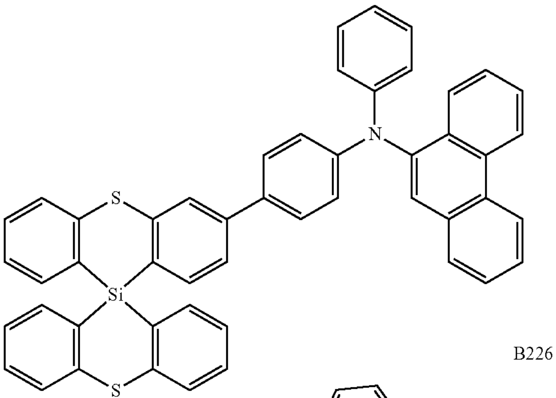
B226
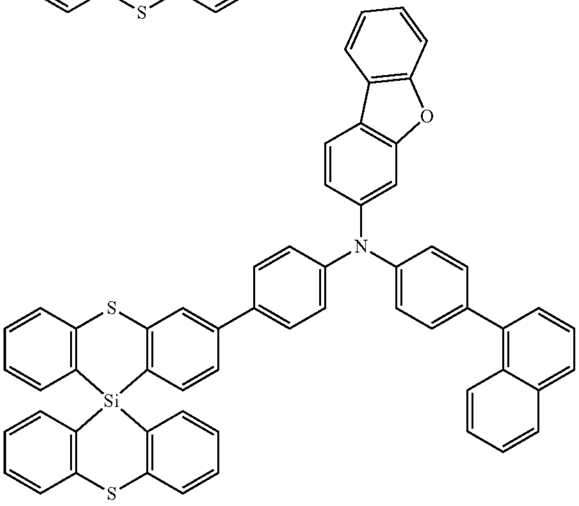
B227
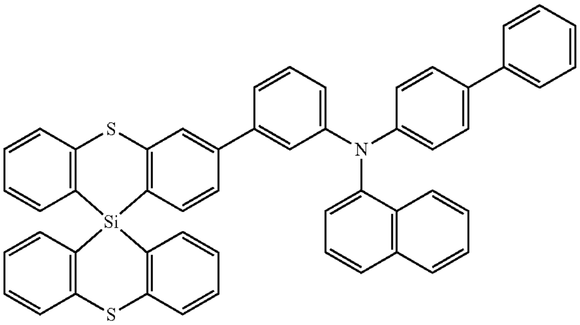
B228
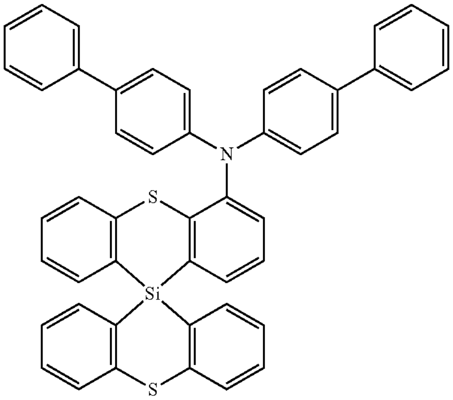
-continued
B229
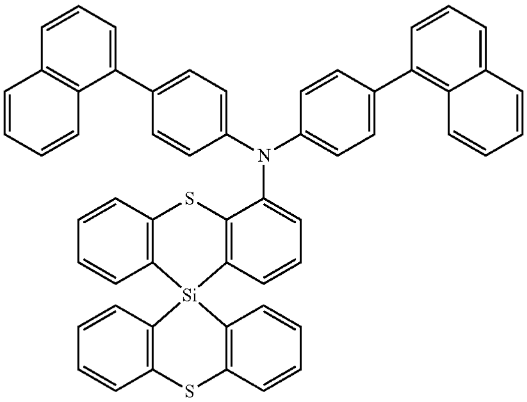
B230
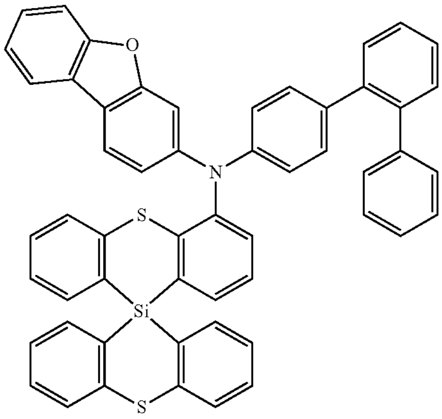
B231
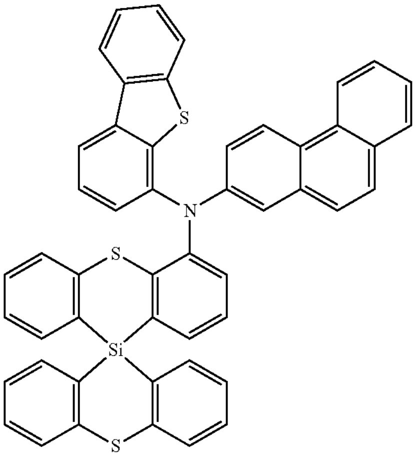

-continued
B232
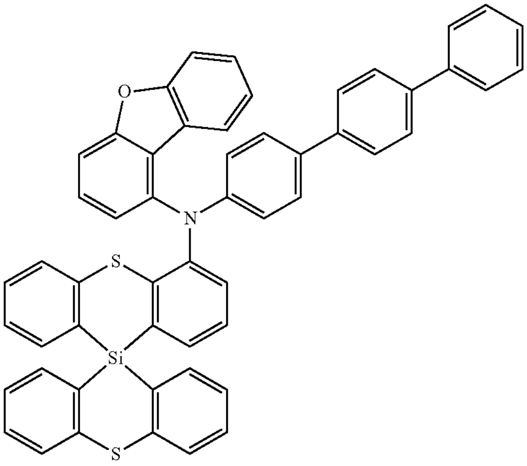
B233
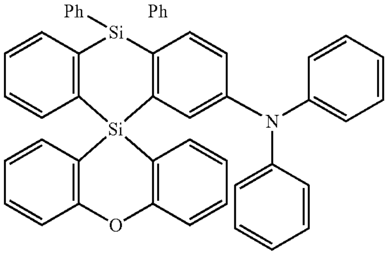
B234
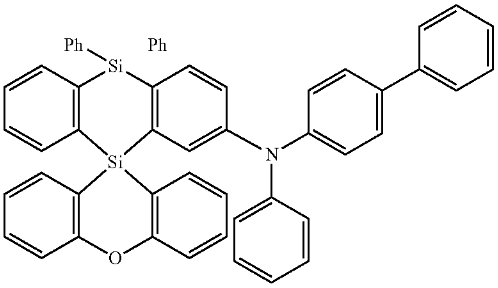
B235
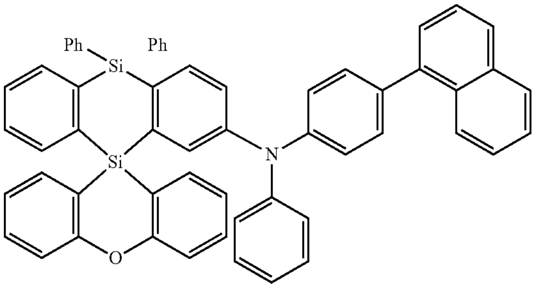
-continued
B236
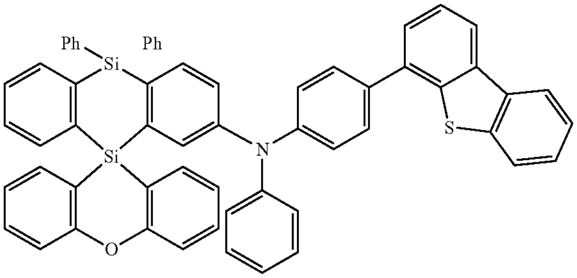
B237
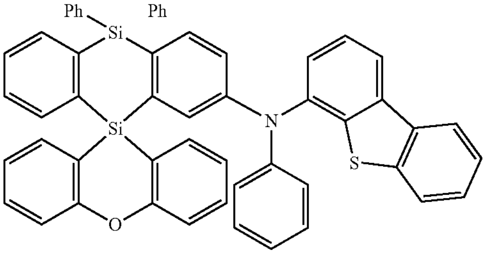
B238
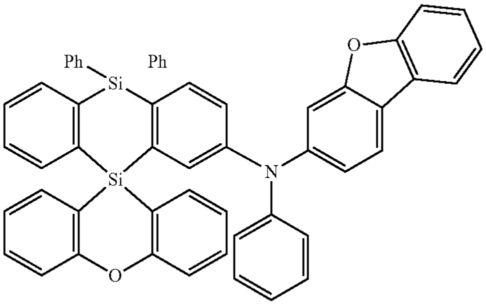
B239
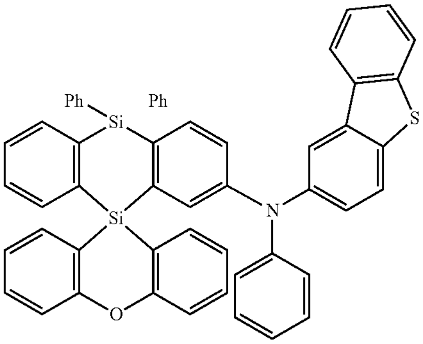
B240
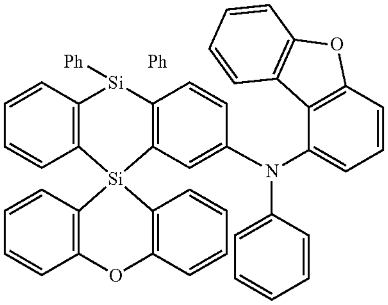

-continued
B241
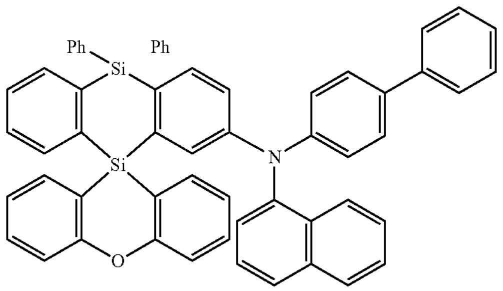
B242
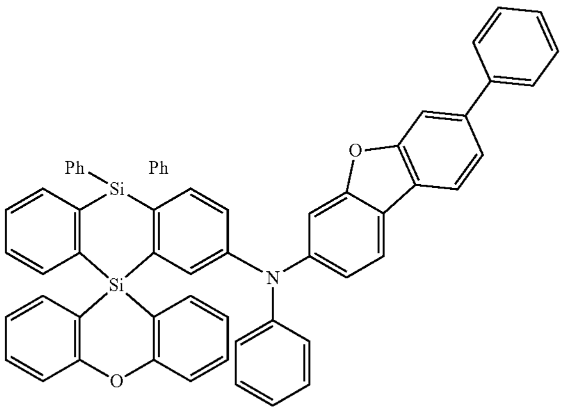
B243
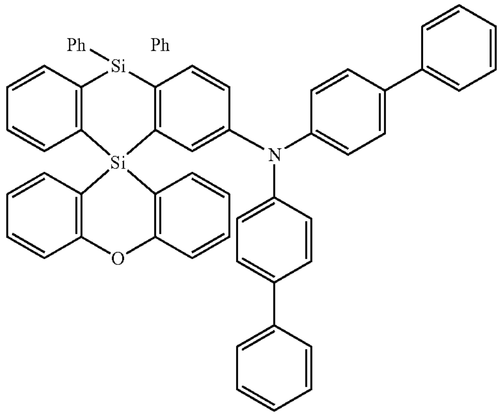
B244
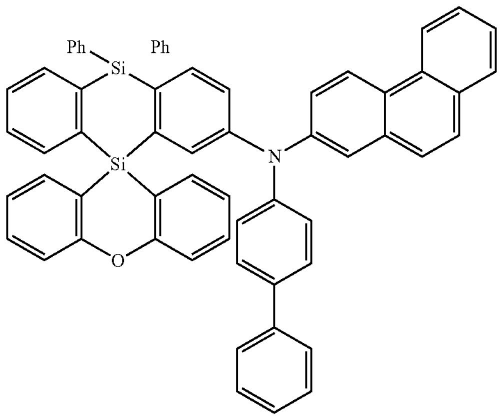
-continued
B245
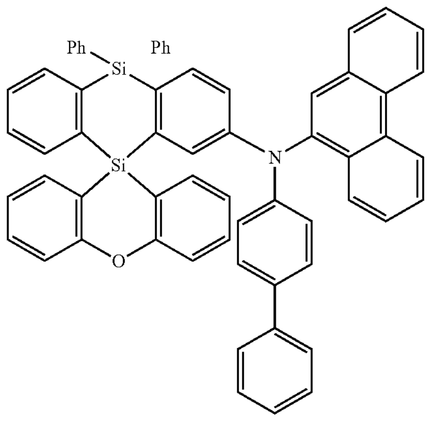
B246
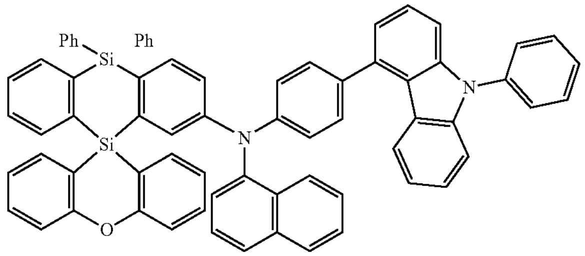
B247
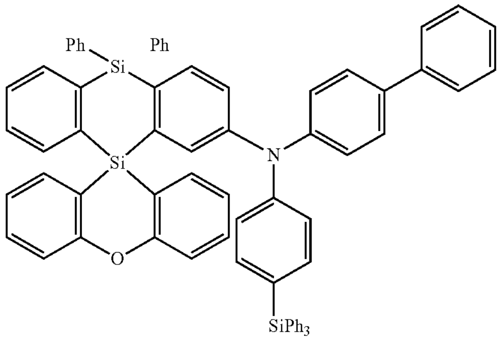
B248
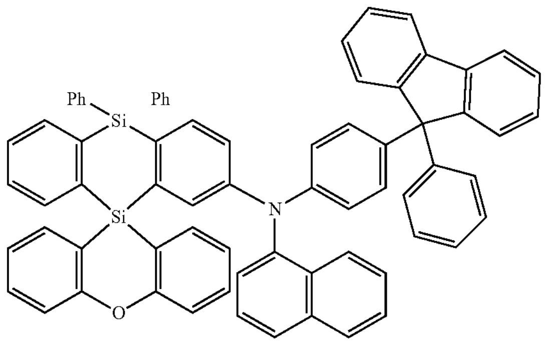

-continued
B249
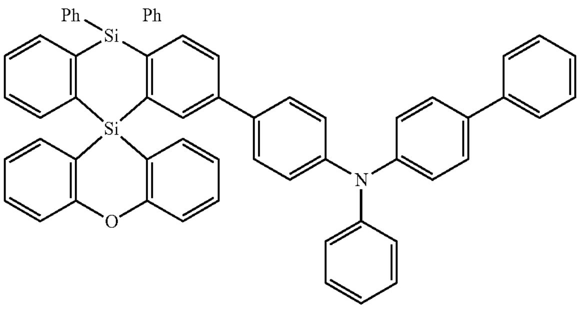
B250
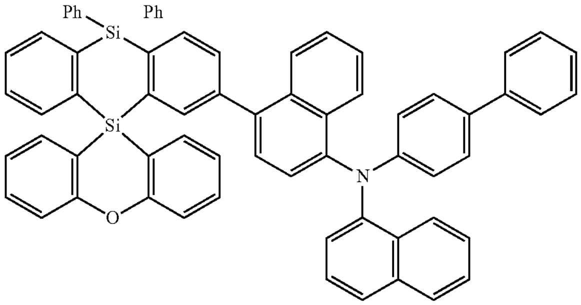
B251
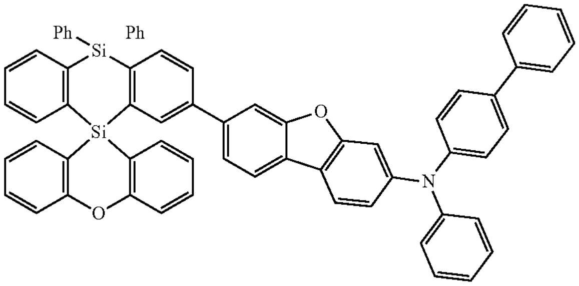
B252
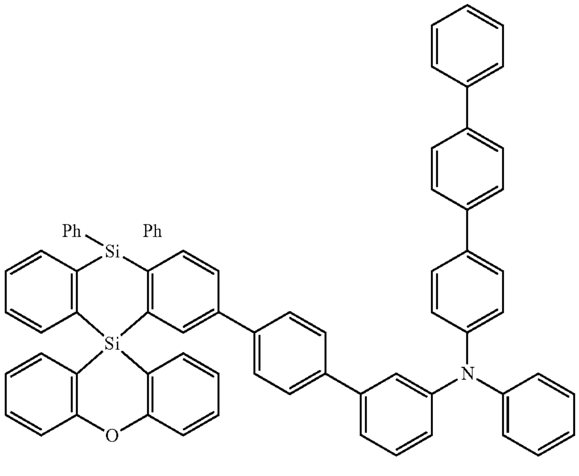
-continued
B253
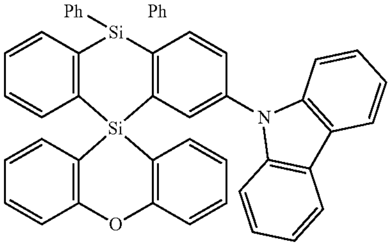
B254
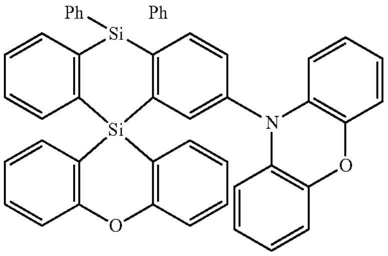
B255
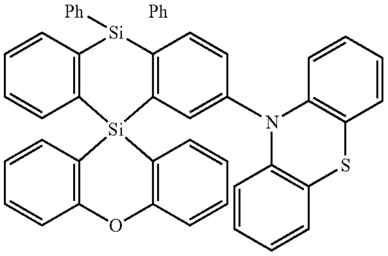
B256
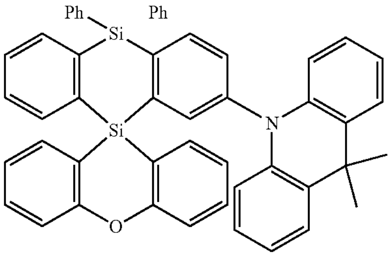
B257
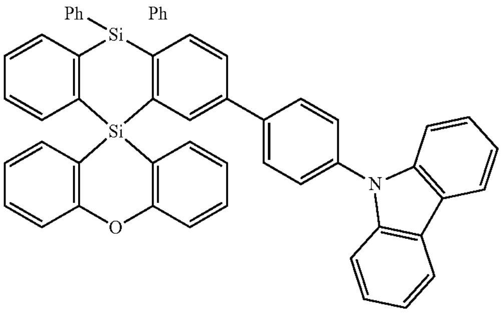

-continued
B258
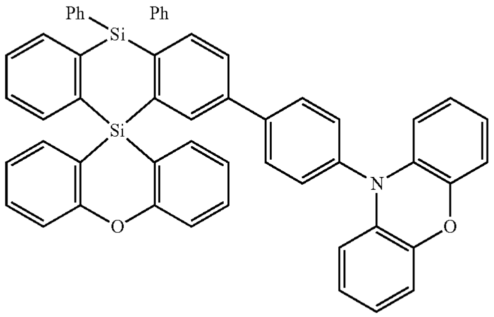
B259
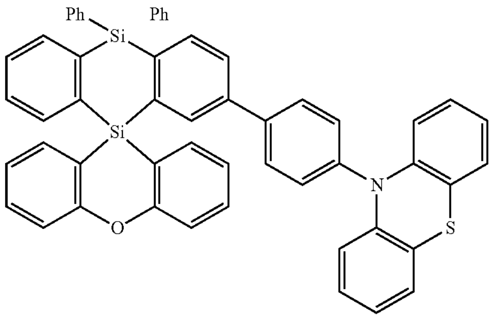
B260
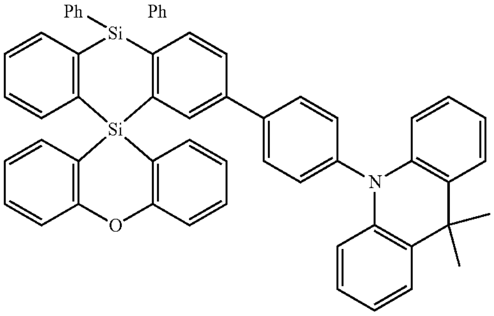
B261
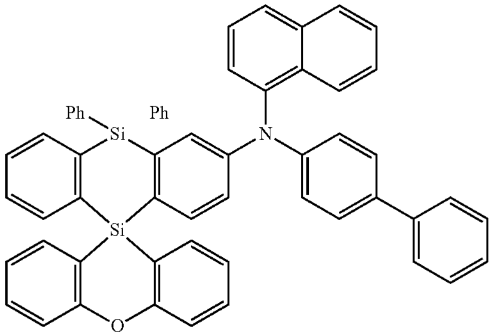
-continued
B262
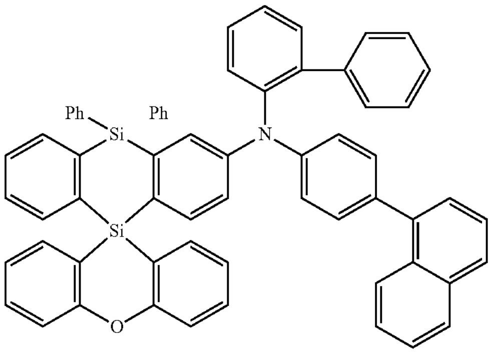
B263
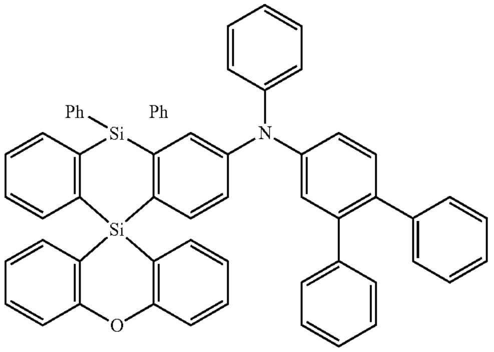
B264
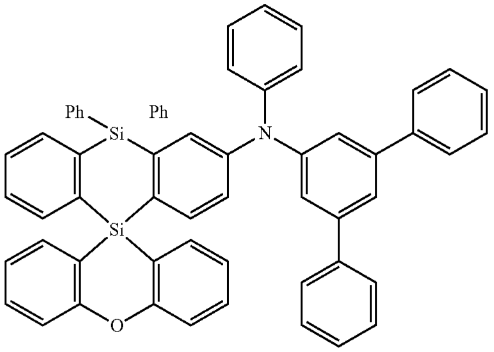
B265
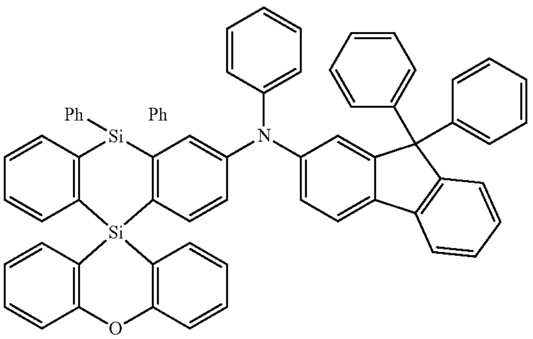

-continued
B266
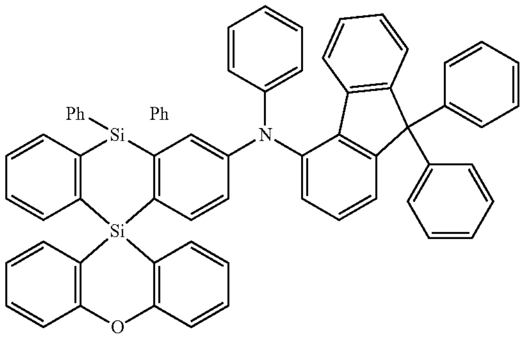
B267
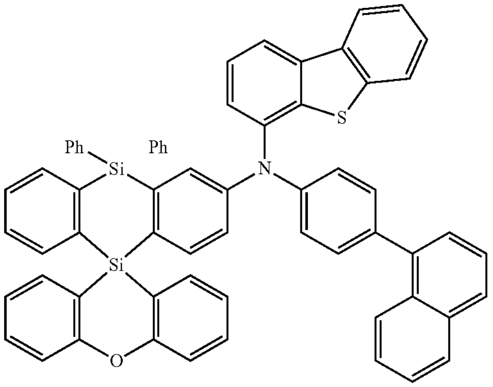
B268
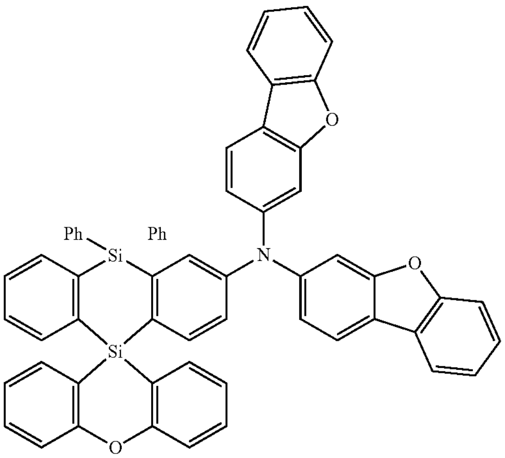
B269
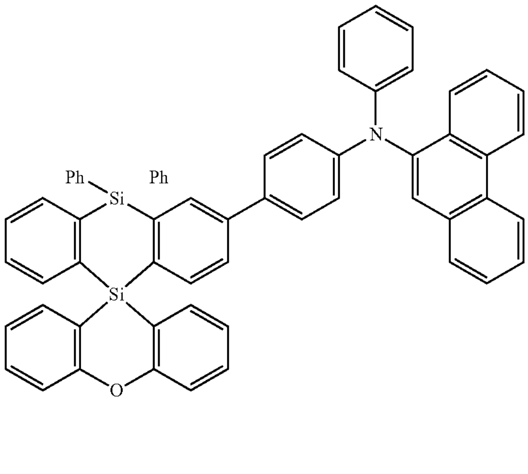
-continued
B270
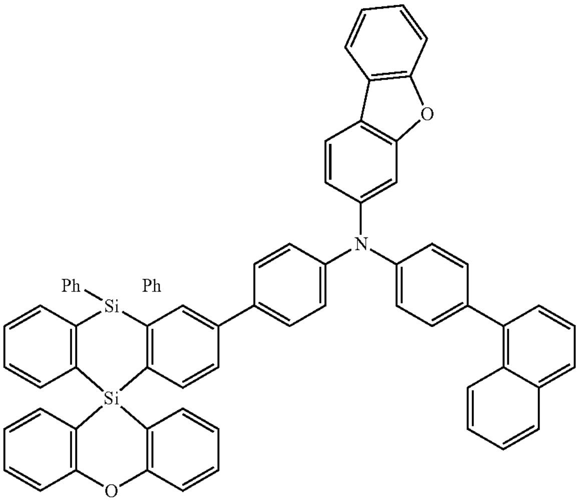
B271
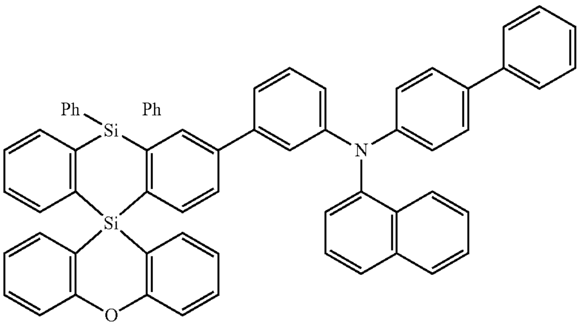
B272
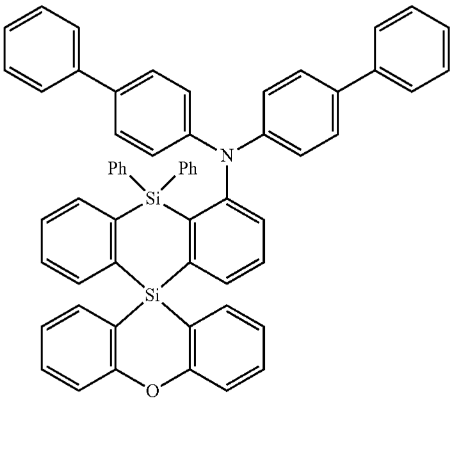

-continued
B273
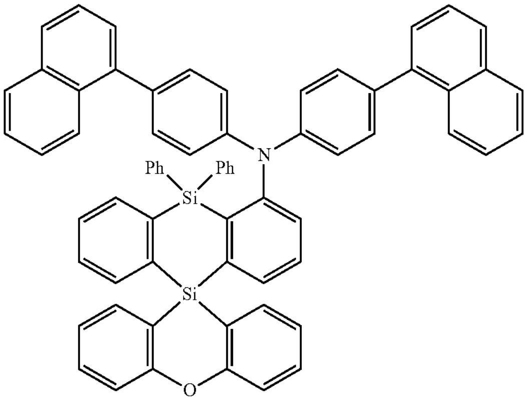
B274
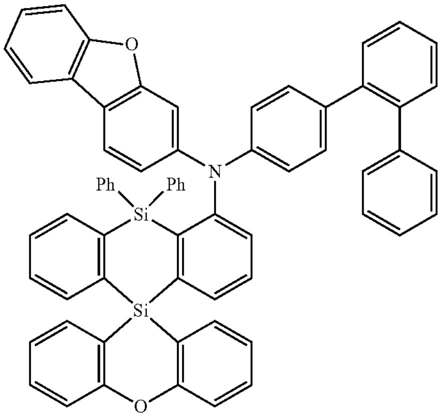
B275
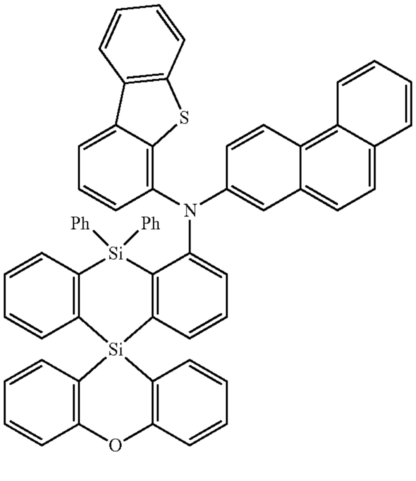
-continued
B276
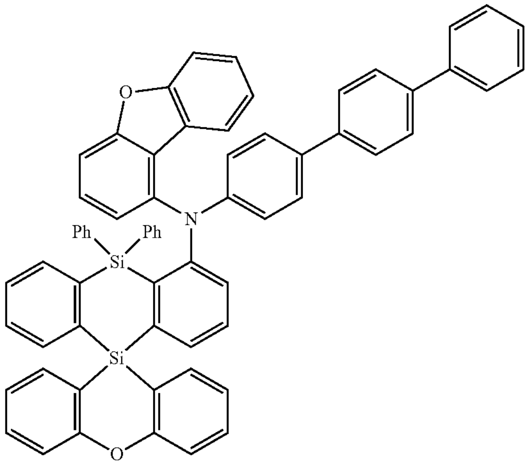
B277
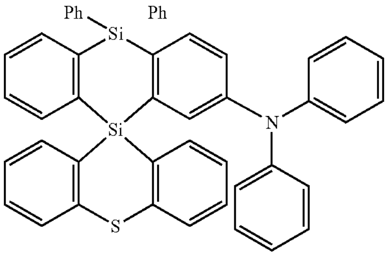
B278
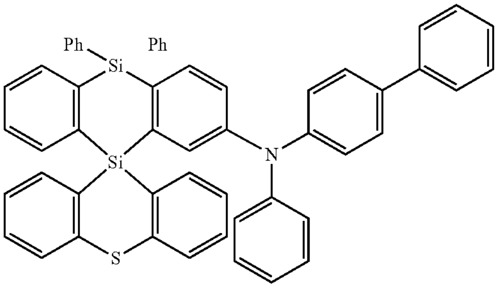
B279
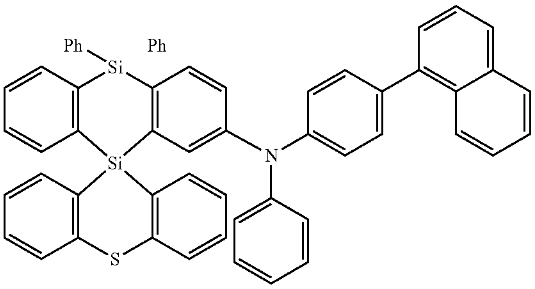

B280
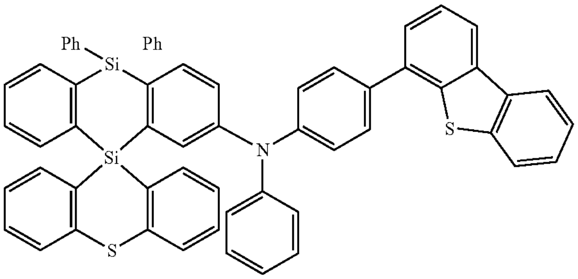
B281
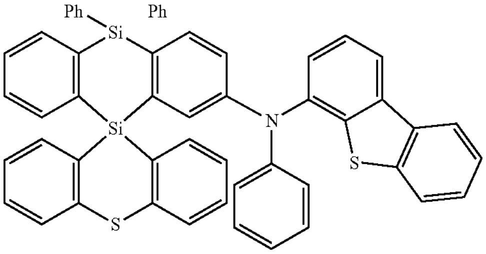
B282
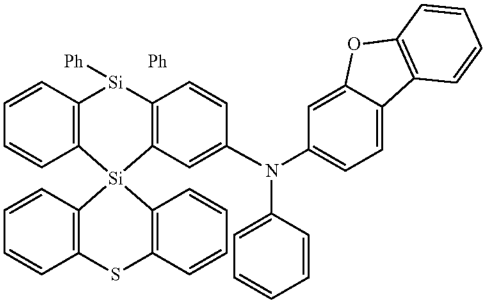
B283
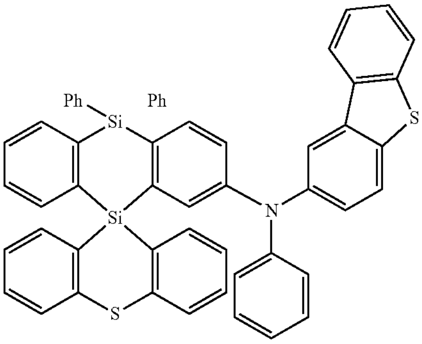
B284
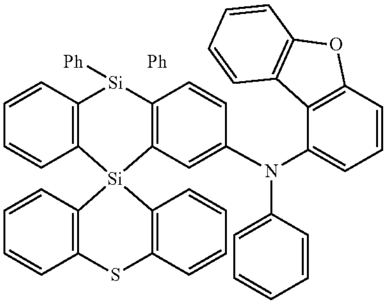
B285
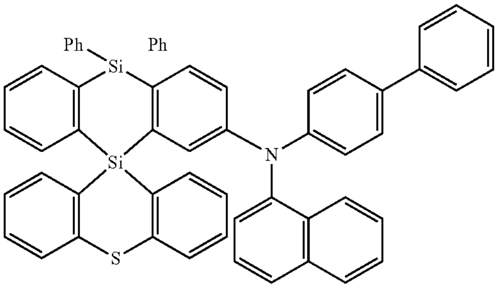
B286
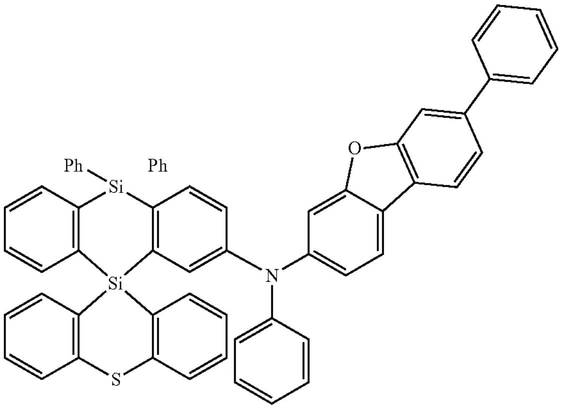
B287
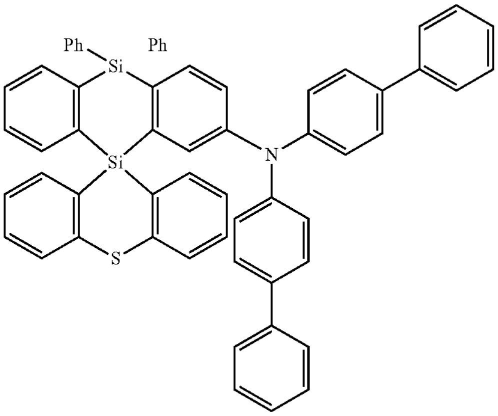
B288
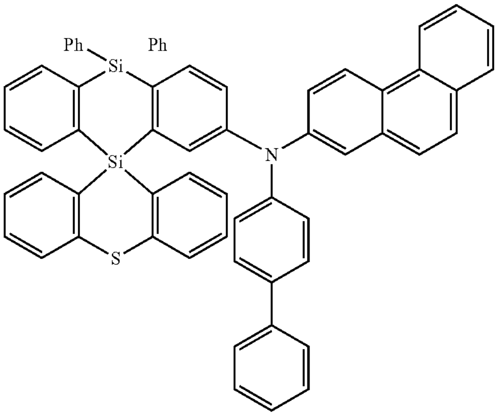

B289
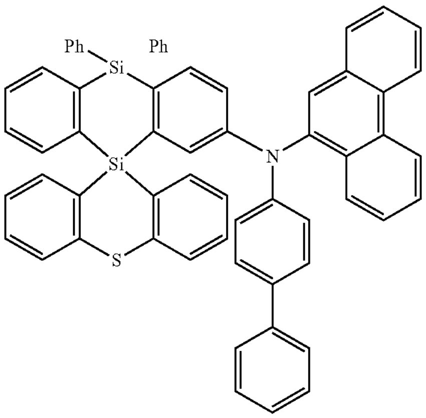
B290
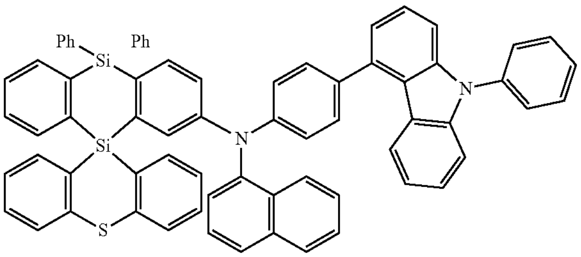
B291
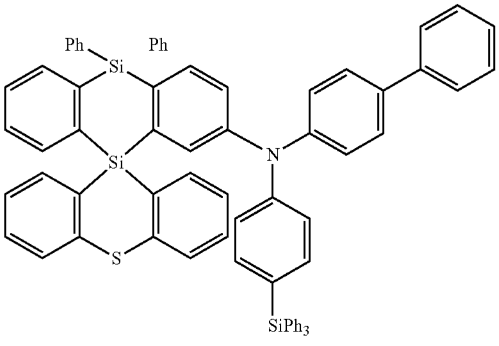
B292
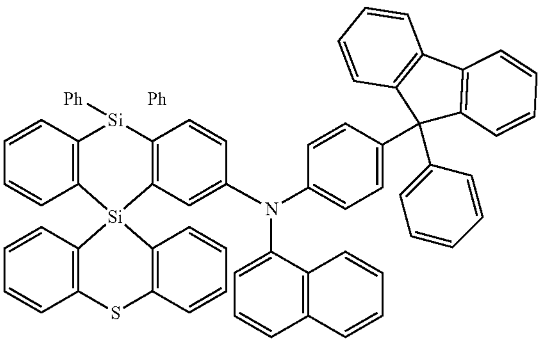
B293
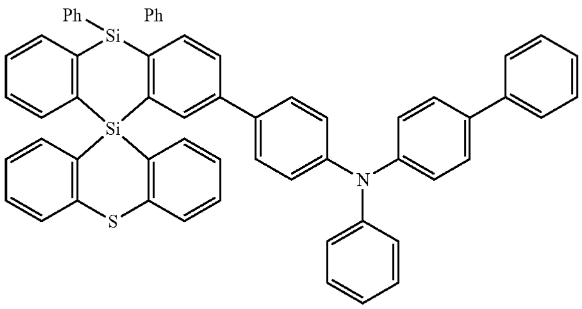
B294
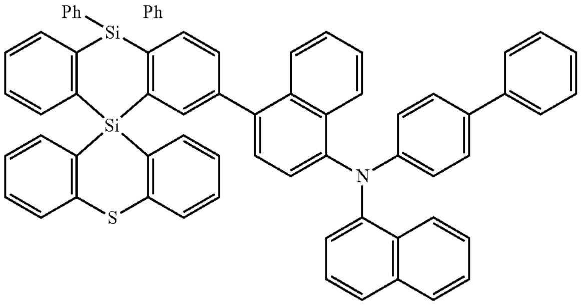
B295
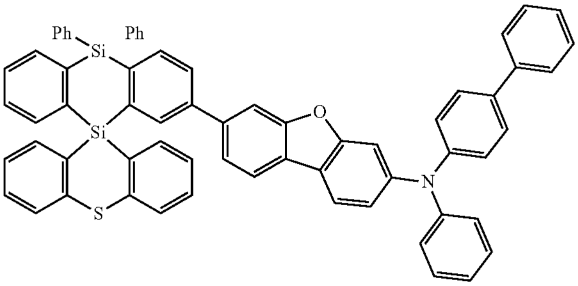
B296
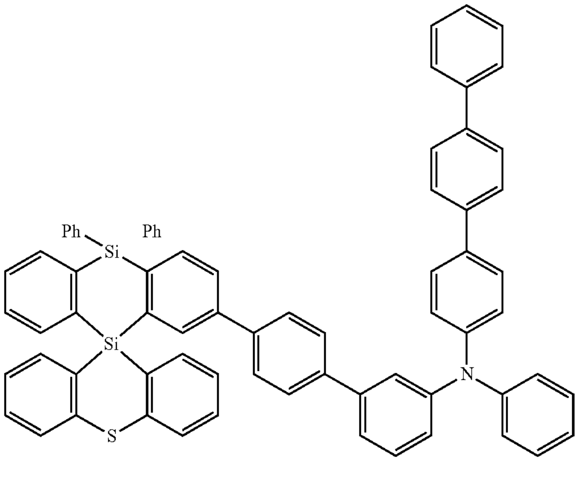

-continued
B297
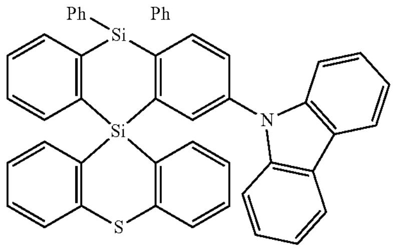
B298
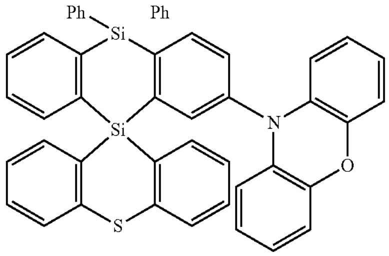
B299
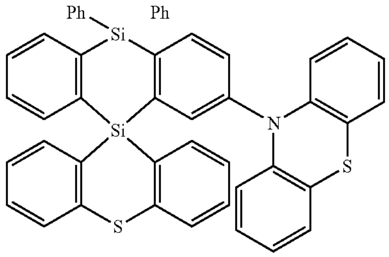
B300
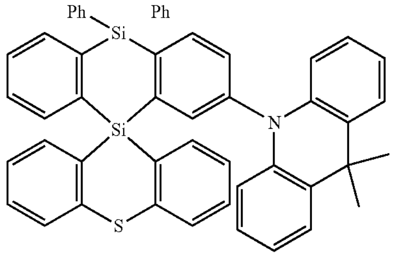
B301
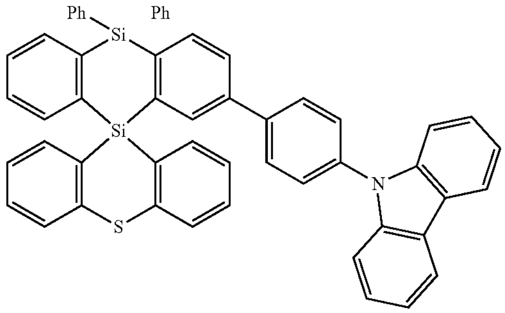
-continued
B302
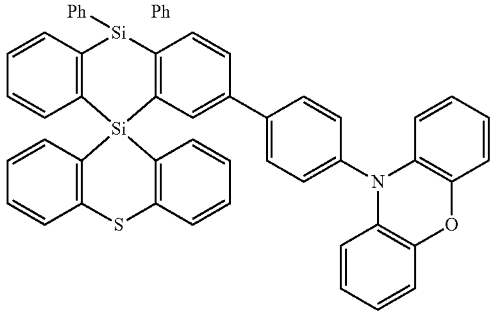
B303
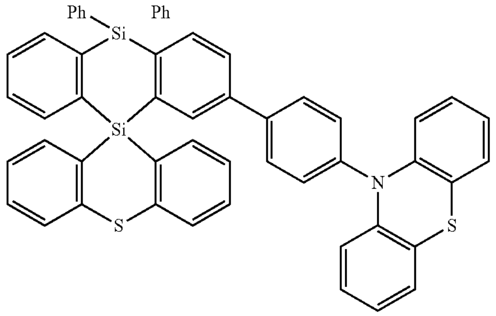
B304
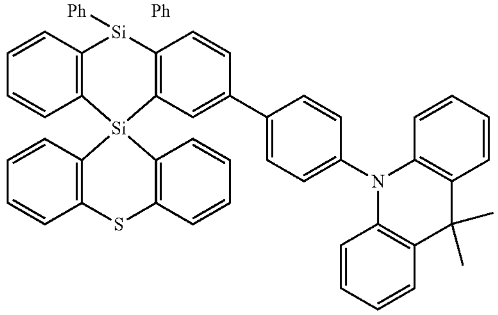
B305
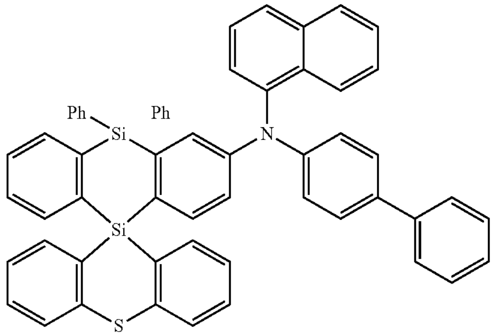

-continued
B306
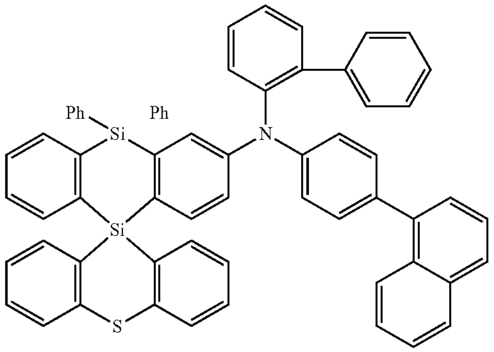
B307
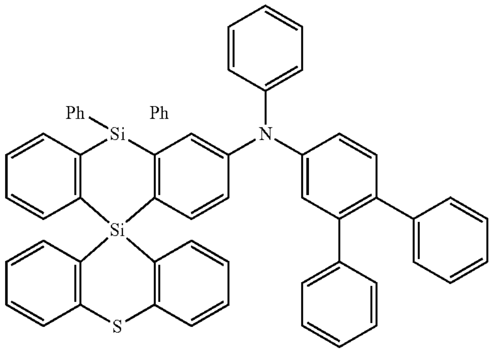
B308
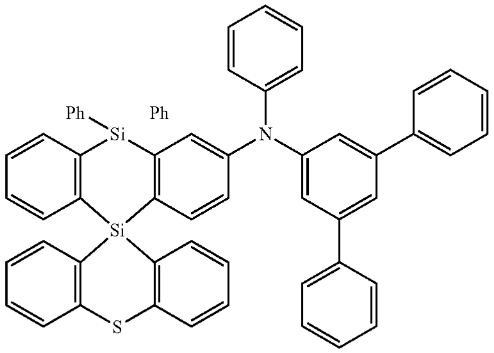
B309
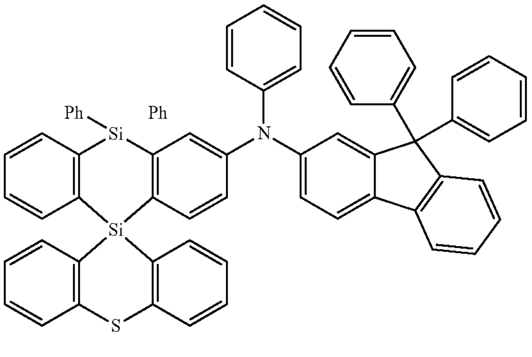
-continued
B310
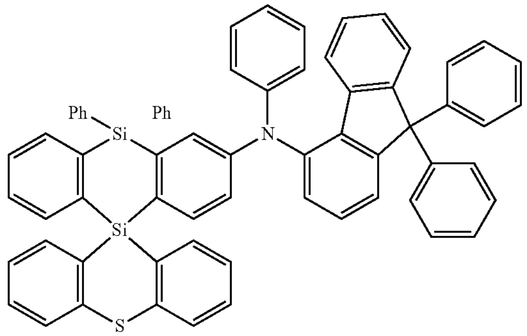
B311
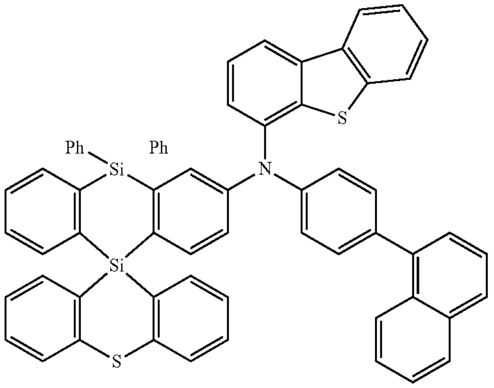
B312
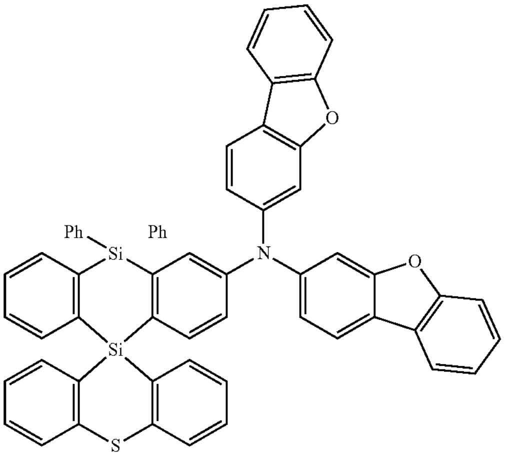
B313
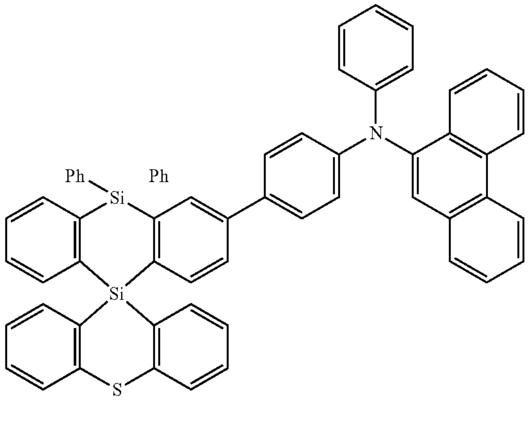

-continued
B314
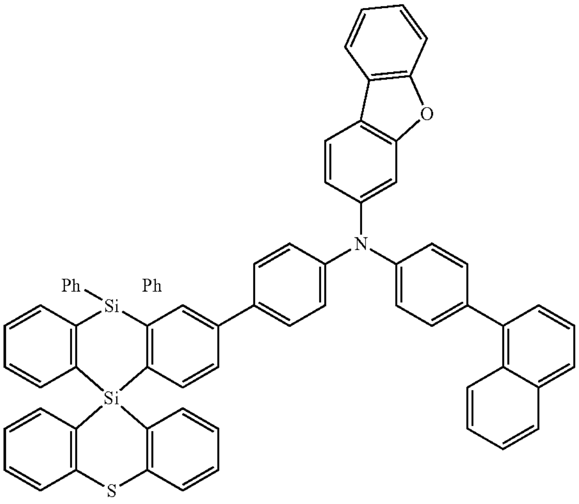
B315
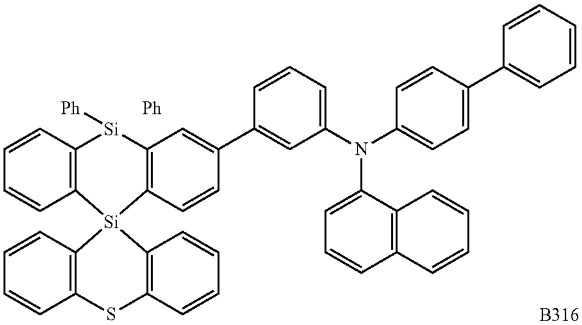
B316
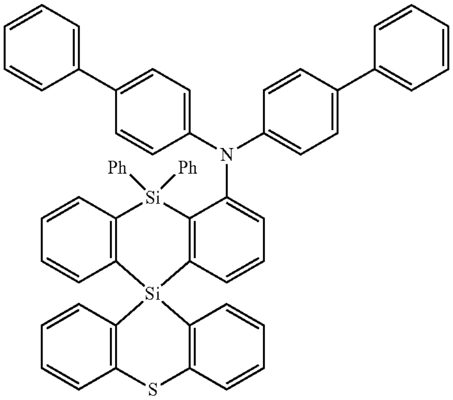
B317
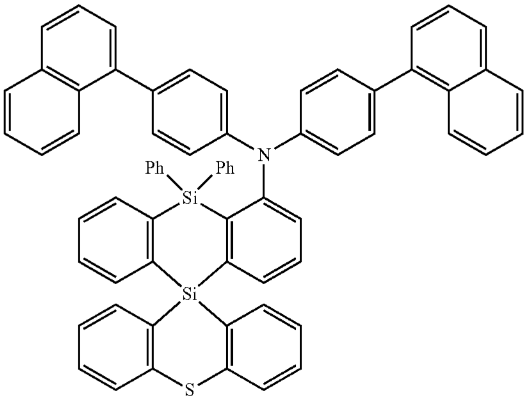
-continued
B318
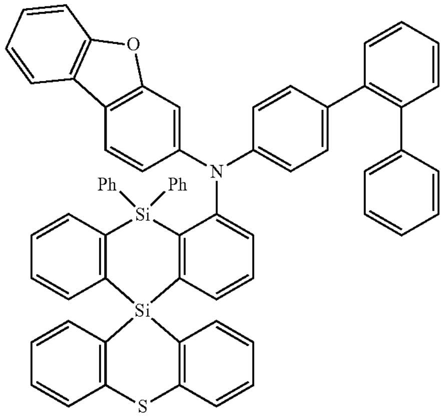
B319
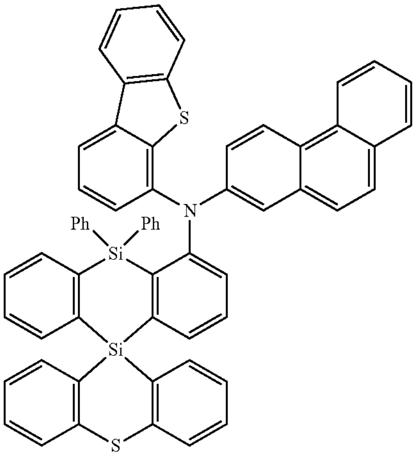
B320
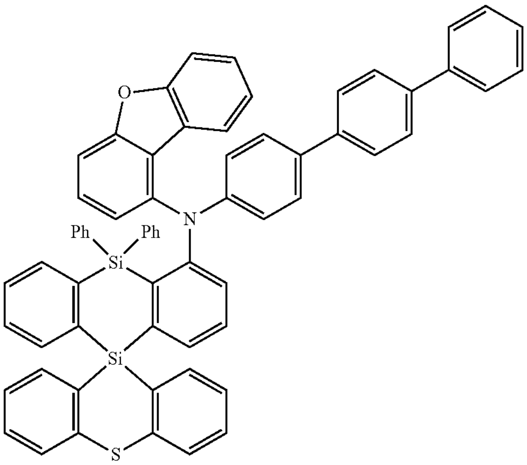
B321
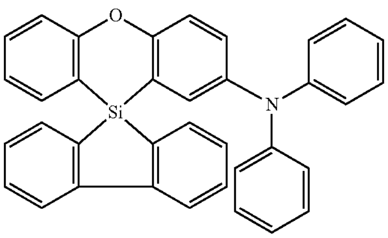

-continued
B322
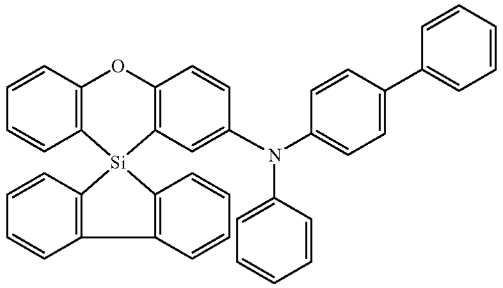
B323
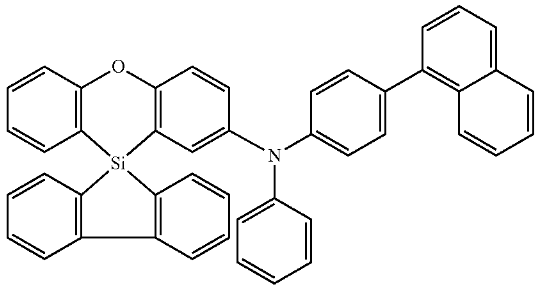
B324
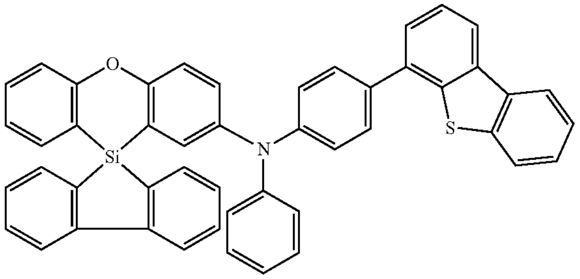
B325
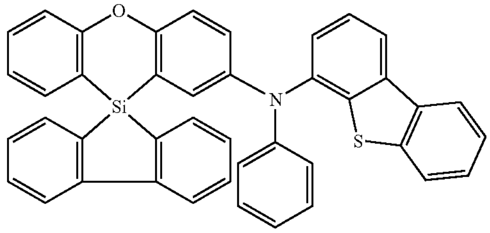
B326
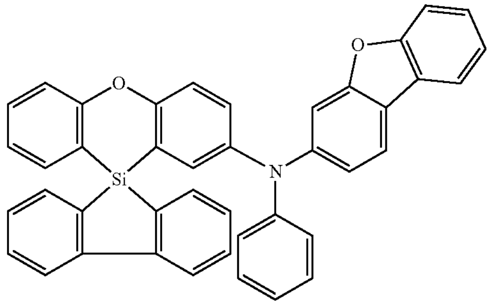
-continued
B327
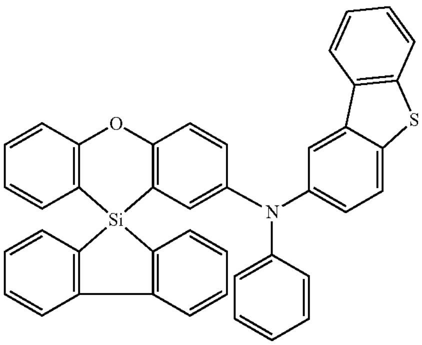
B328
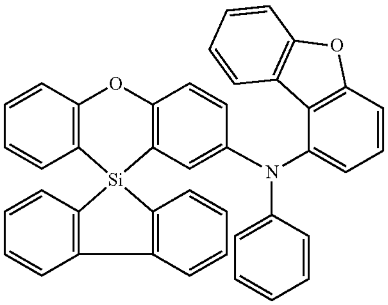
B329
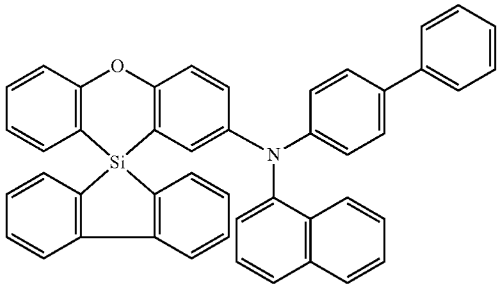
B330
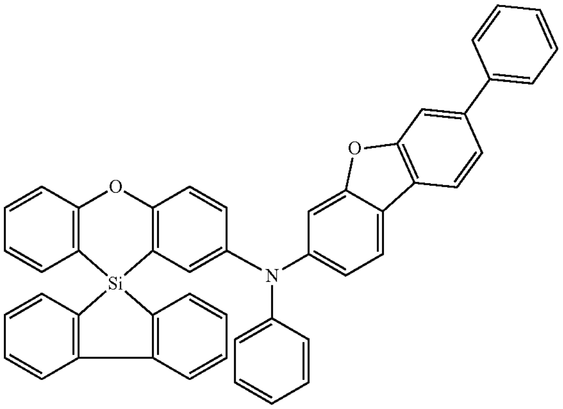

-continued
B331
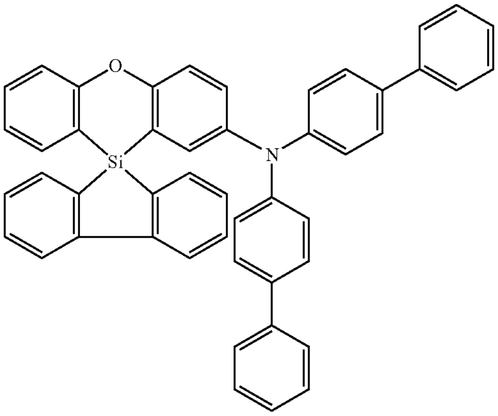
B332
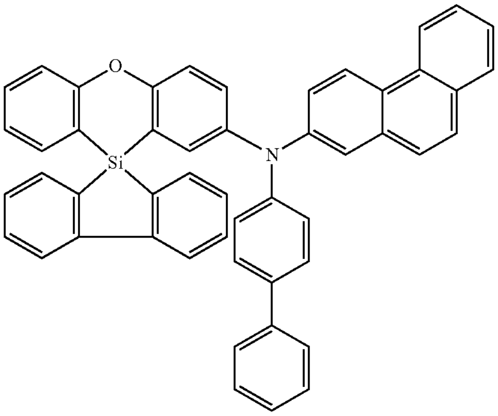
B333
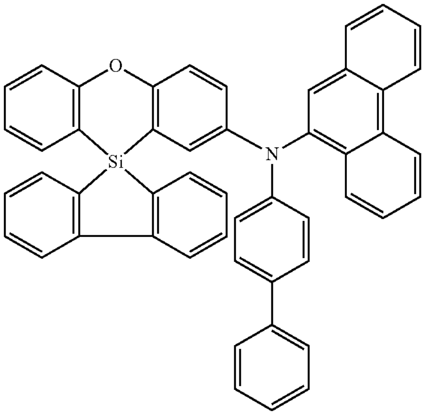
B334
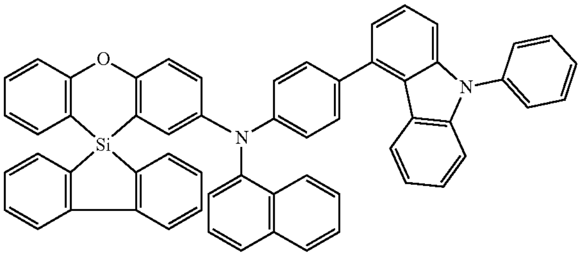
-continued
B335
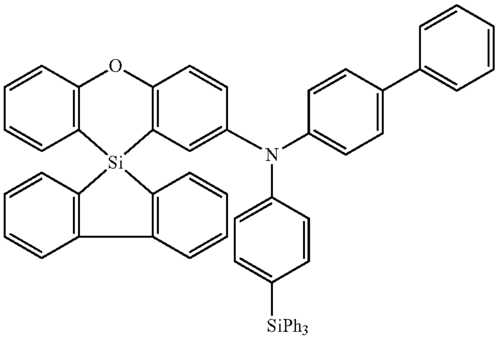
B336
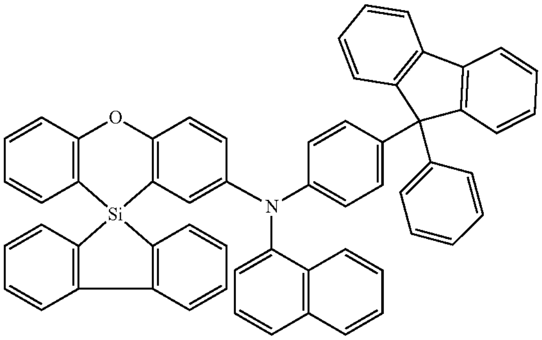
B337
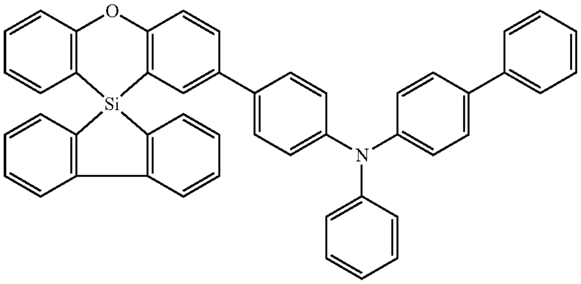
B338
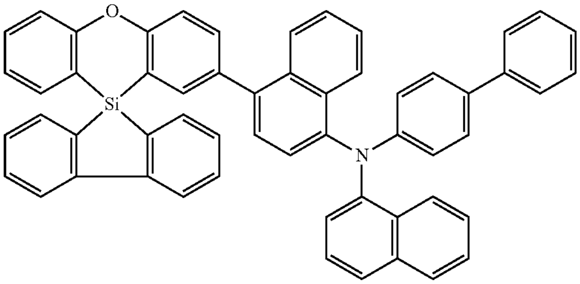
B339
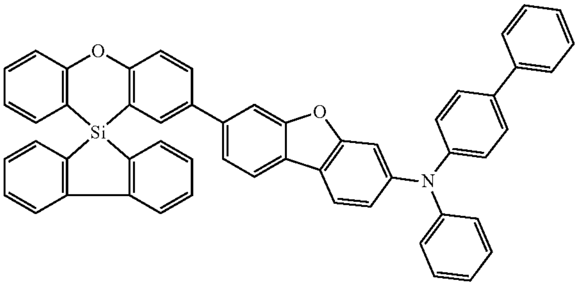

B340
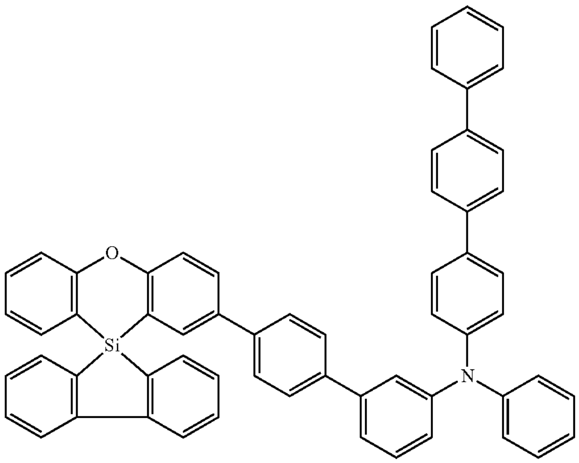
B341
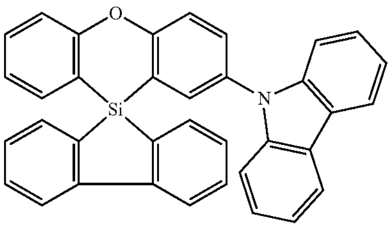
B342
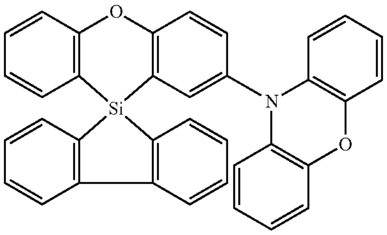
B343
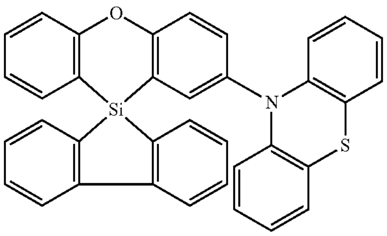
B344
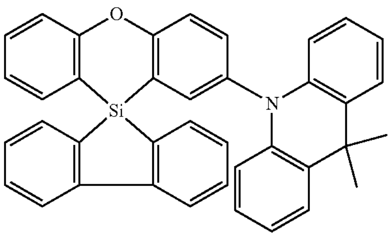
B345
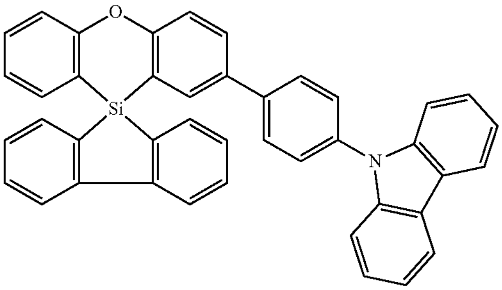
B346
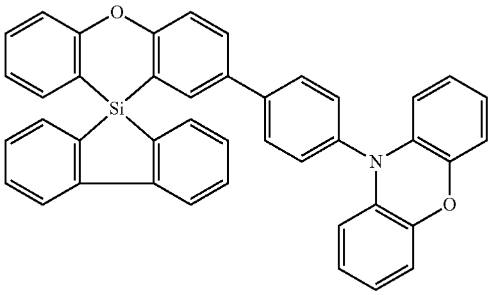
B347
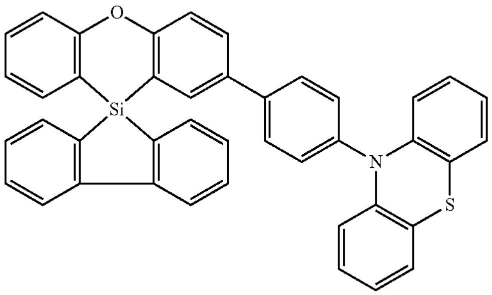
B348
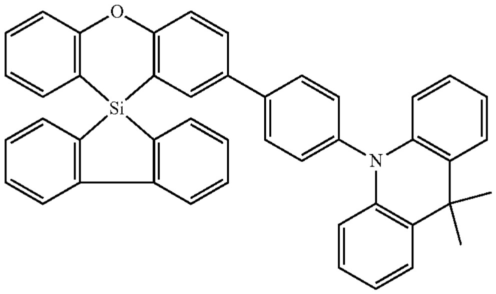
B349
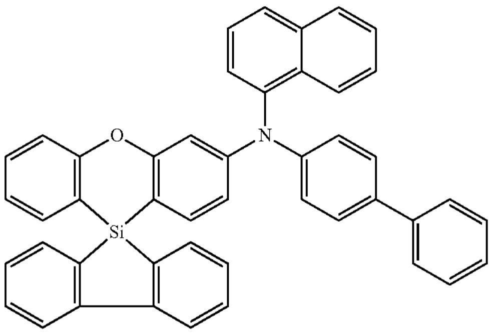

-continued
B350
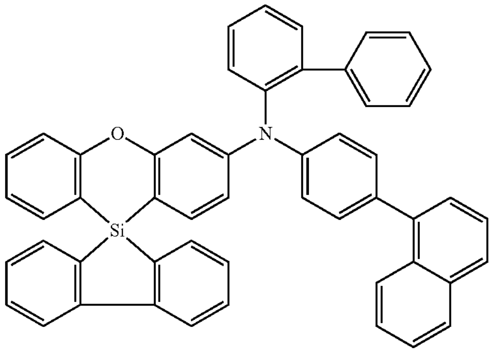
B351
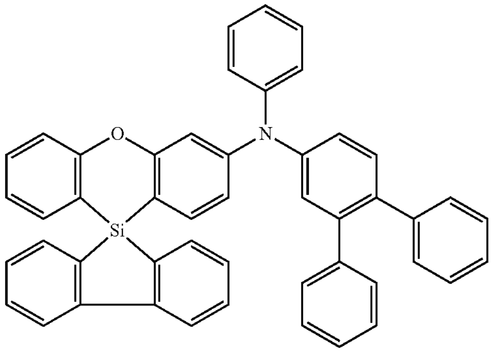
B352
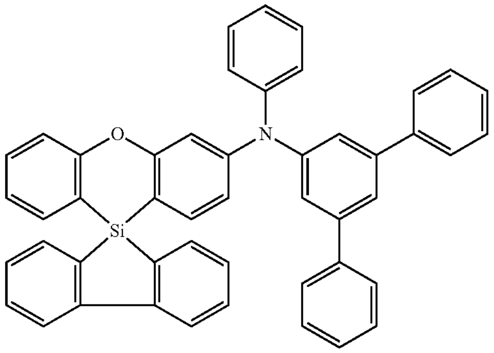
B353
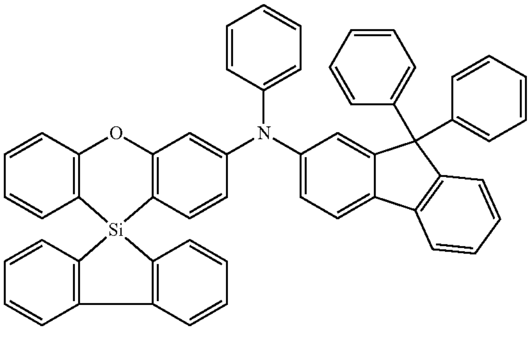
-continued
B354
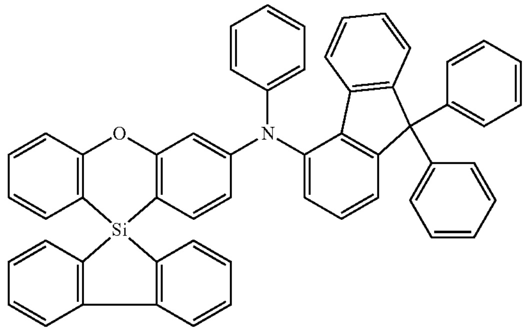
B355
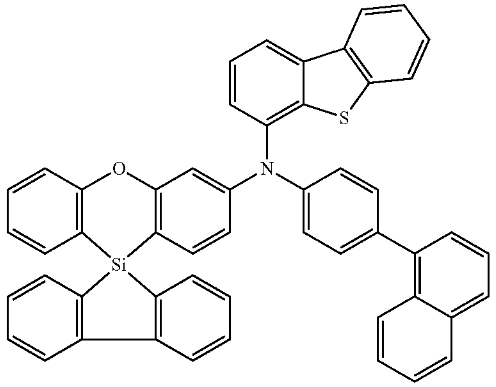
B356
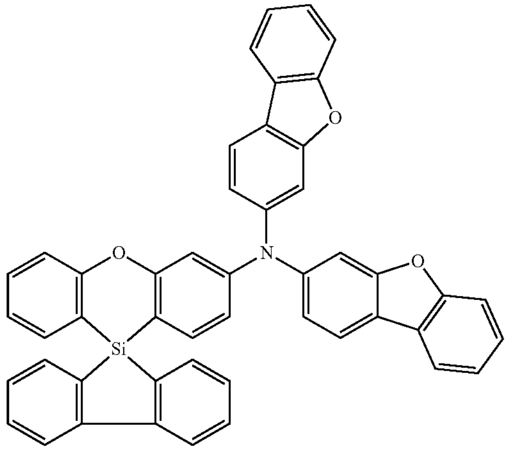
B357
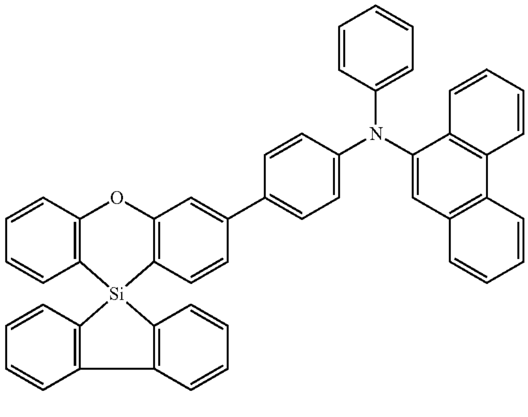

-continued
B358
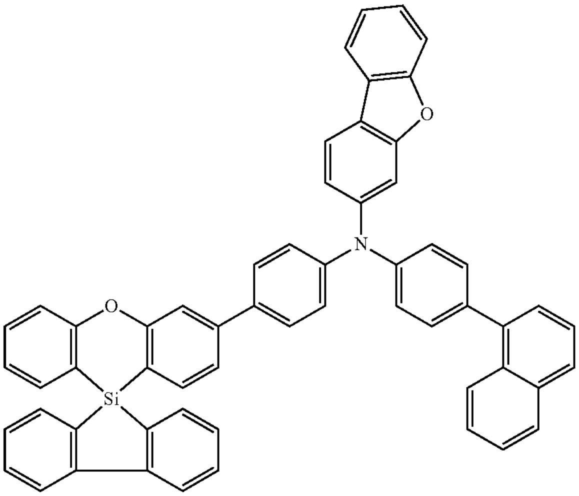
B359
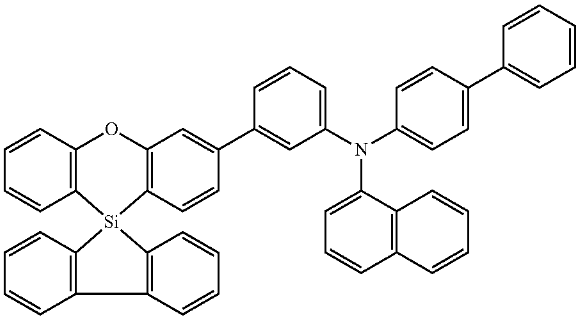
B360
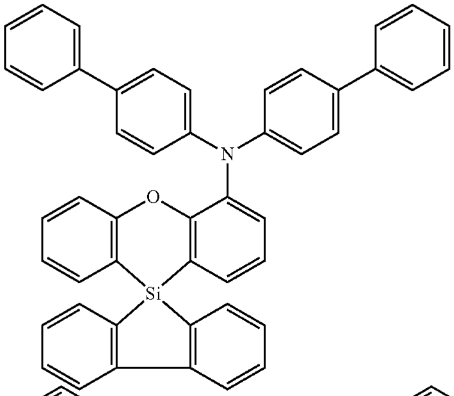
B361
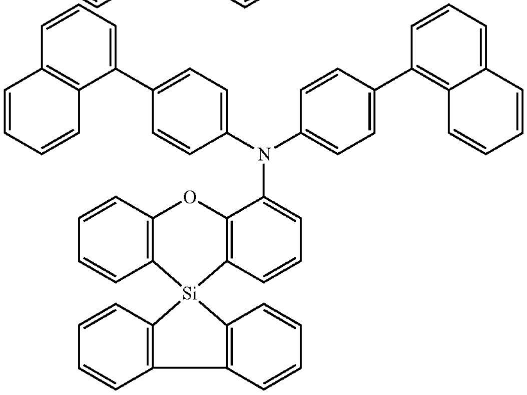
-continued
B362
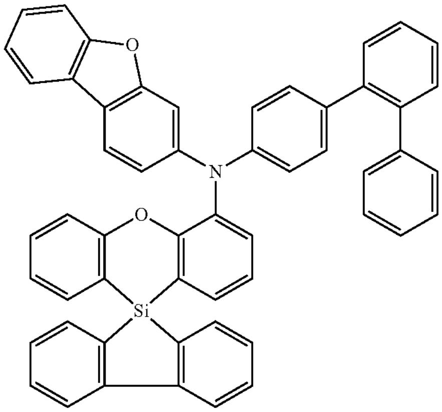
B363
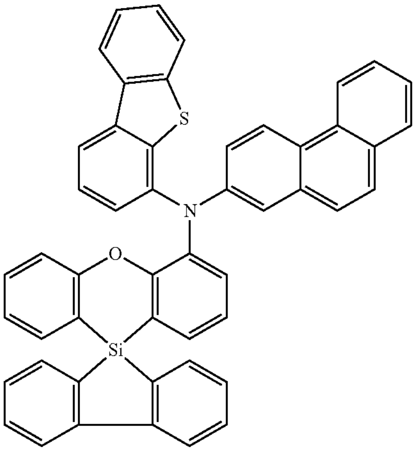
B364
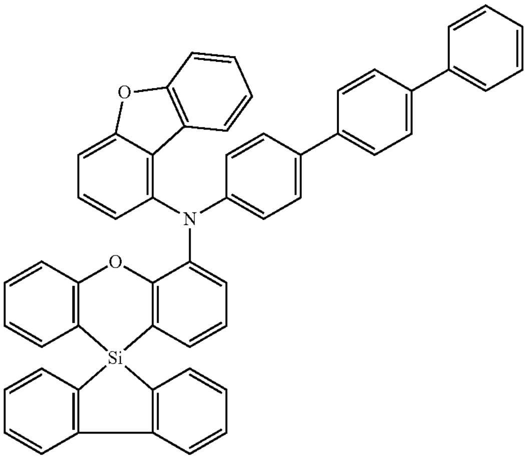
B365
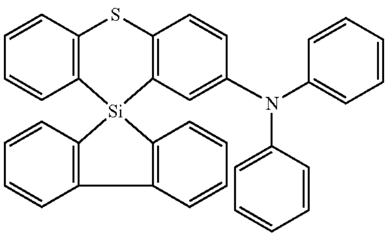

-continued
B366
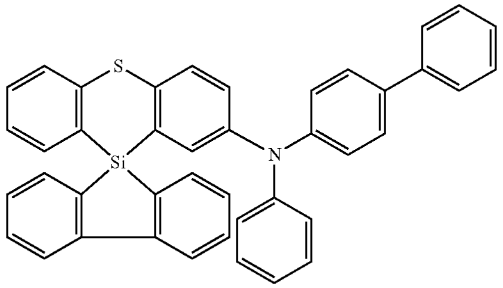
B367
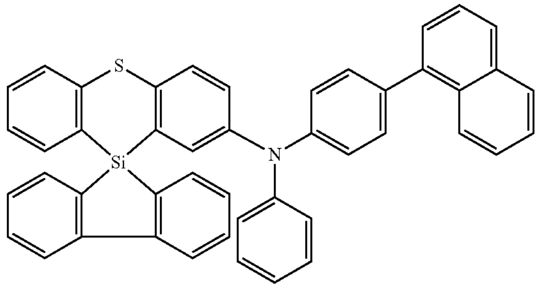
B368
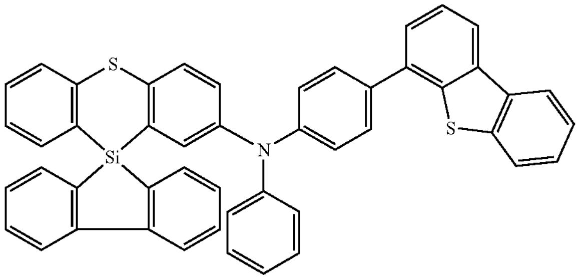
B369
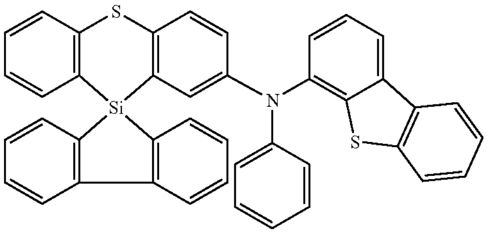
B370
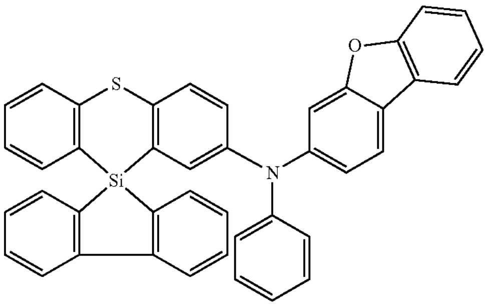
-continued
B371
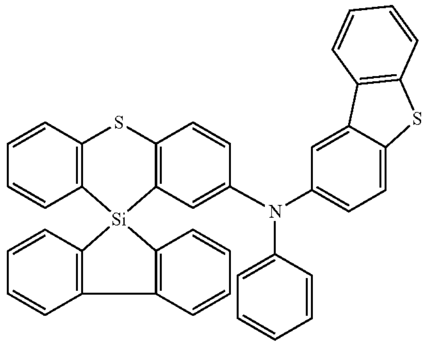
B372
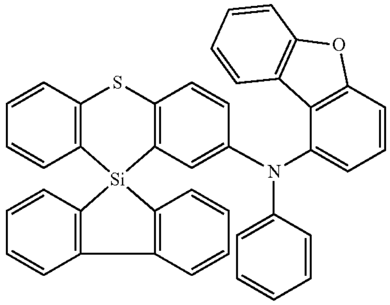
B373
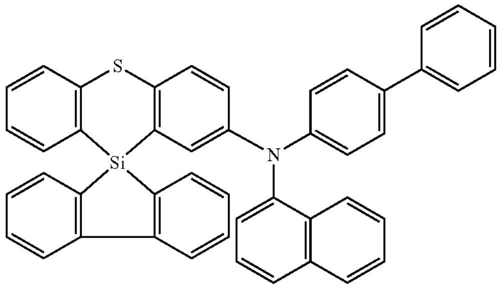
B374
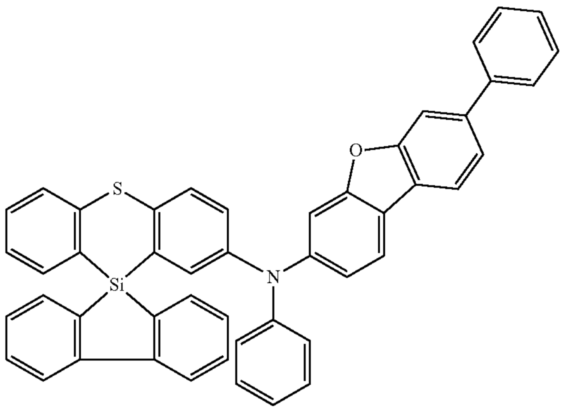

-continued
B375
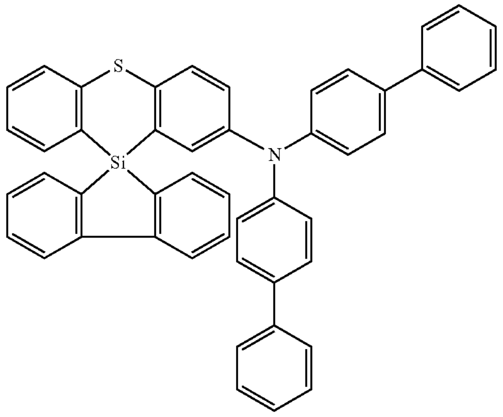
B376
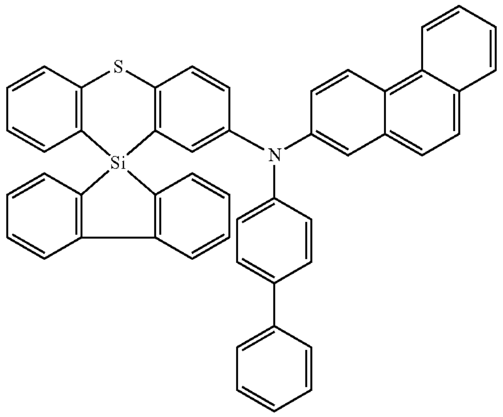
B377
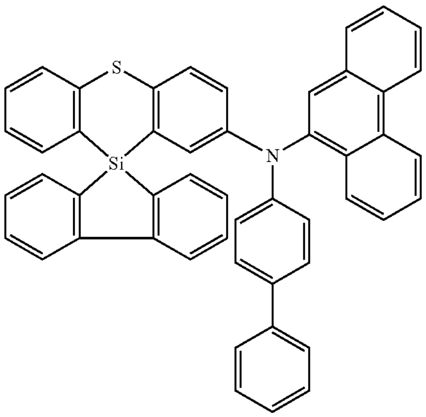
B378
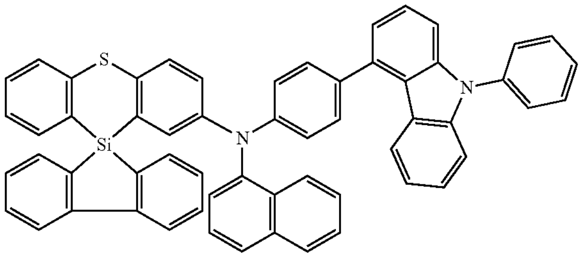
-continued
B379
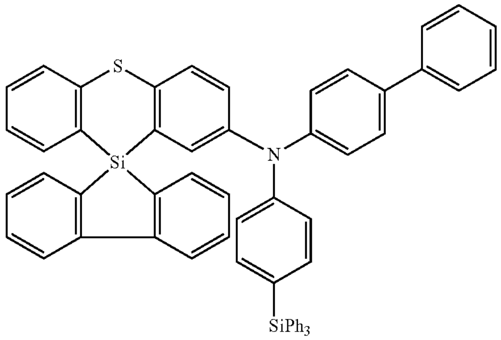
B380
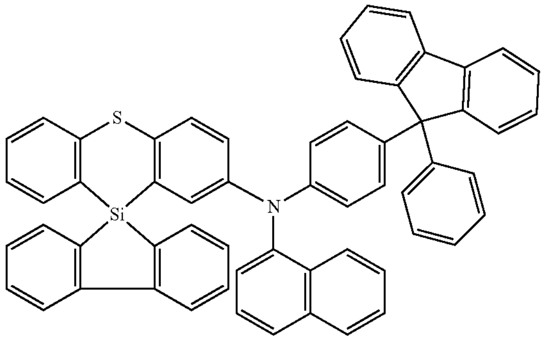
B381
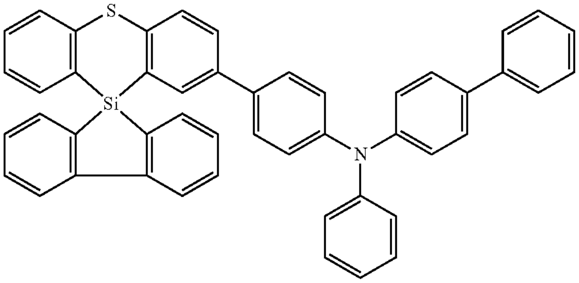
B382
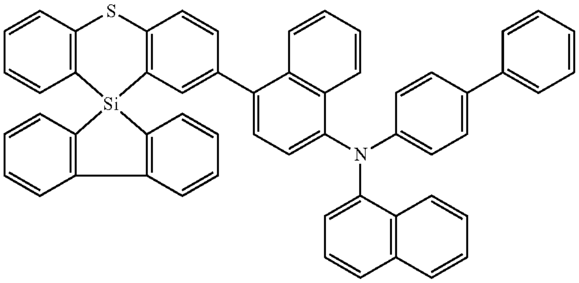
B383
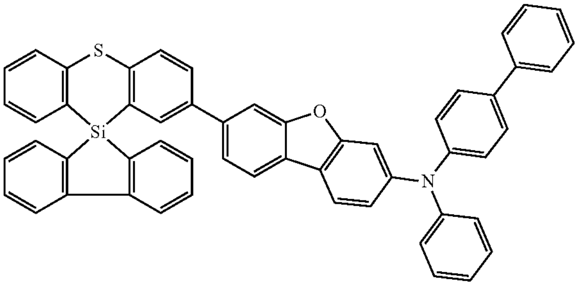

-continued
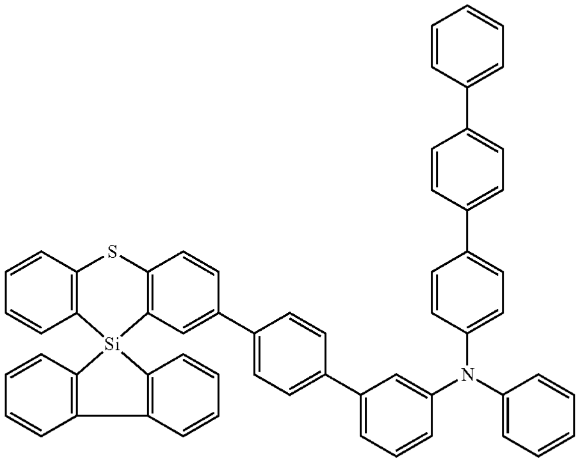
B384
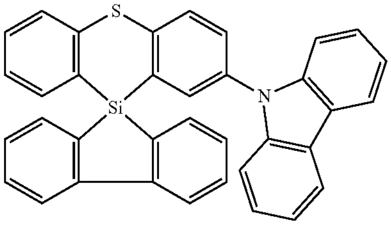
B385
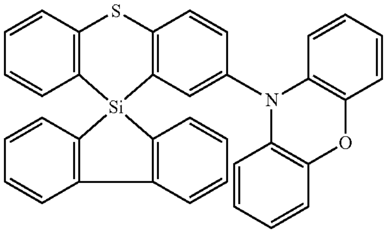
B386
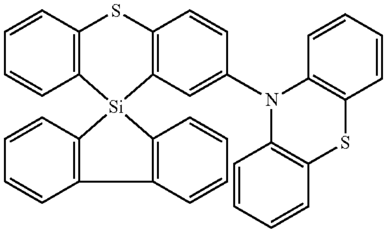
B387
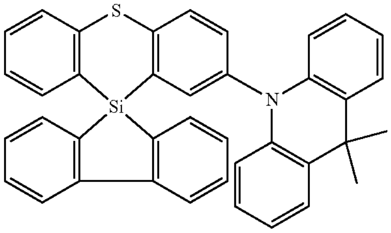
B388
-continued
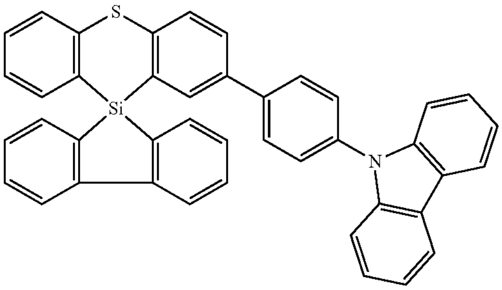
B389
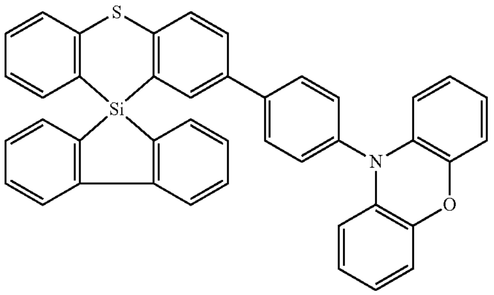
B390
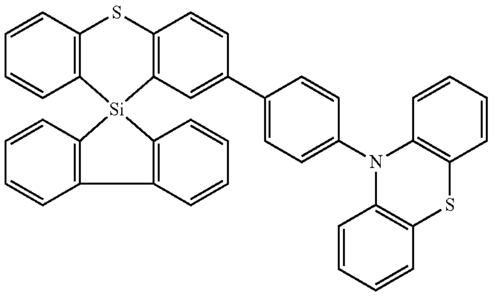
B391
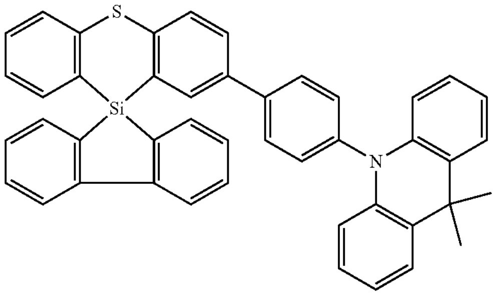
B392
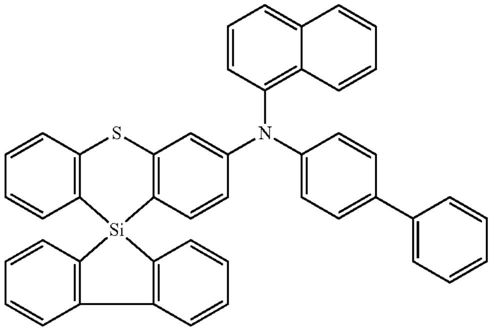
B393

-continued
B394
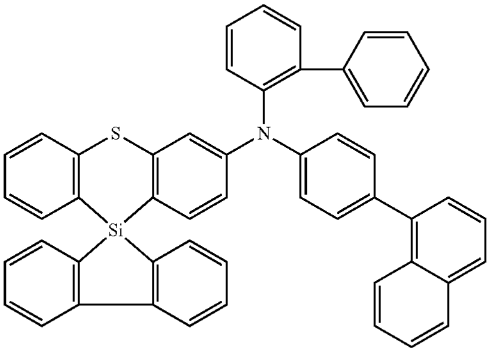
B395
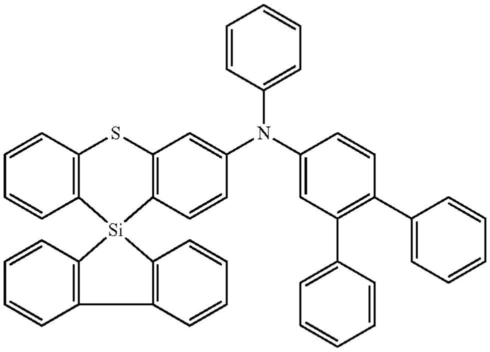
B396
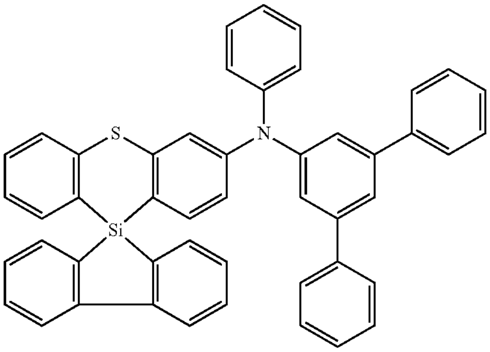
B397
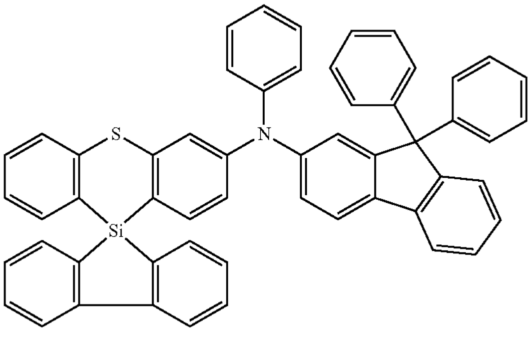
-continued
B398
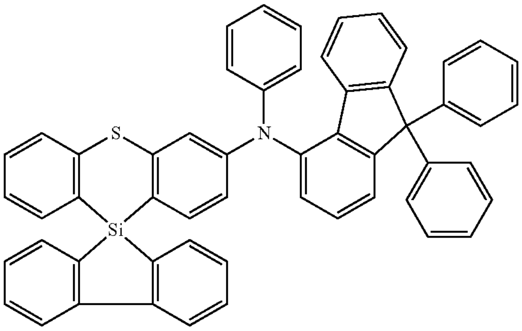
B399
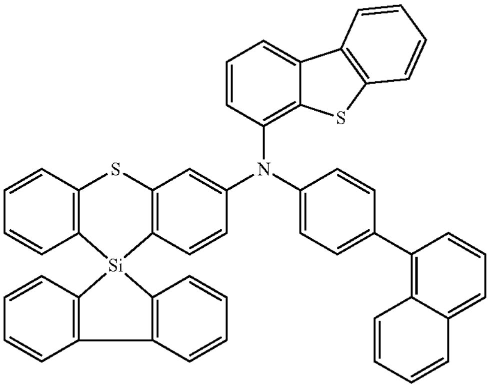
B400
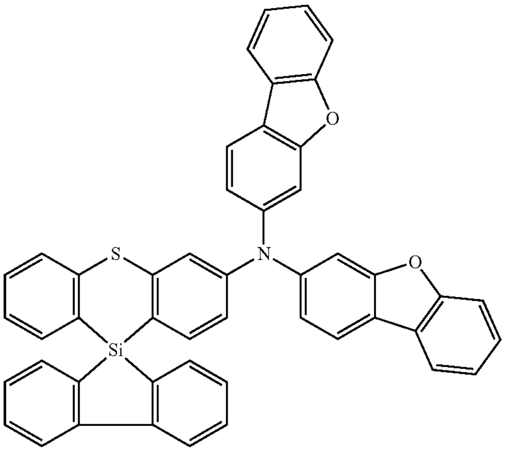
B401
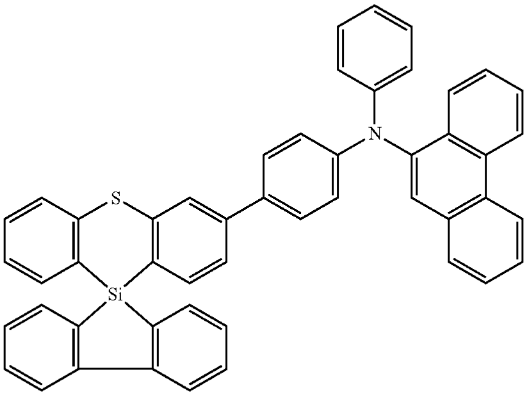

-continued
B402
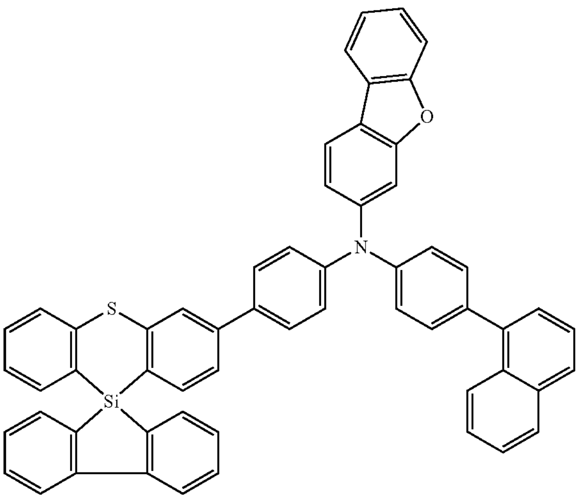
B403
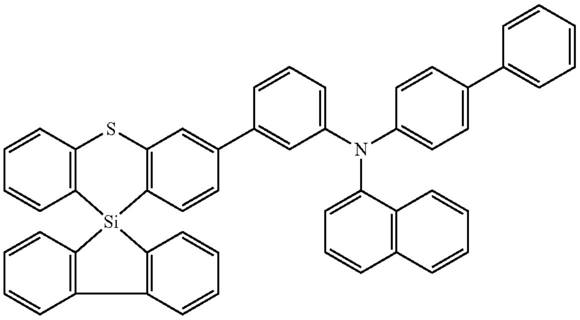
B404
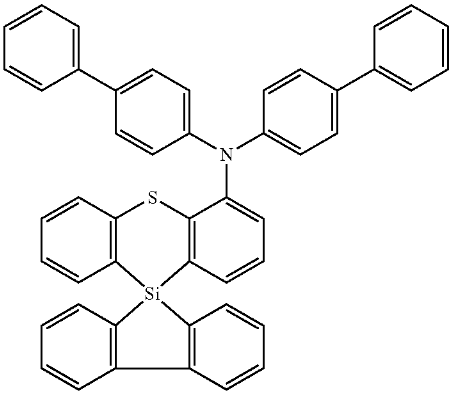
B405
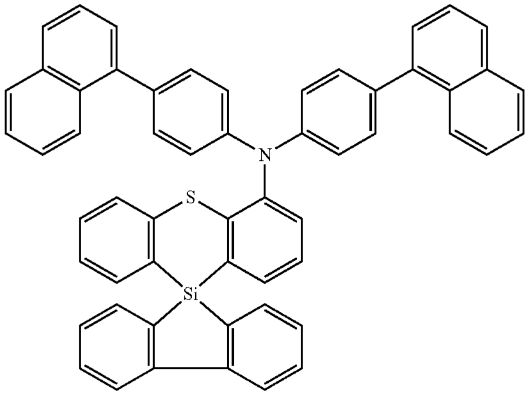
-continued
B406
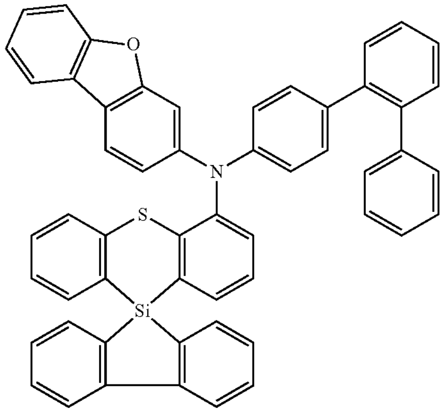
B407
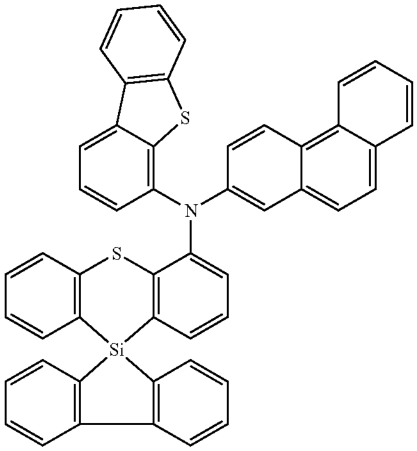
B408
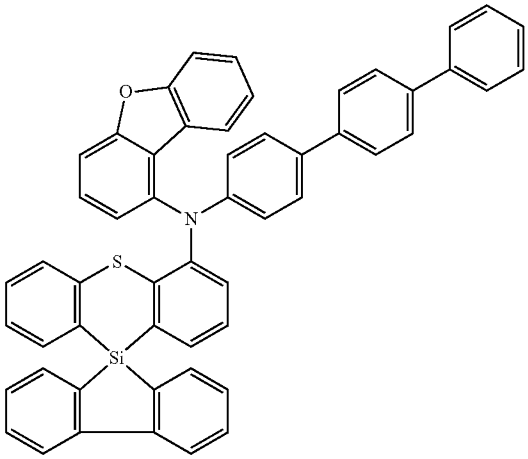
B409
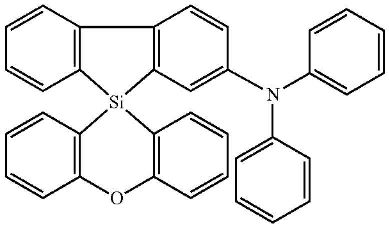

-continued
B410
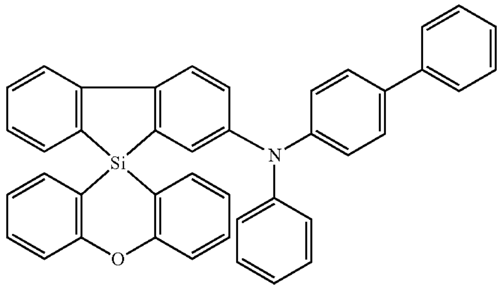
B411
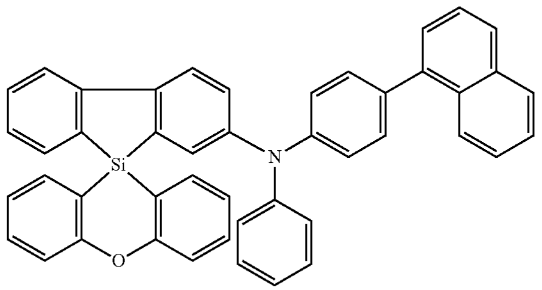
B412
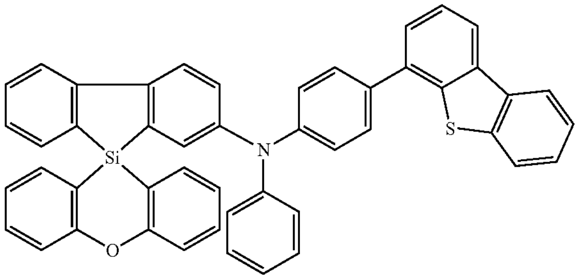
B413
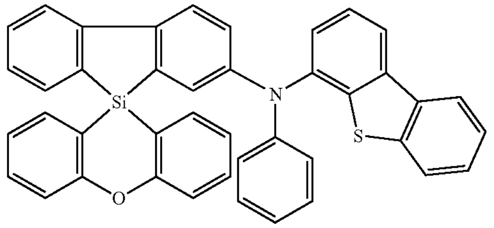
B414
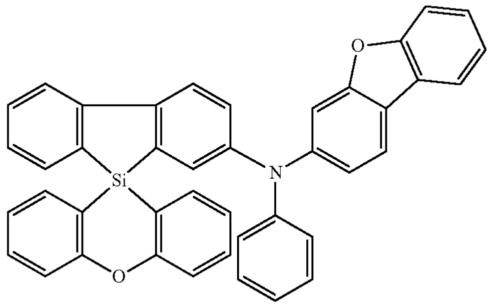
-continued
B415
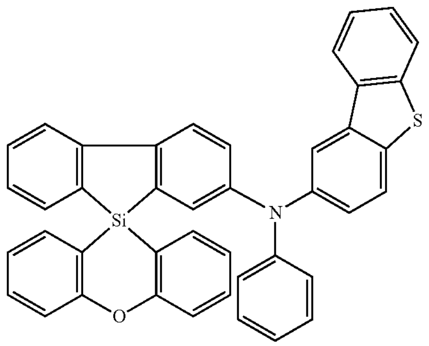
B416
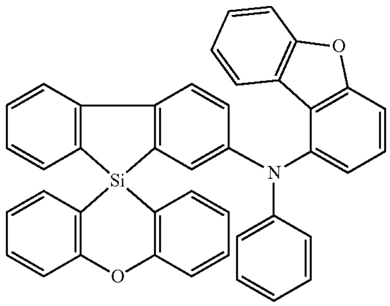
B417
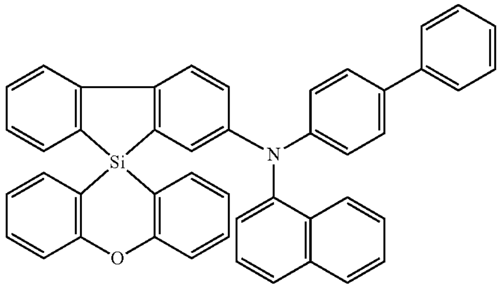
B418
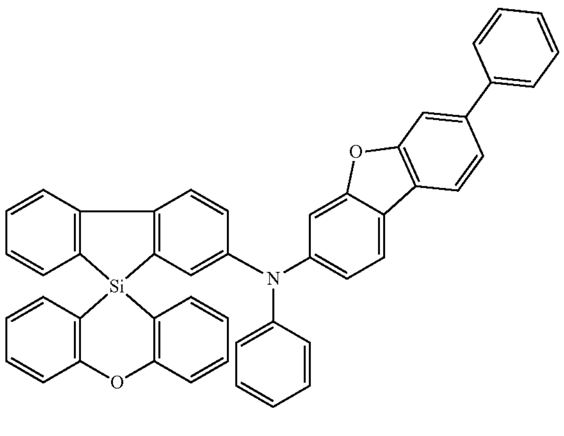

-continued
B419
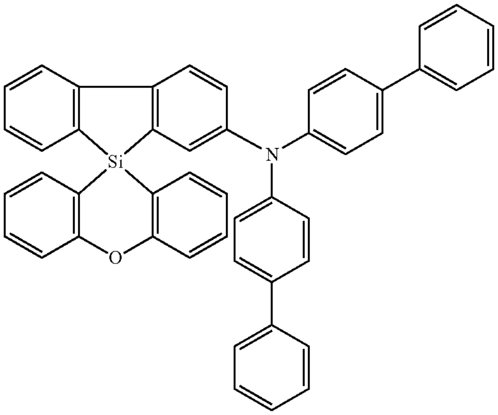
B420
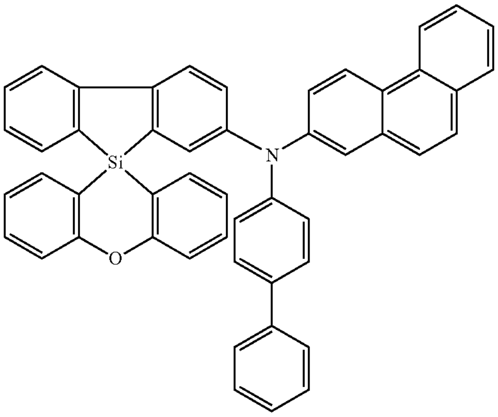
B421
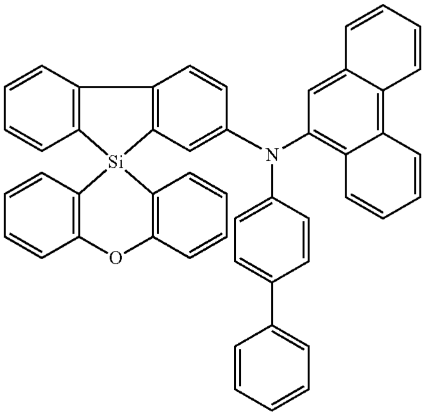
B422
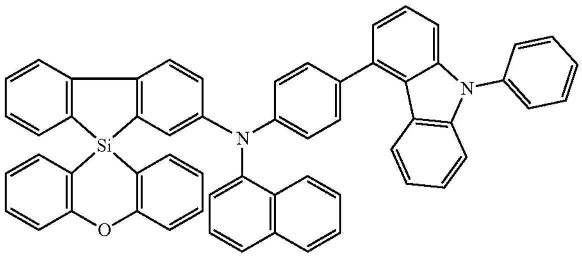
-continued
B423
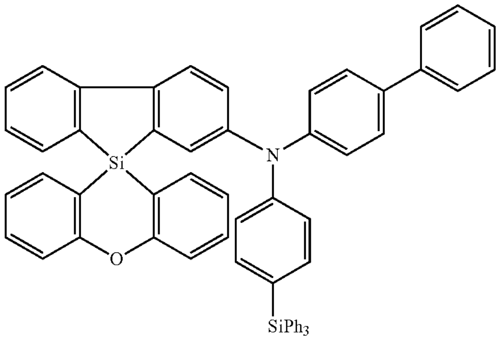
B424
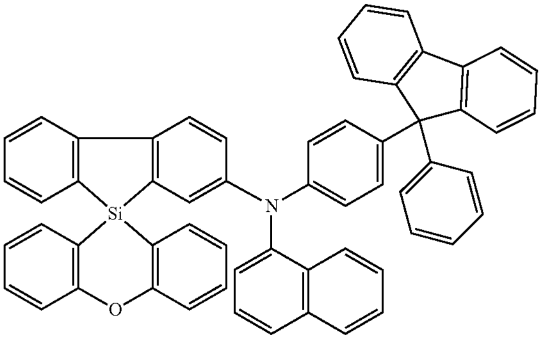
B425
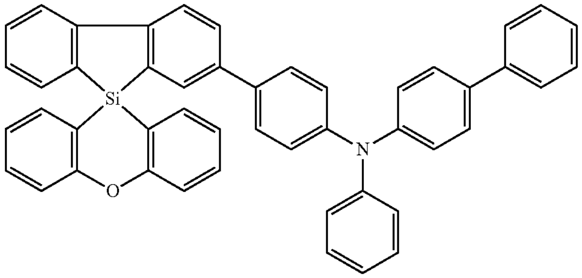
B426
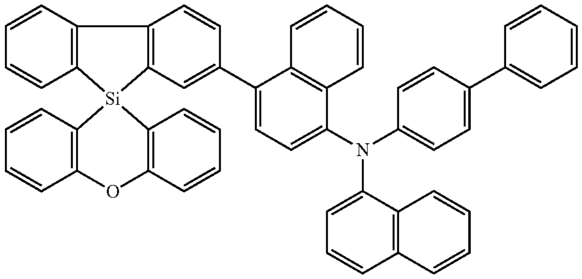
B427
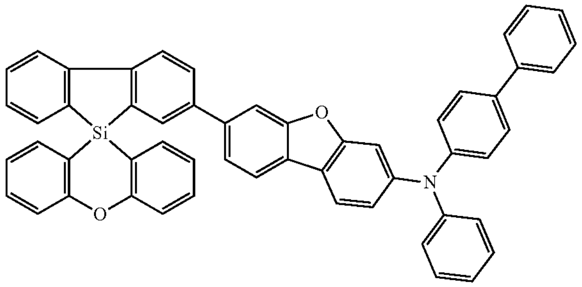

-continued
B428
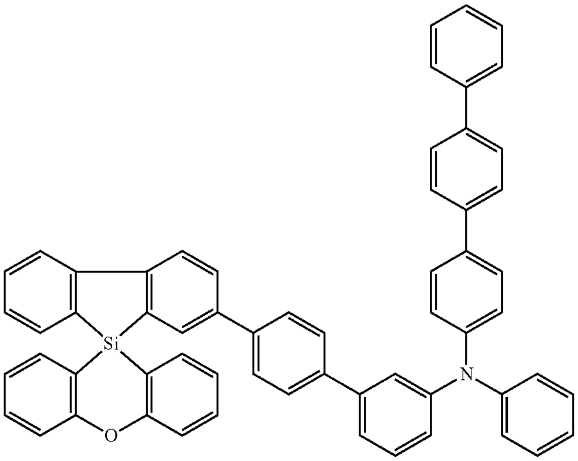
B429
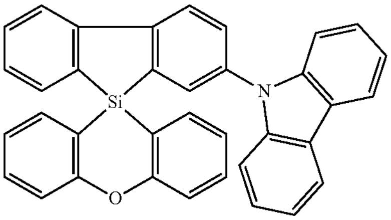
B430
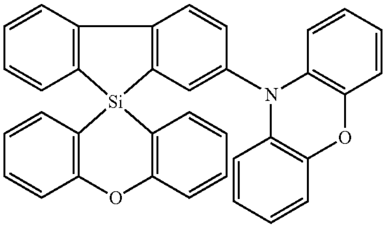
B431
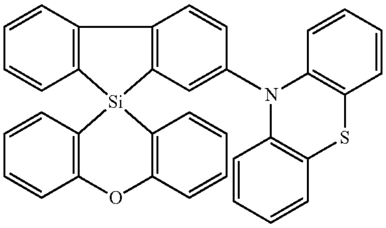
B432
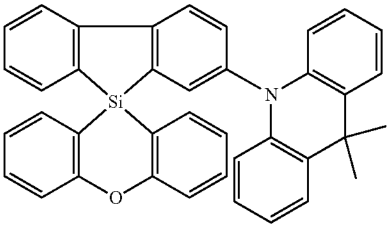
-continued
B433
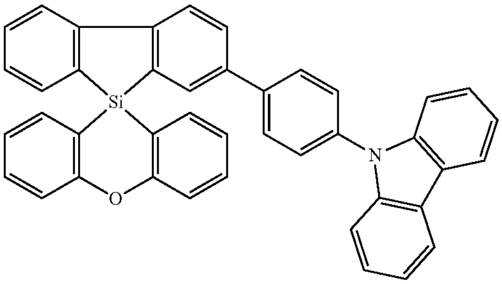
B434
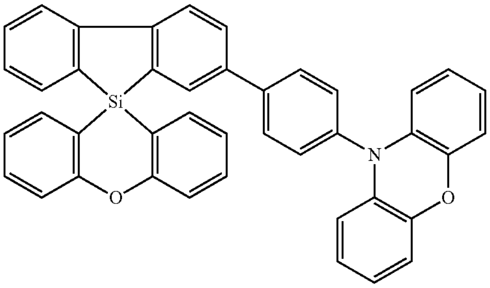
B345
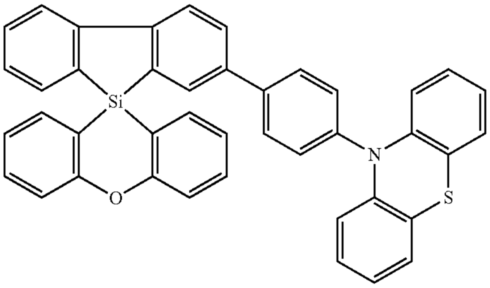
B436
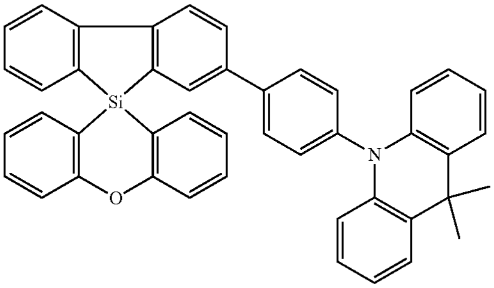
B437
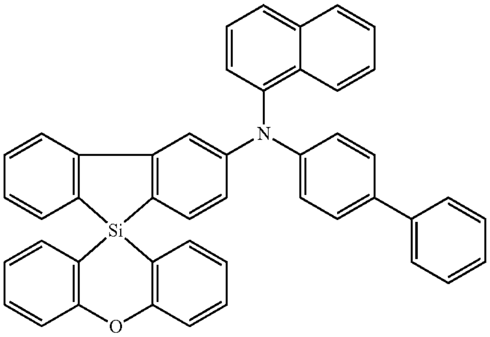

-continued
B438
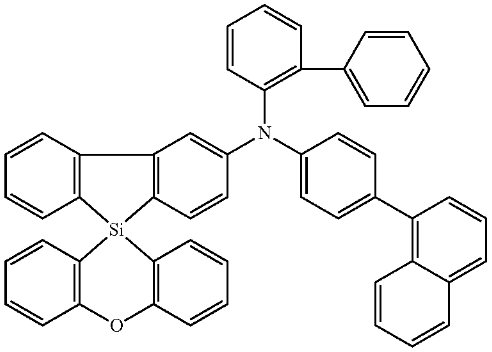
B439
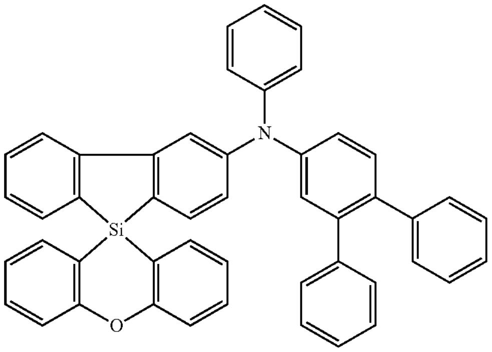
B440
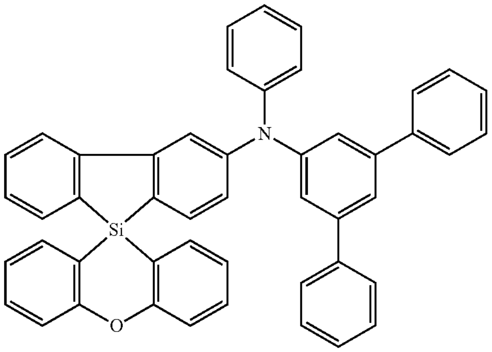
B441
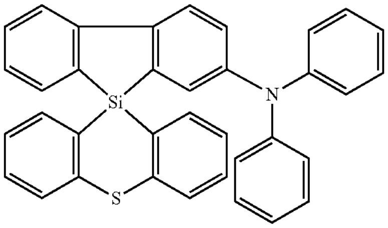
B442
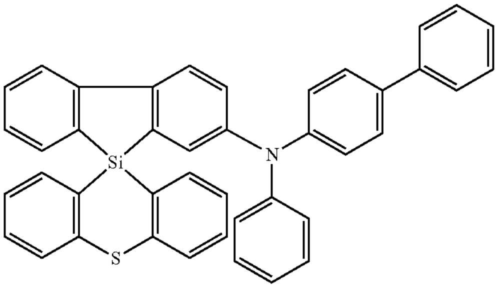
-continued
B443
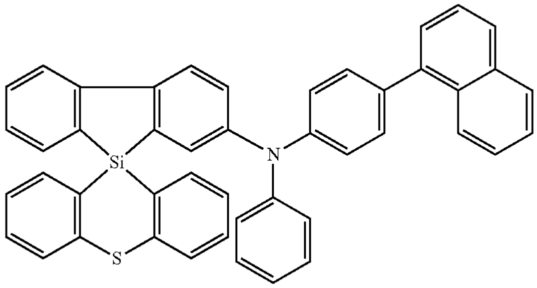
B444
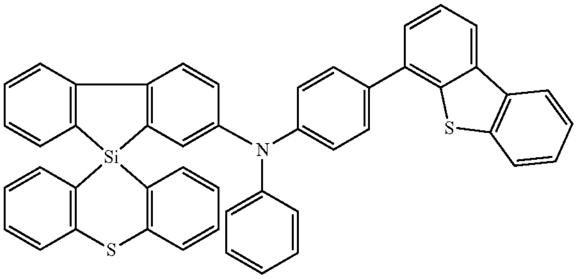
B445
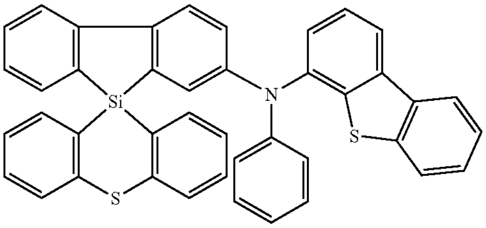
B446
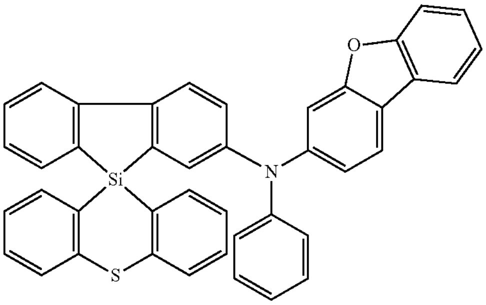
B447
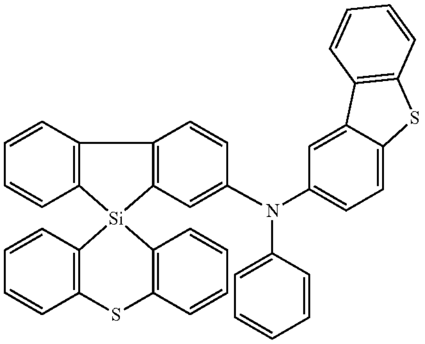

-continued
B448
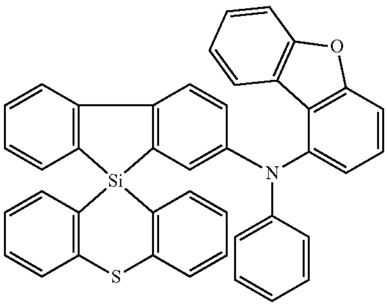
B449
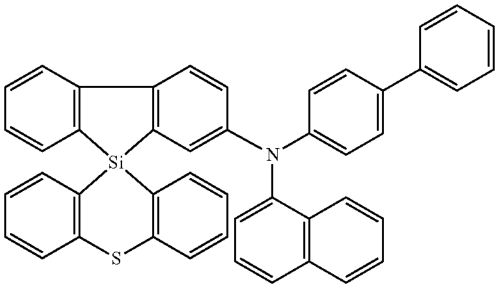
B450
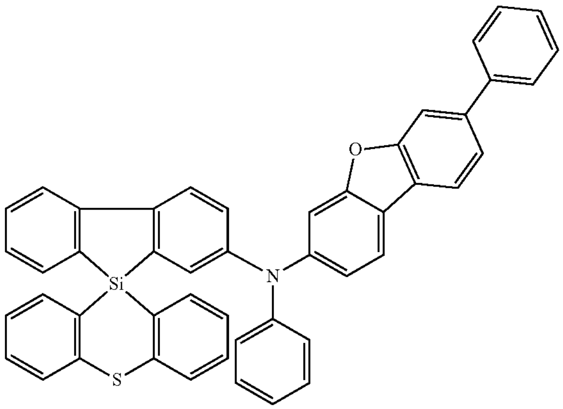
B451
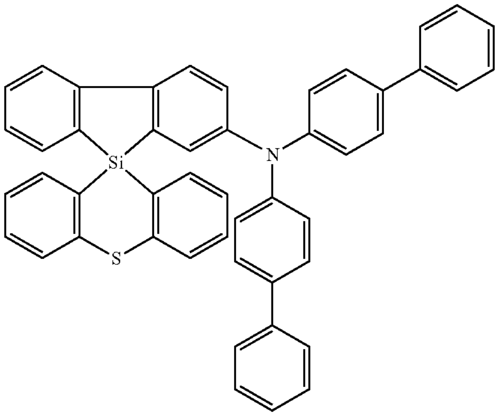
-continued
B452
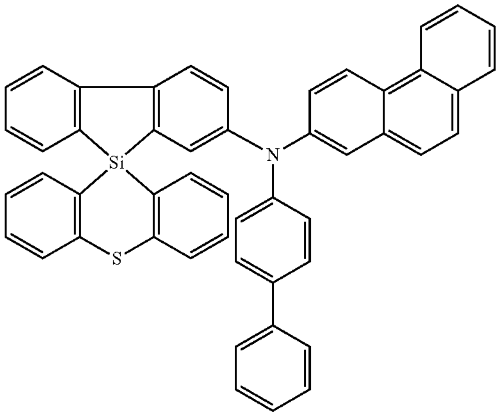
B453
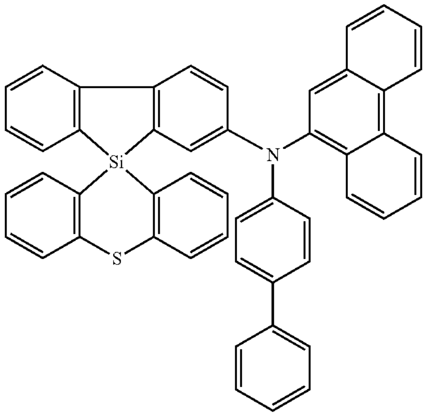
B454
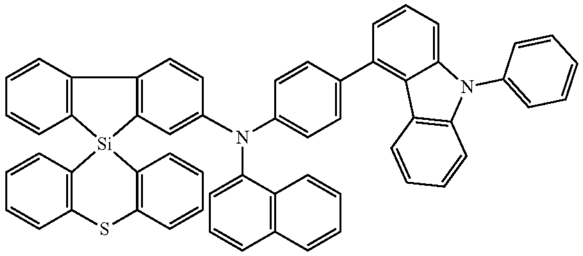
B455
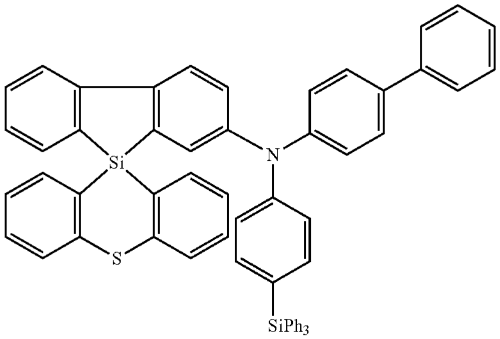

-continued
B456
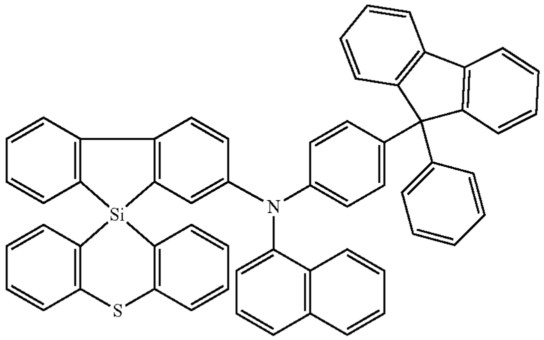
B457
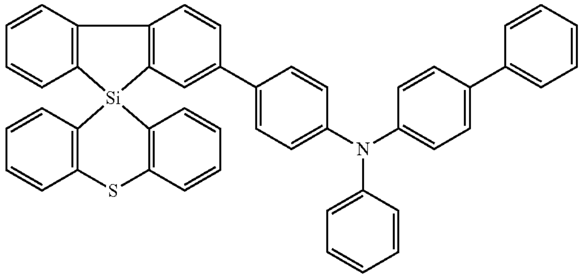
B458
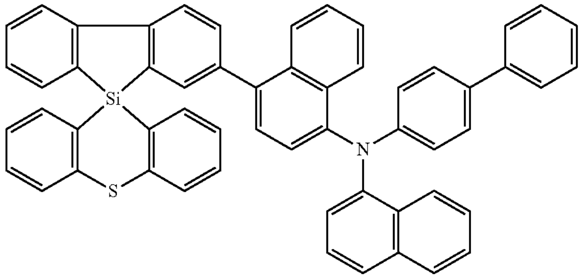
B459
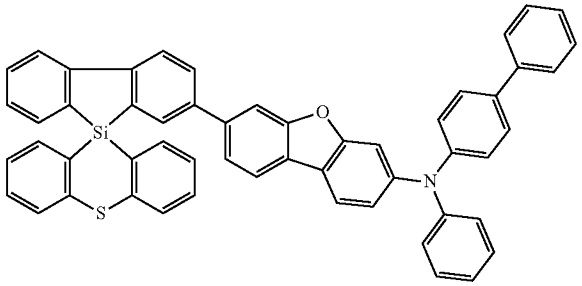
-continued
B460
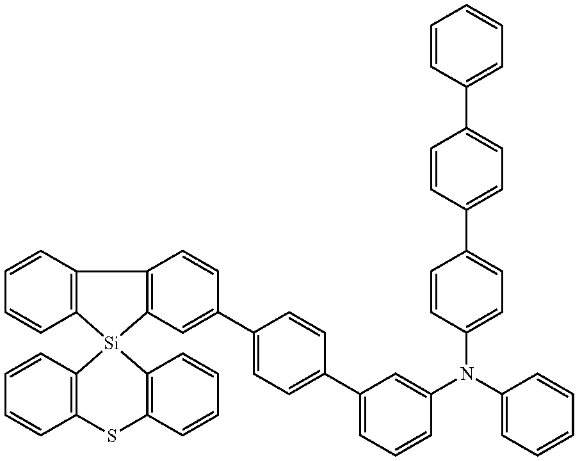
B461
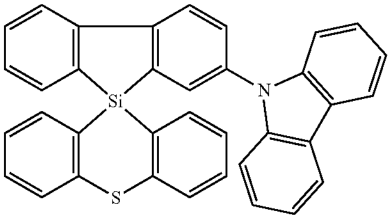
B462
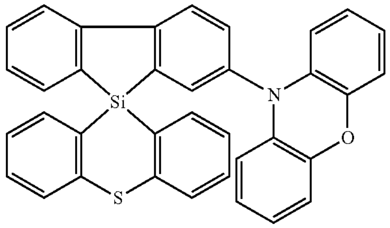
B463
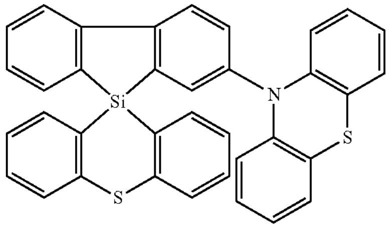
B464
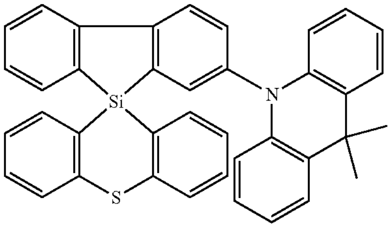

-continued
B465
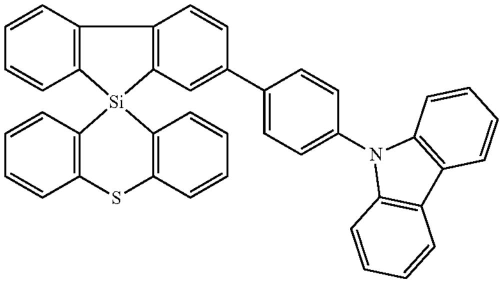
B466
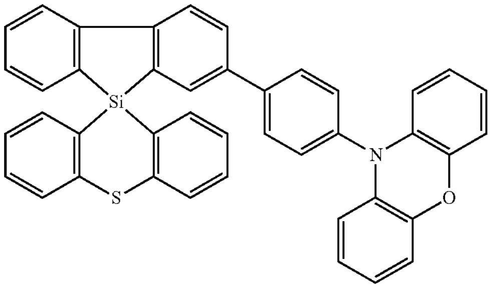
B367
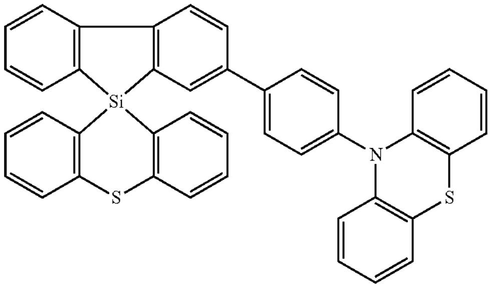
B468
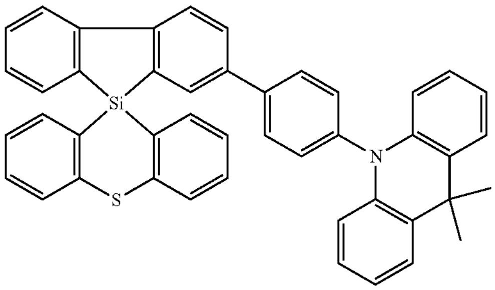
-continued
B469
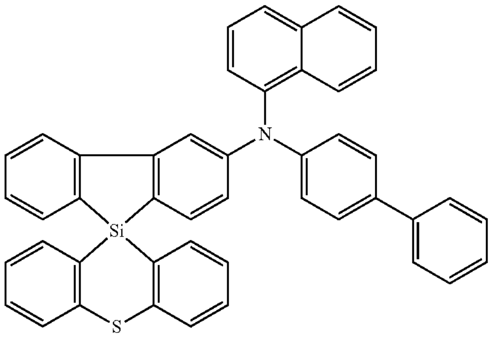
B470
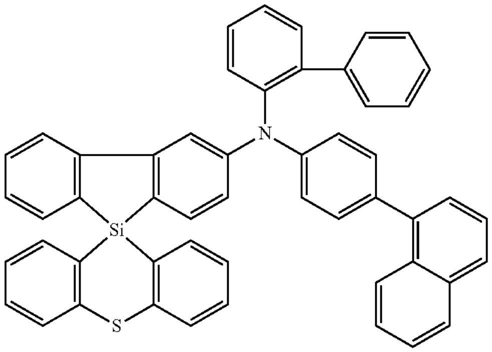
B471
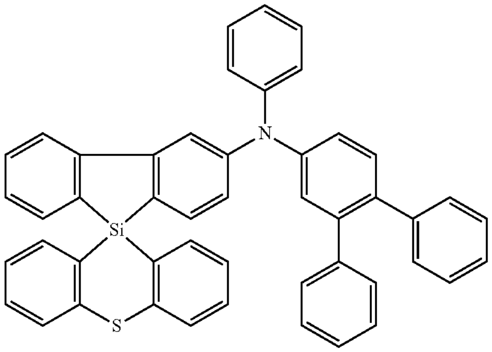
B472
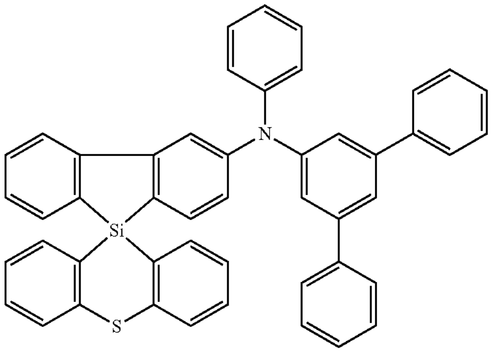

-continued
B473
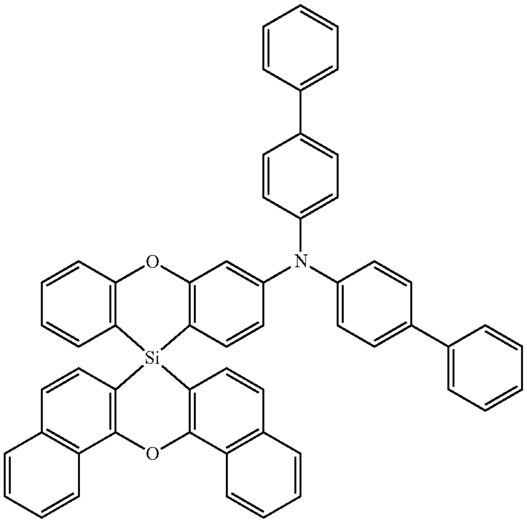
B474
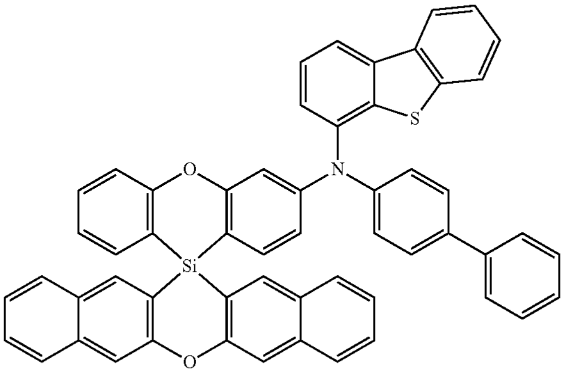
-continued
B475
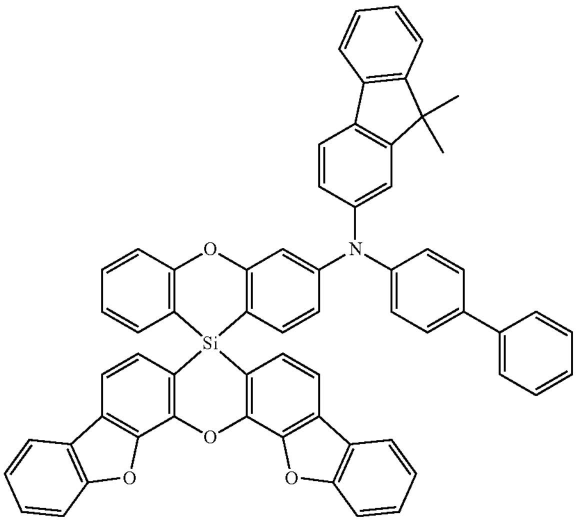
B476
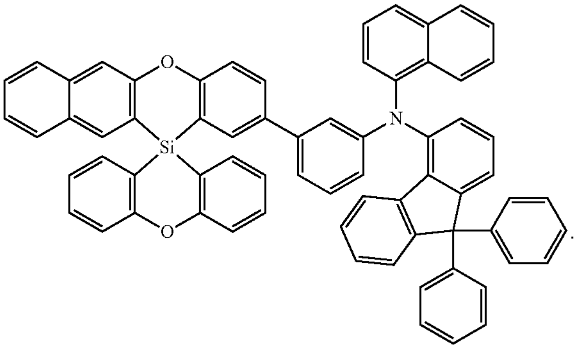
.
* * * * *